US011254711B2

United States Patent
Ammendola et al.

(10) Patent No.: US 11,254,711 B2
(45) Date of Patent: Feb. 22, 2022

(54) ADENOVIRUS POLYNUCLEOTIDES AND POLYPEPTIDES

(71) Applicant: GLAXOSMITHKLINE BIOLOGICALS, SA, Rixensart (BE)

(72) Inventors: Virginia Ammendola, Naples (IT); Stefano Colloca, Rome (IT); Riccardo Cortese, Basel (CH); Fabiana Grazioli, Naples (IT); Alfredo Nicosia, Naples (IT); Alessandra Vitelli, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/735,872

(22) PCT Filed: Jun. 10, 2016

(86) PCT No.: PCT/EP2016/063297
§ 371 (c)(1),
(2) Date: Dec. 12, 2017

(87) PCT Pub. No.: WO2016/198599
PCT Pub. Date: Dec. 15, 2016

(65) Prior Publication Data
US 2020/0140886 A1    May 7, 2020

(30) Foreign Application Priority Data

Jun. 12, 2015  (GB) ..................................... 1510357
Jun. 12, 2015  (WO) ................. PCT/EP2015/063248
Aug. 19, 2015  (GB) ..................................... 1514772

(51) Int. Cl.
| | |
|---|---|
| C07K 14/005 | (2006.01) |
| C12N 15/86 | (2006.01) |
| C07K 14/075 | (2006.01) |
| A61K 39/12 | (2006.01) |
| A61K 39/21 | (2006.01) |
| C07K 14/75 | (2006.01) |
| C12N 15/861 | (2006.01) |
| A61K 39/155 | (2006.01) |
| C12N 7/00 | (2006.01) |
| A61K 39/00 | (2006.01) |

(52) U.S. Cl.
CPC ............ *C07K 14/005* (2013.01); *A61K 39/12* (2013.01); *A61K 39/155* (2013.01); *A61K 39/21* (2013.01); *C07K 14/075* (2013.01); *C07K 14/75* (2013.01); *C12N 7/00* (2013.01); *C12N 15/86* (2013.01); *C12N 15/861* (2013.01); *A61K 2039/5256* (2013.01); *C12N 2710/10321* (2013.01); *C12N 2710/10322* (2013.01); *C12N 2710/10343* (2013.01); *C12N 2710/10371* (2013.01); *C12N 2740/16234* (2013.01); *C12N 2750/14134* (2013.01); *C12N 2750/14143* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | |
|---|---|---|
| 2003/0147920 A1 | 8/2003 | Mossman et al. |
| 2005/0227943 A1 | 10/2005 | Johnson et al. |
| 2009/0104226 A1* | 4/2009 | Perri ....................... A61P 31/14 424/201.1 |
| 2010/0260799 A1 | 10/2010 | Roy et al. |
| 2012/0027788 A1 | 2/2012 | Colloca et al. |
| 2012/0321694 A1 | 12/2012 | Larocque et al. |
| 2014/0314834 A1 | 10/2014 | Paya Cuenca et al. |

FOREIGN PATENT DOCUMENTS

| | | |
|---|---|---|
| CN | 102131920 A | 7/2011 |
| CN | 102300872 A | 12/2011 |
| CN | 103442731 A | 12/2013 |
| CN | 104334188 A | 2/2015 |
| JP | 2007-518414 A | 7/2007 |
| JP | 2011-504751 A | 2/2011 |
| JP | 2011521985 A | 7/2011 |
| JP | 2012516679 A | 7/2012 |
| JP | 2014-504500 A | 2/2014 |
| WO | 2003000283 A1 | 1/2003 |
| WO | 2005071093 A2 | 8/2005 |

(Continued)

OTHER PUBLICATIONS

Lee Hsu et al., Efficacy of adenovirus-vectored respiratory syncytial virus vaccines in a new ferret model, 1994, Vaccine, vol. 12, No. 7, abstract.*
European Communication pursuant to Article 94(3) EPC for European Application No. 16730773.5, dated May 7, 2020.
Astray, R M, et al., "Rabies vaccine development by expression of recombinant viral glycoprotein", Archives of Virology, Springer Wien, AT, vol. 162. No. 2, Oct. 31, 2016, pp. 323-332.
Colloca, et al., "Vaccine Vectors Derived from a Large Collection of Simian Adenoviruses Induce Potent Cellular Immunity Across Multiple Species", Science Translational Medicine, American Association for the Advancement of Science (A A A S), US, vol. 4. No. 115, Jan. 1, 2012. pp. 47-55. XP009166675.

(Continued)

*Primary Examiner* — Benjamin P Blumel
(74) *Attorney, Agent, or Firm* — Birch, Stewart, Kolasch & Birch, LLP

(57) ABSTRACT

There is provided inter alia an isolated polynucleotide, wherein the polynucleotide encodes a polypeptide selected from the group consisting of:
(a) a polypeptide having the amino acid sequence according to SEQ ID NO: 1,
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polypeptide having the amino acid sequence according to SEQ ID NO: 3.

16 Claims, 24 Drawing Sheets
Specification includes a Sequence Listing.

(56) References Cited

FOREIGN PATENT DOCUMENTS

| WO | 2008107370 A1 | 9/2008 |
| --- | --- | --- |
| WO | 2009105084 A2 | 8/2009 |
| WO | 2009136977 A2 | 11/2009 |
| WO | 2009146902 A1 | 12/2009 |
| WO | 2010085984 A1 | 8/2010 |
| WO | 2010086189 A2 | 8/2010 |
| WO | 2011150249 A1 | 12/2011 |
| WO | WO 2012/089231 A1 | 7/2012 |
| WO | 2013006842 A2 | 1/2013 |
| WO | 2013052799 A2 | 4/2013 |
| WO | 2013116965 A1 | 8/2013 |
| WO | WO 2013/139911 A1 | 9/2013 |
| WO | 2014019718 A1 | 2/2014 |
| WO | 2014079842 A1 | 5/2014 |
| WO | 2015189425 A1 | 12/2015 |
| WO | 2016198599 A1 | 12/2016 |

OTHER PUBLICATIONS

Connors M., et al., "Respiratory Syncytial Virus (RSV) F, G, M2 (22K), and N Proteins Each Induce Resistance to RSV Challenge, but Resistance Induced by M2 and N Proteins Is Relatively Short-Lived" Journal of Virology, vol. 65, No. 3, Mar. 1, 1991. pp. 1634-1637.

Database Geneseq [Online], Sep. 24, 2015 (Sep. 24, 2015).

Hennessy, et al.. "Targeting Toll-like receptors: emerging therapeutics?", Nature reviews Drug discovery, vol. 9, Issue 4; Apr. 1, 2010, pp. 293-307.

Hildegund C.J. ERTL et al., "Novel Vaccines to Human Rabies". PLOS Neglected Tropical Diseases, vol. 3, No. 9, Sep. 29, 2009 (Sep. 29, 2009), p. e515.

Mossman, et al., "Development of a CTL vaccine for Her-2/neu usingpeptide-microspheres and adjuvants", Vaccine vol. 23, Issue 27, May 20, 2005, pp. 3545-3554.

Pierantoni A. et al., "Mucosal delivery of a vectored RSV vaccine is safe and elicitsprotective immunity in rodents and nonhuman primates." Molecular Therapy—Methods & Clinical Development, May 20, 2015, vol. 2, No. 15018 pp. 1-11.

Roberts, et al., "Hexon-chimaeric adenovirus serotype 5 vectors circumvent pre-existinq anti-vector immunity." Nature, May 11, 2006, vol. 441, pp. 239-243.

Roy, et al., "Creation of a panel of vectors based on ape adenovirus isolates", The Journal of Gene Medicine, vol. 13, Dec. 17, 2010, pp. 17-25.

Roy, et al., "Complete nucleotide sequences and genome organization of four chimpanzee adenoviruses", Virology, vol. 324, 2004, pp. 361-372.

Tatsis, et al., "Adenoviruses as vaccine vectors", Molecular Therapy, 2004, vol. 10, No. 4, Oct. 2004, p. 616-629.

Wang, et al., "A complex adenovirus vaccine against chikungunya virus provides complete protection against viraemia and arthritis", Vaccine, vol. 29, No. 15, pp. 2803-2809; Jan. 30, 2011.

Xiang Z.Q. et al., "Protection of non-human primates against rabies with an adenovirus recombinant vaccine", Virology, vol. 450, Jan. 9, 2014 (Jan. 9, 2014), pp. 243-249.

Youil et al., "Hexon Gene Switch Strategy for the Generation of Chimeric Recombinant Adenovirus", Human Gene Therapy, 13:311-320, Jan. 2002.

Yu et al., "Toll-like receptors expressed in tumor cells: targets for therapy". Cancer Immunol Immunother, vol. 57, Issue 9; pp. 1271-1278; Feb. 7, 2008.

Zhou, et al., "A Chimpanzee-Origin Adenovirus Vector Expressing the Rabies Virus Glycoprotein as an Oral Vaccine against Inhalation Infection with Rabies Virus". Molecular Therapy, vol. 14, No. 5, Nov. 2006, pp. 662-672.

Furtado et al., "Functional Dissection of Adenovirus VAI RNA," Journal of Virology. Aug. 1989, vol. 63. No. 8, pp. 3423-3434.

\* cited by examiner

```
ChAd3   (365) TPDPSPNCRI ISDKDCKFTLVLTKCGSQ LASV ALAVSGNLASI IGTVASVT FLRFDQNGVLMENSSLLDRQYWN RNGNSTN APYTNAVGFMPNL AA
PanAd3  (364) TPDPSPNCRI ISD KDCKFTLVLTKCGSQ LASV ALAVSGNLSSM GTVSSVT FLRFREDQNGVIMENSSLLDKEYWN RNGNSTN TPYTNAVGFMPNL SA
ChAd17  (365) TPDPSPNCRI ISDKDCKFTLVLTKCGSQ LASV ALAVSGNLAS IDGTVASVT FLRFREDQNGVIMENSSLLDKQYWN RNGNSTN APYTNAVGFMPNL AA
ChAd19  (365) TPDPSPNCRI LSDKDCKFTLVLTKCGSQ LASV ALAVSGNLASI IGTVSSVT FLRFREDQNGVL ENSSLDKQYWN RNGNSTN TPYTNAVGFMPNL AA
ChAd24  (365) TPDPSPNCRI ISDKDCKFTLVLTKCGSQ LASV ALAVSGNLASI IGTVSSVT FLRFDQNGVLMENSSLDKQYWN RNGNSTN ATPYTNAVGFMPNL AA
ChAd155 (401) TPDPSPNCRI VSEKDAKFTLVLTKCGSQVLASVSMLSVKGS LAPISGTVTSAQI VLRFDENGVLLSNSSLDPQYWN YRKGDLTEGTA YTNAVGFMPNL TA
ChAd11  (401) TPDPSPNCRI VSEKDAKFTLVLTKCGSQVLASVSMLSVKGS LAPISGTVT SAQI LRFDENGVLLSNSSLDPQYWN RRKGDLTEGTA YTNAVGFMPNL TA
ChAd20  (401) TPDPSPNCRI VSEKDAKFTLVLTKCGSQVLASVSVLSVKGS LAPISGTVTSAQTVLRFDENGVLLSNSSLDPQYWN RKGDLTEGTAYTNAVGFMPNL TA
ChAd31  (401) TPDPSPNCRI VSEKDAKFTLVLTKCGSQVLASVSVLSVKGS LAPISGTVT SAQIMLRFDENGVLLSNSSLDPQYWN RKGDLTEGTA YTNAVGFMPNL TA
PanAd1  (400) TPDPSPNCRI NSEKDAKILTLVLTKCGSQVLASVSMLSVKGS LAPISGTVT SAQI LRFDENGVLLSNSSLDPQYWN YRKGDSTEGTAYTNAVGFMPNL TA
PanAd2  (400) TPDPSPNCRI NSEKDAKITLVLTKCGSQVLASVSMLSVKGS LAPISGTVT SAQI LRFDENGVLLSNSSLDPQYWN YRKGDSTEGTA YTNAVGFMPNL TA

ChAd3   (465) YPKTQSQTAKNNIVSQVYINGDKSKPMILTITLNGTNE SET QVSHYSMSF WAWESGQYATETFATNSFTFSYIAEQ
PanAd3  (464) YPKTQSQTAKNNIVSEVYLHGDKSKPMILTITLNGTNE SET QVSHYSMSFIWSWDSGKYATETFATNSFTFSYIAEQ
ChAd17  (465) YPKTQSQTAKNNIVSQVYINGDKSKPMILTITLNGTNE SET QVSHYSMSF WAWESGQYATETFATNSFTFSYIAEQ
ChAd19  (465) YPKTQSQTAKNNIVSQVYINGDKSKPMILTITLNGTNE SET QVSHYSMSF WAWESGQYATETFATNSFTFSYIAEQ
ChAd24  (465) YPKTQSQTAKNNIVSQVYINGDKSKPMILTITLNGTNE SET QVSHYSMSF WAWESGQYATETFATNSFTFSYIAEQ
ChAd155 (501) YPKTQSQTAKSNIVSQVYINGDKSKPMILTITLNGTNETG - DATVSTYSMSFSWNWNGSNYINETFQTNSFTFSYIAQE
ChAd11  (501) YPKTQSQTAKSNIVSQVYINGDKSKPMILTITLNGTNETG - DATVSTYSMSFSWNWNGSNYINETFQTNSFTFSYIAQE
ChAd20  (501) YPKTQSQTAKSNIVSQVYINGDKSKPMILTITLNGTNETG - DATVSTYSMSFSWNWNGSNYINGSNYINETFQTNSFTFSYIAQE
ChAd31  (501) YPKTQSQTAKSNIVSQVYINGDKSKPMILTITLNGTNETG - DATVSTYSMSFSWNWNGSNYINETFQTNSFTFSYIAQE
PanAd1  (500) YPKTQSQTAKSNIVSQVYINGDKKPMTLTITLNGTNETG - DATVSTYSMSFSWNWNGSNYINDTFQTNSFTFSYIAQE
PanAd2  (500) YPKTQSQTAKSNIVSQVYINGDKKPMTLTITLNGTNETG - DATVSTYSMSFSWNWNGSNYINTFQTNSFTFSYIAQE
```

A)

B)

IM: Intramuscular. Symbols represent the geometric mean for each group and the error bars represent 95% confidence intervals of the geometric mean.

TSc: Tracheal Scrape cells; LWC: Lung Wash cells; RA: Right Apical (lung lobe cells); RC: Right Cardiac (lung lobe cells); LC: Left Cardiac (lung lobe cells)

L: Lymphocytes; Mo: macrophages; PMN: Polymorphonuclear Leukocytes; Eo; Eosinophils; Con: control

SEQUENCE LISTING

<160> NUMBER OF SEQ ID NOS: 38

<210> SEQ ID NO 1
<211> LENGTH: 578
<212> TYPE: PRT

<213> ORGANISM: Simian adenovirus

<400> SEQUENCE: 1

```
Met Lys Arg Thr Lys Thr Ser Asp Glu Ser Phe Asn Pro Val Tyr Pro
 1               5                  10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
        355                 360                 365

Ala Ile Ile Ala Lys Leu Gly Thr Gly Leu Ser Phe Asp Asn Thr Gly
    370                 375                 380

Ala Ile Thr Val Gly Asn Lys Asn Asp Asp Lys Leu Thr Leu Trp Thr
385                 390                 395                 400
```

-continued

```
Thr Pro Asp Pro Ser Pro Asn Cys Arg Ile Tyr Ser Glu Lys Asp Ala
            405                 410                 415
Lys Phe Thr Leu Val Leu Thr Lys Cys Gly Ser Gln Val Leu Ala Ser
        420                 425                 430
Val Ser Val Leu Ser Val Lys Gly Ser Leu Ala Pro Ile Ser Gly Thr
    435                 440                 445
Val Thr Ser Ala Gln Ile Val Leu Arg Phe Asp Glu Asn Gly Val Leu
450                 455                 460
Leu Ser Asn Ser Ser Leu Asp Pro Gln Tyr Trp Asn Tyr Arg Lys Gly
465                 470                 475                 480
Asp Leu Thr Glu Gly Thr Ala Tyr Thr Asn Ala Val Gly Phe Met Pro
                485                 490                 495
Asn Leu Thr Ala Tyr Pro Lys Thr Gln Ser Gln Thr Ala Lys Ser Asn
            500                 505                 510
Ile Val Ser Gln Val Tyr Leu Asn Gly Asp Lys Ser Lys Pro Met Thr
        515                 520                 525
Leu Thr Ile Thr Leu Asn Gly Thr Asn Glu Thr Gly Asp Ala Thr Val
    530                 535                 540
Ser Thr Tyr Ser Met Ser Phe Ser Trp Asn Trp Asn Gly Ser Asn Tyr
545                 550                 555                 560
Ile Asn Glu Thr Phe Gln Thr Asn Ser Phe Thr Phe Ser Tyr Ile Ala
                565                 570                 575
Gln Glu
```

```
<210> SEQ ID NO 2
<211> LENGTH: 1734
<212> TYPE: DNA
<213> ORGANISM: Simian adenovirus

<400> SEQUENCE: 2
atgaagcgca ccaaaacgtc tgacgagagc ttcaaccccg tgtaccccta tgacacggaa      60
agcggccctc cctccgtccc tttcctcacc cctcccttcg tgtctcccga tggattccaa     120
gaaagtcccc ccggggtcct gtctctgaac ctggccgagc ccctggtcac ttcccacggc     180
atgctcgccc tgaaaatggg aagtggcctc tccctggacg acgctggcaa cctcacctct     240
caagatatca ccaccgctag ccctcccctc aaaaaaacca agaccaacct cagcctagaa     300
acctcatccc cctaactgt gagcacctca ggcgccctca ccgtagcagc cgccgctccc     360
ctggcggtgg ccggcaccct cctcaccatg caatcagagg cccccctgac agtacaggat     420
gcaaaactca ccctggccac caaaggcccc ctgaccgtgt ctgaaggcaa actggccttg     480
caaacatcgg ccccgctgac ggccgctgac agcagcaccc tcacagtcag tgccacacca     540
ccccttagca aagcaatgg cagcttgggt attgacatgc aagcccccat ttacaccacc     600
aatggaaaac taggacttaa ctttggcgct ccctgcatg tggtagacag cctaaatgca     660
ctgactgtag ttactggcca aggtcttacg ataaacggaa cagccctaca aactagagtc     720
tcaggtgccc tcaactatga cacatcagga aacctagaat tgagagctgc aggggtatg     780
cgagttgatg caaatggtca acttatcctt gatgtagctt acccatttga tgcacaaaac     840
aatctcagcc ttaggcttgg acagggaccc ctgtttgtta actctgccca caacttggat     900
gttaactaca acagaggcct ctacctgttc acatctggaa ataccaaaaa gctagaagtt     960
aatatcaaaa cagccaaggg tctcatttat gatgacactg ctatagcaat caatgcgggt    1020
gatgggctac agtttgactc aggctcagat acaaatccat taaaaactaa acttggatta    1080
```

-continued

```
ggactggatt atgactccag cagagccata attgctaaac tgggaactgg cctaagcttt    1140
gacaacacag gtgccatcac agtaggcaac aaaaatgatg acaagcttac cttgtggacc    1200
acaccagacc catcccctaa ctgtagaatc tattcagaga aagatgctaa attcacactt    1260
gttttgacta aatgcggcag tcaggtgttg ccagcgtttt ctgttttatc tgtaaaaggt    1320
agccttgcgc ccatcagtgg cacagtaact agtgctcaga ttgtcctcag atttgatgaa    1380
aatggagttc tactaagcaa ttcttcccct gaccctcaat actggaacta cagaaaaggt    1440
gaccttacag agggcactgc ataccaacgc agtgggatt tatgcccaa cctcacagca    1500 tacccaaaaa cacagagcca aactgctaaa agcaacattg taagtcaggt ttacttgaat    1560
ggggacaaat ccaaacccat gaccctcacc attaccctca atggaactaa tgaaacagga    1620
gatgccacag taagcactta ctccatgtca ttctcatgga actggaatgg aagtaattac    1680
attaatgaaa cgttccaaac caactccttc accttctcct acatcgccca agaa          1734
```

<210> SEQ ID NO 3
<211> LENGTH: 593
<212> TYPE: PRT
<213> ORGANISM: Simian adenovirus

<400> SEQUENCE: 3

```
Met Arg Arg Ala Ala Met Tyr Gln Glu Gly Pro Pro Pro Ser Tyr Glu
1               5                   10                  15

Ser Val Val Gly Ala Ala Ala Ala Pro Ser Ser Pro Phe Ala Ser
            20                  25                  30

Gln Leu Leu Glu Pro Pro Tyr Val Pro Pro Arg Tyr Leu Arg Pro Thr
        35                  40                  45

Gly Gly Arg Asn Ser Ile Arg Tyr Ser Glu Leu Ala Pro Leu Phe Asp
    50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
            100                 105                 110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
    130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
    210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
```

```
            260                 265                 270
Thr Tyr Glu Asp Leu Glu Gly Gly Asn Ile Pro Ala Leu Leu Asp Val
            275                 280                 285

Glu Ala Tyr Gln Asp Ser Leu Lys Glu Asn Glu Ala Gly Gln Glu Asp
        290                 295                 300

Thr Ala Pro Ala Ala Ser Ala Ala Ala Glu Gln Gly Glu Asp Ala Ala
305                 310                 315                 320

Asp Thr Ala Ala Ala Asp Gly Ala Glu Ala Asp Pro Ala Met Val Val
                325                 330                 335

Glu Ala Pro Glu Gln Glu Glu Asp Met Asn Asp Ser Ala Val Arg Gly
            340                 345                 350

Asp Thr Phe Val Thr Arg Gly Glu Glu Lys Gln Ala Glu Ala Glu Ala
        355                 360                 365

Ala Ala Glu Glu Lys Gln Leu Ala Ala Ala Ala Ala Ala Ala Ala Leu
            370                 375                 380

Ala Ala Ala Glu Ala Glu Ser Glu Gly Thr Lys Pro Ala Lys Glu Pro
385                 390                 395                 400

Val Ile Lys Pro Leu Thr Glu Asp Ser Lys Lys Arg Ser Tyr Asn Leu
                405                 410                 415

Leu Lys Asp Ser Thr Asn Thr Ala Tyr Arg Ser Trp Tyr Leu Ala Tyr
            420                 425                 430

Asn Tyr Gly Asp Pro Ser Thr Gly Val Arg Ser Trp Thr Leu Leu Cys
        435                 440                 445

Thr Pro Asp Val Thr Cys Gly Ser Glu Gln Val Tyr Trp Ser Leu Pro
450                 455                 460

Asp Met Met Gln Asp Pro Val Thr Phe Arg Ser Thr Arg Gln Val Ser
465                 470                 475                 480

Asn Phe Pro Val Val Gly Ala Glu Leu Leu Pro Val His Ser Lys Ser
                485                 490                 495

Phe Tyr Asn Asp Gln Ala Val Tyr Ser Gln Leu Ile Arg Gln Phe Thr
            500                 505                 510

Ser Leu Thr His Val Phe Asn Arg Phe Pro Glu Asn Gln Ile Leu Ala
        515                 520                 525

Arg Pro Pro Ala Pro Thr Ile Thr Thr Val Ser Glu Asn Val Pro Ala
530                 535                 540

Leu Thr Asp His Gly Thr Leu Pro Leu Arg Asn Ser Ile Gly Gly Val
545                 550                 555                 560

Gln Arg Val Thr Val Thr Asp Ala Arg Arg Thr Cys Pro Tyr Val
                565                 570                 575

Tyr Lys Ala Leu Gly Ile Val Ser Pro Arg Val Leu Ser Ser Arg Thr
            580                 585                 590

Phe

<210> SEQ ID NO 4
<211> LENGTH: 1779
<212> TYPE: DNA
<213> ORGANISM: Simian adenovirus

<400> SEQUENCE: 4
atgcggcgcg cggcgatgta ccaggaggga cctcctccct cttacgagag cgtggtgggc    60
gcggcggcgg cggcgccctc ttctcccttt gcgtcgcagc tgctggagcc gccgtacgtg   120
cctccgcgct acctgcggcc tacgggggga agaaacagca tccgttactc ggagctggcg   180
cccctgttcg acaccacccg ggtgtacctg gtggacaaca gtcggcgga cgtggcctcc   240
```

```
ctgaactacc agaacgacca cagcaatttt ttgaccacgg tcatccagaa caatgactac    300
agcccgagcg aggccagcac ccagaccatc aatctggatg accggtcgca ctggggcggc    360
gacctgaaaa ccatcctgca caccaacatg cccaacgtga acgagttcat gttcaccaat    420
aagttcaagg cgcgggtgat ggtgtcgcgc tcgcacacca aggaagaccg ggtggagctg    480
aagtacgagt gggtggagtt cgagctgcca gagggcaact actccgagac catgaccatt    540
gacctgatga caacgcgat cgtggagcac tatctgaaag tgggcaggca gaacggggtc     600
ctggagagcg acatcggggt caagttcgac accaggaact tccgcctggg gctggacccc    660
gtgaccgggc tggttatgcc cggggtgtac accaacgagg ccttccatcc cgacatcatc    720
ctgctgcccg gctgcggggt ggacttcact tacagccgcc tgagcaacct cctgggcatc    780
cgcaagcggc agcccttcca ggagggcttc aggatcaccc acgaggacct ggaggggggc    840
aacatccccg cgctcctcga tgtggaggcc taccaggata gcttgaagga aaatgaggcg    900
ggacaggagg ataccgcccc cgccgcctcc gccgccgccg agcagggcga ggatgctgct    960
gacaccgcgg ccgcggacgg ggcagaggcc gaccccgcta tggtggtgga ggctcccgag    1020
caggaggagg acatgaatga cagtgcggtg cgcggagaca ccttcgtcac ccgggggggag   1080 gaaaagcaag cggaggccga ggccgcggcc gaggaaaagc aactggcggc agcagcggcg    1140
gcggcggcgt tggccgcggc ggaggctgag tctgagggga ccaagcccgc caaggagccc    1200
gtgattaagc ccctgaccga agatagcaag aagcgcagtt acaacctgct caaggacagc    1260
accaacaccg cgtaccgcag ctggtacctg gcctacaact acggcgaccc gtcgacgggg    1320
gtgcgctcct ggaccctgct gtgcacgccg gacgtgacct gcggctcgga gcaggtgtac    1380
tggtcgctgc ccgacatgat gcaagacccc gtgaccttcc gctccacgcg gcaggtcagc    1440
aacttcccgg tggtgggcgc cgagctgctg cccgtgcact ccaagagctt ctacaacgac    1500
caggccgtct actcccagct catccgccag ttcacctctc tgacccacgt gttcaatcgc    1560
tttcctgaga accagattct ggcgcgcccg cccgccccca ccatcaccac cgtcagtgaa    1620
aacgttcctg ctctcacaga tcacgggacg ctaccgctgc gcaacagcat cggaggagtc    1680
cagcgagtga ccgttactga cgccagacgc cgcacctgcc cctacgttta caaggccttg    1740
ggcatagtct cgccgcgcgt cctttccagc cgcactttt                           1779
```

<210> SEQ ID NO 5
<211> LENGTH: 964
<212> TYPE: PRT
<213> ORGANISM: Simian adenovirus

<400> SEQUENCE: 5

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Asp Ser Tyr Phe Ser Leu Ser Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

```
Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Thr Gln Thr Ala Glu
130                 135                 140

Glu Ala Gln Asp Glu Glu Asp Glu Ala Glu Ala Glu Glu Glu Met
145                 150                 155                 160

Pro Gln Glu Glu Gln Ala Pro Val Lys Lys Thr His Val Tyr Ala Gln
                165                 170                 175

Ala Pro Leu Ser Gly Glu Lys Ile Thr Lys Asp Gly Leu Gln Ile Gly
            180                 185                 190

Thr Asp Ala Thr Ala Thr Glu Gln Lys Pro Ile Tyr Ala Asp Pro Thr
        195                 200                 205

Phe Gln Pro Glu Pro Gln Ile Gly Glu Ser Gln Trp Asn Glu Ala Asp
    210                 215                 220

Ala Ser Val Ala Gly Gly Arg Val Leu Lys Lys Thr Pro Met Lys
225                 230                 235                 240

Pro Cys Tyr Gly Ser Tyr Ala Arg Pro Thr Asn Ala Asn Gly Gly Gln
                245                 250                 255

Gly Val Leu Val Glu Lys Asp Gly Lys Met Glu Ser Gln Val Asp
            260                 265                 270

Met Gln Phe Phe Ser Thr Ser Glu Asn Ala Arg Asn Glu Ala Asn Asn
        275                 280                 285

Ile Gln Pro Lys Leu Val Leu Tyr Ser Glu Asp Val His Met Glu Thr
    290                 295                 300

Pro Asp Thr His Ile Ser Tyr Lys Pro Ala Lys Ser Asp Asp Asn Ser
305                 310                 315                 320

Lys Val Met Leu Gly Gln Gln Ser Met Pro Asn Arg Pro Asn Tyr Ile
                325                 330                 335

Gly Phe Arg Asp Asn Phe Ile Gly Leu Met Tyr Tyr Asn Ser Thr Gly
            340                 345                 350

Asn Met Gly Val Leu Ala Gly Gln Ala Ser Gln Leu Asn Ala Val Val
        355                 360                 365

Asp Leu Gln Asp Arg Asn Thr Glu Leu Ser Tyr Gln Leu Leu Leu Asp
    370                 375                 380

Ser Met Gly Asp Arg Thr Arg Tyr Phe Ser Met Trp Asn Gln Ala Val
385                 390                 395                 400

Asp Ser Tyr Asp Pro Asp Val Arg Ile Ile Glu Asn His Gly Thr Glu
                405                 410                 415

Asp Glu Leu Pro Asn Tyr Cys Phe Pro Leu Gly Gly Ile Gly Val Thr
            420                 425                 430

Asp Thr Tyr Gln Ala Ile Lys Thr Asn Gly Asn Gly Asn Gly Gly
        435                 440                 445

Asn Thr Thr Trp Thr Lys Asp Glu Thr Phe Ala Asp Arg Asn Glu Ile
    450                 455                 460

Gly Val Gly Asn Asn Phe Ala Met Glu Ile Asn Leu Ser Ala Asn Leu
465                 470                 475                 480

Trp Arg Asn Phe Leu Tyr Ser Asn Val Ala Leu Tyr Leu Pro Asp Lys
                485                 490                 495

Leu Lys Tyr Asn Pro Ser Asn Val Glu Ile Ser Asp Asn Pro Asn Thr
            500                 505                 510

Tyr Asp Tyr Met Asn Lys Arg Val Val Ala Pro Gly Leu Val Asp Cys
```

```
              515                 520                 525
Tyr Ile Asn Leu Gly Ala Arg Trp Ser Leu Asp Tyr Met Asp Asn Val
        530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
                565                 570                 575

Lys Phe Phe Ala Ile Lys Asn Leu Leu Leu Pro Gly Ser Tyr Thr
                580                 585                 590

Tyr Glu Trp Asn Phe Arg Lys Asp Val Asn Met Val Leu Gln Ser Ser
                595                 600                 605

Leu Gly Asn Asp Leu Arg Val Asp Gly Ala Ser Ile Lys Phe Glu Ser
        610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655

Asp Tyr Leu Ser Ala Ala Asn Met Leu Tyr Pro Ile Pro Ala Asn Ala
                660                 665                 670

Thr Asn Val Pro Ile Ser Ile Pro Ser Arg Asn Trp Ala Ala Phe Arg
                675                 680                 685

Gly Trp Ala Phe Thr Arg Leu Lys Thr Lys Glu Thr Pro Ser Leu Gly
        690                 695                 700

Ser Gly Phe Asp Pro Tyr Tyr Thr Tyr Ser Gly Ser Ile Pro Tyr Leu
705                 710                 715                 720

Asp Gly Thr Phe Tyr Leu Asn His Thr Phe Lys Lys Val Ser Val Thr
                725                 730                 735

Phe Asp Ser Ser Val Ser Trp Pro Gly Asn Asp Arg Leu Leu Thr Pro
                740                 745                 750

Asn Glu Phe Glu Ile Lys Arg Ser Val Asp Gly Glu Gly Tyr Asn Val
                755                 760                 765

Ala Gln Cys Asn Met Thr Lys Asp Trp Phe Leu Ile Gln Met Leu Ala
        770                 775                 780

Asn Tyr Asn Ile Gly Tyr Gln Gly Phe Tyr Ile Pro Glu Ser Tyr Lys
785                 790                 795                 800

Asp Arg Met Tyr Ser Phe Phe Arg Asn Phe Gln Pro Met Ser Arg Gln
                805                 810                 815

Val Val Asp Glu Thr Lys Tyr Lys Asp Tyr Gln Gln Val Gly Ile Ile
                820                 825                 830

His Gln His Asn Asn Ser Gly Phe Val Gly Tyr Leu Ala Pro Thr Met
        835                 840                 845

Arg Glu Gly Gln Ala Tyr Pro Ala Asn Phe Pro Tyr Pro Leu Ile Gly
        850                 855                 860

Lys Thr Ala Val Asp Ser Val Thr Gln Lys Lys Phe Leu Cys Asp Arg
865                 870                 875                 880

Thr Leu Trp Arg Ile Pro Phe Ser Ser Asn Phe Met Ser Met Gly Ala
                885                 890                 895

Leu Thr Asp Leu Gly Gln Asn Leu Leu Tyr Ala Asn Ser Ala His Ala
                900                 905                 910

Leu Asp Met Thr Phe Glu Val Asp Pro Met Asp Glu Pro Thr Leu Leu
                915                 920                 925

Tyr Val Leu Phe Glu Val Phe Asp Val Val Arg Val His Gln Pro His
                930                 935                 940
```

Arg Gly Val Ile Glu Thr Val Tyr Leu Arg Thr Pro Phe Ser Ala Gly
945                 950                 955                 960

Asn Ala Thr Thr

<210> SEQ ID NO 6
<211> LENGTH: 2880
<212> TYPE: DNA
<213> ORGANISM: Simian adenovirus

<400> SEQUENCE: 6

| | | | | | |
|---|---|---|---|---|---|
| atggcgaccc | catcgatgat | gccgcagtgg | tcgtacatgc | acatctcggg | ccaggacgcc | 60 |
| tcggagtacc | tgagccccgg | gctggtgcag | ttcgcccgcg | ccaccgagag | ctacttcagc | 120 |
| ctgagtaaca | agtttaggaa | ccccacggtg | gcgcccacgc | acgatgtgac | caccgaccgg | 180 |
| tctcagcgcc | tgacgctgcg | gttcattccc | gtggaccgcg | aggacaccgc | gtactcgtac | 240 |
| aaggcgcggt | tcaccctggc | cgtgggcgac | aaccgcgtgc | tggacatggc | ctccacctac | 300 |
| tttgacatcc | gcggggtgct | ggaccggggt | cccactttca | agccctactc | tggcaccgcc | 360 |
| tacaactccc | tggcccccaa | gggcgctccc | aactcctgcg | agtgggagca | agaggaaact | 420 |
| caggcagttg | aagaagcagc | agaagaggaa | gaagaagatg | ctgacggtca | agctgaggaa | 480 |
| gagcaagcag | ctaccaaaaa | gactcatgta | tatgctcagg | ctccccttc | tggcgaaaaa | 540 |
| attagtaaag | atggtctgca | ataggaacg | gacgctacag | ctacagaaca | aaaacctatt | 600 |
| tatgcagacc | ctacattcca | gcccgaaccc | caaatcgggg | agtcccagtg | gaatgaggca | 660 |
| gatgctacag | tcgccggcgg | tagagtgcta | aagaaatcta | ctcccatgaa | accatgctat | 720 |
| ggttcctatg | caagacccac | aaatgctaat | ggaggtcagg | gtgtactaac | ggcaaatgcc | 780 |
| cagggacagc | tagaatctca | ggttgaaatg | caattctttt | caacttctga | aaacgcccgt | 840 |
| aacgaggcta | acaacattca | gcccaaattg | gtgctgtata | gtgaggatgt | gcacatggag | 900 |
| accccggata | cgcacctttc | ttacaagccc | gcaaaaagcg | atgacaattc | aaaaatcatg | 960 |
| ctgggtcagc | agtccatgcc | caacagacct | aattacatcg | gcttcagaga | caactttatc | 1020 |
| ggcctcatgt | attacaatag | cactggcaac | atgggagtgc | ttgcaggtca | ggcctctcag | 1080 |
| ttgaatgcag | tggtggactt | gcaagacaga | aacacagaac | tgtcctacca | gctcttgctt | 1140 |
| gattccatgg | gtgacagaac | cagatacttt | tccatgtgga | atcaggcagt | ggacagttat | 1200 |
| gacccagatg | ttagaattat | tgaaaatcat | ggaactgaag | acgagctccc | caactattgt | 1260 |
| ttccctctgg | gtggcatagg | ggtaactgac | acttaccagg | ctgttaaaac | caacaatggc | 1320 |
| aataacgggg | gccaggtgac | ttggacaaaa | gatgaaactt | ttgcagatcg | caatgaaata | 1380 |
| ggggtgggaa | acaatttcgc | tatggagatc | aacctcagtg | ccaacctgtg | agaaacttc | 1440 |
| ctgtactcca | acgtggcgct | gtacctacca | gacaagctta | agtacaaccc | ctccaatgtg | 1500 |
| gacatctctg | acaaccccaa | cacctacgat | tacatgaaca | agcgagtggt | ggccccgggg | 1560 |
| ctggtggact | gctacatcaa | cctgggcgcg | cgctggtcgc | tggactacat | ggacaacgtc | 1620 |
| aaccccttca | ccaccaccg | caatgcgggc | ctgcgctacc | gctccatgct | cctgggcaac | 1680 |
| gggcgctacg | tgcccttcca | catccaggtg | ccccagaagt | tctttgccat | caagaacctc | 1740 |
| ctcctcctgc | cgggctccta | cacctacgag | tggaacttca | ggaaggatgt | caacatggtc | 1800 |
| ctccagagct | ctctgggtaa | cgatctcagg | gtgacggggg | ccagcatcaa | gttcgagagc | 1860 |
| atctgcctct | acgccaccct | cttccccatg | gcccacaaca | cggcctccac | gctcgaggcc | 1920 |
| atgctcagga | acgacaccaa | cgaccagtcc | ttcaatgact | acctctccgc | cgccaacatg | 1980 |

| | |
|---|---|
| ctctacccca tacccgccaa cgccaccaac gtccccatct ccatcccctc gcgcaactgg | 2040 |
| gcggccttcc gcggctgggc cttcacccgc tcaagacca aggagacccc ctccctgggc | 2100 |
| tcgggattcg acccctacta cacctactcg ggctccattc cctacctgga cggcaccttc | 2160 |
| tacctcaacc acactttcaa gaaggtctcg gtcaccttcg actcctcggt cagctggccg | 2220 |
| ggcaacgacc gtctgctcac ccccaacgag ttcgagatca gcgctcggt cgacggggag | 2280 |
| ggctacaacg tggcccagtg caacatgacc aaggactggt cctggtccga tgctggcc | 2340 |
| aactacaaca tcggctacca gggcttctac atcccagaga gctacaagga caggatgtac | 2400 |
| tccttcttca ggaacttcca gcccatgagc cggcaggtgg tggaccagac caagtacaag | 2460 |
| gactaccagg aggtgggcat catccaccag cacaacaact cgggcttcgt gggctacctc | 2520 |
| gcccccacca tgcgcgaggg acaggcctac cccgccaact tccccatacc gctcataggc | 2580 |
| aagaccgcgg tcgacagcat cacccagaaa aagttcctct gcgaccgcac cctctggcgc | 2640 |
| atcccccttct ccagcaactt catgtccatg gtgcgctct cggacctggg ccagaacttg | 2700 |
| ctctacgcca actccgccca cgccctcgac atgaccttcg aggtcgaccc catggacgag | 2760 |
| cccacccttc tctatgttct gttcgaagtc tttgacgtgg tccgggtcca ccagccgcac | 2820 |
| cgcggcgtca tcgagaccgt gtacctgcgt acgcccttct cggccggcaa cgccaccacc | 2880 |

<210> SEQ ID NO 7
<211> LENGTH: 37912
<212> TYPE: DNA
<213> ORGANISM: Simian adenovirus

<400> SEQUENCE: 7

| | |
|---|---|
| catcatcaat aatatacctt attttggatt gaagccaata tgataatgag atgggcggcg | 60 |
| cggggcgggg cgcggggcgg gaggcgggtt tggggggggg ccggcgggcg gggcggtgtg | 120 |
| gcggaagtgg actttgtaag tgtggcggat gtgacttgct agtgccgggc gcggtaaaag | 180 |
| tgacgttttc cgtgcgcgac aacgccccg ggaagtgaca ttttttcccgc ggttttttacc | 240 |
| ggatgttgta gtgaatttgg gcgtaaccaa gtaagatttg gccattttcg cgggaaaact | 300 |
| gaaacgggga agtgaaatct gattaatttt gcgttagtca taccgcgtaa tatttgtcta | 360 |
| gggccgaggg actttggccg attacgtgga ggactcgccc aggtgttttt tgaggtgaat | 420 |
| ttccgcgttc cgggtcaaag tctgcgtttt attattatag gatatcccat tgcatacgtt | 480 |
| gtatccatat cataatatgt acatttatat tggctcatgt ccaacattac cgccatgttg | 540 |
| acattgatta ttgactagtt attaatagta atcaattacg ggtcattag ttcatagccc | 600 |
| atatatggag ttccgcgtta cataacttac ggtaaatggc ccgcctggct gaccgcccaa | 660 |
| cgacccccgc ccattgacgt caataatgac gtatgttccc atagtaacgc caatagggac | 720 |
| tttccattga cgtcaatggg tggagtattt acggtaaact gcccacttgg cagtacatca | 780 |
| agtgtatcat atgccaagta cgccccctat tgacgtcaat gacggtaaat ggcccgcctg | 840 |
| gcattatgcc cagtacatga ccttatggga ctttcctact tggcagtaca tctacgtatt | 900 |
| agtcatcgct attaccatgg tgatgcggtt ttggcagtac atcaatgggc gtggatagcg | 960 |
| gtttgactca cggggatttc caagtctcca ccccattgac gtcaatggga gtttgttttg | 1020 |
| gcaccaaaat caacgggact ttccaaaatg tcgtaacaac tccgccccat tgacgcaaat | 1080 |
| gggcggtagg cgtgtacggt gggaggtcta tataagcaga gctctcccta tcagtgatag | 1140 |
| agatctccct atcagtgata gagatcgtcg acgagctcgt ttagtgaacc gtcagatcgc | 1200 |

```
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccgggccc cccctcgagg tcgacggtat cgataagctt cacgctgccg   1380
caagcactca gggcgcaagg gctgctaaag gaagcggaac acgtagaaag ccagtccgca   1440
gaaacggtgc tgaccccgga tgaatgtcag ctactgggct atctggacaa gggaaaacgc   1500
aagcgcaaag agaaagcagg tagcttgcag tgggcttaca tggcgatagc tagactgggc   1560
ggttttatgg acagcaagcg aaccggaatt gccagctggg gcgccctctg gtaaggttgg   1620
gaagccctgc aaagtaaact ggatggcttt cttgccgcca aggatctgat ggcgcagggg   1680
atcaagatct aaccaggagc tatttaatgg caacagttaa ccagctggta cgcaaaccac   1740
gtgctcgcaa agttgcgaaa agcaacgtgc ctgcgctgga agcatgcccg caaaaacgtg   1800
gcgtatgtac tcgtgtatat actaccactc ctaaaaaacc gaactccgcg ctgcgtaaag   1860
tatgccgtgt tcgtctgact aacggtttcg aagtgacttc ctacatcggt ggtgaaggtc   1920
acaacctgca ggagcactcc gtgatcctga tccgtggcgg tcgtgttaaa gacctcccgg   1980
gtgttcgtta ccacaccgta cgtggtgcgc ttgactgctc cggcgttaaa gaccgtaagc   2040
aggctcgttc caagtatggc gtgaagcgtc ctaaggctta atggtagatc tgatcaagag   2100
acaggatgac ggtcgtttcg catgcttgaa caagatggat tgcacgcagg ttctccggcc   2160
gcttgggtgg agaggctatt cggctatgac tgggcacaac agacaatcgg ctgctctgat   2220
gccgccgtgt tccggctgtc agcgcagggg cgcccggttc tttttgtcaa gaccgacctg   2280
tccggtgccc tgaatgaact gcaggacgag gcagcgcggc tatcgtggct ggccacgacg   2340
ggcgttcctt gcgcagctgt gctcgacgtt gtcactgaag cgggaaggga ctggctgcta   2400
ttgggcgaag tgccggggca ggatctcctg tcatctcacc ttgctcctgc cgagaaagta   2460
tccatcatgg ctgatgcaat gcggcggctg catacgcttg atccggctac ctgcccattc   2520
gaccaccaag cgaaacatcg catcgagcga gcacgtactc ggatggaagc cggtcttgtc   2580
gatcaggatg atctggacga agagcatcag gggctcgcgc cagccgaact gttcgccagg   2640
ctcaaggcgc gcatgcccga cggcgaggat ctcgtcgtga cccatggcga tgcctgcttg   2700
ccgaatatca tggtggaaaa tggccgcttt tctggattca tcgactgtgg ccggctgggt   2760
gtggcggacc gctatcagga catagcgttg gctacccgtg atattgctga agagcttggc   2820
ggcgaatggg ctgaccgctt cctcgtgctt tacggtatcg ccgctcccga ttcgcagcgc   2880
atcgccttct atcgccttct tgacgagttc ttctgagcgg gactctgggg ttcgaaatga   2940
ccgaccaagc gacgcccaac ctgccatcac gagatttcga ttccaccgcc gccttctatg   3000
aaaggttggg cttcggaatc gttttccggg acgccggctg atgatcctc cagcgcgggg   3060
atctcatgct ggagttcttc gcccaccccg ggctcgatcc cctcgggggg aatcagaatt   3120
cagtcgacag cggccgcgat ctgctgtgcc ttctagttgc cagccatctg ttgtttgccc   3180
ctcccccgtg ccttccttga ccctggaagg tgccactccc actgtccttt cctaataaaa   3240
tgaggaaatt gcatcgcatt gtctgagtag tgtcattct attctggggg gtggggtggg   3300
gcaggacagc aagggggagg attgggaaga caatagcagg catgctgggg atgcggtggg   3360
ctctatggcc gatcagcgat cgctgaggtg ggtgagtggg cgtggcctgg ggtggtcatg   3420
aaaatatata agttgggggt cttagggtct ctttatttgt gttgcagaga ccgccggagc   3480
catgagcggg agcagcagca gcagcagtag cagcagcgcc ttggatggca gcatcgtgag   3540
cccttatttg acgacgcgga tgccccactg ggccggggtg cgtcagaatg tgatgggctc   3600
```

```
cagcatcgac ggccgacccg tcctgcccgc aaattccgcc acgctgacct atgcgaccgt   3660
cgcggggacg ccgttggacg ccaccgccgc cgccgccgcc accgcagccg cctcggccgt   3720
gcgcagcctg gccacggact ttgcattcct gggaccactg gcgacagggg ctacttctcg   3780
ggccgctgct gccgccgttc gcgatgacaa gctgaccgcc ctgctggcgc agttggatgc   3840
gcttactcgg gaactgggtg acctttctca gcaggtcatg gccctgcgcc agcaggtctc   3900
ctccctgcaa gctggcggga atgcttctcc cacaaatgcc gtttaagata aataaaacca   3960
gactctgttt ggattaaaga aaagtagcaa gtgcattgct ctctttattt cataattttc   4020
cgcgcgcgat aggccctaga ccagcgttct cggtcgttga gggtgcggtg tatcttctcc   4080
aggacgtggt agaggtggct ctggacgttg agatacatgg gcatgagccc gtcccggggg   4140
tggaggtagc accactgcag agcttcatgc tccggggtgg tgttgtagat gatccagtcg   4200
tagcaggagc gctgggcatg gtgcctaaaa atgtccttca gcagcaggcc gatggccagg   4260
gggaggccct tggtgtaagt gtttacaaaa cggttaagtt gggaagggtg cattcgggga   4320
gagatgatgt gcatcttgga ctgtattttt agattggcga tgtttccgcc cagatccctt   4380
ctgggattca tgttgtgcag gaccaccagt acagtgtatc cggtgcactt ggggaatttg   4440
tcatgcagct tagagggaaa agcgtggaag aacttggaga cgcctttgtg gcctcccaga   4500
ttttccatgc attcgtccat gatgatggca atgggcccgc gggaggcagc ttgggcaaag   4560
atatttctgg ggtcgctgac gtcgtagttg tgttccaggg tgaggtcgtc ataggccatt   4620
tttacaaagc gcgggcggag ggtgcccgac tgggggatga tggtcccctc tggccctggg   4680
gcgtagttgc cctcgcagat ctgcatttcc caggccttaa tctcggaggg gggaatcata   4740
tccacctgcg gggcgatgaa gaaaacggtt ccggagccg gggagattaa ctgggatgag   4800
agcaggtttc taagcagctg tgattttcca caaccggtgg gcccataaat aacacctata   4860
accggttgca gctggtagtt tagagagctg cagctgccgt cgtcccggag gagggggcc   4920 acctcgttga gcatgtccct gacgcgcatg ttctccccga ccagatccgc cagaaggcgc   4980
tcgccgccca gggacagcag ctcttgcaag gaagcaaagt ttttcagcgg cttgaggccg   5040
tccgccgtgg gcatgttttt cagggtctgg ctcagcagct ccaggcggtc ccagagctcg   5100
gtgacgtgct ctacggcatc tctatccagc atatctcctc gtttcgcggg ttggggcgac   5160
tttcgctgta gggcaccaag cggtggtcgt ccagcgggc cagagtcatg tccttccatg   5220
ggcgcagggt cctcgtcagg gtggtctggg tcacggtgaa ggggtgcgct ccgggctgag   5280
cgcttgccaa ggtgcgcttg aggctggttc tgctggtgct gaagcgctgc cggtcttcgc   5340
cctgcgcgtc ggccaggtag catttgacca tggtgtcata gtccagcccc tccgcggcgt   5400
gtcccttggc gcgcagcttg cccttggagg tggcgccgca cgaggggcag agcaggctct   5460
tgagcgcgta gagcttgggg gcgaggaaga ccgattcggg ggagtaggcg tccgcgccgc   5520 agacccgca cacggtctcg cactccacca gccaggtgag ctcggggcgc gccgggtcaa   5580
aaaccaggtt tcccccatgc tttttgatgc gtttcttacc tcgggtctcc atgaggtggt   5640
gtccccgctc ggtgacgaag aggctgtccg tgtctccgta daccgacttg agggtctttt   5700
tctccagggg ggtccctcgg tcttcctcgt agaggaactc ggaccactct gagacgaagg   5760
cccgcgtcca ggccaggacg aaggaggcta tgtgggaggg gtagcggtcg ttgtccacta   5820
gggggtccac cttctccaag gtgtgaagac acatgtcgcc ttcctcggcg tccaggaagg   5880
tgattggctt gtaggtgtag gccacgtgac cgggggttcc tgacgggggg gtataaagg   5940
```

```
gggtgggggc gcgctcgtcg tcactctctt ccgcatcgct gtctgcgagg ccagctgct      6000
ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atctttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag gggggcaggg ggtcgagctg ggtctcgtcc gggggtccg     6480
cgtccacggt gaaaccccg gggcgcaggc gcgcgtcgaa gtagtctatc ttgcaacctt      6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcataga    6660
cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg    6780
tgcgggcggg gcgctccgcg cggaagacga tctgcctgaa gatggcatgc gagttggaag    6840
agatggtggg gcgctggaag acgttgaagc tggcgtcctg caggccgacg gcgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttctttttcc    7020
acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tggcccacga tgtagagttc caggaagcgg ggccggccct    7500
ttacggtggg cagcttcttt agctcttcgt aggtgagctc ctcgggcgag gcgaggccgt    7560
gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680
tttttcggg ggtgatgcag tagaaggtga gggggtcttg ctgccagcgg tcccagtcga    7740
gctgcagggc gaggtcgcgc gcggcggtga ccaggcgctc gtcgccccg aatttcatga     7800
ccagcatgaa gggcacgagc tgctttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc acctttcgcc cgcgcacgag gaagccgagg ggaaatctga    8100
gccccccgcc tggctcgcgg catggctggt tctcttctac tttggatgcg tgtccgtctc    8160
cgtctggctc ctcgaggggt gttacggtgg agcggaccac cacgccgcgc gagccgcagg    8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
```

```
cgcagagtcg ggccagggcg cggggcaggt ctaggtggta cctgatctct aggggcgtgt    8400
tggtggcggc gtcgatggct tgcaggagcc cgcagccccg gggggcgacg acggtgcccc    8460
gcggggtggt ggtggtggtg gcggtgcagc tcagaagcgg tgccgcgggc gggcccccgg    8520 aggtagggg  ggctccggtc ccgcgggcag gggcggcagc ggcacgtcgg cgtggagcgc    8580
gggcaggagt tggtgctgtg cccggaggtt gctggcgaag cgacgacgc  ggcggttgat    8640 ctcctggatc tggcgcctct gcgtgaagac gacgggcccg gtgagcttga acctgaaaga    8700
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
gaggtctccg cgtccggcgc gttccacggt ggccgccagg tcgttggaga tgcgcccat    8880 gagctgcgag aaggcgttga gtccgccctc gttccagact cggctgtaga ccacgccccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
cacgaagaag ttcatgaccc agcggcgcaa cgtggattcg ttgatgtccc ccaaggcctc    9120
cagccgttcc atggcctcgt agaagtccac ggcgaagttg aaaaactggg agttgcgcgc    9180
cgacacggtc aactcctcct ccagaagacg gatgagctcg gcgacggtgt cgcgcacctc    9240
gcgctcgaag gctatgggga tctcttcctc cgctagcatc accacctcct cctcttcctc    9300
ctcttctggc acttccatga tggcttcctc ctcttcgggg ggtggcggcg gcggcggtgg    9360 gggaggggc  gctctgcgcc ggcggcgcg  caccggagg  cggtccacga agcgcgcgat    9420
catctccccg cggcggcggc gcatggtctc ggtgacggcg cggccgttct cccggggcg    9480 cagttggaag acgccgccgg acatctggtg ctggggcggg tggccgtgag gcagcgagac    9540
ggcgctgacg atgcatctca acaattgctg cgtaggtacg ccgccgaggg acctgaggga    9600
gtccatatcc accggatccg aaaaccttc  gaggaaggcg tctaaccagt cgcagtcgca    9660
aggtaggctg agcaccgtgg cgggcggcgg ggggtggggg gagtgtctgg cggaggtgct    9720
gctgatgatg taattgaagt aggcggactt gacacggcgg atggtcgaca ggagcaccat    9780
gtccttgggt ccggcctgct ggatgcggag gcggtcggct atgccccagg cttcgttctg    9840
gcatcggcgc aggtccttgt agtagtcttg catgagcctt ccaccggca  cctcttctcc    9900 ttcctcttct gcttcttcca tgtctgcttc ggccctgggg cggcgccgcg ccccctgcc    9960 ccccatgcgc gtgaccccga accccctgag cggttggagc agggccaggt cggcgacgac  10020
gcgctcggcc aggatggcct gctgcacctg cgtgagggtc gtttggaagt catccaagtc  10080
cacgaagcgg tggtaggcgc ccgtgttgat ggtgtaggtg cagttggcca tgacggacca  10140
gttgacggtc tggtggcccg gttgcgacat ctcggtgtac ctgagtcgcg agtaggcgcg  10200
ggagtcgaag acgtagtcgt tgcaagtccg caccaggtac tggtagccca ccaggaagtg  10260
cggcggcggc tggcggtaga ggggccagcc caggtggcg  ggggctccgg gggccaggtc  10320
ttccagcatg aggcggtggt aggcgtagat gtacctggac atccaggtga tacccgcggc  10380
ggtggtggag gcgcgcggga agtcgcgcac ccggttccag atgttgcgca ggggcagaaa  10440
gtgctccatg gtaggcgtgc tctgtccagt cagacgcgcg cagtcgttga tactctagac  10500
cagggaaaac gaaagccggt cagcgggcac tcttccgtgg tctggtgaat agatcgcaag  10560
ggtatcatgg cggagggcct cggttcgagc cccgggtccg ggccgacgg  tccgccatga  10620 tccacgcggt taccgcccgc gtgtcgaacc caggtgtgcg acgtcagaca acggtggagt  10680
```

```
gttccttttg gcgttttttct ggccgggcgc cggcgccgcg taagagacta agccgcgaaa  10740
gcgaaagcag taagtggctc gctccccgta gccggaggga tccttgctaa gggttgcgtt  10800
gcggcgaacc ccggttcgaa tcccgtactc gggccggccg gacccgcggc taaggtgttg  10860
gattggcctc cccctcgtat aaagaccccg cttgcggatt gactccggac acggggacga  10920
gcccctttta ttttttgcttt cccagatgc atccggtgct gcggcagatg cgccccccgc  10980
cccagcagca gcaacaacac cagcaagagc ggcagcaaca gcagcgggag tcatgcaggg  11040 cccccctcacc caccctcggc gggccggcca cctcggcgtc cgcggccgtg tctggcgcct  11100
gcggcggcgg cgggggggccg gctgacgacc ccgaggagcc ccgcggcgc agggccagac  11160 actacctgga cctggaggag ggcgagggcc tggcgcggct gggggcgccg tctcccgagc  11220
gccacccgcg ggtgcagctg aagcgcgact cgcgcgaggc gtacgtgcct cggcagaacc  11280
tgttcaggga ccgcgcgggc gaggagcccg aggagatgcg ggacaggagg ttcagcgcag  11340
ggcgggagct gcggcagggg ctgaaccgcg agcggctgct gcgcgaggag gactttgagc  11400
ccgacgcgcg gacgggatc agccccgcgc gcgcgcacgt ggcggccgcc gacctggtga  11460
cggcgtacga gcagacggtg aaccaggaga tcaacttcca aaagagtttc aacaaccacg  11520
tgcgcacgct ggtggcgcgc gaggaggtga ccatcgggct gatgcacctg tgggactttg  11580
taagcgcgct ggtgcagaac cccaacagca agcctctgac ggcgcagctg ttcctgatag  11640
tgcagcacag cagggacaac gaggcgttta ggacgcgct gctgaacatc accgagcccg  11700
agggtcggtg gctgctggac ctgattaaca tcctgcagag catagtggtg caggagcgca  11760
gcctgagcct ggccgacaag gtggcggcca tcaactactc gatgctgagc ctgggcaagt  11820
tttacgcgcg caagatctac cagacgccgt acgtgcccat agacaaggag gtgaagatcg  11880
acggttttta catgcgcatg gcgctgaagg tgctcaccct gagcgacgac ctgggcgtgt  11940
accgcaacga gcgcatccac aaggccgtga gcgtgagccg gcggcgcgag ctgagcgacc  12000
gcgagctgat gcagacctg cagcgggcgc tggcgggcgc cggcagcggc gacagggagg  12060
cggagtccta cttcgatgcg ggggcggacc tgcgctgggc gcccagccgg cgggccctgg  12120
aggccgcggg ggtccgcgag gactatgacg aggacggcga ggaggatgag gagtacgagc  12180
tagaggaggg cgagtacctg gactaaaccg cgggtggtgt ttccggtaga tgcaagaccc  12240
gaacgtggtg gacccggcgc tgcggcggc tctgcagagc cagccgtccg gccttaactc  12300
ctcagacgac tggcgacagg tcatggaccg catcatgtcg ctgacggcgc gtaacccgga  12360
cgcgttccgg cagcagccgc aggccaacag gctctccgcc atcctggagg cggtggtgcc  12420
tgcgcgctcg aaccccacgc acgagaaggt gctggccata gtgaacgcgc tggccgagaa  12480
cagggccatc cgcccggacg aggccgggct ggtgtacgac gcgctgctgc agcgcgtggc  12540
ccgctacaac agcggcaacg tgcagaccaa cctggaccgg ctggtggggg acgtgcgcga  12600
ggcggtggcg cagcgcgagc gcgcggatcg gcagggcaac ctgggctcca tggtggcgct  12660
gaatgccttc ctgagcacgc agccggccaa cgtgccgcgg gggcaggaag actacaccaa  12720
ctttgtgagc gcgctgcggc tgatggtgac cgagaccccc cagagcgagg tgtaccagtc  12780
gggcccggac tacttcttcc agaccagcag acagggcctg cagacggtga acctgagcca  12840
ggctttcaag aacctgcggg ggctgtgggg cgtgaaggcg cccaccggcg accgggcgac  12900
ggtgtccagc ctgctgacgc ccaactcgcg cctgctgctg ctgctgatcg cgccgttcac  12960
ggacagcggc agcgtgtccc gggacaccta cctgggcac ctgctgaccc tgtaccgcga  13020
ggccatcggg caggcgcagg tggacgagca caccttccag gagatcacca gcgtgagccg  13080
```

```
cgcgctgggg caggaggaca cgagcagcct ggaggcgact ctgaactacc tgctgaccaa    13140
ccggcggcag aagattccct cgctgcacag cctgacctcc gaggaggagc gcatcttgcg    13200
ctacgtgcag cagagcgtga gcctgaacct gatgcgcgac ggggtgacgc ccagcgtggc    13260
gctggacatg accgcgcgca acatggaacc gggcatgtac gccgcgcacc ggccttacat    13320
caaccgcctg atggactacc tgcatcgcgc ggcggccgtg aaccccgagt actttaccaa    13380
cgccatcctg aacccgcact ggctcccgcc gcccgggttc tacagcgggg gcttcgaggt    13440
cccggagacc aacgatggct tcctgtggga cgacatggac gacagcgtgt tctccccgcg    13500
gccgcaggcg ctggcggaag cgtccctgct gcgtcccaag aaggaggagg aggaggaggc    13560
gagtcgccgc cgcggcagca gcggcgtggc ttctctgtcc gagctggggg cggcagccgc    13620
cgcgcgcccc gggtccctgg gcggcagccc ctttccgagc ctggtggggt ctctgcacag    13680
cgagcgcacc acccgccctc ggctgctggg cgaggacgag tacctgaata actccctgct    13740
gcagccggtg cgggagaaaa acctgcctcc cgccttcccc aacaacggga tagagagcct    13800
ggtggacaag atgagcagat ggaagaccta tgcgcaggag cacagggacg cgcctgcgct    13860
ccggccgccc acgcggcgcc agcgccacga ccggcagcgg gggctggtgt gggatgacga    13920
ggactccgcg gacgatagca gcgtgctgga cctgggaggg agcggcaacc cgttcgcgca    13980
cctgcgcccc cgcctgggga ggatgtttta aaaaaaaaaa aaaaaagcaa gaagcatgat    14040
gcaaaaatta aataaaactc accaaggcca tggcgaccga gcgttggttt cttgtgttcc    14100
cttcagtatg cggcgcgcgg cgatgtacca ggagggacct cctccctctt acgagagcgt    14160
ggtgggcgcg gcggcggcgg cgccctcttc tccctttgcg tcgcagctgc tggagccgcc    14220
gtacgtgcct ccgcgctacc tgcggcctac gggggggaga acagcatcc gttactcgga     14280 gctggcgccc ctgttcgaca ccaccgggt gtacctggtg acaacaagt cggcggacgt      14340 ggcctccctg aactaccaga acgaccacg caatttttg accacggtca tccagaacaa      14400
tgactacagc ccgagcgagg ccagcaccca gaccatcaat ctggatgacc ggtcgcactg    14460
gggcggcgac ctgaaaacca tcctgcacac caacatgccc aacgtgaacg agttcatgtt    14520
caccaataag ttcaaggcgc gggtgatggt gtcgcgctcg cacaccaagg aagaccgggt    14580
ggagctgaag tacgagtggg tggagttcga gctgccagag ggcaactact ccgagaccat    14640
gaccattgac ctgatgaaca acgcgatcgt ggagcactat ctgaaagtgg gcaggcagaa    14700
cggggtcctg gagagcgaca tcggggtcaa gttcgacacc aggaacttcc gcctggggct    14760
ggaccccgtg accgggctgg ttatgcccgg ggtgtacacc aacgaggcct tccatcccga    14820
catcatcctg ctgcccggct gcggggtgga cttcacttac agccgcctga caacctcct    14880 gggcatccgc aagcggcagc ccttccagga gggcttcagg atcacctacg aggacctgga    14940 gggggcaac atccccgcgc tcctcgatgt ggaggcctac caggatagct tgaaggaaaa      15000
tgaggcggga caggaggata ccgcccccgc cgcctccgcc gccgcgagc agggcgagga    15060 tgctgctgac accgcggccg cggacggggc agaggccgac cccgctatgg tggtggaggc    15120
tcccgagcag gaggaggaca tgaatgacag tgccggtgcgc ggagacacct tcgtcacccg    15180
gggggaggaa aagcaagcgg aggccgaggc gcgcggccag gaaaagcaac tggcggcagc    15240
agcggcggcg gcggcgttgg ccgcggcgga ggctgagtct gagggacca gcccgccaa     15300 ggagcccgtg attaagcccc tgaccgaaga tagcaagaag cgcagttaca acctgctcaa    15360
ggacagcacc aacaccgcgt accgcagctg gtacctggcc tacaactacg gcgacccgtc    15420
```

```
gacggggggtg cgctcctgga ccctgctgtg cacgccggac gtgacctgcg gctcggagca    15480
ggtgtactgg tcgctgcccg acatgatgca agaccccgtg accttccgct ccacgcggca    15540
ggtcagcaac ttcccggtgg tgggcgccga gctgctgccc gtgcactcca agagcttcta    15600
caacgaccag gccgtctact cccagctcat ccgccagttc acctctctga cccacgtgtt    15660
caatcgcttt cctgagaacc agattctggc gcgcccgccc gcccccacca tcaccaccgt    15720
cagtgaaaac gttcctgctc tcacagatca cgggacgcta ccgctgcgca acagcatcgg    15780
aggagtccag cgagtgaccg ttactgacgc cagacgccgc acctgcccct acgtttacaa    15840
ggccttgggc atagtctcgc cgcgcgtcct ttccagccgc acttttttgag caacaccacc    15900 atcatgtcca tcctgatctc acccagcaat aactccggct ggggactgct gcgcgcgccc    15960
agcaagatgt tcggagggggc gaggaagcgt tccgagcagc accccgtgcg cgtgcgcggg    16020
cacttccgcg cccccctgggg agcgcacaaa cgcggccgcg cggggcgcac caccgtggac    16080
gacgccatcg actcggtggt ggagcaggcg cgcaactaca ggcccgcggt ctctaccgtg    16140
gacgcggcca tccagaccgt ggtgcggggc gcgcggcggt acgccaagct gaagagccgc    16200
cggaagcgcg tggcccgccg ccaccgccgc cgacccgggg ccgccgccaa acgcgccgcc    16260
gcggccctgc ttcgccgggc caagcgcacg ggccgccgcg ccgccatgag ggccgcgcgc    16320
cgcttggccg ccggcatcac cgccgccacc atggcccccc gtacccgaag acgcgcggcc    16380
gccgccgccc ccgccgccat cagtgacatg ccagcaggc gccggggcaa cgtgtactgg    16440
gtgcgcgact cggtgaccgg cacgcgcgtg cccgtgcgct tccgcccccc gcggacttga    16500
gatgatgtga aaaacaaca ctgagtctcc tgctgttgtg tgtatcccag cggcggcggc    16560
gcgcgcagcg tcatgtccaa gcgcaaaatc aaagaagaga tgctccaggt cgtcgcgccg    16620
gagatctatg ggccccgaa gaaggaagag caggattcga agcccgcaa gataaagcgg    16680 gtcaaaaaga aaagaaaga tgatgacgat gccgatgggg aggtggagtt cctgcgcgcc    16740
acggcgccca ggcgcccggt gcagtggaag gggccggcgcg taaagcgcgt cctgcgcccc    16800
ggcaccgcgg tggtcttcac gcccggcgag cgctccaccc ggacttttcaa gcgcgtctat    16860 gacgaggtgt acggcgacga agacctgctg gagcaggcca acgagcgctt cggagagttt    16920
gcttacggga agcgtcagcg ggcgctgggg aaggaggacc tgctggcgct ccgctggac    16980 cagggcaacc ccaccccag tctgaagccc gtgaccctgc agcaggtgct gccgagcagc    17040
gcaccctccg aggcgaagcg gggtctgaag cgcgagggcg gcgacctggc gcccaccgtg    17100
cagctcatgg tgcccaagcg gcagaggctg gaggatgtgc tggagaaaat gaaagtagac    17160
cccggtctgc agccggacat cagggtccgc cccatcaagc aggtggcgcc gggcctcggc    17220
gtgcagaccg tggacgtggt catccccacc ggcaactccc ccgccgccgc caccactacc    17280
gctgcctcca cggacatgga gacacagacc gatcccgccg cagccgcagc cgcagccgcc    17340
gccgcgacct cctcggcgga ggtgcagacg gaccctggc tgccgccggc gatgtcagct    17400
ccccgcgcgc gtcgcgggcg caggaagtac ggcgccgcca acgcgctcct gcccgagtac    17460
gccttgcatc cttccatcgc gcccaccccc ggctaccgag gctataccta ccgcccgcga    17520
agagccaagg gttccacccg ccgtccccgc cgacgcgccg ccgccaccac ccgccgccgc    17580
cgccgcagac gccagcccgc actggctcca gtctccgtga ggaaagtggc gcgcgacgga    17640 cacacccctgg tgctgcccag ggcgcgctac cacccccagca tcgtttaaaa gcctgttgtg    17700
gttcttgcag atatggccct cacttgccgc ctccgttttcc cggtgccggg ataccgagga    17760
ggaagatcgc gccgcaggag gggtctggcc ggccgcggcc tgagcggagg cagccgccgc    17820
```

```
gcgcaccggc ggcgacgcgc caccagccga cgcatgcgcg gcggggtgct gccccctgtta   17880 atcccccctga tcgccgcggc gatcggcgcc gtgcccggga tcgcctccgt ggccttgcaa   17940
gcgtcccaga ggcattgaca gacttgcaaa cttgcaaata tggaaaaaaa aaccccaata   18000
aaaaagtcta gactctcacg ctcgcttggt cctgtgacta ttttgtagaa tggaagacat   18060
caactttgcg tcgctggccc cgcgtcacgg ctcgcgcccg ttcctgggac actggaacga   18120
tatcggcacc agcaacatga gcggtggcgc cttcagttgg ggctctctgt ggagcggcat   18180
taaaagtatc gggtctgccg ttaaaaatta cggctcccgg gcctggaaca gcagcacggg   18240
ccagatgttg agagacaagt tgaaagagca gaacttccag cagaaggtgg tggagggcct   18300
ggcctccggc atcaacgggg tggtggacct ggccaaccag gccgtgcaga ataagatcaa   18360
cagcagactg gaccccggc cgccggtgga ggaggtgccg ccggcgctgg agacggtgtc   18420
ccccgatggg cgtggcgaga agcgcccgcg gcccgatagg gaagagacca ctctggtcac   18480
gcagaccgat gagccgcccc cgtatgagga ggccctgaag caaggtctgc ccaccacgcg   18540
gcccatcgcg cccatggcca ccggggtggt gggccgccac acccccgcca cgctggactt   18600
gcctccgccc gccgatgtgc cgcagcagca gaaggcggca cagccgggcc cgcccgcgac   18660
cgcctcccgt tcctccgccg gtcctctgcg ccgcgcggcc agcggccccc gcgggggggt   18720
cgcgaggcac ggcaactggc agagcacgct gaacagcatc gtgggtctgg gggtgcggtc   18780
cgtgaagcgc cgccgatgct actgaatagc ttagctaacg tgttgtatgt gtgtatgcgc   18840
cctatgtcgc cgccagagga gctgctgagt cgccgccgtt cgcgcgccca ccaccaccgc   18900
cactccgccc ctcaagatgg cgacccatc gatgatgccg cagtggtcgt acatgcacat   18960
ctcgggccag gacgcctcgg agtacctgag ccccggctg gtgcagttcg cccgcgccac   19020
cgagagctac ttcagcctga gtaacaagtt taggaacccc acggtggcgc ccacgcacga   19080
tgtgaccacc gaccggtctc agcgcctgac gctgcggttc attcccgtgg accgcgagga   19140
caccgcgtac tcgtacaagg cgcggttcac cctggccgtg ggcgacaacc gcgtgctgga   19200
catggcctcc acctactttg acatccgcgg ggtgctggac cggggtccca ctttcaagcc   19260
ctactctggc accgcctaca actccctggc ccccaagggc gctcccaact cctgcgagtg   19320
ggagcaagag gaaactcagg cagttgaaga agcagcagaa gaggaagaag aagatgctga   19380
cggtcaagct gaggaagagc aagcagctac caaaaagact catgtatatg ctcaggctcc   19440
cctttctggc gaaaaaatta gtaaagatgg tctgcaaata ggaacggacg ctacagctac   19500
agaacaaaaa cctatttatg cagaccctac attccagccc gaaccccaaa tcggggagtc   19560
ccagtggaat gaggcagatg ctacagtcgc cggcggtaga gtgctaaaga aatctactcc   19620
catgaaacca tgctatggtt cctatgcaag acccacaaat gctaatggag gtcagggtgt   19680
actaacggca aatgcccagg gacagctaga atctcaggtt gaaatgcaat tcttttcaac   19740
ttctgaaaac gcccgtaacg aggctaacaa cattcagccc aaattggtgc tgtatagtaa   19800
ggatgtgcac atggagaccc cggatacgca ccttcttac aagcccgcaa aaagcgatga   19860
caattcaaaa atcatgctgg gtcagcagtc catgcccaac agacctaatt acatcggctt   19920
cagagacaac tttatcggcc tcatgtatta caatagcact ggcaacatgg gagtgcttgc   19980
aggtcaggcc tctcagttga atgcagtggt ggacttgcaa gacagaaaca cagaactgtc   20040
ctaccagctc ttgcttgatt ccatgggtga cagaaccaga tacttttcca tgtggaatca   20100
ggcagtggac agttatgacc cagatgttag aattattgaa aatcatggaa ctgaagacga   20160
```

```
gctccccaac tattgtttcc ctctgggtgg catagggta actgacactt accaggctgt   20220
taaaaccaac aatggcaata acggggggcca ggtgacttgg acaaaagatg aaacttttgc   20280
agatcgcaat gaaatagggg tgggaaacaa tttcgctatg gagatcaacc tcagtgccaa   20340
cctgtggaga aacttcctgt actccaacgt ggcgctgtac ctaccagaca agcttaagta   20400 caaccctcc aatgtggaca tctctgacaa ccccaacacc tacgattaca tgaacaagcg   20460
agtggtggcc ccggggctgg tggactgcta catcaacctg ggcgcgcgct ggtcgctgga   20520
ctacatggac aacgtcaacc ccttcaacca ccaccgcaat gcgggcctgc gctaccgctc   20580
catgctcctg ggcaacgggc gctacgtgcc cttccacatc caggtgcccc agaagttctt   20640
tgccatcaag aacctcctcc tcctgccggg ctcctacacc tacgagtgga acttcaggaa   20700
ggatgtcaac atggtcctcc agagctctct gggtaacgat ctcagggtgg acggggccag   20760
catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct accccatacc cgccaacgcc accaacgtcc ccatctccat   20940
cccctcgcgc aactgggcgg ccttccgcgg ctgggccttc acccgcctca agaccaagga   21000
gaccccctcc ctgggctcgg gattcgaccc ctactacacc tactcgggct ccattcccta   21060
cctggacggc accttctacc tcaaccacac tttcaagaag gtctcggtca ccttcgactc   21120
ctcggtcagc tggccgggca acgaccgtct gctcacccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
caaggacagg atgtactcct tcttcaggaa cttccagccc atgagccggc aggtggtgga   21360
ccagaccaag tacaaggact accaggaggt gggcatcatc caccagcaca acaactcggg   21420
cttcgtgggc tacctcgccc ccaccatgcg cgagggacag gcctaccccg ccaacttccc   21480
ctatccgctc ataggcaaga ccgcggtcga cagcatcacc cagaaaaagt tcctctgcga   21540
ccgcaccctc tggcgcatcc ccttctccag caacttcatg tccatgggtg cgctctcgga   21600
cctgggccag aacttgctct acgccaactc cgcccacgcc ctcgacatga ccttcgaggt   21660
cgaccccatg gacgagccca cccttctcta tgttctgttc gaagtctttg acgtggtccg   21720
ggtccaccag ccgcaccgcg cgtcatcga ccgtgtac ctgcgtacgc ccttctcggc   21780
cggcaacgcc accacctaaa gaagcaagcc gcagtcatcg ccgcctgcat gccgtcgggt   21840
tccaccgagc aagagctcag ggccatcgtc agagacctgg gatgcgggcc ctatttttg   21900 ggcaccttcg acaagcgctt ccctggcttt gtctccccac acaagctggc ctgcgccatc   21960
gtcaacacgg ccggccgcga gaccgggggc gtgcactggc tggccttcgc ctggaacccg   22020
cgctccaaaa catgcttcct ctttgacccc ttcggcttt cggaccagcg gctcaagcaa   22080
atctacgagt cgagtacga gggcttgctg cgtcgcagcg ccatcgcctc ctcgcccgac   22140
cgctgcgtca ccctcgaaaa gtccacccag accgtgcagg ggcccgactc ggccgcctgc   22200
ggtctcttct gctgcatgtt tctgcacgcc tttgtgcact ggcctcagag tcccatggac   22260
cgcaacccca ccatgaactt gctgacgggg gtgcccaact ccatgctcca gagccccag   22320 gtcgagccca ccctgcgccg caaccaggag cagctctaca gcttcctgga gcgccactcg   22380
ccttacttcc gccgcacag cgcacagatc aggagggcca cctccttctg ccacttgcaa   22440
gagatgcaag aagggtaata acgatgtaca cactttttt ctcaataaat ggcatctttt   22500 tattatataca agctctctgg ggtattcatt tcccaccacc acccgccgtt gtcgccatct   22560
```

```
ggctctattt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcgggc   22740
gccgagatct tgaagtcgca gttggggccg ccgccctgcg cgcgcgagtt gcggtacacc   22800
gggttgcagc actggaacac caacagcgcc gggtgcttca cgctggccag cacgctgcgg   22860
tcggagatca gctcggcgtc caggtcctcc gcgttgctca gcgcgaacgg ggtcatcttg   22920
ggcacttgcc gccccaggaa gggcgcgtgc cccggtttcg agttgcagtc gcagcgcagc   22980
gggatcagca ggtgcccgtg cccggactcg gcgttgggt acagcgcgcg catgaaggcc   23040
tgcatctggc ggaaggccat ctgggccttg gcgccctccg agaagaacat gccgcaggac   23100
ttgcccgaga actggtttgc ggggcagctg gcgtcgtgca ggcagcagcg cgcgtcggtg   23160
ttggcgatct gcaccacgtt gcgccccac cggttcttca cgatcttggc cttggacgat   23220
tgctccttca gcgcgcgctg cccgttctcg ctggtcacat ccatctcgat cacatgttcc   23280
ttgttcacca tgctgctgcc gtgcagacac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
acggggttct tcaccatcac cgtggccgcc gcctccgccg cgctttcgct ttccgccccg   23700
ctgttctctt cctcttcctc ctcttcctcg ccgccgccca ctcgcagccc ccgcaccacg   23760
gggtcgtctt cctgcaggcg ctgcaccttg cgcttgccgt tgcgcccctg cttgatgcgc   23820
acgggcgggt tgctgaagcc caccatcacc agcgcggcct cttcttgctc gtcctcgctg   23880
tccagaatga cctccgggga ggggggggttg gtcatcctca gtaccgaggc acgcttcttt   23940
ttcttcctgg gggcgttcgc cagctccgcg gctgcggccg ctgccgaggt cgaaggccga   24000
gggctgggcg tgcgcggcac cagcgcgtcc tgcgagccgt cctcgtcctc ctcggactcg   24060
agacggaggc gggcccgctt cttcgggggc gcgcggggcg gcggaggcgg cggcggcgac   24120
ggagacgggg acgagacatc gtccaggtg ggtggacggc gggccgcgcc gcgtccgcgc   24180
tcggggtgg tctcgcgctg gtcctcttcc cgactggcca tctcccactg ctccttctcc   24240
tataggcaga aagagatcat ggagtctctc atgcgagtcg agaaggagga ggacagccta   24300
accgcccct ctgagccctc caccaccgcc gccaccaccg ccaatgccgc cgcggacgac   24360
gcgcccaccg agaccaccgc cagtaccacc ctccccagcg acgcacccc gctcgagaat   24420
gaagtgctga tcgagcagga cccgggtttt gtgagcggag aggaggatga ggtggatgag   24480
aaggagaagg aggaggtcgc cgcctcagtg ccaaaagagg ataaaaagca agaccaggac   24540
gacgcagata aggatgagac agcagtcggg cggggaacg gaagccatga tgctgatgac   24600
ggctacctag acgtgggaga cgacgtgctg cttaagcacc tgcaccgcca gtgcgtcatc   24660
gtctgcgacg cgctgcagga gcgctgcgaa gtgcccctgg acgtggcgga ggtcagccgc   24720
gcctacgagc ggcacctctt cgcgccgcac gtgcccccca agcgccggga gaacggcacc   24780
tgcgagccca acccgcgtct caacttctac ccggtcttcg cggtacccga ggtgctggcc   24840
acctaccaca tctttttcca aaactgcaag atcccctct cctgccgcgc caaccgcacc   24900
```

-continued

```
cgcgccgaca aaaccctgac cctgcggcag ggcgcccaca tacctgatat cgcctctctg    24960
gaggaagtgc ccaagatctt cgagggtctc ggtcgcgacg agaaacgggc ggcgaacgct    25020
ctgcacggag acagcgaaaa cgagagtcac tcgggggtgc tggtggagct cgagggcgac    25080
aacgcgcgcc tggccgtact caagcgcagc atagaggtca cccactttgc ctacccggcg    25140
ctcaacctgc cccccaaggt catgagtgtg gtcatgggcg agctcatcat gcgccgcgcc    25200
cagcccctgg ccgcggatgc aaacttgcaa gagtcctccg aggaaggcct gcccgcggtc    25260
agcgacgagc agctggcgcg ctggctggag acccgcgacc ccgcgcagct ggaggagcgg    25320
cgcaagctca tgatggccgc ggtgctggtc accgtggagc tcgagtgtct gcagcgcttc    25380
ttcgcggacc ccgagatgca gcgcaagctc gaggagaccc tgcactacac cttccgccag    25440
ggctacgtgc gccaggcctg caagatctcc aacgtggagc tctgcaacct ggtctcctac    25500
ctgggcatcc tgcacgagaa ccgcctcggg cagaacgtcc tgcactccac cctcaaaggg    25560
gaggcgcgcc gcgactacat ccgcgactgc gcctacctct cctctgcta cacctggcag    25620 acggccatgg gggtctggca gcagtgcctg gaggagcgca acctcaagga gctggaaaag    25680
ctcctcaagc gcaccctcag ggacctctgg acgggcttca cgagcgctc ggtggccgcc    25740 gcgctggcgg acatcatctt tcccgagcgc ctgctcaaga ccctgcagca gggcctgccc    25800
gacttcacca gccagagcat gctgcagaac ttcaggactt tcatcctgga gcgctcgggc    25860
atcctgccgg ccacttgctg cgcgctgccc agcgacttcg tgcccatcaa gtacaggag    25920 tgcccgccgc cgctctgggg ccactgctac ctcttccagc tggccaacta cctcgcctac    25980
cactcggacc tcatggaaga cgtgagcggc gagggcctgc tcgagtgcca ctgccgctgc    26040
aacctctgca cgccccaccg ctctctagtc tgcaacccgc agctgctcag cgagagtcag    26100
attatcggta ccttcgagct gcagggtccc tcgcctgacg agaagtccgc ggctccaggg    26160
ctgaaactca ctccggggct gtggacttcc gcctacctac gcaaatttgt acctgaggac    26220
taccacgccc acgagatcag gttctacgaa gaccaatccc gcccgcccaa ggcggagctc    26280
accgcctgcg tcatcaccca ggggcacatc ctgggccaat gcaagccat caacaaagcc    26340 cgccgagagt tcttgctgaa aaagggtcgg ggggtgtacc tggaccccca gtccggcgag    26400 gagctaaaacc cgctaccccc gccgccgccc cagcagcggg accttgcttc ccaggatggc    26460 acccagaaaag aagcagcagc cgccgccgcc gccgcagcca tacatgcttc tggaggaaga    26520
ggaggaggac tgggacagtc aggcagagga ggtttcggac gaggagcagg aggagatgat    26580
ggaagactgg gaggaggaca gcagcctaga cgaggaagct tcagaggccg aagaggtggc    26640
agacgcaaca ccatcgccct cggtcgcagc cccctcgccg gggcccctga atcctccga    26700 acccagcacc agcgctataa cctccgctcc tccggcgccg cgccaccccg cccgcagacc    26760
caaccgtaga tgggacacca caggaaccgg ggtcggtaag tccaagtgcc cgccgccgcc    26820
accgcagcag cagcagcagc agcgccaggg ctaccgctcg tggcgcgggc acaagaacgc    26880
catagtcgcc tgcttgcaag actgcggggg caacatctct ttcgcccgcc gcttcctgct    26940
attccaccac ggggtcgcct ttccccgcaa tgtcctgcat tactaccgtc atctctacag    27000
cccctactgc agcggcgacc cagaggcggc agcggcagcc acagcggcga ccaccaccta    27060
ggaagatatc ctccgcgggc aagacagcgg cagcagcggc caggagaccc gcggcagcag    27120
cggcgggagc ggtgggcgca ctgcgcctct cgcccaacga acccctctcg acccgggagc    27180
tcagacacag gatcttcccc actttgtatg ccatcttcca acagagcaga ggccaggagc    27240
aggagctgaa aataaaaaac agatctctgc gctccctcac ccgcagctgt ctgtatcaca    27300
```

```
aaagcgaaga tcagcttcgg cgcacgctgg aggacgcgga ggcactcttc agcaaatact   27360
gcgcgctcac tcttaaagac tagctccgcg cccttctcga atttaggcgg gagaaaacta   27420
cgtcatcgcc ggccgccgcc cagcccgccc agccgagatg agcaaagaga ttcccacgcc   27480
atacatgtgg agctaccagc cgcagatggg actcgcggcg ggagcggccc aggactactc   27540
cacccgcatg aactacatga gcgcgggacc ccacatgatc tcacaggtca acgggatccg   27600
cgcccagcga aaccaaatac tgctggaaca ggcggccatc accgccacgc cccgccataa   27660
tctcaacccc cgaaattggc ccgccgccct cgtgtaccag gaaacccccct ccgccaccac   27720 cgtactactt ccgcgtgacg cccaggccga agtccagatg actaactcag gggcgcagct   27780
cgcgggcggc tttcgtcacg gggcgcggcc gctccgacca ggtataagac acctgatgat   27840
cagaggccga ggtatccagc tcaacgacga gtcggtgagc tcttcgctcg gtctccgtcc   27900
ggacggaact ttccagctcg ccggatccgg ccgctcttcg ttcacgcccc gccaggcgta   27960
cctgactctg cagacctcgt cctcggagcc ccgctccggc ggcatcggaa ccctccagtt   28020
cgtggaggag ttcgtgccct cggtctactt caaccccttc tcgggacctc ccggacgcta   28080
ccccgaccag ttcattccga actttgacgc ggtgaaggac tcggcggacg gctacgactg   28140
aatgtcaggt gtcgaggcag agcagcttcg cctgagacac ctcgagcact gccgccgcca   28200
caagtgcttc gcccgcggtt ctggtgagtt ctgctacttt cagctacccg aggagcatac   28260
cgaggggccg gcgcacggcg tccgcctgac cacccagggc gaggttacct gttccctcat   28320
ccggagtttt accctccgtc ccctgctagt ggagcgggag cggggtccct gtgtcctaac   28380
tatcgcctgc aactgcccta accctggatt acatcaagat ctttgctgtc atctctgtgc   28440
tgagtttaat aaacgctgag atcagaatct actggggctc ctgtcgccat cctgtgaacg   28500
ccaccgtctt cacccacccc gaccaggccc aggcgaacct cacctgcggt ctgcatcgga   28560
gggccaagaa gtacctcacc tggtacttca acggcacccc ctttgtggtt tacaacagct   28620
tcgacgggga cggagtctcc ctgaaagacc agctctccgg tctcagctac tccatccaca   28680
agaacaccac cctccaactc ttccctcccct acctgccggg aacctacgag tgcgtcaccg   28740
gccgctgcac ccacctcacc cgcctgatcg taaaccagag ctttccggga acagataact   28800
ccctcttccc cagaacagga ggtgagctca ggaaactccc cggggaccag ggcggagacg   28860
taccttcgac ccttgtgggg ttaggatttt ttattaccgg gttgctggct cttttaatca   28920
aagtttcctt gagatttgtt ctttccttct acgtgtatga acacctcaac ctccaataac   28980 tctaccccttt cttcggaatc aggtgacttc tctgaaatcg gcttggtgt gctgcttact   29040 ctgttgattt ttttccttat catactcagc cttctgtgcc tcaggctcgc cgcctgctgc   29100
gcacacatct atatctactg ctggttgctc aagtgcaggg gtcgccaccc aagatgaaca   29160
ggtacatggt cctatcgatc ctaggcctgc tggccctggc ggcctgcagc gccgccaaaa   29220
aagagattac ctttgaggag cccgcttgca atgtaacttt caagcccgag ggtgaccaat   29280
gcaccaccct cgtcaaatgc gttaccaatc atgagaggct gcgcatcgac tacaaaaaca   29340
aaactggcca gtttgcggtc tatagtgtgt ttacgcccgg agacccctct aactactctg   29400
tcaccgtctt ccagggcgga cagtctaaga tattcaatta cactttccct ttttatgagt   29460
tatgcgatgc ggtcatgtac atgtcaaaac agtacaacct gtggcctccc tctcccagg   29520 cgtgtgtgga aaatactggg tcttactgct gtatggcttt cgcaatcact acgctcgctc   29580
taatctgcac ggtgctatac ataaaattca ggcagaggcg aatctttatc gatgaaaaga   29640
```

```
aaatgccttg atcgctaaca ccggctttct atctgcagaa tgaatgcaat cacctcccta    29700
ctaatcacca ccaccctcct tgcgattgcc catgggttga cacgaatcga agtgccagtg    29760
gggtccaatg tcaccatggt gggccccgcc ggcaattcca ccctcatgtg ggaaaaattt    29820
gtccgcaatc aatgggttca tttctgctct aaccgaatca gtatcaagcc cagagccatc    29880
tgcgatgggc aaaatctaac tctgatcaat gtgcaaatga tggatgctgg gtactattac    29940
gggcagcggg gagaaatcat taattactgg cgaccccaca aggactacat gctgcatgta    30000
gtcgaggcac ttcccactac caccccact accacctctc ccaccaccac caccactact    30060
actactacta ctactactac tactactacc actaccgctg cccgccatac ccgcaaaagc    30120
accatgatta gcacaaagcc ccctcgtgct cactcccacg ccggcgggcc catcggtgcg    30180
acctcagaaa ccaccgagct ttgcttctgc caatgcacta acgccagcgc tcatgaactg    30240
ttcgacctgg agaatgagga tgtccagcag agctccgctt gcctgaccca ggaggctgtg    30300
gagcccgttg ccctgaagca gatcggtgat tcaataattg actcttcttc ttttgccact    30360
cccgaatacc ctcccgattc tactttccac atcacgggta ccaaagaccc taacctctct    30420
ttctacctga tgctgctgct ctgtatctct gtggtctctt ccgcgctgat gttactgggg    30480
atgttctgct gcctgatctg ccgcagaaag agaaaagctc gctctcaggg ccaaccactg    30540
atgcccttcc cctacccccc ggattttgca gataacaaga tatgagctcg ctgctgacac    30600
taaccgcttt actagcctgc gctctaaccc ttgtcgcttg cgactcgaga ttccacaatg    30660
tcacagctgt ggcaggagaa aatgttactt tcaactccac ggccgatacc cagtggtcgt    30720
ggagtggctc aggtagctac ttaactatct gcaatagctc cacttccccc ggcatatccc    30780
caaccaagta ccaatgcaat gccagcctgt tcaccctcat caacgcttcc accctggaca    30840
atggactcta tgtaggctat gtacccttttg gtgggcaagg aaagacccac gcttacaacc    30900
tggaagttcg ccagcccaga accactaccc aagcttctcc caccaccacc accaccacca    30960
ccatcaccag cagcagcagc agcagcagcc acagcagcag cagcagatta ttgacttttgg    31020 ttttggccag ctcatctgcc gctacccagg ccatctacag ctctgtgccc gaaaccactc    31080
agatccaccg cccagaaacg accaccgcca ccacccttaca cacctccagc gatcagatgc    31140
cgaccaacat cacccccttg gctcttcaaa tgggacttac aagccccact ccaaaaccag    31200
tggatgcggc cgaggtctcc gccctcgtca atgactgggc ggggctggga atgtggtggt    31260
tcgccatagg catgatggcg ctctgcctgc ttctgctctg gctcatctgc tgcctccacc    31320
gcaggcgagc cagaccccccc atctatagac ccatcattgt cctgaacccc gataatgatg    31380
ggatccatag attggatggc ctgaaaaacc tacttttttc ttttacagta tgataaattg    31440
agacatgcct cgcattttct tgtacatgtt ccttctccca ccttttctgg ggtgttctac    31500
gctggccgct gtgtctcacc tggaggtaga ctgcctctca cccttcactg tctacctgct    31560
ttacggattg gtcaccctca ctctcatctg cagcctaatc acagtaatca tcgccttcat    31620
ccagtgcatt gattacatct gtgtgcgcct cgcatacttc agacaccacc gcagtaccg    31680 agacaggaac attgcccaac ttctaagact gctctaatca tgcataagac tgtgatctgc    31740
cttctgatcc tctgcatcct gcccaccctc acctcctgcc agtacaccac aaaatctccg    31800
cgcaaaagac atgcctcctg ccgcttcacc caactgtgga atatacccaa atgctacaac    31860
gaaaagagcg agctctccga agcttggctg tatggggtca tctgtgtctt agttttctgc    31920
agcactgtct ttgcccctcat aatctacccc tactttgatt tgggatggaa cgcgatcgat    31980
gccatgaatt accccacctt tcccgcaccc gagataattc cactgcgaca agttgtaccc    32040
```

```
gttgtcgtta atcaacgccc cccatcccct acgcccactg aaatcagcta ctttaaccta   32100
acaggcggag atgactgacg ccctagatct agaaatggac ggcatcagta ccgagcagcg   32160
tctcctagag aggcgcaggc aggcggctga gcaagagcgc ctcaatcagg agctccgaga   32220
tctcgttaac ctgcaccagt gcaaaagagg catcttttgt ctggtaaagc aggccaaagt   32280
cacctacgag aagaccggca acagccaccg cctcagttac aaattgccca cccagcgcca   32340
gaagctggtg ctcatggtgg gtgagaatcc catcaccgtc acccagcact cggtagagac   32400
cgaggggtgt ctgcactccc cctgtcgggg tccagaagac ctctgcaccc tggtaaagac   32460
cctgtgcggt ctcagagatt tagtccccct taactaatca aacactggaa tcaataaaaa   32520
gaatcactta cttaaaatca gacagcaggt ctctgtccag tttattcagc agcacctcct   32580
tcccctcctc ccaactctgg tactccaaac gccttctggc ggcaaacttc ctccacaccc   32640
tgaagggaat gtcagattct tgctcctgtc cctccgcacc cactatcttc atgttgttgc   32700
agatgaagcg caccaaaacg tctgacgaga gcttcaaccc cgtgtacccc tatgacacgg   32760
aaagcggccc tccctccgtc cctttcctca cccctccctt cgtgtctccc gatggattcc   32820
aagaaagtcc ccccggggtc ctgtctctga acctggccga gccctggtc  acttcccacg   32880 gcatgctcgc cctgaaaatg ggaagtggcc tctccctgga cgacgctggc aacctcacct   32940
ctcaagatat caccaccgct agccctcccc tcaaaaaaac caagaccaac ctcagcctag   33000
aaacctcatc cccctaact  gtgagcacct caggcgccct caccgtagca gccgccgctc   33060
ccctggcggt ggccggcacc tccctcacca tgcaatcaga ggccccctg  acagtacagg   33120 atgcaaaact caccctggcc accaaaggcc ccctgaccgt gtctgaaggc aaactggcct   33180
tgcaaacatc ggccccgctg acggccgctg acagcagcac cctcacagtc agtgccacac   33240
caccccttag cacaagcaat ggcagcttgg gtattgacat gcaagccccc atttacacca   33300
ccaatggaaa actaggactt aactttggcg ctccccctgca tgtggtagac agcctaaatg   33360
cactgactgt agttactggc caaggtctta cgataaacgg aacagcccta caaactagag   33420
tctcaggtgc cctcaactat gacacatcag gaaacctaga attgagagct gcaggggta   33480 tgcgagttga tgcaaatggt caacttatcc ttgatgtagc ttacccattt gatgcacaaa   33540
acaatctcag ccttaggctt ggacagggac ccctgtttgt taactctgcc cacaacttgg   33600
atgttaacta caacagaggc ctctacctgt tcacatctgg aaataccaaa aagctagaag   33660
ttaatatcaa aacagccaag ggtctcattt atgatgacac tgctatagca atcaatgcgg   33720
gtgatgggct acagtttgac tcaggctcag atacaaatcc attaaaaact aaacttggat   33780
taggactgga ttatgactcc agcagagcca taattgctaa actgggaact ggcctaagct   33840 ttgacaaac  aggtgccatc acagtaggca acaaaaatga tgacaagctt accttgtgga   33900
ccacaccaga cccatcccct aactgtagaa tctattcaga gaaagatgct aaattcacac   33960 ttgtttttgac taaatgcggc agtcaggtgt tggccagcgt ttctgttta  tctgtaaaag   34020 gtagccttgc gcccatcagt ggcacagtaa ctagtgctca gattgtcctc agatttgatg   34080
aaaatggagt tctactaagc aattcttccc ttgaccctca atactggaac tacagaaaag   34140
gtgaccttac agagggcact gcatatacca acgcagtggg atttatgccc aacctcacag   34200
catacccaaa aacacagagc caaactgcta aaagcaacat tgtaagtcag gtttacttga   34260
atggggacaa atccaacccc atgacccctca ccattaccct caatgaaact aatgaaacag   34320
gagatgccac agtaagcact tactccatgt cattctcatg gaactggaat ggaagtaatt   34380
```

```
acattaatga aacgttccaa accaactcct tcaccttctc ctacatcgcc caagaataaa    34440
aagcatgacg ctgttgattt gattcaatgt gtttctgttt tattttcaag cacaacaaaa    34500
tcattcaagt cattcttcca tcttagctta atagacacag tagcttaata gacccagtag    34560
tgcaaagccc cattctagct tataactagt ggagaagtac tcgcctacat gggggtagag    34620
tcataatcgt gcatcaggat agggcggtgg tgctgcagca gcgcgcgaat aaactgctgc    34680
cgccgccgct ccgtcctgca ggaatacaac atggcagtgg tctcctcagc gatgattcgc    34740
accgcccgca gcataaggcg ccttgtcctc cgggcacagc agcgcaccct gatctcactt    34800
aaatcagcac agtaactgca gcacagcacc acaatattgt tcaaaatccc acagtgcaag    34860
gcgctgtatc caaagctcat ggcggggacc acagaaccca cgtggccatc ataccacaag    34920
cgcaggtaga ttaagtggcg acccctcata aacacgctgg acataaacat tacctctttt    34980
ggcatgttgt aattcaccac ctcccggtac catataaacc tctgattaaa catggcgcca    35040
tccaccacca tcctaaacca gctggccaaa acctgcccgc cggctataca ctgcagggaa    35100
ccgggactgg aacaatgaca gtggagagcc caggactcgt aaccatggat catcatgctc    35160
gtcatgatat caatgttggc acaacacagg cacacgtgca tacacttcct caggattaca    35220
agctcctccc gcgttagaac catatcccag ggaacaaccc attcctgaat cagcgtaaat    35280
cccacactgc agggaagacc tcgcacgtaa ctcacgttgt gcattgtcaa agtgttacat    35340
tcgggcagca gcggatgatc ctccagtatg gtagcgcggg tttctgtctc aaaaggaggt    35400
agacgatccc tactgtacgg agtgcgccga gacaaccgag atcgtgttgg tcgtagtgtc    35460
atgccaaatg aacgccgga cgtagtcata tttcctgaag tcttagatct ctcaacgcag    35520
caccagcacc aacacttcgc agtgtaaaag gccaagtgcc gagagagtat atataggaat    35580
aaaagtgac gtaaacgggc aaagtccaaa aaacgcccag aaaaaccgca cgcgaaccta    35640
cgccccgaaa cgaaagccaa aaaacactag acactccctt ccggcgtcaa cttccgcttt    35700
cccacgctac gtcacttgcc ccagtcaaac aaactacata tcccgaactt ccaagtcgcc    35760
acgcccaaaa caccgcctac acctccccgc ccgccggccc gccccaaac ccgcctcccg    35820
ccccgcgccc cgccccgcgc cgcccatctc attatcatat tggcttcaat ccaaaataag    35880
gtatattatt gatgatggtt taaacggatc caattcttga agacgaaagg gcctcgtgat    35940
acgcctattt ttataggtta atgtcatgat aataatggtt tcttagacgt caggtggcac    36000
ttttcgggga aatgtgcgcg gaacccctat ttgtttattt ttctaaatac attcaaatat    36060
gtatccgctc atgagacaat aaccctgata aatgcttcaa taatattgaa aaaggaagag    36120
tatgagtatt caacatttcc gtgtcgccct tattcccttt tttgcggcat tttgccttcc    36180
tgttttgct cacccagaaa cgctggtgaa agtaaaagat gctgaagatc agttgggtgc    36240
acgagtgggt tacatcgaac tggatctcaa cagcggtaag atccttgaga gttttcgccc    36300
cgaagaacgt tttccaatga tgagcacttt taaagttctg ctatgtggcg cggtattatc    36360
ccgtgttgac gccgggcaag agcaactcgg tcgccgcata cactattctc agaatgactt    36420
ggttgagtac tcaccagtca cagaaaagca tcttacggat ggcatgacag taagagaatt    36480
atgcagtgct gccataacca tgagtgataa cactgcggcc aacttacttc tgacaacgat    36540
cggaggaccg aaggagctaa ccgcttttt gcacaacatg gggatcatg taactcgcct    36600
tgatcgttgg gaaccggagc tgaatgaagc cataccaaac gacgagcgtg acaccacgat    36660
gcctgtagca atggcaacaa cgttgcgcaa actattaact ggcgaactac ttactctagc    36720
ttcccggcaa caattaatag actggatgga ggcggataaa gttgcaggac cacttctgcg    36780
```

```
ctcggccctt ccggctggct ggtttattgc tgataaatct ggagccggtg agcgtgggtc    36840
tcgcggtatc attgcagcac tggggccaga tggtaagccc tcccgtatcg tagttatcta    36900
cacgacgggg agtcaggcaa ctatggatga acgaaataga cagatcgctg agataggtgc    36960
ctcactgatt aagcattggt aactgtcaga ccaagtttac tcatatatac tttagattga    37020
tttaaaagga tctaggtgaa gatcctttt gataatctca tgaccaaaat cccttaacgt     37080
gagttttcgt tccactgagc gtcagacccc gtagaaaaga tcaaaggatc ttcttgagat    37140
cctttttttc tgcgcgtaat ctgctgcttg caaacaaaaa aaccaccgct accagcggtg    37200
gtttgtttgc cggatcaaga gctaccaact cttttccga aggtaactgg cttcagcaga     37260
gcgcagatac caaatactgt ccttctagtg tagccgtagt taggccacca cttcaagaac    37320
tctgtagcac cgcctacata cctcgctctg ctaatcctgt taccagtggc tgctgccagt    37380
ggcgataagt cgtgtcttac cgggttggac tcaagacgat agttaccgga taaggcgcag    37440
cggtcgggct gaacggggggg ttcgtgcaca gcccagct tggagcgaac gacctacacc     37500
gaactgagat acctacagcg tgagctatga gaaagcgcca cgcttcccga agggagaaag    37560
gcggacaggt atccggtaag cggcagggtc ggaacaggag agcgcacgag ggagcttcca    37620
gggggaaacg cctggtatct ttatagtcct gtcgggtttc gccacctctg acttgagcgt    37680
cgatttttgt gatgctcgtc aggggggcgg agcctatgga aaaacgccag caacgcggcc    37740 ttttttacggt tcctggcctt ttgctggcct tgaagctgtc cctgatggtc gtcatctacc    37800
tgcctggaca gcatgcctg caacgcgggc atcccgatgc cgccgaagc gagaagaatc      37860 ataatgggga aggccatcca gcctcgcgtc gcagatccga attcgtttaa ac            37912
```

<210> SEQ ID NO 8
<211> LENGTH: 43428
<212> TYPE: DNA
<213> ORGANISM: Simian adenovirus

<400> SEQUENCE: 8

```
catcatcaat aatatacctt attttggatt gaagccaata tgataatgag atgggcggcg     60
cggggcgggg cgcggggcgg gaggcgggtt tggggggcggg ccggcgggcg gggcggtgtg    120
gcggaagtgg actttgtaag tgtggcggat gtgacttgct agtgccgggc gcggtaaaag    180
tgacgttttc cgtgcgcgac aacgccccg ggaagtgaca ttttttcccgc ggttttttacc    240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg ggtcattag ttcatagccc     600 atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
```

```
gtttgactca cggggatttc caagtctcca ccccattgac gtcaatggga gtttgttttg    1020
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg aacggtgca ttggaacgcg gattccccgt gccaagagtg agatcttccg    1320
tttatctagg taccgggccc cccctcgagg tcgacggtat cgataagctt cacgctgccg    1380
caagcactca gggcgcaagg gctgctaaag gaagcggaac acgtagaaag ccagtccgca    1440
gaaacggtgc tgaccccgga tgaatgtcag ctactgggct atctggacaa gggaaaacgc    1500
aagcgcaaag agaaagcagg tagcttgcag tgggcttaca tggcgatagc tagactgggc    1560
ggttttatgg acagcaagcg aaccggaatt gccagctggg gcgccctctg gtaaggttgg    1620
gaagccctgc aaagtaaact ggatggcttt cttgccgcca aggatctgat ggcgcagggg    1680
atcaagatct aaccaggagc tatttaatgg caacagttaa ccagctggta cgcaaaccac    1740
gtgctcgcaa agttgcgaaa agcaacgtgc ctgcgctgga agcatgcccg caaaaacgtg    1800
gcgtatgtac tcgtgtatat actaccactc ctaaaaaacc gaactccgcg ctgcgtaaag    1860
tatgccgtgt tcgtctgact aacggtttcg aagtgacttc ctacatcggt ggtgaaggtc    1920
acaacctgca ggagcactcc gtgatcctga tccgtggcgg tcgtgttaaa gacctcccgg    1980
gtgttcgtta ccacaccgta cgtggtgcgc ttgactgctc cggcgttaaa gaccgtaagc    2040
aggctcgttc caagtatggc gtgaagcgtc ctaaggctta atggtagatc tgatcaagag    2100
acaggatgac ggtcgtttcg catgcttgaa caagatggat tgcacgcagg ttctccggcc    2160
gcttgggtgg agaggctatt cggctatgac tgggcacaac agacaatcgg ctgctctgat    2220
gccgccgtgt tccggctgtc agcgcagggg cgcccggttc tttttgtcaa gaccgacctg    2280
tccggtgccc tgaatgaact gcaggacgag gcagcgcggc tatcgtggct ggccacgacg    2340
ggcgttcctt gcgcagctgt gctcgacgtt gtcactgaag cgggaaggga ctggctgcta    2400
ttgggcgaag tgccggggca ggatctcctg tcatctcacc ttgctcctgc cgagaaagta    2460
tccatcatgg ctgatgcaat gcggcggctg catacgcttg atccggctac ctgcccattc    2520
gaccaccaag cgaaacatcg catcgagcga gcacgtactc ggatggaagc cggtcttgtc    2580
gatcaggatg atctggacga agagcatcag gggctcgcgc cagccgaact gttcgccagg    2640
ctcaaggcgc gcatgcccga cggcgaggat ctcgtcgtga cccatggcga tgcctgcttg    2700
ccgaatatca tggtggaaaa tggccgcttt tctggattca tcgactgtgg ccggctgggt    2760
gtggcggacc gctatcagga catagcgttg gctacccgtg atattgctga agagcttggc    2820
ggcgaatggg ctgaccgctt cctcgtgctt tacggtatcg ccgctcccga ttcgcagcgc    2880
atcgccttct atcgccttct tgacgagttc ttctgagcgg gactctgggg ttcgaaatga    2940
ccgaccaagc gacgcccaac ctgccatcac gagatttcga ttccaccgcc gccttctatg    3000
aaaggttggg cttcggaatc gttttccggg acgccggctg gatgatcctc cagcgcgggg    3060
atctcatgct ggagttcttc gcccaccccg ggctcgatcc cctcgggggg aatcagaatt    3120
cagtcgacag cggccgcgat ctgctgtgcc ttctagttgc cagccatctg ttgtttgccc    3180
ctcccccgtg ccttccttga ccctggaagg tgccactccc actgtccttt cctaataaaa    3240
tgaggaaatt gcatcgcatt gtctgagtag gtgtcattct attctggggg gtggggtggg    3300
gcaggacagc aagggggagg attgggaaga caatagcagg catgctgggg atgcggtggg    3360
```

```
ctctatggcc gatcagcgat cgctgaggtg ggtgagtggg cgtggcctgg ggtggtcatg    3420
aaaatatata agttgggggt cttagggtct ctttatttgt gttgcagaga ccgccggagc    3480
catgagcggg agcagcagca gcagcagtag cagcagcgcc ttggatggca gcatcgtgag    3540
cccttatttg acgacgcgga tgccccactg gccggggtg cgtcagaatg tgatgggctc     3600
cagcatcgac ggccgacccg tcctgcccgc aaattccgcc acgctgacct atgcgaccgt    3660
cgcggggacg ccgttggacg ccaccgccg cgccgccgcc accgcagccg cctcggccgt     3720
gcgcagcctg gccacggact ttgcattcct gggaccactg gcgacagggg ctacttctcg    3780
ggccgctgct gccgccgttc gcgatgacaa gctgaccgcc ctgctggcgc agttggatgc    3840
gcttactcgg gaactgggtg acctttctca gcaggtcatg gccctgcgcc agcaggtctc    3900
ctccctgcaa gctggcggga atgcttctcc cacaaatgcc gtttaagata aataaaacca    3960
gactctgttt ggattaaaga aaagtagcaa gtgcattgct ctctttattt cataattttc    4020
cgcgcgcgat aggccctaga ccagcgttct cggtcgttga gggtgcggtg tatcttctcc    4080
aggacgtggt agaggtggct ctggacgttg agatacatgg gcatgagccc gtcccggggg    4140
tggaggtagc accactgcag agcttcatgc tccggggtgg tgttgtagat gatccagtcg    4200
tagcaggagc gctgggcatg gtgcctaaaa atgtccttca gcagcaggcc gatggccagg    4260
gggaggccct tggtgtaagt gtttacaaaa cggttaagtt gggaagggtg cattcggga     4320 gagatgatgt gcatcttgga ctgtattttt agattggcga tgtttccgcc cagatccctt    4380
ctgggattca tgttgtgcag gaccaccagt acagtgtatc cggtgcactt ggggaatttg    4440
tcatgcagct tagagggaaa agcgtggaag aacttggaga cgcctttgtg gcctcccaga    4500
ttttccatgc attcgtccat gatgatggca atgggcccgc gggaggcagc ttggcaaag    4560 atatttctgg ggtcgctgac gtcgtagttg tgttccaggg tgaggtcgtc ataggccatt    4620
tttacaaagc gcgggcggag ggtgcccgac tggggggatga tggtcccctc tggccctggg   4680
gcgtagttgc cctcgcagat ctgcatttcc caggccttaa tctcggaggg gggaatcata    4740
tccacctgcg gggcgatgaa gaaaacggtt ccggagccgg gggagattaa ctgggatgag    4800
agcaggtttc taagcagctg tgattttcca caaccggtgg gcccataaat aacacctata    4860
accggttgca gctggtagtt tagagagctg cagctgccgt cgtcccggag gaggggggcc    4920
acctcgttga gcatgtccct gacgcgcatg ttctccccga ccagatccgc cagaaggcgc    4980
tcgccgccca gggacagcag ctcttgcaag gaagcaaagt ttttcagcgg cttgaggccg    5040
tccgccgtgg gcatgttttt cagggtctgg ctcagcagct ccaggcggtc ccagagctcg    5100
gtgacgtgct ctacggcatc tctatccagc atatctcctc gtttcgcggg ttggggcgac    5160
tttcgctgta gggcaccaag cggtggtcgt ccagcgggc cagagtcatg tccttccatg     5220
ggcgcagggt cctcgtcagg gtggtctggg tcacggtgaa ggggtgcgct ccgggctgag    5280
cgcttgccaa ggtgcgcttg aggctggttc tgctggtgct gaagcgctgc cggtcttcgc    5340
cctgcgcgtc ggccaggtag catttgacca tggtgtcata gtccagcccc tccgcggcgt    5400 gtccccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520 agacccgca cacggtctcg cactccacca gccaggtgag ctcggggcgc gccgggtcaa     5580
aaaccaggtt tccccatgc ttttgatgc gtttcttacc tcgggtctcc atgaggtggt      5640
gtccccgctc ggtgacgaag aggctgtccg tgtctccgta gaccgacttg aggggtcttt    5700
```

```
tctccagggg ggtccctcgg tcttcctcgt agaggaactc ggaccactct gagacgaagg   5760
cccgcgtcca ggccaggacg aaggaggcta tgtgggaggg gtagcggtcg ttgtccacta   5820
gggggtccac cttctccaag gtgtgaagac acatgtcgcc ttcctcggcg tccaggaagg   5880
tgattggctt gtaggtgtag gccacgtgac cgggggttcc tgacgggggg gtataaaagg   5940
gggtgggggc gcgctcgtcg tcactctctt ccgcatcgct gtctgcgagg ccagctgct    6000 ggggtgagta ttccctctcg aaggcgggca tgacctccgc gctgaggttg tcagtttcca   6060
aaaacgagga ggatttgatg ttcacctgtc ccgaggtgat acctttgagg gtacccgcgt   6120
ccatctggtc agaaaacacg atcttttat tgtccagctt ggtggcgaac gacccgtaga    6180
gggcgttgga gagcagcttg gcgatggagc gcagggtctg gttcttgtcc ctgtcggcgc   6240
gctccttggc cgcgatgttg agctgcacgt actcgcgcgc gacgcagcgc cactcgggga   6300
agacggtggt gcgctcgtcg ggcaccaggc gcacgcgcca gccgcggttg tgcagggtga   6360
ccaggtccac gctggtggcg acctcgccgc gcaggcgctc gttggtccag cagagacggc   6420
cgcccttgcg cgagcagaag gggggcaggg ggtcgagctg gtctcgtcc gggggtccg     6480 cgtccacggt gaaaaccccg gggcgcaggc gcgtcgaa gtagtctatc ttgcaacctt     6540
gcatgtccag cgcctgctgc cagtcgcggg cggcgagcgc gcgctcgtag ggttgagcg    6600 gcgggcccca gggcatgggg tgggtgagtg cggaggcgta catgccgcag atgtcataga   6660
cgtagagggg ctcccgcagg accccgatgt aggtggggta gcagcggccg ccgcggatgc   6720
tggcgcgcac gtagtcatac agctcgtgcg aggggcgag gaggtcgggg cccaggttgg    6780
tgcgggcggg gcgctccgcg cggaagacga tctgcctgaa gatggcatgc gagttggaag   6840
agatggtggg gcgctggaag acgttgaagc tggcgtcctg caggccgacg gcgtcgcgca   6900
cgaaggaggc gtaggagtcg cgcagcttgt gtaccagctc ggcggtgacc tgcacgtcga   6960
gcgcgcagta gtcgagggtc tcgcggatga tgtcatattt agcctgcccc ttctttttcc   7020
acagctcgcg gttgaggaca aactcttcgc ggtctttcca gtactcttgg atcgggaaac   7080
cgtccggttc cgaacggtaa gagcctagca tgtagaactg gttgacggcc tggtaggcgc   7140
agcagccctt ctccacgggg agggcgtagg cctgcgcggc cttgcggagc gaggtgtggg   7200
tcagggcgaa ggtgtccctg accatgactt tgaggtactg gtgcttgaag tcggagtcgt   7260
cgcagccgcc ccgctcccag agcgagaagt cggtgcgctt cttggagcgg gggttgggca   7320
gagcgaaggt gacatcgttg aagaggattt tgcccgcgcg gggcatgaag ttgcgggtga   7380
tgcggaaggg ccccggcact tcagagcggt tgttgatgac ctgggcggcg agcacgatct   7440
cgtcgaagcc gttgatgttg tggcccacga tgtagagttc caggaagcgg ggccggccct   7500
ttacggtggg cagcttcttt agctcttcgt aggtgagctc ctcggcgag gcgaggccgt    7560 gctcggccag ggcccagtcc gcgaggtgcg ggttgtctct gaggaaggac ttccagaggt   7620
cgcgggccag gagggtctgc aggcggtctc tgaaggtcct gaactggcgg cccacggcca   7680
ttttttcggg ggtgatgcag tagaaggtga gggggtcttg ctgccagcgg tcccagtcga   7740
gctgcagggc gaggtcgcgc gcggcggtga ccaggcgctc gtcgcccccg aatttcatga   7800
ccagcatgaa gggcacgagc tgctttccga aggcccccat ccaagtgtag gtctctacat   7860
cgtaggtgac aaagaggcgc tccgtgcgag gatgcgagcc gatcgggaag aactggatct   7920
cccgccacca gttggaggag tggctgttga tgtggtggaa gtagaagtcc cgtcgccggg   7980
ccgaacactc gtgctggctt ttgtaaaagc gagcgcagta ctggcagcgc tgcacgggct   8040
gtacctcatg cacgagatgc acctttcgcc cgcgcacgag gaagccgagg ggaaatctga   8100
```

```
gcccccccgcc tggctcgcgg catggctggt tctcttctac tttggatgcg tgtccgtctc   8160
cgtctggctc ctcgaggggt gttacggtgg agcggaccac cacgccgcgc gagccgcagg   8220
tccagatatc ggcgcgcggc ggtcggagtt tgatgacgac atcgcgcagc tgggagctgt   8280
ccatggtctg gagctcccgc ggcggcggca ggtcagccgg gagttcttgc aggttcacct   8340
cgcagagtcg ggccagggcg cggggcaggt ctaggtggta cctgatctct aggggcgtgt   8400
tggtggcggc gtcgatggct tgcaggagcc cgcagccccg gggggcgacg acggtgcccc   8460
gcggggtggt ggtggtggtg gcggtgcagc tcagaagcgg tgccgcgggc gggcccccgg   8520
aggtaggggg ggctccggtc ccgcgggcag gggcggcagc ggcacgtcgg cgtggagcgc   8580
gggcaggagt tggtgctgtg cccggaggtt gctggcgaag cgacgacgc ggcggttgat    8640 ctcctggatc tggcgcctct gcgtgaagac gacgggcccg tgagcttga acctgaaaga    8700 gagttcgaca gaatcaatct cggtgtcatt gaccgcggcc tggcgcagga tctcctgcac   8760
gtctcccgag ttgtcttggt aggcgatctc ggccatgaac tgctcgatct cttcctcctg   8820
gaggtctccg cgtccggcgc gttccacggt ggccgccagg tcgttggaga tgcgcccat    8880 gagctgcgag aaggcgttga gtccgccctc gttccagact cggctgtaga ccacgccccc   8940
ctggtcatcg cgggcgcgca tgaccacctg cgcgaggttg agctccacgt gccgcgcgaa   9000
gacggcgtag ttgcgcagac gctggaagag gtagttgagg gtggtggcgg tgtgctcggc   9060
cacgaagaag ttcatgaccc agcggcgcaa cgtggattcg ttgatgtccc caaggcctc    9120 cagccgttcc atggcctcgt agaagtccac ggcgaagttg aaaaactggg agttgcgcgc   9180
cgacacggtc aactcctcct ccagaagacg gatgagctcg gcgacggtgt cgcgcacctc   9240
gcgctcgaag gctatgggga tctcttcctc cgctagcatc accacctcct cctcttcctc   9300
ctcttctggc acttccatga tggcttcctc ctcttcgggg ggtggcggcg gcggcggtgg   9360 gggaggggc gctctgcgcc ggcggcggcg caccggagg cggtccacga agcgcgcgat    9420
catctccccg cggcggcggc gcatggtctc ggtgacggcg cggccgttct cccggggggcg   9480 cagttggaag acgccgccgg acatctggtc ctggggcggg tggccgtgag gcagcgagac   9540
ggcgctgacg atgcatctca acaattgctg cgtaggtacg ccgccgaggg acctgaggga   9600
gtccatatcc accggatccg aaaaccttc gaggaaggcg tctaaccagt cgcagtcgca   9660
aggtaggctg agcaccgtgg cgggcggcgg ggggtgggg gagtgtctgg cggaggtgct    9720
gctgatgatg taattgaagt aggcggactt gacacggcgg atggtcgaca ggagcaccat   9780
gtccttgggt ccggcctgct ggatgcggag gcggtcggct atgccccagg cttcgttctg   9840
gcatcggcgc aggtccttgt agtagtcttg catgagcctt ccaccggca cctcttctcc    9900 ttcctcttct gcttcttcca tgtctgcttc ggccctgggg cggcgccgcg ccccctgcc    9960 cccccatgcgc gtgaccccga accccctgag cggttggagc agggccaggt cggcgacgac  10020
gcgctcggcc aggatggcct gctgcacctg cgtgagggtg gtttggaagt catccaagtc  10080
cacgaagcgg tggtaggcgc ccgtgttgat ggtgtaggtg cagttggcca tgacggacca  10140
gttgacggtc tggtggcccg gttgcgacat ctcggtgtac ctgagtcgcg agtaggcgcg  10200
ggagtcgaag acgtagtcgt tgcaagtccg caccaggtac tggtagccca ccaggaagtg  10260
cggcggcggc tggcggtaga ggggccagcg caggtggcg ggggctccgg gggccaggtc   10320
ttccagcatg aggcggtggt aggcgtagat gtacctggac atccaggtga tacccgcggc  10380
ggtggtggag gcgcgcggga agtcgcgcac ccggttccag atgttgcgca ggggcagaaa  10440
```

```
gtgctccatg gtaggcgtgc tctgtccagt cagacgcgcg cagtcgttga tactctagac   10500
cagggaaaac gaaagccggt cagcgggcac tcttccgtgg tctggtgaat agatcgcaag   10560
ggtatcatgg cggagggcct cggttcgagc cccgggtccg ggccggacgg tccgccatga   10620
tccacgcggt taccgcccgc gtgtcgaacc caggtgtgcg acgtcagaca acggtggagt   10680
gttccttttg gcgtttttct ggccgggcgc cggcgccgcg taagagacta agccgcgaaa   10740
gcgaaagcag taagtggctc gctcccgta gccggaggga tccttgctaa gggttgcgtt   10800
gcggcgaacc ccggttcgaa tcccgtactc gggccggccg gacccgcggc taaggtgttg   10860
gattggcctc cccctcgtat aaagaccccg cttgcggatt gactccggac acggggacga   10920
gcccctttta tttttgcttt cccagatgc atccggtgct gcggcagatg cgccccccgc   10980
cccagcagca gcaacaacac cagcaagagc ggcagcaaca gcagcgggag tcatgcaggg   11040 cccctcacc caccctcggc gggccggcca cctcggcgtc cgcggccgtg tctggcgcct   11100
gcggcggcgg cggggggccg gctgacgacc ccgaggagcc cccgcggcgc agggccagac   11160
actacctgga cctggaggag ggcgagggcc tggcgcggct gggggcgccg tctcccgagc   11220
gccacccgcg ggtgcagctg aagcgcgact cgcgcgaggc gtacgtgcct cggcagaacc   11280
tgttcaggga ccgcgcgggc gaggagcccg aggagatgcg ggacaggagg ttcagcgcag   11340
ggcgggagct gcggcagggg ctgaaccgcg agcggctgct gcgcgaggag gactttgagc   11400
ccgacgcgcg gacgggatc agcccgcgc gcgcgcacgt ggcggccgcc gacctggtga   11460
cggcgtacga gcagacggtg aaccaggaga tcaacttcca aaagagtttc aacaaccacg   11520
tgcgcacgct ggtggcgcgc gaggaggtga ccatcgggct gatgcacctg tgggactttg   11580
taagcgcgct ggtgcagaac cccaacagca agcctctgac ggcgcagctg ttcctgatag   11640
tgcagcacag cagggacaac gaggcgttta gggacgcgct gctgaacatc accgagcccg   11700
agggtcggtg gctgctggac ctgattaaca tcctgcagag catagtggtg caggagcgca   11760
gcctgagcct ggccgacaag gtggcggcca tcaactactc gatgctgagc ctgggcaagt   11820
tttacgcgcg caagatctac cagacgccgt acgtgcccat agacaaggag gtgaagatcg   11880
acggttttta catgcgcatg gcgctgaagg tgctcaccct gagcgacgac ctgggcgtgt   11940
accgcaacga gcgcatccac aaggccgtga gcgtgagccg gcggcgcgag ctgagcgacc   12000
gcgagctgat gcacagcctg cagcgggcgc tggcgggcgc cggcagcggc gacagggagg   12060
cggagtccta cttcgatgcg ggggcggacc tgcgctgggc gcccagccgg cgggccctgg   12120
aggccgcggg ggtccgcgag gactatgacg aggacggcga ggaggatgag gagtacgagc   12180
tagaggaggg cgagtacctg gactaaaccg cgggtggtgt ttccggtaga tgcaagaccc   12240
gaacgtggtg gacccggcgc tgcggcggc tctgcagagc cagccgtccg gccttaactc   12300
ctcagacgac tggcgacagg tcatggaccg catcatgtcg ctgacggcgc gtaacccgga   12360
cgcgttccgg cagcagccgc aggccaacag gctctccgcc atcctggagg cggtggtgcc   12420
tgcgcgctcg aaccccacgc acgagaaggt gctggccata gtgaacgcgc tggccgagaa   12480
cagggccatc cgcccggacg aggccgggct ggtgtacgac gcgctgctgc agcgcgtggc   12540
ccgctacaac agcggcaacg tgcagaccaa cctggaccgg ctggtggggg acgtgcgcga   12600
ggcggtggcg cagcgcgagc gcgcggatcg gcagggcaac ctgggctcca tggtggcgct   12660
gaatgccttc ctgagcacgc agccggccaa cgtgccgcgg gggcaggaag actacaccaa   12720
ctttgtgagc gcgctgcggc tgatggtgac cgagaccccc cagagcgagg tgtaccagtc   12780
gggcccggac tacttcttcc agaccagcag acagggcctg cagacggtga acctgagcca   12840
```

```
ggctttcaag aacctgcggg ggctgtgggg cgtgaaggcg cccaccggcg accgggcgac   12900
ggtgtccagc ctgctgacgc ccaactcgcg cctgctgctg ctgctgatcg cgccgttcac   12960
ggacagcggc agcgtgtccc gggacaccta cctgggcac ctgctgaccc tgtaccgcga    13020
ggccatcggg caggcgcagg tggacagaca caccttccag gagatcacca gcgtgagccg   13080
cgcgctgggg caggaggaca cgagcagcct ggaggcgact ctgaactacc tgctgaccaa   13140
ccggcggcag aagattccct cgctgcacag cctgacctcc gaggaggagc gcatcttgcg   13200
ctacgtgcag cagagcgtga gcctgaacct gatgcgcgac ggggtgacgc ccagcgtggc   13260
gctggacatg accgcgcgca acatggaacc gggcatgtac gccgcgcacc ggccttacat   13320
caaccgcctg atggactacc tgcatcgcgc ggcggccgtg aaccccgagt actttaccaa   13380
cgccatcctg aacccgcact ggctcccgcc gcccgggttc tacagcgggg gcttcgaggt   13440
cccggagacc aacgatggct tcctgtggga cgacatggac gacagcgtgt tctccccgcg   13500
gccgcaggcg ctggcggaag cgtccctgct gcgtcccaag aaggaggagg aggaggaggc   13560
gagtcgccgc cgcggcagca gcggcgtggc ttctctgtcc gagctggggg cggcagccgc   13620
cgcgcgcccc gggtccctgg gcggcagccc ctttccgagc ctggtggggt ctctgcacag   13680
cgagcgcacc acccgccctc ggctgctggg cgaggacgag tacctgaata actccctgct   13740
gcagccggtg cgggagaaaa acctgcctcc cgccttcccc aacaacggga tagagagcct   13800
ggtggacaag atgagcagat ggaagaccta tgcgcaggag cacagggacg cgcctgcgct   13860
ccggccgccc acgcggcgcc agcgccacga ccggcagcgg gggctggtgt gggatgacga   13920
ggactccgcg gacgatagca gcgtgctgga cctgggaggg agcggcaacc cgttcgcgca   13980
cctgcgcccc cgcctgggga ggatgtttta aaaaaaaaaa aaaaaagcaa gaagcatgat   14040
gcaaaaatta aataaaactc accaaggcca tggcgaccga gcgttggttt cttgtgttcc   14100
cttcagtatg cggcgcgcgg cgatgtacca ggagggacct cctccctctt acgagagcgt   14160
ggtgggcgcg gcgcggcgg cgccctcttc tcccttttgcg tcgcagctgc tggagccgcc   14220
gtacgtgcct ccgcgctacc tgcggcctac ggggggaga aacagcatcc gttactcgga   14280
gctggcgccc ctgttcgaca ccacccgggt gtacctggtg gacaacaagt cggcggacgt   14340
ggcctccctg aactaccaga acgaccacag caatttttg accacggtca tccagaacaa   14400
tgactacagc ccgagcgagg ccagcaccca gaccatcaat ctggatgacc ggtcgcactg   14460
gggcggcgac ctgaaaacca tcctgcacac caacatgccc aacgtgaacg agttcatgtt   14520
caccaataag ttcaaggcgc gggtgatggt gtcgcgctcg cacaccaagg aagaccgggt   14580
ggagctgaag tacgagtggg tggagttcga gctgccagag ggcaactact ccgagaccat   14640
gaccattgac ctgatgaaca cgcgatcgt ggagcactat ctgaaagtgg gcaggcagaa    14700
cggggtcctg gagagcgaca tcggggtcaa gttcgacacc aggaacttcc gcctggggct   14760
ggaccccgtg accgggctgg ttatgccgg ggtgtacacc aacgaggcct tccatcccga    14820
catcatcctg ctgcccggct gcggggtgga cttcacttac agccgcctga gcaacctcct   14880
gggcatccgc aagcggcagc ccttccagga gggcttcagg atcacctacg aggacctgga   14940
gggggcaac atccccgcgc tcctcgatgt ggaggcctac caggatagct tgaaggaaaa    15000
tgaggcggga caggaggata ccgccccgc cgcctccgcc gccgccgagc agggcgagga   15060
tgctgctgac accgcggccg cggacggggc agaggccgac cccgctatgg tggtgggagc   15120
tcccgagcag gaggaggaca tgaatgacag tgcggtgcgc ggagacacct tcgtcacccg   15180
```

```
gggggaggaa aagcaagcgg aggccgaggc cgcggccgag gaaaagcaac tggcggcagc    15240
agcggcggcg gcggcgttgg ccgcggcgga ggctgagtct gaggggacca agcccgccaa    15300
ggagcccgtg attaagcccc tgaccgaaga tagcaagaag cgcagttaca acctgctcaa    15360
ggacagcacc aacaccgcgt accgcagctg gtacctggcc tacaactacg cgacccgtc     15420 gacggggtg cgctcctgga ccctgctgtg cacgccggac gtgacctgcg gctcggagca    15480
ggtgtactgg tcgctgcccg acatgatgca agacccgtg accttccgct ccacgcggca     15540
ggtcagcaac ttcccggtgg tgggcgccga gctgctgccc gtgcactcca agagcttcta    15600
caacgaccag gccgtctact cccagctcat ccgccagttc acctctctga cccacgtgtt    15660
caatcgcttt cctgagaacc agattctggc gcgcccgccc gcccccacca tcaccaccgt    15720
cagtgaaaac gttcctgctc tcacagatca cgggacgcta ccgctgcgca acagcatcgg    15780
aggagtccag cgagtgaccg ttactgacgc cagacgccgc acctgcccct acgtttacaa    15840
ggccttgggc atagtctcgc cgcgcgtcct ttccagccgc acttttttgag caacaccacc    15900 atcatgtcca tcctgatctc acccagcaat aactccggct ggggactgct gcgcgcgccc    15960
agcaagatgt tcggaggggc gaggaagcgt tccgagcagc accccgtgcg cgtgcgcggg    16020
cacttccgcg ccccctgggg agcgcacaaa cgcggccgcg cggggcgcac caccgtggac    16080
gacgccatcg actcggtggt ggagcaggcg cgcaactaca ggcccgcggt ctctaccgtg    16140
gacgcggcca tccagaccgt ggtgcggggc gcgcggcggt acgccaagct gaagagccgc    16200
cggaagcgcg tggcccgcc ccaccgccgc cgacccgggg ccgccgccaa acgcgccgcc     16260 gcggcccctgc ttcgccgggc caagcgcacg gccgccgcg ccgccatgag ggccgcgcgc    16320
cgcttggccg ccggcatcac cgccgccacc atggccccccc gtacccgaag acgcgcggcc    16380
gccgccgccg ccgccgccat cagtgacatg gccagcaggc gccggggcaa cgtgtactgg    16440
gtgcgcgact cggtgaccgg cacgcgcgtg cccgtgcgct tccgccccccc gcggacttga    16500 gatgatgtga aaaacaaca ctgagtctcc tgctgttgtg tgtatcccag cggcggcggc     16560
gcgcgcagcg tcatgtccaa gcgcaaaatc aaagaagaga tgctccaggt cgtcgcgccg    16620
gagatctatg ggccccccgaa gaaggaagag caggattcga agccccgcaa gataaagcgg    16680
gtcaaaaaga aaagaaaga tgatgacgat gccgatgggg aggtggagtt cctgcgcgcc     16740
acggcgccca ggcgcccggt gcagtggaag ggccggcgcg taaagcgcgt cctgcgcccc    16800
ggcaccgcgg tggtcttcac gcccggcgag cgctccaccc ggacttcaa gcgcgtctat     16860 gacgaggtgt acggcgacga agacctgctg gagcaggcca acgagcgctt cggagagttt    16920
gcttacggga agcgtcagcg ggcgctgggg aaggaggacc tgctggcgct gccgctggac    16980
cagggcaacc ccaccccag tctgaagccc gtgaccctgc agcaggtgct gccgagcagc    17040
gcaccctccg aggcgaagcg gggtctgaag cgcgagggcg gcgacctggc gcccaccgtg    17100
cagctcatgg tgcccaagcg gcagaggctg gaggatgtgc tggagaaaat gaaagtagac    17160
cccggtctgc agccggacat cagggtccgc cccatcaagc aggtggcgcc gggcctcggc    17220
gtgcagaccg tggacgtggt catccccacc ggcaactccc ccgccgccgc caccactacc    17280
gctgcctcca cggacatgga gacacagacc gatcccgccg cagccgcagc cgcagccgcc    17340
gccgcgacct cctcggcgga ggtgcagacg gacccctggc tgccgccggc gatgtcagct    17400
ccccgcgcgc gtcgcggcg caggaagtac ggcgccgcca acgcgctcct gcccgagtac    17460
gccttgcatc cttccatcgc gcccacccc ggctaccgag gctataccta ccgcccgcga    17520
agagccaagg gttccacccg ccgtccccgc cgacgcgccg ccgccaccac ccgccgccgc    17580
```

```
cgccgcagac gccagcccgc actggctcca gtctccgtga ggaaagtggc gcgcgacgga   17640
cacaccctgg tgctgcccag ggcgcgctac caccccagca tcgttttaaaa gcctgttgtg   17700 gttcttgcag atatggccct cacttgccgc ctccgttttcc cggtgccggg ataccgagga   17760
ggaagatcgc gccgcaggag gggtctggcc ggccgcggcc tgagcggagg cagccgccgc   17820
gcgcaccggc ggcgacgcgc caccagccga cgcatgcgcg gcggggtgct gcccctgtta   17880
atccccctga tcgccgcggc gatcggcgcc gtgcccggga tcgcctccgt ggccttgcaa   17940
gcgtcccaga ggcattgaca gacttgcaaa cttgcaaata tggaaaaaaa aaccccaata   18000
aaaaagtcta gactctcacg ctcgcttggt cctgtgacta ttttgtagaa tggaagacat   18060
caactttgcg tcgctggccc cgcgtcacgg ctcgcgcccg ttcctgggac actggaacga   18120
tatcggcacc agcaacatga gcggtggcgc cttcagttgg ggctctctgt ggagcggcat   18180
taaaagtatc gggtctgccg ttaaaaatta cggctcccgg gcctggaaca gcagcacggg   18240
ccagatgttg agagacaagt tgaaagagca gaacttccag cagaaggtgg tggagggcct   18300
ggcctccggc atcaacgggg tggtggacct ggccaaccag gccgtgcaga ataagatcaa   18360
cagcagactg gaccccggc cgccggtgga ggaggtgccg ccggcgctgg agacggtgtc   18420
ccccgatggg cgtggcgaga agcgcccgcg gcccgatagg gaagagacca ctctggtcac   18480
gcagaccgat gagccgcccc cgtatgagga ggccctgaag caaggtctgc ccaccacgcg   18540
gcccatcgcg cccatggcca ccggggtggt gggccgccac accccgcca cgctggactt   18600 gcctccgccc gccgatgtgc cgcagcagca gaaggcggca cagccgggcc cgcccgcgac   18660
cgcctcccgt tcctccgccg gtcctctgcg ccgcgcggcc agcggccccc gcgggggggt   18720
cgcgaggcac ggcaactggc agagcacgct gaacagcatc gtgggtctgg gggtgcggtc   18780
cgtgaagcgc cgccgatgct actgaatagc ttagctaacg tgttgtatgt gtgtatgcgc   18840
cctatgtcgc cgccagagga gctgctgagt cgccgccgtt cgcgcgccca ccaccaccgc   18900
cactccgccc ctcaagatgg cgaccccatc gatgatgccg cagtggtcgt acatgcacat   18960
ctcgggccag gacgcctcgg agtacctgag ccccgggctg gtgcagttcg cccgcgccac   19020
cgagagctac ttcagcctga gtaacaagtt taggaacccc acggtggcgc ccacgcacga   19080
tgtgaccacc gaccggtctc agcgcctgac gctgcggttc attcccgtgg accgcgagga   19140
caccgcgtac tcgtacaagg cgcggttcac cctggccgtg ggcgacaacc gcgtgctgga   19200
catggcctcc acctactttg acatccgcgg ggtgctggac cggggtccca ctttcaagcc   19260
ctactctggc accgcctaca actccctggc ccccaagggc gctcccaact cctgcgagtc   19320
ggagcaagag gaaactcagg cagttgaaga agcagcagaa gaggaagaag aagatgctga   19380
cggtcaagct gaggaagagc aagcagctac caaaaagact catgtatatg ctcaggctcc   19440
cctttctggc gaaaaaatta gtaaagatgg tctgcaaata ggaacggacg ctacagctac   19500
agaacaaaaa cctatttatg cagaccctac attccagccc gaaccccaaa tcggggagtc   19560
ccagtggaat gaggcagatg ctacagtcgc cggcggtaga gtgctaaaga aatctactcc   19620
catgaaacca tgctatggtt cctatgcaag acccacaaat gctaatggag gtcagggtgt   19680
actaacggca aatgcccagg acagctagaa atctcaggtt gaaatgcaat tcttttcaac   19740
ttctgaaaac gcccgtaacg aggctaacaa cattcagccc aaattggtgc tgtatagtga   19800
ggatgtgcac atggagaccc cggatacgca ccttttcttac aagcccgcaa aaagcgatga   19860
caattcaaaa atcatgctgg gtcagcagtc catgcccaac agacctaatt acatcggctt   19920
```

```
cagagacaac tttatcggcc tcatgtatta caatagcact ggcaacatgg gagtgcttgc   19980
aggtcaggcc tctcagttga atgcagtggt ggacttgcaa gacagaaaca cagaactgtc   20040
ctaccagctc ttgcttgatt ccatgggtga cagaaccaga tacttttcca tgtggaatca   20100
ggcagtggac agttatgacc cagatgttag aattattgaa aatcatggaa ctgaagacga   20160
gctccccaac tattgtttcc ctctgggtgg cataggggta actgacactt accaggctgt   20220
taaaaccaac aatggcaata acggggggcca ggtgacttgg acaaaagatg aaacttttgc   20280
agatcgcaat gaaatagggg tgggaaacaa tttcgctatg gagatcaacc tcagtgccaa   20340
cctgtggaga aacttcctgt actccaacgt ggcgctgtac ctaccagaca agcttaagta   20400 caaccccctcc aatgtggaca tctctgacaa ccccaacacc tacgattaca tgaacaagcg   20460
agtggtggcc ccggggctgg tggactgcta catcaacctg ggcgcgcgct ggtcgctgga   20520
ctacatggac aacgtcaacc ccttcaacca ccaccgcaat gcgggcctgc gctaccgctc   20580
catgctcctg ggcaacgggc gctacgtgcc cttccacatc caggtgcccc agaagttctt   20640
tgccatcaag aacctcctcc tcctgccggg ctcctacacc tacgagtgga acttcaggaa   20700
ggatgtcaac atggtcctcc agagctctct gggtaacgat ctcagggtgg acggggccag   20760
catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct accccatacc cgccaacgcc accaacgtcc ccatctccat   20940
cccctcgcgc aactgggcgg ccttccgcgg ctgggccttc acccgcctca agaccaagga   21000
gaccccctcc ctgggctcgg gattcgaccc ctactacacc tactcgggct ccattcccta   21060
cctggacggc accttctacc tcaaccacac tttcaagaag gtctcggtca ccttcgactc   21120
ctcggtcagc tggccgggca acgaccgtct gctcacccccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
caaggacagg atgtactcct tcttcaggaa cttccagccc atgagccggc aggtggtgga   21360
ccagaccaag tacaaggact accaggaggt gggcatcatc caccagcaca caactcggg   21420 cttcgtgggc tacctcgccc ccaccatgcg cgagggacag gcctacccc ccaacttccc   21480 ctatccgctc ataggcaaga ccgcggtcga cagcatcacc cagaaaaagt tcctctgcga   21540 ccgcacccctc tggcgcatcc ccttctccag caacttcatg tccatgggtg cgctctcgga   21600
cctgggccag aacttgctct acgccaactc cgcccacgcc ctcgacatga ccttcgaggt   21660 cgacccccatg gacgagccca cccttctcta tgttctgttc gaagtctttg acgtggtccg   21720
ggtccaccag ccgcaccgcg cgtcatcga gaccgtgtac ctgcgtacgc ccttctcggc   21780
cggcaacgcc accacctaaa gaagcaagcc gcagtcatcg ccgcctgcat gccgtcgggt   21840
tccaccgagc aagagctcag ggccatcgtc agagacctgg gatgcgggcc ctatttttg   21900 ggcaccttcg acaagcgctt ccctggcttt gtctccccac acaagctggc ctgcgccatc   21960
gtcaacacgg ccggccgcga gaccggggc gtgcactggc tggccttcgc ctggaacccg   22020
cgctccaaaa catgcttcct cttttgacccc ttcggctttt cggaccagcg gctcaagcaa   22080
atctacgagt tcgagtacga gggcttgctg cgtcgcagcg ccatcgcctc ctcgcccgac   22140
cgctgcgtca ccctcgaaaa gtccacccag accgtgcagg ggcccgactc ggccgcctgc   22200
ggtctcttct gctgcatgtt tctgcacgcc tttgtgcact ggcctcagag tcccatggac   22260 cgcaaccccca ccatgaactt gctgacgggg gtgcccaact ccatgctcca gagccccag   22320
```

```
gtcgagccca ccctgcgccg caaccaggag cagctctaca gcttcctgga gcgccactcg    22380
ccttacttcc gccgccacag cgcacagatc aggagggcca cctccttctg ccacttgcaa    22440
gagatgcaag aagggtaata acgatgtaca cactttttt ctcaataaat ggcatctttt     22500
tatttataca agctctctgg ggtattcatt tcccaccacc acccgccgtt gtcgccatct    22560
ggctctattt agaaatcgaa agggttctgc cgggagtcgc cgtgcgccac gggcagggac    22620
acgttgcgat actggtagcg ggtgccccac ttgaactcgg gcaccaccag gcgaggcagc    22680
tcggggaagt tttcgctcca caggctgcgg gtcagcacca gcgcgttcat caggtcgggc    22740
gccgagatct tgaagtcgca gttggggccg ccgccctgcg cgcgcgagtt gcggtacacc    22800
gggttgcagc actggaacac caacagcgcc gggtgcttca cgctggccag cacgctgcgg    22860
tcggagatca gctcggcgtc caggtcctcc gcgttgctca gcgcgaacgg ggtcatcttg    22920
ggcacttgcc gccccaggaa gggcgcgtgc cccggtttcg agttgcagtc gcagcgcagc    22980
gggatcagca ggtgcccgtg cccggactcg gcgttgggt acagcgcgcg catgaaggcc     23040
tgcatctggc ggaaggccat ctgggccttg gcgccctccg agaagaacat gccgcaggac    23100
ttgcccgaga actggtttgc ggggcagctg cgtcgtgca ggcagcagcg cgcgtcggtg     23160
ttggcgatct gcaccacgtt gcgcccccac cggttcttca cgatcttggc cttggacgat    23220
tgctccttca gcgcgcgctg cccgttctcg ctggtcacat ccatctcgat cacatgttcc    23280
ttgttcacca tgctgctgcc gtgcagacac ttcagctcgc cctccgtctc ggtgcagcgg    23340
tgctgccaca gcgcgcagcc cgtgggctcg aaagacttgt aggtcacctc cgcgaaggac    23400
tgcaggtacc cctgcaaaaa gcggcccatc atggtcacga aggtcttgtt gctgctgaag    23460
gtcagctgca gcccgcggtg ctcctcgttc agccaggtct tgcacacggc cgccagcgcc    23520
tccacctggt cgggcagcat cttgaagttc accttcagct cattctccac gtggtacttg    23580
tccatcagcg tgcgcgccgc ctccatgccc ttctcccagg ccgacaccag cggcaggctc    23640
acggggttct tcaccatcac cgtggccgcc gcctccgccg cgctttcgct ttccgccccg    23700
ctgttctctt cctcttcctc ctcttcctcg ccgccgccca ctcgcagccc cgcaccacg     23760
gggtcgtctt cctgcaggcg ctgcaccttg cgcttgccgt tgcgcccctg cttgatgcgc    23820
acgggcgggt tgctgaagcc caccatcacc agcgcggcct cttcttgctc gtcctcgctg    23880
tccagaatga cctccgggga ggggggttg gtcatcctca gtaccgaggc acgcttcttt     23940
ttcttcctgg gggcgttcgc cagctccgcg gctgcggccg ctgccgaggt cgaaggccga    24000
gggctgggcg tgcgcggcac cagcgcgtcc tgcgagccgt cctcgtcctc ctcggactcg    24060
agacggaggc gggcccgctt cttcgggggc gcgcggggcg gcggaggcgg cggcggcgac    24120
ggagacgggg acgagacatc gtccaggtg ggtggacggc gggccgcgcc gcgtccgcgc     24180
tcggggtgg tctcgcgctg gtcctcttcc cgactggcca tctcccactg ctccttctcc     24240
tataggcaga aagagatcat ggagtctctc atgcgagtcg agaaggagga ggacagccta    24300
accgcccct ctgagccctc caccaccgcc gccaccaccg ccaatgccgc cgcggacgac      24360
gcgcccaccg agaccaccgc cagtaccacc ctcccccagcg acgcaccccc gctcgagaat   24420
gaagtgctga tcgagcagga cccgggtttt gtgagcggag aggaggatga ggtggatgag    24480
aaggagaagg aggaggtcgc cgcctcagtg ccaaaagagg ataaaaagca agaccaggac    24540
gacgcagata aggatgagac agcagtcggg cgggggaacg gaagccatga tgctgatgac    24600
ggctacctag acgtgggaga cgacgtgctg cttaagcacc tgcaccgcca gtgcgtcatc    24660
```

```
gtctgcgacg cgctgcagga gcgctgcgaa gtgccctgg acgtggcgga ggtcagccgc    24720
gcctacgagc ggcacctctt cgcgccgcac gtgcccccca agcgccggga gaacggcacc    24780
tgcgagccca acccgcgtct caacttctac ccggtcttcg cggtacccga ggtgctggcc    24840
acctaccaca tctttttcca aaactgcaag atccccctct cctgccgcgc caaccgcacc    24900
cgcgccgaca aaaccctgac cctgcggcag ggcgcccaca tacctgatat cgcctctctg    24960
gaggaagtgc ccaagatctt cgagggtctc ggtcgcgacg agaaacgggc ggcgaacgct    25020
ctgcacggag acagcgaaaa cgagagtcac tcggggggtgc tggtggagct cgagggcgac    25080
aacgcgcgcc tggccgtact caagcgcagc atagaggtca cccactttgc ctacccggcg    25140
ctcaacctgc cccccaaggt catgagtgtg gtcatgggcg agctcatcat gcgccgcgcc    25200
cagcccctgg ccgcggatgc aaacttgcaa gagtcctccg aggaaggcct gcccgcggtc    25260
agcgacgagc agctggcgcg ctggctggag acccgcgacc ccgcgcagct ggaggagcgg    25320
cgcaagctca tgatggccgc ggtgctggtc accgtggagc tcgagtgtct gcagcgcttc    25380
ttcgcggacc ccgagatgca gcgcaagctc gaggagaccc tgcactacac cttccgccag    25440
ggctacgtgc gccaggcctg caagatctcc aacgtggagc tctgcaacct ggtctcctac    25500
ctgggcatcc tgcacgagaa ccgcctcggg cagaacgtcc tgcactccac cctcaaaggg    25560
gaggcgcgcc gcgactacat ccgcgactgc gcctacctct cctctgcta cacctggcag    25620 acggccatgg gggtctggca gcagtgcctg gaggagcgca acctcaagga gctggaaaag    25680
ctcctcaagc gcaccctcag ggacctctgg acgggcttca acgagcgctc ggtggccgcc    25740
gcgctggcgg acatcatctt tcccgagcgc ctgctcaaga ccctgcagca gggcctgccc    25800
gacttcacca gccagagcat gctgcagaac ttcaggactt tcatcctgga gcgctcgggc    25860
atcctgccgg ccacttgctg cgcgctgccc agcgacttcg tgcccatcaa gtacaggggag    25920 tgcccgccgc cgctctgggg ccactgctac ctcttccagc tggccaacta cctcgcctac    25980
cactcggacc tcatggaaga cgtgagcggc gagggcctgc tcgagtgcca ctgccgctgc    26040
aacctctgca cgccccaccg ctctctagtc tgcaacccgc agctgctcag cgagagtcag    26100
attatcggta ccttcgagct gcagggtccc tcgcctgacg agaagtccgc ggctccaggg    26160
ctgaaactca ctccggggct gtggacttcc gcctacctac gcaaatttgt acctgaggac    26220
taccacgccc acgagatcag gttctacgaa gaccaatccc gcccgcccaa ggcggagctc    26280
accgcctgcg tcatcaccca ggggcacatc ctgggccaat gcaagccat caacaaagcc    26340 cgccgagagt tcttgctgaa aaagggtcgg ggggtgtacc tggacccccca gtccggcgag    26400 gagctaaacc cgctaccccc gccgccgccc cagcagcggg accttgcttc ccaggatggc    26460
acccagaaag aagcagcagc cgccgccgcc gccgcagcca tacatgcttc tggaggaaga    26520
ggaggaggac tgggacagtc aggcagagga ggtttcggac gaggagcagg aggagatgat    26580
ggaagactgg gaggaggaca gcagcctaga cgaggaagct tcagaggccg aagaggtggc    26640
agacgcaaca ccatcgccct cggtcgcagc ccctcgccg gggcccctga atcctccga    26700 acccagcacc agcgctataa cctccgctcc tccggcgccg cgccacccg cccgcagacc    26760 caaccgtaga tgggacacca caggaaccgg ggtcggtaag tccaagtgcc cgccgccgcc    26820
accgcagcag cagcagcagc agcgccaggg ctaccgctcg tggcgcgggc acaagaacgc    26880
catagtcgcc tgcttgcaag actgcggggg caacatctct ttcgcccgcc gcttcctgct    26940
attccaccac ggggtcgcct ttccccgcaa tgtcctgcat tactaccgtc atctctacag    27000
cccctactgc agcggcgacc cagaggcggc agcggcagcc acagcggcga ccaccaccta    27060
```

```
ggaagatatc ctccgcgggc aagacagcgg cagcagcggc caggagaccc gcggcagcag   27120
cggcgggagc ggtgggcgca ctgcgcctct cgcccaacga acccctctcg acccgggagc   27180
tcagacacag gatcttcccc actttgtatg ccatcttcca acagagcaga ggccaggagc   27240
aggagctgaa aataaaaaac agatctctgc gctccctcac ccgcagctgt ctgtatcaca   27300
aaagcgaaga tcagcttcgg cgcacgctgg aggacgcgga ggcactcttc agcaaatact   27360
gcgcgctcac tcttaaagac tagctccgcg cccttctcga atttaggcgg gagaaaacta   27420
cgtcatcgcc ggccgccgcc cagcccgccc agccgagatg agcaaagaga ttcccacgcc   27480
atacatgtgg agctaccagc cgcagatggg actcgcggcg ggagcggccc aggactactc   27540
cacccgcatg aactacatga gcgcgggacc ccacatgatc tcacaggtca cgggatccg   27600 cgcccagcga aaccaaatac tgctggaaca ggcggccatc accgccacgc cccgccataa   27660 tctcaaccccc cgaaattggc ccgccgccct cgtgtaccag gaaacccct ccgccaccac   27720 cgtactactt ccgcgtgacg cccaggccga agtccagatg actaactcag gggcgcagct   27780
cgcgggcggc tttcgtcacg gggcgcggcc gctccgacca ggtataagac acctgatgat   27840
cagaggccga ggtatccagc tcaacgacga gtcggtgagc tcttcgctcg gtctccgtcc   27900
ggacggaact ttccagctcg ccggatccgg ccgctcttcg ttcacgcccc gccaggcgta   27960
cctgactctg cagacctcgt cctcggagcc ccgctccggc ggcatcggaa ccctccagtt   28020
cgtggaggag ttcgtgccct cggtctactt caacccctt tcgggacctc ccggacgcta   28080
ccccgaccag ttcattccga actttgacgc ggtgaaggac tcggcggacg gctacgactg   28140
aatgtcaggt gtcgaggcag agcagcttcg cctgagacac ctcgagcact gccgccgcca   28200
caagtgcttc gcccgcggtt ctggtgagtt ctgctacttt cagctacccg aggagcatac   28260
cgaggggccg gcgcacggcg tccgcctgac cacccagggc gaggttacct gttccctcat   28320
ccggagtttt accctccgtc ccctgctagt ggagcgggag cggggtccct gtgtcctaac   28380
tatcgcctgc aactgcccta accctggatt acatcaagat ctttgctgtc atctctgtgc   28440
tgagtttaat aaacgctgag atcagaatct actgggctc ctgtcgccat cctgtgaacg   28500
ccaccgtctt cacccacccc gaccaggccc aggcgaacct cacctgcggt ctgcatcgga   28560
gggccaagaa gtacctcacc tggtacttca acggcacccc cttttgtggtt tacaacagct   28620 tcgacgggga cggagtctcc ctgaaagacc agctctccgg tctcagctac tccatccaca   28680
agaacaccac cctccaactc ttccctcct acctgccggg aacctacgag tgcgtcaccg   28740
gccgctgcac ccacctcacc cgcctgatcg taaaccagag cttccgggga acagataact   28800
ccctcttccc cagaacagga ggtgagctca ggaaactccc cggggaccag ggcggagacg   28860
taccttcgac ccttgtgggg ttaggatttt ttattaccgg gttgctggct cttttaatca   28920
aagtttcctt gagatttgtt ctttccttct acgtgtatga acacctcaac ctccaataac   28980
tctacccttt cttcggaatc aggtgacttc tctgaaatcg gcttggtgt gctgcttact   29040 ctgttgattt ttttccttat catactcagc cttctgtgcc tcaggctcgc cgcctgctgc   29100
gcacacatct atatctactg ctggttgctc aagtgcaggg gtcgccaccc aagatgaaca   29160
ggtacatggt cctatcgatc ctaggcctgc tggccctggc ggcctgcagc gccgccaaaa   29220
aagagattac ctttgaggag cccgcttgca atgtaacttt caagcccgag ggtgaccaat   29280
gcaccaccct cgtcaaatgc gttaccaatc atgagaggct gcgcatcgac tacaaaaaca   29340
aaactggcca gtttgcggtc tatagtgtgt ttacgcccgg agaccctct aactactctg   29400
```

```
tcaccgtctt ccagggcgga cagtctaaga tattcaatta cactttccct ttttatgagt    29460
tatgcgatgc ggtcatgtac atgtcaaaac agtacaacct gtggcctccc tctccccagg    29520
cgtgtgtgga aaatactggg tcttactgct gtatggcttt cgcaatcact acgctcgctc    29580
taatctgcac ggtgctatac ataaaattca ggcagaggcg aatctttatc gatgaaaaga    29640
aaatgccttg atcgctaaca ccggctttct atctgcagaa tgaatgcaat cacctcccta    29700
ctaatcacca ccaccctcct tgcgattgcc catgggttga cacgaatcga agtgccagtg    29760
gggtccaatg tcaccatggt gggccccgcc ggcaattcca ccctcatgtg ggaaaaattt    29820
gtccgcaatc aatgggttca tttctgctct aaccgaatca gtatcaagcc cagagccatc    29880
tgcgatgggc aaaatctaac tctgatcaat gtgcaaatga tggatgctgg gtactattac    29940
gggcagcggg gagaaatcat taattactgg cgaccccaca aggactacat gctgcatgta    30000
gtcgaggcac ttcccactac caccccccact accacctctc ccaccaccac caccactact    30060
actactacta ctactactac tactactacc actaccgctg cccgccatac ccgcaaaagc    30120
accatgatta gcacaaagcc ccctcgtgct cactcccacg ccggcgggcc catcggtgcg    30180
acctcagaaa ccaccgagct ttgcttctgc caatgcacta acgccagcgc tcatgaactg    30240
ttcgacctgg agaatgagga tgtccagcag agctccgctt gcctgaccca ggaggctgtg    30300
gagcccgttg ccctgaagca gatcggtgat tcaataattg actcttcttc ttttgccact    30360
cccgaatacc ctcccgattc tactttccac atcacgggta ccaaagaccc taacctctct    30420
ttctacctga tgctgctgct ctgtatctct gtggtctctt ccgcgctgat gttactgggg    30480
atgttctgct gcctgatctg ccgcagaaag agaaaagctc gctctcaggg ccaaccactg    30540
atgcccttcc cctacccccc ggattttgca gataacaaga tatgagctcg ctgctgacac    30600
taaccgcttt actagcctgc gctctaaccc ttgtcgcttg cgactcgaga ttccacaatg    30660
tcacagctgt ggcaggagaa aatgttactt tcaactccac ggccgatacc cagtggtcgt    30720
ggagtggctc aggtagctac ttaactatct gcaatagctc cacttccccc ggcatatccc    30780
caaccaagta ccaatgcaat gccagcctgt tcaccctcat caacgcttcc accctggaca    30840
atggactcta tgtaggctat gtaccctttg gtgggcaagg aaagacccac gcttacaacc    30900
tggaagttcg ccagcccaga accactaccc aagcttctcc caccaccacc accaccacca    30960
ccatcaccag cagcagcagc agcagcagcc acagcagcag cagcagatta ttgactttgg    31020
ttttggccag ctcatctgcc gctacccagg ccatctacag ctctgtgccc gaaaccactc    31080
agatccaccg cccagaaacg accaccgcca ccacccctaca cacctccagc gatcagatgc    31140
cgaccaacat caccccccttg gctcttcaaa tgggacttac aagcccccact ccaaaaccag    31200
tggatgcggc cgaggtctcc gccctcgtca atgactgggc ggggctggga atgtggtggt    31260
tcgccatagg catgatggcg ctctgcctgc ttctgctctg gctcatctgc tgcctccacc    31320
gcaggcgagc cagacccccc atctatagac ccatcattgt cctgaacccc gataatgatg    31380
ggatccatag attggatggc ctgaaaaacc tacttttttc ttttacagta tgataaattg    31440
agacatgcct cgcatttttct tgtacatgtt ccttctccca ccttttctgg ggtgttctac    31500
gctggccgct gtgtctcacc tggaggtaga ctgcctctca cccttcactg tctacctgct    31560
ttacggattg gtcaccctca ctctcatctg cagcctaatc acagtaatca tcgccttcat    31620
ccagtgcatt gattacatct gtgtgcgcct cgcatacttc agacaccacc cgcagtaccg    31680
agacaggaac attgcccaac ttctaagact gctctaatca tgcataagac tgtgatctgc    31740
cttctgatcc tctgcatcct gcccaccctc acctcctgcc agtacaccac aaaatctccg    31800
```

```
cgcaaaagac atgcctcctg ccgcttcacc caactgtgga atatacccaa atgctacaac    31860
gaaaagagcg agctctccga agcttggctg tatggggtca tctgtgtctt agttttctgc    31920
agcactgtct ttgccctcat aatctacccc tactttgatt tgggatggaa cgcgatcgat    31980
gccatgaatt accccacctt tcccgcaccc gagataattc cactgcgaca agttgtaccc    32040
gttgtcgtta atcaacgccc cccatcccct acgccactg aaatcagcta ctttaaccta    32100
acaggcggag atgactgacg ccctagatct agaaatggac ggcatcagta ccgagcagcg    32160
tctcctagag aggcgcaggc aggcggctga gcaagagcgc tcaatcagg agctccgaga    32220 tctcgttaac ctgcaccagt gcaaagagg catcttttgt ctggtaaagc aggccaaagt    32280
cacctacgag aagaccggca acagccaccg cctcagttac aaattgccca cccagcgcca    32340
gaagctggtg ctcatggtgg gtgagaatcc catcaccgtc acccagcact cggtagagac    32400
cgaggggtgt ctgcactccc cctgtcgggg tccagaagac ctctgcaccc tggtaaagac    32460
cctgtgcggt ctcagagatt tagtcccctt taactaatca aacactggaa tcaataaaaa    32520
gaatcactta cttaaaatca gacagcaggt ctctgtccag tttattcagc agcacctcct    32580 tccccctcctc ccaactctgg tactccaaac gccttctggc ggcaaacttc ctccacaccc    32640
tgaagggaat gtcagattct tgctcctgtc cctccgcacc cactatcttc atgttgttgc    32700
agatgaagcg caccaaaacg tctgacgaga gcttcaaccc cgtgtacccc tatgacacgg    32760
aaagcggccc tccctccgtc cctttcctca cccctccctt cgtgtctccc gatggattcc    32820
aagaaagtcc ccccggggtc ctgtctctga acctggccga gccctggtc acttcccacg    32880 gcatgctcgc cctgaaaatg ggaagtggcc tctccctgga cgacgctggc aacctcacct    32940
ctcaagatat caccaccgct agccctcccc tcaaaaaaac caagaccaac ctcagcctag    33000
aaacctcatc ccccctaact gtgagcacct caggcgccct caccgtagca gccgccgctc    33060
ccctggcggt ggccggcacc tccctcacca tgcaatcaga ggcccccctg acagtacagg    33120
atgcaaaact caccctggcc accaaaggcc ccctgaccgt gtctgaaggc aaactggcct    33180
tgcaaacatc ggccccgctg acggccgctg acagcagcac cctcacagtc agtgccacac    33240
caccccttag cacaagcaat ggcagcttgg gtattgacat gcaagccccc atttacacca    33300
ccaatggaaa actaggactt aactttggcg ctccctgca tgtggtagac agcctaaatg    33360
cactgactgt agttactggc caaggtctta cgataaacgg aacagcccta caaactagag    33420
tctcaggtgc cctcaactat gacacatcag gaaacctaga attgagagct gcaggggta    33480 tgcgagttga tgcaaatggt caacttatcc ttgatgtagc ttacccattt gatgcacaaa    33540
acaatctcag ccttaggctt ggacagggac ccctgtttgt taactctgcc cacaacttgg    33600
atgttaacta caacagaggc ctctacctgt tcacatctgg aaataccaaa aagctagaag    33660
ttaatatcaa aacagccaag ggtctcattt atgatgacac tgctatagca atcaatgcgg    33720
gtgatgggct acagtttgac tcaggctcag atacaaatcc attaaaaact aaacttggat    33780
taggactgga ttatgactcc agcagagcca taattgctaa actgggaact ggcctaagct    33840
ttgacaacac aggtgccatc acagtaggca acaaaaatga tgacaagctt accttgtgga    33900
ccacaccaga cccatcccct aactgtgaaa tctattcaga gaaagatgct aaattcacac    33960
ttgttttgac taaatgcggc agtcaggtgt tggccagcgt ttctgtttta tctgtaaaag    34020
gtagccttgc gccatcagt ggcacagtaa ctagtgctca gattgtcctc agatttgatg    34080
aaaatggagt tctactaagc aattcttccc ttgaccctca atactggaac tacagaaaag    34140
```

```
gtgaccttac agagggcact gcatatacca acgcagtggg atttatgccc aacctcacag    34200
catacccaaa aacacagagc caaactgcta aaagcaacat tgtaagtcag gtttacttga    34260
atggggacaa atccaaaccc atgaccctca ccattaccct caatggaact aatgaaacag    34320
gagatgccac agtaagcact tactccatgt cattctcatg gaactggaat ggaagtaatt    34380
acattaatga aacgttccaa accaactcct tcaccttctc ctacatcgcc caagaataaa    34440
aagcatgacg ctgttgattt gattcaatgt gtttctgttt tattttcaag cacaacaaaa    34500
tcattcaagt cattcttcca tcttagctta atagacacag tagcttaata gacccagtag    34560
tgcaaagccc cattctagct tataactagt ggagaagtac tcgcctacat gggggtagag    34620
tcataatcgt gcatcaggat agggcggtgg tgctgcagca gcgcgcgaat aaactgctgc    34680
cgccgccgct ccgtcctgca ggaatacaac atggcagtgg tctcctcagc gatgattcgc    34740
accgcccgca gcataaggcg ccttgtcctc cgggcacagc agcgcaccct gatctcactt    34800
aaatcagcac agtaactgca gcacagcacc acaatattgt tcaaaatccc acagtgcaag    34860
gcgctgtatc caaagctcat ggcggggacc acagaaccca cgtggccatc ataccacaag    34920
cgcaggtaga ttaagtggcg acccctcata aacacgctgg acataaacat tacctctttt    34980
ggcatgttgt aattcaccac ctcccggtac catataaacc tctgattaaa catggcgcca    35040
tccaccacca tcctaaacca gctggccaaa acctgcccgc cggctataca ctgcagggaa    35100
ccgggactgg aacaatgaca gtggagagcc caggactcgt aaccatggat catcatgctc    35160
gtcatgatat caatgttggc acaacacagg cacacgtgca tacacttcct caggattaca    35220
agctcctccc gcgttagaac catatcccag ggaacaaccc attcctgaat cagcgtaaat    35280
cccacactgc agggaagacc tcgcacgtaa ctcacgttgt gcattgtcaa agtgttacat    35340
tcgggcagca gcggatgatc ctccagtatg gtagcgcggg tttctgtctc aaaaggaggt    35400
agacgatccc tactgtacgg agtgcgccga dacaaccgag atcgtgttgg tcgtagtgtc    35460
atgccaaatg gaacgccgga cgtagtcata tttcctgaag tcttagatct ctcaacgcag    35520
caccagcacc aacacttcgc agtgtaaaag gccaagtgcc gagagagtat atataggaat    35580
aaaaagtgac gtaaacgggc aaagtccaaa aaacgcccag aaaaaccgca cgcgaaccta    35640
cgccccgaaa cgaaagccaa aaaacactag acactcccTt ccggcgtcaa cttccgcttt    35700
cccacgctac gtcacttgcc ccagtcaaac aaactacata tcccgaactt ccaagtcgcc    35760
acgcccaaaa caccgcctac acctcccccgc ccgccggccc gccccccaaac ccgcctcccg    35820 ccccgcgccc cgccccgcgc cgcccatctc attatcatat tggcttcaat ccaaaataag    35880
gtatattatt gatgatggtt taaacggatc ctctagagtc gacctgcagg catgcaagct    35940
tgagtattct atagtgtcac ctaaatagct tggcgtaatc atggtcatag ctgtttcctg    36000
tgtgaaattg ttatccgctc acaattccac acaacatacg agccggaagc ataaagtgta    36060
aagcctgggg tgcctaatga gtgagctaac tcacattaat tgcgttgcgc tcactgcccg    36120
ctttccagtc gggaaacctg tcgtgccagc tgcattaatg aatcggccaa cgcgaacccc    36180
ttgcggccgc ccgggccgtc gaccaattct catgtttgac agcttatcat cgaatttctg    36240
ccattcatcc gcttattatc acttattcag gcgtagcaac caggcgttta agggcaccaa    36300
taactgcctt aaaaaaatta cgccccgccc tgccactcat cgcagtactg ttgtaattca    36360
ttaagcattc tgccgacatg gaagccatca caaacggcat gatgaacctg aatcgccagc    36420
ggcatcagca ccttgtcgcc ttgcgtataa tatttgccca tggtgaaaac gggggcgaag    36480
aagttgtcca tattggccac gtttaaatca aaactggtga aactcaccca gggattggct    36540
```

```
gagacgaaaa acatattctc aataaaccct ttagggaaat aggccaggtt ttcaccgtaa    36600
cacgccacat cttgcgaata tatgtgtaga aactgccgga aatcgtcgtg gtattcactc    36660
cagagcgatg aaaacgtttc agtttgctca tggaaaacgg tgtaacaagg gtgaacacta    36720
tcccatatca ccagctcacc gtctttcatt gccatacgga attccggatg agcattcatc    36780
aggcgggcaa gaatgtgaat aaaggccgga taaaacttgt gcttattttt ctttacggtc    36840
tttaaaaagg ccgtaatatc cagctgaacg gtctggttat aggtacattg agcaactgac    36900
tgaaatgcct caaaatgttc tttacgatgc cattgggata tatcaacggt ggtatatcca    36960 gtgattttt tctccatttt agcttcctta gctcctgaaa atctcgataa ctcaaaaaat     37020
acgcccggta gtgatcttat ttcattatgg tgaaagttgg aacctcttac gtgccgatca    37080
acgtctcatt ttcgccaaaa gttggcccag ggcttcccgg tatcaacagg gacaccagga    37140
tttatttatt ctgcgaagtg atcttccgtc acaggtattt attcgcgata agctcatgga    37200
gcggcgtaac cgtcgcacag gaaggacaga gaaagcgcgg atctgggaag tgacggacag    37260
aacggtcagg acctggattg gggaggcggt tgccgccgct gctgctgacg gtgtgacgtt    37320
ctctgttccg gtcacaccac atacgttccg ccattcctat gcgatgcaca tgctgtatgc    37380
cggtataccg ctgaaagttc tgcaaagcct gatgggacat aagtccatca gttcaacgga    37440
agtctacacg aaggttttg cgctggatgt ggctgcccgg caccgggtgc agtttgcgat     37500
gccggagtct gatgcggttg cgatgctgaa acaattatcc tgagaataaa tgccttggcc    37560
tttatatgga aatgtggaac tgagtggata tgctgttttt gtctgttaaa cagagaagct    37620
ggctgttatc cactgagaag cgaacgaaac agtcgggaaa atctcccatt atcgtagaga    37680
tccgcattat taatctcagg agcctgtgta gcgtttatag gaagtagtgt tctgtcatga    37740
tgcctgcaag cggtaacgaa aacgatttga atatgccttc aggaacaata gaaatcttcg    37800
tgcggtgtta cgttgaagtg gagcggatta tgtcagcaat ggacagaaca acctaatgaa    37860
cacagaacca tgatgtggtc tgtccttta cagccagtag tgctcgccgc agtcgagcga     37920
cagggcgaag ccctcgagtg agcgaggaag caccagggaa cagcacttat atattctgct    37980
tacacacgat gcctgaaaaa acttcccttg gggttatcca cttatccacg gggatatttt    38040
tataattatt ttttttatag tttttagatc ttctttttta gagcgccttg taggcccttta    38100 tccatgctgg ttctagagaa ggtgttgtga caaattgccc tttcagtgtg acaaatcacc    38160
ctcaaatgac agtcctgtct gtgacaaatt gcccttaacc ctgtgacaaa ttgccctcag    38220
aagaagctgt ttttttcacaa agttatccct gcttattgac tcttttttat ttagtgtgac    38280
aatctaaaaa cttgtcacac ttcacatgga tctgtcatgg cggaaacagc ggttatcaat    38340
cacaagaaac gtaaaatag cccgcgaatc gtccagtcaa acgacctcac tgaggcggca    38400
tatagtctct cccgggatca aaaacgtatg ctgtatctgt tcgttgacca gatcagaaaa    38460
tctgatggca ccctacagga acatgacggt atctgcgaga tccatgttgc taaatatgct    38520
gaaatattcg gattgacctc tgcggaagcc agtaaggata tacggcaggc attgaagagt    38580
ttcgcgggga aggaagtggt ttttatcgc cctgaagagg atgccggcga tgaaaaggc     38640 tatgaatctt ttccttggtt tatcaaacgt gcgcacagtc catccagagg gctttacagt    38700
gtacatatca acccatatct cattcccttc tttatcgggt tacagaaccg gtttacgcag    38760
tttcggctta gtgaaacaaa agaaatcacc aatccgtatg ccatgcgttt atacgaatcc    38820
ctgtgtcagt atcgtaagcc ggatggctca ggcatcgtct ctctgaaaat cgactggatc    38880
```

```
atagagcgtt accagctgcc tcaaagttac cagcgtatgc ctgacttccg ccgccgcttc   38940
ctgcaggtct gtgttaatga gatcaacagc agaactccaa tgcgcctctc atacattgag   39000
aaaaagaaag gccgccagac gactcatatc gtattttcct tccgcgatat cacttccatg   39060
acgacaggat agtctgaggg ttatctgtca cagatttgag ggtggttcgt cacatttgtt   39120
ctgacctact gagggtaatt tgtcacagtt ttgctgtttc cttcagcctg catggatttt   39180
ctcatacttt ttgaactgta attttttaagg aagccaaatt tgagggcagt ttgtcacagt   39240
tgatttcctt ctctttccct tcgtcatgtg acctgatatc gggggttagt tcgtcatcat   39300
tgatgagggt tgattatcac agtttattac tctgaattgg ctatccgcgt gtgtacctct   39360
acctggagtt tttcccacgg tggatatttc ttcttgcgct gagcgtaaga gctatctgac   39420
agaacagttc ttcttttgctt cctcgccagt tcgctcgcta tgctcggtta cacggctgcg   39480
gcgagcgcta gtgataataa gtgactgagg tatgtgctct tcttatctcc ttttgtagtg   39540
ttgctcttat tttaaacaac tttgcggttt tttgatgact ttgcgatttt gttgttgctt   39600
tgcagtaaat tgcaagattt aataaaaaaa cgcaaagcaa tgattaaagg atgttcagaa   39660
tgaaactcat ggaaacactt aaccagtgca taaacgctgg tcatgaaatg acgaaggcta   39720
tcgccattgc acagtttaat gatgacagcc cggaagcgag gaaaataacc cggcgctgga   39780
gaataggtga agcagcggat ttagttgggg tttcttctca ggctatcaga gatgccgaga   39840
aagcagggcg actaccgcac ccggatatgg aaattcgagg acgggttgag caacgtgttg   39900
gttatacaat tgaacaaatt aatcatatgc gtgatgtgtt tggtacgcga ttgcgacgtg   39960
ctgaagacgt atttccaccg gtgatcgggg ttgctgccca taaaggtggc gtttacaaaa   40020
cctcagtttc tgttcatctt gctcaggatc tggctctgaa ggggctacgt gttttgctcg   40080
tggaaggtaa cgacccccag ggaacagcct caatgtatca cggatgggta ccagatcttc   40140
atattcatgc agaagacact ctcctgcctt tctatcttgg ggaaaaggac gatgtcactt   40200
atgcaataaa gccccacttgc tggccggggc ttgacattat tccttcctgt ctggctctgc   40260
accgtattga aactgagtta atgggcaaat tgatgaagg taaactgccc accgatccac   40320
acctgatgct ccgactggcc attgaaactg ttgctcatga ctatgatgtc atagttattg   40380
acagcgcgcc taacctgggt atcggcacga ttaatgtcgt atgtgctgct gatgtgctga   40440
ttgttcccac gcctgctgag ttgtttgact acacctccgc actgcagttt ttcgatatgc   40500
ttcgtgatct gctcaagaac gttgatctta aagggttcga gcctgatgta cgtatttttgc   40560
ttaccaaata cagcaatagt aatggctctc agtccccgtg gatggaggag caaattcggg   40620
atgcctgggg aagcatggtt ctaaaaaatg ttgtacgtga aacggatgaa gttggtaaag   40680
gtcagatccg gatgagaact gttttttgaac aggccattga tcaacgctct tcaactggtg   40740
cctggagaaa tgctctttct atttgggaac ctgtctgcaa tgaaattttc gatcgtctga   40800
ttaaaccacg ctgggagatt agataatgaa gcgtgcgcct gttattccaa aacatacgct   40860
caatactcaa ccggttgaag atacttcgtt atcgacacca gctgccccga tggtggattc   40920
gttaattgcg cgcgtaggag taatggctcg cggtaatgcc attactttgc ctgtatgtgg   40980
tcgggatgtg aagtttactc ttgaagtgct ccggggtgat agtgttgaga agacctctcg   41040
ggtatggtca ggtaatgaac gtgaccagga gctgcttact gaggacgcac tggatgatct   41100
catcccttct tttctactga ctggtcaaca gacaccggcg ttcggtcgaa gagtatctgg   41160
tgtcatagaa attgccgatg ggagtcgccg tcgtaaagct gctgcactta ccgaaagtga   41220
ttatcgtgtt ctggttggcg agctggatga tgagcagatg gctgcattat ccagattggg   41280
```

```
taacgattat cgcccaacaa gtgcttatga acgtggtcag cgttatgcaa gccgattgca    41340
gaatgaattt gctggaaata tttctgcgct ggctgatgcg gaaatatttt cacgtaagat    41400
tattacccgc tgtatcaaca ccgccaaatt gcctaaatca gttgttgctc ttttttctca    41460
ccccggtgaa ctatctgccc ggtcaggtga tgcacttcaa aaagccttta cagataaaga    41520
ggaattactt aagcagcagg catctaacct tcatgagcag aaaaaagctg gggtgatatt    41580
tgaagctgaa gaagttatca ctcttttaac ttctgtgctt aaaacgtcat ctgcatcaag    41640
aactagttta agctcacgac atcagtttgc tcctggagcg acagtattgt ataagggcga    41700
taaaatggtg cttaacctgg acaggtctcg tgttccaact gagtgtatag agaaaattga    41760
ggccattctt aaggaacttg aaaagccagc accctgatgc gaccacgttt tagtctacgt    41820
ttatctgtct ttacttaatg tcctttgtta caggccagaa agcataactg gcctgaatat    41880
tctctctggg cccactgttc cacttgtatc gtcggtctga taatcagact gggaccacgg    41940
tcccactcgt atcgtcggtc tgattattag tctgggacca cggtcccact cgtatcgtcg    42000
gtctgattat tagtctggga ccacggtccc actcgtatcg tcggtctgat aatcagactg    42060
ggaccacggt cccactcgta tcgtcggtct gattattagt ctgggaccat ggtcccactc    42120
gtatcgtcgg tctgattatt agtctgggac cacggtccca ctcgtatcgt cggtctgatt    42180
attagtctgg aaccacggtc ccactcgtat cgtcggtctg attattagtc tgggaccacg    42240
gtcccactcg tatcgtcggt ctgattatta gtctgggacc acgatcccac tcgtgttgtc    42300
ggtctgatta tcggtctggg accacggtcc cacttgtatt gtcgatcaga ctatcagcgt    42360
gagactacga ttccatcaat gcctgtcaag gcaagtatt gacatgtcgt cgtaacctgt    42420
agaacggagt aacctcggtg tgcggttgta tgcctgctgt ggattgctgc tgtgtcctgc    42480
ttatccacaa cattttgcgc acggttatgt ggacaaaata cctggttacc caggccgtgc    42540
cggcacgtta accgggctgc atccgatgca agtgtgtcgc tgtcgacgag ctcgcgagct    42600
cggacatgag gttgccccgt attcagtgtc gctgatttgt attgtctgaa gttgttttta    42660
cgttaagttg atgcagatca attaatacga tacctgcgtc ataattgatt atttgacgtg    42720
gtttgatggc ctccacgcac gttgtgatat gtagatgata atcattatca ctttacgggt    42780
cctttccggt gatccgacag gttacggggc ggcgacctcg cgggttttcg ctatttatga    42840
aaattttccg gtttaaggcg tttccgttct tcttcgtcat aacttaatgt ttttatttaa    42900 aatacccctct gaaagaaag gaaacgacag gtgctgaaag cgagcttttt ggcctctgtc    42960
gtttcctttc tctgttttg tccgtggaat gaacaatgga agtccgagct catcgctaat    43020
aacttcgtat agcatacatt atacgaagtt atattcgatg cggccgcaag gggttcgcgt    43080
cagcgggtgt tggcgggtgt cggggctggc ttaactatgc ggcatcagag cagattgtac    43140
tgagagtgca ccatatgcgg tgtgaaatac cgcacagatg cgtaaggaga aataccgca    43200 tcaggcgcca ttcgccattc aggctgcgca actgttggga agggcgatcg gtgcgggcct    43260
cttcgctatt acgccagctg gcgaaagggg gatgtgctgc aaggcgatta agttgggtaa    43320
cgccagggtt ttcccagtca cgacgttgta aaacgacggc cagtgaattg taatacgact    43380
cactataggg cgaattcgag ctcggtaccc ggggatcctc gtttaaac                 43428
```

<210> SEQ ID NO 9
<211> LENGTH: 45227
<212> TYPE: DNA
<213> ORGANISM: Simian adenovirus

```
<400> SEQUENCE: 9
catcatcaat aatataccttt attttggatt gaagccaata tgataatgag atgggcggcg     60
cggggcgggg cgcggggcgg gaggcgggtt tggggcggg ccggcgggcg ggcggtgtg      120 gcggaagtgg actttgtaag tgtggcggat gtgacttgct agtgccgggc gcggtaaaag    180
tgacgttttc cgtgcgcgac aacgccccg ggaagtgaca ttttccccgc ggttttacc     240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660 cgaccccgc ccattgacgt caataatgac gtatgttccc atagtaacgc caatagggac     720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga cttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgcccat tgacgcaaat    1080 gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccgggccc ccctcgagg tcgacggtat cgataagctt cacgctgccg    1380
caagcactca gggcgcaagg gctgctaaag gaagcggaac acgtagaaag ccagtccgca   1440
gaaacggtgc tgacccggga tgaatgtcag ctactgggct atctggacaa gggaaaacgc   1500
aagcgcaaag agaaagcagg tagcttgcag tgggcttaca tggcgatagc tagactgggc   1560
ggttttatgg acagcaagcg aaccggaatt gccagctggg gcgccctctg gtaaggttgg   1620
gaagccctgc aaagtaaact ggatggcttt cttgccgcca aggatctgat ggcgcagggg   1680
atcaagatct aaccaggagc tatttaatgg caacagttaa ccagctggta cgcaaaccac   1740
gtgctcgcaa agttgcgaaa agcaacgtgc ctgcgctgga agcatgcccg caaaaacgtg   1800
gcgtatgtac tcgtgtatat actaccactc ctaaaaaacc gaactccgcg ctgcgtaaag   1860
tatgccgtgt tcgtctgact aacggtttcg aagtgacttc ctacatcggt ggtgaaggtc   1920
acaacctgca ggagcactcc gtgatcctga tccgtggcgg tcgtgttaaa gacctcccgg   1980
gtgttcgtta ccacaccgta cgtggtgcgc ttgactgctc cggcgttaaa gaccgtaagc   2040
aggctcgttc caagtatggc gtgaagcgtc ctaaggctta atggtagatc tgatcaagag   2100
acaggatgac ggtcgtttcg catgcttgaa caagatggat tgcacgcagg ttctccggcc   2160
gcttgggtgg agaggctatt cggctatgac tgggcacaac agacaatcgg ctgctctgat   2220
gccgccgtgt tccggctgtc agcgcagggg cgcccggttc tttttgtcaa gaccgacctg   2280
tccggtgccc tgaatgaact gcaggacgag gcagcgcggc tatcgtggct ggccacgacg   2340
```
ggcgttcctt gcgcagctgt gctcgacgtt gtcactgaag cgggaaggga ctggctgcta 2400 

ttgggcgaag tgccggggca ggatctcctg tcatctcacc ttgctcctgc cgagaaagta 2460
tccatcatgg ctgatgcaat gcggcggctg catacgcttg atccggctac ctgcccattc 2520
gaccaccaag cgaaacatcg catcgagcga gcacgtactc ggatggaagc cggtcttgtc 2580
gatcaggatg atctggacga agagcatcag gggctcgcgc cagccgaact gttcgccagg 2640
ctcaaggcgc gcatgcccga cggcgaggat ctcgtcgtga cccatggcga tgcctgcttg 2700
ccgaatatca tggtggaaaa tggccgcttt tctggattca tcgactgtgg ccggctgggt 2760
gtggcggacc gctatcagga catagcgttg gctacccgtg atattgctga agagcttggc 2820
ggcgaatggg ctgaccgctt cctcgtgctt tacggtatcg ccgctcccga ttcgcagcgc 2880
atcgccttct atcgccttct tgacgagttc ttctgagcgg gactctgggg ttcgaaatga 2940
ccgaccaagc gacgcccaac ctgccatcac gagatttcga ttccaccgcc gccttctatg 3000
aaaggttggg cttcggaatc gttttccggg acgccggctg gatgatcctc cagcgcgggg 3060
atctcatgct ggagttcttc gcccaccccg ggctcgatcc cctcgggggg aatcagaatt 3120
cagtcgacag cggccgcgat ctgctgtgcc ttctagttgc cagccatctg ttgtttgccc 3180
ctcccccgtg ccttccttga ccctggaagg tgccactccc actgtccttt cctaataaaa 3240
tgaggaaatt gcatcgcatt gtctgagtag gtgtcattct attctggggg gtggggtggg 3300
gcaggacagc aagggggagg attgggaaga caatagcagg catgctgggg atgcggtggg 3360
ctctatggcc gatcagcgat cgctgaggtg ggtgagtggg cgtggcctgg ggtggtcatg 3420
aaaatatata agttgggggt cttagggtct ctttatttgt gttgcagaga ccgccggagc 3480
catgagcggg agcagcagca gcagcagtag cagcagcgcc ttggatggca gcatcgtgag 3540
cccttatttg acgacgcgga tgccccactg ggccggggtg cgtcagaatg tgatgggctc 3600
cagcatcgac ggccgacccg tcctgcccgc aaattccgcc acgctgacct atgcgaccgt 3660
cgcggggacg ccgttggacg ccaccgccgc cgccgccgcc accgcagccg cctcggccgt 3720
gcgcagcctg gccacggact ttgcattcct gggaccactg gcgacagggg ctacttctcg 3780
ggccgctgct gccgccgttc gcgatgacaa gctgaccgcc ctgctggcgc agttggatgc 3840
gcttactcgg gaactgggtg acctttctca gcaggtcatg gccctgcgcc agcaggtctc 3900
ctccctgcaa gctggcggga atgcttctcc cacaaatgcc gtttaagata aataaaacca 3960
gactctgttt ggattaaaga aaagtagcaa gtgcattgct ctctttattt cataattttc 4020
cgcgcgcgat aggccctaga ccagcgttct cggtcgttga gggtgcggtg tatcttctcc 4080
aggacgtggt agaggtggct ctggacgttg agatacatgg gcatgagccc gtcccggggg 4140
tggaggtagc accactgcag agcttcatgc tccggggtgg tgttgtagat gatccagtcg 4200
tagcaggagc gctgggcatg gtgcctaaaa atgtccttca gcagcaggcc gatggccagg 4260
gggaggccct tggtgtaagt gtttacaaaa cggttaagtt gggaagggtg cattcgggga 4320
gagatgatgt gcatcttgga ctgtattttt agattggcga tgtttccgcc cagatccctt 4380
ctgggattca tgttgtgcag gaccaccagt acagtgtatc cggtgcactt ggggaatttg 4440
tcatgcagct tagagggaaa agcgtggaag aacttggaga cgcctttgtg gcctcccaga 4500
ttttccatgc attcgtccat gatgatggca atgggcccgc gggaggcagc ttgggcaaag 4560
atatttctgg ggtcgctgac gtcgtagttg tgttccaggg tgaggtcgtc ataggccatt 4620
tttacaaagc gcgggcggag ggtgcccgac tgggggatga tggtcccctc tggccctggg 4680

```
gcgtagttgc cctcgcagat ctgcatttcc caggccttaa tctcggaggg gggaatcata      4740
tccacctgcg gggcgatgaa gaaaacggtt tccggagccg gggagattaa ctgggatgag      4800
agcaggtttc taagcagctg tgattttcca caaccggtgg gcccataaat aacacctata      4860
accggttgca gctggtagtt tagagagctg cagctgccgt cgtcccggag gagggggggcc      4920 acctcgttga gcatgtccct gacgcgcatg ttctccccga ccagatccgc cagaaggcgc      4980
tcgccgccca gggacagcag ctcttgcaag gaagcaaagt ttttcagcgg cttgaggccg      5040
tccgccgtgg gcatgttttt cagggtctgg ctcagcagct ccaggcggtc ccagagctcg      5100
gtgacgtgct ctacggcatc tctatccagc atatctcctc gtttcgcggg ttggggcgac      5160
tttcgctgta gggcaccaag cggtggtcgt ccagcggggc cagagtcatg tccttccatg      5220
ggcgcagggt cctcgtcagg gtggtctggg tcacggtgaa ggggtgcgct ccgggctgag      5280
cgcttgccaa ggtgcgcttg aggctggttc tgctggtgct gaagcgctgc cggtcttcgc      5340
cctgcgcgtc ggccaggtag catttgacca tggtgtcata gtccagcccc tccgcggcgt      5400
gtcccttggc gcgcagcttg cccttggagg tggcgccgca cgaggggcag agcaggctct      5460
tgagcgcgta gagcttgggg gcgaggaaga ccgattcggg ggagtaggcg tccgcgccgc      5520
agaccccgca cacggtctcg cactccacca gccaggtgag ctcggggcgc gccgggtcaa      5580
aaaccaggtt tccccatgc tttttgatgc gtttcttacc tcgggtctcc atgaggtggt       5640
gtccccgctc ggtgacgaag aggctgtccg tgtctccgta gaccgacttg aggggtcttt      5700
tctccagggg ggtccctcgg tcttcctcgt agaggaactc ggaccactct gagacgaagg      5760
cccgcgtcca ggccaggacg aaggaggcta tgtgggaggg gtagcggtcg ttgtccacta      5820
gggggtccac cttctccaag gtgtgaagac acatgtcgcc ttcctcggcg tccaggaagg      5880
tgattggctt gtaggtgtag gccacgtgac cgggggttcc tgacgggggg gtataaaagg      5940 gggtggggc gcgctcgtcg tcactctctt ccgcatcgct gtctgcgagg ccagctgct       6000 ggggtgagta ttccctctcg aaggcgggca tgacctccgc gctgaggttg tcagtttcca      6060
aaaacgagga ggatttgatg ttcacctgtc ccgaggtgat acctttgagg gtacccgcgt      6120
ccatctggtc agaaaacacg atcttttttat tgtccagctt ggtggcgaac gacccgtaga     6180
gggcgttgga gagcagcttg gcgatggagc gcagggtctg gttcttgtcc ctgtcggcgc      6240
gctccttggc cgcgatgttg agctgcacgt actcgcgcgc gacgcagcgc cactcgggga      6300
agacggtggt gcgctcgtcg ggcaccaggc gcacgcgcca gccgcggttg tgcagggtga      6360
ccaggtccac gctggtggcg acctcgccgc gcaggcgctc gttggtccag cagagacggc      6420
cgcccttgcg cgagcagaag gggggcaggg ggtcgagctg ggtctcgtcc gggggggtccg     6480 cgtccacggt gaaacccccg gggcgcaggc gcgcgtcgaa gtagtctatc ttgcaacctt      6540
gcatgtccag cgcctgctgc cagtcgcggg cggcgagcgc gcgctcgtag gggttgagcg      6600
gcgggcccca gggcatgggg tgggtgagtg cggaggcgta catgccgcag atgtcataga      6660
cgtagagggg ctcccgcagg accccgatgt aggtggggta gcagcggccg ccgcggatgc      6720
tggcgcgcac gtagtcatac agctcgtgcg agggggcgag gaggtcgggg cccaggttgg      6780
tgcgggcggg gcgctccgcg cggaagacga tctgcctgaa gatggcatgc gagttggaag      6840
agatggtggg gcgctggaag acgttgaagc tggcgtcctg caggccgacg gcgtcgcgca      6900
cgaaggaggc gtaggagtcg cgcagcttgt gtaccagctc ggcggtgacc tgcacgtcga      6960
gcgcgcagta gtcgagggtc tcgcggatga tgtcatattt agcctgcccc ttcttttcc       7020 acagctcgcg gttgaggaca aactcttcgc ggtctttcca gtactcttgg atcgggaaac      7080
```

```
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcgaagggg ccccggcact tcagagcggt tgttgatgac ctgggcggcg agcacgatct    7440
cgtcgaagcc gttgatgttg tgcccacga  tgtagagttc caggaagcgg ggccggccct    7500
ttacggtggg cagcttcttt agctcttcgt aggtgagctc ctcgggcgag gcgaggccgt    7560
gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680
ttttttcggg ggtgatgcag tagaaggtga gggggtcttg ctgccagcgg tcccagtcga    7740
gctgcagggc gaggtcgcgc gcggcggtga ccaggcgctc gtcgccccg  aatttcatga    7800
ccagcatgaa gggcacgagc tgctttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc acctttcgcc cgcgcacgag aagccgagg  ggaaatctga    8100
gccccccgcc tggctcgcgg catggctggt tctcttctac tttggatgcg tgtccgtctc    8160
cgtctggctc ctcgaggggt gttacggtgg agcggaccac cacgccgcgc gagccgcagg    8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
cgcagagtcg ggccagggcg cggggcaggt ctaggtggta cctgatctct aggggcgtgt    8400
tggtggcggc gtcgatggct tgcaggagcc cgcagccccg ggggcgacg  acggtgcccc    8460
gcggggtggt ggtggtggtg gcggtgcagc tcagaagcgg tgccgcgggc gggcccccgg    8520
aggtagggg  ggctccggtc ccgcgggcag gggcggcagc ggcacgtcgg cgtggagcgc    8580
gggcaggagt tggtgctgtg cccggaggtt gctggcgaag gcgacgacgc ggcggttgat    8640
ctcctggatc tggcgcctct gcgtgaagac gacgggcccg gtgagcttga acctgaaaga    8700
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
gaggtctccg cgtccggcgc gttccacggt ggccgccagg tcgttggaga tgcgcccat    8880
gagctgcgag aaggcgttga gtccgccctc gttccagact cggctgtaga ccacgccccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
cacgaagaag ttcatgaccc agcggcgcaa cgtggattcg ttgatgtccc ccaaggcctc    9120
cagccgttcc atggcctcgt agaagtccac ggcgaagttg aaaaactggg agttgcgcgc    9180
cgacacggtc aactcctcct ccagaagacg gatgagctcg cgacggtgt  cgcgcacctc    9240
gcgctcgaag gctatgggga tctcttcctc cgctagcatc accacctcct cctcttcctc    9300
ctcttctggc acttccatga tggcttcctc ctcttcgggg ggtggcggcg gcggcggtgg    9360
gggagggggc gctctgcgcc ggcggcggcg caccggggagg cggtccacga agcgcgcgat    9420
```

-continued

| | |
|---|---|
| catctcccccg cggcggcggc gcatggtctc ggtgacggcg cggccgttct cccgggggcg | 9480 |
| cagttggaag acgccgccgg acatctggtg ctggggcggg tggccgtgag gcagcgagac | 9540 |
| ggcgctgacg atgcatctca acaattgctg cgtaggtacg ccgccgaggg acctgaggga | 9600 |
| gtccatatcc accggatccg aaaacctttc gaggaaggcg tctaaccagt cgcagtcgca | 9660 |
| aggtaggctg agcaccgtgg cgggcggcgg ggggtgggggg gagtgtctgg cggaggtgct | 9720 |
| gctgatgatg taattgaagt aggcggactt gacacggcgg atggtcgaca ggagcaccat | 9780 |
| gtccttgggt ccggcctgct ggatgcggag gcggtcggct atgccccagg cttcgttctg | 9840 |
| gcatcggcgc aggtccttgt agtagtcttg catgagcctt ccaccggca cctcttctcc | 9900 |
| ttcctcttct gcttcttcca tgtctgcttc ggccctgggg cggcgccgcg cccccctgcc | 9960 |
| ccccatgcgc gtgaccccga acccctgag cggttggagc agggccaggt cggcgacgac | 10020 |
| gcgctcggcc aggatggcct gctgcacctg cgtgagggtg gtttggaagt catccaagtc | 10080 |
| cacgaagcgg tggtaggcgc ccgtgttgat ggtgtaggtg cagttggcca tgacggacca | 10140 |
| gttgacggtc tggtggcccg gttgcgacat ctcggtgtac ctgagtcgcg agtaggcgcg | 10200 |
| ggagtcgaag acgtagtcgt tgcaagtccg caccaggtac tggtagccca ccaggaagtg | 10260 |
| cggcggcggc tggcggtaga ggggccagcc cagggtggcg ggggctccgg gggccaggtc | 10320 |
| ttccagcatg aggcggtggt aggcgtagat gtacctggac atccaggtga tacccgcggc | 10380 |
| ggtggtggag gcgcgcggga agtcgcgcac ccggttccag atgttgcgca ggggcagaaa | 10440 |
| gtgctccatg gtaggcgtgc tctgtccagt cagacgcgcg cagtcgttga tactctagac | 10500 |
| cagggaaaac gaaagccggt cagcgggcac tcttccgtgg tctggtgaat agatcgcaag | 10560 |
| ggtatcatgg cggagggcct cggttcgagc cccgggtccg ggccggacgg tccgccatga | 10620 |
| tccacgcggt taccgcccgc gtgtcgaacc caggtgtgcg acgtcagaca acggtggagt | 10680 |
| gttccttttg gcgttttttct ggccgggcgc cggcgccgcg taagagacta agccgcgaaa | 10740 |
| gcgaaagcag taagtggctc gctccccgta gccggaggga tccttgctaa gggttgcgtt | 10800 |
| gcggcgaacc ccggttcgaa tcccgtactc gggccggccg gacccgcggc taaggtgttg | 10860 |
| gattggcctc cccctcgtat aaagaccccg cttgcggatt gactccggac acggggacga | 10920 |
| gccccttttta tttttgcttt cccagatgc atccggtgct gcggcagatg cgcccccgc | 10980 |
| cccagcagca gcaacaacac cagcaagagc ggcagcaaca gcagcgggag tcatgcaggg | 11040 |
| cccccctcacc caccctcggc gggccggcca cctcggcgtc cgcggccgtg tctggcgcct | 11100 |
| gcggcggcgg cgggggggccg gctgacgacc ccgaggagcc cccgcggcgc agggccagac | 11160 |
| actacctgga cctggaggag ggcgagggcc tggcgcggct gggggcgccg tctcccgagc | 11220 |
| gccaccccgcg ggtgcagctg aagcgcgact cgcgcgaggc gtacgtgcct cggcagaacc | 11280 |
| tgttcaggga ccgcgcgggc gaggagcccg aggagatgcg ggacaggagg ttcagcgcag | 11340 |
| ggcgggagct gcggcagggg ctgaaccgcg agcggctgct gcgcgaggag gactttgagc | 11400 |
| ccgacgcgcg gacgggatc agccccgcgc gcgcgcacgt ggcggccgcc gacctggtga | 11460 |
| cggcgtacga gcagacggtg aaccaggaga tcaacttcca aaagagtttc aacaaccacg | 11520 |
| tgcgcacgct ggtggcgcgc gaggaggtga ccatcgggct gatgcacctg tgggactttg | 11580 |
| taagcgcgct ggtgcagaac cccaacagca agcctctgac ggcgcagctg ttcctgatag | 11640 |
| tgcagcacag cagggacaac gaggcgttta gggacgcgct gctgaacatc accgagcccg | 11700 |
| agggtcggtg gctgctggac ctgattaaca tcctgcagag catagtggtg caggagcgca | 11760 |
| gcctgagcct ggccgacaag gtggcggcca tcaactactc gatgctgagc ctgggcaagt | 11820 |

```
tttacgcgcg caagatctac cagacgccgt acgtgcccat agacaaggag gtgaagatcg  11880
acggttttta catgcgcatg gcgctgaagg tgctcaccct gagcgacgac ctgggcgtgt  11940
accgcaacga gcgcatccac aaggccgtga gcgtgagccg gcggcgcgag ctgagcgacc  12000
gcgagctgat gcacagcctg cagcgggcgc tggcgggcgc cggcagcggc gacagggagg  12060
cggagtccta cttcgatgcg ggggcggacc tgcgctgggc gcccagccgg cgggccctgg  12120
aggccgcggg ggtccgcgag gactatgacg aggacggcga ggaggatgag gagtacgagc  12180
tagaggaggg cgagtacctg gactaaaccg cgggtggtgt ttccggtaga tgcaagaccc  12240
gaacgtggtg gacccggcgc tgcgggcggc tctgcagagc cagccgtccg gccttaactc  12300
ctcagacgac tggcgacagg tcatggaccg catcatgtcg ctgacggcgc gtaacccgga  12360
cgcgttccgg cagcagccgc aggccaacag gctctccgcc atcctggagg cggtggtgcc  12420
tgcgcgctcg aaccccacgc acgagaaggt gctggccata gtgaacgcgc tggccgagaa  12480
cagggccatc cgcccggacg aggccgggct ggtgtacgac gcgctgctgc agcgcgtggc  12540
ccgctacaac agcggcaacg tgcagaccaa cctggaccgg ctggtggggg acgtgcgcga  12600
ggcggtggcg cagcgcgagc gcgcggatcg gcagggcaac ctgggctcca tggtggcgct  12660
gaatgccttc ctgagcacgc agccggccaa cgtgccgcgg gggcaggaag actacaccaa  12720
ctttgtgagc gcgctgcggc tgatggtgac cgagaccccc cagagcgagg tgtaccagtc  12780
gggcccggac tacttcttcc agaccagcag acagggcctg cagacggtga acctgagcca  12840
ggctttcaag aacctgcggg ggctgtgggg cgtgaaggcg cccaccggcg accgggcgac  12900
ggtgtccagc ctgctgacgc ccaactcgcg cctgctgctg ctgctgatcg cgccgttcac  12960
ggacagcggc agcgtgtccc gggacaccta cctggggcac ctgctgaccc tgtaccgcga  13020
ggccatcggg caggcgcagg tggacgagca caccttccag gagatcacca gcgtgagccg  13080
cgcgctgggg caggaggaca cgagcagcct ggaggcgact ctgaactacc tgctgaccaa  13140
ccggcggcag aagattccct cgctgcacag cctgacctcc gaggaggagc gcatcttgcg  13200
ctacgtgcag cagagcgtga gcctgaacct gatgcgcgac ggggtgacgc ccagcgtggc  13260
gctggacatg accgcgcgca acatggaacc gggcatgtac gccgcgcacc ggccttacat  13320
caaccgcctg atggactacc tgcatcgcgc ggcggccgtg aaccccgagt actttaccaa  13380
cgccatcctg aacccgcact ggctcccgcc gcccgggttc tacagcgggg gcttcgaggt  13440
cccggagacc aacgatggct tcctgtggga cgacatggac gacagcgtgt tctccccgcg  13500
gccgcaggcg ctggcggaag cgtccctgct gcgtcccaag aaggaggagg aggaggagc  13560 gagtcgccgc cgcggcagca gcggcgtggc ttctctgtcc gagctggggg cggcagccgc  13620
cgcgcgcccc gggtccctgg gcggcagccc ctttccgagc ctggtggggt ctctgcacag  13680
cgagcgcacc acccgccctc ggctgctggg cgaggacgag tacctgaata actccctgct  13740
gcagccggtg cgggagaaaa acctgcctcc cgccttcccc aacaacggga tagagagcct  13800
ggtggacaag atgagcagat ggaagaccta tgcgcaggag cacagggacg cgcctgcgct  13860
ccggccgccc acgcggcgcc agcgccacga ccggcagcgg gggctggtgt gggatgacga  13920
ggactccgcg gacgatagca gcgtgctgga cctgggaggg agcggcaacc cgttcgcgca  13980
cctgcgcccc cgcctgggga ggatgttta aaaaaaaaa aaaaagcaa gaagcatgat  14040 gcaaaaatta aataaaactc accaaggcca tggcgaccga gcgttggttt cttgtgttcc  14100
cttcagtatg cggcgcgcgg cgatgtacca ggagggacct cctccctctt acgagagcgt  14160
```

```
ggtgggcgcg gcggcggcgg cgccctcttc tccctttgcg tcgcagctgc tggagccgcc   14220
gtacgtgcct ccgcgctacc tgcggcctac ggggggagga aacagcatcc gttactcgga   14280
gctggcgccc ctgttcgaca ccacccgggt gtacctggtg acaacaagt cggcggacgt    14340
ggcctccctg aactaccaga acgaccacag caatttttg accacggtca tccagaacaa    14400
tgactacagc ccgagcgagg ccagcaccca gaccatcaat ctggatgacc ggtcgcactg   14460
gggcggcgac ctgaaaacca tcctgcacac caacatgccc aacgtgaacg agttcatgtt   14520
caccaataag ttcaaggcgc gggtgatggt gtcgcgctcg cacaccaagg aagaccgggt   14580
ggagctgaag tacgagtggg tggagttcga gctgccagag ggcaactact ccgagaccat   14640
gaccattgac ctgatgaaca acgcgatcgt ggagcactat ctgaaagtgg gcaggcagaa   14700
cggggtcctg gagagcgaca tcgggtcaa gttcgacacc aggaacttcc gcctggggct    14760
ggaccccgtg accgggctgg ttatgcccgg ggtgtacacc aacgaggcct tccatcccga   14820
catcatcctg ctgcccggct gcggggtgga cttcacttac agccgcctga gcaacctcct   14880
gggcatccgc aagcggcagc ccttccagga gggcttcagg atcacctacg aggacctgga   14940
gggggggcaac atccccgcgc tcctcgatgt ggaggcctac caggatagct tgaaggaaaa   15000
tgaggcggga caggaggata ccgccccgc cgcctccgcc gccgccgagc agggcgagga   15060
tgctgctgac accgcggccg cggacggggc agaggccgac cccgctatgg tggtggaggc   15120
tcccgagcag gaggaggaca tgaatgacag tgccggtgcg cggagacacct tcgtcacccg    15180
gggggaggaa aagcaagcgg aggccgaggc cgcggccgag aaaagcaac tggcggcagc    15240
agcggcggcg cgcgcgttgg ccgcggcgga ggctgagtct gaggggacca gcccgccaa    15300
ggagcccgtg attaagcccc tgaccgaaga tagcaagaag cgcagttaca acctgctcaa   15360
ggacagcacc aacaccgcgt accgcagctg gtacctggcc tacaactacg gcgacccgtc   15420
gacggggggtg cgctcctgga ccctgctgtg cacgccggac gtgacctgcg gctcggagca   15480
ggtgtactgg tcgctgcccg acatgatgca agacccgtg accttccgct ccacgcggca    15540
ggtcagcaac ttcccggtgg tgggcgccga gctgctgccc gtgcactcca agagcttcta   15600
caacgaccag gccgtctact cccagctcat ccgccagttc acctctctga cccacgtgtt   15660
caatcgcttt cctgagaacc agattctggc gcgcccgccc gcccccacca tcaccaccgt   15720
cagtgaaaac gttcctgctc tcacagatca cgggacgcta ccgctgcgca acagcatcgg   15780
aggagtccag cgagtgaccg ttactgacgc cagacgccgc acctgccct acgtttacaa   15840
ggccttgggc atagtctcgc gcgcgtcct ttccagccgc acttttgag caacaccacc     15900
atcatgtcca tcctgatctc acccagcaat aactccggct ggggactgct gcgcgcgccc   15960
agcaagatgt tcgagggggc gaggaagcgt tccgagcagc accccgtgcg cgtgcgcggg   16020
cacttccgcg cccctggg agcgcacaaa cgcggccgcg cggggcgcac caccgtggac     16080
gacgccatcg actcggtggt ggagcaggcg cgcaactaca ggcccgcggt ctctaccgtg   16140
gacgcggcca tccagaccgt ggtgcggggc gcgcggcggg acgccaagct gaagagccgc   16200
cggaagcgcg tggcccgccg ccaccgccgc cgacccgggg ccgccgccaa acgcgccgcc   16260
gcggccctgc ttcgccgggc caagcgcacg gccgccgcg ccgccatgag gccgcgcgc     16320
cgcttggccg ccggcatcac cgccgccacc atggccccc gtacccgaag acgcgcggcc   16380
gccgccgccg ccgccgccat cagtgacatg ccagcaggc gccggggcaa cgtgtactgg   16440
gtgcgcgact cggtgaccgg cacgcgcgtg ccgtgcgct tccgcccccc gcggacttga   16500
gatgatgtga aaaaacaaca ctgagtctcc tgctgttgtg tgtatcccag cggcggcggc   16560
```

```
gcgcgcagcg tcatgtccaa gcgcaaaatc aaagaagaga tgctccaggt cgtcgcgccg    16620
gagatctatg ggcccccgaa gaaggaagag caggattcga agccccgcaa gataaagcgg    16680
gtcaaaaaga aaagaaaga tgatgacgat gccgatgggg aggtggagtt cctgcgcgcc     16740
acggcgccca ggcgcccggt gcagtggaag ggccggcgcg taaagcgcgt cctgcgcccc    16800
ggcaccgcgg tggtcttcac gcccggcgag cgctccaccc ggactttcaa gcgcgtctat    16860
gacgaggtgt acggcgacga agacctgctg gagcaggcca acgagcgctt cggagagttt    16920
gcttacggga agcgtcagcg ggcgctgggg aaggaggacc tgctggcgct gccgctggac    16980
cagggcaacc ccaccccag tctgaagccc gtgaccctgc agcaggtgct gccgagcagc     17040
gcaccctccg aggcgaagcg gggtctgaag cgcgagggcg gcgacctggc gcccaccgtg    17100
cagctcatgg tgcccaagcg gcagaggctg gaggatgtgc tggagaaaat gaaagtagac    17160
cccggtctgc agccggacat cagggtccgc cccatcaagc aggtggcgcc gggcctcggc    17220
gtgcagaccg tggacgtggt catccccacc ggcaactccc ccgccgccgc caccactacc    17280
gctgcctcca cggacatgga gacacagacc gatcccgccg cagccgcagc cgcagccgcc    17340
gccgcgacct cctcggcgga ggtgcagacg gaccccctggc tgccgccggc gatgtcagct   17400
ccccgcgcgc gtcgcgggcg caggaagtac ggcgccgcca acgcgctcct gcccgagtac    17460
gccttgcatc cttccatcgc gcccaccccc ggctaccgag gctataccta ccgcccgcga    17520
agagccaagg gttccaccccg ccgtccccgc cgacgcgccg ccgccaccac ccgccgccgc    17580
cgccgcagac gccagcccgc actggctcca gtctccgtga ggaaagtggc gcgcgacgga    17640
cacaccctgg tgctgcccag ggcgcgctac caccccagca tcgtttaaaa gcctgttgtg    17700
gttcttgcag atatggccct cacttgccgc ctccgtttcc cggtgccggg ataccgagga    17760
ggaagatcgc gccgcaggag gggtctggcc ggccgcggcc tgagcggagg cagccgccgc    17820
gcgcaccggc ggcgacgcgc caccagccga cgcatgcgcg gcggggtgct gcccctgtta    17880 atcccctga tcgccgcggc gatcggcgcc gtgcccggga tcgcctccgt ggccttgcaa     17940
gcgtcccaga ggcattgaca gacttgcaaa cttgcaaata tggaaaaaaa aaccccaata    18000
aaaaagtcta gactctcacg ctcgcttggt cctgtgacta ttttgtagaa tggaagacat    18060
caactttgcg tcgctggccc cgcgtcacgg ctcgcgcccg ttcctgggac actggaacga    18120
tatcggcacc agcaacatga gcggtggcgc cttcagttgg ggctctctgt ggagcggcat    18180
taaaagtatc gggtctgccg ttaaaaatta cggctcccgg gcctggaaca gcagcacggg    18240
ccagatgttg agagacaagt tgaaagagca gaacttccag cagaaggtgg tggagggcct    18300
ggcctccggc atcaacgggg tggtggacct ggccaaccag gccgtgcaga ataagatcaa    18360
cagcagactg gaccccggc cgccggtgga ggaggtgccg ccggcgctgg agacggtgtc     18420
ccccgatggg cgtggcgaga agcgcccgcg gcccgatagg gaagagacca ctctggtcac    18480
gcagaccgat gagccgcccc cgtatgagga ggccctgaag caaggtctgc ccaccacgcg    18540
gcccatcgcg cccatggcca ccggggtggt gggccgccac accccgccca cgctggactt    18600
gcctccgccc gccgatgtgc cgcagcagca gaaggcggca cagccgggcc cgcccgcgac    18660
cgcctcccgt tcctccgccg gtcctctgcg ccgcgcggcc agcggccccc gcgggggggt    18720
cgcgaggcac ggcaactggc agagcacgct gaacagcatc gtgggtctgg gggtgcggtc    18780
cgtgaagcgc cgccgatgct actgaatagc ttagctaacg tgtttgtatgt gtgtatgcgc    18840 cctatgtcgc cgccagagga gctgctgagt cgccgccgtt cgcgcgccca ccaccaccgc    18900
```

```
cactccgccc ctcaagatgg cgaccccatc gatgatgccg cagtggtcgt acatgcacat   18960
ctcgggccag gacgcctcgg agtacctgag ccccgggctg gtgcagttcg cccgcgccac   19020
cgagagctac ttcagcctga gtaacaagtt taggaacccc acggtggcgc ccacgcacga   19080
tgtgaccacc gaccggtctc agcgcctgac gctgcggttc attcccgtgg accgcgagga   19140
caccgcgtac tcgtacaagg cgcggttcac cctggccgtg ggcgacaacc gcgtgctgga   19200
catggcctcc acctactttg acatccgcgg ggtgctggac cggggtccca ctttcaagcc   19260
ctactctggc accgcctaca actccctggc ccccaagggc gctcccaact cctgcgagtg   19320
ggagcaagag gaaactcagg cagttgaaga agcagcagaa gaggaagaag aagatgctga   19380
cggtcaagct gaggaagagc aagcagctac caaaaagact catgtatatg ctcaggctcc   19440
cctttctggc gaaaaaatta gtaaagatgg tctgcaaata ggaacggacg ctacagctac   19500
agaacaaaaa cctatttatg cagaccctac attccagccc gaaccccaaa tcggggagtc   19560
ccagtggaat gaggcagatg ctacagtcgc cggcggtaga gtgctaaaga aatctactcc   19620
catgaaacca tgctatggtt cctatgcaag acccacaaat gctaatggag gtcagggtgt   19680
actaacggca aatgcccagg acagctagaa tctcaggtt gaaatgcaat tcttttcaac   19740
ttctgaaaac gcccgtaacg aggctaacaa cattcagccc aaattggtgc tgtatagtaa   19800
ggatgtgcac atggagaccc cggatacgca cctttcttac aagcccgcaa aaagcgatga   19860
caattcaaaa atcatgctgg gtcagcagtc catgcccaac agacctaatt acatcggctt   19920
cagagacaac tttatcggcc tcatgtatta caatagcact ggcaacatgg gagtgcttgc   19980
aggtcaggcc tctcagttga atgcagtggt ggacttgcaa gacagaaaca cagaactgtc   20040
ctaccagctc ttgcttgatt ccatgggtga cagaaccaga tacttttcca tgtggaatca   20100
ggcagtggac agttatgacc agatgttag aattattgaa aatcatggaa ctgaagacga   20160
gctccccaac tattgtttcc ctctgggtgg catagggta actgacactt accaggctgt   20220
taaaaccaac aatggcaata acgggggcca ggtgacttgg acaaaagatg aaactttgc   20280
agatcgcaat gaaatagggg tgggaaacaa tttcgctatg gagatcaacc tcagtgccaa   20340
cctgtggaga aacttcctgt actccaacgt ggcgctgtac ctaccagaca agcttaagta   20400
caacccctcc aatgtggaca tctctgacaa ccccaacacc tacgattaca tgaacaagcg   20460
agtggtggcc ccggggctgg tggactgcta catcaacctg ggcgcgcgct ggtcgctgga   20520
ctacatggac aacgtcaacc ccttcaacca ccaccgcaat gcgggcctgc gctaccgctc   20580
catgctcctg ggcaacgggc gctacgtgcc cttccacatc caggtgcccc agaagttctt   20640
tgccatcaag aacctcctcc tcctgccggg ctcctacacc tacgagtgga acttcaggaa   20700
ggatgtcaac atggtcctcc agagctctct gggtaacgat ctcagggtgg acggggccag   20760
catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct accccatacc cgccaacgcc accaacgtcc ccatctccat   20940
cccctcgcgc aactgggcgg ccttccgcgg ctgggccttc acccgcctca agaccaagga   21000
gacccctcc ctgggctcgg attcgaccc ctactacacc tactcgggct ccattcccta   21060
cctggacggc accttctacc tcaaccacac tttcaagaag gtctcggtca ccttcgactc   21120
ctcggtcagc tggccgggca acgaccgtct gctcacccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
```

```
caaggacagg atgtactcct tcttcaggaa cttccagccc atgagccggc aggtggtgga   21360
ccagaccaag tacaaggact accaggaggt gggcatcatc caccagcaca caactcggg    21420
cttcgtgggc tacctcgccc ccaccatgcg cgagggacag gcctaccccg ccaacttccc   21480
ctatccgctc ataggcaaga ccgcggtcga cagcatcacc cagaaaaagt tcctctgcga   21540
ccgcaccctc tggcgcatcc ccttctccag caacttcatg tccatgggtg cgctctcgga   21600
cctgggccag aacttgctct acgccaactc cgcccacgcc ctcgacatga ccttcgaggt   21660
cgaccccatg gacgagccca cccttctcta tgttctgttc gaagtctttg acgtggtccg   21720
ggtccaccag ccgcaccgcg gcgtcatcga gaccgtgtac ctgcgtacgc ccttctcggc   21780
cggcaacgcc accacctaaa gaagcaagcc gcagtcatcg ccgcctgcat gccgtcgggt   21840
tccaccgagc aagagctcag ggccatcgtc agagacctgg gatgcgggcc ctattttttg   21900
ggcaccttcg acaagcgctt ccctggcttt gtctccccac acaagctggc ctgcgccatc   21960
gtcaacacgg ccgccgcga gaccgggggc gtgcactggc tggccttcgc ctggaacccg    22020
cgctccaaaa catgcttcct cttttgacccc ttcggctttt cggaccagcg gctcaagcaa  22080
atctacgagt tcgagtacga gggcttgctg cgtcgcagcg ccatcgcctc ctcgcccgac   22140
cgctgcgtca ccctcgaaaa gtccacccag accgtgcagg ggcccgactc ggccgcctgc   22200
ggtctcttct gctgcatgtt tctgcacgcc tttgtgcact ggcctcagag tcccatggac   22260
cgcaaccccca ccatgaactt gctgacgggg gtgcccaact ccatgctcca gagccccag    22320
gtcgagccca ccctgcgccg caaccaggag cagctctaca gcttcctgga gcgccactcg   22380
ccttacttcc gccgccacag cgcacagatc aggagggcca cctccttctg ccacttgcaa   22440
gagatgcaag aagggtaata acgatgtaca cactttttt ctcaataaat ggcatctttt    22500
tatttataca agctctctgg ggtattcatt tcccaccacc acccgccgtt gtcgccatct   22560
ggctctattt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcgggc   22740
gccgagatct tgaagtcgca gttggggccg ccgccctgcg cgcgcgagtt gcggtacacc   22800
gggttgcagc actggaacac caacagcgcc gggtgcttca cgctggccag cacgctgcgg   22860
tcggagatca gctcggcgtc caggtcctcc gcgttgctca gcgcgaacgg ggtcatcttg   22920
ggcacttgcc gccccaggaa gggcgcgtgc cccggtttcg agttgcagtc gcagcgcagc   22980
gggatcagca ggtgcccgtg cccggactcg gcgttgggt acagcgcgcg catgaaggcc    23040
tgcatctggc ggaaggccat ctgggccttg gcgccctccg agaagaacat gccgcaggac   23100
ttgcccgaga actggtttgc ggggcagctg gcgtcgtgca ggcagcagcg cgcgtcggtg   23160
ttggcgatct gcaccacgtt gcgcccccac cggttcttca cgatcttggc cttggacgat   23220
tgctccttca gcgcgcgctg cccgttctcg ctggtcacat ccatctcgat cacatgttcc   23280
ttgttcacca tgctgctgcc gtgcagacac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
```

```
acggggttct tcaccatcac cgtggccgcc gcctccgccg cgctttcgct ttccgccccg    23700
ctgttctctt cctcttcctc ctcttcctcg ccgccgccca ctcgcagccc ccgcaccacg    23760
gggtcgtctt cctgcaggcg ctgcaccttg cgcttgccgt tgcgcccctg cttgatgcgc    23820
acgggcgggt tgctgaagcc caccatcacc agcgcggcct cttcttgctc gtcctcgctg    23880
tccagaatga cctccgggga gggggggttg gtcatcctca gtaccgaggc acgcttcttt    23940
ttcttcctgg gggcgttcgc cagctccgcg gctgcggccg ctgccgaggt cgaaggccga    24000
gggctgggcg tgcgcggcac cagcgcgtcc tgcgagccgt cctcgtcctc ctcggactcg    24060
agacggaggc gggcccgctt cttcggggc gcgcggggcg gcggaggcgg cggcggcgac    24120
ggagacgggg acgagacatc gtccagggtg ggtggacggc gggccgcgcc gcgtccgcgc    24180
tcggggtgg tctcgcgctg gtcctcttcc cgactggcca tctcccactg ctccttctcc    24240
tataggcaga aagagatcat ggagtctctc atgcgagtcg agaaggagga ggacagccta    24300
accgccccct ctgagccctc caccaccgcc gccaccaccg ccaatgccgc cgcggacgac    24360
gcgcccaccg agaccaccgc cagtaccacc ctccccagcg acgcacccccc gctcgagaat    24420
gaagtgctga tcgagcagga cccgggtttt gtgagcggag aggaggatga ggtggatgag    24480
aaggagaagg aggaggtcgc cgcctcagtg ccaaaagagg ataaaaagca agaccaggac    24540
gacgcagata aggatgagac agcagtcggg cggggaacg gaagccatga tgctgatgac    24600
ggctacctag acgtgggaga cgacgtgctg cttaagcacc tgcaccgcca gtgcgtcatc    24660
gtctgcgacg cgctgcagga gcgctgcgaa gtgcccctgg acgtggcgga ggtcagccgc    24720
gcctacgagc ggcacctctt cgcgccgcac gtgcccccca agcgccggga gaacggcacc    24780
tgcgagccca cccgcgtctc aacttctac ccggtcttcg cggtacccga ggtgctggcc    24840
acctaccaca tctttttcca aaactgcaag atcccctct cctgccgcgc caaccgcacc    24900
ccgcgccgaca aaaccctgac cctgcggcag ggcgcccaca tacctgatat cgcctctctg    24960
gaggaagtgc ccaagatctt cgagggtctc ggtcgcgacg agaaacgggc ggcgaacgct    25020
ctgcacggag acagcgaaaa cgagagtcac tcggggtgc tggtggagct cgagggcgac    25080
aacgcgcgc tggccgtact caagcgcagc atagaggtca cccactttgc ctacccggcg    25140
ctcaacctgc cccccaaggt catgagtgtg gtcatgggcg agctcatcat cgccgcgcc    25200
cagcccctgg ccgcggatgc aaacttgcaa gagtcctccg aggaaggcct gcccgcggtc    25260
agcgacgagc agctggcgcg ctggctggag accgcgacc ccgcgcagct ggaggagcgg    25320
cgcaagctca tgatgccgc ggtgctggtc accgtggagc tcgagtgtct gcagcgcttc    25380
ttcgcggacc ccgagatgca gcgcaagctc gaggagaccc tgcactacac cttccgccag    25440
ggctacgtgc gccaggcctg caagatctcc aacgtggagc tctgcaacct ggtctcctac    25500
ctgggcatcc tgcacgagaa ccgcctcggg cagaacgtcc tgcactccac cctcaaaggg    25560
gaggcgcgcc gcgactacat ccgcgactgc gcctacctct cctctgcta cacctggcag    25620
acggccatgg ggtctggca gcagtgcctg gaggagcgca acctcaagga gctggaaaag    25680
ctcctcaagc gcaccctcag ggacctctgg acgggcttca acgagcgctc ggtggccgcc    25740
gcgctggcg acatcatctt tcccgagcgc ctgctcaaga ccctgcagca gggcctgccc    25800
gacttcacca gccagagcat gctgcagaac ttcaggactt tcatcctgga gcgctcgggc    25860
atcctgccgg ccacttgctg cgcgctgccc agcgacttcg tgcccatcaa gtacagggag    25920
tgcccgccgc cgcctctgggg ccactgctac ctcttccagc tggccaacta cctgcctac    25980
cactcggacc tcatggaaga cgtgagcggc gagggcctgc tcgagtgcca ctgccgctgc    26040
```

```
aacctctgca cgccccaccg ctctctagtc tgcaacccgc agctgctcag cgagagtcag   26100
attatcggta ccttcgagct gcagggtccc tcgcctgacg agaagtccgc ggctccaggg   26160
ctgaaactca ctccggggct gtggacttcc gcctacctac gcaaatttgt acctgaggac   26220
taccacgccc acgagatcag gttctacgaa gaccaatccc gcccgcccaa ggcggagctc   26280
accgcctgcg tcatcaccca ggggcacatc ctgggccaat tgcaagccat caacaaagcc   26340
cgccgagagt tcttgctgaa aaagggtcgg ggggtgtacc tggacccca gtccggcgag   26400
gagctaaacc cgctacccc gccgccgccc cagcagcggg accttgcttc ccaggatggc   26460
acccagaaag aagcagcagc cgccgccgcc gccgcagcca tacatgcttc tggaggaaga   26520
ggaggaggac tgggacagtc aggcagagga ggtttcggac gaggagcagg aggagatgat   26580
ggaagactgg gaggaggaca gcagcctaga cgaggaagct tcagaggccg aagaggtggc   26640
agacgcaaca ccatcgccct cggtcgcagc cccctcgccg gggcccctga atcctccga   26700
acccagcacc agcgctataa cctccgctcc tccggcgccg cgccacccg cccgcagacc   26760
caaccgtaga tgggacacca caggaaccgg ggtcggtaag tccaagtgcc cgccgccgcc   26820
accgcagcag cagcagcagc agcgccaggg ctaccgctcg tggcgcgggc acaagaacgc   26880
catagtcgcc tgcttgcaag actgcggggg caacatctct ttcgcccgcc gcttcctgct   26940
attccaccac ggggtcgcct ttccccgcaa tgtcctgcat tactaccgtc atctctacag   27000
cccctactgc agcggcgacc cagaggcggc agcggcagcc acagcggcga ccaccaccta   27060
ggaagatatc ctccgcgggc aagacagcgg cagcagcggc caggagaccc gcggcagcag   27120
cggcgggagc ggtgggcgca ctgcgcctct cgcccaacga accctctcg acccgggagc   27180
tcagacacag gatcttcccc actttgtatg ccatcttcca acagagcaga ggccaggagc   27240
aggagctgaa aataaaaaac agatctctgc gctccctcac ccgcagctgt ctgtatcaca   27300
aaagcgaaga tcagcttcgg cgcacgctgg aggacgcgga ggcactcttc agcaaatact   27360
gcgcgctcac tcttaaagac tagctccgcg cccttctcga atttaggcgg gagaaaacta   27420
cgtcatcgcc ggccgccgcc cagcccgccc agccgagatg agcaaagaga ttcccacgcc   27480
atacatgtgg agctaccagc cgcagatggg actcgcggcg ggagcggccc aggactactc   27540
cacccgcatg aactacatga gcgcgggacc ccacatgatc tcacaggtca acgggatccg   27600
cgcccagcga aaccaaatac tgctggaaca ggcggccatc accgccacgc cccgccataa   27660
tctcaacccc cgaaattggc ccgccgccct cgtgtaccag gaaacccct ccgccaccac   27720
cgtactactt ccgcgtgacg cccaggccga agtccagatg actaactcag gggcgcagct   27780
cgcgggcggc tttcgtcacg gggcgcggcc gctccgacca ggtataagac acctgatgat   27840
cagaggccga ggtatccagc tcaacgacga gtcggtgagc tcttcgctcg gtctccgtcc   27900
ggacggaact ttccagctcg ccggatccgg ccgctcttcg ttcacgcccc gccaggcgta   27960
cctgactctg cagacctcgt cctcggagcc ccgctccggc ggcatcggaa ccctccagtt   28020
cgtggaggag ttcgtgccct cggtctactt caacccctcc tcgggacctc ccggacgcta   28080
ccccgaccag ttcattccga actttgacgc ggtgaaggac tcggcggacg gctacgactg   28140
aatgtcaggt gtcgaggcag agcagcttcg cctgagacac ctcgagcact gccgccgcca   28200
caagtgcttc gcccgcggtt ctggtgagtt ctgctacttt cagctacccg aggagcatac   28260
cgaggggccg gcgcacggcg tccgcctgac cacccagggc gaggttacct gttccctcat   28320
ccgggagttt accctccgtc ccctgctagt ggagcgggag cggggtccct gtgtcctaac   28380
```

```
tatcgcctgc aactgcccta accctggatt acatcaagat ctttgctgtc atctctgtgc  28440
tgagtttaat aaacgctgag atcagaatct actggggctc ctgtcgccat cctgtgaacg  28500
ccaccgtctt cacccacccc gaccaggccc aggcgaacct cacctgcggt ctgcatcgga  28560
gggccaagaa gtacctcacc tggtacttca acggcacccc ctttgtggtt tacaacagct  28620
tcgacgggga cggagtctcc ctgaaagacc agctctccgg tctcagctac tccatccaca  28680
agaacaccac cctccaactc ttccctccct acctgccggg aacctacgag tgcgtcaccg  28740
gccgctgcac ccacctcacc cgcctgatcg taaaccagag ctttccggga acagataact  28800
ccctcttccc cagaacagga ggtgagctca ggaaactccc cggggaccag ggcggagacg  28860
taccttcgac ccttgtgggg ttaggatttt ttattaccgg gttgctggct cttttaatca  28920
aagtttcctt gagatttgtt ctttccttct acgtgtatga acacctcaac ctccaataac  28980
tctacccttt cttcggaatc aggtgacttc tctgaaatcg ggcttggtgt gctgcttact  29040
ctgttgattt ttttccttat catactcagc cttctgtgcc tcaggctcgc cgcctgctgc  29100
gcacacatct atatctactg ctggttgctc aagtgcaggg gtcgccaccc aagatgaaca  29160
ggtacatggt cctatcgatc ctaggcctgc tggccctggc ggcctgcagc gccgccaaaa  29220
aagagattac ctttgaggag cccgcttgca atgtaacttt caagcccgag ggtgaccaat  29280
gcaccaccct cgtcaaatgc gttaccaatc atgagaggct gcgcatcgac tacaaaaaca  29340
aaactggcca gtttgcggtc tatagtgtgt ttacgcccgg agacccctct aactactctg  29400
tcaccgtctt ccagggcgga cagtctaaga tattcaatta cactttccct ttttatgagt  29460
tatgcgatgc ggtcatgtac atgtcaaaac agtacaacct gtggcctccc tctccccagg  29520
cgtgtgtgga aaatactggg tcttactgct gtatggcttt cgcaatcact acgctcgctc  29580
taatctgcac ggtgctatac ataaaattca ggcagaggcg aatctttatc gatgaaagaa  29640
aaatgccttg atcgctaaca ccggctttct atctgcagaa tgaatgcaat cacctcccta  29700
ctaatcacca ccaccctcct tgcgattgcc catgggttga cacgaatcga agtgccagtg  29760
gggtccaatg tcaccatggt gggccccgcc ggcaattcca ccctcatgtg ggaaaaattt  29820
gtccgcaatc aatgggttca tttctgctct aaccgaatca gtatcaagcc cagagccatc  29880
tgcgatgggc aaaatctaac tctgatcaat gtgcaaatga tggatgctgg gtactattac  29940
gggcagcggg gagaaatcat taattactgg cgaccccaca aggactacat gctgcatgta  30000
gtcgaggcac ttcccactac cacccccact accacctctc ccaccaccac caccactact  30060
actactacta ctactactac tactactacc actaccgctg cccgccatac ccgcaaaagc  30120
accatgatta gcacaaagcc ccctcgtgct cactcccacg ccggcgggcc catcggtgcg  30180
acctcagaaa ccaccgagct ttgcttctgc caatgcacta acgccagcgc tcatgaactg  30240
ttcgacctgg agaatgagga tgtccagcag agctccgctt gcctgaccca ggaggctgtg  30300
gagcccgttg ccctgaagca gatcggtgat tcaataattg actcttcttc ttttgccact  30360
cccgaatacc ctcccgattc tactttccac atcacgggta ccaaagaccc taacctctct  30420
ttctacctga tgctgctgct ctgtatctct gtggtctctt ccgcgctgat gttactgggg  30480
atgttctgct gcctgatctg ccgcagaaag agaaaagctc gctctcaggg ccaaccactg  30540
atgcccttcc cctaccccccc ggattttgca gataacaaga tatgagctcg ctgctgacac  30600
taaccgcttt actagcctgc gctctaaccc ttgtcgcttg cgactcgaga ttccacaatg  30660
tcacagctgt ggcaggagaa aatgttactt tcaactccac ggccgatacc cagtggtcgt  30720
ggagtggctc aggtagctac ttaactatct gcaatagctc cacttccccc ggcatatccc  30780
```

```
caaccaagta ccaatgcaat gccagcctgt tcaccctcat caacgcttcc accctggaca   30840
atggactcta tgtaggctat gtacccttttg gtgggcaagg aaagacccac gcttacaacc   30900
```



```
caaccaagta ccaatgcaat gccagcctgt tcaccctcat caacgcttcc accctggaca   30840
atggactcta tgtaggctat gtacccttttg gtgggcaagg aaagacccac gcttacaacc   30900
tggaagttcg ccagcccaga accactaccc aagcttctcc caccaccacc accaccacca   30960
ccatcaccag cagcagcagc agcagcagcc acagcagcag cagcagatta ttgactttgg   31020
ttttggccag ctcatctgcc gctacccagg ccatctacag ctctgtgccc gaaaccactc   31080
agatccaccg cccagaaacg accaccgcca ccaccctaca cacctccagc gatcagatgc   31140
cgaccaacat cacccccttg gctcttcaaa tgggacttac aagcccccact ccaaaaccag   31200
tggatgcggc cgaggtctcc gccctcgtca atgactgggc ggggctggga atgtggtggt   31260
tcgccatagg catgatggcg ctctgcctgc ttctgctctg gctcatctgc tgcctccacc   31320
gcaggcgagc cagaccccccc atctatagac ccatcattgt cctgaacccc gataatgatg   31380
ggatccatag attggatggc ctgaaaaacc tacttttttc ttttacagta tgataaattg   31440
agacatgcct cgcattttct tgtacatgtt ccttctccca ccttttctgg ggtgttctac   31500
gctggccgct gtgtctcacc tggaggtaga ctgcctctca cccttcactg tctacctgct   31560
ttacggattg gtcaccctca ctctcatctg cagcctaatc acagtaatca tcgccttcat   31620
ccagtgcatt gattacatct gtgtgcgcct cgcatacttc agacaccacc cgcagtaccg   31680
agacaggaac attgcccaac ttctaagact gctctaatca tgcataagac tgtgatctgc   31740
cttctgatcc tctgcatcct gcccaccctc acctcctgcc agtacaccac aaaatctccg   31800
cgcaaaagac atgcctcctg ccgcttcacc caactgtgga atatacccaa atgctacaac   31860
gaaaagagcg agctctccga agcttggctg tatgggtgtca tctgtgtctt agttttctgc   31920
agcactgtct ttgccctcat aatctacccc tactttgatt tgggatggaa cgcgatcgat   31980
gccatgaatt accccaccctt tcccgcaccc gagataattc cactgcgaca agttgtaccc   32040
gttgtcgtta atcaacgccc cccatcccct acgcccactg aaatcagcta ctttaaccta   32100
acaggcggag atgactgacg ccctagatct agaaatggac ggcatcagta ccgagcagcg   32160
tctcctagag aggcgcaggc aggcggctga gcaagagcgc ctcaatcagg agctccgaga   32220
tctcgttaac ctgcaccagt gcaaaagagg catctttttgt ctggtaaagc aggccaaagt   32280
cacctacgag aagaccggca acagccaccg cctcagttac aaattgccca cccagcgcca   32340
gaagctggtg ctcatggtgg gtgagaatcc catcaccgtc acccagcact cggtagagac   32400
cgaggggtgt ctgcactccc cctgtcgggg tccagaagac ctctgcaccc tggtaaagac   32460
cctgtgcggt ctcagagatt tagtcccctt taactaatca aacactggaa tcaataaaaa   32520
gaatcactta cttaaaatca gacagcaggt ctctgtccag tttattcagc agcacctcct   32580
tcccctcctc ccaactctgg tactccaaac gccttctggc ggcaaacttc ctccacaccc   32640
tgaagggaat gtcagattct tgctcctgtc cctccgcacc cactatcttc atgttgttgc   32700
agatgaagcg caccaaaacg tctgacgaga gcttcaaccc cgtgtacccc tatgacacgg   32760
aaagcggccc tccctccgtc ccttttcctca cccctcccctt cgtgtctccc gatggattcc   32820
aagaaagtcc cccgggggtc ctgtctctga acctggccga gccctggtc acttcccacg   32880
gcatgctcgc cctgaaaatg ggaagtggcc tctccctgga cgacgctggc aacctcacct   32940
ctcaagatat caccaccgct agccctcccc tcaaaaaaac caagaccaac ctcagcctag   33000
aaacctcatc cccctaact gtgagcacct caggcgccct caccgtagca gccgccgctc   33060
ccctggcggt ggccggcacc tccctcacca tgcaatcaga ggccccccctg acagtacagg   33120
```

```
atgcaaaact cacccctggcc accaaaggcc ccctgaccgt gtctgaaggc aaactggcct    33180
tgcaaacatc ggccccgctg acggccgctg acagcagcac cctcacagtc agtgccacac    33240
caccccttag cacaagcaat ggcagcttgg gtattgacat gcaagccccc atttacacca    33300
ccaatggaaa actaggactt aactttggcg ctcccctgca tgtggtagac agcctaaatg    33360
cactgactgt agttactggc caaggtctta cgataaacgg aacagcccta caaactagag    33420
tctcaggtgc cctcaactat gacacatcag gaaacctaga attgagagct gcaggggta    33480 tgcgagttga tgcaaatggt caacttatcc ttgatgtagc ttacccattt gatgcacaaa    33540
acaatctcag cctt aggctt ggacagggac ccctgtttgt taactctgcc cacaacttgg    33600
atgttaacta caacagaggc ctctacctgt tcacatctgg aaataccaaa aagctagaag    33660
ttaatatcaa aacagccaag ggtctcattt atgatgacac tgctatagca atcaatgcgg    33720
gtgatgggct acagtttgac tcaggctcag atacaaatcc attaaaaact aaacttggat    33780
taggactgga ttatgactcc agcagagcca taattgctaa actggaact ggcctaagct    33840 ttgacaacac aggtgccatc acagtaggca acaaaaatga tgacaagctt accttgtgga    33900
ccacaccaga cccatcccct aactgtagaa tctattcaga gaaagatgct aaattcacac    33960
ttgttttgac taaatgcggc agtcaggtgt tggccagcgt ttctgttta tctgtaaaag    34020 gtagccttgc gcccatcagt ggcacagtaa ctagtgctca gattgtcctc agatttgatg    34080
aaaatggagt tctactaagc aattcttccc ttgaccctca atactggaac tacagaaaag    34140
gtgaccttac agagggcact gcatatacca acgcagtggg atttatgccc aacctcacag    34200 cataccaaa aacacagagc caaactgcta aaagcaacat tgtaagtcag gtttacttga    34260
atggggacaa atccaaaccc atgaccctca ccattaccct caatggaact aatgaaacag    34320
gagatgccac agtaagcact tactccatgt cattctcatg gaactggaat ggaagtaatt    34380
acattaatga aacgttccaa accaactcct tcaccttctc ctacatcgcc caagaataaa    34440
aagcatgacg ctgttgattt gattcaatgt gttctgtttt tattttcaag cacaacaaaa    34500
tcattcaagt cattcttcca tcttagctta atagacacag tagcttaata gacccagtag    34560
tgcaaagccc cattctagct tatagatcag acagtgataa ttaaccacca ccaccaccat    34620 acctttgat tcaggaaatc atgatcatca caggatccta gtcttcaggc cgcccctcc    34680 ctcccaagac acagaataca cagtcctctc ccccgactg gctttaaata caccatctg    34740 gttggtcaca gacatgttct taggggttat attccacacg gtctcctgcc gcgccaggcg    34800
ctcgtcggtg atgttgataa actctcccgg cagctcgctc aagttcacgt cgctgtccag    34860
cggctgaacc tccggctgac gcgataactg tgcgaccggc tgctggacga acggaggccg    34920
cgcctacaag ggggtagagt cataatcctc ggtcaggata gggcggtgat gcagcagcag    34980
cgagcgaaac atctgctgcc gccgccgctc cgtccggcag gaaaacaaca cgccggtggt    35040
ctcctccgcg ataatccgca ccgcccgcag catcagcttc ctcgttctcc gcgcgcagca    35100 cctcacccctt atctcgctca aatcggcgca gtaggtacag cacagcacca cgatgttatt    35160
catgatccca cagtgcaggg cgctgtatcc aaagctcatg ccgggaacca ccgcccccac    35220
gtggccatcg taccacaagc gcacgtaaat caagtgtcga cccctcatga acgcgctgga    35280
cacaaacatt acttccttgg gcatgttgta attcaccacc tcccggtacc agataaacct    35340
ctggttgaac agggcacctt ccaccaccat cctgaaccaa gaggccagaa cctgcccacc    35400
ggctatgcac tgcagggaac ccgggttgga acaatgacaa tgcagactcc aaggctcgta    35460
accgtggatc atccggctgc tgaaggcatc gatgttggca caacacagac acacgtgcat    35520
```

```
gcactttctc atgattagca gctcttccct cgtcaggatc atatcccaag gaataaccca   35580
ttcttgaatc aacgtaaaac ccacacagca gggaaggcct cgcacataac tcacgttgtg   35640
catggtcagc gtgttgcatt ccggaaacag cggatgatcc tccagtatcg aggcgcgggt   35700
ctccttctca cagggaggta aagggtccct gctgtacgga ctgcgccggg acgaccgaga   35760
tcgtgttgag cgtagtgtca tggaaagggg aacgccggac gtggtcatac ttcttgaagc   35820
agaaccaggt tcgcgcgtgg caggcctcct tgcgtctgcg gtctcgccgt ctagctcgct   35880
ccgtgtgata gttgtagtac agccactccc gcagagcgtc gaggcgcacc ctggcttccg   35940
gatctatgta gactccgtct tgcaccgcgg ccctgataat atccaccacc gtagaataag   36000
caacacccag ccaagcaata cactcgctct gcgagcggca gacaggagga gcgggcagag   36060
atgggagaac catgataaaa aacttttttt aaagaatatt ttccaattct tcgaaagtaa   36120
gatctatcaa gtggcagcgc tcccctccac tggcgcggtc aaactctacg gccaaagcac   36180
agacaacggc atttctaaga tgttccttaa tggcgtccaa aagacacacc gctctcaagt   36240
tgcagtaaac tatgaatgaa aacccatccg gctgattttc caatatagac gcgccggcag   36300
cgtccaccaa acccagataa ttttcttctc tccagcggtt tacgatctgt ctaagcaaat   36360
cccttatatc aagtccgacc atgccaaaaa tctgctcaag agcgccctcc accttcatgt   36420
acaagcagcg catcatgatt gcaaaaattc aggttcttca gagacctgta taagattcaa   36480
aatgggaaca ttaacaaaaa ttcctctgtc gcgcagatcc cttcgcaggg caagctgaac   36540
ataatcagac aggtccgaac ggaccagtga ggccaaatcc ccaccaggaa ccagatccag   36600
agaccctata ctgattatga cgcgcatact cggggctatg ctgaccagcg tagcgccgat   36660
gtaggcgtgc tgcatgggcg gcgagataaa atgcaaagtg ctggttaaaa aatcaggcaa   36720
agcctcgcgc aaaaaagcta acacatcata atcatgctca tgcaggtagt tgcaggtaag   36780
ctcaggaacc aaaacggaat aacacacgat tttcctctca aacatgactt cgcggatact   36840
gcgtaaaaca aaaattata aataaaaat taattaaata acttaaacat tggaagcctg   36900
tctcacaaca ggaaaaacca ctttaatcaa cataagacgg ccacgggca tgccggcata   36960 gccgtaaaaa aattggtccc cgtgattaac aagtaccaca gacagctccc cggtcatgtc   37020
gggggtcatc atgtgagact ctgtatacac gtctggattg tgaacatcag acaaacaaag   37080
aaatcgagcc acgtagcccg gaggtataat cacccgcagg cggaggtaca gcaaaacgac   37140
ccccatagga ggaatcacaa aattagtagg agaaaaaaat acataaacac cagaaaaacc   37200
ctgttgctga ggcaaaatag cgccctcccg atccaaaaca acataaagcg cttccacagg   37260
agcagccata acaaagaccc gagtcttacc agtaaaagaa aaaagatctc tcaacgcagc   37320
accagcacca acacttcgca gtgtaaaagg ccaagtgccg agagagtata tagaagata   37380 aaaagtgacg taaacgggca aagtccaaaa aacgcccaga aaaccgcac gcgaacctac   37440 gccccgaaac gaaagccaaa aaacactaga cactcccttc cggcgtcaac ttccgctttc   37500
ccacgctacg tcacttgccc cagtcaaaca aactacatat cccgaacttc caagtcgcca   37560
cgcccaaaac accgcctaca cctcccccgcc cgccggcccg cccccaaacc cgcctcccgc   37620
cccgcgcccc gccccgcgcc gcccatctca ttatcatatt ggcttcaatc caaaataagg   37680
tatattattg atgatggttt aaacggatcc tctagagtcg acctgcaggc atgcaagctt   37740
gagtattcta tagtgtcacc taaatagctt ggcgtaatca tggtcatagc tgtttcctgt   37800
gtgaaattgt tatccgctca caattccaca caacatacga gccggaagca taagtgtaa   37860
```

-continued

| | | | | | |
|---|---|---|---|---|---|
| agcctggggt | gcctaatgag | tgagctaact | cacattaatt | gcgttgcgct | cactgcccgc 37920 |
| tttccagtcg | ggaaacctgt | cgtgccagct | gcattaatga | atcggccaac | gcgaacccct 37980 |
| tgcggccgcc | cgggccgtcg | accaattctc | atgtttgaca | gcttatcatc | gaatttctgc 38040 |
| cattcatccg | cttattatca | cttattcagg | cgtagcaacc | aggcgtttaa | gggcaccaat 38100 |
| aactgcctta | aaaaaattac | gccccgccct | gccactcatc | gcagtactgt | tgtaattcat 38160 |
| taagcattct | gccgacatgg | aagccatcac | aaacggcatg | atgaacctga | atcgccagcg 38220 |
| gcatcagcac | cttgtcgcct | tgcgtataat | atttgcccat | ggtgaaaacg | ggggcgaaga 38280 |
| agttgtccat | attggccacg | tttaaatcaa | aactggtgaa | actcacccag | ggattggctg 38340 |
| agacgaaaaa | catattctca | ataaacccgtt | tagggaaata | ggccaggttt | tcaccgtaac 38400 |
| acgccacatc | ttgcgaatat | atgtgtagaa | actgccggaa | atcgtcgtgg | tattcactcc 38460 |
| agagcgatga | aaacgtttca | gtttgctcat | ggaaaacggt | gtaacaaggg | tgaacactat 38520 |
| cccatatcac | cagctcaccg | tctttcattg | ccatacggaa | ttccggatga | gcattcatca 38580 |
| ggcgggcaag | aatgtgaata | aaggccggat | aaaacttgtg | cttattttc | tttacggtct 38640 |
| ttaaaaggc | cgtaatatcc | agctgaacgg | tctggttata | ggtacattga | gcaactgact 38700 |
| gaaatgcctc | aaaatgttct | ttacgatgcc | attgggatat | atcaacggtg | gtatatccag 38760 |
| tgattttttt | ctccatttta | gcttccttag | ctcctgaaaa | tctcgataac | tcaaaaaata 38820 |
| cgcccggtag | tgatcttatt | tcattatggt | gaaagttgga | acctcttacg | tgccgatcaa 38880 |
| cgtctcattt | tcgccaaaag | ttggcccagg | gcttcccggt | atcaacaggg | acaccaggat 38940 |
| ttatttattc | tgcgaagtga | tcttccgtca | caggtattta | ttcgcgataa | gctcatggag 39000 |
| cggcgtaacc | gtcgcacagg | aaggacagag | aaagcgcgga | tctgggaagt | gacggacaga 39060 |
| acggtcagga | cctggattgg | ggaggcggtt | gccgccgctg | ctgctgacgg | tgtgacgttc 39120 |
| tctgttccgg | tcacaccaca | tacgttccgc | cattcctatg | cgatgcacat | gctgtatgcc 39180 |
| ggtataccgc | tgaaagttct | gcaaagcctg | atgggacata | agtccatcag | ttcaacggaa 39240 |
| gtctacacga | aggttttttgc | gctggatgtg | gctgcccggc | accgggtgca | gtttgcgatg 39300 |
| ccggagtctg | atgcgttgc | gatgctgaaa | caattatcct | gagaataaat | gccttggcct 39360 |
| ttatatggaa | atgtggaact | gagtggatat | gctgttttg | tctgttaaac | agagaagctg 39420 |
| gctgttatcc | actgagaagc | gaacgaaaca | gtcgggaaaa | tctcccatta | tcgtagagat 39480 |
| ccgcattatt | aatctcagga | gcctgtgtag | cgtttatagg | aagtagtgtt | ctgtcatgat 39540 |
| gcctgcaagc | ggtaacgaaa | acgatttgaa | tatgccttca | ggaacaatag | aaatcttcgt 39600 |
| gcggtgttac | gttgaagtgg | agcggattat | gtcagcaatg | gacagaacaa | cctaatgaac 39660 |
| acagaaccat | gatgtggtct | gtccttttac | agccagtagt | gctcgccgca | gtcgagcgac 39720 |
| agggcgaagc | cctcgagtga | gcgaggaagc | accagggaac | agcacttata | tattctgctt 39780 |
| acacacgatg | cctgaaaaaa | cttcccttgg | ggttatccac | ttatccacgg | ggatatttt 39840 |
| ataattattt | tttttatagt | ttttagatct | tctttttag | agcgccttgt | aggcctttat 39900 |
| ccatgctggt | tctagagaag | gtgttgtgac | aaattgccct | tcagtgtga | caaatcaccc 39960 |
| tcaaatgaca | gtcctgtctg | tgacaaattg | cccttaaccc | tgtgacaaat | tgccctcaga 40020 |
| agaagctgtt | ttttcacaaa | gttatccctg | cttattgact | cttttttatt | tagtgtgaca 40080 |
| atctaaaaac | ttgtcacact | tcacatggat | ctgtcatggc | ggaaacagcg | gttatcaatc 40140 |
| acaagaaacg | taaaaatagc | ccgcgaatcg | tccagtcaaa | cgacctcact | gaggcggcat 40200 |
| atagtctctc | ccgggatcaa | aaacgtatgc | tgtatctgtt | cgttgaccag | atcagaaaat 40260 |

```
ctgatggcac cctacaggaa catgacggta tctgcgagat ccatgttgct aaatatgctg   40320
aaatattcgg attgacctct gcggaagcca gtaaggatat acggcaggca ttgaagagtt   40380
tcgcggggaa ggaagtggtt ttttatcgcc ctgaagagga tgccggcgat gaaaaaggct   40440
atgaatcttt tccttggttt atcaaacgtg cgcacagtcc atccagaggg ctttacagtg   40500
tacatatcaa cccatatctc attcccttct ttatcgggtt acagaaccgg tttacgcagt   40560
ttcggcttag tgaaacaaaa gaaatcacca atccgtatgc catgcgttta tacgaatccc   40620
tgtgtcagta tcgtaagccg gatggctcag gcatcgtctc tctgaaaatc gactggatca   40680
tagagcgtta ccagctgcct caaagttacc agcgtatgcc tgacttccgc cgccgcttcc   40740
tgcaggtctg tgttaatgag atcaacagca gaactccaat gcgcctctca tacattgaga   40800
aaaagaaagg ccgccagacg actcatatcg tattttcctt ccgcgatatc acttccatga   40860
cgacaggata gtctgagggt tatctgtcac agatttgagg gtggttcgtc acatttgttc   40920
tgacctactg agggtaattt gtcacagttt tgctgtttcc ttcagcctgc atggattttc   40980
tcatactttt tgaactgtaa ttttaagga agccaaattt gagggcagtt tgtcacagtt   41040
gatttccttc tctttccctt cgtcatgtga cctgatatcg ggggtagtt cgtcatcatt   41100 gatgagggtt gattatcaca gtttattact ctgaattggc tatccgcgtg tgtacctcta   41160
cctggagttt ttcccacggt ggatatttct tcttgcgctg agcgtaagag ctatctgaca   41220
gaacagttct tctttgcttc ctcgccagtt cgctcgctat gctcggttac acggctgcgg   41280
cgagcgctag tgataataag tgactgaggt atgtgctctt cttatctcct tttgtagtgt   41340
tgctcttatt ttaaacaact ttgcggtttt ttgatgactt tgcgattttg ttgttgcttt   41400
gcagtaaatt gcaagattta ataaaaaaac gcaaagcaat gattaaagga tgttcagaat   41460
gaaactcatg gaaacactta accagtgcat aaacgctggt catgaaatga cgaaggctat   41520
cgccattgca cagtttaatg atgacagccc ggaagcgagg aaaataaccc ggcgctggag   41580
aataggtgaa gcagcggatt tagttggggt ttcttctcag gctatcagag atgccgagaa   41640
agcagggcga ctaccgcacc cggatatgga aattcgagga cgggttgagc aacgtgttgg   41700
ttatacaatt gaacaaatta atcatatgcg tgatgtgttt ggtacgcgat tgcgacgtgc   41760
tgaagacgta tttccaccgg tgatcggggt tgctgcccat aaaggtggcg tttacaaaac   41820
ctcagtttct gttcatcttg ctcaggatct ggctctgaag gggctacgtg ttttgctcgt   41880
ggaaggtaac gacccccagg gaacagcctc aatgtatcac ggatgggtac cagatcttca   41940
tattcatgca gaagacactc tcctgccttt ctatcttggg gaaaaggacg atgtcactta   42000
tgcaataaag cccacttgct ggccgggct tgacattatt ccttcctgtc tggctctgca   42060
ccgtattgaa actgagttaa tgggcaaatt tgatgaaggt aaactgccca ccgatccaca   42120
cctgatgctc cgactggcca ttgaaactgt tgctcatgac tatgatgtca tagttattga   42180
cagcgcgcct aacctgggta tcggcacgat taatgtcgta tgtgctgctg atgtgctgat   42240
tgttcccacg cctgctgagt tgtttgacta cacctccgca ctgcagtttt tcgatatgct   42300
tcgtgatctg ctcaagaacg ttgatcttaa agggttcgag cctgatgtac gtattttgct   42360
taccaaatac agcaatagta atggctctca gtccccgtgg atggaggagc aaattcggga   42420
tgcctgggga agcatggttc taaaaaatgt tgtacgtgaa acggatgaag ttggtaaagg   42480
tcagatccgg atgagaactg ttttttgaaca ggccattgat caacgctctt caactggtgc   42540
ctggagaaat gctctttcta tttgggaacc tgtctgcaat gaaattttcg atcgtctgat   42600
```

```
taaaccacgc tgggagatta gataatgaag cgtgcgcctg ttattccaaa acatacgctc    42660
aatactcaac cggttgaaga tacttcgtta tcgacaccag ctgccccgat ggtggattcg    42720
ttaattgcgc gcgtaggagt aatggctcgc ggtaatgcca ttactttgcc tgtatgtggt    42780
cgggatgtga agtttactct tgaagtgctc cggggtgata tgttgagaa gacctctcgg     42840 gtatggtcag gtaatgaacg tgaccaggag ctgcttactg aggacgcact ggatgatctc    42900
atcccttctt ttctactgac tggtcaacag acaccggcgt tcggtcgaag agtatctggt    42960
gtcatagaaa ttgccgatgg gagtcgccgt cgtaaagctg ctgcacttac cgaaagtgat    43020
tatcgtgttc tggttggcga gctggatgat gagcagatgg ctgcattatc cagattgggt    43080
aacgattatc gcccaacaag tgcttatgaa cgtggtcagc gttatgcaag ccgattgcag    43140
aatgaatttg ctggaaatat ttctgcgctg gctgatgcgg aaaatatttc acgtaagatt    43200 attaccgct gtatcaacac cgccaaattg cctaaatcag ttgttgctct ttttctcac     43260 cccggtgaac tatctgcccg gtcaggtgat gcacttcaaa aagcctttac agataaagag    43320
gaattactta agcagcaggc atctaacctt catgagcaga aaaaagctgg ggtgatattt    43380
gaagctgaag aagttatcac tcttttaact tctgtgctta aaacgtcatc tgcatcaaga    43440
actagtttaa gctcacgaca tcagtttgct cctggagcga cagtattgta aagggcgat    43500 aaaatggtgc ttaacctgga caggtctcgt gttccaactg agtgtataga gaaaattgag    43560
gccattctta aggaacttga aaagccagca ccctgatgcg accacgtttt agtctacgtt    43620
tatctgtctt tacttaatgt cctttgttac aggccagaaa gcataactgg cctgaatatt    43680
ctctctgggc ccactgttcc acttgtatcg tcggtctgat aatcagactg ggaccacggt    43740
cccactcgta tcgtcggtct gattattagt ctgggaccac ggtcccactc gtatcgtcgg    43800
tctgattatt agtctgggac cacggtccca ctcgtatcgt cggtctgata atcagactgg    43860
gaccacggtc ccactcgtat cgtcggtctg attattagtc tgggaccatg gtcccactcg    43920
tatcgtcggt ctgattatta gtctgggacc acggtcccac tcgtatcgtc ggtctgatta    43980
ttagtctgga accacggtcc cactcgtatc gtcggtctga ttattagtct gggaccacgg    44040
tcccactcgt atcgtcggtc tgattattag tctgggacca cgatcccact cgtgttgtcg    44100
gtctgattat cggtctggga ccacggtccc acttgtattg tcgatcagac tatcagcgtg    44160
agactacgat tccatcaatg cctgtcaagg gcaagtattg acatgtcgtc gtaacctgta    44220
gaacggagta acctcggtgt gcggttgtat gcctgctgtg gattgctgct gtgtcctgct    44280
tatccacaac attttgcgca cggttatgtg gacaaaatac ctggttaccc aggccgtgcc    44340
ggcacgttaa ccgggctgca tccgatgcaa gtgtgtcgct gtcgacgagc tcgcgagctc    44400
ggacatgagg ttgccccgta ttcagtgtcg ctgatttgta ttgtctgaag ttgttttttac   44460 gttaagttga tgcagatcaa ttaatacgat acctgcgtca taattgatta tttgacgtgg    44520
tttgatggcc tccacgcacg ttgtgatatg tagatgataa tcattatcac tttacgggtc    44580
ctttccggtg atccgacagg ttacggggcg gcgacctcgc gggttttcgc tatttatgaa    44640
aattttccgg tttaaggcgt ttccgttctt cttcgtcata acttaatgtt tttatttaaa    44700
ataccctctg aaaagaaagg aaacgacagg tgctgaaagc gagcttttg gcctctgtcg     44760 tttcctttct ctgttttgt ccgtggaatg aacaatggaa gtccgagctc atcgctaata     44820
acttcgtata gcatacatta tacgaagtta tattcgatgc ggccgcaagg ggttcgcgtc    44880
agcgggtgtt ggcgggtgtc ggggctggct taactatgcg gcatcagagc agattgtact    44940
gagagtgcac catatgcggt gtgaaatacc gcacagatgc gtaaggagaa aataccgcat    45000
```

```
caggcgccat tcgccattca ggctgcgcaa ctgttgggaa gggcgatcgg tgcgggcctc    45060
ttcgctatta cgccagctgg cgaaaggggg atgtgctgca aggcgattaa gttgggtaac    45120
gccagggttt tcccagtcac gacgttgtaa aacgacggcc agtgaattgt aatacgactc    45180
actatagggc gaattcgagc tcggtacccg gggatcctcg tttaaac                  45227

<210> SEQ ID NO 10
<211> LENGTH: 37830
<212> TYPE: DNA
<213> ORGANISM: Simian adenovirus

<400> SEQUENCE: 10
catcatcaat aatataccct attttggatt gaagccaata tgataatgag atgggcggcg      60
cggggcggga ggcgggtccg ggggcgggcc ggcgggcggg gcggtgtggc ggaagtggac     120
tttgtaagtg tggcggatgt gacttgctag tgccgggcgc ggtaaaagtg acgttttccg     180
tgcgcgacaa cgcccacggg aagtgacatt tttcccgcgg ttttttaccgg atgttgtagt    240 gaatttgggc gtaaccaagt aagatttggc cattttcgcg ggaaaactga aacggggaag     300
tgaaatctga ttaatttcgc gttagtcata ccgcgtaata tttgtcgagg gccgagggac     360
tttggccgat tacgtggagg actcgcccag gtgttttttg aggtgaattt ccgcgttccg    420
ggtcaaagtc tccgttttat tattatagtc agctgacgcg gagtgtattt ataccctctg    480
atctcgtcaa gtggccactc ttgagtgcca gcgagtagag ttttctcctc tgccgctctc    540
cgctccgctc cgctcggctc tgacaccggg gaaaaaatga gacatttcac ctacgatggc    600
ggtgtgctca ccggccagct ggctgctgaa gtcctggaca ccctgatcga ggaggtattg    660
gccgataatt atcctcccctc gactccttttt gagccaccta cacttcacga actctacgat    720
ctggatgtgg tggggcccag cgatccgaac gagcaggcgg tttccagttt ttttccagag    780
tccatgttgt tggccagcca ggaggggggtc gaacttgaga cccctcctcc gatcgtggat    840
tcccccgatc cgccgcagct gactaggcag cccgagcgct gtgcgggacc tgagactatg    900
ccccagctgc tacctgaggt gatcgatctc acctgtaatg agtctggttt tccacccagc    960
gaggatgagg acgaagaggg tgagcagttt gtgttagatt ctgtggaaca acccgggcga   1020
ggatgcaggt cttgtcaata tcaccggaaa aacacaggag actcccagat tatgtgttct   1080
ctgtgttata tgaagatgac ctgtatgttt atttacagta agtttatcat ctgtgggcag   1140
gtgggctata gtgtgggtgg tggtctttgg ggggtttttt aatatatgtc aggggttatg   1200
ctgaagactt ttttattgtg atttttaaag gtccagtgtc tgagcccgag caagaacctg   1260
aaccggagcc tgagccttct cgccccagga gaaagcctgt aatcttaact agacccagcg   1320
caccggtagc gagaggcctc agcagcgcgg agaccaccga ctccggtgct tcctcatcac   1380
ccccggagat tcaccccctg gtgcccctgt gtcccgttaa gcccgttgcc gtgagagtca   1440
gtgggcggcg gtctgctgtg gagtgcattg aggacttgct ttttgattca caggaacctt   1500
tggacttgag cttgaaacgc cccaggcatt aaacctggtc acctggactg aatgagttga   1560
cgcctatgtt tgcttttgaa tgacttaatg tgtatagata taaagagtg agataatgtt    1620 ttaattgcat ggtgtgttta acttgggcgg agtctgctgg gtatataagc ttccctgggc   1680
taaacttggt tacacttgac ctcatggagg cctgggagtg tttggagaac tttgccggag   1740
ttcgtgcctt gctggacgag agctctaaca ataccctcttg gtggtggagg tatttgtggg   1800 gctctccccca gggcaagtta gtttgtagaa tcaaggagga ttacaagtgg gaatttgaag   1860
```

```
agcttttgaa atcctgtggt gagctattgg attctttgaa tctaggccac caggctctct   1920
tccaggagaa ggtcatcagg actttggatt tttccacacc ggggcgcatt gcagccgcgg   1980
ttgcttttct agcttttttg aaggatagat ggagcgaaga gacccacttg agttcgggct   2040
acgtcctgga ttttctggcc atgcaactgt ggagagcatg gatcagacac aagaacaggc   2100
tgcaactgtt gtcttccgtc cgcccgttgc tgattccggc ggaggagcaa caggccgggt   2160
cagaggaccg ggcccgtcgg gatccggagg agagggcacc gaggccgggc gagaggagcg   2220
cgctgaacct gggaaccggg ctgagcggcc atccacatcg ggagtgaatg tcgggcaggt   2280
ggtggatctt tttccagaac tgcggcggat tttgactatt agggaggatg gcaatttgt    2340 taagggtctt aagagggaga ggggggcttc tgagcataac gaggaggcca gtaatttagc   2400
ttttagcttg atgaccagac accgtccaga gtgcatcact tttcagcaga ttaaggacaa   2460
ttgtgccaat gagttggatc tgtttgggtca gaagtatagc atagagcagc tgaccactta   2520
ctggctgcag ccgggtgatg atctggagga agctattagg gtgtatgcta aggtggccct   2580
gcggcccgat tgcaagtaca agctcaaggg gctggtgaat atcaggaatt gttgctacat   2640
ttctggcaac ggggcggagg tggagataga gaccgaagac agggtggctt tcagatgcag   2700
catgatgaat atgtggccgg gggtgctggg catggacggg gtggtgatta tgaatgtgag   2760
gttcacgggg cccaacttta acggcacggt gttttgggg aacaccaacc tggtcctgca    2820
cggggtgagc ttctatgggt ttaacaacac ctgtgtggag gcctggaccg atgtgaaggt   2880
ccgcggttgc gccttttatg gatgttggaa ggccatagtg agccgcccta agagcaggag   2940
ttccattaag aaatgcttgt ttgagaggtg caccttgggg atcctggccg agggcaactg   3000
cagggtgcgc cacaatgtgg cctccgagtg cggttgcttc atgctagtca gagagcgtggc   3060 ggtaatcaag cataatatgg tgtgcggcaa cagcgaggac aaggcctcac agatgctgac   3120
ctgcacggat ggcaactgcc acttgctgaa gaccatccat gtaaccagcc acagccggaa   3180
ggcctggccc gtgttcgagc acaacttgct gacccgctgc tccttgcatc tgggcaacag   3240
gcggggggtg ttcctgccct atcaatgcaa ctttagtcac accaagatct tgctagagcc   3300
cgagagcatg tccaaggtga acttgaacgg ggtgtttgac atgaccatga agatctggaa   3360
ggtgctgagg tacgacgaga ccaggtcccg gtgcagaccc tgcgagtgcg ggggcaagca   3420
tatgaggaac cagcccgtga tgctggatgt gaccgaggag ctgaggacag accacttggt   3480
tctggcctgc accagggccg agtttggttc tagcgatgaa gacacagatt gaggtgggtg   3540
agtgggcgtg gcctggggtg gtcatgaaaa tatataagtt gggggtctta gggtctcttt   3600
atttgtgttg cagagaccgc cggagccatg agcgggagca gcagcagcag cagtagcagc   3660
agcgccttgg atggcagcat cgtgagccct tatttgacga cgcggatgcc ccactgggcc   3720
ggggtgcgtc agaatgtgat gggctccagc atcgacggcc gacccgtcct gcccgcaaat   3780
tccgccacgc tgacctatgc gaccgtcgcg gggacgccgt tggacgccac cgccgccgcc   3840
gccgccaccg cagccgcctc ggccgtgcgc agcctggcca cggactttgc attcctggga   3900
ccactggcga caggggctac ttctcgggcc gctgctgccg ccgttcgcga tgacaagctg   3960
accgccctgc tggcgcagtt ggatgcgctt actcggaac tgggtgacct ttctcagcag    4020
gtcatggccc tgcgccagca ggtctcctcc ctgcaagctg gcgggaatgc ttctcccaca   4080
aatgccgttt aagataaata aaaccagact ctgtttggat taaagaaaag tagcaagtgc   4140
attgctctct ttatttcata attttccgcg cgcgatagcc cctagaccag cgttctcggt   4200
cgttgagggt gcggtgtatc ttctccagga cgtggtagag gtggctctgg acgttgagat   4260
```

```
acatgggcat gagcccgtcc cgggggtgga ggtagcacca ctgcagagct tcatgctccg   4320
gggtggtgtt gtagatgatc cagtcgtagc aggagcgctg ggcatggtgc ctaaaaatgt   4380
ccttcagcag caggccgatg gccagggggc ggcccttggt gtaagtgttt acaaaacggt   4440
taagttggga agggtgcatt cggggagaga tgatgtgcat cttggactgt atttttagat   4500
tggcgatgtt tccgcccaga tcccttctgg gattcatgtt gtgcaggacc accagtacag   4560
tgtatccggt gcacttgggg aatttgtcat gcagcttaga gggaaaagcg tggaagaact   4620
tggagacgcc tttgtggcct cccagatttt ccatgcattc gtccatgatg atggcaatgg   4680
gcccgcggga ggcagcttgg gcaaagatat ttctggggtc gctgacgtcg tagttgtgtt   4740
ccagggtgag gtcgtcatag gccattttta caaagcgcgg gcggagggtg cccgactggg   4800
ggatgatggt cccctctggc cctggggcgt agttgccctc gcagatctgc atttcccagg   4860
ccttaatctc ggagggggga atcatatcca cctgcggggc gatgaagaaa acggtttccg   4920
gagccgggga gattaactgg gatgagagca ggtttctaag cagctgtgat tttccacaac   4980
cggtgggccc ataaataaca cctataaccg gttgcagctg gtagtttaga gagctgcagc   5040
tgccgtcgtc ccggaggagg ggggccacct cgttgagcat gtccctgacg cgcatgttct   5100
ccccgaccag atccgccaga aggcgctcgc cgcccaggga cagcagctct tgcaaggaag   5160
caaagttttt cagcggcttg aggccgtccg ccgtgggcat gttttcagg gtctggctca   5220 gcagctccag gcggtcccag agctcggtga cgtgctctac ggcatctcta tccagcatat   5280
ctcctcgttt cgcgggttgg ggcgactttc gctgtagggc accaagcggt ggtcgtccag   5340
cggggccaga gtcatgtcct tccatgggcg cagggtcctc gtcagggtgg tctgggtcac   5400
ggtgaagggg tgcgctccgg gctgagcgct tgccaaggtg cgcttgaggc tggttctgct   5460
ggtgctgaag cgctgccggt cttcgccctg cgcgtcggcc aggtagcatt tgaccatggt   5520
gtcatagtcc agcccctccg cggcgtgtcc cttggcgcgc agcttgccct tggaggtggc   5580
gccgcacgag gggcagagca ggctcttgag cgcgtagagc ttggggcga ggaagaccga   5640 ttcgggggag taggcgtccg cgccgcagac cccgcacacg gtctcgcact ccaccagcca   5700
ggtgagctcg gggcgcgccg ggtcaaaaac caggtttccc ccatgctttt tgatgcgttt   5760
cttacctcgg gtctccatga ggtggtgtcc ccgctcggtg acgaagaggc tgtccgtgtc   5820
tccgtagacc gacttgaggg gtcttttctc caggggggtc cctcggtctt cctcgtagag   5880
gaactcggac cactctgaga cgaaggcccg cgtccaggcc aggacgaagg aggctatgtg   5940
ggaggggtag cggtcgttgt ccactagggg gtccaccttc tccaaggtgt gaagacacat   6000
gtcgccttcc tcggcgtcca ggaaggtgat tggcttgtag gtgtaggcca cgtgaccggg   6060
ggttcctgac gggggggtat aaagggggt gggggcgcgc tcgtcgtcac tctcttccgc   6120
atcgctgtct gcgagggcca gctgctgggg tgagtattcc ctctcgaagg cgggcatgac   6180
ctccgcgctg aggttgtcag tttccaaaaa cggaggaggt tgatgttca cctgtcccga   6240 ggtgatacct ttgagggtac ccgcgtccat ctggtcagaa aacacgatct ttttattgtc   6300
cagcttggtg gcgaacgacc cgtagagggc gttggagagc agcttggcga tggagcgcag   6360
ggtctggttc ttgtccctgt cggcgcgctc cttggccgcg atgttgagct gcacgtactc   6420
gcgcgcgacg cagcgccact cggggaagac ggtggtgcgc tcgtcgggca ccaggcgcac   6480
gcgccagccg cggttgtgca gggtgaccag gtccacgctg gtggcgacct cgccgcgcag   6540
gcgctcgttg gtccagcaga gacggccgcc cttgcgcgag cagaaggggg gcaggggtc   6600
```

```
gagctgggtc tcgtccgggg ggtccgcgtc cacggtgaaa accccggggc gcaggcgcgc   6660
gtcgaagtag tctatcttgc aaccttgcat gtccagcgcc tgctgccagt cgcgggcggc   6720
gagcgcgcgc tcgtaggggt tgagcggcgg gccccagggc atggggtggg tgagtgcgga   6780
ggcgtacatg ccgcagatgt catagacgta gaggggctcc cgcaggaccc cgatgtaggt   6840
ggggtagcag cggccgccgc ggatgctggc gcgcacgtag tcatacagct cgtgcgaggg   6900
ggcgaggagg tcggggccca ggttggtgcg ggcggggcgc tccgcgcgga agacgatctg   6960
cctgaagatg gcatgcgagt tggaagagat ggtggggcgc tggaagacgt tgaagctggc   7020
gtcctgcagg ccgacggcgt cgcgcacgaa ggaggcgtag gagtcgcgca gcttgtgtac   7080
cagctcggcg gtgacctgca cgtcgagcgc gcagtagtcg agggtctcgc ggatgatgtc   7140
atatttagcc tgccccttct ttttccacag ctcgcggttg aggacaaact cttcgcggtc   7200
tttccagtac tcttggatcg ggaaaccgtc cggttccgaa cggtaagagc ctagcatgta   7260
gaactggttg acggcctggt aggcgcagca gcccttctcc acggggaggg cgtaggcctg   7320
cgcggccttg cggagcgagg tgtgggtcag ggcgaaggtg tccctgacca tgactttgag   7380
gtactggtgc ttgaagtcgg agtcgtcgca gccgccccgc tcccagagcg agaagtcggt   7440
gcgcttcttg gagcggggggt tgggcagagc gaaggtgaca tcgttgaaga ggattttgcc   7500
cgcgcggggc atgaagttgc gggtgatgcg gaagggcccc ggcacttcag agcggttgtt   7560
gatgacctgg gcggcgagca cgatctcgtc gaagccgttg atgttgtggc ccacgatgta   7620
gagttccagg aagcggggcc ggccctttac ggtgggcagc ttctttagct cttcgtaggt   7680
gagctcctcg ggcgaggcga ggccgtgctc ggccagggcc cagtccgcga ggtgcgggtt   7740
gtctctgagg aaggacttcc agaggtcgcg ggccaggagg gtctgcaggc ggtctctgaa   7800
ggtcctgaac tggcggccca cggccatttt ttcgggggtg atgcagtaga aggtgagggg   7860
gtcttgctgc cagcggtccc agtcgagctg cagggcgagg tcgcgcgcgg cggtgaccag   7920
gcgctcgtcg cccccgaatt tcatgaccag catgaagggc acgagctgct ttccgaaggc   7980
ccccatccaa gtgtaggtct ctacatcgta ggtgacaaag aggcgctccg tgcgaggatg   8040
cgagccgatc gggaagaact ggatctcccg ccaccagttg gaggagtggc tgttgatgtg   8100
gtggaagtag aagtcccgtc gccgggccga acactcgtgc tggcttttgt aaaagcgagc   8160
gcagtactgg cagcgctgca cgggctgtac ctcatgcacg agatgcacct ttcgcccgcg   8220
cacgaggaag ccgaggggaa atctgagccc cccgcctggc tcgcggcatg gctggttctc   8280
ttctactttg gatgcgtgtc cgtctccgtc tggctcctcg aggggtgtta cggtggagcg   8340
gaccaccacg ccgcgcgagc cgcaggtcca gatatcggcg cgcggcggtc ggagtttgat   8400
gacgacatcg cgcagctggg agctgtccat ggtctggagc tcccgcggcg gcggcaggtc   8460
agccgggagt tcttgcaggt tcacctcgca gagtcgggcc agggcgcggg gcaggtctag   8520
gtggtacctg atctctaggg gcgtgttggt ggcggcgtcg atggcttgca ggagcccgca   8580
gccccggggg gcgacgacgg tgcccgcgcg ggtggtggtg gtggtggcgg tgcagctcag   8640
aagcggtgcc gcgggcgggc ccccggaggt aggggggggct ccggtcccgc gggcaggggc   8700
ggcagcggca cgtcgcgtg gagcgcgggc aggagttggt gctgtgcccg gaggttgctg   8760
gcgaaggcga cgacgcggcg gttgatctcc tggatctggc gcctctgcgt gaagacgacg   8820
ggcccggtga gcttgaacct gaaagagagt tcgacagaat caatctcggt gtcattgacc   8880
gcggcctggc gcaggatctc ctgcacgtct cccgagttgt cttggtaggc gatctcggcc   8940
atgaactgct cgatctcttc ctcctggagg tctccgcgtc cggcgcgttc cacggtggcc   9000
```

-continued

```
gccaggtcgt tggagatgcg ccccatgagc tgcgagaagg cgttgagtcc gccctcgttc    9060
cagactcggc tgtagaccac gccccccctgg tcatcgcggg cgcgcatgac cacctgcgcg   9120
aggttgagct ccacgtgccg cgcgaagacg gcgtagttgc gcagacgctg aagaggtag    9180
ttgagggtgg tggcggtgtg ctcggccacg aagaagttca tgacccagcg cgcaacgtg    9240
gattcgttga tgtcccccaa ggcctccagc cgttccatgg cctcgtagaa gtccacggcg   9300
aagttgaaaa actgggagtt gcgcgccgac acggtcaact cctcctccag aagacggatg   9360
agctcggcga cggtgtcgcg cacctcgcgc tcgaaggcta tggggatctc ttcctccgct   9420
agcatcacca cctcctcctc ttcctcctct tctggcactt ccatgatggc ttcctcctct   9480
tcgggggtg gcggcggcgg cggtggggga ggggcgctc tgcgccggcg gcggcgcacc     9540
gggaggcggt ccacgaagcg cgcgatcatc tccccgcggc ggcggcgcat ggtctcggtg   9600
acggcgcggc cgttctcccg ggggcgcagt tggaagacgc cgccggacat ctggtgctgg   9660
ggcgggtggc cgtgaggcag cgagacggcg ctgacgatga tctcaacaa ttgctgcgta    9720
ggtacgccgc cgagggacct gagggagtcc atatccaccg gatccgaaaa cctttcgagg   9780
aaggcgtcta accagtcgca gtcgcaaggt aggctgagca ccgtggcggg cggcgggggg   9840
tgggggagt gtctggcgga ggtgctgctg atgatgtaat tgaagtaggc ggacttgaca    9900
cggcggatgg tcgacaggag caccatgtcc ttgggtccgg cctgctggat gcggaggcgg   9960
tcggctatgc cccaggcttc gttctggcat cggcgcaggt ccttgtagta gtcttgcatg  10020
agcctttcca ccggcacctc ttctccttcc tcttctgctt cttccatgtc tgcttcggcc  10080
ctggggcggc gccgcgcccc cctgccccc atgcgcgtga ccccgaaccc cctgagcggt   10140
tggagcaggg ccaggtcggc gacgacgcgc tcggccagga tggcctgctg cacctgcgtg  10200
agggtggttt ggaagtcatc caagtccacg aagcggtggt aggcgcccgt gttgatggtg  10260
taggtgcagt tggccatgac ggaccagttg acggtctggt ggcccggttg cgacatctcg  10320
gtgtacctga gtcgcgagta ggcgcgggag tcgaagacgt agtcgttgca agtccgcacc  10380
aggtactggt agcccaccag gaagtgcggc ggcggctggc ggtagagggg ccagcgcagg  10440
gtggcggggg ctccggggc caggtcttcc agcatgaggc ggtggtaggc gtagatgtac   10500
ctggacatcc aggtgatacc cgcggcggtg gtggaggcgc gcgggaagtc gcgcacccgg  10560
ttccagatgt tgcgcagggg cagaaagtgc tccatggtag gcgtgctctg tccagtcaga  10620
cgcgcgcagt cgttgatact ctagaccagg gaaaacgaaa gccggtcagc gggcactctt  10680
ccgtggtctg tgtgaatagat cgcaagggta tcatggcgga gggcctcggt tcgagccccg  10740
ggtccgggcc ggacggtccg ccatgatcca cgcggttacc gcccgcgtgt cgaacccagg  10800
tgtgcgacgt cagacaacgg tggagtgttc cttttggcgt ttttctggcc gggcgccggc  10860
gccgcgtaag agactaagcc gcgaaagcga aagcagtaag tggctcgctc cccgtagccg  10920
gagggatcct tgctaagggt tgcgttgcgg cgaaccccgg ttcgaatccc gtactcgggc  10980
cggccggacc cgcggctaag gtgttggatt ggcctccccc tcgtataaag acccccgcttg 11040
cggattgact ccggacacgg ggacgagccc ctttttatttt tgctttcccc agatgcatcc 11100
ggtgctgcgg cagatgcgcc ccccgcccca gcagcagcaa caacaccagc aagagcggca  11160
gcaacagcag cgggagtcat gcagggcccc ctcacccacc ctcggcgggc cggccacctc  11220
ggcgtccgcg gccgtgtctg gcgcctgcgg cggcggcggg gggccggctg acgacccga    11280
ggagcccccg cggcgcaggg ccagacacta cctggacctg gaggagggcg agggcctggc  11340
```

```
gcggctgggg gcgccgtctc ccgagcgcca cccgcgggtg cagctgaagc gcgactcgcg    11400
cgaggcgtac gtgcctcggc agaacctgtt cagggaccgc gcgggcgagg agcccgagga    11460
gatgcgggac aggaggttca gcgcagggcg ggagctgcgg caggggctga accgcgagcg    11520
gctgctgcgc gaggaggact ttgagcccga cgcgcggacg gggatcagcc ccgcgcgcgc    11580
gcacgtggcg gccgccgacc tggtgacggc gtacgagcag acggtgaacc aggagatcaa    11640
cttccaaaag agtttcaaca accacgtgcg cacgctggtg gcgcgcgagg aggtgaccat    11700
cgggctgatg cacctgtggg actttgtaag cgcgctggtg cagaacccca acagcaagcc    11760
tctgacggcg cagctgttcc tgatagtgca gcacagcagg gacaacgagg cgtttaggga    11820
cgcgctgctg aacatcaccg agcccgaggg tcggtggctg ctggacctga ttaacatcct    11880
gcagagcata gtggtgcagg agcgcagcct gagcctggcc gacaaggtgg cggccatcaa    11940
ctactcgatg ctgagcctgg gcaagtttta cgcgcgcaag atctaccaga cgccgtacgt    12000
gcccatagac aaggaggtga agatcgacgg tttttacatg cgcatggcgc tgaaggtgct    12060
caccctgagc gacgacctgg gcgtgtaccg caacgagcgc atccacaagg ccgtgagcgt    12120
gagccggcgg cgcgagctga gcgaccgcga gctgatgcac agcctgcagc gggcgctggc    12180
gggcgccggc agcggcgaca gggaggcgga gtcctacttc gatgcggggg cggacctgcg    12240
ctgggcgccc agccggcggg ccctggaggc cgcgggggtc cgcgaggact atgacgagga    12300
cggcgaggag gatgaggagt acgagctaga ggagggcgag tacctggact aaaccgcggg    12360
tggtgtttcc ggtagatgca agacccgaac gtggtggacc cggcgctgcg ggcggctctg    12420
cagagccagc cgtccggcct taactcctca gacgactggc gacaggtcat ggaccgcatc    12480
atgtcgctga cggcgcgtaa cccggacgcg ttccggcagc agccgcaggc caacaggctc    12540
tccgccatcc tggaggcggt ggtgcctgcg cgctcgaacc ccacgcacga gaaggtgctg    12600
gccatagtga acgcgctggc cgagaacagg gccatccgcc cggacgaggc cgggctggtg    12660
tacgacgcgc tgctgcagcg cgtggcccgc tacaacagcg gcaacgtgca gaccaacctg    12720
gaccggctgg tgggggacgt gcgcgaggcg gtggcgcagc gcgagcgcgc ggatcggcag    12780
ggcaacctgg gctccatggt ggcgctgaat gccttcctga gcacgcagcc ggccaacgtg    12840
ccgcgggggc aggaagacta caccaacttt gtgagcgcgc tgcggctgat ggtgaccgag    12900
accccccaga gcgaggtgta ccagtcgggc ccggactact tcttccagac cagcagacag    12960
ggcctgcaga cggtgaacct gagccaggct ttcaagaacc tgcgggggct gtggggcgtg    13020
aaggcgccca ccggcgaccg ggcgacggtg tccagcctgc tgacgcccaa ctcgcgcctg    13080
ctgctgctgc tgatcgcgcc gttcacggac agcggcagcg tgtcccggga cacctacctg    13140
gggcacctgc tgaccctgta ccgcgaggcc atcgggcagg cgcaggtgga cgagcacacc    13200
ttccaggaga tcaccagcgt gagccgcgcg ctggggcagg aggacacgag cagcctggag    13260
gcgactctga actacctgct gaccaaccgg cggcagaaga ttccctcgct gcacagcctg    13320
acctccgagg aggagcgcat cttgcgctac gtgcagcaga gcgtgagcct gaacctgatg    13380
cgcgacgggg tgacgcccag cgtggcgctg gacatgaccg cgcgcaacat ggaaccgggc    13440
atgtacgccg cgcaccggcc ttacatcaac cgcctgatgg actacctgca tcgcgcggcc    13500
gccgtgaacc ccgagtactt taccaacgcc atcctgaacc cgcactggct cccgccgccc    13560
gggttctaca cgcggggctt cgaggtcccg gagaccaacg atggcttcct gtgggacgac    13620
atggacgaca gcgtgttctc cccgcggccg caggcgctgg cggaagcgtc cctgctgcgt    13680
cccaagaagg aggaggagga ggaggcgagt cgccgccgcg gcagcagcgg cgtggcttct    13740
```

```
ctgtccgagc tgggggcggc agccgccgcg cgccccgggt ccctgggcgg cagccccttt    13800
ccgagcctgg tggggtctct gcacagcgag cgcaccaccc gccctcggct gctgggcgag    13860
gacgagtacc tgaataactc cctgctgcag ccggtgcggg agaaaaacct gcctcccgcc    13920
ttccccaaca acgggataga gagcctggtg gacaagatga gcagatggaa gacctatgcg    13980
caggagcaca gggacgcgcc tgcgctccgg ccgcccacgc ggcgccagcg ccacgaccgg    14040 cagcggggc tggtgtggga tgacgaggac tccgcggacg atagcagcgt gctggacctg     14100
ggagggagcg gcaacccgtt cgcgcacctg cgcccccgcc tggggaggat gttttaaaaa    14160 aaaaaaaaa aagcaagaag catgatgcaa aaattaaata aaactcacca aggccatggc     14220
gaccgagcgt tggtttcttg tgttcccttc agtatgcggc gcgcggcgat gtaccaggag    14280
ggacctcctc cctcttacga gagcgtggtg ggcgcggcgg cggcggcgcc ctcttctccc    14340
tttgcgtcgc agctgctgga gccgccgtac gtgcctccgc gctacctgcg gcctacgggg    14400
gggagaaaca gcatccgtta ctcggagctg gcgcccctgt tcgacaccac ccgggtgtac    14460
ctggtggaca acaagtcggc ggacgtggcc tccctgaact accagaacga ccacagcaat    14520
tttttgacca cggtcatcca gaacaatgac tacagcccga gcgaggccag cacccagacc    14580
atcaatctgg atgaccggtc gcactggggc ggcgacctga aaccatcct gcacaccaac     14640 atgcccaacg tgaacgagtt catgttcacc aataagttca aggcgcgggt gatggtgtcg    14700
cgctcgcaca ccaaggaaga ccgggtggag ctgaagtacg agtgggtgga gttcgagctg    14760
ccagagggca actactccga gaccatgacc attgacctga tgaacaacgc gatcgtggag    14820
cactatctga aagtgggcag gcagaacggg gtcctggaga gcgacatcgg ggtcaagttc    14880
gacaccagga acttccgcct ggggctggac cccgtgaccg ggctggttat gcccggggtg    14940
tacaccaacg aggccttcca tcccgacatc atcctgctgc ccggctgcgg ggtggacttc    15000
acttacagcc gcctgagcaa cctcctgggc atccgcaagc ggcagcccTT ccaggagggc    15060
ttcaggatca cctacgagga cctggagggg ggcaacatcc ccgcgctcct cgatgtggag    15120
gcctaccagg atagcttgaa ggaaaatgag gcgggacagg aggataccgc ccccgccgcc    15180
tccgccgccg ccgagcaggg cgaggatgct gctgacaccg cggccgcgga cggggcagag    15240
gccgaccccg ctatggtggt ggaggctccc gagcaggagg aggacatgaa tgacagtgcg    15300
gtgcgcggag acaccttcgt cacccggggg gaggaaaagc aagcggaggc cgaggccgcg    15360
gccgaggaaa agcaactggc ggcagcagcg gcggcggcgg cgttggccgc ggcggaggct    15420
gagtctgagg ggaccaagcc cgccaaggag cccgtgatta gcccctgac cgaagatagc     15480 aagaagcgca gttacaacct gctcaaggac agcaccaaca ccgcgtaccg cagctggtac    15540
ctggcctaca actacggcga cccgtcgacg ggggtgcgct cctggaccct gctgtgcacg    15600
ccggacgtga cctgcggctc ggagcaggtg tactggtcgc tgcccgacat gatgcaagac    15660
cccgtgacct tccgctccac gcggcaggtc agcaacttcc cggtggtggg cgccgagctg    15720
ctgcccgtgc actccaagag cttctacaac gaccaggccg tctactccca gctcatccgc    15780
cagttcacct ctctgaccca cgtgttcaat cgctttcctg agaaccagat tctggcgcgc    15840
ccgccccgcc ccaccatcac caccgtcagt gaaaacgttc ctgctctcac agatcacggg    15900
acgctaccgc tgcgcaacag catcggagga gtccagcgag tgaccgttac tgacgccaga    15960
cgccgcacct gccctacgt ttacaaggcc ttgggcatag tctcgccgcg cgtcctttcc     16020
agccgcactt tttgagcaac accaccatca tgtccatcct gatctcaccc agcaataact    16080
```

```
ccggctgggg actgctgcgc gcgcccagca agatgttcgg aggggcgagg aagcgttccg   16140
agcagcaccc cgtgcgcgtg cgcgggcact tccgcgcccc ctggggagcg cacaaacgcg   16200
gccgcgcggg gcgcaccacc gtggacgacg ccatcgactc ggtggtggag caggcgcgca   16260
actacaggcc cgcggtctct accgtggacg cggccatcca gaccgtggtg cggggcgcgc   16320
ggcggtacgc caagctgaag agccgccgga agcgcgtggc ccgccgccac cgccgccgac   16380
ccggggccgc cgccaaacgc gccgccgcgg ccctgcttcg ccgggccaag cgcacgggcc   16440
gccgcgccgc catgagggcc gcgcgccgct tggccgccgg catcaccgcc gccaccatgg   16500 cccccccgtac ccgaagacgc gcggccgccg ccgccgccgc cgccatcagt gacatggcca   16560
gcaggcgccg gggcaacgtg tactgggtgc gcgactcggt gaccggcacg cgcgtgcccg   16620
tgcgcttccg ccccccgcgg acttgagatg atgtgaaaaa acaacactga gtctcctgct   16680
gttgtgtgta tcccagcggc ggcggcgcgc gcagcgtcat gtccaagcgc aaaatcaaag   16740
aagagatgct ccaggtcgtc gcgccggaga tctatgggcc cccgaagaag gaagagcagg   16800
attcgaagcc ccgcaagata aagcgggtca aaaagaaaaa gaaagatgat gacgatgccg   16860
atggggaggt ggagttcctg cgcgccacgg cgcccaggcg cccggtgcag tggaagggcc   16920
ggcgcgtaaa gcgcgtcctg cgccccgcca ccgcggtggt cttcacgccc ggcgagcgct   16980
ccacccggac tttcaagcgc gtctatgacg aggtgtacgg cgacgaagac ctgctggagc   17040
aggccaacga gcgcttcgga gagttttgctt acggaagcg tcagcgggcg ctggggaagg   17100
aggacctgct ggcgctgccg ctggaccagg gcaaccccac ccccagtctg aagcccgtga   17160
ccctgcagca ggtgctgccg agcagcgcac cctccgaggc gaagcggggt ctgaagcgcg   17220
agggcggcga cctggcgccc accgtgcagc tcatggtgcc caagcggcag aggctggagg   17280
atgtgctgga gaaaatgaaa gtagacccg gtctgcagcc ggacatcagg gtccgcccca   17340
tcaagcaggt ggcgccgggc ctcggcgtgc agaccgtgga cgtggtcatc cccaccggca   17400
actcccccgc cgccgccacc actaccgctg cctccacgga catggagaca cagaccgatc   17460
ccgccgcagc cgcagccgca gccgccgccg cgacctcctc ggcggaggtg cagacggacc   17520
cctggctgcc gccggcgatg tcagctcccc gcgcgcgtcg cgggcgcagg aagtacggcg   17580
ccgccaacgc gctcctgccc gagtacgcct tgcatccttc catcgcgccc accccgggct   17640
accgaggcta tacctaccgc ccgcgaagag ccaagggttc caccccgccgt ccccgccgac   17700 gcgccgccgc caccacccgc cgccgccgcc gcagacgcca gcccgcactg gctccagtct   17760
ccgtgaggaa agtggcgcgc gacggacaca ccctggtgct gcccagggcg cgctaccacc   17820
ccagcatcgt ttaaaagcct gttgtggttc ttgcagatat ggccctcact tgccgcctcc   17880
gtttcccggt gccgggatac cgaggaggaa gatcgcgccg caggaggggt ctggccggcc   17940
gcggcctgag cggaggcagc cgccgcgcgc accggcggcg acgcgccacc agccgacgca   18000
tgcgcggcgg ggtgctgccc ctgttaatcc ccctgatcgc cgcggcgatc ggcgccgtgc   18060
ccgggatcgc ctccgtggcc ttgcaagcgt cccagaggca ttgacagact tgcaaacttg   18120
caaatatgga aaaaaaaacc ccaataaaaa agtctagact ctcacgctcg cttggtcctg   18180
tgactatttt gtagaatgga agacatcaac tttgcgtcgc tggccccgcg tcacggctcg   18240
cgcccgttcc tgggacactg gaacgatatc ggcaccagca acatgagcgg tggcgccttc   18300
agttggggct ctctgtggag cggcattaaa agtatcgggt ctgccgttaa aaattacggc   18360
tcccgggcct ggaacagcag cacgggccag atgttgagag acaagttgaa agagcagaac   18420
ttccagcaga aggtggtgga gggcctggcc tccggcatca acgggtggt ggacctggcc   18480
```

```
aaccaggccg tgcagaataa gatcaacagc agactggacc cccggccgcc ggtggaggag   18540
gtgccgccgg cgctggagac ggtgtccccc gatgggcgtg gcgagaagcg cccgcggccc   18600
gatagggaag agaccactct ggtcacgcag accgatgagc cgcccccgta tgaggaggcc   18660
ctgaagcaag gtctgcccac cacgcggccc atcgcgccca tggccaccgg ggtggtgggc   18720
cgccacaccc ccgccacgct ggacttgcct ccgcccgccg atgtgccgca gcagcagaag   18780
gcggcacagc cgggccccgcc cgcgaccgcc tcccgttcct ccgccggtcc tctgcgccgc   18840
gcggccagcg gcccccgcgg ggggtcgcg aggcacggca actggcagag cacgctgaac   18900
agcatcgtgg gtctgggggt gcggtccgtg aagcgccgcc gatgctactg aatagcttag   18960
ctaacgtgtt gtatgtgtgt atgcgcccta tgtcgccgcc agaggagctg ctgagtcgcc   19020
gccgttcgcg cgcccaccac caccgccact ccgcccctca agatggcgac ccatcgatg   19080
atgccgcagt ggtcgtacat gcacatctcg ggccaggacg cctcggagta cctgagcccc   19140
gggctggtgc agttcgcccg cgccaccgag agctacttca gcctgagtaa caagtttagg   19200
aaccccacgg tggcgcccac gcacgatgtg accaccgacc ggtctcagcg cctgacgctg   19260
cggttcattc ccgtggaccg cgaggacacc gcgtactcgt acaaggcgcg gttcaccctg   19320
gccgtgggcg acaaccgcgt gctggacatg gcctccacct actttgacat ccgcggggtg   19380
ctggaccggg gtcccacttt caagccctac tctggcaccg cctacaactc cctgccccc    19440
aagggcgctc ccaactcctg cgagtgggag caagaggaaa ctcaggcagt tgaagaagca   19500
gcagaagagg aagaagaaga tgctgacggt caagctgagg aagagcaagc agctaccaaa   19560
aagactcatg tatatgctca ggctcccctt tctggcgaaa aaattagtaa agatggtctg   19620
caaataggaa cggacgctac agctacagaa caaaaaccta tttatgcaga ccctacattc   19680
cagcccgaac cccaaatcgg ggagtcccag tggaatgagg cagatgctac agtcgccggc   19740
ggtagagtgc taaagaaatc tactcccatg aaaccatgct atggttccta tgcaagaccc   19800
acaaatgcta atggaggtca gggtgtacta acggcaaatg cccagggaca gctagaatct   19860
caggttgaaa tgcaattctt ttcaacttct gaaaacgccc gtaacgaggc taacaacatt   19920
cagcccaaat tggtgctgta tagtgaggat gtgcacatgg agaccccgga tacgcacctt   19980
tcttacaagc ccgcaaaaag cgatgacaat tcaaaaatca tgctgggtca gcagtccatg   20040
cccaacagac ctaattacat cggcttcaga gacaacttta tcggcctcat gtattacaat   20100
agcactggca acatgggagt gcttgcaggt caggcctctc agttgaatgc agtggtggac   20160
ttgcaagaca gaaacacaga actgtcctac cagctcttgc ttgattccat gggtgacaga   20220
accagatact tttccatgtg gaatcaggca gtggacagtt atgacccaga tgttagaatt   20280
attgaaaatc atggaactga agacgagctc cccaactatt gtttccctct gggtggcata   20340
ggggtaactg acacttacca ggctgttaaa accaacaatg caataacgg gggccaggtg    20400
acttggacaa aagatgaaac ttttgcagat cgcaatgaaa taggggtggg aaacaatttc   20460
gctatggaga tcaacctcag tgccaacctg tggagaaact tcctgtactc caacgtggcg   20520
ctgtacctac cagacaagct taagtacaac ccctccaatg tggacatctc tgacaacccc   20580
aacacctacg attacatgaa caagcgagtg gtggccccgg ggctggtgga ctgctacatc   20640
aacctgggcg cgcgctggtc gctggactac atggacaacg tcaaccccctt caaccaccac   20700
cgcaatgcgg gcctgcgcta ccgctccatg ctcctgggca cgggcgcta cgtgcccttc   20760
cacatccagg tgccccagaa gttctttgcc atcaagaacc tcctcctcct gccgggctcc   20820
```

```
tacacctacg agtggaactt caggaaggat gtcaacatgg tcctccagag ctctctgggt    20880
aacgatctca gggtggacgg ggccagcatc aagttcgaga gcatctgcct ctacgccacc    20940
ttcttcccca tggcccacaa cacggcctcc acgctcgagg ccatgctcag gaacgacacc    21000
aacgaccagt ccttcaatga ctacctctcc gccgccaaca tgctctaccc catacccgcc    21060
aacgccacca acgtccccat ctccatcccc tcgcgcaact gggcggcctt ccgcggctgg    21120
gccttcaccc gcctcaagac caaggagacc ccctccctgg gctcgggatt cgaccctac    21180 tacacctact cgggctccat tccctacctg gacggcacct tctacctcaa ccacactttc    21240
aagaaggtct cggtcacctt cgactcctcg gtcagctggc cgggcaacga ccgtctgctc    21300 accccaacg agttcgagat caagcgctcg gtcgacgggg agggctacaa cgtggcccag    21360
tgcaacatga ccaaggactg gttcctggtc cagatgctgg ccaactacaa catcggctac    21420
cagggcttct acatcccaga gagctacaag gacaggatgt actccttctt caggaacttc    21480
cagcccatga gccggcaggt ggtggaccag accaagtaca aggactacca ggaggtgggc    21540
atcatccacc agcacaacaa ctcgggcttc gtgggctacc tcgcccccac catgcgcgag    21600
ggacaggcct acccccgccaa cttcccctat ccgctcatag gcaagaccgc ggtcgacagc    21660
atcacccaga aaaagttcct ctgcgaccgc accctctggc gcatcccctt ctccagcaac    21720
ttcatgtcca tgggtgcgct ctcggacctg gccagaact tgctctacgc caactccgcc    21780
cacgccctcg acatgacctt cgaggtcgac cccatggacg agcccaccct tctctatgtt    21840
ctgttcgaag tcttttgacgt ggtccgggtc caccagccgc accgcggcgt catcgagacc    21900
gtgtacctgc gtacgcccctt ctcggccggc aacgccacca cctaaagaag caagccgcag    21960
tcatcgccgc ctgcatgccg tcgggttcca ccgagcaaga gctcagggcc atcgtcagag    22020
acctgggatg cgggccctat tttttgggca ccttcgacaa gcgcttccct ggctttgtct    22080
ccccacacaa gctggcctgc gccatcgtca acacggccgg ccgcgagacc gggggcgtgc    22140
actggctggc cttcgcctgg aacccgcgct ccaaaacatg cttcctcttt gaccccttcg    22200
gcttttcgga ccagcggctc aagcaaatct acgagttcga gtacgagggc ttgctgcgtc    22260
gcagcgccat cgcctcctcg cccgaccgct gcgtcaccct cgaaaagtcc acccagaccg    22320
tgcaggggcc cgactcggcc gcctgcggtc tcttctgctg catgtttctg cacgcctttg    22380
tgcactggcc tcagagtccc atggaccgca accccaccat gaacttgctg acggggggtgc    22440 ccaactccat gctccagagc cccaggtcg agcccaccct gcgccgcaac caggagcagc    22500
tctacagctt cctggagcgc cactcgcctt acttccgccg ccacagcgca cagatcagga    22560
gggccacctc cttctgccac ttgcaagaga tgcaagaagg gtaataacga tgtacacact    22620
ttttttctca ataaatggca tcttttttatt tatacaagct ctctggggta ttcatttccc    22680
accaccaccc gccgttgtcg ccatctggct ctatttagaa atcgaaaggg ttctgccggg    22740
agtcgccgtg cgccacgggc agggacacgt tgcgatactg gtagcgggtg ccccacttga    22800
actcgggcac caccaggcga ggcagctcgg ggaagttttc gctccacagg ctgcgggtca    22860
gcaccagcgc gttcatcagg tcgggcgccg agatcttgaa gtcgcagttg gggccgccgc    22920
cctgcgcgcg cgagttgcgg tacaccgggt tgcagcactg gaacaccaac agcgccgggt    22980
gcttcacgct ggccagcacg ctgcggtcgg agatcagctc ggcgtccagg tcctccgcgt    23040
tgctcagcgc gaacgggtc atcttgggca cttccgccc caggaagggc gcgtgccccg    23100
gtttcgagtt gcagtcgcag cgcagcggga tcagcaggtg cccgtgcccg gactcggcgt    23160
tggggtacag cgcgcgcatg aaggcctgca tctggcggaa ggccatctgg gccttggcgc    23220
```

```
cctccgagaa gaacatgccg caggacttgc ccgagaactg gtttgcgggg cagctggcgt   23280
cgtgcaggca gcagcgcgcg tcggtgttgg cgatctgcac cacgttgcgc ccccaccggt   23340
tcttcacgat cttggccttg gacgattgct ccttcagcgc gcgctgcccg ttctcgctgg   23400
tcacatccat ctcgatcaca tgttccttgt tcaccatgct gctgccgtgc agacacttca   23460
gctcgccctc cgtctcggtg cagcggtgct gccacagcgc gcagcccgtg ggctcgaaag   23520
acttgtaggt cacctccgcg aaggactgca ggtaccnctg caaaaagcgg cccatcatgg   23580
tcacgaaggt cttgttgctg ctgaaggtca gctgcagccc gcggtgctcc tcgttcagcc   23640
aggtcttgca cacggccgcc agcgcctcca cctggtcggg cagcatcttg aagttcacct   23700
tcagctcatt ctccacgtgg tacttgtcca tcagcgtgcg cgccgcctcc atgcccttct   23760
cccaggccga caccagcggc aggctcacgg ggttcttcac catcaccgtg gccgccgcct   23820
ccgccgcgct ttcgctttcc gccccgctgt tctcttcctc ttcctcctct tcctcgccgc   23880
cgcccactcg cagcccccgc accacggggt cgtcttcctg caggcgctgc accttgcgct   23940
tgccgttgcg cccctgcttg atgcgcacgg gcgggttgct gaagcccacc atcaccagcg   24000
cggcctcttc ttgctcgtcc tcgctgtcca gaatgacctc cggggagggg gggttggtca   24060
tcctcagtac cgaggcacgc ttcttttttct tcctggggnc gttcgccagc tccgcggctg   24120
cggccgctgc cgaggtcgaa ggccgagggc tgggcgtgcg cggcaccagc gcgtcctgcg   24180
agccgtcctc gtcctcctcg gactcgagac ggaggcgggc ccgcttcttc gggggcgcgc   24240
ggggcggcgg aggcggcggc ggcgacgag acggggacga acatcgtcc agggtgggtg   24300
gacggcgggc cgcgccgcgt ccgcgctcgg gggtggtctc gcgctggtcc tcttcccgac   24360
tggccatctc ccactgctcc ttctcctata ggcagaaaga gatcatggag tctctcatgc   24420
gagtcgagaa ggaggaggac agcctaaccg ccccctctga gccctccacc accgccgcca   24480
ccaccgccaa tgccgccgcg gacgacgcgc ccaccgagac caccgccagt accaccctcc   24540
ccagcgacgc accccgctc gagaatgaag tgctgatcga gcaggacccg ggttttgtga   24600
gcggagagga ggatgaggtg gatgagaagg agaaggagga ggtcgccgcc tcagtgccaa   24660
aagaggataa aaagcaagac caggacgacg cagataagga tgagacagca gtcgggcggg   24720
ggaacggaag ccatgatgct gatgacggct acctagacgt gggagacgac gtgctgctta   24780
agcacctgca ccgccagtgc gtcatcgtct gcgacgcgct gcaggagcgc tgcgaagtgc   24840
ccctggacgt ggcggaggtc agccgcgcct acgagcggca cctcttcgcg ccgcacgtgc   24900
ccccaagcg ccggggagaac ggcacctgcg agcccaaccc gcgtctcaac ttctacccgg   24960
tcttcgcggt acccgaggtg ctggccacct accacatctt tttccaaaac tgcaagatcc   25020
ccctctcctg ccgcgccaac cgcacccgcg ccgacaaaac cctgaccctg cggcagggcg   25080
cccacatacc tgatatcgcc tctctggagg aagtgcccaa gatcttcgag ggtctcggtc   25140
gcgacgagaa acgggcggcg aacgctctgc acggagacg cgaaaacgag agtcactcgg   25200
gggtgctggt ggagctcgag ggcgacaacg cgcgcctggc cgtactcaag cgcagcatag   25260
aggtcaccca ctttgcctac ccggcgctca acctgccccc caaggtcatg agtgtggtca   25320
tgggcgagct catcatgcgc cgcgcccagc ccctggccgc ggatgcaaac ttgcaagagt   25380
cctccgagga aggcctgccc gcggtcagcg acgagcagct ggcgcgctgg ctggagaccc   25440
gcgaccccgc gcagctggag gagcggcgca agctcatgat ggccgcggtg ctggtcaccg   25500
tggagctcga gtgtctgcag cgcttcttcg cggacccga gatgcagcgc aagctcgagg   25560
```

```
agaccctgca ctacaccttc cgccagggct acgtgcgcca ggcctgcaag atctccaacg   25620
tggagctctg caacctggtc tcctacctgg gcatcctgca cgagaaccgc ctcgggcaga   25680
acgtcctgca ctccacccctc aaggggagg cgcgccgcga ctacatccgc gactgcgcct   25740
acctcttcct ctgctacacc tggcagacgg ccatggggt ctggcagcag tgcctggagg   25800
agcgcaacct caaggagctg aaaagctcc tcaagcgcac cctcagggac ctctggacgg   25860
gcttcaacga gcgctcggtg gccgccgcgc tggcggacat catctttccc gagcgcctgc   25920
tcaagaccct gcagcagggc ctgcccgact tcaccagcca gagcatgctg cagaacttca   25980
ggactttcat cctggagcgc tcgggcatcc tgccggccac ttgctgcgcg ctgcccagcg   26040
acttcgtgcc catcaagtac agggagtgcc cgccgccgct ctggggccac tgctacctct   26100
tccagctggc caactacctc gcctaccact cggacctcat ggaagacgtg agcggcgagg   26160
gcctgctcga gtgccactgc cgctgcaacc tctgcacgcc ccaccgctct ctagtctgca   26220
acccgcagct gctcagcgag agtcagatta tcggtacctt cgagctgcag ggtccctcgc   26280
ctgacgagaa gtccgcggct ccagggctga aactcactcc ggggctgtgg acttccgcct   26340
acctacgcaa atttgtacct gaggactacc acgcccacga gatcaggttc tacgaagacc   26400
aatcccgccc gcccaaggcg gagctcaccg cctgcgtcat cacccagggg cacatcctgg   26460
gccaattgca agccatcaac aaagcccgcc gagagttctt gctgaaaaag ggtcgggggg   26520
tgtacctgga cccccagtcc ggcgaggagc taaacccgct accccccgcg ccgcccccagc   26580 agcgggacct tgcttcccag gatggcaccc agaaagaagc agcagccgcc gccgccgccg   26640
cagccataca tgcttctgga ggaagaggag gaggactggg acagtcaggc agaggaggtt   26700
tcggacgagg agcaggagga gatgatggaa gactgggagg aggacagcag cctagacgag   26760
gaagcttcag aggccgaaga ggtggcagac gcaacaccat cgccctcggt cgcagccccc   26820
tcgccggggc ccctgaaatc ctccgaaccc agcaccagcg ctataacctc cgctcctccg   26880
gcgccggcgc caccccgccg cagacccaac cgtagatggg acaccacagg aaccggggtc   26940
ggtaagtcca agtgcccgcc gccgccaccg cagcagcagc agcagcagcg ccagggctac   27000
cgctcgtggc gcgggcacaa gaacgccata gtcgcctgct tgcaagactg cggggggcaac   27060 atctctttcg cccgccgctt cctgctattc caccacgggg tcgcctttcc ccgcaatgtc   27120
ctgcattact accgtcatct ctacagcccc tactgcagcg cgacccagag ggcggcagcg   27180
gcagccacag cggcgaccac cacctaggaa gatatcctcc gcgggcaaga cagcggcagc   27240
agcggccagg agaccgcgg cagcagcggc gggagcggtg ggcgcactgc gcctctcgcc   27300
caacgaaccc ctctcgaccc gggagctcag acacaggatc ttccccactt tgtatgccat   27360
cttccaacag agcagaggcc aggagcagga gctgaaaata aaaaacagat ctctgcgctc   27420
cctcacccgc agctgtctgt atcacaaaag cgaagatcag cttcggcgca cgctggagga   27480
cgcggaggca ctcttcagca aatactgcgc gctcactctt aaagactagc tccgcgccct   27540
tctcgaattt aggcgggaga aaactacgtc atcgccggcc gccgcccagc ccgcccagcc   27600
gagatgagca aagagattcc cacgccatac atgtggagct accagccgca gatgggactc   27660
gcggcgggag cggcccagga ctactccacc cgcatgaact acatgagcgc gggacccccac   27720 atgatctcac aggtcaacgg gatccgcgcc cagcgaaacc aaatactgct ggaacaggcg   27780
gccatcaccg ccacgcccccg ccataatctc aaccccccgaa attggccgc cgccctcgtg   27840 taccaggaaa ccccctccgc caccaccgta ctacttccgc gtgacgccca ggccgaagtc   27900
cagatgacta actcaggggc gcagctcgcg ggcggctttc gtcacggggc gcggccgctc   27960
```

```
cgaccaggta taagacacct gatgatcaga ggccgaggta tccagctcaa cgacgagtcg  28020
gtgagctctt cgctcggtct ccgtccggac ggaactttcc agctcgccgg atccggccgc  28080
tcttcgttca cgccccgcca ggcgtacctg actctgcaga cctcgtcctc ggagcccgc   28140 tccggcggca tcggaaccct ccagttcgtg gaggagttcg tgccctcggt ctacttcaac  28200
cccttctcgg gacctcccgg acgctacccc gaccagttca ttccgaactt tgacgcggtg  28260
aaggactcgc ggacggcta cgactgaatg tcaggtgtcg aggcagagca gcttcgcctg   28320
agacacctcg agcactgccg ccgccacaag tgcttcgccc gcggttctgg tgagttctgc  28380
tactttcagc tacccgagga gcataccgag gggccggcgc acggcgtccg cctgaccacc  28440
cagggcgagg ttacctgttc cctcatccgg gagtttaccc tccgtcccct gctagtggag  28500
cgggagcggg gtccctgtgt cctaactatc gcctgcaact gccctaaccc tggattacat  28560
caagatcttt gctgtcatct ctgtgctgag tttaataaac gctgagatca gaatctactg  28620
gggctcctgt cgccatcctg tgaacgccac cgtcttcacc caccccgacc aggcccaggc  28680
gaacctcacc tgcggtctgc atcggagggc caagaagtac ctcacctggt acttcaacgg  28740 caccccttt gtggtttaca acagcttcga cgggacgga gtctccctga aagaccagct    28800
ctccggtctc agctactcca tccacaagaa caccacccctc caactcttcc ctccctacct  28860
gccgggaacc tacgagtgcg tcaccggccg ctgcacccac ctcacccgcc tgatcgtaaa  28920
ccagagcttt ccgggaacag ataactccct cttccccaga acaggaggtg agctcaggaa  28980 actcccggg gaccagggcg gagacgtacc ttcgacccctt gtggggttag gattttttat   29040
taccgggttg ctggctcttt taatcaaagt ttccttgaga tttgttcttt ccttctacgt  29100
gtatgaacac ctcaacctcc aataactcta cccctttctcc ggaatcaggt gacttctctg  29160
aaatcgggct tggtgtgctg cttactctgt tgatttttt ccttatcata ctcagccttc     29220
tgtgcctcag gctcgccgcc tgctgcgcac acatctatat ctactgctgg ttgctcaagt  29280 gcagggtcg ccacccaaga tgaacaggta catggtccta tcgatcctag gcctgctggc    29340
cctggcggcc tgcagcgccg ccaaaaaaga gattacctttt gaggagcccg cttgcaatgt  29400
aactttcaag cccgagggtg accaatgcac caccctcgtc aaatgcgtta ccaatcatga  29460
gaggctgcgc atcgactaca aaaacaaaac tggccagttt gcggtctata gtgtgtttac  29520
gcccggagac ccctctaact actctgtcac cgtcttccag ggcggacagt ctaagatatt    29580
caattacact ttccctttt atgagttatg cgatgcggtc atgtacatgt caaaacagta    29640
caacctgtgg cctccctctc cccaggcgtg tgtggaaaat actgggtctt actgctgtat  29700
ggctttcgca atcactacgc tcgctctaat ctgcacggtg ctatacataa aattcaggca   29760
gaggcgaatc tttatcgatg aaaagaaaat gccttgatcg ctaacaccgg ctttctatct  29820
gcagaatgaa tgcaatcacc tccctactaa tcaccaccac cctccttgcg attgccatg   29880 ggttgacacg aatcgaagtg ccagtggggt ccaatgtcac catggtgggc cccgccggca  29940
attccaccct catgtgggaa aaatttgtcc gcaatcaatg ggttcatttc tgctctaacc  30000
gaatcagtat caagcccaga gccatctgcg atgggcaaaa tctaactctg atcaatgtgc  30060
aaatgatgga tgctgggtac tattacgggc agcggggaga aatcattaat tactggcgac  30120
cccacaagga ctacatgctg catgtagtcg aggcacttcc cactaccacc cccactacca   30180
cctctcccac caccaccacc actactacta ctactactac tactactact actaccacta   30240
ccgctgcccg ccataccgc aaaagcacca tgattagcac aaagcccct cgtgctcact    30300
```

```
cccacgccgg cgggcccatc ggtgcgacct cagaaaccac cgagctttgc ttctgccaat   30360
gcactaacgc cagcgctcat gaactgttcg acctggagaa tgaggatgtc cagcagagct   30420
ccgcttgcct gacccaggag gctgtggagc ccgttgccct gaagcagatc ggtgattcaa   30480
taattgactc ttcttctttt gccactcccg aataccctcc cgattctact ttccacatca   30540
cgggtaccaa agaccctaac ctctctttct acctgatgct gctgctctgt atctctgtgg   30600
tctcttccgc gctgatgtta ctggggatgt tctgctgcct gatctgccgc agaaagagaa   30660
aagctcgctc tcagggccaa ccactgatgc ccttccccta cccccggat tttgcagata    30720 acaagatatg agctcgctgc tgacactaac cgctttacta gcctgcgctc taaccccttgt  30780 cgcttgcgac tcgagattcc acaatgtcac agctgtggca ggagaaaatg ttactttcaa   30840
ctccacggcc gatacccagt ggtcgtggag tggctcaggt agctacttaa ctatctgcaa   30900
tagctccact tcccccggca tatccccaac caagtaccaa tgcaatgcca gcctgttcac   30960
cctcatcaac gcttccaccc tggacaatgg actctatgta ggctatgtac cctttggtgg   31020
gcaaggaaag acccacgctt acaacctgga agttcgccag cccagaacca ctacccaagc   31080
ttctcccacc accaccacca ccaccaccat caccagcagc agcagcagca gcagccacag   31140
cagcagcagc agattattga ctttggtttt ggccagctca tctgccgcta cccaggccat   31200
ctacagctct gtgcccgaaa ccactcagat ccaccgccca gaaacgacca ccgccaccac   31260
cctacacacc tccagcgatc agatgccgac caacatcacc cccttggctc ttcaaatggg   31320
acttacaagc cccactccaa aaccagtgga tgcggccgag gtctccgccc tcgtcaatga   31380
ctgggcgggg ctgggaatgt ggtggttcgc cataggcatg atggcgctct gcctgcttct   31440
gctctggctc atctgctgcc tccaccgcag gcgagccaga ccccccatct atagacccat   31500
cattgtcctg aaccccgata atgatgggat ccatagattg gatggcctga aaaacctact   31560
tttttctttt acagtatgat aaattgagac atgcctcgca ttttcttgta catgttcctt   31620
ctcccacctt ttctggggtg ttctacgctg gccgctgtgt ctcacctgga ggtagactgc   31680
ctctcaccct tcactgtcta cctgctttac ggattggtca ccctcactct catctgcagc   31740
ctaatcacag taatcatcgc cttcatccag tgcattgatt acatctgtgt gcgcctcgca   31800
tacttcagac accacccgca gtaccgagac aggaacattg cccaacttct aagactgctc   31860
taatcatgca taagactgtg atctgccttc tgatcctctg catcctgccc accctcacct   31920
cctgccagta caccacaaaa tctccgcgca aaagacatgc ctcctgccgc ttcacccaac   31980
tgtggaatat acccaaatgc tacaacgaaa agagcgagct ctccgaagct tggctgtatg   32040
gggtcatctg tgtcttagtt ttctgcagca ctgtctttgc cctcataatc taccccact    32100 ttgatttggg atggaacgcg atcgatgcca tgaattaccc cacctttccc gcacccgaga   32160
taattccact gcgacaagtt gtacccgttg tcgttaatca acgcccccca tccctacgc    32220 ccactgaaat cagctacttt aacctaacag gcggagatga ctgacgccct agatctagaa   32280
atggacggca tcagtaccga gcagcgtctc ctagagaggc gcaggcaggc ggctgagcaa   32340
gagcgcctca atcaggagct ccgagatctc gttaacctgc accagtgcaa aagaggcatc   32400
ttttgtctgg taaagcaggc caaagtcacc tacgagaaga ccggcaacag ccaccgcctc   32460
agttacaaat tgcccaccca cgccagaag  ctggtgctca tggtgggtga gaatcccatc   32520
accgtcaccc agcactcggt agagaccgag gggtgtctgc actcccctg tcggggtcca   32580 gaagacctct gcaccctggt aaagaccctg tgcggtctca gagatttagt ccccttaac    32640 taatcaaaca ctggaatcaa taaaagaat cacttactta aaatcagaca gcaggtctct    32700
```

```
gtccagttta ttcagcagca cctccttccc ctcctcccaa ctctggtact ccaaacgcct   32760
tctggcggca aacttcctcc acaccctgaa gggaatgtca gattcttgct cctgtccctc   32820
cgcacccact atcttcatgt tgttgcagat gaagcgcacc aaaacgtctg acgagagctt   32880
caaccccgtg taccoctatg acacggaaag cggcoctccc tccgtccctt tcctcacccc   32940
tcccttcgtg tctcccgatg gattccaaga aagtccccc ggggtcctgt ctctgaacct   33000
ggccgagccc ctggtcactt cccacggcat gctcgccctg aaaatgggaa gtggcctctc   33060
cctggacgac gctggcaacc tcacctctca agatatcacc accgctagcc ctccctcaa   33120 aaaaaccaag accaacctca gcctagaaac ctcatccccc ctaactgtga gcacctcagg   33180
cgccctcacc gtagcagccg ccgctcccct ggcggtggcc ggcacctccc tcaccatgca   33240
atcagaggcc cccctgacag tacaggatgc aaaactcacc ctggccacca aggcccct   33300 gaccgtgtct gaaggcaaac tggccttgca acatcggcc ccgctgacgg ccgctgacag   33360 cagcacoctc acagtcagtg ccacaccacc ccttagcaca agcaatggca gcttgggtat   33420
tgacatgcaa gcccccattt acaccaccaa tggaaaacta ggacttaact ttggcgctcc   33480
cctgcatgtg gtagacagcc taaatgcact gactgtagtt actggccaag gtcttacgat   33540
aaacggaaca gccctacaaa ctagagtctc aggtgccctc aactatgaca catcaggaaa   33600
cctagaattg agagctgcag ggggtatgcg agttgatgca aatggtcaac ttatccttga   33660
tgtagcttac ccatttgatg cacaaaacaa tctcagcctt aggcttggac agggaccct   33720 gtttgttaac tctgcccaca acttggatgt taactacaac agaggcctct acctgttcac   33780
atctggaaat accaaaaagc tagaagttaa tatcaaaaca gccaagggtc tcatttatga   33840
tgacactgct atagcaatca atgcgggtga tgggctacag tttgactcag gctcagatac   33900
aaatccatta aaaactaaac ttggattagg actggattat gactccagca gagccataat   33960
tgctaaactg ggaactggcc taagctttga caacacaggt gccatcacag taggcaacaa   34020
aaatgatgac aagcttacct tgtggaccac accagaccca tcccctaact gtagaatcta   34080
ttcagagaaa gatgctaaat tcacacttgt tttgactaaa tgcggcagtc aggtgttggc   34140
cagcgtttct gttttatctg taaaaggtag ccttgcgccc atcagtggca cagtaactag   34200
tgctcagatt gtcctcagat ttgatgaaaa tggagttcta ctaagcaatt cttcccttga   34260
ccctcaatac tggaactaca gaaaaggtga ccttacagag ggcactgcat ataccaacgc   34320
agtgggattt atgcccaacc tcacagcata cccaaaaaca cagagccaaa ctgctaaaag   34380
caacattgta agtcaggttt acttgaatgg ggacaaatcc aaacccatga ccctcaccat   34440
taccctcaat ggaactaatg aaacaggaga tgccacagta agcacttact ccatgtcatt   34500
ctcatggaac tggaatggaa gtaattacat taatgaaacg ttccaaacca actccttcac   34560
cttctcctac atcgcccaag aataaaaagc atgacgctgt tgatttgatt caatgtgttt   34620
ctgttttatt ttcaagcaca acaaaatcat tcaagtcatt cttccatctt agcttaatag   34680
acacagtagc ttaatagacc cagtagtgca aagcccatt ctagcttata gatcagacag   34740
tgataattaa ccaccaccac caccataccct tttgattcag gaaatcatga tcatcacagg   34800
atcctagtct tcaggccgcc ccctccctcc caagacacag aatacacagt cctctccccc   34860
cgactggctt taaataacac catctggttg gtcacagaca tgttcttagg ggttatattc   34920
cacacggtct cctgccgcgc caggcgctcg tcggtgatgt tgataaactc tcccggcagc   34980
tcgctcaagt tcacgtcgct gtccagcggc tgaacctccg gctgacgcga taactgtgcg   35040
```

```
accggctgct ggacgaacgg aggccgcgcc tacaaggggg tagagtcata atcctcggtc   35100
aggatagggc ggtgatgcag cagcagcgag cgaaacatct gctgccgccg ccgctccgtc   35160
cggcaggaaa acaacacgcc ggtggtctcc tccgcgataa tccgcaccgc ccgcagcatc   35220
agcttcctcg ttctccgcgc gcagcacctc acccttatct cgctcaaatc ggcgcagtag   35280
gtacagcaca gcaccacgat gttattcatg atcccacagt gcagggcgct gtatccaaag   35340
ctcatgccgg gaaccaccgc ccccacgtgg ccatcgtacc acaagcgcac gtaaatcaag   35400
tgtcgacccc tcatgaacgc gctggacaca acattactt ccttgggcat gttgtaattc   35460
accacctccc ggtaccagat aaacctctgg ttgaacaggg caccttccac caccatcctg   35520
aaccaagagg ccagaacctg cccaccggct atgcactgca gggaacccgg gttggaacaa   35580
tgacaatgca gactccaagg ctcgtaaccg tggatcatcc ggctgctgaa ggcatcgatg   35640
ttggcacaac acagacacac gtgcatgcac tttctcatga ttagcagctc ttccctcgtc   35700
aggatcatat cccaaggaat aacccattct tgaatcaacg taaaacccac acagcaggga   35760
aggcctcgca cataactcac gttgtgcatg gtcagcgtgt tgcattccgg aaacagcgga   35820
tgatcctcca gtatcgaggc gcgggtctcc ttctcacagg gaggtaaagg gtccctgctg   35880
tacggactgc gccgggacga ccgagatcgt gttgagcgta gtgtcatgga aaagggaacg   35940
ccggacgtgg tcatacttct tgaagcagaa ccaggttcgc gcgtggcagg cctccttgcg   36000
tctgcggtct cgccgtctag ctcgctccgt gtgatagttg tagtacagcc actcccgcag   36060
agcgtcgagg cgcaccctgg cttccggatc tatgtagact ccgtcttgca ccgcggccct   36120
gataatatcc accaccgtag aataagcaac acccagccaa gcaatacact cgctctgcga   36180
gcggcagaca ggaggagcgg gcagagatgg gagaaccatg ataaaaaact tttttttaaag   36240 aatattttcc aattcttcga aagtaagatc tatcaagtgg cagcgctccc ctccactggc   36300
gcggtcaaac tctacggcca aagcacagac aacggcattt ctaagatgtt ccttaatggc   36360
gtccaaaaga cacaccgctc tcaagttgca gtaaactatg aatgaaaacc catccggctg   36420
attttccaat atagacgcgc cggcagcgtc caccaaaccc agataatttt cttctctcca   36480
gcggtttacg atctgtctaa gcaaatccct tatatcaagt ccgaccatgc caaaaatctg   36540
ctcaagagcg ccctccacct tcatgtacaa gcagcgcatc atgattgcaa aaattcaggt   36600
tcttcagaga cctgtataag attcaaaatg ggaacattaa caaaaattcc tctgtcgcgc   36660
agatcccttc gcagggcaag ctgaacataa tcagacaggt ccgaacggac cagtgaggcc   36720
aaatccccac caggaaccag atccagagac cctatactga ttatgacgcg catactcggg   36780
gctatgctga ccagcgtagc gccgatgtag gcgtgctgca tgggcggcga gataaaatgc   36840
aaagtgctgg ttaaaaaatc aggcaaagcc tcgcgcaaaa aagctaacac atcataatca   36900
tgctcatgca ggtagttgca ggtaagctca ggaaccaaaa cggaataaca cacgattttc   36960
ctctcaaaca tgacttcgcg gatactgcgt aaaacaaaaa attataaata aaaaattaat   37020
taaataactt aaacattgga agcctgtctc acaacaggaa aaaccacttt aatcaacata   37080
agacgggcca cggcatgcc ggcatagccg taaaaaaatt ggtccccgtg attaacaagt   37140
accacagaca gctccccggt catgtcgggg gtcatcatgt gagactctgt atacacgtct   37200
ggattgtgaa catcagacaa acaaagaaat cgagccacgt agcccggagg tataatcacc   37260
cgcaggcgga ggtacagcaa aacgaccccc ataggaggaa tcacaaaatt agtaggagaa   37320
aaaaatacat aaacaccaga aaaacccgt tgctgaggca aatagcgcc ctcccgatcc   37380 aaaacaacat aaagcgcttc cacaggagca gccataacaa agacccgagt cttaccagta   37440
```

```
aaagaaaaaa gatctctcaa cgcagcacca gcaccaacac ttcgcagtgt aaaaggccaa    37500
gtgccgagag agtatatata ggaataaaaa gtgacgtaaa cgggcaaagt ccaaaaaacg    37560
cccagaaaaa ccgcacgcga acctacgccc cgaaacgaaa gccaaaaaac actagacact    37620
cccttccggc gtcaacttcc gctttcccac gctacgtcac ttcccccggt caaacaaact    37680
acatatcccg aacttccaag tcgccacgcc caaaacaccg cctacacctc cccgcccgcc    37740
ggcccgcccc cggacccgcc tcccgccccg cgccgcccat ctcattatca tattggcttc    37800
aatccaaaat aaggtatatt attgatgatg                                    37830

<210> SEQ ID NO 11
<211> LENGTH: 37559
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
catcatcaat aatataccttt attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag     180
tgacgttttc cgtgcgcgac aacgcccccg ggaagtgaca tttttcccgc ggttttttacc    240 ggatgttgta gtgaatttgg gcgtaaccaa gtaagatttg gccatttttcg cgggaaaact    300 gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660 cgaccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta taagcaga gctctcccta tcagtgatag   1140 agatctcct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccagatat cgccaccatg gaactgctga tcctgaaggc caacgccatc   1380
accaccatcc tgaccgccgt gaccttctgc ttcgccagcg ccagaacat caccgaggaa   1440 ttctaccaga gcacctgtag cgccgtgagc aagggctacc tgagcgccct gagaaccggc   1500
tggtacacca gcgtgatcac catcgagctg agcaacatca agaaaacaa gtgcaacggc   1560
```

```
accgacgcca aagtgaagct gatcaagcag gaactggaca agtacaagaa cgccgtgacc    1620
gagctgcagc tgctgatgca gagcaccccc gccaccaaca accgggccag acgggagctg    1680
ccccggttca tgaactacac cctgaacaac gccaaaaaga ccaacgtgac cctgagcaag    1740
aagcggaagc ggcggttcct gggctttctg ctgggcgtgg gcagcgccat tgccagcggc    1800
gtggccgtgt ctaaggtgct gcacctggaa ggcgaagtga acaagatcaa gagcgccctg    1860
ctgagcacca acaaggccgt ggtgtccctg agcaacggcg tgagcgtgct gaccagcaag    1920
gtgctggatc tgaagaacta catcgacaag cagctgctgc ccatcgtgaa caagcagagc    1980
tgcagcatca gcaacatcga cagtgatc gagttccagc agaagaacaa ccggctgctg    2040
gaaatcaccc gggagttcag cgtgaacgcc ggcgtgacca cccctgtgtc cacctacatg    2100
ctgaccaaca gcgagctgct gagcctgatc aacgacatgc ccatcaccaa cgaccagaaa    2160
aagctgatga gcaacaacgt gcagatcgtg cggcagcaga gctactccat catgtccatc    2220
atcaaagaag aggtgctggc ctacgtggtg cagctgcccc tgtacggcgt gatcgacacc    2280
ccctgctgga agctgcacac cagcccctg tgcaccacca acaccaaaga gggcagcaac    2340
atctgcctga cccggaccga cagaggctgg tactgcgaca cgccggcag cgtgtcattc    2400 tttccacagg ccgagacatg caaggtgcag agcaaccggg tgttctgcga caccatgaac    2460
agcctgaccc tgcccctccga agtgaacctg tgcaacgtgg acatcttcaa ccccaagtac    2520
gactgcaaga tcatgacctc caagaccgac gtgtccagct ccgtgatcac ctccctgggc    2580
gccatcgtgt cctgctacgg caagaccaag tgcaccgcca gcaacaagaa ccggggcatc    2640
atcaagacct tcagcaacgg ctgcgactac gtgtccaaca ggggggtgga caccgtgtcc    2700
gtgggcaaca ccctgtacta cgtgaacaaa caggaaggca gagcctgta cgtgaagggc    2760 gagcccatca tcaacttcta cgaccccctg gtgttcccca cgacgagtt cgacgccagc    2820 atcagccagg tgaacgagaa gatcaaccag agcctggcct tcatccggaa gtccgacgag    2880
ctgctgcaca atgtgaatgc cggcaagtcc accaccaacc ggaagcggag agcccctgtg    2940
aagcagaccc tgaacttcga cctgctgaag ctggccggcg acgtggagag caatcccggc    3000
cctatggccc tgagcaaagt gaaactgaac gatacactga acaaggacca gctgctgtcc    3060
agcagcaagt acaccatcca gcggagcacc ggcgacagca tcgatacccc caactacgac    3120
gtgcagaagc acatcaacaa gctgtgcggc atgctgctga tcacagagga cgccaaccac    3180
aagttcaccg gcctgatcgg catgctgtac gccatgagcc ggctgggccg ggaggacacc    3240
atcaagatcc tgcgggacgc cggctaccac gtgaaggcca atggcgtgga cgtgaccaca    3300
caccggcagg acatcaacgg caaagaaatg aagttcgagg tgctgaccct ggccagcctg    3360
accaccgaga tccagatcaa tatcgagatc gagagccgga agtcctacaa gaaaatgctg    3420
aaagaaatgg gcgaggtggc ccccgagtac agacacgaca gccccgactg cggcatgatc    3480
atcctgtgta tcgccgccct ggtgatcaca aagctggccg ctggcgacag atctggcctg    3540
acagccgtga tcagacgggc caacaatgtg ctgaagaacg agatgaagcg gtacaagggc    3600
ctgctgccca aggacattgc caacagcttc tacgaggtgt cgagaagta cccccacttc    3660 atcgacgtgt tcgtgcactt cggcattgcc cagagcagca ccagaggcgg ctccagagtg    3720
gagggcatct tcgccggcct gttcatgaac gcctacggcg ctggccaggt gatgctgaga    3780
tggggcgtgc tggccaagag cgtgaagaac atcatgctgg ccacgccag cgtgcaggcc    3840 gagatggaac aggtggtgga ggtgtacgag tacgcccaga gctgggcgg agaggccggc    3900 ttctaccaca tcctgaacaa ccctaaggcc tccctgctgt ccctgaccca gttcccccac    3960
```

```
ttctccagcg tggtgctggg aaatgccgcc ggactgggca tcatgggcga gtaccggggc    4020 accccccagaa accaggacct gtacgacgcc gccaaggcct acgccgagca gctgaaagaa    4080
aacggcgtga tcaactacag cgtgctggac ctgaccgctg aggaactgga agccatcaag    4140
caccagctga acccccaagga caacgacgtg agctgggag gcggaggatc tggcggcgga    4200
ggcatgagca gacggaaccc ctgcaagttc gagatccggg ccactgcct gaacggcaag    4260 cggtgccact tcagccacaa ctacttcgag tggcccctc atgctctgct ggtgcggcag    4320
aacttcatgc tgaaccggat cctgaagtcc atggacaaga gcatcgacac cctgagcgag    4380
atcagcggag ccgccgagct ggacagaacc gaggaatatg ccctgggcgt ggtgggagtg    4440
ctggaaagct acatcggctc catcaacaac atcacaaagc agagcgcctg cgtggccatg    4500
agcaagctgc tgacagagct gaacagcgac gacatcaaga agctgaggga caacgaggaa    4560
ctgaacagcc ccaagatccg ggtgtacaac accgtgatca gctacattga gcaaccgc    4620 aagaacaaca agcagaccat ccatctgctg aagcggctgc ccgccgacgt gctgaaaaag    4680
accatcaaga cacccctgga catccacaag tccatcacca tcaacaatcc caaagaaagc    4740
accgtgtctg acaccaacga tcacgccaag aacaacgaca ccacctgatg agcggccgcg    4800
atctgctgtg ccttctagtt gccagccatc tgttgtttgc ccctcccccg tgccttcctt    4860
gaccctggaa ggtgccactc ccactgtcct ttcctaataa aatgaggaaa ttgcatcgca    4920
ttgtctgagt aggtgtcatt ctattctggg gggtggggtg gggcaggaca gcaaggggga    4980
ggattgggaa gacaatagca ggcatgctgg ggatgcggtg ggctctatgg ccgatcagcg    5040
atcgctgagg tgggtgagtg ggcgtggcct ggggtggtca tgaaaatata taagttgggg    5100
gtcttagggt ctcttttattt tgttgcaga gaccgccgga gccatgagcg ggagcagcag    5160
cagcagcagt agcagcagcg ccttggatgg cagcatcgtg agcccttatt tgacgacgcg    5220
gatgccccac tgggccgggg tgcgtcagaa tgtgatgggc tccagcatcg acggccgacc    5280
cgtcctgccc gcaaattccg ccacgctgac ctatgcgacc gtcgcgggga cgccgttgga    5340
cgccaccgcc gccgccgccg ccaccgcagc cgcctcggcc gtgcgcagcc tggccacgga    5400 cttttgcattc ctgggaccac tggcgacagg ggctacttct cgggccgctg ctgccgccgt    5460
tcgcgatgac aagctgaccg ccctgctggc gcagttggat gcgcttactc gggaactggg    5520
tgacctttct cagcaggtca tggccctgcg ccagcaggtc tcctccctgc aagctggcgg    5580
gaatgcttct cccacaaatg ccgtttaaga taaataaaac cagactctgt ttggattaaa    5640
gaaaagtagc aagtgcattg ctctctttat ttcataattt tccgcgcgcg ataggcccta    5700
gaccagcgtt ctcggtcgtt gagggtgcgg tgtatcttct ccaggacgtg gtagaggtgg    5760
ctctggacgt tgagatacat gggcatgagc ccgtcccggg ggtggaggta gcaccactgc    5820
agagcttcat gctccggggt ggtgttgtag atgatccagt cgtagcagga gcgctgggca    5880
tggtgcctaa aaatgtcctt cagcagcagg ccgatgccca gggggaggcc cttggtgtaa    5940
gtgtttacaa aacggttaag ttgggaaggg tgcattcggg gagagatgat gtgcatcttg    6000
gactgtattt ttagattggc gatgtttccg cccagatccc ttctgggatt catgttgtgc    6060
aggaccacca gtacagtgta tccggtgcac ttggggaatt tgtcatgcag cttagaggga    6120
aaagcgtgga agaacttgga gacgcctttg tggcctccca gattttccat gcattcgtcc    6180
atgatgatgg caatgggccc gcgggaggca gcttgggcaa agatatttct ggggtcgctg    6240
acgtcgtagt tgtgttccag ggtgaggtcg tcataggcca tttttacaaa gcgcgggcgg    6300
```

```
agggtgcccg actgggggat gatggtcccc tctggccctg gggcgtagtt gccctcgcag    6360
atctgcattt cccaggcctt aatctcggag gggggaatca tatccacctg cggggcgatg    6420
aagaaaacgg tttccggagc cggggagatt aactgggatg agagcaggtt tctaagcagc    6480
tgtgattttc cacaaccggt gggcccataa ataacaccta taaccggttg cagctggtag    6540
tttagagagc tgcagctgcc gtcgtcccgg aggagggggg ccacctcgtt gagcatgtcc    6600
ctgacgcgca tgttctcccc gaccagatcc gccagaaggc gctcgccgcc cagggacagc    6660
agctcttgca aggaagcaaa gttttcagc ggcttgaggc cgtccgccgt gggcatgttt     6720
ttcagggtct ggctcagcag ctccaggcgg tcccagagct cggtgacgtg ctctacggca    6780
tctctatcca gcatatctcc tcgtttcgcg ggttggggcg actttcgctg tagggcacca    6840
agcggtggtc gtccagcggg gccagagtca tgtccttcca tgggcgcagg gtcctcgtca    6900
gggtggtctg ggtcacggtg aagggtgcg ctccgggctg agcgcttgcc aaggtgcgct     6960
tgaggctggt tctgctggtg ctgaagcgct gccggtcttc gccctgcgcg tcggccaggt    7020
agcatttgac catggtgtca tagtccagcc cctccgcggc gtgtcccttg gcgcgcagct    7080
tgcccttgga ggtggcgccg cacgaggggc agagcaggct cttgagcgcg tagagcttgg    7140
gggcgaggaa gaccgattcg ggggagtagg cgtccgcgcc gcagacccg cacacggtct     7200 cgcactccac cagccaggtg agctcggggc gcgccgggtc aaaaaccagg tttccccat    7260 gcttttttgat gcgtttctta cctcgggtct ccatgaggtg gtgtccccgc tcggtgacga    7320
agaggctgtc cgtgtctccg tagaccgact tgagggggtct tttctccagg ggggtccctc   7380
ggtcttcctc gtagaggaac tcggaccact ctgagacgaa ggcccgcgtc caggccagga    7440
cgaaggaggc tatgtgggag gggtagcggt cgttgtccac taggggtcc accttctcca     7500 aggtgtgaag acacatgtcg ccttcctcgg cgtccaggaa ggtgattggc ttgtaggtgt    7560
aggccacgtg accggggggtt cctgacgggg gggtataaaa gggggtgggg gcgcgctcgt   7620
cgtcactctc ttccgcatcg ctgtctgcga gggccagctg ctggggtgag tattccctct    7680
cgaaggcggg catgacctcc gcgctgaggt tgtcagtttc caaaaacgag gaggatttga    7740
tgttcacctg tcccgaggtg atacctttga gggtacccgc gtccatctgg tcagaaaaca    7800
cgatcttttt attgtccagc ttggtggcga acgacccgta gagggcgttg gagagcagct    7860
tggcgatgga gcgcagggtc tggttcttgt ccctgtcggc gcgctccttg gccgcgatgt    7920
tgagctgcac gtactcgcgc gcgacgcagc gccactcggg gaagacggtg gtgcgctcgt    7980
cgggcaccag gcgcacgcgc cagccgcggt tgtgcagggt gaccaggtcc acgctggtgg    8040
cgacctcgcc gcgcaggcgc tcgttggtcc agcagagacg gccgcccttg cgcgagcaga    8100
aggggggcag ggggtcgagc tgggtctcgt ccgggggtc cgcgtccacg gtgaaaaccc     8160
cggggcgcag gcgcgcgtcg aagtagtcta tcttgcaacc ttgcatgtcc agcgcctgct    8220
gccagtcgcg ggcggcgagc gcgcgctcgt agggggttgag cggcgggccc cagggcatgg   8280
ggtgggtgag tgcggaggcg tacatgccgc agatgtcata gacgtagagg ggctcccgca    8340
ggaccccgat gtaggtgggg tagcagcggc cgccgcggat gctggcgcgc acgtagtcat    8400
acagctcgtg cgaggggggcg aggaggtcgg ggcccaggtt ggtgcgggcg gggcgctccg   8460
cgcggaagac gatctgcctg aagatggcat gcgagttgga agagatggtg gggcgctgga    8520
agacgttgaa gctggcgtcc tgcaggccga cggcgtcgcg cacgaaggag cgtaggagt     8580 cgcgcagctt gtgtaccagc tcggcggtga cctgcacgtc gagcgcgcag tagtcgaggg    8640
tctcgcggat gatgtcatat ttagcctgcc ccttctttt ccacagctcg cggttgagga     8700
```

```
caaactcttc gcggtctttc cagtactctt ggatcgggaa accgtccggt tccgaacggt   8760
aagagcctag catgtagaac tggttgacgg cctggtaggc gcagcagccc ttctccacgg   8820
ggagggcgta ggcctgcgcg gccttgcgga gcgaggtgtg ggtcagggcg aaggtgtccc   8880
tgaccatgac tttgaggtac tggtgcttga agtcggagtc gtcgcagccg ccccgctccc   8940
agagcgagaa gtcggtgcgc ttcttggagc ggggttggg cagagcgaag gtgacatcgt   9000
tgaagaggat tttgcccgcg cggggcatga agttgcgggt gatgcggaag ggccccggca   9060
cttcagagcg gttgttgatg acctgggcgg cgagcacgat ctcgtcgaag ccgttgatgt   9120
tgtggcccac gatgtagagt tccaggaagc ggggccggcc ctttacggtg gcagcttct    9180
ttagctcttc gtaggtgagc tcctcgggcg aggcgaggcc gtgctcggcc agggcccagt   9240
ccgcgaggtg cgggttgtct ctgaggaagg acttccagag gtcgcgggcc aggagggtct   9300
gcaggcggtc tctgaaggtc ctgaactggc ggcccacggc cattttttcg ggggtgatgc   9360
agtagaaggt gaggggtct tgctgccagc ggtcccagtc gagctgcagg gcgaggtcgc   9420
gcgcggcggt gaccaggcgc tcgtcgcccc cgaatttcat gaccagcatg aagggcacga   9480
gctgctttcc gaaggccccc atccaagtgt aggtctctac atcgtaggtg acaaagaggc   9540
gctccgtgcg aggatgcgag ccgatcggga agaactggat ctcccgccac cagttggagg   9600
agtggctgtt gatgtggtgg aagtagaagt cccgtcgccg ggccgaacac tcgtgctggc   9660
ttttgtaaaa gcgagcgcag tactggcagc gctgcacggg ctgtacctca tgcacgagat   9720
gcacctttcg cccgcgcacg aggaagccga ggggaaatct gagcccccg cctggctcgc    9780
ggcatggctg gttctcttct actttggatg cgtgtccgtc tccgtctggc tcctcgaggg   9840
gtgttacggt ggagcggacc accacgccgc gcgagccgca ggtccagata tcggcgcgcg   9900
gcggtcggag tttgatgacg acatcgcgca gctgggagct gtccatggtc tggagctccc   9960
gcggcggcgg caggtcagcc gggagttctt gcaggttcac ctcgcagagt cgggccaggg  10020
cgcggggcag gtctaggtgg tacctgatct ctaggggcgt gttggtggcg gcgtcgatgg  10080
cttgcaggag cccgcagccc cgggggggcga cgacggtgcc ccgcggggtg gtggtggtgg  10140
tggcggtgca gctcagaagc ggtgccgcgg gcggcccccc ggaggtaggg ggggctccgg  10200
tcccgcgggc aggggcggca gcggcacgtc ggcgtggagc gcgggcagga gttggtgctg  10260
tgcccggagg ttgctggcga aggcgacgac gcggcggttg atctcctgga tctggcgcct  10320
ctgcgtgaag acgacgggcc cggtgagctt gaacctgaaa gagagttcga cagaatcaat  10380
ctcggtgtca ttgaccgcgg cctggcgcag gatctcctgc acgtctcccg agttgtcttg  10440
gtaggcgatc tcggccatga actgctcgat ctcttcctcc tggaggtctc cgcgtccggc  10500
gcgttccacg gtgccgcca ggtcgttgga gatgcgcccc atgagctgcg agaaggcgtt   10560
gagtccgccc tcgttccaga ctcggctgta gaccacgccc ccctggtcat cgcgggcgcg  10620
catgaccacc tgcgcgaggt tgagctccac gtgccgcgcg aagacggcgt agttgcgcag  10680
acgctggaag aggtagttga gggtggtggc ggtgtgctcg gccacgaaga agttcatgac  10740
ccagcggcgc aacgtggatt cgttgatgtc ccccaaggcc tccagccgtt ccatggcctc  10800
gtagaagtcc acgcgaagt tgaaaaactg ggagttgcgc gccgacacgg tcaactcctc   10860
ctccagaaga cggatgagct cggcgacggt gtcgcgcacc tcgcgctcga aggctatggg  10920
gatctcttcc tccgctagca tcaccacctc ctcctcttcc tcctcttctg gcacttccat  10980
gatggcttcc tcctcttcgg ggggtggcgg cggcggcggt gggggagggg gcgctctgcg  11040
```

```
ccggcggcgg cgcaccggga ggcggtccac gaagcgcgcg atcatctccc cgcggcggcg   11100
gcgcatggtc tcggtgacgg cgcggccgtt ctcccggggg cgcagttgga agacgccgcc   11160
ggacatctgg tgctggggcg ggtggccgtg aggcagcgag acggcgctga cgatgcatct   11220
caacaattgc tgcgtaggta cgccgccgag ggacctgagg gagtccatat ccaccggatc   11280
cgaaaacctt tcgaggaagg cgtctaacca gtcgcagtcg caaggtaggc tgagcaccgt   11340
ggcgggcggc gggggtgggg gggagtgtct ggcggaggtg ctgctgatga tgtaattgaa   11400
gtaggcggac ttgacacggc ggatggtcga caggagcacc atgtccttgg gtccggcctg   11460
ctggatgcgg aggcggtcgg ctatgcccca ggcttcgttc tggcatcggc gcaggtcctt   11520
gtagtagtct tgcatgagcc tttccaccgg cacctcttct ccttcctctt ctgcttcttc   11580
catgtctgct tcggccctgg ggcggcgccg cgccccctg ccccccatgc gcgtgacccc   11640
gaaccccctg agcggttgga gcagggccag gtcggcgacg acgcgctcgg ccaggatggc   11700
ctgctgcacc tgcgtgaggg tggtttggaa gtcatccaag tccacgaagc ggtggtaggc   11760
gcccgtgttg atggtgtagg tgcagttggc catgacggac cagttgacgg tctggtggcc   11820
cggttgcgac atctcggtgt acctgagtcg cgagtaggcg cgggagtcga agacgtagtc   11880
gttgcaagtc cgcaccaggt actggtagcc caccaggaag tgcggcggcg gctggcggta   11940
gaggggccag cgcagggtgg cgggggctcc ggggccagg tcttccagca tgaggcggtg   12000
gtaggcgtag atgtacctgg acatccaggt gatacccgcg gcggtggtgg aggcgcgcgg   12060
gaagtcgcgc acccggttcc agatgttgcg caggggcaga aagtgctcca tggtaggcgt   12120
gctctgtcca gtcagacgcg cgcagtcgtt gatactctag accagggaaa acgaaagccg   12180
gtcagcgggc actcttccgt ggtctggtga atagatcgca agggtatcat ggcggagggc   12240
ctcggttcga gccccgggtc cgggccgac ggtccgccat gatccacgcg gttaccgccc   12300
gcgtgtcgaa cccaggtgtg cgacgtcaga caacggtgga gtgttccttt tggcgttttt   12360
ctggccgggc gccggcgccg cgtaagagac taagccgcga aagcgaaagc agtaagtggc   12420
tcgctccccg tagccggagg gatccttgct aagggttgcg ttgcggcgaa ccccggttcg   12480
aatcccgtac tcgggccggc cggacccgcg gctaaggtgt tggattggcc tccccctcgt   12540
ataaagaccc cgcttgcgga ttgactccgg acacggggac gagcccctt tattttgct    12600 ttccccagat gcatccggtg ctgcggcaga tgcgccccc gccccagcag cagcaacaac    12660
accagcaaga gcggcagcaa cagcagcggg agtcatgcag ggcccctca cccaccctcg    12720 gcgggccggc cacctcggcg tccgcggccg tgtctggcgc ctgcggcggc ggcgggggc    12780 cggctgacga ccccgaggag cccccgcggc gcagggccag acactacctg gacctggagg   12840
agggcgaggg cctggcgcgg ctgggggcgc cgtctcccga gcgccacccg cgggtgcagc   12900
tgaagcgcga ctcgcgcgag gcgtacgtgc ctcggcagaa cctgttcagg gaccgcgcgg   12960
gcgaggagcc cgaggagatg cgggacagga ggttcagcgc agggcgggag ctgcggcagg   13020
ggctgaaccg cgagcggctg ctgcgcgagg aggactttga gcccgacgcg cggacgggga   13080
tcagccccgc gcgcgcgcac gtggcggccg ccgacctggt gacggcgtac gagcagacgg   13140
tgaaccagga gatcaacttc caaaagagtt caacaacca cgtgcgcacg ctggtggcgc    13200
gcgaggaggt gaccatcggg ctgatgcacc tgtgggactt tgtaagcgcg ctggtgcaga   13260
accccaacag caagcctctg acggcgcagc tgttcctgat agtgcagcac agcagggaca   13320
acgaggcgtt tagggacgcg ctgctgaaca tcaccgagcc cgagggtcgg tggctgctgg   13380
acctgattaa catcctgcag agcatagtgg tgcaggagcg cagcctgagc ctggccgaca   13440
```

```
aggtggcggc catcaactac tcgatgctga gcctgggcaa gttttacgcg cgcaagatct   13500
accagacgcc gtacgtgccc atagacaagg aggtgaagat cgacggtttt tacatgcgca   13560
tggcgctgaa ggtgctcacc ctgagcgacg acctgggcgt gtaccgcaac gagcgcatcc   13620
acaaggccgt gagcgtgagc cggcggcgcg agctgagcga ccgcgagctg atgcacagcc   13680
tgcagcgggc gctggcgggc gccggcagcg gcgacaggga ggcggagtcc tacttcgatg   13740 cggggggcgga cctgcgctgg gcgcccagcc ggcgggccct ggaggccgcg ggggtccgcg   13800
aggactatga cgaggacggc gaggaggatg aggagtacga gctagaggag ggcgagtacc   13860
tggactaaac cgcgggtggt gtttccggta gatgcaagac ccgaacgtgg tggacccggc   13920
gctgcgggcg gctctgcaga gccagccgtc cggccttaac tcctcagacg actggcgaca   13980
ggtcatggac cgcatcatgt cgctgacggc gcgtaacccg gacgcgttcc ggcagcagcc   14040
gcaggccaac aggctctccg ccatcctgga ggcggtggtg cctgcgcgct cgaaccccac   14100
gcacgagaag gtgctggcca tagtgaacgc gctggccgag aacagggcca tccgcccgga   14160
cgaggccggg ctggtgtacg acgcgctgct gcagcgcgtg gcccgctaca acagcggcaa   14220
cgtgcagaca aacctggacc ggctggtggg ggacgtgcgc gaggcggtgg cgcagcgcga   14280
gcgcgcggat cggcagggca acctgggctc catggtggcg ctgaatgcct tcctgagcac   14340
gcagccggcc aacgtgccgc gggggcagga agactacacc aactttgtga gcgcgctgcg   14400
gctgatggtg accgagaccc cccagagcga ggtgtaccag tcgggcccgg actacttctt   14460
ccagaccagc agacagggcc tgcagacggt gaacctgagc caggcttttca agaacctgcg   14520 ggggctgtgg ggcgtgaagg cgcccaccgg cgaccgggcg acggtgtcca gcctgctgac   14580
gcccaactcg cgcctgctgc tgctgctgat cgcgccgttc acggacagcg gcagcgtgtc   14640
ccgggacacc tacctggggc acctgctgac cctgtaccgc gaggccatcg gcaggcgca   14700 ggtggacgag cacaccttcc aggagatcac cagcgtgagc cgcgcgctgg ggcaggagga   14760
cacgagcagc ctggaggcga ctctgaacta cctgctgacc aaccggcggc agaagattcc   14820
ctcgctgcac agcctgacct ccgaggagga gcgcatcttg cgctacgtgc agcagagcgt   14880
gagcctgaac ctgatgcgcg acggggtgac gcccagcgtg gcgctggaca tgaccgcgcg   14940
caacatggaa ccgggcatgt acgccgcgca ccggccttac atcaaccgcc tgatggacta   15000
cctgcatcgc gcggcggccg tgaacccga gtactttacc aacgccatcc tgaacccgca   15060
ctggctcccg ccgcccgggt tctacagcgg gggcttcgag gtcccggaga ccaacgatgg   15120
cttcctgtgg gacgacatgg acgacagcgt gttctccccg cggccgcagg cgctggcgga   15180
agcgtccctg ctgcgtccca agaaggagga ggaggaggag gcgagtcgcc gccgcggcag   15240
cagcggcgtg gcttctctgt ccgagctggg ggcggcagcc gccgcgcgcc ccgggtccct   15300
gggcggcagc ccctttccga gcctggtggg gtctctgcac agcgagcgca ccacccgccc   15360
tcggctgctg ggcgaggacg agtacctgaa taactccctg ctgcagccgg tgcgggagaa   15420
aaacctgcct cccgccttcc ccaacaacgg gatagagagc ctggtggaca agatgagcag   15480
atggaagacc tatgcgcagg agcacaggga cgcgcctgcg ctccggccgc ccacgcgcg   15540 ccagcgccac gaccggcagc gggggctggt gtgggatgac gaggactccg cggacgatag   15600
cagcgtgctg gacctgggag ggagcggcaa cccgttcgcg cacctgcgcc cccgcctggg   15660
gaggatgttt taaaaaaaaa aaaaaaagc aagaagcatg atgcaaaat taaataaaac   15720 tcaccaaggc catggcgacc gagcgttggt ttcttgtgtt cccttcagta tgcggcgcgc   15780
```

-continued

```
ggcgatgtac caggagggac ctcctccctc ttacgagagc gtggtgggcg cggcggcggc    15840
ggcgccctct tctcccttttg cgtcgcagct gctggagccg ccgtacgtgc ctccgcgcta    15900
cctgcggcct acgggggggga gaaacagcat ccgttactcg gagctggcgc ccctgttcga   15960
caccacccgg gtgtacctgg tggacaacaa gtcggcggac gtggcctccc tgaactacca    16020
gaacgaccac agcaattttt tgaccacggt catccagaac aatgactaca gcccgagcga    16080
ggccagcacc cagaccatca atctggatga ccggtcgcac tggggcggcg acctgaaaac    16140
catcctgcac accaacatgc ccaacgtgaa cgagttcatg ttcaccaata agttcaaggc    16200
gcgggtgatg gtgtcgcgct cgcacaccaa ggaagaccgg gtggagctga agtacgagtg    16260
ggtggagttc gagctgccag agggcaacta ctccgagacc atgaccattg acctgatgaa    16320
caacgcgatc gtggagcact atctgaaagt gggcaggcag aacggggtcc tggagagcga    16380
catcggggtc aagttcgaca ccaggaactt ccgcctgggg ctggaccccg tgaccgggct    16440
ggttatgccc ggggtgtaca ccaacgaggc cttccatccc gacatcatcc tgctgcccgg    16500
ctgcgggtgg gacttcactt acagccgcct gagcaacctc ctgggcatcc gcaagcggca    16560
gcccttccag gagggcttca ggatcaccta cgaggacctg gaggggggca acatccccgc    16620
gctcctcgat gtggaggcct accaggatag cttgaaggaa aatgaggcgg acaggagga    16680
taccgccccc gccgcctccg ccgccgccga gcagggcgag gatgctgctg acaccgcggc    16740
cgcggacggg gcagaggccg accccgctat ggtggtggag gctcccgagc aggaggagga    16800
catgaatgac agtgcggtgc gcggagacac cttcgtcacc cggggggagg aaaagcaagc    16860
ggaggccgag gccgcggccg aggaaaagca actggcggca gcagcggcgg cggcggcgtt    16920
ggccgcggcg gaggctgagt ctgaggggac caagcccgcc aaggagcccg tgattaagcc    16980
cctgaccgaa gatagcaaga agcgcagtta caacctgctc aaggacagca ccaacaccgc    17040
gtaccgcagc tggtacctgg cctacaacta cggcgacccg tcgacggggg tgcgctcctg    17100
gaccctgctg tgcacgccgg acgtgacctg cggctcggag caggtgtact ggtcgctgcc    17160
cgacatgatg caagaccccg tgaccttccg ctccacgcgg caggtcagca acttcccggt    17220
ggtgggcgcc gagctgctgc ccgtgcactc caagagcttc tacaacgacc aggccgtcta    17280
ctcccagctc atccgccagt tcacctctct gacccacgtg ttcaatcgct ttcctgagaa    17340
ccagattctg gcgcgcccgc ccgccccac catcaccacc gtcagtgaaa acgttcctgc    17400
tctcacagat cacgggacgc taccgctgcg caacagcatc ggaggagtcc agcgagtgac    17460
cgttactgac gccagacgcc gcacctgccc ctacgtttac aaggccttgg gcatagtctc    17520
gccgcgcgtc cttttccagcc gcactttttg agcaacacca ccatcatgtc catcctgatc    17580
tcacccagca ataactccgg ctggggactg ctgcgcgcgc ccagcaagat gttcggaggg    17640
gcgaggaagc gttccgagca gcaccccgtg cgcgtgcgcg ggcacttccg cgcccctgg    17700
ggagcgcaca aacgcggccg cgcggggcgc accaccgtgg acgacgccat cgactcggtg    17760
gtggagcagg cgcgcaacta caggcccgcg gtctctaccg tggacgcggc catccagacc    17820
gtggtgcggg gcgcgcggcg gtacgccaag ctgaagagcc gccggaagcg cgtggcccgc    17880
cgccaccgcc gccgacccgg ggccgccgcc aaacgcgccg ccgcggccct gcttcgccgg    17940
gccaagcgca cgggccgccg cgccgccatg agggccgcgc gccgcttggc cgccggcatc    18000
accgccgcca ccatggcccc ccgtacccga agacgcgcgg ccgccgccgc cgccgccgc    18060
atcagtgaca tggccagcag gcgccgggc aacgtgtact gggtgcgcga ctcggtgacc    18120
ggcacgcgcg tgcccgtgcg cttccgcccc ccgcggactt gagatgatgt gaaaaaacaa    18180
```

```
cactgagtct cctgctgttg tgtgtatccc agcggcggcg gcgcgcgcag cgtcatgtcc   18240
aagcgcaaaa tcaaagaaga gatgctccag gtcgtcgcgc cggagatcta tgggcccccg   18300
aagaaggaag agcaggattc gaagcccgc aagataaagc gggtcaaaaa gaaaagaaa    18360 gatgatgacg atgccgatgg ggaggtggag ttcctgcgcg ccacggcgcc caggcgcccg   18420
gtgcagtgga agggccggcg cgtaaagcgc gtcctgcgcc ccggcaccgc ggtggtcttc   18480
acgcccggcg agcgctccac ccggactttc aagcgcgtct atgacgaggt gtacggcgac   18540
gaagacctgc tggagcaggc caacgagcgc ttcggagagt ttgcttacgg gaagcgtcag   18600
cgggcgctgg ggaaggagga cctgctggcg ctgccgctgg accagggcaa ccccacccc    18660 agtctgaagc ccgtgaccct gcagcaggtg ctgccgagca gcgcaccctc cgaggcgaag   18720
cggggtctga agcgcgaggg cggcgacctg gcgcccaccg tgcagctcat ggtgcccaag   18780
cggcagaggc tggaggatgt gctggagaaa atgaaagtag accccggtct gcagccggac   18840
atcagggtcc gccccatcaa gcaggtggcg ccgggcctcg gcgtgcagac cgtggacgtg   18900
gtcatcccca ccggcaactc ccccgccgcc gccaccacta ccgctgcctc cacggacatg   18960
gagacacaga ccgatcccgc cgcagccgca gccgcagccg ccgccgcgac ctcctcggcg   19020
gaggtgcaga cggacccctg gctgccgccg gcgatgtcag ctccccgcgc gcgtcgcggg   19080
cgcaggaagt acgcgccgc caacgcgctc ctgcccgagt acgccttgca tccttccatc   19140
gcgcccaccc ccggctaccg aggctatacc taccgcccgc gaagagccaa gggttccacc   19200
cgccgtcccc gccgacgcgc cgccgccacc accgccgcc gccgccgcag acgccagccc    19260
gcactggctc cagtctccgt gaggaaagtg gcgcgcgacg gacacaccct ggtgctgccc   19320
agggcgcgct accaccccag catcgtttaa aagcctgttg tggttcttgc agatatggcc   19380
ctcacttgcc gcctccgttt cccggtgccg ggataccgag gaggaagatc gcgccgcagg   19440
aggggtctgg ccggccgcgg cctgagcgga ggcagccgcc gcgcgcaccg gcggcgacgc   19500
gccaccagcc gacgcatgcg cggcggggtg ctgcccctgt taatcccct gatcgccgcg   19560 gcgatcggcg ccgtgcccgg gatcgcctcc gtggccttgc aagcgtccca gaggcattga   19620
cagacttgca aacttgcaaa tatggaaaaa aaacccccaa taaaaaagtc tagactctca   19680
cgctcgcttg gtcctgtgac tattttgtag aatggaagac atcaactttg cgtcgctggc   19740
cccgcgtcac ggctcgcgcc cgttcctggg acactggaac gatatcggca ccagcaacat   19800
gagcggtggc gccttcagtt ggggctctct gtggagcggc attaaaagta tcgggtctgc   19860
cgttaaaaat tacggctccc gggcctggaa cagcagcacg ggccagatgt tgagagacaa   19920
gttgaaagag cagaacttcc agcagaaggt ggtggagggc ctggcctccg gcatcaacgg   19980
ggtggtggac ctggccaacc aggccgtgca gaataagatc aacagcagac tggaccccg    20040 gccgccggtg gaggaggtgc cgccggcgct ggagacggtg tcccccgatg ggcgtggcga   20100
gaagcgcccg cggcccgata gggaagagac cactctggtc acgcagaccg atgagccgcc   20160
cccgtatgag gaggccctga agcaaggtct gcccaccacg cggcccatcg cgcccatggc   20220
caccggggtg gtgggccgcc acaccccgc cacgctggac ttgcctccgc ccgccgatgt   20280
gccgcagcag cagaaggcgg cacagccggg cccgcccgcg accgcctccc gttcctccgc   20340
cggtcctctg cgccgcgcgg ccagcggccc ccgcgggggg gtcgcgaggc acggcaactg   20400
gcagagcacg ctgaacagca tcgtgggtct gggggtgcgg tccgtgaagc ccgccgatg    20460 ctactgaata gcttagctaa cgtgttgtat gtgtgtatgc gccctatgtc gccgccagag   20520
```

```
gagctgctga gtcgccgccg ttcgcgcgcc caccaccacc gccactccgc ccctcaagat   20580
ggcgacccca tcgatgatgc cgcagtggtc gtacatgcac atctcggcc  aggacgcctc   20640
ggagtacctg agccccgggc tggtgcagtt cgcccgcgcc accgagagct acttcagcct   20700
gagtaacaag tttaggaacc ccacggtggc gcccacgcac gatgtgacca ccgaccggtc   20760
tcagcgcctg acgctgcggt tcattcccgt ggaccgcgag gacaccgcgt actcgtacaa   20820
ggcgcggttc accctggccg tgggcgacaa ccgcgtgctg gacatggcct ccacctactt   20880
tgacatccgc ggggtgctgg accggggtcc cactttcaag ccctactctg gcaccgccta   20940
caactccctg gcccccaagg gcgctcccaa ctcctgcgag tgggagcaag aggaaactca   21000
ggcagttgaa gaagcagcag aagaggaaga agaagatgct gacggtcaag ctgaggaaga   21060
gcaagcagct accaaaaaga ctcatgtata tgctcaggct ccccttcctg gcgaaaaaat   21120
tagtaaagat ggtctgcaaa taggaacgga cgctacagct acagaacaaa aacctattta   21180
tgcagaccct acattccagc ccgaacccca aatcggggag tcccagtgga atgaggcaga   21240
tgctacagtc gccggcggta gagtgctaaa gaaatctact cccatgaaac catgctatgg   21300
ttcctatgca agacccacaa atgctaatgg aggtcagggt gtactaacgg caaatgccca   21360
gggacagcta gaatctcagg ttgaaatgca attcttttca acttctgaaa cgcccgtaa    21420
cgaggctaac aacattcagc ccaaattggt gctgtatagt gaggatgtgc acatggagac   21480
cccggatacg caccttcctt acaagcccgc aaaaagcgat gacaattcaa aaatcatgct   21540
gggtcagcag tccatgccca acagacctaa ttacatcggc ttcagagaca actttatcgg   21600
cctcatgtat tacaatagca ctggcaacat gggagtgctt gcaggtcagg cctctcagtt   21660
gaatgcagtg gtggacttgc aagacagaaa cacagaactg tcctaccagc tcttgcttga   21720
ttccatgggt gacagaacca gatacttttc catgtggaat caggcagtgg acagttatga   21780
cccagatgtt agaattattg aaaatcatgg aactgaagac gagctcccca actattgttt   21840
ccctctgggt ggcataggg  taactgacac ttaccaggct gttaaaacca caatggcaa    21900
taacgggggc caggtgactt ggacaaaaga tgaaactttt gcagatcgca atgaaatagg   21960
ggtgggaaac aatttcgcta tggagatcaa cctcagtgcc aacctgtgga gaaacttcct   22020
gtactccaac gtggcgctgt acctaccaga caagcttaag tacaaccccct ccaatgtgga   22080
catctctgac aaccccaaca cctacgatta catgaacaag cgagtggtgg ccccggggct   22140
ggtggactgc tacatcaacc tgggcgcgcg ctggtcgctg gactacatgg acaacgtcaa   22200
ccccttcaac caccaccgca atgcgggcct gcgctaccgc tccatgctcc tgggcaacgg   22260
gcgctacgtg cccttccaca tccaggtgcc ccagaagttc tttgccatca gaacctcct    22320
cctcctgccg ggctcctaca cctacgagtg gaacttcagg aaggatgtca acatggtcct   22380
ccagagctct ctgggtaacg atctcagggt ggacggggcc agcatcaagt tcgagagcat   22440
ctgcctctac gccaccttct tccccatggc ccacaacacg gcctcacgc tcgaggccat    22500
gctcaggaac gacaccaacg accagtcctt caatgactac ctctccgccg ccaacatgct   22560
ctaccccata cccgccaacg ccaccaacgt cccccatctcc atccctcgc gcaactgggc    22620
ggccttccgc ggctgggcct tcacccgcct caagaccaag gagacccctc cctgggctc    22680
gggattcgac ccctactaca cctactcggg ctccattccc tacctggacg gcaccttcta   22740
cctcaaccac actttcaaga aggtctcggt caccttcgac tcctcggtca gctggccggg   22800
caacgaccgt ctgctcaccc ccaacgagtt cgagatcaag cgctcggtcg acggggaggg   22860
ctacaacgtg gcccagtgca acatgaccaa ggactggttc ctggtccaga tgctggccaa   22920
```

```
ctacaacatc ggctaccagg gcttctacat cccagagagc tacaaggaca ggatgtactc    22980
cttcttcagg aacttccagc ccatgagccg gcaggtggtg gaccagacca agtacaagga    23040
ctaccaggag gtgggcatca tccaccagca caacaactcg ggcttcgtgg gctacctcgc    23100
ccccaccatg cgcgagggac aggcctaccc cgccaacttc ccctatccgc tcataggcaa    23160
gaccgcggtc gacagcatca cccagaaaaa gttcctctgc gaccgcaccc tctggcgcat    23220 cccctctcc agcaacttca tgtccatggg tgcgctctcg gacctgggcc agaacttgct    23280
ctacgccaac tccgcccacg ccctcgacat gaccttcgag gtcgaccca tggacgagcc    23340 cacccttctc tatgttctgt tcgaagtctt tgacgtggtc cgggtccacc agccgcaccg    23400
cggcgtcatc gagaccgtgt acctgcgtac gcccttctcg gccggcaacg ccaccaccta    23460
aagaagcaag ccgcagtcat cgccgcctgc atgccgtcgg gttccaccga gcaagagctc    23520
agggccatcg tcagagacct gggatgcggg ccctattttt tgggcacctt cgacaagcgc    23580
ttccctggct ttgtctcccc acacaagctg gcctgcgcca tcgtcaacac ggccggccgc    23640
gagaccgggg gcgtgcactg gctggccttc gcctggaacc cgcgctccaa acatgcttc    23700 ctctttgacc ccttcggctt ttcggaccag cggctcaagc aaatctacga gttcgagtac    23760
gagggcttgc tgcgtcgcag cgccatcgcc tcctcgcccg accgctgcgt caccctcgaa    23820
aagtccaccc agaccgtgca ggggcccgac tcggccgcct gcggtctctt ctgctgcatg    23880
tttctgcacg cctttgtgca ctggcctcag agtcccatgg accgcaaccc caccatgaac    23940
ttgctgacgg gggtgcccaa ctccatgctc cagagccccc aggtcgagcc caccctgcgc    24000
cgcaaccagg agcagctcta cagcttcctg gagccgccact cgccttactt ccgccgccac    24060
agcgcacaga tcaggagggc cacctccttc tgccacttgc aagagatgca agaagggtaa    24120
taacgatgta cacactttt ttctcaataa atggcatctt tttatttata caagctctct    24180
ggggtattca tttcccacca ccacccgccg ttgtcgccat ctggctctat ttagaaatcg    24240
aaagggttct gccgggagtc gccgtgcgcc acgggcaggg acacgttgcg atactggtag    24300
cgggtgcccc acttgaactc gggcaccacc aggcgaggca gctcggggaa gttttcgctc    24360
cacaggctgc gggtcagcac cagcgcgttc atcaggtcgg gcgccagat cttgaagtcg    24420 cagttggggc cgccgccctg cgcgcgcgag ttgcggtaca ccgggttgca gcactggaac    24480
accaacagcg ccgggtgctt cacgctggcc agcacgctgc ggtcggagat cagctcggcg    24540
tccaggtcct ccgcgttgct cagcgcgaac ggggtcatct tgggcacttg ccgccccagg    24600
aagggcgcgt gccccggttt cgagttgcag tcgcagcgca gcgggatcag caggtgcccg    24660
tgcccggact cggcgttggg gtacagcgcg cgcatgaagg cctgcatctg gcggaaggcc    24720
atctgggcct tggcgccctc cgagaagaac atgccgcagg acttgcccga gaactggttt    24780
gcggggcagc tggcgtcgtg caggcagcag cgcgcgtcgg tgttggcgat ctgcaccacg    24840
ttgcgccccc accggttctt cacgatcttg gccttggacg attgctcctt cagcgcgcgc    24900
tgcccgttct cgctggtcac atccatctcg atcacatgtt ccttgttcac catgctgctg    24960
ccgtgcagac acttcagctc gccctccgtc tcggtcagc ggtgctgcca cagcgcgcag    25020
cccgtgggct cgaaagactt gtaggtcacc tccgcgaagg actgcaggta ccctgcaaa    25080 aagcggccca tcatggtcac gaaggtcttg ttgctgctga aggtcagctg cagcccgcgg    25140
tgctcctcgt tcagccaggt cttgcacacg gccgccagcg cctccacctg gtcgggcagc    25200
atcttgaagt tcaccttcag ctcattctcc acgtggtact tgtccatcag cgtgcgcgcc    25260
```

```
gcctccatgc ccttctccca ggccgacacc agcggcaggc tcacggggtt cttcaccatc    25320
accgtggccg ccgcctccgc cgcgctttcg ctttccgccc cgctgttctc ttcctcttcc    25380
tcctcttcct cgccgccgcc cactcgcagc ccccgcacca cggggtcgtc ttcctgcagg    25440
cgctgcacct tgcgcttgcc gttgcgcccc tgcttgatgc gcacgggcgg gttgctgaag    25500
cccaccatca ccagcgcggc ctcttcttgc tcgtcctcgc tgtccagaat gacctccggg    25560
gagggggggt tggtcatcct cagtaccgag gcacgcttct ttttcttcct ggggcgttc     25620
gccagctccg cggctgcggc cgctgccgag gtcgaaggcc gagggctggg cgtgcgcggc    25680
accagcgcgt cctgcgagcc gtcctcgtcc tcctcggact cgagacggag gcgggcccgc    25740
ttcttcgggg gcgcgcgggg cggcggaggc ggcggcggcg acggagacgg ggacgagaca    25800
tcgtccaggg tgggtggacg gcgggccgcg ccgcgtccgc gctcgggggt ggtctcgcgc    25860
tggtcctctt cccgactggc catctcccac tgctccttct cctataggca gaaagagatc    25920
atggagtctc tcatgcgagt cgagaaggag gaggacagcc taaccgcccc ctctgagccc    25980
tccaccaccg ccgccaccac cgccaatgcc gccgcgacg acgcgccac cgagaccacc      26040
gccagtacca ccctccccag cgacgcaccc ccgctcgaga tgaagtgct gatcgagcag     26100
gacccgggtt ttgtgagcgg agaggaggat gaggtggatg agaaggagaa ggaggaggtc    26160
gccgcctcag tgccaaaaga ggataaaaag caagaccagg acgacgcaga taaggatgag    26220
acagcagtcg ggcgggggaa cggaagccat gatgctgatg acggctacct agacgtggga    26280
gacgacgtgc tgcttaagca cctgcaccgc cagtgcgtca tcgtctgcga cgcgctgcag    26340
gagcgctgcg aagtgcccct ggacgtggcg gaggtcagcc gcgcctacga gcggcacctc    26400
ttcgcgccgc acgtgccccc caagcgccgg gagaacggca cctgcgagcc caacccgcgt    26460
ctcaacttct acccggtctt cgcggtaccc gaggtgctgg ccacctacca catcttttc     26520
caaaactgca agatccccct ctcctgccgc gccaaccgca cccgcgccga caaaaccctg    26580
accctgcgga agggcgccca catacctgat atcgcctctc tggaggaagt gcccaagatc    26640
ttcgagggtc tcggtcgcga cgagaaacgg gcggcgaacg ctctgcacgg agacagcgaa    26700
aacgagagtc actcggggt gctggtggag ctcgagggca caacgcgcg cctggccgta     26760
ctcaagcgca gcatagaggt cacccacttt gcctacccgg cgctcaacct gccccccaag    26820
gtcatgagtg tggtcatggg cgagctcatc atgcgccgcg cccagcccct ggccgcggat    26880
gcaaacttgc aagagtcctc cgaggaaggc ctgcccgcgg tcagcgacga gcagctggcg    26940
cgctggctgg agaccgcgga ccccgcgcag ctggaggagc ggcgcaagct catgatggcc    27000
gcggtgctgg tcaccgtgga gctcgagtgt ctgcagcgct tcttcgcgga ccccgagatg    27060
cagcgcaagc tcgaggagac cctgcactac accttccgcc agggctacgt gcgccaggcc    27120
tgcaagatct ccaacgtgga gctctgcaac ctggtctcct acctgggcat cctgcacgag    27180
aaccgcctcg gcagaacgt cctgcactcc accctcaaag gggaggcgcg ccgcgactac     27240
atccgcgact gcgcctacct cttcctctgc tacacctggc agacggccat gggggtctgg    27300
cagcagtgcc tggaggagcg caacctcaag gagctggaaa agctcctcaa gcgcaccctc    27360
agggacctct ggacgggctt caacgagcgc tcggtggccg ccgcgctggc ggacatcatc    27420
tttcccgagc gcctgctcaa gaccctgcag cagggcctgc ccgacttcac cagccagagc    27480
atgctgcaga acttcaggac tttcatcctg gagcgctcgg gcatcctgcc ggccacttgc    27540
tgcgcgctgc ccagcgactt cgtgcccatc aagtacaggg agtgcccgcc gccgctctgg    27600
ggccactgct acctcttcca gctggccaac tacctcgcct accactcgga cctcatggaa    27660
```

```
gacgtgagcg gcgagggcct gctcgagtgc cactgccgct gcaacctctg cacgccccac   27720
cgctctctag tctgcaaccc gcagctgctc agcgagagtc agattatcgg taccttcgag   27780
ctgcagggtc cctcgcctga cgagaagtcc gcggctccag ggctgaaact cactccgggg   27840
ctgtggactt ccgcctacct acgcaaattt gtacctgagg actaccacgc ccacgagatc   27900
aggttctacg aagaccaatc ccgcccgccc aaggcggagc tcaccgcctg cgtcatcacc   27960
caggggcaca tcctgggcca attgcaagcc atcaacaaag cccgccgaga gttcttgctg   28020
aaaaagggtc gggggtgta cctggacccc cagtccggcg aggagctaaa cccgctaccc   28080
ccgccgccgc cccagcagcg ggaccttgct tcccaggatg gcacccagaa agaagcagca   28140
gccgccgccg ccgccgcagc catacatgct tctggaggaa gaggaggagg actgggacag   28200
tcaggcagag gaggtttcgg acgaggagca ggaggagatg atggaagact gggaggagga   28260
cagcagccta gacgaggaag cttcagaggc cgaagaggtg gcagacgcaa caccatcgcc   28320
ctcggtcgca gcccctcgc cggggcccct gaaatcctcc gaacccagca ccagcgctat   28380
aacctccgct cctccggcgc cggcgccacc cgcccgcaga cccaaccgta gatgggacac   28440
cacaggaacc ggggtcggta agtccaagtg cccgccgccg ccaccgcagc agcagcagca   28500
gcagcgccag ggctaccgct cgtggcgcgg gcacaagaac gccatagtcg cctgcttgca   28560
agactgcggg ggcaacatct cttttcgcccg ccgcttcctg ctattccacc acggggtcgc   28620 cttttccccgc aatgtcctgc attactaccg tcatctctac agcccctact gcagcggcga   28680
cccagaggcg gcagcggcag ccacagcggc gaccaccacc taggaagata tcctccgcgg   28740
gcaagacagc ggcagcagcg gccaggagac ccgcggcagc agcggcggga gcggtgggcg   28800
cactgcgcct ctcgcccaac gaaccctct cgacccggga gctcagacac aggatcttcc   28860
ccactttgta tgccatcttc caacagagca gaggccagga gcaggagctg aaaataaaaa   28920
acagatctct gcgctcccte acccgcagct gtctgtatca caaaagcgaa gatcagcttc   28980
ggcgcacgct ggaggacgcg gaggcactct tcagcaaata ctgcgcgctc actcttaaag   29040
actagctccg cgcccttctc gaatttaggc gggagaaaac tacgtcatcg ccggccgccg   29100
cccagcccgc ccagccgaga tgagcaaaga gattcccacg ccatacatgt ggagctacca   29160
gccgcagatg ggactcgcgg cgggagcggc ccaggactac tccacccgca tgaactacat   29220
gagcgcggga ccccacatga tctcacaggt caacgggatc cgcgcccagc gaaaccaaat   29280
actgctggaa caggcggcca tcaccgccac gccccgccat aatctcaacc cccgaaattg   29340 gccccgccgcc ctcgtgtacc aggaaacccc ctccgccacc accgtactac ttccgcgtga   29400
cgcccaggcc gaagtccaga tgactaactc aggggcgcag ctcgcgggcg gctttcgtca   29460
cggggcgcgg ccgctccgac caggtataag acacctgatg atcagaggcc gaggtatcca   29520
gctcaacgac gagtcggtga gctcttcgct cggtctccgt ccggacggaa ctttccagct   29580
cgccggatcc ggccgctctt cgttcacgcc ccgccaggcg tacctgactc tgcagacctc   29640
gtcctcggag ccccgctccg gcggcatcgg aaccctccag ttcgtggagg agttcgtgcc   29700
ctcggtctac ttcaacccct tctcgggacc tccggacgc tacccgacc agttcattcc   29760 gaactttgac gcggtgaagg actcggcgga cggctacgac tgaatgtcag gtgtcgaggc   29820
agagcagctt cgcctgagac acctcgagca ctgccgccgc cacaagtgct tcgcccgcgg   29880
ttctggtgag ttctgctact ttcagctacc cgaggagcat accgagggc cggcgcacgg   29940 cgtccgcctg accacccagg gcgaggttac ctgttccctc atccgggagt ttaccctccg   30000
```

```
tcccctgcta gtggagcggg agcggggtcc ctgtgtccta actatcgcct gcaactgccc    30060
taaccctgga ttacatcaag atctttgctg tcatctctgt gctgagttta ataaacgctg    30120
agatcagaat ctactggggc tcctgtcgcc atcctgtgaa cgccaccgtc ttcacccacc    30180
ccgaccaggc ccaggcgaac ctcacctgcg gtctgcatcg gagggccaag aagtacctca    30240
cctggtactt caacggcacc cccttgtgg tttacaacag cttcgacggg gacggagtct    30300
ccctgaaaga ccagctctcc ggtctcagct actccatcca caagaacacc accctccaac    30360
tcttccctcc ctacctgccg ggaacctacg agtgcgtcac cggccgctgc acccacctca    30420
cccgcctgat cgtaaaccag agctttccgg gaacagataa ctccctcttc cccagaacag    30480
gaggtgagct caggaaactc cccggggacc agggcggaga cgtaccttcg acccttgtgg    30540
ggttaggatt ttttattacc gggttgctgg ctcttttaat caaagttttcc ttgagatttg    30600 ttctttcctt ctacgtgtat gaacacctca acctccaata actctaccct tcttcggaa    30660 tcaggtgact tctctgaaat cgggcttggt gtgctgctta ctctgttgat ttttttcctt    30720
atcatactca gccttctgtg cctcaggctc gccgcctgct gcgcacacat ctatatctac    30780
tgctggttgc tcaagtgcag gggtcgccac ccaagatgaa caggtacatg gtcctatcga    30840
tcctaggcct gctggccctg gcggcctgca gcgccgccaa aaaagagatt acctttgagg    30900
agcccgcttg caatgtaact ttcaagcccg agggtgacca atgcaccacc ctcgtcaaat    30960
gcgttaccaa tcatgagagg ctgcgcatcg actacaaaaa caaaactggc cagttttgcg    31020
tctatagtgt gtttacgccc ggagacccct ctaactactc tgtcaccgtc ttccagggcg    31080
gacagtctaa gatattcaat tacactttcc ctttttatga gttatgcgat gcggtcatgt    31140
acatgtcaaa acagtacaac ctgtggcctc cctctcccca ggcgtgtgtg gaaaatactg    31200
ggtcttactg ctgtatggct ttcgcaatca ctacgctcgc tctaatctgc acggtgctat    31260
acataaaatt caggcagagg cgaatcttta tcgatgaaaa gaaaatgcct tgatcgctaa    31320
caccggcttt ctatctgcag aatgaatgca atcacctccc tactaatcac caccaccctc    31380
cttgcgattg cccatgggtt gacacgaatc gaagtgccag tggggtccaa tgtcaccatg    31440
gtgggccccg ccggcaattc caccctcatg tgggaaaaat ttgtccgcaa tcaatgggtt    31500
catttctgct ctaaccgaat cagtatcaag cccagagcca tctgcgatgg gcaaaatcta    31560
actctgatca atgtgcaaat gatggatgct gggtactatt acgggcagcg gggagaaatc    31620
attaattact ggcgacccca caaggactac atgctgcatg tagtcgaggc acttcccact    31680
accaccccca ctaccacctc tcccaccacc accaccacta ctactactac tactactact    31740
actactacta ccactaccgc tgcccgccat acccgcaaaa gcaccatgat tagcacaaag    31800 cccctcgtg ctcactccca cgccggcggg cccatcggtg cgacctcaga accaccgag    31860 ctttgcttct gccaatgcac taacgccagc gctcatgaac tgttcgacct ggagaatgag    31920
gatgtccagc agagctccgc ttgcctgacc caggaggctg tggagcccgt tgccctgaag    31980
cagatcggtg attcaataat tgactcttct tcttttgcca ctcccgaata ccctcccgat    32040
tctactttcc acatcacggg taccaaagac cctaacctct cttctacct gatgctgctg    32100 ctctgtatct ctgtggtctc ttccgcgctg atgttactgg gatgttctg ctgcctgatc    32160 tgccgcagaa agagaaaagc tcgctctcag ggccaaccac tgatgcccctt ccctaccccc    32220 ccggattttg cagataacaa gatatgagct cgctgctgac actaaccgct ttactagcct    32280
gcgctctaac ccttgtcgct tgcgactcga gattccacaa tgtcacagct gtggcaggag    32340
aaaatgttac tttcaactcc acggccgata cccagtggtc gtggagtggc tcaggtagct    32400
```

```
acttaactat ctgcaatagc tccacttccc ccggcatatc cccaaccaag taccaatgca   32460
atgccagcct gttcaccctc atcaacgctt ccaccctgga caatggactc tatgtaggct   32520
atgtacccct tggtgggcaa ggaaagaccc acgcttacaa cctggaagtt cgccagccca   32580
gaaccactac ccaagcttct cccaccacca ccaccaccac caccatcacc agcagcagca   32640
gcagcagcag ccacagcagc agcagcagat tattgacttt ggttttggcc agctcatctg   32700
ccgctaccca ggccatctac agctctgtgc ccgaaaccac tcagatccac cgcccagaaa   32760
cgaccaccgc caccacccta cacacctcca gcgatcagat gccgaccaac atcacccccct   32820 tggctcttca aatgggactt acaagcccca ctccaaaacc agtggatgcg gccgaggtct   32880
ccgccctcgt caatgactgg gcggggctgg gaatgtggtg gttcgccata ggcatgatgg   32940
cgctctgcct gcttctgctc tggctcatct gctgcctcca ccgcaggcga gccagacccc   33000
ccatctatag acccatcatt gtcctgaacc ccgataatga tgggatccat agattggatg   33060
gcctgaaaaa cctacttttt tcttttacag tatgataaat tgagacatgc ctcgcatttt   33120
cttgtacatg ttccttctcc cacctttttct ggggtgttct acgctggccg ctgtgtctca   33180
cctggaggta gactgcctct cacccttcac tgtctacctg ctttacggat tggtcaccct   33240
cactctcatc tgcagcctaa tcacagtaat catcgccttc atccagtgca ttgattacat   33300
ctgtgtgcgc ctcgcatact tcagacacca cccgcagtac cgagacagga acattgccca   33360
acttctaaga ctgctctaat catgcataag actgtgatct gccttctgat cctctgcatc   33420
ctgcccaccc tcacctcctg ccagtacacc acaaaatctc cgcgcaaaag acatgcctcc   33480
tgccgcttca cccaactgtg gaatataccc aaatgctaca acgaaaagag cgagctctcc   33540
gaagcttggc tgtatgggt catctgtgtc ttagttttct gcagcactgt ctttgccctc   33600
ataatctacc cctactttga tttgggatgg aacgcgatcg atgccatgaa ttaccccacc   33660
tttcccgcac ccgagataat tccactgcga caagttgtac ccgttgtcgt taatcaacgc   33720
cccccatccc ctacgcccac tgaaatcagc tactttaacc taacaggcgg agatgactga   33780
cgccctagat ctagaaatgg acggcatcag taccgagcag cgtctcctag agaggcgcag   33840
gcaggcggct gagcaagagc gcctcaatca ggagctccga gatctcgtta acctgcacca   33900
gtgcaaaaga ggcatctttt gtctggtaaa gcaggccaaa gtcacctacg agaagaccgg   33960
caacagccac cgcctcagtt acaaattgcc cacccagcgc cagaagctgg tgctcatggt   34020
gggtgagaat cccatcaccg tcacccagca ctcggtagag accgaggggt gtctgcactc   34080
cccctgtcgg ggtccagaag acctctgcac cctggtaaag accctgtgcg gtctcagaga   34140
tttagtcccc tttaactaat caaacactgg aatcaataaa aagaatcact tacttaaaat   34200
cagacagcag gtctctgtcc agtttattca gcagcacctc cttcccctcc tcccaactct   34260
ggtactccaa acgccttctg gcggcaaact tcctccacac cctgaaggga atgtcagatt   34320
cttgctcctg tccctccgca cccactatct tcatgttgtt gcagatgaag cgcaccaaaa   34380
cgtctgacga gagcttcaac cccgtgtacc cctatgacac ggaaagcggc cctccctccg   34440
tccctttcct caccccctccc ttcgtgtctc ccgatggatt ccaagaaagt cccccggggg   34500
tcctgtctct gaacctggcc gagccctggg tcacttccca cggcatgctc gccctgaaaa   34560
tgggaagtgg cctctccctg gacgacgctg gcaacctcac ctctcaagat atcaccaccg   34620 ctagcccctcc cctcaaaaaa accaagacca acctcagcct agaaacctca tccccctaa   34680 ctgtgagcac ctcaggcgcc ctcaccgtag cagccgccgc tcccctggcg gtggccggca   34740
```

```
cctccctcac catgcaatca gaggcccccc tgacagtaca ggatgcaaaa ctcaccctgg    34800
ccaccaaagg cccctgacc gtgtctgaag gcaaactggc cttgcaaaca tcggcccgc     34860 tgacggccgc tgacagcagc accctcacag tcagtgccac accaccctt agcacaagca    34920 atggcagctt gggtattgac atgcaagccc ccatttacac caccaatgga aaactaggac    34980
ttaactttgg cgctcccctg catgtggtag acagcctaaa tgcactgact gtagttactg    35040
gccaaggtct tacgataaac ggaacagccc tacaaactag agtctcaggt gccctcaact    35100
atgacacatc aggaaaccta gaattgagag ctgcagggg tatgcgagtt gatgcaaatg     35160
gtcaacttat ccttgatgta gcttacccat ttgatgcaca aaacaatctc agccttaggc    35220
ttggacaggg acccctgttt gttaactctg cccacaactt ggatgttaac tacaacagag    35280
gcctctacct gttcacatct ggaaatacca aaaagctaga agttaatatc aaaacagcca    35340 aggtctcat ttatgatgac actgctatag caatcaatgc gggtgatggg ctacagtttg     35400
actcaggctc agatacaaat ccattaaaaa ctaaacttgg attaggactg gattatgact    35460
ccagcagagc cataattgct aaactgggaa ctggcctaag cttgacaac acaggtgcca     35520 tcacagtagg caacaaaaat gatgacaagc ttaccttgtg gaccacacca gacccatccc    35580
ctaactgtag aatctattca gagaaagatg ctaaattcac acttgtttg actaaatgcg     35640 gcagtcaggt gttggccagc gtttctgttt tatctgtaaa aggtagcctt gcgcccatca    35700
gtggcacagt aactagtgct cagattgtcc tcagatttga tgaaaatgga gttctactaa    35760
gcaattcttc ccttgacccct caatactgga actacagaaa aggtgacctt acagagggca    35820
ctgcatatac caacgcagtg ggatttatgc ccaacctcac agcataccca aaaacacaga    35880
gccaaactgc taaaagcaac attgtaagtc aggtttactt gaatggggac aaatccaaac    35940
ccatgaccct caccattacc ctcaatggaa ctaatgaaac aggagatgcc acagtaagca    36000
cttactccat gtcattctca tggaactgga atggaagtaa ttacattaat gaaacgttcc    36060
aaaccaactc cttcaccttc tcctacatcg cccaagaata aaaagcatga cgctgttgat    36120
ttgattcaat gtgtttctgt tttattttca agcacaacaa aatcattcaa gtcattcttc    36180
catcttagct taatagacac agtagcttaa tagacccagt agtgcaaagc cccattctag    36240
cttataacta gtggagaagt actcgcctac atgggggtag agtcataatc gtgcatcagg    36300
ataggggggt ggtgctgcag cagcgcgcga ataaactgct gccgccgccg ctccgtcctg    36360
caggaataca acatggcagt ggtctcctca gcgatgattc gcaccgcccg cagcataagg    36420
cgccttgtcc tccgggcaca gcagcgcacc ctgatctcac ttaaatcagc acagtaactg    36480
cagcacagca ccacaatatt gttcaaaatc ccacagtgca aggcgctgta tccaaagctc    36540
atggcgggga ccacagaacc cacgtggcca tcataccaca agcgcaggta gattaagtgg    36600
cgacccctca taaacacgct ggacataaac attacctctt ttggcatgtt gtaattcacc    36660
acctcccggt accatataaa cctctgatta aacatggcgc catccaccac catcctaaac    36720
cagctggcca aaacctgccc gccggctata cactgcaggg aaccgggact ggaacaatga    36780
cagtggagag cccaggactc gtaaccatgg atcatcatgc tcgtcatgat atcaatgttg    36840
gcacaacaca ggcacacgtg catacacttc ctcaggatta caagctcctc ccgcgttaga    36900
accatatccc agggaacaac ccattcctga atcagcgtaa atcccacact gcagggaaga    36960
cctcgcacgt aactcacgtt gtgcattgtc aaagtgttac attcgggcag cagcggatga    37020
tcctccagta tggtagcgcg ggtttctgtc tcaaaaggag gtagacgatc cctactgtac    37080
ggagtgcgcc gagacaaccg agatcgtgtt ggtcgtagtg tcatgccaaa tggaacgccg    37140
```

```
gacgtagtca tatttcctga agtcttagat ctctcaacgc agcaccagca ccaacacttc   37200
gcagtgtaaa aggccaagtg ccgagagagt atatatagga ataaaaagtg acgtaaacgg   37260
gcaaagtcca aaaacgccc agaaaaaccg cacgcgaacc tacgccccga aacgaaagcc    37320
aaaaaacact agacactccc ttccggcgtc aacttccgct ttcccacgct acgtcacttg   37380
ccccagtcaa acaaactaca tatcccgaac ttccaagtcg ccacgcccaa aacaccgcct   37440
acacctcccc gcccgccggc ccgccccaa acccgcctcc cgccccgcgc ccgcccccgc    37500
gccgcccatc tcattatcat attggcttca atccaaaata aggtatatta ttgatgatg    37559
```

<210> SEQ ID NO 12
<211> LENGTH: 1109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

```
ggagttccgc gttacataac ttacggtaaa tggcccgcct ggctgaccgc ccaacgaccc     60
ccgcccattg acgtcaataa tgacgtatgt tcccatagta acgccaatag ggactttcca   120
ttgacgtcaa tgggtggagt atttacggta aactgcccac ttggcagtac atcaagtgta   180
tcatatgcca agtacgcccc ctattgacgt caatgacggt aaatggcccg cctggcatta   240
tgcccagtac atgaccttat gggactttcc tacttggcag tacatctacg tattagtcat   300
cgctattacc atggtcgagg tgagccccac gttctgcttc actctcccca tctccccccc   360
ctccccaccc ccaattttgt atttatttat tttttaatta ttttgtgcag cgatgggggc   420 ggggggggg ggggcgcgc gccaggcggg gcggggcggg gcgaggggcg gggcggggcg    480
aggcggagag gtgcggcggc agccaatcag agcggcgcgc tccgaaagtt tccttttatg   540
gcgaggcggc ggcggcggcg gccctataaa aagcgaagcg ctccctatca gtgatagaga   600
tctccctatc agtgatagag atcgtcgacg agctcgcggc gggcgggagt cgctgcgcgc   660
tgccttcgcc ccgtgccccg ctccgccgcc gcctcgcgcc gcccgcccg gctctgactg    720 accgcgttac taaaacaggt aagtccggcc tccgcgccgg ttttggcgc ctcccgcggg    780 cgcccccctc ctcacggcga gcgctgccac gtcagacgaa gggcgcagcg agcgtcctga   840
tccttccgcc cggacgctca ggacagcggc ccgctgctca taagactcgg ccttagaacc   900
ccagtatcag cagaaggaca ttttaggacg ggacttgggt gactctaggg cactggtttt   960
ctttccagag agcggaacag gcgaggaaaa gtagtccctt ctcggcgatt ctgcggaggg   1020
atctccgtgg ggcggtgaac gccgatgatg cctctactaa ccatgttcat gttttcttt   1080 tttttctaca ggtcctgggt gacgaacag                                    1109
```

<210> SEQ ID NO 13
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13

```
atacggacta gtggagaagt actcgcctac atg                                 33
```

<210> SEQ ID NO 14
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 14
atacggaaga tctaagactt caggaaatat gactac                         36

<210> SEQ ID NO 15
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 15
attcagtgta caggcgcgcc aaagcatgac gctgttgatt tgattc               46

<210> SEQ ID NO 16
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 16
actaggacta gttataagct agaatggggc tttgc                          35

<210> SEQ ID NO 17
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 17
ttaatagaca cagtagctta atagacccag tagtgcaaag ccccattcta gcttataacc    60
cctatttgtt tatttttct                                            79

<210> SEQ ID NO 18
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 18
atatatactc tctcggcact tggccttta cactgcgaag tgttggtgct ggtgctgcgt    60
tgagagatct ttatttgtta actgttaatt gtc                            93

<210> SEQ ID NO 19
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 19
ttaatagaca cagtagctta ata                                          23

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
ggaagggagt gtctagtgtt                                              20

<210> SEQ ID NO 21
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
caatgggcgt ggatagcggt ttgac                                        25

<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
cagcatgcct gctattgtc                                               19

<210> SEQ ID NO 23
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
catctacgta ttagtcatcg ctattacca                                    29

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
gacttggaaa tccccgtgag t                                            21
```

<210> SEQ ID NO 25
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 25
acatcaatgg gcgtggatag cggtt                                              25

<210> SEQ ID NO 26
<211> LENGTH: 592
<212> TYPE: DNA
<213> ORGANISM: Woodchuck hepatitis virus

<400> SEQUENCE: 26
taatcaacct ctggattaca aaatttgtga agattgact ggtattctta actatgttgc          60
tccttttacg ctatgtggat acgctgcttt aatgcctttg tatcatgcta ttgcttcccg        120
tatggctttc attttctcct ccttgtataa atcctggttg ctgtctcttt atgaggagtt        180
gtggcccgtt gtcaggcaac gtggcgtggt gtgcactgtg tttgctgacg caaccccac         240 tggttggggc attgccacca cctgtcagct cctttccggg actttcgctt tccccctccc        300
tattgccacg gcggaactca tcgccgcctg ccttgcccgc tgctggacag gggctcggct        360
gttgggcact gacaattccg tggtgttgtc ggggaaatca tcgtcctttc cttggctgct        420
cgcctgtgtt gccacctgga ttctgcgcgg gacgtcctc tgctacgtcc cttcggccct        480
caatccagcg gaccttcctt cccgcggcct gctgccggct ctgcggcctc ttccgcgtct        540
tcgccttcgc cctcagacga gtcggatctc cctttgggcc gcctcccgc ct                592

<210> SEQ ID NO 27
<211> LENGTH: 543
<212> TYPE: PRT
<213> ORGANISM: Simian adenovirus

<400> SEQUENCE: 27

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

```
Gln Thr Ser Ala Pro Leu Thr Ala Ala Asp Ser Ser Thr Leu Thr Val
                165                 170                 175

Ser Ala Thr Pro Pro Ile Asn Val Ser Gly Ser Leu Gly Leu Asp
        180                 185                 190

Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
210                 215                 220

Thr Gly Asn Gly Leu Thr Val Asp Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asn Val
            260                 265                 270

Ala Tyr Pro Phe Asp Ala Gln Asn Asn Leu Ser Leu Arg Leu Gly Gln
        275                 280                 285

Gly Pro Leu Tyr Ile Asn Thr Asp His Asn Leu Asp Leu Asn Cys Asn
        290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
        370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Arg Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
        450                 455                 460

Tyr Pro Lys Thr Gln Ser Gln Thr Ala Lys Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
        530                 535                 540
```

<210> SEQ ID NO 28
<211> LENGTH: 541
<212> TYPE: PRT
<213> ORGANISM: Simian adenovirus

```
<400> SEQUENCE: 28

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Thr Lys Thr Asn
                85                  90                  95

Leu Ser Leu Gln Thr Ser Ala Pro Leu Thr Val Ser Ser Gly Ser Leu
                100                 105                 110

Thr Val Ala Ala Ala Pro Leu Ala Val Ala Gly Thr Ser Leu Thr
                115                 120                 125

Met Gln Ser Gln Ala Pro Leu Thr Val Gln Asp Ala Lys Leu Gly Leu
    130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Gly
                165                 170                 175

Thr Thr Pro Pro Ile Ser Val Ser Ser Gly Ser Leu Gly Leu Asp Met
            180                 185                 190

Glu Asp Pro Met Tyr Thr His Asp Gly Lys Leu Gly Ile Arg Ile Gly
        195                 200                 205

Gly Pro Leu Gln Val Val Asp Ser Leu His Thr Leu Thr Val Val Thr
    210                 215                 220

Gly Asn Gly Ile Thr Val Ala Asn Asn Ala Leu Gln Thr Lys Val Ala
225                 230                 235                 240

Gly Ala Leu Gly Tyr Asp Ser Ser Gly Asn Leu Glu Leu Arg Ala Ala
                245                 250                 255

Gly Gly Met Arg Ile Asn Thr Gly Gly Gln Leu Ile Leu Asp Val Ala
            260                 265                 270

Tyr Pro Phe Asp Ala Gln Asn Asn Leu Ser Leu Arg Leu Gly Gln Gly
        275                 280                 285

Pro Leu Tyr Val Asn Thr Asn His Asn Leu Asp Leu Asn Cys Asn Arg
    290                 295                 300

Gly Leu Thr Thr Thr Thr Ser Ser Asn Thr Thr Lys Leu Glu Thr Lys
305                 310                 315                 320

Ile Asp Ser Gly Leu Asp Tyr Asn Ala Asn Gly Ala Ile Ile Ala Lys
                325                 330                 335

Leu Gly Thr Gly Leu Thr Phe Asp Asn Thr Gly Ala Ile Thr Val Gly
            340                 345                 350

Asn Thr Gly Asp Asp Lys Leu Thr Leu Trp Thr Thr Pro Asp Pro Ser
        355                 360                 365

Pro Asn Cys Arg Ile His Ala Asp Lys Asp Lys Phe Thr Leu Val Leu
    370                 375                 380

Thr Lys Cys Gly Ser Gln Ile Leu Ala Ser Val Ala Ala Leu Ala Val
385                 390                 395                 400

Ser Gly Asn Leu Ser Ser Met Thr Gly Thr Val Ser Ser Val Thr Ile
                405                 410                 415
```

```
Phe Leu Arg Phe Asp Gln Asn Gly Val Leu Met Glu Asn Ser Ser Leu
            420                 425                 430

Asp Lys Glu Tyr Trp Asn Phe Arg Asn Gly Asn Ser Thr Asn Ala Thr
            435                 440                 445

Pro Tyr Thr Asn Ala Val Gly Phe Met Pro Asn Leu Ser Ala Tyr Pro
            450                 455                 460

Lys Thr Gln Ser Gln Thr Ala Lys Asn Ile Val Ser Glu Val Tyr
465             470                 475                 480

Leu His Gly Asp Lys Ser Lys Pro Met Ile Leu Thr Ile Thr Leu Asn
                485                 490                 495

Gly Thr Asn Glu Ser Ser Glu Thr Ser Gln Val Ser His Tyr Ser Met
                500                 505                 510

Ser Phe Thr Trp Ser Trp Asp Ser Gly Lys Tyr Ala Thr Glu Thr Phe
            515                 520                 525

Ala Thr Asn Ser Phe Thr Phe Ser Tyr Ile Ala Glu Gln
            530                 535                 540
```

<210> SEQ ID NO 29
<211> LENGTH: 543
<212> TYPE: PRT
<213> ORGANISM: Simian adenovirus

<400> SEQUENCE: 29

```
Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Ser Thr Thr Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Ala Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Leu Thr Val
                165                 170                 175

Ser Ser Thr Pro Pro Ile Ser Val Ser Ser Gly Ser Leu Gly Leu Asp
            180                 185                 190

Met Glu Asp Pro Met Tyr Thr His Asp Gly Lys Leu Gly Ile Arg Ile
        195                 200                 205

Gly Gly Pro Leu Arg Val Val Asp Ser Leu His Thr Leu Thr Val Val
    210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
```

```
                    245                 250                 255
Ala Gly Gly Met Arg Ile Asp Ala Asn Gly Gln Leu Ile Leu Asp Val
            260                 265                 270

Ala Tyr Pro Phe Asp Ala Gln Asn Asn Leu Ser Leu Arg Leu Gly Gln
            275                 280                 285

Gly Pro Leu Tyr Val Asn Thr Asp His Asn Leu Asp Leu Asn Cys Asn
            290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
                340                 345                 350

Gly Asn Thr Gly Asp Asp Lys Leu Thr Leu Trp Thr Thr Pro Asp Pro
                355                 360                 365

Ser Pro Asn Cys Arg Ile His Ser Asp Lys Asp Cys Lys Phe Thr Leu
            370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Val Ala Ser Val
                405                 410                 415

Thr Ile Phe Leu Arg Phe Asp Gln Asn Gly Val Leu Met Glu Asn Ser
                420                 425                 430

Ser Leu Asp Lys Gln Tyr Trp Asn Phe Arg Asn Gly Asn Ser Thr Asn
            435                 440                 445

Ala Ala Pro Tyr Thr Asn Ala Val Gly Phe Met Pro Asn Leu Ala Ala
            450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
            515                 520                 525

Thr Phe Ala Thr Asn Ser Phe Thr Phe Ser Tyr Ile Ala Glu Gln
            530                 535                 540

<210> SEQ ID NO 30
<211> LENGTH: 543
<212> TYPE: PRT
<213> ORGANISM: Simian adenovirus

<400> SEQUENCE: 30

Met Lys Arg Thr Lys Thr Ser Asp Lys Ser Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
65                  70                  75                  80
```

```
Gln Asp Val Thr Thr Thr Pro Pro Leu Lys Lys Thr Lys Thr Asn
             85                  90                  95

Leu Ser Leu Glu Thr Ser Ala Pro Leu Thr Val Ser Thr Ser Gly Ala
            100                 105                 110

Leu Thr Leu Ala Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
            130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Ser Val Ser Ser Gly Ser Leu Gly Leu Asp
                180                 185                 190

Met Glu Asp Pro Met Tyr Thr His Asp Gly Lys Leu Gly Ile Arg Ile
                195                 200                 205

Gly Gly Pro Leu Arg Val Val Asp Ser Leu His Thr Leu Thr Val Val
            210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
                260                 265                 270

Ala Tyr Pro Phe Asp Ala Gln Asn Asn Leu Ser Leu Arg Leu Gly Gln
                275                 280                 285

Gly Pro Leu Tyr Val Asn Thr Asp His Asn Leu Asp Leu Asn Cys Asn
            290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
                325                 330                 335

Lys Leu Gly Thr Gly Val Ser Phe Asp Ser Thr Gly Ala Leu Ser Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
            370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
            435                 440                 445

Ala Thr Pro Tyr Thr Asn Ala Val Gly Phe Met Pro Asn Leu Ala Ala
            450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
```

-continued

```
                500                 505                 510
Ser Met Ser Phe Thr Trp Ala Trp Glu Ser Gly Gln Tyr Ala Thr Glu
            515                 520                 525
Thr Phe Ala Thr Asn Ser Phe Thr Phe Ser Tyr Ile Ala Glu Gln
        530                 535                 540

<210> SEQ ID NO 31
<211> LENGTH: 543
<212> TYPE: PRT
<213> ORGANISM: Simian adenovirus

<400> SEQUENCE: 31

Met Lys Arg Thr Lys Thr Ser Asp Glu Ser Phe Asn Pro Val Tyr Pro
1               5                   10                  15
Tyr Asp Thr Glu Asn Gly Pro Pro Ser Val Pro Phe Leu Thr Pro Pro
            20                  25                  30
Phe Val Ser Pro Asp Gly Phe Gln Glu Ser Pro Pro Gly Val Leu Ser
        35                  40                  45
Leu Asn Leu Ala Glu Pro Leu Val Thr Ser His Gly Met Leu Ala Leu
    50                  55                  60
Lys Met Gly Ser Gly Leu Ser Leu Asp Asp Ala Gly Asn Leu Thr Ser
65                  70                  75                  80
Gln Asp Val Thr Thr Thr Pro Pro Leu Lys Lys Thr Lys Thr Asn
                85                  90                  95
Leu Ser Leu Glu Thr Ser Ala Pro Leu Thr Val Ser Thr Ser Gly Ala
            100                 105                 110
Leu Thr Leu Ala Ala Ala Ala Pro Leu Ala Val Ala Gly Thr Ser Leu
        115                 120                 125
Thr Met Gln Ser Glu Ala Pro Leu Thr Val Gln Asp Ala Lys Leu Thr
    130                 135                 140
Leu Ala Thr Lys Gly Pro Leu Thr Val Ser Glu Gly Lys Leu Ala Leu
145                 150                 155                 160
Gln Thr Ser Ala Pro Leu Thr Ala Ala Asp Ser Ser Thr Leu Thr Val
                165                 170                 175
Ser Ala Thr Pro Pro Ile Asn Val Ser Ser Gly Ser Leu Gly Leu Asp
            180                 185                 190
Met Glu Asn Pro Met Tyr Thr His Asp Gly Lys Leu Gly Ile Arg Ile
        195                 200                 205
Gly Gly Pro Leu Arg Val Val Asp Ser Leu His Thr Leu Thr Val Val
    210                 215                 220
Thr Gly Asn Gly Ile Ala Val Asp Asn Asn Ala Leu Gln Thr Arg Val
225                 230                 235                 240
Thr Gly Ala Leu Gly Tyr Asp Thr Ser Gly Asn Leu Gln Leu Arg Ala
                245                 250                 255
Ala Gly Gly Met Arg Ile Asp Ala Asn Gly Gln Leu Ile Leu Asp Val
            260                 265                 270
Ala Tyr Pro Phe Asp Ala Gln Asn Asn Leu Ser Leu Arg Leu Gly Gln
        275                 280                 285
Gly Pro Leu Tyr Val Asn Thr Asp His Asn Leu Asp Leu Asn Cys Asn
    290                 295                 300
Arg Gly Leu Thr Thr Thr Thr Asn Asn Thr Lys Lys Leu Glu Thr
305                 310                 315                 320
Lys Ile Gly Ser Gly Leu Asp Tyr Asp Thr Asn Gly Ala Val Ile Ile
                325                 330                 335
```

```
Lys Leu Gly Thr Gly Val Ser Phe Asp Ser Thr Gly Ala Leu Ser Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
        370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Thr Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Ile Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 32
<211> LENGTH: 578
<212> TYPE: PRT
<213> ORGANISM: Simian adenovirus

<400> SEQUENCE: 32

Met Lys Arg Thr Lys Thr Ser Asp Glu Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Val Thr Thr Thr Pro Pro Leu Lys Lys Thr Lys Thr Asn
                85                  90                  95

Leu Ser Leu Glu Thr Ser Ala Pro Leu Thr Val Ser Thr Ser Gly Ala
            100                 105                 110

Leu Thr Leu Ala Ala Ala Val Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Ile
                165                 170                 175
```

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
            195                 200                 205

Gly Ala Pro Leu His Val Val Asp Ser Leu Asn Ala Leu Thr Val Val
            210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Ser Ser Gly Asn Leu Glu Leu Arg Ala
            245                 250                 255

Ala Gly Gly Met Arg Val Asp Ala Asn Gly Lys Leu Ile Leu Asp Val
            260                 265                 270

Ala Tyr Pro Phe Asp Ala Gln Asn Asn Leu Ser Leu Arg Leu Gly Gln
            275                 280                 285

Gly Pro Leu Phe Val Asn Ser Ala His Asn Leu Asp Val Asn Tyr Asn
            290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
            325                 330                 335

Ile Asn Pro Gly Asp Gly Leu Glu Phe Gly Ser Gly Ser Asp Thr Asn
            340                 345                 350

Pro Leu Lys Thr Lys Leu Gly Leu Gly Leu Glu Tyr Asp Ser Ser Arg
            355                 360                 365

Ala Ile Ile Ala Lys Leu Gly Thr Gly Leu Ser Phe Asp Asn Thr Gly
            370                 375                 380

Ala Ile Thr Val Gly Asn Lys Asn Asp Lys Leu Thr Leu Trp Thr
385                 390                 395                 400

Thr Pro Asp Pro Ser Pro Asn Cys Arg Ile Tyr Ser Glu Lys Asp Ala
            405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
            435                 440                 445

Val Thr Ser Ala Gln Ile Ile Leu Arg Phe Asp Glu Asn Gly Val Leu
            450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
            485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Ile
            515                 520                 525

Leu Thr Ile Thr Leu Asn Gly Thr Asn Glu Thr Gly Asp Ala Thr Val
            530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
            565                 570                 575

Gln Glu

```
<210> SEQ ID NO 33
<211> LENGTH: 578
<212> TYPE: PRT
<213> ORGANISM: Simian adenovirus

<400> SEQUENCE: 33

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
        355                 360                 365

Ala Ile Ile Ala Lys Leu Gly Thr Gly Leu Ser Phe Asp Asn Thr Gly
    370                 375                 380
```

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
            405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
            435                 440                 445

Val Thr Ser Ala Gln Ile Val Leu Arg Phe Asp Glu Asn Gly Val Leu
            450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
            485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
            515                 520                 525

Leu Thr Ile Thr Leu Asn Gly Thr Asn Glu Thr Gly Asp Ala Thr Val
            530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
            565                 570                 575

Gln Glu

<210> SEQ ID NO 34
<211> LENGTH: 578
<212> TYPE: PRT
<213> ORGANISM: Simian adenovirus

<400> SEQUENCE: 34

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
            85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
            130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
            165                 170                 175

```
Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
        355                 360                 365

Ala Ile Ile Ala Lys Leu Gly Thr Gly Leu Ser Phe Asp Asn Thr Gly
    370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
        435                 440                 445

Val Thr Ser Ala Gln Ile Val Leu Arg Phe Asp Glu Asn Gly Val Leu
    450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
        515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 35
```

<211> LENGTH: 577
<212> TYPE: PRT
<213> ORGANISM: Simian adenovirus

<400> SEQUENCE: 35

```
Met Lys Arg Ala Lys Thr Ser Asp Glu Thr Phe Asn Pro Val Tyr Pro
1               5                   10                  15
Tyr Asp Thr Glu Asn Gly Pro Pro Ser Val Pro Phe Leu Thr Pro Pro
            20                  25                  30
Phe Val Ser Pro Asp Gly Phe Gln Glu Ser Pro Pro Gly Val Leu Ser
        35                  40                  45
Leu Arg Leu Ser Glu Pro Leu Val Thr Ser His Gly Met Leu Ala Leu
50                  55                  60
Lys Met Gly Asn Gly Leu Ser Leu Asp Asp Ala Gly Asn Leu Thr Ser
65                  70                  75                  80
Gln Asp Val Thr Thr Val Thr Pro Pro Leu Lys Lys Thr Lys Thr Asn
                85                  90                  95
Leu Ser Leu Gln Thr Ser Ala Pro Leu Thr Val Ser Ser Gly Ser Leu
            100                 105                 110
Thr Val Ala Ala Ala Pro Leu Ala Val Ala Gly Thr Ser Leu Thr
        115                 120                 125
Met Gln Ser Gln Ala Pro Leu Thr Val Gln Asp Ala Lys Leu Gly Leu
130                 135                 140
Ala Thr Gln Gly Pro Leu Thr Val Ser Glu Gly Lys Leu Thr Leu Gln
145                 150                 155                 160
Thr Ser Ala Pro Leu Thr Ala Ala Asp Ser Ser Thr Leu Thr Val Ser
                165                 170                 175
Ala Thr Pro Pro Leu Ser Thr Ser Asn Gly Ser Leu Ser Ile Asp Met
            180                 185                 190
Gln Ala Pro Ile Tyr Thr Thr Asn Gly Lys Leu Ala Leu Asn Ile Gly
        195                 200                 205
Ala Pro Leu His Val Val Asp Thr Leu Asn Ala Leu Thr Val Val Thr
210                 215                 220
Gly Gln Gly Leu Thr Ile Asn Gly Arg Ala Leu Gln Thr Arg Val Thr
225                 230                 235                 240
Gly Ala Leu Ser Tyr Asp Thr Glu Gly Asn Ile Gln Leu Gln Ala Gly
                245                 250                 255
Gly Gly Met Arg Ile Asp Asn Asn Gly Gln Leu Ile Leu Asn Val Ala
            260                 265                 270
Tyr Pro Phe Asp Ala Gln Asn Asn Leu Ser Leu Arg Leu Gly Gln Gly
        275                 280                 285
Pro Leu Ile Val Asn Ser Ala His Asn Leu Asp Leu Asn Leu Asn Arg
290                 295                 300
Gly Leu Tyr Leu Phe Thr Ser Gly Asn Thr Lys Lys Leu Glu Val Asn
305                 310                 315                 320
Ile Lys Thr Ala Lys Gly Leu Phe Tyr Asp Gly Thr Ala Ile Ala Ile
                325                 330                 335
Asn Ala Gly Asp Gly Leu Gln Phe Gly Ser Gly Ser Asp Thr Asn Pro
            340                 345                 350
Leu Gln Thr Lys Leu Gly Leu Gly Leu Glu Tyr Asp Ser Asn Lys Ala
        355                 360                 365
Ile Ile Thr Lys Leu Gly Thr Gly Leu Ser Phe Asp Asn Thr Gly Ala
370                 375                 380
Ile Thr Val Gly Asn Lys Asn Asp Asp Lys Leu Thr Leu Trp Thr Thr
```

```
                385                 390                 395                 400
Pro Asp Pro Ser Pro Asn Cys Arg Ile Asn Ser Glu Lys Asp Ala Lys
                        405                 410                 415

Leu Thr Leu Val Leu Thr Lys Cys Gly Ser Gln Val Leu Ala Ser Val
                        420                 425                 430

Ser Val Leu Ser Val Lys Gly Ser Leu Ala Pro Ile Ser Gly Thr Val
                        435                 440                 445

Thr Ser Ala Gln Ile Val Leu Arg Phe Asp Glu Asn Gly Val Leu Leu
                450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
                        485                 490                 495

Leu Thr Ala Tyr Pro Lys Thr Gln Ser Gln Thr Ala Lys Ser Asn Ile
                500                 505                 510

Val Ser Gln Val Tyr Leu Asn Gly Asp Lys Thr Lys Pro Met Thr Leu
                515                 520                 525

Thr Ile Thr Leu Asn Gly Thr Asn Glu Thr Gly Asp Ala Thr Val Ser
                530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                        565                 570                 575

Glu

<210> SEQ ID NO 36
<211> LENGTH: 577
<212> TYPE: PRT
<213> ORGANISM: Simian adenovirus

<400> SEQUENCE: 36

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Pro Gly Val Leu Ser
                35                  40                  45

Leu Arg Leu Ser Glu Pro Leu Val Thr Ser His Gly Met Leu Ala Leu
            50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                        85                  90                  95

Leu Ser Leu Gln Thr Ser Ala Pro Leu Thr Val Ser Ser Gly Ser Leu
                100                 105                 110

Thr Val Ala Ala Ala Pro Leu Ala Val Ala Gly Thr Ser Leu Thr
                115                 120                 125

Met Gln Ser Gln Ala Pro Leu Thr Val Gln Asp Ala Lys Leu Gly Leu
            130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                        165                 170                 175

Ala Thr Pro Pro Leu Ser Thr Ser Asn Gly Ser Leu Ser Ile Asp Met
```

```
                180             185             190
Gln Ala Pro Ile Tyr Thr Thr Asn Gly Lys Leu Ala Leu Asn Ile Gly
            195                 200                 205
Ala Pro Leu His Val Val Asp Thr Leu Asn Ala Leu Thr Val Val Thr
            210                 215                 220
Gly Gln Gly Leu Thr Ile Asn Gly Arg Ala Leu Gln Thr Arg Val Thr
225                 230                 235                 240
Gly Ala Leu Ser Tyr Asp Thr Glu Gly Asn Ile Gln Leu Gln Ala Gly
            245                 250                 255
Gly Gly Met Arg Ile Asp Asn Asn Gly Gln Leu Ile Leu Asn Val Ala
            260                 265                 270
Tyr Pro Phe Asp Ala Gln Asn Asn Leu Ser Leu Arg Leu Gly Gln Gly
            275                 280                 285
Pro Leu Ile Val Asn Ser Ala His Asn Leu Asp Leu Asn Leu Asn Arg
            290                 295                 300
Gly Leu Tyr Leu Phe Thr Ser Gly Asn Thr Lys Lys Leu Glu Val Asn
305                 310                 315                 320
Ile Lys Thr Ala Lys Gly Leu Phe Tyr Asp Gly Thr Ala Ile Ala Ile
            325                 330                 335
Asn Ala Gly Asp Gly Leu Gln Phe Gly Ser Gly Ser Asp Thr Asn Pro
            340                 345                 350
Leu Gln Thr Lys Leu Gly Leu Gly Leu Glu Tyr Asp Ser Asn Lys Ala
            355                 360                 365
Ile Ile Thr Lys Leu Gly Thr Gly Leu Ser Phe Asp Asn Thr Gly Ala
            370                 375                 380
Ile Thr Val Gly Asn Lys Asn Asp Asp Lys Leu Thr Leu Trp Thr Thr
385                 390                 395                 400
Pro Asp Pro Ser Pro Asn Cys Arg Ile Asn Ser Glu Lys Asp Ala Lys
            405                 410                 415
Leu Thr Leu Val Leu Thr Lys Cys Gly Ser Gln Val Leu Ala Ser Val
            420                 425                 430
Ser Val Leu Ser Val Lys Gly Ser Leu Ala Pro Ile Ser Gly Thr Val
            435                 440                 445
Thr Ser Ala Gln Ile Val Leu Arg Phe Asp Glu Asn Gly Val Leu Leu
450                 455                 460
Ser Asn Ser Ser Leu Asp Pro Gln Tyr Trp Asn Tyr Arg Lys Gly Asp
465                 470                 475                 480
Ser Thr Glu Gly Thr Ala Tyr Thr Asn Ala Val Gly Phe Met Pro Asn
            485                 490                 495
Leu Thr Ala Tyr Pro Lys Thr Gln Ser Gln Thr Ala Lys Ser Asn Ile
            500                 505                 510
Val Ser Gln Val Tyr Leu Asn Gly Asp Lys Thr Lys Pro Met Thr Leu
            515                 520                 525
Thr Ile Thr Leu Asn Gly Thr Asn Glu Thr Gly Asp Ala Thr Val Ser
            530                 535                 540
Thr Tyr Ser Met Ser Phe Ser Trp Asn Trp Asn Gly Ser Asn Tyr Ile
545                 550                 555                 560
Asn Asp Thr Phe Gln Thr Asn Ser Phe Thr Phe Ser Tyr Ile Ala Gln
            565                 570                 575
Glu

<210> SEQ ID NO 37
<211> LENGTH: 1145
```

```
<212> TYPE: PRT
<213> ORGANISM: Respiratory syncytial virus

<400> SEQUENCE: 37

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Asn Asp Met Pro Ile Thr Asn Asp Gln Lys Lys Leu
            260                 265                 270

Met Ser Asn Asn Val Gln Ile Val Arg Gln Gln Ser Tyr Ser Ile Met
        275                 280                 285

Ser Ile Ile Lys Glu Glu Val Leu Ala Tyr Val Val Gln Leu Pro Leu
    290                 295                 300

Tyr Gly Val Ile Asp Thr Pro Cys Trp Lys Leu His Thr Ser Pro Leu
305                 310                 315                 320

Cys Thr Thr Asn Thr Lys Glu Gly Ser Asn Ile Cys Leu Thr Arg Thr
                325                 330                 335

Asp Arg Gly Trp Tyr Cys Asp Asn Ala Gly Ser Val Ser Phe Phe Pro
            340                 345                 350

Gln Ala Glu Thr Cys Lys Val Gln Ser Asn Arg Val Phe Cys Asp Thr
        355                 360                 365

Met Asn Ser Leu Thr Leu Pro Ser Glu Val Asn Leu Cys Asn Val Asp
    370                 375                 380

Ile Phe Asn Pro Lys Tyr Asp Cys Lys Ile Met Thr Ser Lys Thr Asp
385                 390                 395                 400
```

```
Val Ser Ser Ser Val Ile Thr Ser Leu Gly Ala Ile Val Ser Cys Tyr
                405                 410                 415
Gly Lys Thr Lys Cys Thr Ala Ser Asn Lys Asn Arg Gly Ile Ile Lys
            420                 425                 430
Thr Phe Ser Asn Gly Cys Asp Tyr Val Ser Asn Lys Gly Val Asp Thr
        435                 440                 445
Val Ser Val Gly Asn Thr Leu Tyr Tyr Val Asn Lys Gln Glu Gly Lys
450                 455                 460
Ser Leu Tyr Val Lys Gly Glu Pro Ile Ile Asn Phe Tyr Asp Pro Leu
465                 470                 475                 480
Val Phe Pro Ser Asp Glu Phe Asp Ala Ser Ile Ser Gln Val Asn Glu
                485                 490                 495
Lys Ile Asn Gln Ser Leu Ala Phe Ile Arg Lys Ser Asp Glu Leu Leu
            500                 505                 510
His Asn Val Asn Ala Gly Lys Ser Thr Thr Asn Arg Lys Arg Arg Ala
        515                 520                 525
Pro Val Lys Gln Thr Leu Asn Phe Asp Leu Leu Lys Leu Ala Gly Asp
530                 535                 540
Val Glu Ser Asn Pro Gly Pro Met Ala Leu Ser Lys Val Lys Leu Asn
545                 550                 555                 560
Asp Thr Leu Asn Lys Asp Gln Leu Leu Ser Ser Ser Lys Tyr Thr Ile
                565                 570                 575
Gln Arg Ser Thr Gly Asp Ser Ile Asp Thr Pro Asn Tyr Asp Val Gln
            580                 585                 590
Lys His Ile Asn Lys Leu Cys Gly Met Leu Leu Ile Thr Glu Asp Ala
        595                 600                 605
Asn His Lys Phe Thr Gly Leu Ile Gly Met Leu Tyr Ala Met Ser Arg
610                 615                 620
Leu Gly Arg Glu Asp Thr Ile Lys Ile Leu Arg Asp Ala Gly Tyr His
625                 630                 635                 640
Val Lys Ala Asn Gly Val Asp Val Thr Thr His Arg Gln Asp Ile Asn
                645                 650                 655
Gly Lys Glu Met Lys Phe Glu Val Leu Thr Leu Ala Ser Leu Thr Thr
            660                 665                 670
Glu Ile Gln Ile Asn Ile Glu Ile Glu Ser Arg Lys Ser Tyr Lys Lys
        675                 680                 685
Met Leu Lys Glu Met Gly Glu Val Ala Pro Glu Tyr Arg His Asp Ser
690                 695                 700
Pro Asp Cys Gly Met Ile Ile Leu Cys Ile Ala Ala Leu Val Ile Thr
705                 710                 715                 720
Lys Leu Ala Ala Gly Asp Arg Ser Gly Leu Thr Ala Val Ile Arg Arg
                725                 730                 735
Ala Asn Asn Val Leu Lys Asn Glu Met Lys Arg Tyr Lys Gly Leu Leu
            740                 745                 750
Pro Lys Asp Ile Ala Asn Ser Phe Tyr Glu Val Phe Glu Lys Tyr Pro
        755                 760                 765
His Phe Ile Asp Val Phe Val His Phe Gly Ile Ala Gln Ser Ser Thr
770                 775                 780
Arg Gly Gly Ser Arg Val Glu Gly Ile Phe Ala Gly Leu Phe Met Asn
785                 790                 795                 800
Ala Tyr Gly Ala Gly Gln Val Met Leu Arg Trp Gly Val Leu Ala Lys
                805                 810                 815
```

```
Ser Val Lys Asn Ile Met Leu Gly His Ala Ser Val Gln Ala Glu Met
                820                 825                 830
Glu Gln Val Val Glu Val Tyr Glu Tyr Ala Gln Lys Leu Gly Gly Glu
        835                 840                 845
Ala Gly Phe Tyr His Ile Leu Asn Asn Pro Lys Ala Ser Leu Leu Ser
850                 855                 860
Leu Thr Gln Phe Pro His Phe Ser Ser Val Val Leu Gly Asn Ala Ala
865                 870                 875                 880
Gly Leu Gly Ile Met Gly Glu Tyr Arg Gly Thr Pro Arg Asn Gln Asp
                885                 890                 895
Leu Tyr Asp Ala Ala Lys Ala Tyr Ala Glu Gln Leu Lys Glu Asn Gly
                900                 905                 910
Val Ile Asn Tyr Ser Val Leu Asp Leu Thr Ala Glu Glu Leu Glu Ala
                915                 920                 925
Ile Lys His Gln Leu Asn Pro Lys Asp Asn Asp Val Glu Leu Gly Gly
                930                 935                 940
Gly Gly Ser Gly Gly Gly Gly Met Ser Arg Arg Asn Pro Cys Lys Phe
945                 950                 955                 960
Glu Ile Arg Gly His Cys Leu Asn Gly Lys Arg Cys His Phe Ser His
                965                 970                 975
Asn Tyr Phe Glu Trp Pro Pro His Ala Leu Leu Val Arg Gln Asn Phe
                980                 985                 990
Met Leu Asn Arg Ile Leu Lys Ser  Met Asp Lys Ser Ile  Asp Thr Leu
                995                 1000                 1005
Ser Glu  Ile Ser Gly Ala Ala  Glu Leu Asp Arg Thr  Glu Glu Tyr
    1010                1015                1020
Ala Leu  Gly Val Val Gly Val  Leu Glu Ser Tyr Ile  Gly Ser Ile
    1025                1030                1035
Asn Asn  Ile Thr Lys Gln Ser  Ala Cys Val Ala Met  Ser Lys Leu
    1040                1045                1050
Leu Thr  Glu Leu Asn Ser Asp  Asp Ile Lys Lys Leu  Arg Asp Asn
    1055                1060                1065
Glu Glu  Leu Asn Ser Pro Lys  Ile Arg Val Tyr Asn  Thr Val Ile
    1070                1075                1080
Ser Tyr  Ile Glu Ser Asn Arg  Lys Asn Asn Lys Gln  Thr Ile His
    1085                1090                1095
Leu Leu  Lys Arg Leu Pro Ala  Asp Val Leu Lys Lys  Thr Ile Lys
    1100                1105                1110
Asn Thr  Leu Asp Ile His Lys  Ser Ile Thr Ile Asn  Asn Pro Lys
    1115                1120                1125
Glu Ser  Thr Val Ser Asp Thr  Asn Asp His Ala Lys  Asn Asn Asp
    1130                1135                1140
Thr Thr
    1145

<210> SEQ ID NO 38
<211> LENGTH: 1502
<212> TYPE: DNA
<213> ORGANISM: Human immunodeficiency virus

<400> SEQUENCE: 38
atgggtgcta gggcttctgt gctgtctggt ggtgagctgg acaagtggga gaagatcagg      60
ctgaggcctg gtggcaagaa gaagtacaag ctaaagcaca ttgtgtgggc ctccagggag     120
ctggagaggt ttgctgtgaa ccctggcctg ctggagacct ctgaggggtg caggcagatc     180
```

```
ctgggccagc tccagccctc cctgcaaaca ggctctgagg agctgaggtc cctgtacaac      240
acagtggcta ccctgtactg tgtgcaccag aagattgatg tgaaggacac caaggaggcc      300
ctggagaaga ttgaggagga gcagaacaag tccaagaaga aggcccagca ggctgctgct      360
ggcacaggca actccagcca ggtgtcccag aactacccca ttgtgcagaa cctccagggc      420
cagatggtgc accaggccat ctccccccgg accctgaatg cctgggtgaa ggtggtggag      480
gagaggcctt ctcccctgag gtgatcccca tgttctctgc cctgtctgag ggtgccaccc      540
cccaggacct gaacaccatg ctgaacacag tggggggcca tcaggctgcc atgcagatgc      600
tgaaggagac catcaatgag gaggctgctg agtgggacag gctgcatcct gtgcacgctg      660
gccccattgc ccccggccag atgagggagc ccaggggctc tgacattgct ggcaccacct      720
ccaccctcca ggagcagatt ggctggatga ccaacaaccc ccccatccct gtgggggaaa      780
tctacaagag gtggatcatc ctgggcctga acaagattgt gaggatgtac tcccccacct      840
ccatcctgga catcaggcag gccccaaggg agcccttcag ggactatgtg gacaggttct      900
acaagaccct gagggctgag caggcctccc aggaggtgaa gaactggatg acagagaccc      960
tgctggtgca gaatgccaac cctgactgca agaccatcct gaaggccctg ggccctgctg     1020
ccaccctgga ggagatgatg acagcctgcc aggggtggg ggggccctggt cacaaggcca     1080 gggtgctggc tgaggccatg tcccaggtga ccaactccgc caccatcatg atgcagaggg     1140
gcaacttcag gaaccagagg aagacagtga agtgcttcaa ctgtggcaag gtgggccaca     1200
ttgccaagaa ctgtagggcc cccaggaaga agggctgctg gaagtgtggc aaggagggcc     1260
accagatgaa ggactgcaat gagaggcagg ccaacttcct gggcaaaatc tggccctccc     1320
acaagggcag gcctggcaac ttcctccagt ccaggcctga gcccacagcc cctcccgagg     1380
agtccttcag gtttggggag gagaagacca ccccagcca gaagcaggag cccattgaca     1440
aggagctgta ccccctggcc tccctgaggt ccctgtttgg caacgacccc tcctcccagt     1500
aa                                                                   1502
```

ADENOVIRUS POLYNUCLEOTIDES AND POLYPEPTIDES

FIELD OF THE INVENTION

The present invention relates to isolated polynucleotide and polypeptide sequences derived from novel chimp adenovirus ChAd155, as well as to recombinant polynucleotides, vectors, adenoviruses and compositions comprising said polynucleotide and polypeptide sequences.

BACKGROUND OF THE INVENTION

Adenovirus has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Recombinant adenoviruses are useful in gene therapy and as vaccines. Viral vectors based on chimpanzee adenovirus represent an alternative to the use of human derived Ad vectors for the development of genetic vaccines. Adenoviruses isolated from chimpanzees are closely related to adenoviruses isolated from humans as demonstrated by their efficient propagation in cells of human origin. However, since human and chimp adenoviruses are close relatives, serologic cross reactivity between the two virus species is possible.

There is a demand for vectors which effectively deliver molecules to a target and minimize the effect of pre-existing immunity to selected adenovirus serotypes in the population. One aspect of pre-existing immunity that is observed in humans is humoral immunity, which can result in the production and persistence of antibodies that are specific for adenoviral proteins. The humoral response elicited by adenovirus is mainly directed against the three major structural capsid proteins: fiber, penton and hexon.

Vectors, compositions and methods of the present invention may have one or more following improved characteristics over the prior art, including but not limited to higher productivity, improved immunogenicity and increased transgene expression. Vectors of the present invention may find use in the expression of one or more immunogens useful to immunise a human or non-human animal against a pathogen.

Respiratory syncytial virus (RSV) is a highly contagious human pathogen that causes respiratory tract infections in people of all ages. During the first year of life, 50-70% of infants are infected with RSV and essentially all children have had an RSV infection by their second birthday. The risk for severe RSV-associated lower respiratory tract infections (LRTI) is highest in infants below 6 months of age and is a leading cause for hospitalization. Infection with RSV does not confer full protective immunity. Symptomatic RSV re-infections are common later in life and continue throughout adulthood. These re-infections generally go undiagnosed because they usually present as common acute upper respiratory tract infections. In more vulnerable persons (e.g., immunocompromised adults or elderly), re-infections can however also lead to severe disease.

To date, no vaccine is available against RSV and treatment of RSV disease is largely symptomatic and supportive care. The antiviral drug ribavirin is currently the only approved antiviral therapy for RSV treatment, but its use is restricted to severe hospitalized cases due to uncertainties regarding its efficacy, difficulty in administration (aerosol) and high cost [American Academy of Pediatrics Subcommittee on Diagnosis and Management of Bronchiolitis, 2006]. RSV-specific monoclonal antibodies (palivizumab, Synagis™, Medimmune) are indicated for the prevention of serious LRTIs requiring hospitalization caused by RSV in children at high risk for RSV disease but are not indicated or recommended in the general, healthy infant population due to high cost and the need for repeated administration.

In the late 1960s, a formalin-inactivated whole virus RSV vaccine (FI-RSV) tested in clinical trials led to more severe clinical symptoms upon subsequent natural infection with RSV in children under the age of two [Kim, 1969; Chin, 1969]). This experience has led to heightened safety concerns with pediatric RSV vaccine candidates. Since that time, several investigational vaccines have been and continue to be explored, including live attenuated viral vaccines and those based upon purified or recombinant viral proteins. However there is not yet a licensed vaccine for the prevention of RSV disease.

SUMMARY OF THE INVENTION

There is provided an isolated polynucleotide, wherein the polynucleotide encodes a polypeptide selected from the group consisting of:
(a) a polypeptide having the amino acid sequence according to SEQ ID NO: 1,
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polypeptide having the amino acid sequence according to SEQ ID NO: 3.

Also provided is a recombinant polynucleotide comprising a polynucleotide selected from the group consisting of:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polynucleotide which encodes a polypeptide having the amino acid sequence according to SEQ ID NO: 3.

Also provided is a recombinant vector comprising a polynucleotide selected from the group consisting of:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polynucleotide which encodes a polypeptide having the amino acid sequence according to SEQ ID NO: 3.

Also provided is a recombinant adenovirus comprising at least one polynucleotide or polypeptide selected from the group consisting of:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(f) a polypeptide having the amino acid sequence according to SEQ ID NO: 3.

Also provided is a composition comprising at least one of the following:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(f) a polypeptide having the amino acid sequence according to SEQ ID NO: 3,
(g) a vector comprising a polynucleotide as described in (a), (b) or (c) above, and
(h) a recombinant adenovirus comprising a polynucleotide as described in (a), (b) or (c) above, and a pharmaceutically acceptable excipient.

Also provided is a cell comprising at least one of the following:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(f) a polypeptide having the amino acid sequence according to SEQ ID NO: 3,
(g) a vector comprising a polynucleotide as described in (a), (b) or (c) above, and
(h) a recombinant adenovirus comprising a polynucleotide as described in (a), (b) or (c) above.

Also provided is an isolated adenoviral polypeptide selected from the group consisting of:
(a) a polypeptide having the amino acid sequence according to SEQ ID NO: 1,
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polypeptide having the amino acid sequence according to SEQ ID NO: 3.

Also provided is an isolated polynucleotide, vector, recombinant adenovirus, composition or cell comprising or consisting of the sequence according to SEQ ID NO: 6.

DESCRIPTION OF THE FIGURES

FIG. 1A-C—Alignment of fiber protein sequences from the indicated simian adenoviruses.
ChAd3 (SEQ ID NO:27)
PanAd3 (SEQ ID NO:28)
ChAd17 (SEQ ID NO:29)
ChAd19 (SEQ ID NO:30)
ChAd24 (SEQ ID NO:31)
ChAd155 (SEQ ID NO:1)
ChAd11 (SEQ ID NO:32)
ChAd20 (SEQ ID NO:33)
ChAd31 (SEQ ID NO:34)
PanAd1 (SEQ ID NO:35)
PanAd2 (SEQ ID NO:36)
FIG. 2—Flow diagram for production of specific ChAd155 BAC and plasmid vectors
FIG. 3—Species C BAC Shuttle #1365 schematic
FIG. 4—pArsChAd155 Ad5E4orf6-2 (#1490) schematic
FIG. 5—pChAd155/RSV schematic
FIG. 6—BAC ChAd155/RSV schematic
FIG. 7—Productivty of ChAd3 and ChAd155 vectors expressing an HIV Gag transgene (Experiment 1)
FIG. 8—Productivity of ChAd3 and ChAd155 vectors expressing an HIV Gag transgene (Experiment 2)
FIG. 9—Productivity of PanAd3 and ChAd155 vectors expressing RSV transgene
FIG. 10—Expression levels of ChAd3 and ChAd155 vectors expressing an HIV Gag transgene
FIG. 11—Expression levels of PanAd3 and ChAd155 vectors expressing an HIV Gag transgene—Western Blot
FIG. 12—Immunogenicity of ChAd3 and ChAd155 vectors expressing an HIV Gag transgene—IFN-gamma ELISpot
FIG. 13—Immunogenicity of PanAd3 and ChAd155 vectors expressing an HIV Gag transgene—IFN-gamma ELISpot
FIG. 14—Schematic of the synthetic DNA fragment used to express RSV antigens by the ChAd155-RSV vector
FIG. 15—Anti-F antibody titers induced by ChAd155-RSV and PanAd3-RSV in BALB/c mice
FIG. 16—RSV titers in nasal tissues (A) and lung homogenates (B), RSV neutralizing antibody (C) and pathology score (D) after viral challenge
FIG. 17—Kinetics of induction of bRSV-specific IgG (A) and RSV neutralizing antibodies (B)
FIG. 18—Kinetics of mean virus titers in nasopharyngeal swabs detected up to day 6 post bRSV challenge
FIG. 19—Effect of vaccination on bRSV replication in the lower respiratory tract
FIG. 20—Effect of vaccination on gross pneumonic consolidation 6 days post bRSV challenge
FIG. 21—Effect of vaccination on the pulmonary inflammatory response 6 days post bRSV challenge

DESCRIPTION OF THE SEQUENCES

Figure 2:
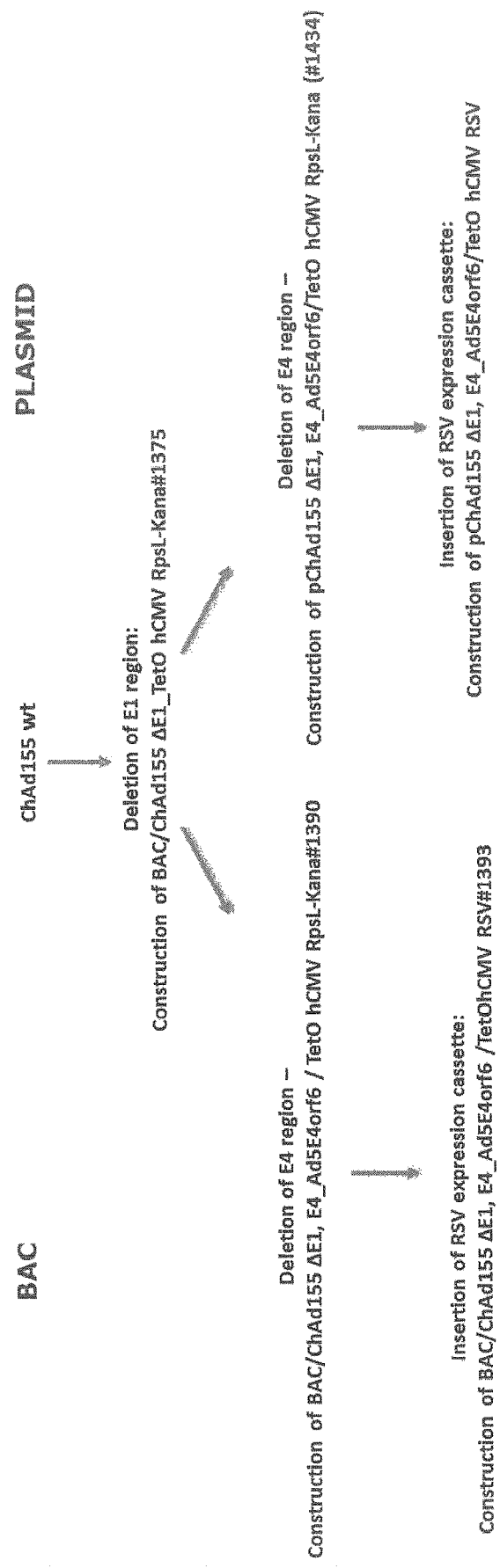

SEQ ID NO: 1—Polypeptide sequence of ChAd155 fiber
SEQ ID NO: 2—Polynucleotide sequence encoding ChAd155 fiber
SEQ ID NO: 3—Polypeptide sequence of ChAd155 penton
SEQ ID NO: 4—Polynucleotide sequence encoding ChAd155 penton
SEQ ID NO: 5—Polypeptide sequence of ChAd155 hexon
SEQ ID NO: 7—Polynucleotide sequence encoding ChAd155#1434
SEQ ID NO: 8—Polynucleotide sequence encoding ChAd155#1390
SEQ ID NO: 9—Polynucleotide sequence encoding ChAd155#1375
SEQ ID NO: 10—Polynucleotide sequence encoding wild type ChAd155
SEQ ID NO: 11—Polynucleotide sequence encoding ChAd155/RSV
SEQ ID NO: 12—Polynucleotide sequence encoding the CASI promoter
SEQ ID NO: 13—Ad5orf6 primer 1 polynucleotide sequence
SEQ ID NO: 14—Ad5orf6 primer 2 polynucleotide sequence
SEQ ID NO: 15—BAC/CHAd155 ΔE1_TetO hCMV RpsL-Kana primer 1 polynucleotide sequence
SEQ ID NO: 16—BAC/CHAd155 ΔE1_TetO hCMV RpsL-Kana (#1375) primer 2 polynucleotide sequence
SEQ ID NO: 17—1021-FW E4 Del Step1 primer polynucleotide sequence
SEQ ID NO: 18—1022-RW E4 Del Step1 primer polynucleotide sequence
SEQ ID NO: 19—1025-FW E4 Del Step2 primer polynucleotide sequence
SEQ ID NO: 20—1026-RW E4 Del Step2 primer polynucleotide sequence
SEQ ID NO: 21—91-SubMonte FW primer polynucleotide sequence
SEQ ID NO: 22—890-BghPolyA RW primer polynucleotide sequence
SEQ ID NO: 23—CMVfor primer polynucleotide sequence
SEQ ID NO: 24—CMVrev primer polynucleotide sequence
SEQ ID NO: 25—CMVFAM-TAMRA qPCR probe polynucleotide sequence
SEQ ID NO: 26—Woodchuck Hepatitis Virus Posttranscriptional Regulatory Element (WPRE) polynucleotide sequence
SEQ ID NO: 27—Amino acid sequence for the fiber protein of ChAd3
SEQ ID NO: 28—Amino acid sequence for the fiber protein of PanAd3
SEQ ID NO: 29—Amino acid sequence for the fiber protein of ChAd17
SEQ ID NO: 30—Amino acid sequence for the fiber protein of ChAd19
SEQ ID NO: 31—Amino acid sequence for the fiber protein of ChAd24
SEQ ID NO: 32—Amino acid sequence for the fiber protein of ChAd11
SEQ ID NO: 33—Amino acid sequence for the fiber protein of ChAd20
SEQ ID NO: 34—Amino acid sequence for the fiber protein of ChAd31
SEQ ID NO: 35—Amino acid sequence for the fiber protein of PanAd1
SEQ ID NO: 36—Amino acid sequence for the fiber protein of PanAd2
SEQ ID NO: 37—RSV FΔTM-N-M2-1 amino acid sequence
SEQ ID NO: 38—HIV Gag polynucleotide sequence

DETAILED DESCRIPTION OF THE INVENTION

Adenovirus

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The virus genome is a linear, double-stranded DNA. The virus DNA is intimately associated with the highly basic protein VII and a small peptide pX (formerly termed mu). Another protein, V, is packaged with this DNA-protein complex and provides a structural link to the capsid via protein VI. The virus also contains a virus-encoded protease, which is necessary for processing of some of the structural proteins to produce mature infectious virus.

The adenoviral genome is well characterized. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles, is activated.

Adenoviruses are species-specific and different serotypes, i.e., types of viruses that are not cross-neutralized by antibodies, have been isolated from a variety of mammalian species. For example, more than 50 serotypes have been isolated from humans which are divided into six subgroups (A-F; B is subdivided into B1 and B2) based on sequence homology and on their ability to agglutinate red blood cells (Tatsis and Ertl *Molecular Therapy* (2004) 10:616-629). Numerous adenoviruses have been isolated from nonhuman simians such as chimpanzees, bonobos, rhesus macaques and gorillas, and they are classified into the same human groups based on phylogenetic relationships based on hexon or fiber sequences (Colloca et al. (2012) ScienceTranslational Medicine 4:1-9; Roy et al. (2004) *Virology* 324: 361-372; Roy et al. (2010) *Journal of Gene Medicine* 13:17-25).

Adenovirus Capsid Proteins Including the Fiber Protein and Polynucleotides Encoding these Proteins As outlined above, the adenoviral capsid comprises three major proteins, hexon, penton and fiber. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable (Tatsis and Ertl *Molecular Therapy* (2004) 10:616-629).

Penton is another adenoviral capsid protein that forms a pentameric base to which fiber attaches. The trimeric fiber protein protrudes from the penton base at each of the 12 vertices of the capsid and is a knobbed rod-like structure. A remarkable difference in the surface of adenovirus capsids compared to that of most other icosahedral viruses is the presence of the long, thin fiber protein. The primary role of the fiber protein is the tethering of the viral capsid to the cell surface via its interaction with a cellular receptor.

The fiber proteins of many adenovirus serotypes share a common architecture: an N-terminal tail, a central shaft made of repeating sequences, and a C-terminal globular knob domain (or "head"). The central shaft domain consists of a variable number of beta-repeats. The beta-repeats connect to form an elongated structure of three intertwined spiralling strands that is highly rigid and stable. The shaft connects the N-terminal tail with the globular knob structure, which is responsible for interaction with the target cellular receptor. The globular nature of the adenovirus knob domain presents large surfaces for binding the receptor laterally and apically. The effect of this architecture is to project the receptor-binding site far from the virus capsid, thus freeing the virus from steric constraints presented by the relatively flat capsid surface.

Although fibers of many adenovirus serotypes have the same overall architecture, they have variable amino acid sequences that influence their function as well as structure. For example, a number of exposed regions on the surface of the fiber knob present an easily adaptable receptor binding site. The globular shape of the fiber knob allows receptors to bind at the sides of the knob or on top of the fiber knob. These binding sites typically lie on surface-exposed loops connecting beta-strands that are poorly conserved among human adenoviruses. The exposed side chains on these loops give the knob a variety of surface features while preserving the tertiary and quaternary structure. For example, the electrostatic potential and charge distributions at the knob surfaces can vary due to the wide range of isoelectric points in the fiber knob sequences, from pI approximately 9 for Ad 8, Ad 19, and Ad 37 to approximately 5 for subgroup B adenoviruses. As a structurally complex virus ligand, the fiber protein allows the presentation of a variety of binding surfaces (knob) in a number of orientations and distances (shaft) from the viral capsid.

One of the most obvious variations between some serotypes is fiber length. Studies have shown that the length of the fiber shaft strongly influences the interaction of the knob and the virus with its target receptors. Further, fiber proteins between serotypes can also vary in their ability to bend. Although beta-repeats in the shaft form a highly stable and regular structure, electron microscopy (EM) studies have shown distinct hinges in the fiber. Analysis of the protein sequence from several adenovirus serotype fibers pinpoints a disruption in the repeating sequences of the shaft at the third beta-repeat from the N-terminal tail, which correlates strongly with one of the hinges in the shaft, as seen by EM. The hinges in the fiber allow the knob to adopt a variety of orientations relative to the virus capsid, which may circumvent steric hindrances to receptor engagement requiring the correct presentation of the receptor binding site on the knob. For example, the rigid fibers of subgroup D Ads thus require a flexible receptor or one prepositioned for virus attachment, as they are unable to bend themselves. (Nicklin et al *Molecular Therapy* 2005 12:384-393)

The identification of specific cell receptors for different Ad serotypes and the knowledge of how they contribute to tissue tropism have been achieved through the use of fiber pseudotyping technology. Although Ads of some subgroups use CAR as a primary receptor, it is becoming clear that many Ads use alternate primary receptors, leading to vastly different tropism in vitro and in vivo. The fibers of these serotypes show clear differences in their primary and tertiary structures, such as fiber shaft rigidity, the length of the fiber shaft, and the lack of a CAR binding site and/or the putative HSPG binding motif, together with the differences in net charge within the fiber knob. Pseudotyping Ad 5 particles with an alternate fiber shaft and knob therefore provides an opportunity to remove important cell binding domains and, in addition, may allow more efficient (and potentially more cell-selective) transgene delivery to defined cell types compared to that achieved with Ad 5. Neutralization of fiber-pseudotyped Ad particles may also be reduced if the fibers used are from Ads with lower seroprevalence in humans or experimental models, a situation that favours successful administration of the vector (Nicklin et al *Molecular Therapy* (2005) 12:384-393). Furthermore, full length fiber as well as isolated fiber knob regions, but not hexon or penton alone, are capable of inducing dendritic cell maturation and are associated with induction of a potent CD8+ T cell response (Molinier-Frenkel et al. *J. Biol. Chem.* (2003) 278:37175-37182). Taken together, adenoviral fiber plays an important role in at least receptor-binding and immunogenicity of adenoviral vectors.

Figure 1A:
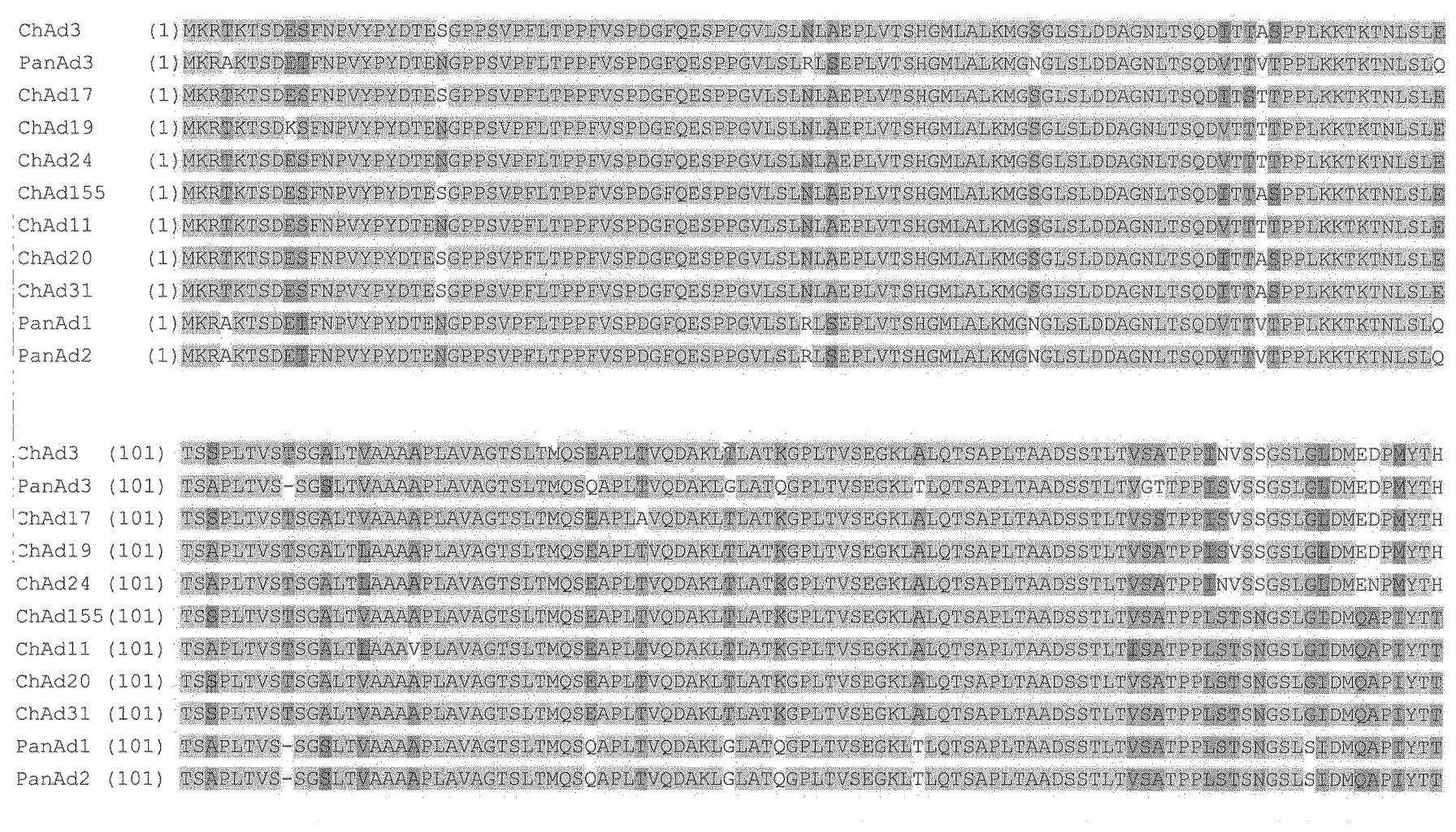
Figure 1B:
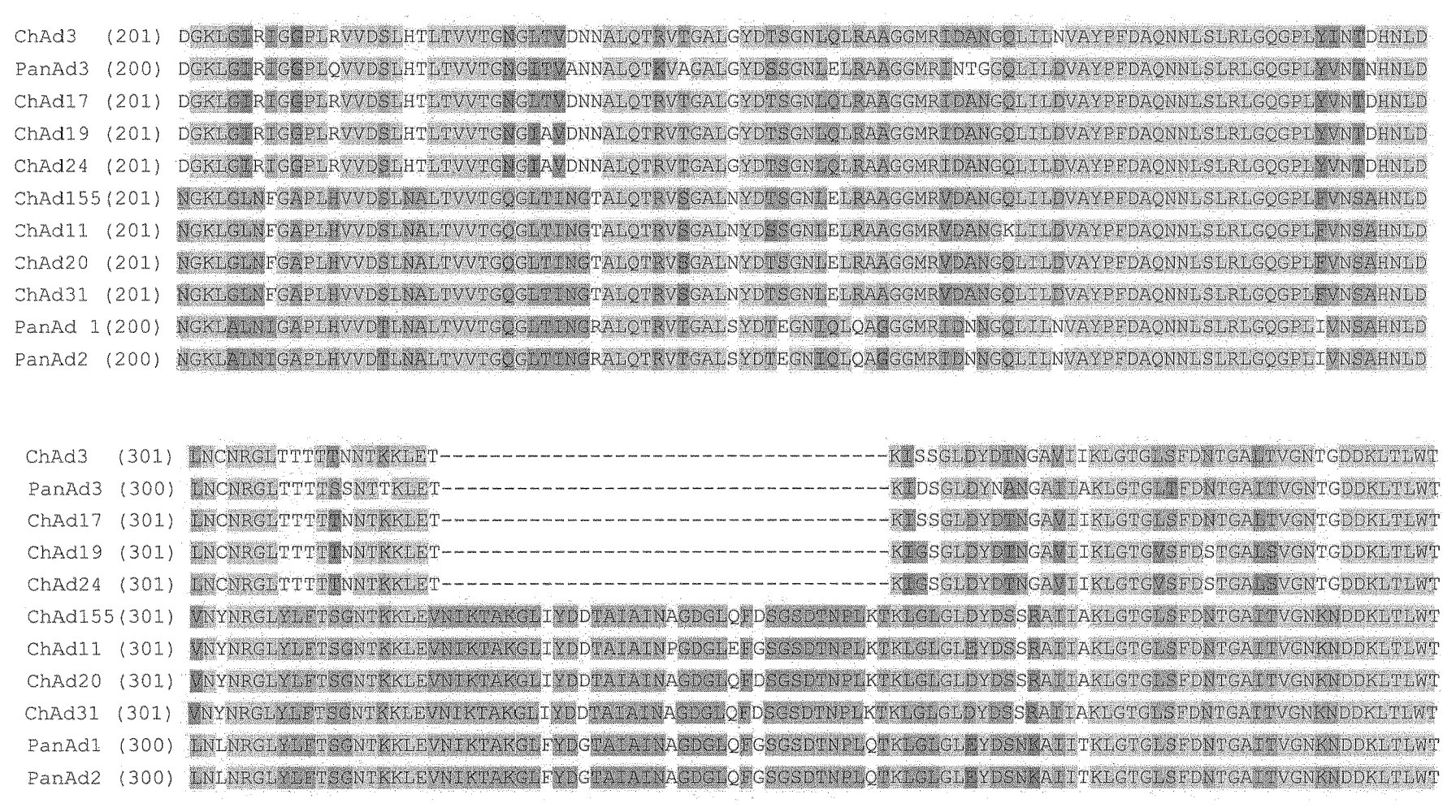

Illustrating the differences between the fiber proteins of Group C simian adenoviruses is the alignment provided in FIG. 1. A striking feature is that the fiber sequences of these adenoviruses can be broadly grouped into having a long fiber, such as ChAd155, or a short fiber, such as ChAd3. This length differential is due to a 36 amino acid deletion at approximately position 321 in the short fiber relative to the long fiber. In addition, there are a number of amino acid substitutions that differ between the short versus long fiber subgroup yet are consistent within each subgroup. While the exact function of these differences have not yet been elucidated, given the function and immunogenicity of fiber, they are likely to be significant. It has been shown that one of the determinants of viral tropism is the length of the fiber shaft. It has been demonstrated that an Ad5 vector with a shorter shaft has a lower efficiency of binding to CAR receptor and a lower infectivity (Ambriović-Ristov A. et al.: Virology. (2003) 312(2):425-33): It has been speculated that this impairment is the results of an increased rigidity of the shorter fiber leading to a less efficient attachment to the cell receptor (Wu, E et al.: J Virol. (2003) 77(13): 7225-7235). These studies may explain the improved properties of ChAd155 carrying a longer and more flexible fiber in comparison with the previously described ChAd3 and PanAd3 carrying a fiber with a shorter shaft.

In one aspect of the invention there is provided isolated fiber, penton and hexon capsid polypeptides of chimp adenovirus ChAd155 and isolated polynucleotides encoding the fiber, penton and hexon capsid polypeptides of chimp adenovirus ChAd155.

All three capsid proteins are expected to contribute to low seroprevalence and can, thus, be used independently from each other or in combination to suppress the affinity of an adenovirus to preexisting neutralizing antibodies, e.g. to manufacture a recombinant adenovirus with a reduced seroprevalence. Such a recombinant adenovirus may be a chimeric adenovirus with capsid proteins from different serotypes with at least a fiber protein from ChAd155.

The ChAd155 fiber polypeptide sequence is provided in SEQ ID NO: 1.

The ChAd155 penton polypeptide sequence is provided in SEQ ID NO: 3.

The ChAd155 hexon polypeptide sequence is provided in SEQ ID NO: 5.

Polypeptides, Recombinant Adenoviruses, Compositions or Cells Comprising Polypeptide Sequences of ChAd155 Fiber or a Functional Derivative Thereof Suitably the isolated polypeptide, recombinant adenovirus, composition or cell of the invention comprises a polypeptide having the amino acid sequence according to SEQ ID NO: 1.

Suitably the polypeptide, recombinant adenovirus, composition or cell of the invention comprises a polypeptide which is a functional derivative of a polypeptide having the amino acid sequence according to SEQ ID NO: 1, wherein the functional derivative has an amino acid sequence which is at least 80% identical over its entire length to the amino acid sequence of SEQ ID NO: 1. Suitably the functional derivative of a polypeptide having the amino acid sequence according to SEQ ID NO: 1 has an amino acid sequence which is at least 80% identical, such as at least 85.0% identical, such as at least 90% identical, such as at least 91.0% identical, such as at least 93.0% identical, such as at least 95.0% identical, such as at least 97.0% identical, such as at least 98.0% identical, such as at least 99.0% identical, such as at least 99.2% identical, such as at least 99.4% identical, such as 99.5% identical, such as at least 99.6% identical, such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the polypeptide, recombinant adenovirus, composition or cell according to the invention further comprises:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 50.0% identical over its entire length to the amino acid sequence of SEQ ID NO: 3, and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of a polypeptide having the amino acid sequence according to SEQ ID NO: 3 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 3. Alternatively the functional derivative has no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 3.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

Polypeptides, Recombinant Adenoviruses, Compositions or Cells Comprising Polypeptide Sequences of ChAd155 Penton Suitably the polypeptide, recombinant adenovirus, composition or cell of the invention comprises a polypeptide having the amino acid sequence according to SEQ ID NO: 3.

Suitably the polypeptide, recombinant adenovirus, composition or cell of the invention further comprises:
(a) a polypeptide having the amino acid sequence according to SEQ ID NO: 1; or
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1 and/or
(a) a polypeptide having the amino acid sequence according to SEQ ID NO: 5; or (b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

Suitably the functional derivative of a polypeptide having the amino acid sequence according to SEQ ID NO: 1 has an amino acid sequence which is at least 60.0% identical, such as at least 70.0% identical, such as at least 80.0% identical, such as at least 85.0% identical, such as at least 87.0% identical, such as at least 89.0% identical, such as at least 91.0% identical, such as at least 93.0% identical, such as at least 95.0% identical, such as at least 97.0% identical, such as at least 98.0% identical, such as at least 99.0% identical, such as at least 99.2%, such as at least 99.4%, such as 99.5% identical, such as at least 99.6%, such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 99.0%, such as at least 99.0%, such as at least 99.2%, such as at least 99.4%, such as 99.5% identical, such as at least 99.6%, such as at least 99.8% identical, such as 99.9% identical over its entire length to the amino acid sequence of SEQ ID NO:5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

Isolated Polynucleotides, Vectors, Recombinant Adenoviruses, Compositions or Cells Comprising Polynucleotides Encoding ChAd155 Fiber or a Functional Derivative Thereof Suitably the isolated polynucleotide, vector, recombinant adenovirus, composition or cell of the invention comprises a polynucleotide which encodes a polypeptide having the amino acid sequence according to SEQ ID NO: 1. Suitably the polynucleotide has a sequence according to SEQ ID NO: 2.

Alternatively, the polynucleotide, vector, recombinant adenovirus, composition or cell of the invention comprises a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1. Suitably the functional derivative of a polypeptide having the amino acid sequence according to SEQ ID NO: 1 has an amino acid sequence which is at least 80% identical, such as at least 85.0% identical, such as at least 90% identical, such as at least 91.0% identical, such as at least 93.0% identical, such as at least 95.0% identical, such as at least 97.0% identical, such as at least 98.0% identical, such as at least 99.0% identical, such as at least 99% identical, such as at least 99.4% identical, such as at least 99.6% identical, such as at least 99.8% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the polynucleotide, vector, recombinant adenovirus, composition or cell of the invention further comprises a polynucleotide encoding:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 50.0% identical over its entire length to the amino acid sequence of SEQ ID NO: 3, and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of the polypeptide having the amino acid sequence according to SEQ ID NO: 3 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99%, such as at least 99.4%, such as at least 99.6%, such as at least 99.8% identical over its entire length to the amino acid sequence of SEQ ID NO: 3. Alternatively the functional derivative has no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 3.

Suitably the functional derivative of the polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 98.0%, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

Isolated Polynucleotides, Vectors, Recombinant Adenoviruses, Compositions or Cells Comprising Polynucleotides Encoding ChAd155 Penton Suitably the isolated polynucleotide, vector, recombinant adenovirus, composition or cell of the invention comprises a polynucleotide which encodes a polypeptide having the amino acid sequence according to SEQ ID NO: 3. Suitably the polynucleotide has a sequence according to SEQ ID NO: 4.

Suitably the polynucleotide, vector, recombinant adenovirus, composition or cell of the invention further comprises a polynucleotide encoding:

(a) a polypeptide having the amino acid sequence according to SEQ ID NO: 1; or
(b) a functional derivative of a polypeptide having the amino acid sequence according to SEQ ID NO: 1, wherein the functional derivative has an amino acid sequence which is at least 50% identical over its entire length to the amino acid sequence of SEQ ID NO: 1 and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of a polypeptide having the amino acid sequence according to SEQ ID NO: 1 has an amino acid sequence which is at least 60.0% identical, such as at least 70.0% identical, such as at least 80.0% identical, such as at least 85.0% identical, such as at least 87.0% identical, such as at least 89.0% identical, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 98.0%, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

ChAd155 Backbones

The invention provides isolated polynucleotide sequences of chimp adenovirus ChAd155, including that of wild type, unmodified ChAd155 (SEQ ID NO: 10) and modified backbone constructs of ChAd155. These modified backbone constructs include ChAd155#1434 (SEQ ID NO: 7), ChAd155#1390 (SEQ ID NO: 8) and ChAd155#1375 (SEQ ID NO: 9). ChAd155 backbones may be used in the construction of recombinant replication-competent or replication-incompetent adenoviruses for example for the delivery of transgenes.

Annotation of the ChAd155 wild type sequence (SEQ ID NO: 10) sequence is provided below.

| LOCUS | ChAd155 37830 bp DNA linear 10 JUN. 2015 |
|---|---|
| DEFINITION | Chimp adenovirus 155, complete genome. |
| COMMENT | Annotation according to alignment of ChAd155 against the human Adenovirus 2 reference strain NC_001405 Two putative ORFs in the E3 region added manually |

| FEATURES | Location/Qualifiers |
|---|---|
| source | 1..37830 |
| | /organism="Chimpanzee adenovirus 155" |
| | /mol_type="genomic DNA" |
| | /acronym="ChAd155" |
| repeat_region | 1..101 |
| | /standard_name="ITR" |
| | /rpt_type=inverted |
| gene | 466..1622 |
| | /gene="E1A" |
| TATA_signal | 466..471 |
| | /gene="E1A" |

| | | | | | |
|---|---|---|---|---|---|
| prim_transcript | 497..1622 /gene="E1A" | | misc_RNA | 10671..10832 /gene="VAI" /product="VAI" | |
| CDS | join(577..1117,1231..1532) /gene="E1A" /product="E1A_280R" | | gene | 10902..11072 /gene="VAII" | |
| CDS | join(577..979,1231..1532) /gene="E1A" /product="E1A_243R" | | misc_RNA | 10902..11072 /gene="VAII" /product="VAII" | |
| polyA_signal | 1600..1605 /gene="E1A" | | CDS | 11093..12352 /gene="L1" /product="L1_52K" | |
| gene | 1662..4131 /gene="E1B" | | CDS | 12376..14157 /gene="L1" /product="L1_pIIIa" | |
| TATA_signal | 1662..1667 /gene="E1B" | | polyA_signal | 14197..14202 /gene="L1" | |
| prim_transcript | 1692..4131 /gene="E1B" | | CDS | 14254..16035 /gene="L2" /product="L2_penton" | |
| CDS | 1704..2267 /gene="E1B" /product="E1B_19K" | | CDS | 16050..16646 /gene="L2" /product="L2_pVII" | |
| CDS | 2009..3532 /gene="E1B" /product="E1B_55K" | | CDS | 16719..17834 /gene="L2" /product="L2_V" | |
| gene | 3571..4131 /gene="IX" | | CDS | 17859..18104 /gene="L2" /product="L2_pX" | |
| TATA_signal | 3571..3576 /gene="IX" | | polyA_signal | 18143..18148 /gene="L2" | |
| prim_transcript | 3601..4131 /gene="IX" | | CDS | 18196..18951 /gene="L3" /product="L3_pVI" | |
| CDS | 3628..4092 /gene="IX" /product="IX" | | CDS | 19063..21945 /gene="L3" /product="L3_hexon" | |
| polyA_signal | 4097..4102 /note="E1B, IX" | | CDS | 21975..22604 /gene="L3" /product="L3_protease" | |
| gene | complement(4117..27523) /gene="E2B" | | polyA_signal | 22630..22635 /gene="L3" | |
| prim_transcript | complement(4117..27494) /gene="E2B" | | gene | complement(22632..27523) /gene="E2A" | |
| gene | complement(4117..5896) /gene="IVa2" | | prim_transcript | complement(22632..27494) /gene="E2A" | |
| prim_transcript | complement(4117..5896) /gene="IVa2" | | gene | complement(22632..26357) /gene="E2A-L" | |
| CDS | complement(join(4151..5487,5766..5778)) /gene="IVa2" /product="E2B_IVa2" | | prim_transcript | complement(22632..26328) /gene="E2A-L" | |
| polyA_signal | complement(4150..4155) /note="IVa2, E2B" | | polyA_signal | complement(22649..22654) /note="E2A, E2A-L" | |
| CDS | complement(join(5257..8838,14209..14217)) /gene="E2B" /product="E2B_polymerase" | | CDS | complement(22715..24367) /gene="E2A" /note="DBP; genus-common; DBP family" /codon_start=1 /product="E2A" | |
| gene | 6078..34605 /gene="L5" | | CDS | 24405..26915 /gene="L4" /product="L4_100k" | |
| gene | 6078..28612 /gene="L4" | | TATA_signal | complement(26352..26357) /gene="E2A-L" | |
| gene | 6078..22658 /gene="L3" | | CDS | join(26602..26941,27147..27529) /gene="L4" /product="L4_33K" | |
| gene | 6078..18164 /gene="L2" | | CDS | 26602..27207 /gene="L4" /product="L4_22K" | |
| gene | 6078..14216 /gene="L1" | | TATA_signal | complement(27518..27523) /note="E2A, E2B; nominal" | |
| TATA_signal | 6078..6083 /note="L" | | CDS | 27604..28287 /gene="L4" /product="L4_pVIII" | |
| prim_transcript | 6109..34605 /gene="L5" | | gene | 27969..32686 /gene="E3B" | |
| prim_transcript | 6109..28612 /gene="L4" | | gene | 27969..31611 /gene="E3A" | |
| prim_transcript | 6109..22658 /gene="L3" | | TATA_signal | 27969..27974 /note="E3A, E3B" | |
| prim_transcript | 6109..18164 /gene="L2" | | | | |
| prim_transcript | 6109..14216 /gene="L1" | | | | |
| CDS | join(8038..8457,9722..9742) /gene="L1" /product="L1_13.6K" | | | | |
| CDS | complement(join(8637..10640,14209..14217)) /gene="E2B" /product="E2B_pTP" | | | | |
| gene | 10671..10832 /gene="VAI" | | | | |

-continued

| | |
|---|---|
| prim_transcript | 27998..32686<br>/gene="E3B" |
| prim_transcript | 27998..31611<br>/gene="E3A" |
| CDS | 28288..28605<br>/gene="E3A"<br>/product="E3 ORF1" |
| polyA_signal | 28594..28599<br>/gene="L4" |
| CDS | 29103..29303<br>/gene="E3A"<br>/product="E3 ORF2" |
| CDS | 29300..29797<br>/gene="E3A"<br>/product="E3 ORF3" |
| CDS | 29826..30731<br>/gene="E3A"<br>/product="E3 ORF4" |
| CDS | 30728..31579<br>/gene="E3A"<br>/product="E3 ORF5" |
| CDS | 31283..31579<br>/gene="E3A"<br>/product="E3 ORF6" |
| polyA_signal | 31578..31584<br>/gene="E3A" |
| CDS | 31591..31863<br>/gene="E3B"<br>/product="E3 ORF7" |
| CDS | 31866..32264<br>/gene="E3B"<br>/product="E3 ORF8" |
| CDS | 32257..32643<br>/gene="E3B"<br>/product="E3 ORF9" |
| polyA_signal | 32659..32664<br>/gene="E3B" |
| gene | complement(<32678..32838)<br>/gene="U" |
| CDS | complement(<32678..32838)<br>/gene="U"<br>/note="exon encoding C terminus unidentified; genus-common"<br>/product="protein U" |
| CDS | 32849..34585<br>/gene="L5"<br>/product="L5_fiber" |
| polyA_signal | 34581..34586<br>/gene="L5" |
| gene | complement(34611..37520)<br>/gene="E4" |
| prim_transcript | complement(34611..37490)<br>/gene="E4" |
| polyA_signal | complement(34625..34630)<br>/gene="E4" |
| CDS | complement(join(34794..35069,35781..35954))<br>/gene="E4"<br>/product="E4 ORF7" |
| CDS | complement(35070..35954)<br>/gene="E4"<br>/product="E4 ORF6" |
| CDS | complement(35875..36219)<br>/gene="E4"<br>/product="E4 ORF4" |
| CDS | complement(36235..36582)<br>/gene="E4"<br>/product="E4 ORF3" |
| CDS | complement(36579..36971)<br>/gene="E4"<br>/product="E4 ORF2" |
| CDS | complement(37029..37415)<br>/gene="E4"<br>/product="E4 ORF1" |
| TATA_signal | complement(37515..37520)<br>/gene="E4" |
| repeat_region | 37740..37830<br>/standard_name="ITR"<br>/rpt_type=inverted |

In one embodiment, fragments of the sequences of SEQ ID NO: 7, 8, 9, 10 and their complementary strands, cDNA and RNA complementary thereto are provided. Suitably, fragments are at least 15 nucleotides in length, more suitably 30 nucleotides in length, more suitably 60 nucleotides in length, more suitably 120 nucleotides in length, more suitably 240, more suitably 480 nucleotides in length and encompass functional fragments, i.e., fragments which are of biological interest. For example, a functional fragment can express a desired adenoviral product or may be useful in production of recombinant viral vectors. Such fragments include the gene sequences listed above.

Gene products of the ChAd155 adenovirus, such as proteins, enzymes, and fragments thereof, which are encoded by the adenoviral nucleic acids described herein are provided. Such proteins include those encoded by the open reading frames identified above and the proteins encoded by the polynucleotides provided in the Sequence Listing.

Further ChAd155 Polynucleotides and Polypeptides

In some embodiments the polynucleotide of the invention comprises a polynucleotide encoding a fiber polypeptide; a penton polypeptide; a hexon polypeptide and penton polypeptide; a hexon polypeptide and fiber polypeptide; penton polypeptide and fiber polypeptide; or hexon polypeptide, penton polypeptide and fiber polypeptide of the invention; and may further comprise additional adenoviral polynucleotides, suitably ChAd155 polynucleotides. Thus, suitably the polynucleotide according to the invention comprises one or more of the following, the sequence coordinates relative to SEQ ID NO:10 provided in the previous annotation:

(a) an adenoviral 5'-inverted terminal repeat (ITR);
(b) an adenoviral E1A region, or a fragment thereof selected from among the E1A_280R and E1A_243R regions;
(c) an adenoviral E1B or IX region, or a fragment thereof selected from among the group consisting of the E1B_19K, E1B_55K and IX regions;
(d) an adenoviral E2B region; or a fragment thereof selected from among the group consisting of the E2B_pTP, E2B_polymerase and E2B_IVa2 regions;
(e) an adenoviral L1 region, or a fragment thereof, said fragment encoding an adenoviral protein selected from the group consisting of the L1_13.6K, L1_52K and L1_pIIIa protein;
(f) an adenoviral L2 region or a L2 region comprising a polynucleotide encoding the penton protein of the invention, or a fragment thereof, said fragment encoding an adenoviral protein selected from the group consisting of the L2_penton protein, the L2_pVII protein, the L2_V protein and the L2_pX protein;
(g) an adenoviral L3 region or a L3 region comprising a polynucleotide encoding the hexon protein of the invention, or a fragment thereof, said fragment encoding an adenoviral protein selected from the group consisting of the L3_pVI protein, the L3_hexon protein and the L3_protease protein;
(h) an adenoviral E2A region;
(i) an adenoviral L4 region, or a fragment thereof said fragment encoding an adenoviral protein selected from the group consisting of the L4_100 k protein, the L4_33K protein, the L4_22K protein and protein L4_VIII;
(j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region or a L5 region comprising a polynucleotide encoding the L5_fiber fiber polypeptide of the invention (l) an adenoviral (such as Ad5) E4 region, or a fragment thereof selected from the group consisting of E4 ORF7, E4 ORF6, E4 ORF4, E4 ORF3, E4 ORF2, and E4 ORF1; in particular ORF6 of said E4 region;

(m) an adenoviral 3'-ITR; and/or (n) an adenoviral VAI or VAII RNA region, preferably an adenoviral VAI or VAII RNA region from an adenovirus other than ChAd155, more preferably from Ad5.

DEFINITIONS

Suitably the polynucleotides or polypeptides of the invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

Suitably the polynucleotides of the invention are recombinant. Recombinant means that the polynucleotide is the product of at least one of cloning, restriction or ligation steps, or other procedures that result in a polynucleotide that is distinct from a polynucleotide found in nature. A recombinant adenovirus is an adenovirus comprising a recombinant polynucleotide. A recombinant vector is a vector comprising a recombinant polynucleotide. 'A recombinant virus' includes progeny of the original recombinant virus. 'A recombinant vector' includes replicates of the original recombinant vector. 'A recombinant polynucleotide' includes replicates of the original recombinant polynucleotide.

Suitably, the polypeptide sequence of the present invention contains at least one alteration with respect to a native sequence. Suitably, the polynucleotide sequences of the present invention contain at least one alteration with respect to a native sequence. For example, a polynucleotide introduced by genetic engineering techniques into a plasmid or vector derived from a different species (and often a different genus, subfamily or family) is a heterologous polynucleotide. A promoter removed from its native coding sequence and operatively linked to a coding sequence with which it is not naturally found linked is a heterologous promoter. A specific recombination site that has been cloned into a genome of a virus or viral vector, wherein the genome of the virus does not naturally contain it, is a heterologous recombination site. A heterologous nucleic acid sequence also includes a sequence naturally found in an adenoviral genome, but located at a non-native position within the adenoviral vector.

Typically, "heterologous" means derived from a genotypically distinct entity from that of the rest of the entity to which it is being compared. A heterologous nucleic acid sequence refers to any nucleic acid sequence that is not isolated from, derived from, or based upon a naturally occurring nucleic acid sequence of the adenoviral vector. "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

A "functional derivative" of a polypeptide suitably refers to a modified version of a polypeptide, e.g. wherein one or more amino acids of the polypeptide may be deleted, inserted, modified and/or substituted. A derivative of an unmodified adenoviral capsid protein is considered functional if, for example:

(a) an adenovirus comprising the derivative capsid protein within its capsid retains substantially the same or a lower seroprevalence compared to an adenovirus comprising the unmodified capsid protein and/or (b) an adenovirus comprising the derivative capsid protein within its capsid retains substantially the same or a higher host cell infectivity compared to an adenovirus comprising the unmodified capsid protein and/or (c) an adenovirus comprising the derivative capsid protein within its capsid retains substantially the same or a higher immunogenicity compared to an adenovirus comprising the unmodified capsid protein and or (d) an adenovirus comprising the derivative capsid protein within its capsid retains substantially the same or a higher level of transgene productivity compared to an adenovirus comprising the unmodified capsid protein.

Properties (a)-(d) above may suitably be measured using the methods described in the Examples section below.

Suitably, the polypeptide, vector or recombinant adenovirus has a low seroprevalence in a human population. "Low seroprevalence" may mean having a reduced pre-existing neutralizing antibody level as compared to human adenovirus 5 (Ad5). Similarly or alternatively, "low seroprevalence" may mean less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titre (defined as a 50% neutralisation titer >200) using methods as described in Aste-Amézaga et al., Hum. Gene Ther. (2004) 15(3):293-304.

The terms polypeptide, peptide and protein are used interchangeably herein.

The term "simian" is typically meant to encompass non-human primates, for example Old World monkeys, New World monkeys, apes and gibbons. In particular, simian may refer to nonhuman apes such as chimpanzees (*Pan troglodyte*), bonobos (*Pan paniscus*) and gorillas (genus Gorilla). Non-ape simians may include rhesus macaques (*Macaca mulatta*)

Sequence Comparison

For the purposes of comparing two closely-related polynucleotide or polypeptide sequences, the "% identity" between a first sequence and a second sequence may be calculated using an alignment program, such as BLAST® (available at blast.ncbi.nlm.nih.gov, last accessed 9 Mar. 2015) using standard settings. The % identity is the number of identical residues divided by the number of residues in the reference sequence, multiplied by 100. The % identity figures referred to above and in the claims are percentages calculated by this methodology. An alternative definition of % identity is the number of identical residues divided by the number of aligned residues, multiplied by 100. Alternative methods include using a gapped method in which gaps in the alignment, for example deletions in one sequence relative to the other sequence, are accounted for in a gap score or a gap cost in the scoring parameter. For more information, see the BLAST® fact sheet available at ftp.ncbi.nlm.nih.gov/pub/factsheets/HowTo_BLASTGuide.pdf, last accessed on 9 Mar. 2015.

Sequences that preserve the functionality of the polynucleotide or a polypeptide encoded thereby are likely to be more closely identical. Polypeptide or polynucleotide sequences are said to be the same as or identical to other polypeptide or polynucleotide sequences, if they share 100% sequence identity over their entire length.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced percent sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

Suitably substitutions in the sequences of the present invention may be conservative substitutions. A conservative substitution comprises the substitution of an amino acid with another amino acid having a chemical property similar to the amino acid that is substituted (see, for example, Stryer et al, Biochemistry, 5$^{th}$ Edition 2002, pages 44-49). Preferably, the conservative substitution is a substitution selected from the group consisting of: (i) a substitution of a basic amino acid with another, different basic amino acid; (ii) a substitution of an acidic amino acid with another, different acidic amino acid; (iii) a substitution of an aromatic amino acid with another, different aromatic amino acid; (iv) a substitution of a non-polar, aliphatic amino acid with another, different non-polar, aliphatic amino acid; and (v) a substitution of a polar, uncharged amino acid with another, different polar, uncharged amino acid. A basic amino acid is preferably selected from the group consisting of arginine, histidine, and lysine. An acidic amino acid is preferably aspartate or glutamate. An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v).

Vectors and Recombinant Adenovirus

The ChAd155 sequences of the invention are useful as therapeutic agents and in construction of a variety of vector systems, recombinant adenovirus and host cells. Suitably the term "vector" refers to a nucleic acid that has been substantially altered (e.g., a gene or functional region that has been deleted and/or inactivated) relative to a wild type sequence and/or incorporates a heterologous sequence, i.e., nucleic acid obtained from a different source (also called an "insert"), and replicating and/or expressing the inserted polynucleotide sequence, when introduced into a cell (e.g., a host cell). For example, the insert may be all or part of the ChAd155 sequences described herein. In addition or alternatively, a ChAd155 vector may be a ChAd155 adenovirus comprising one or more deletions or inactivations of viral genes, such as E1 or other viral gene or functional region described herein. Such a ChAd155, which may or may not comprise a heterologous sequence, is often called a "backbone" and may be used as is or as a starting point for additional modifications to the vector.

A vector may be any suitable nucleic acid molecule including naked DNA, a plasmid, a virus, a cosmid, phage vector such as lambda vector, an artificial chromosome such as a BAC (bacterial artificial chromosome), or an episome. Alternatively, a vector may be a transcription and/or expression unit for cell-free in vitro transcription or expression, such as a T7-compatible system. The vectors may be used alone or in combination with other adenoviral sequences or fragments, or in combination with elements from non-adenoviral sequences. The ChAd155 sequences are also useful in antisense delivery vectors, gene therapy vectors, or vaccine vectors. Thus, further provided are gene delivery vectors, and host cells which contain the ChAd155 sequences.

The term "replication-competent" adenovirus refers to an adenovirus which can replicate in a host cell in the absence of any recombinant helper proteins comprised in the cell. Suitably, a "replication-competent" adenovirus comprises the following intact or functional essential early genes: E1A, E1B, E2A, E2B, E3 and E4. Wild type adenoviruses isolated from a particular animal will be replication competent in that animal.

The term "replication-incompetent" or "replication-defective" adenovirus refers to an adenovirus which is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Particularly suitably E1 and optionally E3 and/or E4 are deleted. If deleted, the aforementioned deleted gene region will suitably not be considered in the alignment when determining % identity with respect to another sequence.

The present invention provides vectors such as recombinant adenovirus that deliver a protein, suitably a heterologous protein, to cells, either for therapeutic or vaccine purposes. A vector may include any genetic element including naked DNA, a phage, transposon, cosmid, episome, plasmid, or a virus. Such vectors contain DNA of ChAd155 as disclosed herein and a minigene. By "minigene" (or "expression cassette") is meant the combination of a selected heterologous gene (transgene) and the other regulatory elements necessary to drive translation, transcription and/or expression of the gene product in a host cell.

Typically, a ChAd155-derived adenoviral vector is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the minigene).

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5 ' cis-elements necessary for packaging and replication; i.e., the 5' ITR sequences (which function as origins of replication) and the native 5 ' packaging enhancer domains (that contain sequences necessary for packaging linear Ad genomes and enhancer elements for the E1 promoter). The 3' end of the adenoviral genome includes the 3 ' cis-elements (including the ITRs) necessary for packaging and encapsidation. Suitably, a recombinant adenovirus contains both 5' and 3' adenoviral cis-elements and the minigene (suitably containing a transgene) is located between the 5' and 3' adenoviral sequences. A ChAd155-based adenoviral vector may also contain additional adenoviral sequences.

Suitably, ChAd155-based vectors contain one or more adenoviral elements derived from the adenoviral ChAd155 genome of the invention. In one embodiment, the vectors contain adenoviral ITRs from ChAd155 and additional adenoviral sequences from the same adenoviral serotype. In another embodiment, the vectors contain adenoviral sequences that are derived from a different adenoviral serotype than that which provides the ITRs.

As defined herein, a pseudotyped adenovirus refers to an adenovirus in which the capsid proteins of the adenovirus are from a different adenovirus than the adenovirus which provides the ITRs.

Further, chimeric or hybrid adenoviruses may be constructed using the adenoviruses described herein using techniques known to those of skill in the art (e.g., U.S. Pat. No. 7,291,498).

ITRs and any other adenoviral sequences present in the vector of the present invention may be obtained from many sources. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other chimp or from human adenoviruses are described in the published literature (for example, U.S. Pat. No. 5,240,846). The DNA sequences of a number of adenovirus types are available from GenBank, including type Ad5 (GenBank Accession Number M73370). The adenovirus sequences may be obtained from any known adenovirus serotype, such as serotypes 2, 3, 4, 7, 12 and 40, and further including any of the presently identified human types. Similarly adenoviruses known to infect nonhuman animals (e.g., simians) may also be employed in the vector constructs of this invention (e.g., U.S. Pat. No. 6,083,716). The viral sequences, helper viruses (if needed), and recombinant viral particles, and other vector components and sequences employed in the construction of the vectors described herein may be obtained as described below.

Sequence, Vector and Adenovirus Production

The sequences of the invention may be produced by any suitable means, including recombinant production, chemical synthesis, or other synthetic means. Suitable production techniques are well known to those of skill in the art. Alternatively, peptides can also be synthesized by well known solid phase peptide synthesis methods.

The adenoviral plasmids (or other vectors) may be used to produce adenoviral vectors. In one embodiment, the adenoviral vectors are adenoviral particles which are replication-incompetent.

In one embodiment, the adenoviral particles are rendered replication-incompetent by deletions in the E1A and/or E1B genes. Alternatively, the adenoviruses are rendered replication-incompetent by another means, optionally while retaining the E1A and/or E1B genes. Similarly, in some embodiments, reduction of an immune response to the vector may be accomplished by deletions in the E2B and/or DNA polymerase genes. The adenoviral vectors can also contain other mutations to the adenoviral genome, e.g., temperature-sensitive mutations or deletions in other genes. In other embodiments, it is desirable to retain an intact E1A and/or E1B region in the adenoviral vectors. Such an intact E1 region may be located in its native location in the adenoviral genome or placed in the site of a deletion in the native adenoviral genome (e.g., in the E3 region).

In the construction of adenovirus vectors for delivery of a gene to a mammalian (such as human) cell, a range of modified adenovirus nucleic acid sequences can be employed in the vectors. For example, all or a portion of the adenovirus delayed early gene E3 may be eliminated from the adenovirus sequence which forms a part of the recombinant virus. The function of E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of the invention contains a deletion in the delayed early gene E2A. Deletions may also be made in any of the late genes L1 to L5 of the adenovirus genome. Similarly, deletions in the intermediate genes IX and IVa2 may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2A and E3 genes, or of the E1 and E3 genes, or of E1, E2A and E4 genes, with or without deletion of E3, and so on. Any one or more of the E genes may suitably be replaced with an E gene (or one or more E gene open reading frames) sourced from a different strain of adenovirus. Particularly suitably the ChAd155 E1 and E3 genes are deleted and the ChAd155E4 gene is replaced with E4Ad5orf6. As discussed above, such deletions and/or substitutions may be used in combination with other mutations, such as temperature-sensitive mutations, to achieve a desired result.

An adenoviral vector lacking one or more essential adenoviral sequences (e.g., E1A, E1B, E2A, E2B, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell.

Complementation of Replication-Incompetent Vectors

To generate recombinant adenoviruses deleted in any of the genes described above, the function of the deleted gene region, if essential to the replication and infectivity of the virus, must be supplied to the recombinant virus by a helper virus or cell line, i.e., a complementation or packaging cell line.

Helper Viruses

Depending upon the adenovirus gene content of the viral vectors employed to carry the minigene, a helper adenovirus or non-replicating virus fragment may be used to provide sufficient adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains adenovirus genes in addition, suitably, to one or more of the sequences described herein. Such a helper virus is suitably used in combination with an E1 expressing (and optionally additionally E3 expressing) cell line.

A helper virus may optionally contain a reporter gene. A number of such reporter genes are known to the art as well as described herein. The presence of a reporter gene on the helper virus which is different from the transgene on the adenovirus vector allows both the adenoviral vector and the helper virus to be independently monitored. This reporter is used to enable separation between the resulting recombinant virus and the helper virus upon purification.

Complementation Cell Lines

In many circumstances, a cell line expressing the one or more missing genes which are essential to the replication and infectivity of the virus, such as human E1, can be used to transcomplement a chimp adenoviral vector. This is particularly advantageous because, due to the diversity between the chimp adenovirus sequences of the invention and the human adenovirus sequences found in currently available packaging cells, the use of the current human E1-containing cells prevents the generation of replication-competent adenoviruses during the replication and production process.

Alternatively, if desired, one may utilize the sequences provided herein to generate a packaging cell or cell line that expresses, at a minimum, the E1 gene from ChAd155 under the transcriptional control of a promoter for expression in a selected parent cell line. Inducible or constitutive promoters may be employed for this purpose. Examples of such promoters are described in detail elsewhere in this document. A parent cell is selected for the generation of a novel cell line expressing any desired ChAd155 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209.

Such E1-expressing cell lines are useful in the generation of recombinant adenovirus E1 deleted vectors. Additionally, or alternatively, cell lines that express one or more adenoviral gene products, e.g., E1A, E1B, E2A, E3 and/or E4, can be constructed using essentially the same procedures as used in the generation of recombinant viral vectors. Such cell lines can be utilised to transcomplement adenovirus vectors deleted in the essential genes that encode those products, or to provide helper functions necessary for packaging of a helper-dependent virus (e.g., adeno-associated virus). The preparation of a host cell involves techniques such as assembly of selected DNA sequences.

In another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells.

Host cells may be selected from among any mammalian species, including, without limitation, cells such as A549, WEHI, 3T3, 10'I'I/2, HEK 293 cells or Per.C6 (both of which express functional adenoviral E1) [Fallaux, 1998], Saos, C2C12, L cells, HT1080, HepG2 and primary fibroblast, hepatocyte and myoblast cells derived from mammals including human, monkey, mouse, rat, rabbit, and hamster.

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. *PLOS One* (2013) 8(e55435):1-9). Procell92.S is adapted for growth in suspension conditions and is useful for producing adenoviral vectors expressing toxic proteins (www.okairos.com/e/inners.php?m=00084, last accessed 13 Apr. 2015).

Assembly of a Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1 \times 10^4$ cells to about 1×10$^{13}$ cells, and preferably about 10$^5$ cells. However, the relative amounts of vector DNA to host cells may be adjusted, taking into consideration such factors as the selected vector, the delivery method and the host cells selected.

Introduction into the host cell of the vector may be achieved by any means known in the art, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Introduction of vectors into the host cell may also be accomplished using techniques known to the skilled person. Suitably, standard transfection techniques are used, e.g., CaPC transfection or electroporation.

Assembly of the selected DNA sequences of the adenovirus (as well as the transgene and other vector elements) into various intermediate plasmids, and the use of the plasmids and vectors to produce a recombinant viral particle are all achieved using conventional techniques. Such techniques include conventional cloning techniques of cDNA, use of overlapping oligonucleotide sequences of the adenovirus genomes, polymerase chain reaction, and any suitable method which provides the desired nucleotide sequence. Standard transfection and co-transfection techniques are employed, e.g., CaPC precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The resulting recombinant adenoviruses are useful in transferring a selected transgene to a selected cell. In in vivo experiments with the recombinant virus grown in the packaging cell lines, the E1-deleted recombinant adenoviral vectors of the invention demonstrate utility in transferring a transgene to a non-simian mammal, preferably a human, cell.

Transgenes

The transgene is a nucleic acid sequence, heterologous to the vector sequences flanking the transgene, which encodes a protein of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, the transgene may be a therapeutic transgene or an immunogenic transgene. Alternatively, a transgene sequence may include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In one embodiment, the transgene is a non-marker sequence encoding a product which is useful in biology and medicine, such as a therapeutic transgene or an immunogenic transgene such as proteins, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a protein to induce a T cell and/or a humoral immune response to the protein.

Accordingly, in one embodiment the present invention provides a recombinant vector according to the present invention comprising an expression cassette comprising an immunogenic transgene derived from a pathogen. In certain embodiments the pathogen is a respiratory virus. Thus, the present invention provides a recombinant ChAd155-derived adenoviral vector comprising an expression cassette comprising an immunogenic transgene derived from human respiratory syncytial virus (RSV). In one embodiment the recombinant ChAd155-derived adenoviral vector of the present invention comprises an RSV F antigen and RSV M and N antigens. More specifically, the nucleic acid encodes an RSV FΔTM antigen (fusion (F) protein deleted of the transmembrane and cytoplasmic regions), and RSV M2-1 (transcription anti-termination) and N (nucleocapsid) antigens. In certain embodiments, a recombinant vector comprises a nucleic acid sequence (for example within an expression cassette) which encodes a sequence according to SEQ ID NO: 37. In one embodiment, the recombinant vector consists essentially of a polynucleotide having a sequence according to SEQ IS NO: 11.

Regulatory Elements

In addition to the transgene the vector also includes conventional control elements which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

In some embodiments, the Woodchuck Hepatitis Virus Posttranscriptional Regulatory Element (WPRE) (Zuffrey et al. (1999) J Virol; 73(4):2886-9) may be operably linked to the transgene. An exemplary WPRE is provided in SEQ ID NO: 26.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter, the SV40 promoter, the dihydrofolate reductase promoter, the β-actin promoter, the phosphoglycerol kinase (PGK) promoter, and the EF1a promoter (Invitrogen).

In some embodiments, the promoter is a CASI promoter (see, for example, WO2012/115980). The CASI promoter is a synthetic promoter which contains a portion of the CMV enhancer, a portion of the chicken beta-actin promoter, and a portion of the UBC enhancer. In some embodiments, the CASI promoter can include a nucleic acid sequence having at least about 90%, at least about 95%, at least about 96%, at least about 97%, at least about 98%, at least about 99%, or more, sequence identity to SEQ ID NO: 12. In some embodiments, the promoter comprises or consists of a nucleic acid sequence of SEQ ID NO: 12.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 378:1766-1769 (1995), see also Harvey et al, Curr. Opin. Chem. Biol, 2:512-518 (1998)). Other systems include the FK506 dimer, VP16 or p65 using castradiol, diphenol murislerone, the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). The effectiveness of some inducible promoters increases over time. In such cases one can enhance the effectiveness of such systems by inserting multiple repressors in tandem, e.g., TetR linked to a TetR by an IRES.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The transgene may be operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al, Nat. Biotech., 17:241-245 (1999)). Examples of promoters that are tissue-specific are known for liver (albumin, Miyatake et al, J. Virol, 71:5124-32 (1997); hepatitis B virus core promoter, Sandig et al, Gene Ther., 3:1002-9 (1996); alpha-fetoprotein (AFP), Arbuthnot et al., Hum. Gene Ther., 7: 1503-14 (1996)), bone osteocalcin (Stein et al, Mol. Biol. Rep., 24:185-96 (1997)); bone sialoprotein (Chen et al., J. Bone Miner. Res., 11:654-64 (1996)), lymphocytes (CD2, Hansal et al, J. Immunol, 161:1063-8 (1998); immunoglobulin heavy chain; T cell receptor chain), neuronal such as neuron-specific enolase (NSE) promoter (Andersen et al, Cell. Mol. Neurobiol, 13:503-15 (1993)), neurofilament light-chain gene (Piccioli et al, Proc. Natl. Acad. Sci. USA, 88:5611-5 (1991)), and the neuron-specific vgf gene (Piccioli et al, Neuron, 15:373-84 (1995)), among others.

Optionally, vectors carrying transgenes encoding therapeutically useful or immunogenic products may also include selectable markers or reporter genes which may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication.

These vectors are generated using the techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Therapeutics and Prophylaxis

The recombinant ChAd155-based vectors are useful for gene transfer to a human or non-simian mammal in vitro, ex vivo, and in vivo.

The recombinant adenovirus vectors described herein can be used as expression vectors for the production of the products encoded by the heterologous transgenes in vitro. For example, the recombinant replication-incompetent adenovirus containing a transgene may be transfected into a complementation cell line as described above.

A ChAd155-derived recombinant adenoviral vector provides an efficient gene transfer vehicle that can deliver a selected transgene to a selected host cell in vivo or ex vivo even where the organism has neutralizing antibodies to one or more adenovirus serotypes. In one embodiment, the vector and the cells are mixed ex vivo; the infected cells are cultured using conventional methodologies; and the transduced cells are re-infused into the patient. These techniques are particularly well suited to gene delivery for therapeutic purposes and for immunisation, including inducing protective immunity.

Immunogenic Transgenes

The recombinant ChAd155 vectors may also be as administered in immunogenic compositions. An immunogenic composition as described herein is a composition comprising one or more recombinant ChAd155 vector capable of inducing an immune response, for example a humoral (e.g., antibody) and/or cell-mediated (e.g., a cytotoxic T cell) response, against a transgene product delivered by the vector following delivery to a mammal, suitably a human. A recombinant adenovirus may comprise (suitably in any of its gene deletions) a gene encoding a desired immunogen and may therefore be used in a vaccine. The recombinant adenoviruses can be used as prophylactic or therapeutic vaccines against any pathogen for which the antigen(s) crucial for induction of an immune response and able to limit the spread of the pathogen has been identified and for which the cDNA is available.

Accordingly, in one embodiment the present invention provides the use of a recombinant adenovirus according to the present invention in the treatment of disease cause by a pathogen. In one embodiment, such treatment is prophylaxis. In one embodiment, the present invention provides the use of a recombinant adenovirus in the generation of an immune response against a pathogen. In certain embodiments the pathogen is a respiratory virus.

Thus, the present invention provides the use of a recombinant ChAd155-derived adenoviral vector comprising an expression cassette comprising an immunogenic transgene derived from human respiratory syncytial virus (RSV) in the treatment or prophylaxis of RSV infection. In one embodiment the recombinant ChAd155-derived adenoviral vector of the present invention comprises an RSV F antigen and RSV M and N antigens. More specifically, the nucleic acid encodes an RSV FΔTM antigen (fusion (F) protein deleted of the transmembrane and cytoplasmic regions), and RSV M2-1 (transcription anti-termination) and N (nucleocapsid) antigens. Particularly, the transgene encodes an RSV antigen as set out in SEQ ID NO: 37.

In further embodiments, the present invention provides the use of a recombinant adenovirus according to the present invention in the manufacture of a medicament for the generation of an immune response against a pathogen. Thus, the present invention provides the use of a recombinant ChAd155-derived adenoviral vector comprising an expression cassette comprising an immunogenic transgene derived from human respiratory syncytial virus (RSV) in the manufacture of a medicament for the treatment or prophylaxis of RSV infection. More specifically, the transgene encodes an RSV FΔTM antigen (fusion (F) protein deleted of the transmembrane and cytoplasmic regions), and RSV M2-1 (transcription anti-termination) and N (nucleocapsid) antigens. Particularly, the transgene encodes an RSV antigen as set out in SEQ ID NO: 37, for example, in one embodiment the trangene compises a polynucleotide of SEQ ID NO: 11.

In one embodiment the present invention provides a method of treatment or prevention of a disease cause by a pathogen, comprising the administration of an effective amount of a recombinant adenovirus according to the present invention, for example a ChAd155-derived adenovirus, comprising an expression cassette comprising an immunogenic transgene derived from the pathogen. In certain embodiments the pathogen is human respiratory syncytial virus (RSV). In one embodiment the present invention provides a method of generating or enhancing an immune response directed against human respiratory syncytial virus (RSV) comprising the administration of a recombinant adenovirus according to the present invention. Particularly, the method of generating or enhancing an immune response comprises the administration of an effective amount of a ChAd155-derived adenovirus comprising a transgene encoding an RSV antigen as set out in SEQ ID NO: 37, for example, in one embodiment the trangene compises a polynucleotide of SEQ ID NO: 11.

In one embodiment, the present invention provides an immunogenic composition comprising a recombinant adenovirus according to the present invention, for example a ChAd155-derived adenovirus, including an expression cassette comprising an immunogenic transgene derived from a pathogen, for example human respiratory syncytial virus (RSV), and a pharmaceutically acceptable excipient.

Such vaccine or other immunogenic compositions may be formulated in a suitable delivery vehicle. Generally, doses for the immunogenic compositions are in the range defined below under 'Delivery Methods and Dosage'. The levels of immunity of the selected gene can be monitored to determine the need, if any, for boosters. Following an assessment of antibody titers in the serum, optional booster immunizations may be desired.

In one embodiment an immunogenic composition comprising a recombinant ChAd155-derived adenoviral vector of the present invention comprising an expression cassette containing a transgene encoding an RSV F antigen and RSV M and N antigens. More specifically, the transgene encodes an RSV FΔTM antigen (fusion (F) protein deleted of the transmembrane and cytoplasmic regions), and RSV M2-1 (transcription anti-termination) and N (nucleocapsid) antigens. Particularly, the transgene encodes an RSV antigen as set out in SEQ ID NO: 37, for example, in one embodiment the trangene compises a polynucleotide of SEQ ID NO: 11. Optionally, a vaccine or immunogenic composition of the invention may be formulated to contain other components, including, e.g., adjuvants, stabilizers, pH adjusters, preservatives and the like. Examples of suitable adjuvants are provided below under 'Adjuvants'. Such an adjuvant can be administered with a priming DNA vaccine encoding an antigen to enhance the antigen-specific immune response compared with the immune response generated upon priming with a DNA vaccine encoding the antigen only. Alternatively, such an adjuvant can be administered with a polypeptide antigen which is administered in an administration regimen involving the ChAd155 vectors of the invention (as described below under 'Administration Regimens'.

The recombinant adenoviruses are administered in an immunogenic amount, that is, an amount of recombinant adenovirus that is effective in a route of administration to transfect the desired target cells and provide sufficient levels of expression of the selected gene to induce an immune response. Where protective immunity is provided, the recombinant adenoviruses are considered to be vaccine compositions useful in preventing infection and/or recurrent disease.

Immunogens expressed by the inventive vectors which are useful to immunize a human or non-human animal against other pathogens include, e.g., bacteria, fungi, parasitic microorganisms or multicellular parasites which infect human and non-human vertebrates, or from a cancer cell or tumor cell. For example, immunogens may be selected from a variety of viral families. Examples of viral families against which an immune response would be desirable include respiratory viruses such as respiratory syncytial virus (RSV) and other paramyxoviruses such as human metapneumovirus, hMPV and parainfluenza viruses (PIV).

Infection with RSV does not confer full protective immunity. Infection in infancy is followed by symptomatic RSV re-infections which continue throughout adulthood. These re-infections generally go undiagnosed because they usually present as common acute upper respiratory tract infections. In more vulnerable persons (e.g., immunocompromised adults or elderly), re-infections can however also lead to severe disease. Both arms of the immune system (humoral and cellular immunity) are involved in protection from severe disease [American Academy of Pediatrics Subcommittee on Diagnosis and Management of Bronchiolitis. Diagnosis and management of bronchiolitis. *Pediatrics.* 2006; 118: 1774-93.

Boukhvalova M S and Blanco J C. The cotton rat Sigmodon hyspidus model of respiratory syncytial virus infection. *Curr Top Microbiol Immunol.* 2013; 372: 347-58.

Cardenas S, Auais A and Piedimonte G. Palivizumab in the prophylaxis of respiratory syncytial virus infection. *Expert Rev Anti Infect Ther.* 2005; 3(5): 719-26.

Castilow E M and Varga S M. Overcoming T cell-mediated immunopathology to achieve safe RSV vaccination. *Future Virol.* 2008; 3(5): 445-454.

Chin J, Magoff in R L, Shearer L A, et al., Field evaluation of a respiratory syncytial virus vaccine and a trivalent parainfluenza virus vaccine in a pediatric population. *Am J Epidemiol.* 1969; 89(4): 449-63.

Colloca S, Barnes E, Folgori A, et al., Vaccine vectors derived from a large collection of simian adenoviruses induce potent cellular immunity across multiple species. *Sci Transl Med.* 2012; 4(115): p. 115ra2.

Donnelly M L, Luke G, Mehrotra A, et al., Analysis of the aphthovirus 2A/2B polyprotein 'cleavage' mechanism indicates not a proteolytic reaction, but a novel translational effect: a putative ribosomal 'skip'. *J Gen Virol.* 2001; 82(Pt 5): 1013-25.

Fallaux, F J et al, (1998), Hum Gene Ther, 9:1909-1917

Guvenel, 2014].

The humoral immune response is capable of neutralizing the virus and inhibiting viral replication, thereby playing a major role in protection against lower respiratory RSV infection and severe disease [American Academy of Pediatrics Subcommittee on Diagnosis and Management of Bronchiolitis. Diagnosis and management of bronchiolitis. *Pediatrics.* 2006; 118: 1774-93.

Boukhvalova M S and Blanco J C. The cotton rat Sigmodon hyspidus model of respiratory syncytial virus infection. *Curr Top Microbiol Immunol.* 2013; 372: 347-58.

Cardenas S, Auais A and Piedimonte G. Palivizumab in the prophylaxis of respiratory syncytial virus infection. *Expert Rev Anti Infect Ther.* 2005; 3(5): 719-26.

Castilow E M and Varga S M. Overcoming T cell-mediated immunopathology to achieve safe RSV vaccination. *Future Virol.* 2008; 3(5): 445-454.

Chin J, Magoff in R L, Shearer L A, et al., Field evaluation of a respiratory syncytial virus vaccine and a trivalent parainfluenza virus vaccine in a pediatric population. *Am J Epidemiol.* 1969; 89(4): 449-63.

Colloca S, Barnes E, Folgori A, et al., Vaccine vectors derived from a large collection of simian adenoviruses induce potent cellular immunity across multiple species. *Sci Transl Med.* 2012; 4(115): p. 115ra2.

Donnelly M L, Luke G, Mehrotra A, et al., Analysis of the aphthovirus 2A/2B polyprotein 'cleavage' mechanism indicates not a proteolytic reaction, but a novel translational effect: a putative ribosomal 'skip'. *J Gen Virol.* 2001; 82(Pt 5): 1013-25.

Fallaux, F J et al, (1998), Hum Gene Ther, 9:1909-1917

Guvenel A K, Chiu C and Openshaw P J. Current concepts and progress in RSV vaccine development. *Expert Rev Vaccines.* 2014; 13(3): 333-44.

Hertz, M I, Englund J A, Snover D, et al., Respiratory syncytial virus-induced acute lung injury in adult patients with bone marrow transplants: a clinical approach and review of the literature. *Medicine* (Baltimore). 1989; 68(5): 269-81.

Kim H W, Canchola J G, Brandt C D et al., Respiratory syncytial virus disease in infants despite prior administration of antigenic inactivated vaccine. *Am J Epidemiol.* 1969; 89(4): 422-34.

Magro M, Andreu D, Gómez-Puertas P, et al., Neutralization of human respiratory syncytial virus infectivity by antibodies and low-molecular-weight compounds targeted against the fusion glycoprotein. *J Virol.* 2010; 84(16): 7970-82.

Piedra, 2003]. Passive immunization, in the form of Immunoglobulin G (IgG) RSV-neutralizing monoclonal antibodies (Synagis) given prophylactically, has been shown to prevent RSV disease to some extent in premature infants and newborns with bronchopulmonary dysplasia or underlying cardiopulmonary disease [American Academy of Pediatrics Subcommittee on Diagnosis and Management of Bronchiolitis. Diagnosis and management of bronchiolitis. *Pediatrics.* 2006; 118: 1774-93.

Boukhvalova M S and Blanco J C. The cotton rat Sigmodon hyspidus model of respiratory syncytial virus infection. *Curr Top Microbiol Immunol.* 2013; 372: 347-58.

Cardenas, 2005].

T cells are also involved in the control of RSV disease. Lethal RSV infections have been described in patients with low CD8 T cells counts, as in the case of severe combined immunodeficiency, bone marrow and lung transplant recipients [

Hertz, 1989]. The histopathology of fatal cases of RSV infection of newborns shows that there is a relative paucity of CD8 T cells in the lung infiltrate [Welliver, 2007]. Moreover, the presence of CD8 T cells producing Interferon-gamma (IFN-γ) has been associated with diminished Th2 responses and reduced eosinophilia in animal models of RSV [

Castilow, 2008;

Stevens, 2009].

The recombinant vectors described herein are expected to be highly efficacious at inducing cytolytic T cells and antibodies directed to the inserted heterologous antigenic protein expressed by the vector.

Suitable antigens of RSV which are useful as immunogens to immunize a human or non-human animal can be selected from: the fusion protein (F), the attachment protein (G), the matrix protein (M2) and the nucleoprotein (N). The term "F protein" or "fusion protein" or "F protein polypeptide" or "fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein" or "matrix protein" or "M protein polypeptide" refers to a polypeptide or protein having all or part of an amino acid sequence of an RSV Matrix protein and may include either or both of the M2-1 (which may be written herein as M2.1) and M2-2 gene products. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008-114149), which is incorporated herein by reference for the purpose of disclosing the nucleic acid and polypeptide sequences of RSV F and G proteins suitable for use in present invention. In an embodiment, the RSV F protein can be an ectodomain of an RSV F Protein (FΔTM).

Exemplary M and N protein nucleic acids and protein sequences can be found, e.g., in US published application number 2014/0141042 (WO2012/089833), which are incorporated herein for purpose of disclosing the nucleic acid and polypeptide sequences of RSV M and N proteins suitable for use in present invention.

Suitably, for use with in present invention, a transgene nucleic acid encodes an RSV F antigen and RSV M and N antigens. More specifically, the nucleic acid encodes an RSV FΔTM antigen (fusion (F) protein deleted of the transmembrane and cytoplasmic regions), and RSV M2-1 (transcription anti-termination) and N (nucleocapsid) antigens.

Fusion (F) Protein Deleted of the Transmembrane and Cytoplasmic Regions (F0ΔTM)

The RSV F protein is a major surface antigen and mediates viral fusion to target cells. The F protein is an antigen which is highly conserved among RSV subgroups and strains. The F protein is a target for neutralizing antibodies, including the prophylactic RSV-neutralizing monoclonal antibody Synagis. Deletion of the transmembrane region and cytoplasmic tail permits secretion of the FΔTM protein. Neutralizing antibodies including Synagis, that recognize this soluble form of the F protein, inhibit RSV infectivity in vitro [American Academy of Pediatrics Subcommittee on Diagnosis and Management of Bronchiolitis. Diagnosis and management of bronchiolitis. *Pediatrics*. 2006; 118: 1774-93.

Boukhvalova M S and Blanco J C. The cotton rat Sigmodon hyspidus model of respiratory syncytial virus infection. *Curr Top Microbiol Immunol*. 2013; 372: 347-58.

Cardenas S, Auais A and Piedimonte G. Palivizumab in the prophylaxis of respiratory syncytial virus infection. *Expert Rev Anti Infect Ther*. 2005; 3(5): 719-26.

Castilow E M and Varga S M. Overcoming T cell-mediated immunopathology to achieve safe RSV vaccination. *Future Virol*. 2008; 3(5): 445-454.

Chin J, Magoffin R L, Shearer L A, et al., Field evaluation of a respiratory syncytial virus vaccine and a trivalent parainfluenza virus vaccine in a pediatric population. *Am J Epidemiol*. 1969; 89(4): 449-63.

Colloca S, Barnes E, Folgori A, et al., Vaccine vectors derived from a large collection of simian adenoviruses induce potent cellular immunity across multiple species. *Sci Transl Med*. 2012; 4(115): p. 115ra2.

Donnelly M L, Luke G, Mehrotra A, et al., Analysis of the aphthovirus 2A/2B polyprotein 'cleavage' mechanism indicates not a proteolytic reaction, but a novel translational effect: a putative ribosomal 'skip'. *J Gen Virol*. 2001; 82(Pt 5): 1013-25.

Fallaux, F J et al, (1998), Hum Gene Ther, 9:1909-1917

Guvenel A K, Chiu C and Openshaw P J. Current concepts and progress in RSV vaccine development. *Expert Rev Vaccines*. 2014; 13(3): 333-44.

Hertz, M I, Englund J A, Snover D, et al., Respiratory syncytial virus-induced acute lung injury in adult patients with bone marrow transplants: a clinical approach and review of the literature. *Medicine* (Baltimore). 1989; 68(5): 269-81.

Kim H W, Canchola J G, Brandt C D et al., Respiratory syncytial virus disease in infants despite prior administration of antigenic inactivated vaccine. *Am J Epidemiol*. 1969; 89(4): 422-34.

Magro, 2010].

Nucleocapsid (N) Protein

The N protein is an internal (non-exposed) antigen, highly conserved between RSV strains and known to be a source of many T cell epitopes [Townsend, 1984]. The N protein is essential for the replication and transcription of the RSV genome. The primary function of the N protein is to encapsulate the virus genome for the purposes of RNA transcription, replication and packaging and protects it from ribonucleases.

Transcription Anti-Termination (M2-1) Protein

The M2-1 protein is a transcription anti-termination factor that is important for the efficient synthesis of full-length messenger RNAs (mRNAs) as well as for the synthesis of polycistronic readthrough mRNAs, which are characteristic of non-segmented negative-strand RNA viruses. M2-1 is an internal (non-exposed) antigen, which is highly conserved between RSV strains and known to be a source of many T cell epitopes [Townsend, 1984].

In one embodiment, the present invention provides a recombinant ChAd155 vector comprising a transgene encoding an RSV FΔTM antigen, and RSV M2-1 and N antigens wherein a self-cleavage site is included between the RSV FΔTM antigen and the RSV M2-1 and a flexible linker is included between the RSV M2-1 and N antigens. In one embodiment a suitable transgene nucleic acid encodes the polypeptide represented by SEQ ID NO:37

In one embodiment, the immunogen may be from a retrovirus, for example a lentivirus such as the Human Immunodeficiency Virus (HIV). In such an embodiment, immunogens may be derived from HIV-1 or HIV-2.

The HIV genome encodes a number of different proteins, each of which can be immunogenic in its entirety or as a fragment when expressed by vectors of the present invention. Envelope proteins include gp120, gp41 and Env precursor gp160, for example. Non-envelope proteins of HIV include for example internal structural proteins such as the products of the gag and pol genes and other non-structural proteins such as Rev, Nef, Vif and Tat. In an embodiment the vector of the invention encodes one or more polypeptides comprising HIV Gag.

The Gag gene is translated as a precursor polyprotein that is cleaved by protease to yield products that include the matrix protein (p17), the capsid (p24), the nucleocapsid (p9), p6 and two space peptides, p2 and p1, all of which are examples of fragments of Gag.

The Gag gene gives rise to the 55-kilodalton (kD) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6, all of which are examples of fragments of Gag. In one embodiment, the vectors of the present invention comprise a Gag polypeptide of SEQ ID NO: 38.

Adjuvants

An "adjuvant" as used herein refers to a composition that enhances the immune response to an immunogen. Examples of such adjuvants include but are not limited to inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immunostimulatory complexes (ISCOMS), liposomes, or biodegradable microspheres), virosomes, bacterial adjuvants (e.g. monophosphoryl lipid A, such as 3-de-O-acylated monophosphoryl lipid A (3D-MPL), or muramyl peptides), synthetic adjuvants (e.g. non-ionic block copolymers, muramyl peptide analogues, or synthetic lipid A), synthetic polynucleotides adjuvants (e.g polyarginine or polylysine) and immunostimulatory oligonucleotides containing unmethylated CpG dinucleotides ("CpG").

One suitable adjuvant is monophosphoryl lipid A (MPL), in particular 3-de-O-acylated monophosphoryl lipid A (3D-MPL). Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099 and EP 0 729 473 B1; Hilgers et al., 1986, Int. Arch. Allergy. Immunol., 79(4):392-6; Hilgers et al., 1987, Immunology, 60(1):141-6; and EP 0 549 074 B11).

Saponins are also suitable adjuvants (see Lacaille-Dubois, M and Wagner H, A review of the biological and pharmacological activities of saponins. Phytomedicine vol 2 pp 363-386 (1996)). For example, the saponin Quil A (derived from the bark of the South American tree Quillaja Saponaria Molina), and fractions thereof, are described in U.S. Pat. No. 5,057,540 and Kensil, Crit. Rev. Ther. Drug Carrier Syst., 1996, 12:1-55; and EP 0 362 279 B1. Purified fractions of Quil A are also known as immunostimulants, such as QS21 and QS17; methods of their production is disclosed in U.S. Pat. No. 5,057,540 and EP 0 362 279 B1. Also described in these references is QS7 (a non-haemolytic fraction of Quil-A). Use of QS21 is further described in Kensil et al. (1991, J. Immunology, 146: 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Another adjuvant is an immunostimulatory oligonucleotide containing unmethylated CpG dinucleotides ("CpG") (Krieg, Nature 374:546 (1995)). CpG is an abbreviation for cytosine-guanosine dinucleotide motifs present in DNA. CpG is known as an adjuvant when administered by both systemic and mucosal routes (WO 96/02555, EP 468520, Davis et al, J. Immunol, 1998, 160:870-876; McCluskie and Davis, J. Immunol., 1998, 161:4463-6). CpG, when formulated into vaccines, may be administered in free solution together with free antigen (WO 96/02555) or covalently conjugated to an antigen (WO 98/16247), or formulated with a carrier such as aluminium hydroxide (Brazolot-Millan et al., Proc. Natl. Acad. Sci., USA, 1998, 95:15553-8).

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide (EP 0 689 454) or oil in water emulsions (WO 95/17210); QS21 may be formulated with cholesterol containing liposomes (WO 96/33739), oil in water emulsions (WO 95/17210) or alum (WO 98/15287); CpG may be formulated with alum (Brazolot-Millan, supra) or with other cationic carriers.

Combinations of adjuvants may be utilized in the present invention, in particular a combination of a monophosphoryl lipid A and a saponin derivative (see, e.g., WO 94/00153; WO 95/17210; WO 96/33739; WO 98/56414; WO 99/12565; WO 99/11241), more particularly the combination of QS21 and 3D-MPL as disclosed in WO 94/00153, or a composition where the QS21 is quenched in cholesterol-containing liposomes (DQ) as disclosed in WO 96/33739. Alternatively, a combination of CpG plus a saponin such as QS21 is an adjuvant suitable for use in the present invention. A potent adjuvant formulation involving QS21, 3D-MPL & tocopherol in an oil in water emulsion is described in WO 95/17210 and is another formulation for use in the present invention. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminium salt (e.g. as described in WO00/23105). A further exemplary adjuvant comprises QS21 and/or MPL and/or CpG. QS21 may be quenched in cholesterol-containing liposomes as disclosed in WO 96/33739.

Other suitable adjuvants include alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

It has been found (WO 2007/062656, which published as US 2011/0293704 and is incorporated by reference for the purpose of disclosing invariant chain sequences) that the fusion of the invariant chain to an antigen which is comprised by an expression system used for vaccination increases the immune response against said antigen, if it is administered with an adenovirus. Accordingly, in one embodiment of the invention, the immunogenic transgene may be co-expressed with invariant chain in a recombinant ChAd155 viral vector.

In another embodiment, the invention provides the use of the capsid of ChAd155 (optionally an intact or recombinant viral particle or an empty capsid is used) to induce an immunomodulatory effect response, or to enhance or adjuvant a cytotoxic T cell response to another active agent by delivering a ChAd155 capsid to a subject. The ChAd155 capsid can be delivered alone or in a combination regimen with an active agent to enhance the immune response thereto. Advantageously, the desired effect can be accomplished without infecting the host with an adenovirus.

Administration Regimens

Commonly, the ChAd155 recombinant adenoviral vectors will be utilized for delivery of therapeutic or immunogenic molecules (such as proteins). It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g. one, two, three, four or more). Thus, a regimen may involve delivery of a recombinant adenovirus with a first capsid, delivery with a recombinant adenovirus with a second capsid, and delivery with a recombinant adenovirus with a third capsid. A variety of other regimens which use the adenovirus capsids of the invention alone, in combination with one another, or in combination with other adenoviruses (which are preferably immunologically non-crossreactive) will be apparent to those of skill in the art. Optionally, such a regimen may involve administration of recombinant adenovirus with capsids of other non-human primate adenoviruses, human adenoviruses, or artificial sequences such as are described herein.

The adenoviral vectors of the invention are particularly well suited for therapeutic regimens in which multiple adenoviral-mediated deliveries of transgenes are desired, e.g., in regimens involving redelivery of the same transgene or in combination regimens involving delivery of other transgenes. Such regimens may involve administration of a ChAd155 adenoviral vector, followed by re-administration with a vector from the same serotype adenovirus. Particularly desirable regimens involve administration of a ChAd155 adenoviral vector, in which the source of the adenoviral capsid sequences of the vector delivered in the first administration differs from the source of adenoviral capsid sequences of the viral vector utilized in one or more of the subsequent administrations. For example, a therapeutic regimen involves administration of a ChAd155 vector and repeat administration with one or more adenoviral vectors of the same or different serotypes.

In another example, a therapeutic regimen involves administration of an adenoviral vector followed by repeat administration with a ChAd155 vector which has a capsid which differs from the source of the capsid in the first delivered adenoviral vector, and optionally further administration with another vector which is the same or, preferably, differs from the source of the adenoviral capsid of the vector in the prior administration steps. These regimens may deliver the same or different therapeutic or immunogenic molecules. These regimens are not limited to delivery of adenoviral vectors constructed using the ChAd155 sequences. Rather, these regimens can readily utilize other adenoviral sequences, including, without limitation, other adenoviral sequences including other non-human primate adenoviral sequences, or human adenoviral sequences, in combination with the ChAd155 vectors.

In a further example, a therapeutic regimen may involve either simultaneous (such as co-administration) or sequential (such as a prime-boost) delivery of (i) one or more ChAd155 adenoviral vectors and (ii) a further component such as non-adenoviral vectors, non-viral vectors, and/or a variety of other therapeutically useful compounds or molecules such as antigenic proteins optionally simultaneously administered with adjuvant. These regimens may deliver the same or different therapeutic or immunogenic molecules.

Examples of co-administration include homo-lateral co-administration and contra-lateral co-administration (further described below under 'Delivery Methods and Dosage').

Suitable non-adenoviral vectors for use in simultaneous or particularly in sequential delivery (such as prime-boost) with one or more ChAd155 adenoviral vectors include one or more poxviral vectors. Suitably, the poxviral vector belongs to the subfamily chordopoxvirinae, more suitably to a genus in said subfamily selected from the group consisting of orthopox, parapox, yatapox, avipox (suitably canarypox (ALVAC) or fowlpox (FPV)) and molluscipox. Even more suitably, the poxviral vector belongs to the orthopox and is selected from the group consisting of vaccinia virus, NYVAC (derived from the Copenhagen strain of vaccinia), Modified Vaccinia Ankara (MVA), cowpoxvirus and monkeypox virus. Most suitably, the poxviral vector is MVA.

"Simultaneous" administration suitably refers to the same ongoing immune response. Preferably both components are administered at the same time (such as simultaneous administration of both DNA and protein), however, one component could be administered within a few minutes (for example, at the same medical appointment or doctor's visit), within a few hours. Such administration is also referred to as co-administration. In some embodiments, co-administration may refer to the administration of an adenoviral vector, an adjuvant and a protein component. In other embodiments, co-administration refers to the administration of an adenoviral vector and another viral vector, for example a second adenoviral vector or a poxvirus such as MVA. In other embodiments, co-administration refers to the administration of an adenoviral vector and a protein component, which is optionally adjuvanted.

In another embodiment, a therapeutic regimen involves the administration of an immunogenic composition to a pregnant mother and subsequent administration of a further immunogenic composition to the infant after birth, for example 1, 2, 3, 4, 5, 6, 7 or 8 months after birth. Antibodies generated as a result of the maternal immunisation can cross the placenta to provide passive immunisation of the gestational infant. In one embodiment the maternal immunisation is by administration of a recombinant protein antigen and the infant immunisation is by administration of a recombinant adenoviral vector according to the present invention. In another embodiment the maternal immunisation is by administration of a recombinant adenoviral vector according to the present invention and the infant immunisation is by administration of a recombinant protein antigen. In another embodiment both the maternal and infant immunisation is by administration of a recombinant adenoviral vector according to the present invention.

Thus, the present invention provides the use of a recombinant ChAd155-derived adenoviral vector according to the present invention in the generation of an immune response against RSV in an infant, particularly an infant born to a mother immunised against RSV during pregnancy. Accordingly, the present invention provides the use of a recombinant ChAd155-derived adenoviral vector comprising an immunogenic transgene derived from human respiratory syncytial virus (RSV) in the manufacture of a medicament for the generation of an immune response in an infant. Desirably, particularly the infant born to a mother immunised against RSV during her pregnancy. More specifically, the transgene encodes an RSV FΔTM antigen (fusion (F) protein deleted of the transmembrane and cytoplasmic regions), and RSV M2-1 (transcription anti-termination) and N (nucleocapsid) antigens. Particularly, the transgene encodes an RSV antigen as set out in SEQ ID NO: 37, for example, in one embodiment the trangene compises a polynucleotide of SEQ ID NO: 11.

A prime-boost regimen may be used. Prime-boost refers to two separate immune responses in the same individual: (i) an initial priming of the immune system followed by (ii) a secondary or boosting of the immune system many weeks or months after the primary immune response has been established.

Such a regimen may involve the administration of a recombinant ChAd155 vector to prime the immune system to second, booster, administration with a traditional antigen, such as a protein (optionally co-administered with adjuvant), or a recombinant virus carrying the sequences encoding such an antigen (e.g., WO 00/11140). Alternatively, an immunization regimen may involve the administration of a recombinant ChAd155 vector to boost the immune response to a vector (either viral or DNA-based) encoding an antigen. In another alternative, an immunization regimen involves administration of a protein followed by booster with a recombinant ChAd155 vector encoding the antigen. In one example, the prime-boost regimen can provide a protective immune response to the virus, bacteria or other organism from which the antigen is derived. In another embodiment, the prime-boost regimen provides a therapeutic effect that can be measured using conventional assays for detection of the presence of the condition for which therapy is being administered.

Preferably, a boosting composition is administered about 2 to about 27 weeks after administering the priming composition to the subject. The administration of the boosting composition is accomplished using an effective amount of a boosting composition containing or capable of delivering the same antigen or a different antigen as administered by the priming vaccine. The boosting composition may be composed of a recombinant viral vector derived from the same viral source or from another source. Alternatively, the boosting composition can be a composition containing the same antigen as encoded in the priming vaccine, but in the form of a protein, which composition induces an immune response in the host. The primary requirements of the boosting composition are that the antigen of the composition is the same antigen, or a cross-reactive antigen, as that encoded by the priming composition.

Delivery Methods and Dosage

The vector may be prepared for administration by being suspended or dissolved in a pharmaceutically or physiologically acceptable carrier such as isotonic saline; isotonic salts solution or other formulations that will be apparent to those skilled in the art. The appropriate carrier will be evident to those skilled in the art and will depend in large part upon the route of administration. The compositions described herein may be administered to a mammal in a sustained release formulation using a biodegradable biocompatible polymer, or by on-site delivery using micelles, gels and liposomes.

In some embodiments, the recombinant adenovirus of the invention is administered to a subject by intramuscular injection, intravaginal injection, intravenous injection, intraperitoneal injection, subcutaneous injection, epicutaneous administration, intradermal administration, nasal administration or oral administration.

If the therapeutic regimen involves co-administration of one or more ChAd155 adenoviral vectors and a further component, each formulated in different compositions, they are favourably administered co-locationally at or near the same site. For example, the components can be administered (e.g. via an administration route selected from intramuscular, transdermal, sub-cutaneous) to the same side or extremity ("co-lateral" administration) or to opposite sides or extremities ("contra-lateral" administration).

Dosages of the viral vector will depend primarily on factors such as the condition being treated, the age, weight and health of the patient, and may thus vary among patients. For example, a therapeutically effective adult human or veterinary dosage of the viral vector generally contains $1\times10^5$ to $1\times10^{15}$ viral particles, such as from $1\times10^8$ to $1\times10^{12}$ (e.g., $1\times10^8$, $2.5\times10^8$, $5\times10^8$, $1\times10^9$, $1.5\times10^9$, $2.5\times10^9$, $5\times10^9$, $1\times10^{10}$, $1.5\times10^{10}$, $2.5\times10^{10}$, $5\times10^{10}$, $1\times10^{11}$, $1.5\times10^{11}$, $2.5\times10^{11}$, $5\times10^{11}$, $1\times10^{12}$ particles). Alternatively, a viral vector can be administered at a dose that is typically from $1\times10^5$ to $1\times10^{10}$ plaque forming units (PFU), such as $1\times10^5$ PFU, $2.5\times10^5$ PFU, $5\times10^5$ PFU, $1\times10^6$ PFU, $2.5\times10^6$ PFU, $5\times10^6$ PFU; $1\times10^7$ PFU, $2.5\times10^7$ PFU, $5\times10^7$ PFU, $1\times10^8$ PFU, $2.5\times10^8$ PFU, $5\times10^8$ PFU, $1\times10^9$ PFU, $2.5\times10^9$ PFU, $5\times10^9$ PFU, or $1\times10^{10}$ PFU. Dosages will vary depending upon the size of the animal and the route of administration. For example, a suitable human or veterinary dosage (for about an 80 kg animal) for intramuscular injection is in the range of about $1\times10^9$ to about $5\times10^{12}$ particles per mL, for a single site. Optionally, multiple sites of administration may be used. In another example, a suitable human or veterinary dosage may be in the range of about $1\times10^{11}$ to about $1\times10^{15}$ particles for an oral formulation.

The viral vector can be quantified by Quantitative PCR Analysis (Q-PCR), for example with primers and probe designed on CMV promoter region using as standard curve serial dilution of plasmid DNA containing the vector genome with expression cassette including HCMV promoter. The copy number in the test sample is determined by the parallel line analysis method. Alternative methods for vector particle quantification can be analytical HPLC or spectrophotometric method based on A260 nm.

An immunologically effective amount of a nucleic acid may suitably be between 1 ng and 100 mg. For example, a suitable amount can be from 1 µg to 100 mg. An appropriate amount of the particular nucleic acid (e.g., vector) can readily be determined by those of skill in the art. Exemplary effective amounts of a nucleic acid component can be between 1 ng and 100 µg, such as between 1 ng and 1 µg (e.g., 100 ng-1 µg), or between 1 µg and 100 µg, such as 10 ng, 50 ng, 100 ng, 150 ng, 200 ng, 250 ng, 500 ng, 750 ng, or 1 µg. Effective amounts of a nucleic acid can also include from 1 µg to 500 µg, such as between 1 µg and 200 µg, such as between 10 and 100 µg, for example 1 µg, 2 µg, 5 µg, 10 µg, 20 µg, 50 µg, 75 µg, 100 µg, 150 µg, or 200 µg. Alternatively, an exemplary effective amount of a nucleic acid can be between 100 µg and 1 mg, such as from 100 µg to 500 µg, for example, 100 µg, 150 µg, 200 µg, 250 µg, 300 µg, 400 µg, 500 µg, 600 µg, 700 µg, 800 µg, 900 µg or 1 mg.

Generally a human dose will be in a volume of between 0.1 ml and 2 ml. Thus the composition described herein can be formulated in a volume of, for example 0.1, 0.15, 0.2, 0.5, 1.0, 1.5 or 2.0 ml human dose per individual or combined immunogenic components.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

If one or more priming and/or boosting steps are used, this step may include a single dose that is administered hourly, daily, weekly or monthly, or yearly. As an example, mammals may receive one or two doses containing between about 10 µg to about 50 µg of plasmid in carrier. The amount or site of delivery is desirably selected based upon the identity and condition of the mammal.

The therapeutic levels of, or level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the recombinant ChAd155 vectors may be delivered in a single administration or in various combination regimens, e.g., in combination with a regimen or course of treatment involving other active ingredients or in a prime-boost regimen.

The present invention will now be further described by means of the following non-limiting examples.

EXAMPLES

Example 1: Isolation of ChAd155

Wild type chimpanzee adenovirus type 155 (ChAd155) was isolated from a healthy young chimpanzee housed at the New Iberia Research Center facility (New Iberia Research Center; The University of Louisiana at Lafayette) using standard procedures as described in Colloca et al. (2012) and WO 2010086189, which is hereby incorporated by reference for the purpose of describing adenoviral isolation and characterization techniques Example 2: ChAd155 Vector Construction The ChAd155 viral genome was then cloned in a plasmid or in a BAC vector and subsequently modified (FIG. 2) to carry the following modifications in different regions of the ChAd155 viral genome:
a) deletion of the E1 region (from bp 449 to bp 3529) of the viral genome;
b) deletion of the E4 region (from bp 34731 to bp 37449) of the viral genome;
c) insertion of the E4orf6 derived from human Ad5.

2.1: Deletion of E1 Region: Construction of BAC/ChAd155 ΔE1 TetO hCMV RpsL-Kana #1375

Figure 3:
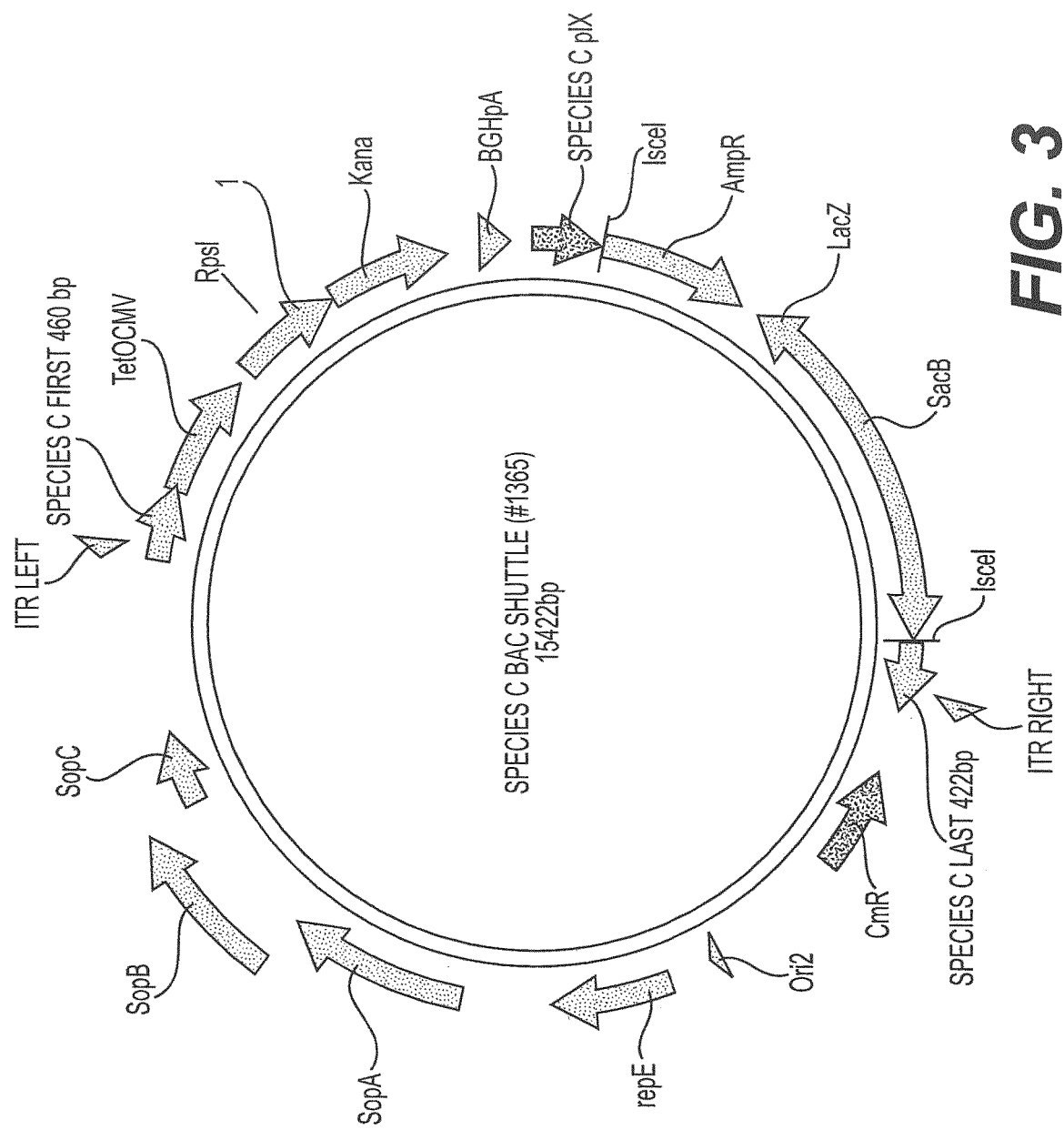

The ChAd155 viral genome was cloned into a BAC vector by homologous recombination in *E. coli* strain BJ5183 electroporation competent cells (Stratagene catalog no. 2000154) co-transformed with ChAd155 viral DNA and Subgroup C BAC Shuttle (#1365). As shown in the schematic of FIG. 3, the Subgroup C Shuttle is a BAC vector derived from pBeloBAC11 (GenBank U51113, NEB) and which is dedicated to the cloning of ChAd belonging to species C and therefore contains the pIX gene and DNA fragments derived from right and left ends (including right and left ITRs) of species C ChAd viruses.

The Species C BAC Shuttle also contains a RpsL-Kana cassette inserted between left end and the pIX gene. In addition, an Amp-LacZ-SacB selection cassette, flanked by IScel restriction sites, is present between the pIX gene and right end of the viral genome. In particular, the BAC Shuttle comprised the following features: Left ITR: bp 27 to 139, hCMV(tetO) RpsL-Kana cassette: bp 493 to 3396, pIX gene: bp 3508 to 3972, IScel restriction sites: bp 3990 and 7481, Amp-LacZ-SacB selection cassette: bp 4000 to 7471, Right ITR: bp 7805 to 7917.

BJ5183 cells were co-transformed by electroporation with ChAd155 purified viral DNA and Subgroup C BAC Shuttle vector digested with IScel restriction enzyme and then purified from gel. Homologous recombination occurring between pIX gene and right ITR sequences (present at the ends of Species C BAC Shuttle linearized DNA) and homologous sequences present in ChAd155 viral DNA lead to the insertion of ChAd155 viral genomic DNA in the BAC shuttle vector. At the same time, the viral E1 region was deleted and substituted by the RpsL-Kana cassette, generating BAC/ChAd155 ΔE1/TetO hCMV RpsL-Kana #1375.

2.2: Plasmid Construction by Homologous Recombination in *E. coli* BJ5183

2.2.1: Deletion of E4 Region—Construction of pChAd155 ΔE1, E4 Ad5E4Orf6/TetO hCMV RpsL-Kana (#1434)

To improve propagation of the vector, a deletion of the E4 region spanning from nucleotide 34731-37449 (ChAd155 wild type sequence) was introduced in the vector backbone by replacing the native E4 region with Ad5 E4orf6 coding sequence using a strategy involving several steps of cloning and homologous recombination in *E. coli*. The E4 coding region was completely deleted while the E4 native promoter and polyadenylation signal were conserved. To this end, a shuttle vector was constructed to allow the insertion of Ad5orf6 by replacing the ChAd155 native E4 region by homologous recombination in *E. coli* BJ5183 as detailed below.

Construction of pARS SpeciesC Ad5E4Orf6-1

A DNA fragment containing Ad5orf6 was obtained by PCR using Ad5 DNA as template, with the oligonucleotides 5'-ATACGGACTAGTGGAGAAGTACTCGCCTACATG-3' (SEQ ID NO: 13) and 5'-ATACGGAAGATCTAA-GACTTCAGGAAATATGACTAC-3' (SEQ ID NO: 14). The PCR fragment was digested with BglII and SpeI and cloned into Species C RLD-EGFP shuttle digested with BglII and SpeI, generating the plasmid pARS Species C Ad5orf6-1. Details regarding the shuttle can be found in Colloca et al, Sci. Transl. Med. (2012) 4:115ra.

Construction of pARS SpeciesC Ad5E4Orf6-2

Figure 4:
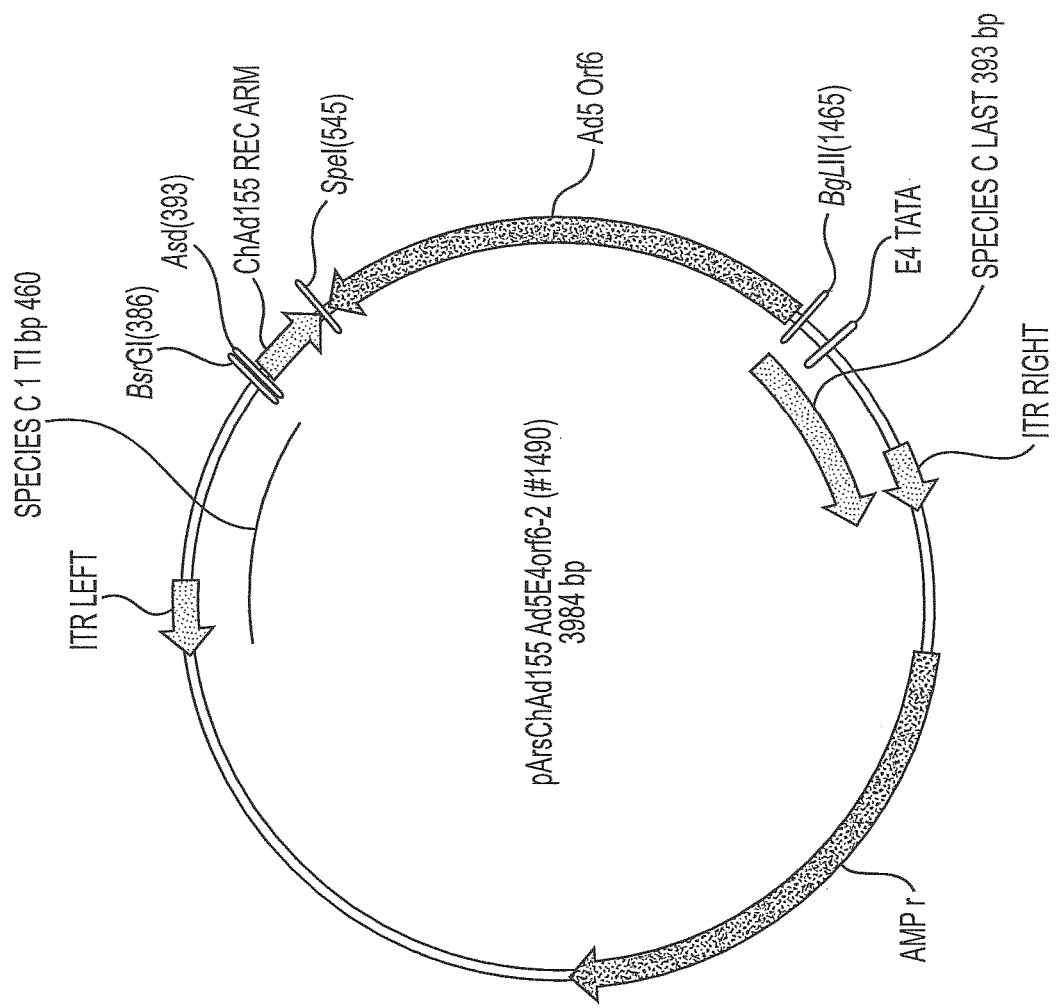
Figure 5:
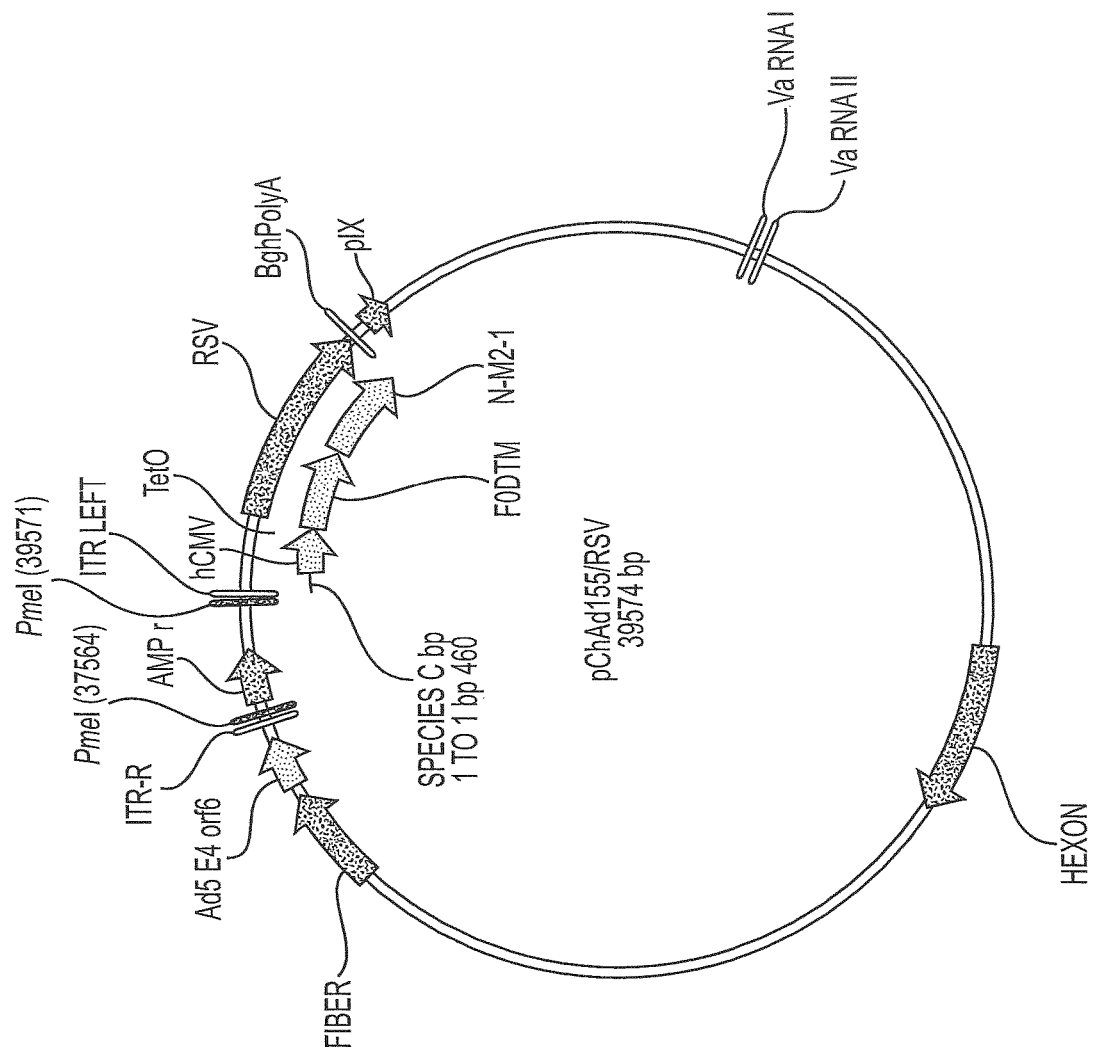

To delete the E4 region, a 177 bp DNA fragment spanning bp 34586 to bp 34730 of the ChAd155 wt sequence (SEQ ID NO: 10) was amplified by PCR using the plasmid BAC/ChAd155 ΔE1_TetO hCMV RpsL-Kana (#1375) as a template with the following oligonucleotides: 5'-ATTCA-GTGTACAGGCGCGCCAAAGCATGACGCTGTTGAT-TTGATTC-3' (SEQ ID NO: 15) and 5'-ACTAGGACTAGT-TATAAGCTAGAATGGGGCTTTGC-3' (SEQ ID NO: 16). The PCR fragment was digested with BsrGI and SpeI and cloned into pARS SubGroupC Ad5orf6-1 digested with BsrGI and SpeI, generating the plasmid pARS SpeciesC Ad5orf6-2 (#1490). A schematic diagram of this shuttle plasmid is provided in FIG. 4. In particular, the shuttle plasmid comprised the following features: Left ITR: bp 1 to 113, Species C first 460 bp: bp 1 to 460, ChAd155 wt (bp 34587 to bp 34724 of SEQ ID NO:10): bp 516 to 650, Ad5 orf6: bp 680 and 1561, Species C last 393 bp: bp 1567 to 1969, Right ITR: bp 1857 to 1969.

Construction of pChAd155 ΔE1, E4 Ad5E4Orf6/TetO hCMV RpsL-Kana (#1434)

The resulting plasmid pARS SubGroupC Ad5orf6-2 was then used to replace the E4 region within the ChAd155 backbone with Ad5orf6. To this end the plasmid BAC/ChAd155 ΔE1_TetO hCMV RpsL-Kana (#1375) was digested with PacI/PmeI and co-transformed into BJ5183 cells with the digested plasmid pARS SubGroupC Ad5orf6-2 BsrGI/AscI, to obtain the pChAd155 ΔE1, E4_Ad5E4orf6/TetO hCMV RpsL-Kana (#1434) pre-adeno plasmid.

Figure 6:
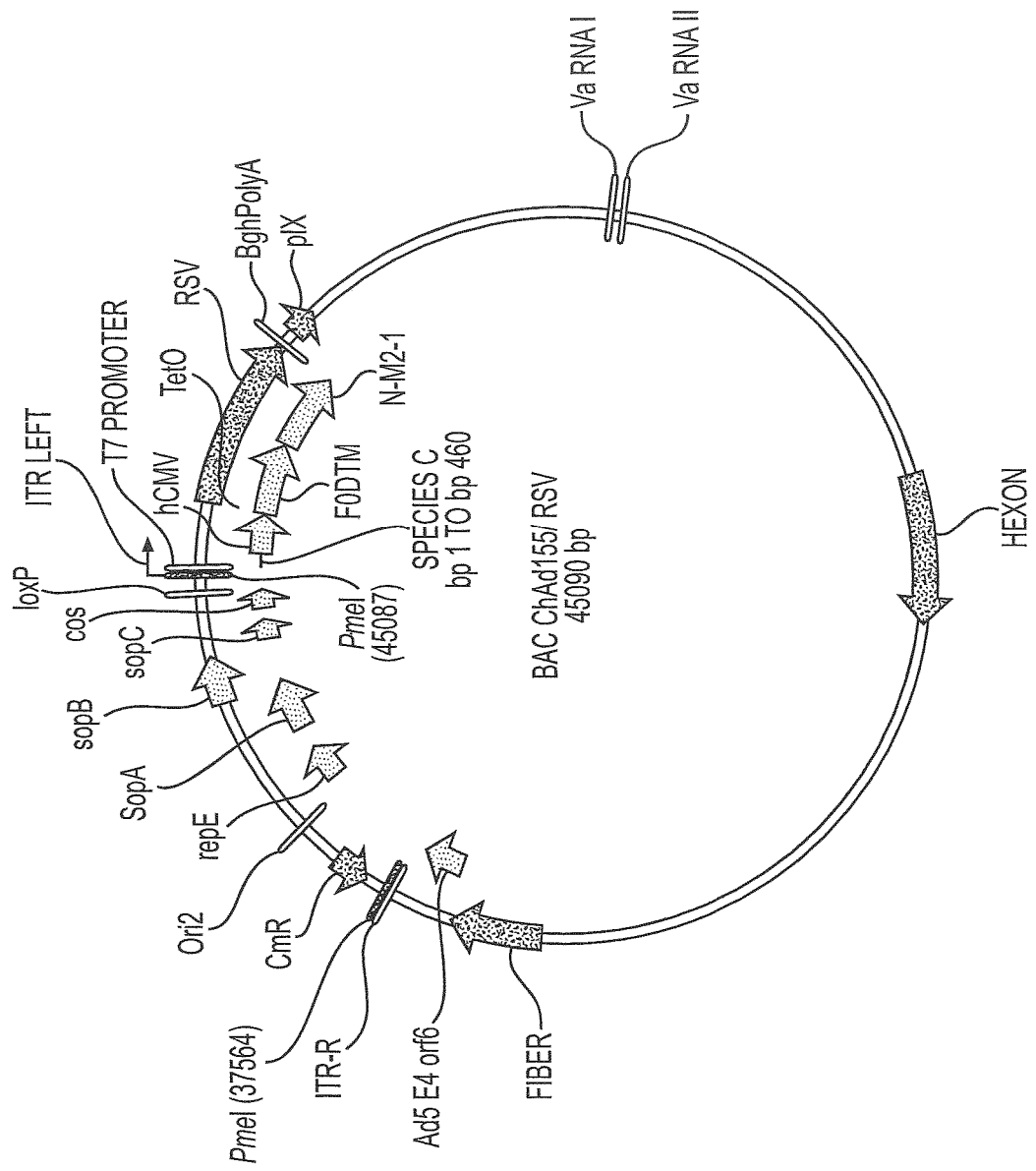

2.2.2: Insertion of RSV Expression Cassette—Construction of pChAd155 ΔE1, E4 Ad5E4Orf6/TetO hCMV RSV The vaccine antigens are computational consensus sequences derived from the alignment of many different subgroup A RSV isolates retrieved from the National Centre for Biotechnology Information (NCBI) database. For each antigen the protein consensus sequence was derived using Multiple Sequence Comparison by Log-Expectation (MUSCLE) version 3.6 by alignment of all non-identical sequences and applying the majority rule. When blasted, the derived consensus sequence of the F protein was found to differ by only one amino acid from a natural annotated variant: embCAA26143.1. The consensus N protein also had only one amino acid different from the annotated variant ID:1494470, while the M2-1 protein was identical to the variant P04545. Finally, each antigenic sequence was codon-optimized for expression in eukaryotic cells, chemically synthesized and assembled. The construct, shown in FIG. 14 and SEQ ID NO: 37 contains the aphtovirus Foot and Mouth Disease Virus 2A region (18 amino acids) between the soluble F protein FΔTM and the other two RSV antigens, which mediates polyprotein processing by a translational effect known as ribosomal skip [American Academy of Pediatrics Subcommittee on Diagnosis and Management of Bronchiolitis. Diagnosis and management of bronchiolitis. *Pediatrics.* 2006; 118: 1774-93.

Boukhvalova M S and Blanco J C. The cotton rat Sigmodon hyspidus model of respiratory syncytial virus infection. *Curr Top Microbiol Immunol.* 2013; 372: 347-58.

Cardenas S, Auais A and Piedimonte G. Palivizumab in the prophylaxis of respiratory syncytial virus infection. *Expert Rev Anti Infect Ther.* 2005; 3(5): 719-26.

Castilow E M and Varga S M. Overcoming T cell-mediated immunopathology to achieve safe RSV vaccination. *Future Virol.* 2008; 3(5): 445-454.

Chin J, Magoff in R L, Shearer L A, et al., Field evaluation of a respiratory syncytial virus vaccine and a trivalent parainfluenza virus vaccine in a pediatric population. *Am J Epidemiol.* 1969; 89(4): 449-63.

Colloca S, Barnes E, Folgori A, et al., Vaccine vectors derived from a large collection of simian adenoviruses induce potent cellular immunity across multiple species. *Sci Transl Med.* 2012; 4(115): p. 115ra2.

Donnelly, 2001]. After transfection into mammalian cells, cleavage occurs and the soluble F protein is detected in the cell culture supernatant. The fusion protein N-M2-1 is instead expressed and detected in the intracellular fraction.

An RSV cassette was cloned into a linearised pre-adeno acceptor vector via homologous recombination in *E. coli* by exploiting the homology existing between HCMV promoter and BGH polyA sequences. The plasmid pvjTetOhCMV-bghpolyA_RSV was cleaved with SfiI and SpeI to excise the 4.65 Kb fragment containing the HCMV promoter with tetO, RSV and BGHpolyA sequence. The resulting RSV 4.65 Kb fragment was cloned by homologous recombination into the pChAd155 ΔE1, E4_Ad5E4orf6/TetO hCMV RpsL-Kana (#1434) acceptor vector carrying the RpsL-Kana selection cassette under control of HCMV and BGHpA. The acceptor pre-adeno plasmid was linearized with the restriction endonuclease SnaBI. The resulting construct was the pChAd155 ΔE1, E4_Ad5E4orf6/TetO hCMV RSV vector (FIG. 5).

2.3: BAC Vector Construction by Recombineering 2.3.1: Deletion of E4 Region—Construction of BAC/ChAd155 ΔE1, E4 Ad5E4Orf6/TetO hCMV RpsL-Kana #1390

A deletion of the E4 region spanning from nucleotide 34731-37449 of the ChAd155 wt sequence was introduced in the vector backbone by replacing this native E4 region with the Ad5 E4orf6 coding sequence using a strategy involving two different steps of recombineering in *E. coli* SW102 competent cells.

The first step resulted in insertion of a selection cassette including the suicide gene SacB, ampicillin-R gene and lacZ (Amp-LacZ-SacB selection cassette) in the E4 region of ChAd155, for the purpose of positive/negative selection of recombinants.

First Step—Substitution of ChAd155 Native E4 Region with Amp-LacZ-SacB Selection Cassette The Amp-LacZ-SacB selection cassette was amplified by PCR using the oligonucleotides provided below containing E4 flanking sequences to allow homologous recombination: 1021-FW E4 Del Step1 (5'-TTAATAGACACAGTAGCT-TAATAGACCCAGTAGTGCAAAGCCCCATTCTAGCT-TATAA CCCCTATTTGTTTATTTTTCT-3') (SEQ ID NO: 17) and 1022-RW E4 Del Step1 (5' ATATATA-CTCTCTCGGCACTTGGCCTTTTACACTGCGAAGTG-TTGGTGCTGGTGCTGCGTT GAGAGATCTTTATTTG-TTAACTGTTAATTGTC-3') (SEQ ID NO: 18).

The PCR product was used to transform *E. coli* SW102 competent cells containing the pAdeno plasmid BAC/ChAd155 (DE1) tetO hCMV—RpsLKana #1375. The transformation of SW102 cells allowed the insertion of the selection cassette in the E4 region of ChAd155 via lambda (λ) Red-mediated homologous recombination, thus obtaining BAC/ChAd155 (DE1) TetOhCMV-RpsL Kana #1379 (including Amp-LacZ-SacB cassette by substituting ChAd155 native E4 region).

Second Step—Substitution of Amp-lacZ-SacB Selection Cassette with Ad5E4Orf6 Region The resulting plasmid BAC/ChAd155 (DE1) TetOhCMV—RpsL Kana #1379 (with Amp-LacZ-SacB cassette in place of ChAd155 E4 region) was then manipulated to replace the Amp-lacZ-SacB selection cassette with Ad5orf6 within the ChAd155 backbone. To this end, a DNA fragment containing the Ad5orf6 region was obtained by PCR, using the oligonucleotides 1025-FW E4 Del Step2 (5'-TTAATAGACACAGTAGCTTAATA-3') (SEQ ID NO: 19) and 1026-RW E4 Del Step2 (5'-GGAAGG-GAGTGTCTAGTGTT-3') (SEQ ID NO: 20). The resulting DNA fragment was introduced into *E. coli* SW102 competent cells containing the pAdeno plasmid BAC/ChAd155 (DE1) TetOhCMV—RpsL Kana)#1379, resulting in a final plasmid BAC/ChAd155 (ΔE1, E4 Ad5E4orf6) TetOhCMV—RpsL Kana #1390 containing Ad5orf6 substituting the native ChAd155 E4 region.

2.3.2: Insertion of RSV Expression Cassette: Construction of BAC/ChAd155 ΔE1, E4_Ad5E4Orf6/TetOhCMV RSV #1393

An RSV transgene was cloned into the BAC/ChAd155 ΔE1, E4_Ad5E4orf6/TetOhCMV RpsL Kana #1390 vector by substituting the RpsL-Kana selection cassette. The construction strategy was based on two different steps of recombineering in *E. coli* SW102 competent cells.

First Step—Substitution of RpsL-Kana Cassette with Amp-LacZ-SacB Selection Cassette The Amp-LacZ-SacB selection cassette was obtained from plasmid BAC/ChAd155 (DE1) TetO hCMV Amp-LacZ-SacB #1342 by PCR using the oligonucleotides 91-SubMonte FW (5'-CAATGGGCGTGGA-TAGCGGTTTGAC-3') (SEQ ID NO: 21) and 890-Bgh-PolyA RW (5'-CAGCATGCCTGCTATTGTC-3') (SEQ ID NO: 22). The product was transformed into *E. coli* SW102 competent cells containing the pAdeno plasmid BAC/ChAd155 (DE1, E4 Ad5E4orf6) TetOhCMV—RpsL Kana #1390, resulting in BAC/ChAd155 (DE1, E4 Ad5E4orf6) TetOhCMV—Amp-LacZ-SacB #1386.

Second Step—Substitution of Amp-lacZ-SacB Selection Cassette with RSV Transgene The RSV transgene was inserted in plasmid BAC/ChAd155 (DE1, E4 Ad5E4orf6) TetOhCMV—Amp-LacZ-SacB #1386 by replacing the Amp-lacZ-SacB selection cassette by homologous recombination. To this end, the plasmid pvjTetOhCMV-bghpolyA_RSV #1080 (containing an RSV expression cassette) was cleaved with SpeI and SfiI to excise the 4.4 Kb fragment including the HCMV promoter, RSV and BGHpolyA. The resulting RSV 4.4 Kb fragment was transformed into *E. coli* SW102 competent cells containing the pAdeno plasmid BAC/ChAd155 (DE1, E4 Adr5E4orf6) TetOhCMV—Amp-LacZ-SacB #1386, resulting in the final plasmid BAC/ChAd155 ΔE1, E4_Ad5E4orf6/TetO hCMV RSV #1393. The structure of the BAC carrying ChAd155/RSV (SEQ ID NO: 11) is illustrated in FIG. 6. In particular, ChAd155/RSV comprised the following features: Species C Left ITR: bp 1 to 113, hCMV(tetO) bp 467 to 1311, RSV gene: bp 1348 to 4785, bghpolyA: bp 4815 to 5032, Ad5E4orf6: bp 36270 to 37151, Species C Right ITR: bp 37447 to 37559.

Example 3: Vector Production

The productivity of ChAd155 was evaluated in comparison to ChAd3 and PanAd3 in the Procell 92 cell line.

3.1: Production of Vectors Comprising an HIV Gag Transgene

Figure 7:
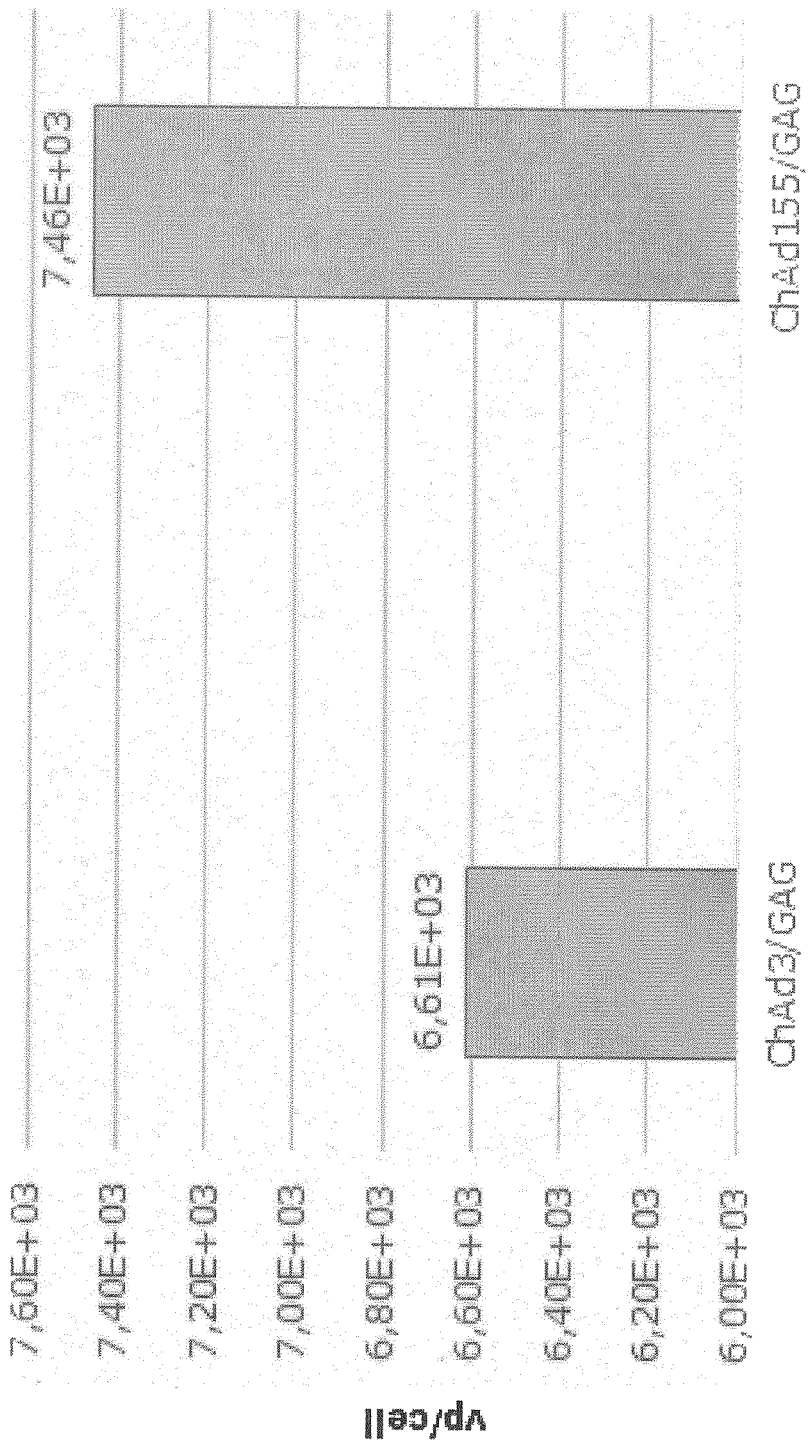

Vectors expressing the HIV Gag protein were prepared as described above (ChAd155/GAG) or previously (ChAd3/GAG Colloca et al, Sci. Transl. Med. (2012) 4:115ra). ChAd3/GAG and ChAd155/GAG were rescued and amplified in Procell 92 until passages 3 (P3); P3 lysates were used to infect 2 T75 flasks of Procell 92 cultivated in monolayer with each vector. A multiplicity of infection (MOI) of 100 vp/cell was used for both infection experiments. The infected cells were harvested when full CPE was evident (72 hours post-infection) and pooled; the viruses were released from the infected cells by 3 cycles of freeze/thaw (−70°/37° C.) then the lysate was clarified by centrifugation. The clarified lysates were quantified by Quantitative PCR Analysis with primers and probe complementary to the CMV promoter region. The oligonucleotide sequences are the following: CMVfor 5'-CATCTACGTATTAGTCATCGCTATTACCA-3' (SEQ ID NO: 23), CMVrev 5'-GACTTGGAAATCCCCGTGAGT-3' (SEQ ID NO: 24), CMVFAM-TAMRA probe 5'-ACATCAATGGGCGTGGAT-AGCGGTT-3' (SEQ ID NO: 25) (QPCRs were run on ABI Prism 7900 Sequence detector—Applied Biosystem). The resulting volumetric titers (vp/ml) measured on clarified lysates and the specific productivity expressed in virus particles per cell (vp/cell) are provided in Table 1 below and illustrated in FIG. 7.

TABLE 1

Vector productivity from P3 lysates.

| Vector | vp/ml | Total vp (20 ml conc.) | vp/cell |
|---|---|---|---|
| ChAd3/GAG | 9.82E+09 | 1.96E+11 | 6.61E+03 |
| ChAd155/GAG | 1.11E+10 | 2.22E+11 | 7.46E+03 |

Figure 8:
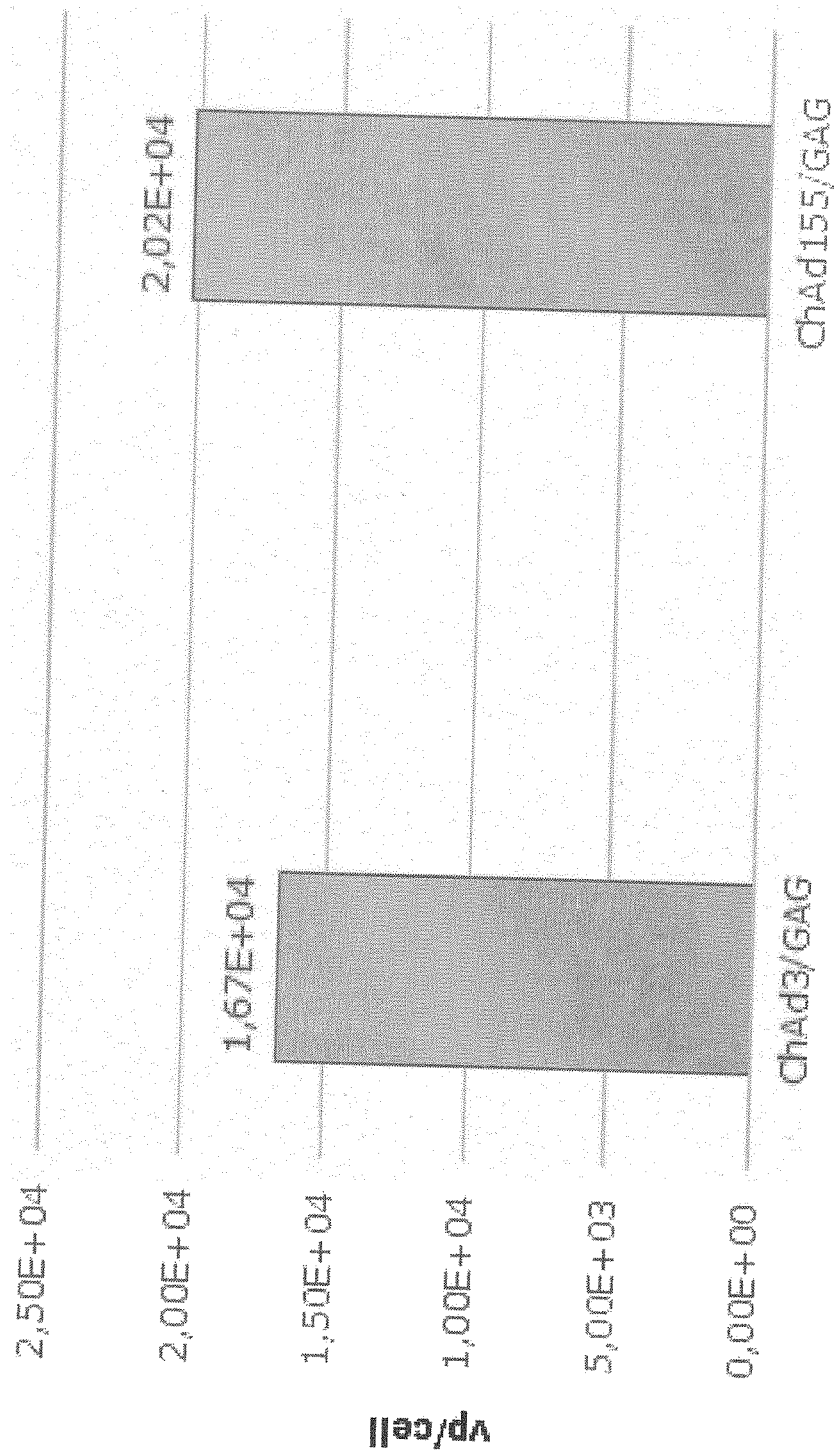

To confirm the higher productivity of the ChAd155 vector expressing HIV Gag transgene, a second experiment was performed by using purified viruses as inoculum. To this end, Procell 92 cells were seeded in a T25 Flask and infected with ChAd3/GAG and ChAd155/GAG when the confluence of the cells was about 80%, using a MOI=100 vp/cell of infection. The infected cells were harvested when full CPE was evident; the viruses were released from the infected cells by freeze/thaw and clarified by centrifugation. The clarified lysates were quantified by Quantitative PCR Analysis by using following primers and probe: CMVfor 5'-CATCTACGTATTAGTCATCGCTATTACCA-3' (SEQ ID NO: 23), CMV rev GACTTGGAAATCCCCGTGAGT (SEQ ID NO: 24), CMV FAM-TAMRA probe 5'-ACATCAATGGGCGTGGATAGCGGTT-3' (SEQ ID NO: 25) complementary to the CMV promoter region (samples were analysed on an ABI Prism 7900 Sequence detector—Applied Biosystems). The resulting volumetric titers (vp/ml) measured on clarified lysates and the specific productivity expressed in virus particles per cell (vp/cell) are provided in Table 2 below and illustrated in FIG. 8.

TABLE 2

Vector productivity from purified viruses.

| Vector | vp/ml | Total vp/T25 flask (5 ml of lysate) | vp/cell |
|---|---|---|---|
| ChAd3/GAG | 1.00E+10 | 5.00E+10 | 1.67E+04 |
| ChAd155/GAG | 1.21E+10 | 6.05E+10 | 2.02E+04 |

3.2: Production of Vectors Comprising an RSV Transgene

Figure 9:
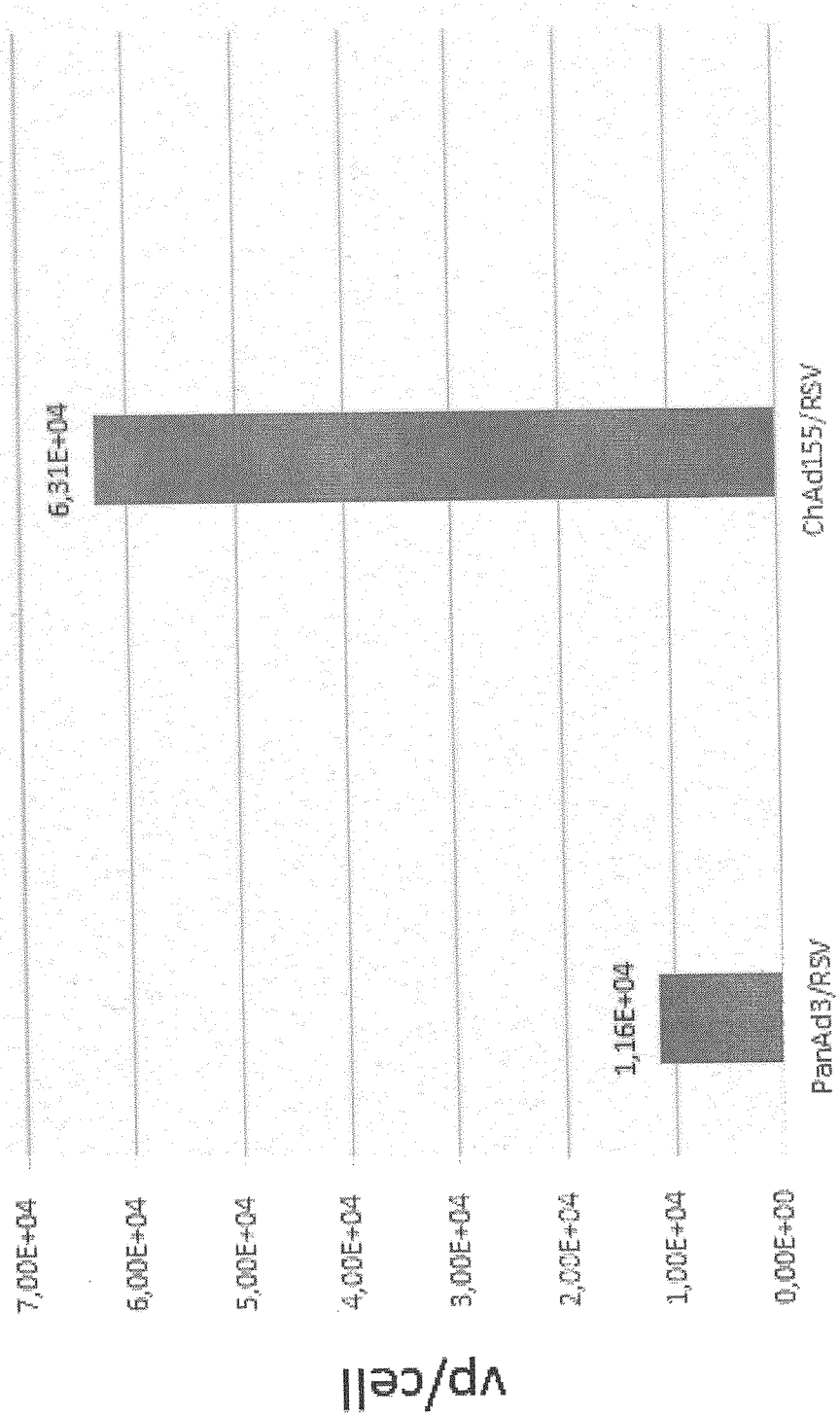

A different set of experiments were performed to evaluate the productivity of RSV vaccine vectors in Procell 92.S cultivated in suspension. The experiment compared PanAd3/RSV (described in WO2012/089833) and Chad155/RSV in parallel by infecting Procell 92.S at a cell density of $5\times10^5$ cells/ml. The infected cells were harvested 3 days post infection; the virus was released from the infected cells by 3 cycles of freeze/thaw and the lysate was clarified by centrifugation. The clarified lysates were then quantified by Quantitative PCR Analysis as reported above. The volumetric productivity and the cell specific productivity are provided in Table 3 below and illustrated in FIG. 9.

TABLE 3

| Virus | Volumetric productivity (Vp/ml) | Total vp | Cell specific productivity (vp/cell) |
|---|---|---|---|
| PanAd3/RSV | 5.82E+09 | 2.91E+11 | 1.16E+4 |
| ChAd155/RSV | 3.16E+10 | 1.58E+12 | 6.31E+04 |

Figure 10:
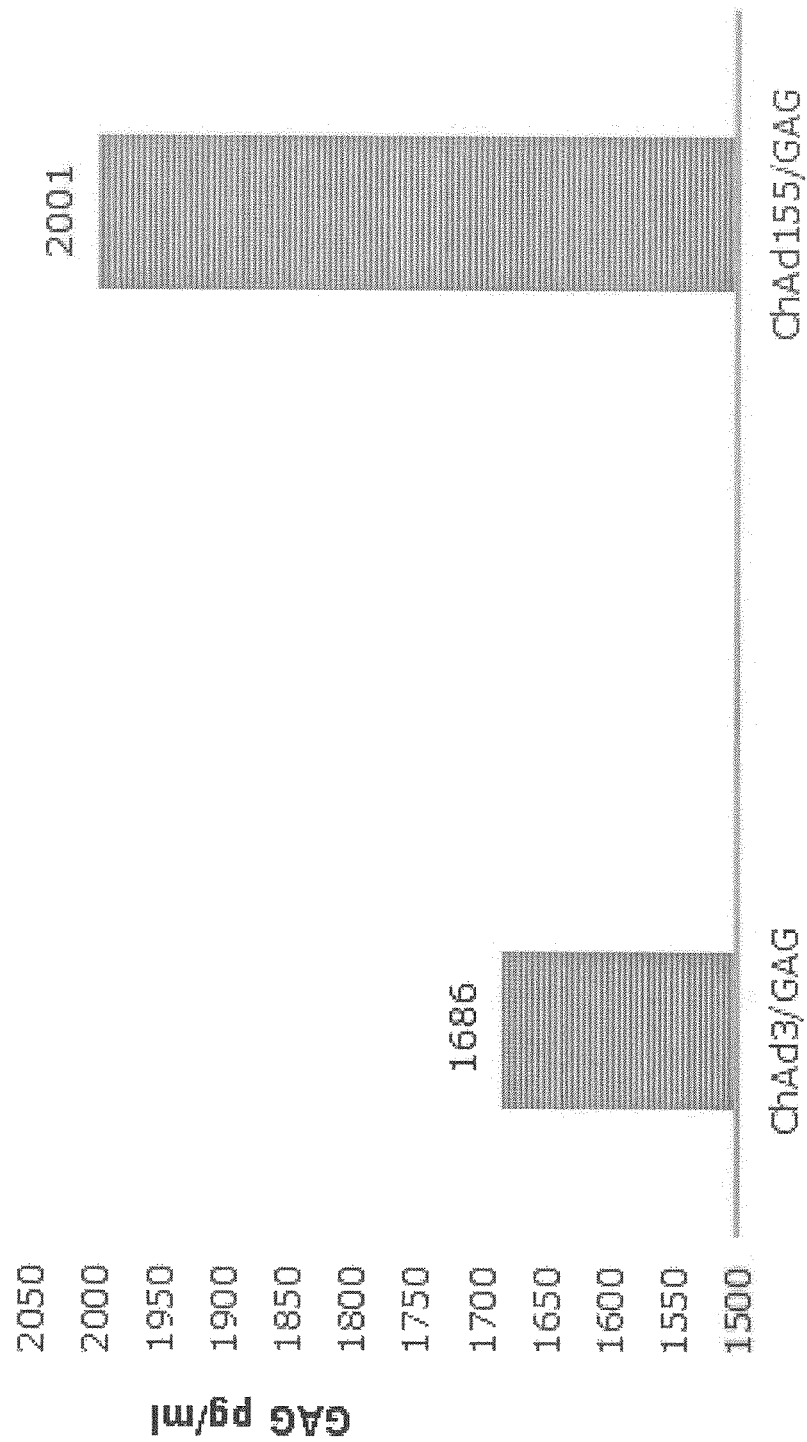

Example 4: Transgene Expression Levels 4.1: Expression Level of HIV Gag Transgene Expression levels were compared in parallel experiments by infecting HeLa cells with ChAd3 and ChAd155 vectors comprising an HIV Gag transgene. HeLa cells were seeded in 24 well plates and infected in duplicate with ChAd3/GAG and ChAd155/GAG purified viruses using a MOI=250 vp/cell. The supernatants of HeLa infected cells were harvested 48 hours post-infection, and the production of secreted HIV GAG protein was quantified by using a commercial ELISA Kit (HIV-1 p24 ELISA Kit, PerkinElmer Life Science). The quantification was performed according to the manufacturer's instruction by using an HIV-1 p24 antigen standard curve. The results, expressed in pg/ml of GAG protein, are illustrated in FIG. 10.

4.1: Expression Level of RSV F Transgene

Expression levels were compared in parallel experiments by infecting HeLa cells with the above-described PanAd3 and ChAd155 vectors comprising an RSV F transgene. To this end, HeLa cells were seeded in 6 well plates and infected in duplicate with PanAd3/RSV and ChAd155/RSV purified viruses using a MOI=500 vp/cell. The supernatants were harvested 48 hours post-infection, and the production of secreted RSV F protein was quantified by ELISA. Five different dilutions of the supernatants were transferred to microplate wells which are coated with a commercial mouse anti-RSV F monoclonal antibody. The captured antigen was revealed using a secondary anti-RSV F rabbit antiserum followed by Biotin-conjugated anti-rabbit IgG, then by adding Streptavidin-AP conjugate (BD Pharmingen cat. 554065). The quantification was performed by using an RSV F protein (Sino Biological cat. 11049-V08B) standard curve. The results obtained, expressed as ug/ml of RSV F protein, are provided in Table 4 below.

TABLE 4

| Sample | μg/ml RSV F protein |
|---|---|
| ChAd155/RSV | 5.9 |
| PanAd3/RSV | 4 |

Figure 11:
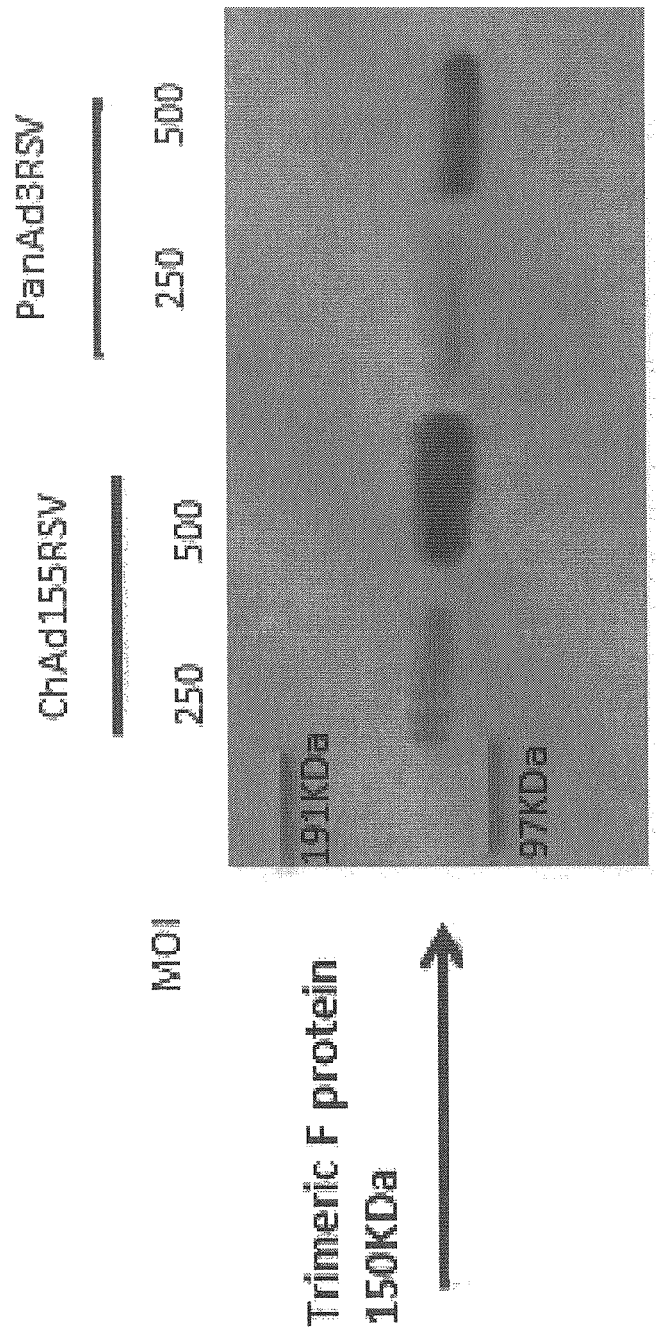

A western blot analysis was also performed to confirm the higher level of transgene expression provided by the ChAd155 RSV vector relative to the PanAd3 RSV vector. HeLa cells plated in 6 well plates were infected with PanAd3/RSV and ChAd155/RSV purified viruses using MOI=250 and 500 vp/cell. The supernatants of HeLa infected cells were harvested and the production of secreted RSV F protein were analysed by non-reducing SDS gel followed by Western Blot analysis. Equivalent quantities of supernatants were loaded on non-reducing SDS gel; after electrophoresis separation, the proteins were transferred to a nitrocellulose membrane to be probed with an anti-RSV F mouse monoclonal antibody (clone RSV-F-3 catalog no: ABIN308230 available at antibodies-online.com (last accessed 13 Apr. 2015). After the incubation with primary antibody, the membrane was washed and then incubated with anti-mouse HRP conjugate secondary antibody. Finally the assay was developed by electrochemiluminescence using standard techniques (ECL detection reagents Pierce catalog no W3252282). The Western Blot results are shown in FIG. 11. A band of about 170 kD indicated by the arrow was revealed by monoclonal antibody mAb 13 raised against the F protein, which corresponds to the expected weight of trimeric F protein. It can be seen that the ChAd155 RSV vector produced a darker band at both MOI=250 and 500 vp/cell.

Figure 12:
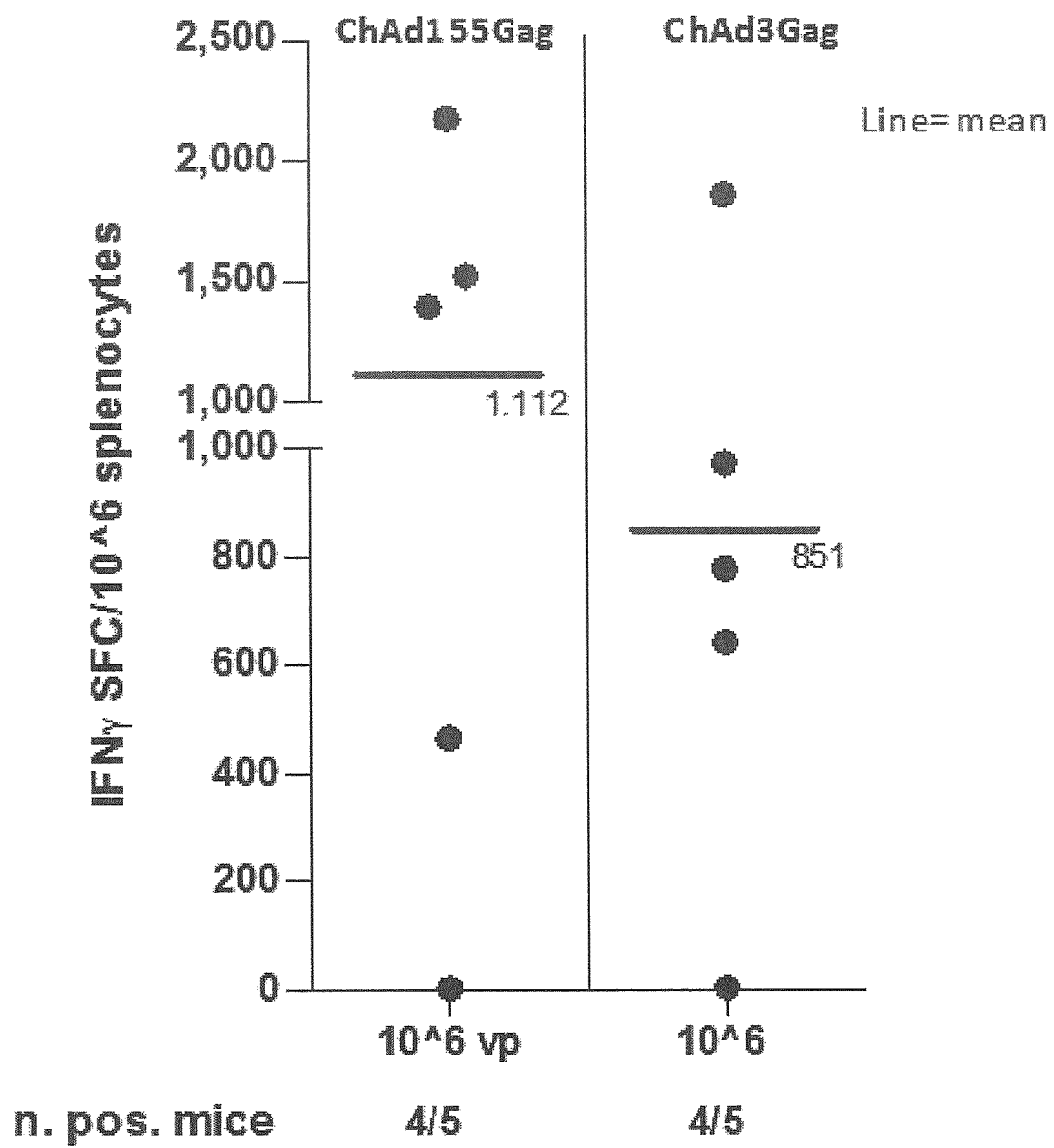

Example 5: Evaluation of Immunological Potency by Mouse Immunization Experiments 5.1: Immunogenicity of Vectors Comprising the HIV Gag Transgene The immunogenicity of the ChAd155/GAG vector was evaluated in parallel with the ChAd3/GAG vector in BALB/c mice (5 per group). The experiment was performed by injecting $10^6$ viral particles intramuscularly. T-cell response was measured 3 weeks after the immunization by ex vivo IFN-gamma enzyme-linked immunospot (ELISpot) using a GAG CD8+ T cell epitope mapped in BALB/c mice. The results are shown in FIG. 12, expressed as IFN-gamma Spot Forming Cells (SFC) per million of splenocytes. Each dot represents the response in a single mouse, and the line corresponds to the mean for each dose group. Injected dose in number of virus particles and frequency of positive mice to the CD8 immunodominant peptide are shown on the x axis.

5.2 Immunogenicity of Vectors Comprising the RSV Transgene

Preclinical studies to evaluate the immunogenicity of the vaccine candidate ChAd155-RSV were performed in inbred BALB/c mice (5.2.1). The vaccine efficacy was also evaluated in cotton rats after intranasal (IN) challenge with RSV through measurement of viral load in lower (lung) or upper (nasal tissue) respiratory tract (5.2.2). Finally, the vaccine was tested in young seronegative calves, which is a model that mimics natural RSV infection (5.2.3).

5.2.1—Inbred Mice

ChAd155-RSV was tested in the BALB/c mouse strain to evaluate its immunological potency. Dose escalation in inbred mice is the standard assay that has enabled the ranking of chimpanzee adenoviral vectors immunological potency in mice with results that have been confirmed consistently across species (non-human primates and humans) [Colloca, 2012].

Figure 13:
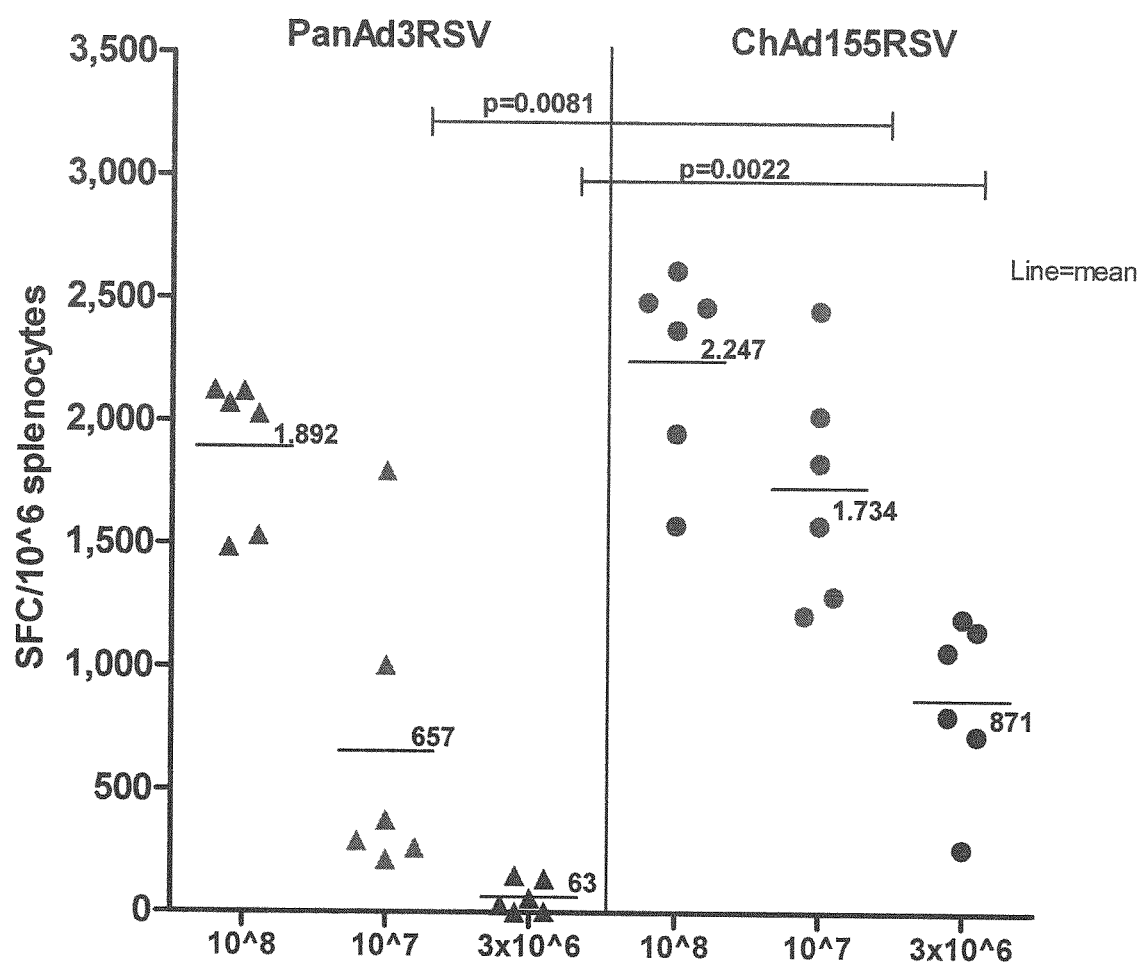
Figure 14:
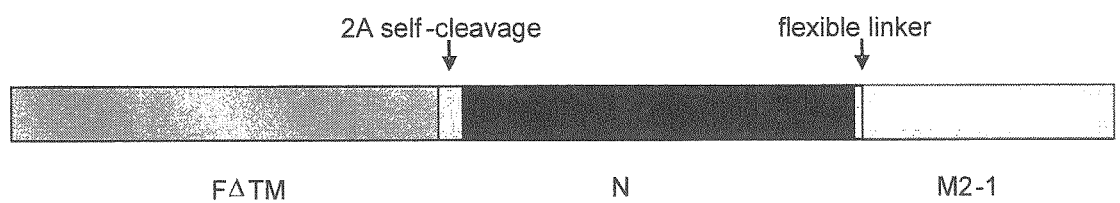

The immunological potency of the PanAd3/RSV and ChAd155/RSV vectors was evaluated in BALB/c mice. Both vectors were injected intramuscularly at doses of $3\times10^6$, $10^7$, and $10^8$ vp. Three weeks after vaccination the splenocytes of immunized mice were isolated and analyzed by IFN-gamma-ELISpot using as antigens immunodominant peptide F and M epitopes mapped in BALB/c mice. The levels of immune-responses were reduced in line with decreasing dosage (as expected) but immune responses were clearly higher in the groups of mice immunized with ChAd155/RSV vector compared to the equivalent groups of mice immunized with PanAd3/RSV vaccine (FIG. 13). In FIG. 13, symbols show individual mouse data, expressed as IFN-gamma Spot Forming Cells (SFC)/million splenocytes, calculated as the sum of responses to the three immunodominant epitopes ($F_{51-66}$ $F_{85-93}$ and $M2-1_{282-290}$) and corrected for background. Horizontal lines represent the mean number of IFN-gamma SFC/million splenocytes for each dose group. A T cell dose response was observed in ChAd155-RSV immunized mice with all mice responding even at the low $3\times10^6$ vp dosage. PanAd3-RSV induced comparable responses at the highest dosage, while ChAd155-RSV induced higher responses at the two lower dosages (FIG. 13).

Figure 15:
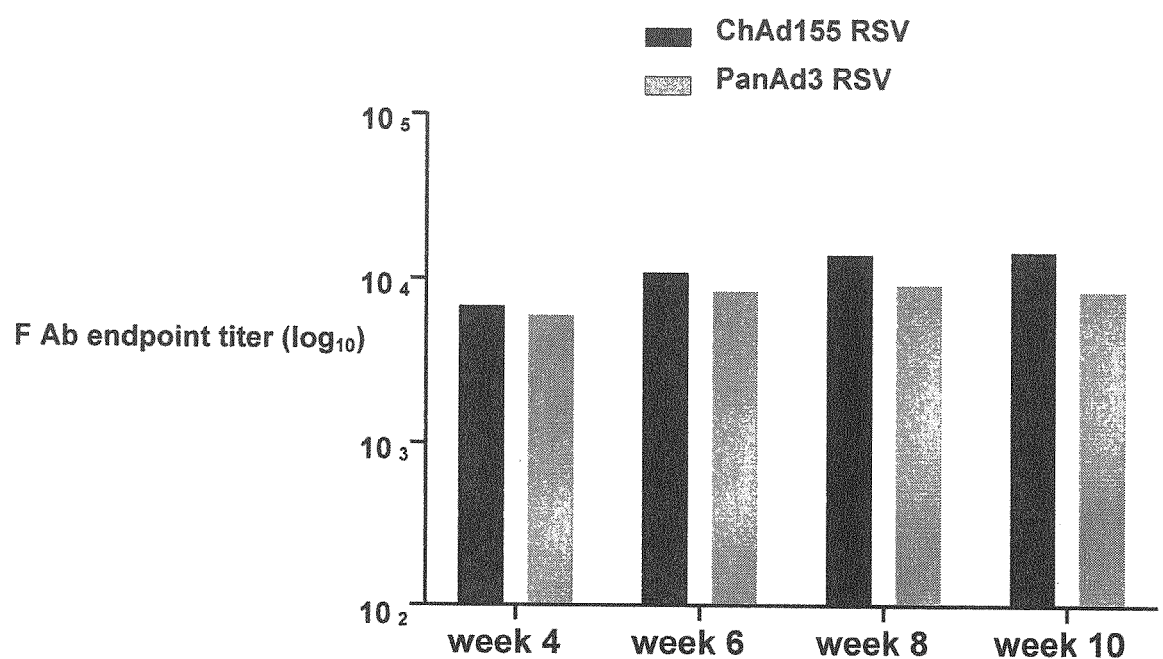

In a second study, a group of BALB/c mice received ChAd155-RSV and another group received PanAd3-RSV, IM at a single dose of $5\times10^6$ vp. The mice (n=5/group) were subsequently bled every two weeks starting from Week 4 post-vaccination up to Week 10, to monitor induction and maintenance of anti F antibodies. Pooled sera from immunized mice were tested in Enzyme-Linked Immunosorbent Assay (ELISA) on coated RSV-F protein. FIG. 15 shows RSV F Immunoglobulin G (IgG) titers, measured by ELISA in pooled sera from immunized mice at different time points from vaccination. Pooled sera serial dilutions were plated in RSV-F protein coated ELISA wells, and the binding of specific IgG revealed using a goat anti-mouse IgG conjugated to Alkaline Phosphatase (AP) and p-Nitrophenyl Phosphate (pNPP) substrate. The reaction was allowed to proceed over time and read at 405 nanometres (nm) during fixed time points. Data are expressed as endpoint titers calculated as the dilution of serum giving an optical density $(OD)_{405}$ reading greater than three Standard Deviations (SDs) above the mean of pre-immune sera at a 1:100 dilution. Antibody responses to RSV F protein were induced by ChAd155-RSV and maintained over a period of 10 weeks after a single IM administration of $5\times10^8$ vp, and antibody titers were 1.5-fold higher at plateau than those induced by PanAd3-RSV (FIG. 15).

5.2.2—Cotton Rats

Methodology

Five groups of female, 6-8 weeks old cotton rats (8 rats/group) were immunized by the intramusculat (IM) route with $5\times10^8$ or $5\times10^7$ vp of ChAd155-RSV or PanAd3-RSV (see Table 5). A control group was left unvaccinated. Seven weeks after vaccination, the animals were challenged by intranasal (IN) inoculation with a $10^5$ pfu standard dose of RSV A (Long strain). Five days after challenge, the animals were sacrificed, the nasal tissue harvested for viral titration, and the lung en bloc collected and bisected for viral titration (left lobes) and histopathology (right lobes, Groups A, D, E only). RSV titers in nasal tissue or lung homogenates collected five days after RSV challenge were determined by a standard plaque assay on permissive cells (HEp-2 cells). FFPE lung sections were stained with Hematoxylin/Eosin. Four parameters of pulmonary inflammation were evaluated: peribronchiolitis (PB), perivasculitis (PV), interstitial pneumonia (IP), and alveolitis (A). Slides were scored blind on a 0-4 severity scale, and values were then converted to a 0-100% histopathology score. The animals were also bled at Day 0 and at the time of challenge, for RSV neutralizing antibody titration by standard plaque assay on permissive cells (Vero cells).

Neutralizing antibody titers were determined as the reciprocal of the serum dilutions at which 60% of the virus was neutralized compared to virus control.

TABLE 5

Dosing scheme of cotton rats

| Group | Vaccine | Immunization dose |
|---|---|---|
| A | Control | — |
| B | PanAd3-RSV IM | $5 \times 10^8$ vp |
| C | PanAd3-RSV IM | $5 \times 10^7$ vp |
| D | ChAd155-RSV IM | $5 \times 10^8$ vp |
| E | ChAd155-RSV IM | $5 \times 10^7$ vp |

Immunogenicity and Efficacy Results

Figure 16:
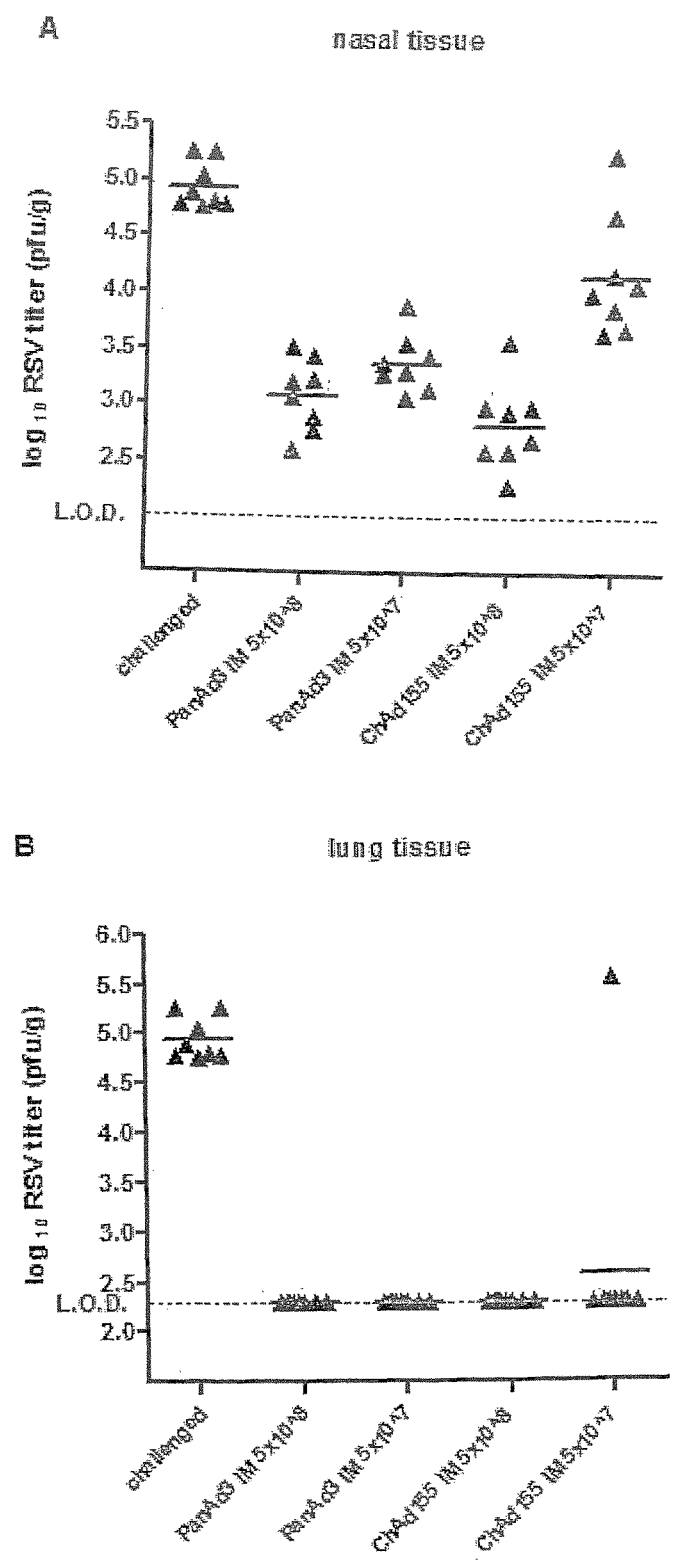
Figure 16:
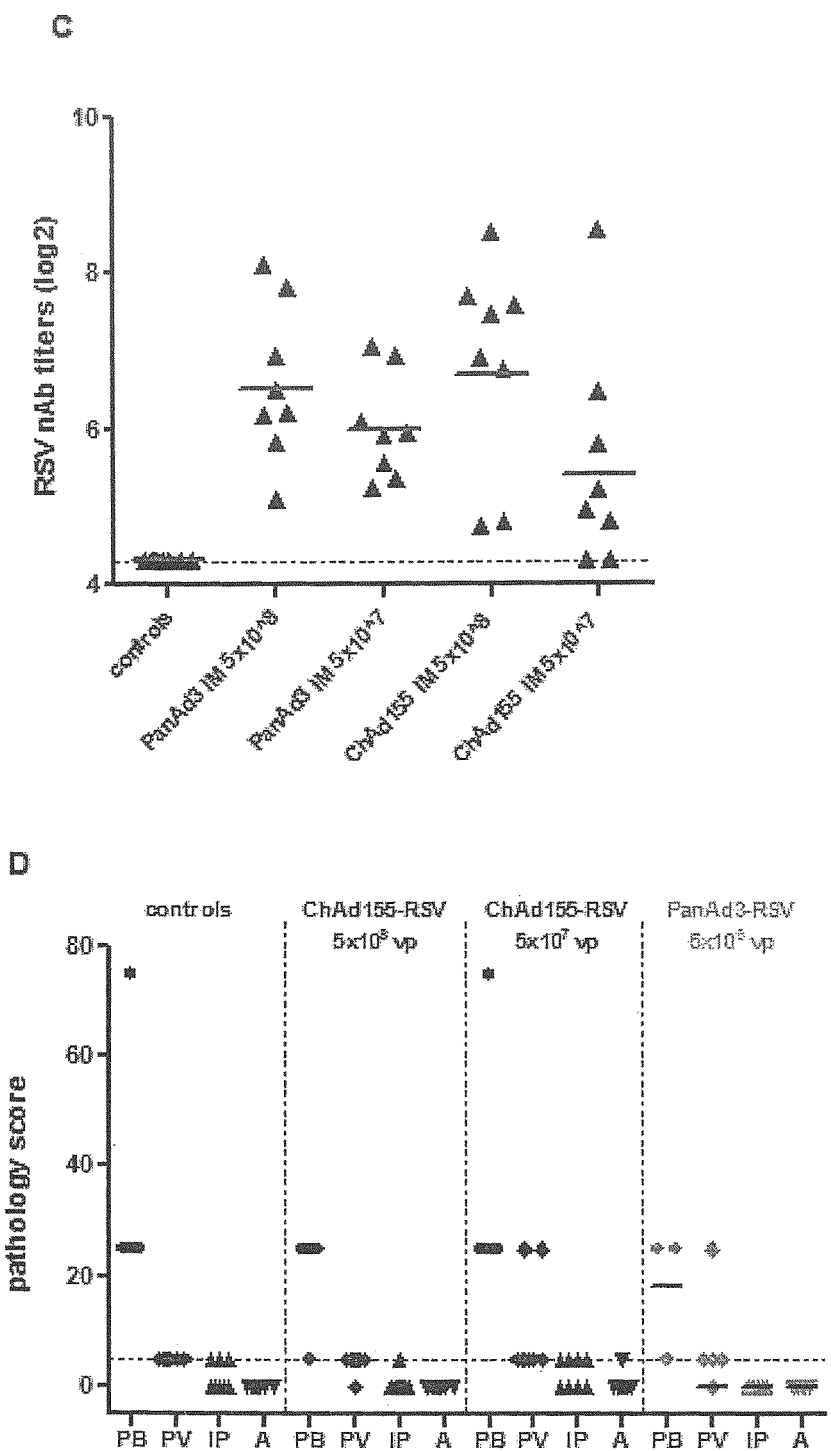

FIG. 16 panels A and B show the RSV viral titers from nasal tissue and lung homogenates, respectively, by plaque assay. RSV titers in nasal tissue or lung homogenates collected five days after RSV challenge were determined by a standard plaque assay on permissive cells. Data are expressed as RSV plaque forming units per gram of tissue (pfu/g). intramuscular ChAd155-RSV at both dosages completely abolished viral replication in the lung, apart from one animal at the lowest dosage. Infection of the upper respiratory tract was also significantly reduced (between 1 and 2 logs lower RSV titers recovered from nasal tissue) in a dose-dependent manner compared to unvaccinated control animals.

It has been previously shown that in cotton rats a serum neutralizing antibody titer of 1:100 or greater confers protection from viral replication in the lung [Prince, 1985]. In this study both vectors administered IM at $5\times10^8$ vp induced RSV neutralizing antibodies in the range of the protective threshold while titers decreased with a lower vaccine dosage (FIG. 16 panel C). Nevertheless, the vaccination prevented viral replication in the lung even when serum antibody levels were below 1:100, suggesting a role for other immune effector mechanisms. RSV neutralizing antibody titers are expressed as the serum dilution reducing plaques by 60% compared to control.

Safety Results

Lung histopathology was performed five days post-infection to assess whether vaccination with ChAd155-RSV induced vaccine-enhanced pathology. Four parameters of pulmonary inflammation were evaluated according to the presence of inflammatory cells in different areas of the lung structure: peribronchiolitis (PB, inflammatory cell infiltration around the bronchioles), perivasculitis (PV, inflammatory cell infiltration around the small blood vessels), interstitial pneumonia (IP, inflammatory cell infiltration and thickening of alveolar walls), and alveolitis (A, cells within the alveolar space). Formalin-fixed, paraffin-embedded lung sections were stained with Hematoxylin/Eosin. Slides were scored blind on a 0-4 severity scale, and values were then converted to a 0-100% histopathology score. The dashed line (set at 5%) represents the threshold for significant pathology. Histopathology data for PanAd3-RSV (depicted in grey) derive from a previous study. Among the four parameters, the presence of inflammatory infiltrate in the alveolar walls (interstitial pneumonia [IP]), and more importantly in the alveolar space, (alveolitis [A]), is considered predictive for enhanced disease and lung pathology [Prince, 2001]. The results of the lung histopathology analysis (FIG. 16 panel D) showed that IM ChAd155-RSV did not induce significant IP and A pathology scores. The low levels of IP and A observed were consistent with what has been observed during RSV acute infection and secondary RSV re-infection [American Academy of Pediatrics Subcommittee on Diagnosis and Management of Bronchiolitis. Diagnosis and management of bronchiolitis. *Pediatrics*. 2006; 118: 1774-93.

Boukhvalova, 2013], and were comparable to values observed with PanAd3-RSV in previous studies.

In FIG. 16, dashed horizontal lines represent limit of detection (LOD) for each assay in panels A, B and C. In panel D The dashed horizontal line (set at 5%) represents the threshold for significant pathology.

5.2.3—Seronegative Calves

Bovine RSV (bRSV) causes respiratory disease in young calves that is very similar to that observed in human infants. In addition, bovine RSV is genetically and antigenically related to human RSV. The newborn calf bRSV model a relevant animal model for evaluation of safety of human RSV vaccines Methodology Three groups of five colostrum-restricted calves were vaccinated on two occasions, four weeks apart, with $5\times10^{10}$ vp ChAd155-RSV or comparator PanAd3-RSV, as indicated in Table 6.

TABLE 6

Dosing scheme of newborn calves

| Group | Vaccination 1 | Dose | Vaccination 2 | Dose |
|---|---|---|---|---|
| A | PanAd3-RSV IM | $5 \times 10^{10}$ vp | PanAd3-RSV IM | $5 \times 10^{10}$ vp |
| B | ChAd155-RSV IM | $5 \times 10^{10}$ vp | ChAd155-RSV IM | $5 \times 10^{10}$ vp |
| C | PanAd3-control IM | $5 \times 10^{10}$ vp | PanAd3-control IM | $5 \times 10^{10}$ vp |

Group C was mock-vaccinated with PanAd3 adenovectors containing unrelated antigens. The animals were challenged four weeks after the second vaccination by IN (10 mL) and intratracheal (IT) (10 mL) administration of $10^4$ pfu of bRSV Snook strain. Six days after the infection, when the virus replication peaked in the lung and in the nose causing maximal pulmonary pathology, the animals were sacrificed. In this model, due to the IN/IT routes of administration of the challenge inoculum, very few, if any, clinical signs are observed in challenged control animals. Therefore, the effects of vaccination on bRSV challenge were studied by nasopharyngeal excretion of bRSV, analysis of levels of bRSV in lung homogenate, development of gross pneumonic lesions and analysis of leukocytes in broncho-alveolar lavage (BAL). Antibody responses (antibody and neutralizing titers) induced after vaccination and/or challenge were also investigated.

Figure 17:
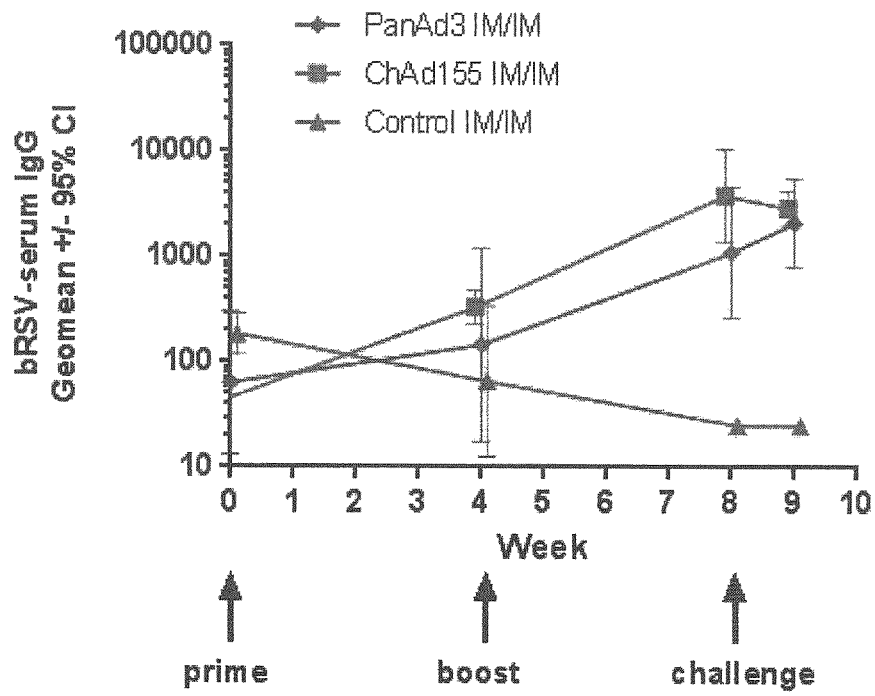
Figure 17:
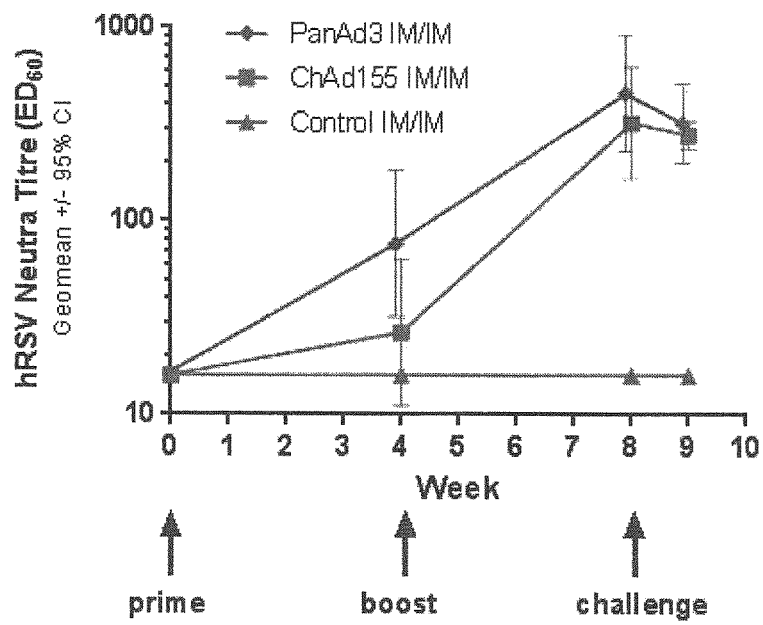

Immunogenicity Results
Effect of Vaccination on Induction of bRSV-Specific Serum IgG Kinetics of the mean bRSV-specific serum IgG antibody and human RSV (hRSV) neutralizing titers throughout the course of the vaccination are shown per study group in FIG. 17. The graph shows the geometric mean value of each study group. Levels of bRSV-specific IgG were determined using bRSV (Snook strain)-infected fetal calf kidney (FCK) cell lysate as antigen [Taylor, 1995]. A lysate of mock-infected FCK cells was used as a control antigen.

Two out of five animals in each group receiving an RSV immunogen showed low levels of maternal bRSV-specific antibodies at the start of the vaccination. Nevertheless, all animals responded to the vaccines and reached high levels ($\log_{10}$=3-3.5) of bRSV-specific antibodies after the boost (FIG. 17A). All the calves in the control group had detectable bRSV-specific antibodies at the start of the vaccination which declined during the study and were not detectable on the day of the challenge. In conclusion, PanAd3-RSV and ChAd155-RSV displayed similar potency in eliciting antibody responses.

No hRSV neutralizing response could be detected before vaccination. After a single dose, all animals vaccinated with PanAd3-RSV and 2 out of 5 animals vaccinated with ChAd155-RSV had measurable RSV neutralizing antibodies (FIG. 17B). A marked boost was observed after the second dose for both vaccines. No further enhancement of the hRSV neutralizing response was observed 1 week after challenge.

Efficacy Results
Effect of Vaccination on Nasopharyngeal Excretion of bRSV

Figure 18:
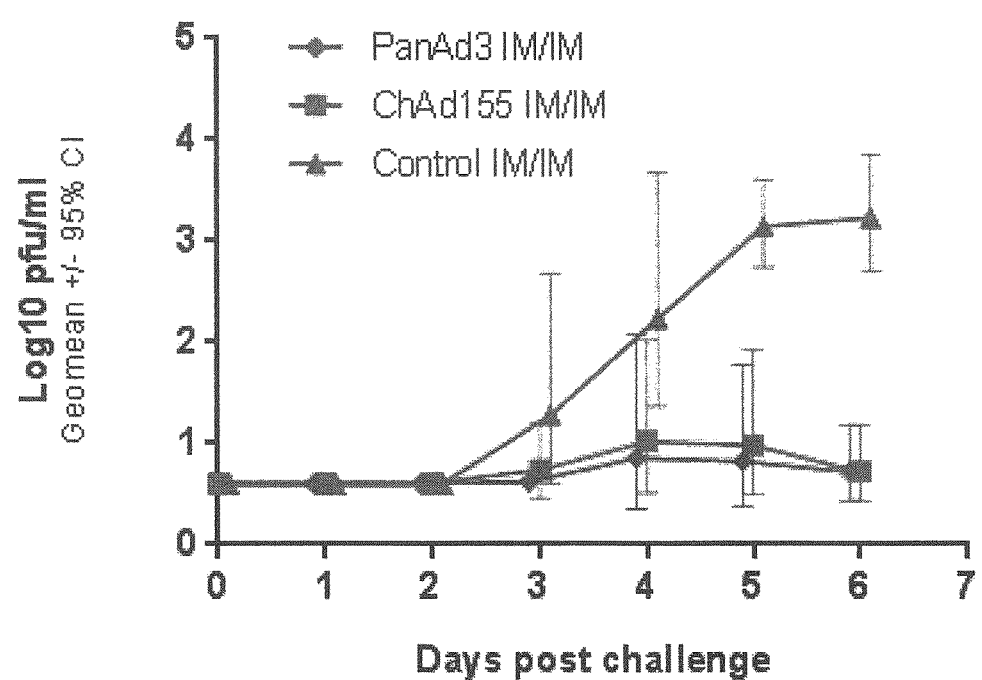

Following bRSV challenge, nasopharynx swabs were obtained daily and the bRSV titers within the samples determined. As shown in FIG. 18, titers in the control group increased from day 3 to day 6. bRSV replication appeared to be significantly reduced in calves that had received either of the adenovector RSV constructs.

Effect of Vaccination on Replication of bRSV in the Lower Respiratory Tract.

Figure 19:
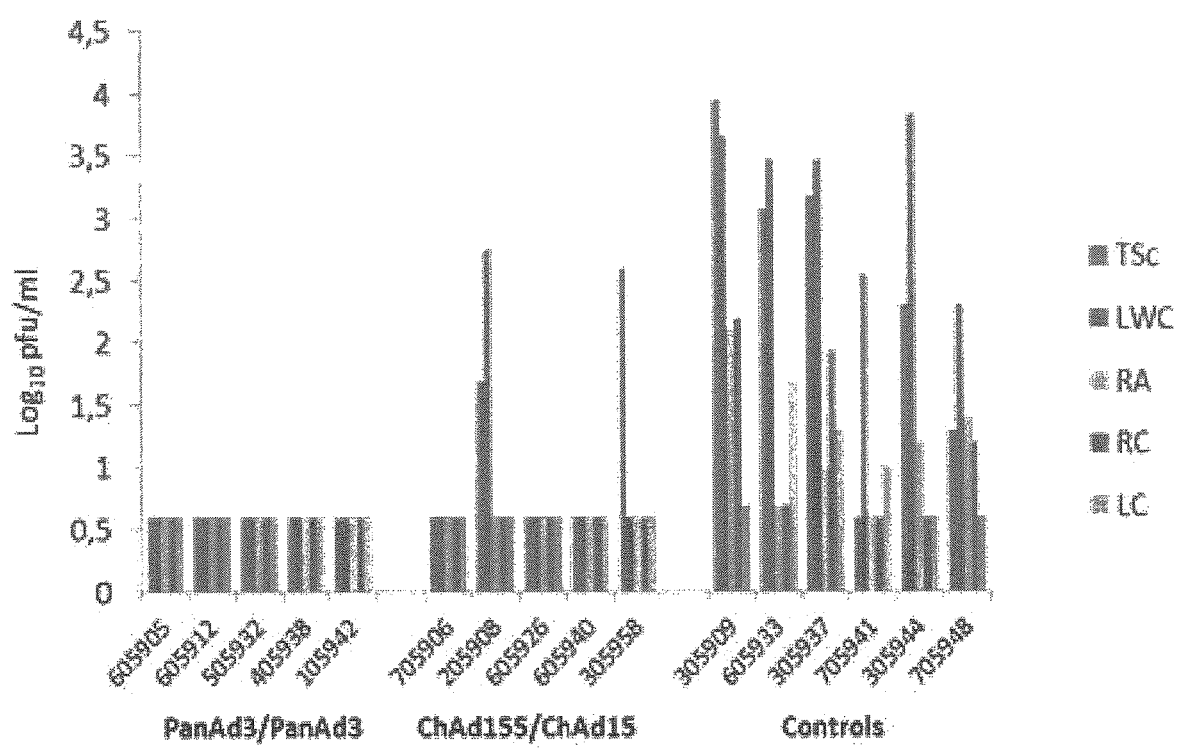

Six days after bRSV challenge, high titers of bRSV were detected in lung wash cells (LWC) and lung lobe homogenates (RA, RC and LC) of all of the control calves, and from tracheal scrape (TSc) samples in 5 out of 6 of the control calves (FIG. 19). In contrast, bRSV was detected at low titers from the TSc samples of 2 and from LWC of 1 of the calves which reveived ChAd155-RSV, while it was undetectable in all samples from the calves which received PanAd3-RSV.

Effect of Vaccination on Pulmonary Pathology

Figure 20:
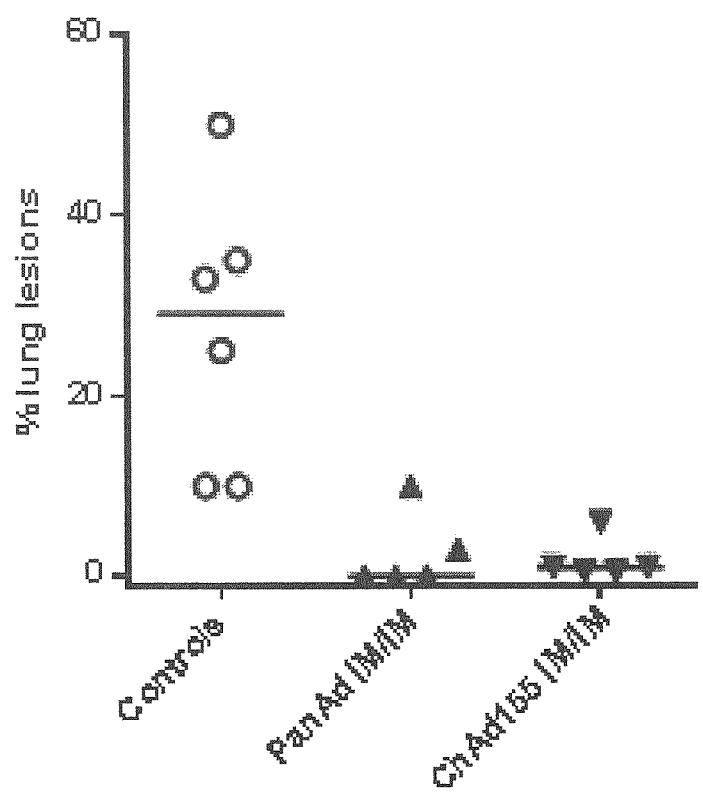
Figure 21:
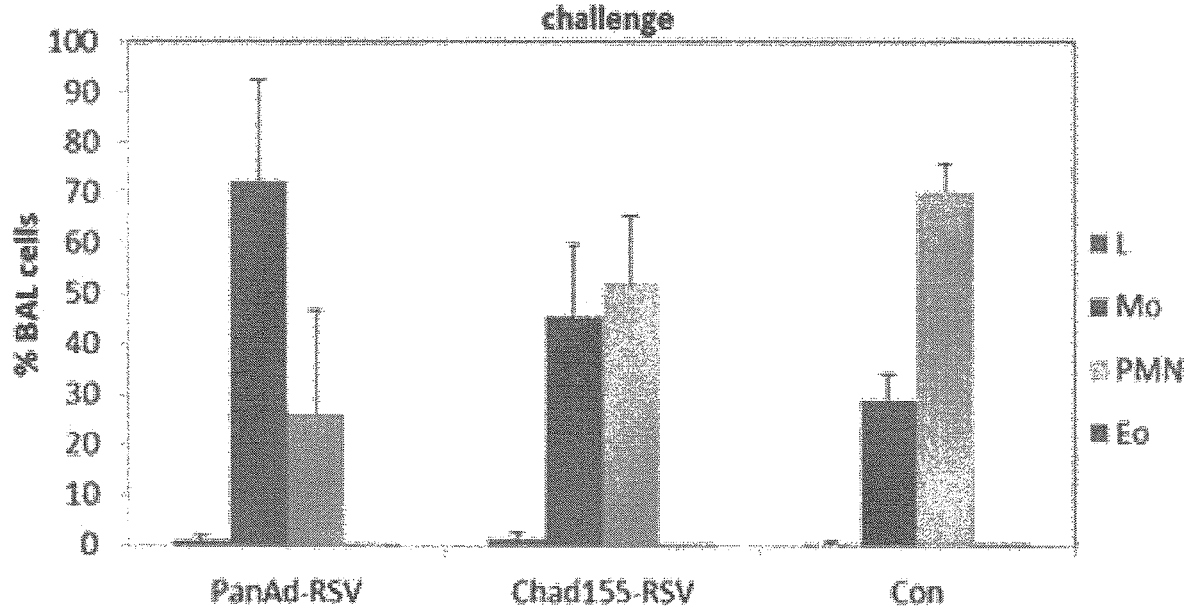

Six days after bRSV challenge, extensive gross pneumonic consolidation was observed in 6 out of 6 control calves (FIG. 20). In contrast, there was little or no gross pneumonic consolidation in the calves that had received either of the adenovector RSV constructs. FIG. 21 quantifies the mean proportion±SD of lymphocytes (L), macrophages (Mo), polymorphonuclear leukocytes (PMN) and eosinophils (Eo) in BAL, 6 days after bRSV challenge. Approximately 70% of the cells in BAL from control calves were PMN. A lower proportion of PMN was found in BAL from calves which received ChAd155-RSV or PanAd3-RSV, indicating a reduced pulmonary inflammation. Importantly, eosinophils were very few or undetectable in the lungs of calves which received ChAd155-RSV or PanAd3-RSV suggesting the absence of vaccine-induced disease exacerbation.

CONCLUSION

Taken together the results reported above demonstrated that ChAd155 is an improved adenoviral vector in comparison to ChAd3 and PanAd3 vectors. ChAd155 was shown to be more productive therefore facilitating the manufacture process, able to express higher level of transgene in vitro and also in vivo providing a stronger T-cell response and at least as potent an antibody response against the antigens expressed in animal models. Protective immunity is achieved without signs of vaccine-induced enhanced pulmonary pathology.

REFERENCES

American Academy of Pediatrics Subcommittee on Diagnosis and Management of Bronchiolitis. Diagnosis and management of bronchiolitis. *Pediatrics*. 2006; 118: 1774-93.

Boukhvalova M S and Blanco J C. The cotton rat Sigmodon hyspidus model of respiratory syncytial virus infection. *Curr Top Microbiol Immunol*. 2013; 372: 347-58.

Cardenas S, Auais A and Piedimonte G. Palivizumab in the prophylaxis of respiratory syncytial virus infection. *Expert Rev Anti Infect Ther*. 2005; 3(5): 719-26.

Castilow E M and Varga S M. Overcoming T cell-mediated immunopathology to achieve safe RSV vaccination. *Future Virol*. 2008; 3(5): 445-454.

Chin J, Magoff in R L, Shearer L A, et al., Field evaluation of a respiratory syncytial virus vaccine and a trivalent parainfluenza virus vaccine in a pediatric population. *Am J Epidemiol*. 1969; 89(4): 449-63.

Colloca S, Barnes E, Folgori A, et al., Vaccine vectors derived from a large collection of simian adenoviruses induce potent cellular immunity across multiple species. *Sci Transl Med*. 2012; 4(115): p. 115ra2.

Donnelly M L, Luke G, Mehrotra A, et al., Analysis of the aphthovirus 2A/2B polyprotein 'cleavage' mechanism indicates not a proteolytic reaction, but a novel translational effect: a putative ribosomal 'skip'. *J Gen Virol*. 2001; 82(Pt 5): 1013-25.

Fallaux, F J et al, (1998), Hum Gene Ther, 9:1909-1917

Guvenel A K, Chiu C and Openshaw P J. Current concepts and progress in RSV vaccine development. *Expert Rev Vaccines*. 2014; 13(3): 333-44.

Hertz, M I, Englund J A, Snover D, et al., Respiratory syncytial virus-induced acute lung injury in adult patients with bone marrow transplants: a clinical approach and review of the literature. *Medicine* (Baltimore). 1989; 68(5): 269-81.

Kim H W, Canchola J G, Brandt C D et al., Respiratory syncytial virus disease in infants despite prior administration of antigenic inactivated vaccine. *Am J Epidemiol*. 1969; 89(4): 422-34.

Magro M, Andreu D, Gómez-Puertas P, et al., Neutralization of human respiratory syncytial virus infectivity by antibodies and low-molecular-weight compounds targeted against the fusion glycoprotein. *J Virol.* 2010; 84(16): 7970-82.

Piedra P A, Jewell A M, Cron S G, et al., Correlates of immunity to respiratory syncytial virus (RSV) associated-hospitalization: establishment of minimum protective threshold levels of serum neutralizing antibodies. *Vaccine.* 2003; 21(24): 3479-82.

Prince G A, Curtis S J, Yim K C, et al., Vaccine-enhanced respiratory syncytial virus disease in cotton rats following immunization with Lot 100 or a newly prepared reference vaccine. *J. Gen. Virol.* 2001; 82: 2881-88.

Prince G A, Horswood R L and Chanock R M. Quantitative aspects of passive immunity to respiratory syncytial virus infection in infant cotton rats. *J Virol.* 1985; 55(3): 517-20.

Stevens W W, Sun J, Castillo J P, et al., Pulmonary eosinophilia is attenuated by early responding CD8(+) memory T cells in a murine model of RSV vaccine-enhanced disease. *Viral Immunol.* 2009; 22(4): 243-51.

Taylor G, Thomas L H, Wyld S G, et al., Role of T-lymphocyte subsets in recovery from respiratory syncytial virus infection in calves. *J Virol.* 1995; 69(11): 6658-64.

Townsend A R and Skehel J J. The influenza A virus nucleoprotein gene controls the induction of both subtype specific and cross-reactive cytotoxic T cells. *J Exp Med.* 1984; 160(2): 552-63.

Welliver T P, Garofalo R P, Hosakote Y, et al., Severe human lower respiratory tract illness caused by respiratory syncytial virus and influenza virus is characterized by the absence of pulmonary cytotoxic lymphocyte responses. *J Infect Dis.* 2007. 195(8): 1126-36.

DESCRIPTION OF THE SEQUENCES

Polypeptide sequence of ChAd155 fiber

SEQ ID NO: 1

```
MKRTKTSDESFNPVYPYDTESGPPSVPFLTPPFVSPDGFQESPPGVLSLNLAEPLVTSHGMLALKMGSGLS
LDDAGNLTSQDITTASPPLKKTKTNLSLETSSPLTVSTSGALTVAAAAPLAVAGTSLTMQSEAPLTVQDAK
LTLATKGPLTVSEGKLALQTSAPLTAADSSTLTVSATPPLSTSNGSLGIDMQAPIYTTNGKLGLNFGAPLH
VVDSLNALTVVTGQGLTINGTALQTRVSGALNYDTSGNLELRAAGGMRVDANGQLILDVAYPFDAQNN
LSLRLGQGPLFVNSAHNLDVNYNRGLYLFTSGNTKKLEVNIKTAKGLIYDDTAIAINAGDGLQFDSGSDT
NPLKTKLGLGLDYDSSRAIIAKLGTGLSFDNTGAITVGNKNDDKLTLWTTPDPSPNCRIYSEKDAKFTLVL
TKCGSQVLASVSVLSVKGSLAPISGTVTSAQIVLRFDENGVLLSNSSLDPQYWNYRKGDLFEGTAYTNAV
GFMPNLTAYPKTQSQTAKSNIVSQVYLNGDKSKPMTLTITLNGTNETGDATVSTYSMSFSWNWNGSNYI
NETFQTNSFTFSYIAQE
```

Polynucleotide sequence encoding ChAd155 fiber

SEQ ID NO: 2

```
ATGAAGCGCACCAAAACGTCTGACGAGAGCTTCAACCCCGTGTACCCCTATGACACGGAAAGCGGCC
CTCCCTCCGTCCCTTTCCTCACCCCTCCCTTCGTGTCTCCCGATGGATTCCAAGAAAGTCCCCCCGGGG
TCCTGTCTCTGAACCTGGCCGAGCCCCTGGTCACTTCCCACGGCATGCTCGCCCTGAAAATGGGAAGT
GGCCTCTCCCTGGACGACGCTGGCAACCTCACCTCTCAAGATATCACCACCGCTAGCCCTCCCCTCAA
AAAAACCAAGACCAACCTCAGCCTAGAAACCTCATCCCCCCTAACTGTGAGCACCTCAGGCGCCCTC
ACCGTAGCAGCCGCCGCTCCCCTGGCGGTGGCCGGCACCTCCCTCACCATGCAATCAGAGGCCCCCC
TGACAGTACAGGATGCAAAACTCACCCTGGCCACCAAAGGCCCCCTGACCGTGTCTGAAGGCAAACT
GGCCTTGCAAACATCGGCCCCGCTGACGGCCGCTGACAGCAGCACCCTCACAGTCAGTGCCACACCA
CCCCTTAGCACAAGCAATGGCAGCTTGGGTATTGACATGCAAGCCCCCATTTACACCACCAATGGAA
AACTAGGACTTAACTTTGGCGCTCCCCTGCATGTGGTAGACAGCCTAAATGCACTGACTGTAGTTACT
GGCCAAGGTCTTACGATAAACGGAACAGCCCTACAAACTAGAGTCTCAGGTGCCCTCAACTATGACA
CATCAGGAAACCTAGAATTGAGAGCTGCAGGGGGTATGCGAGTTGATGCAAATGGTCAACTTATCCT
TGATGTAGCTTACCCATTTGATGCACAAAACAATCTCAGCCTTAGGCTTGGACAGGGACCCCTGTTTG
TTAACTCTGCCCACAACTTGGATGTTAACTACAACAGAGGCCTCTACCTGTTCACATCTGGAAATACC
AAAAAGCTAGAAGTTAATATCAAAACAGCCAAGGGTCTCATTTATGATGACACTGCTATAGCAATCA
ATGCGGGTGATGGGCTACAGTTTGACTCAGGCTCAGATACAAATCCATTAAAAACTAAACTTGGATT
AGGACTGGATTATGACTCCAGCAGAGCCATAATTGCTAAACTGGGAACTGGCCTAAGCTTTGACAAC
ACAGGTGCCATCACAGTAGGCAACAAAAATGATGACAAGCTTACCTTGTGGACCACACCAGACCCAT
```

-continued

CCCCTAACTGTAGAATCTATTCAGAGAAAGATGCTAAATTCACACTTGTTTTGACTAAATGCGGCAGT

CAGGTGTTGGCCAGCGTTTCTGTTTTATCTGTAAAAGGTAGCCTTGCGCCCATCAGTGGCACAGTAAC

TAGTGCTCAGATTGTCCTCAGATTTGATGAAAATGGAGTTCTACTAAGCAATTCTTCCCTTGACCCTC

AATACTGGAACTACAGAAAAGGTGACCTTACAGAGGGCACTGCATATACCAACGCAGTGGGATTTAT

GCCCAACCTCACAGCATACCCAAAAACACAGAGCCAAACTGCTAAAAGCAACATTGTAAGTCAGGTT

TACTTGAATGGGGACAAATCCAAACCCATGACCCTCACCATTACCCTCAATGGAACTAATGAAACAG

GAGATGCCACAGTAAGCACTTACTCCATGTCATTCTCATGGAACTGGAATGGAAGTAATTACATTAA

TGAAACGTTCCAAACCAACTCCTTCACCTTCTCCTACATCGCCCAAGAA

Polypeptide sequence of ChAd155 penton                                    SEQ ID NO: 3

MRRAAMYQEGPPPSYESVVGAAAAAPSSPFASQLLEPPYVPPRYLRPTGGRNSIRYSELAPLFDTTRVYLV

DNKSADVASLNYQNDHSNFLTTVIQNNDYSPSEASTQTINLDDRSHWGGDLKTILHTNMPNVNEFMFTN

KFKARVMVSRSHTKEDRVELKYEWVEFELPEGNYSETMTIDLMNNAIVEHYLKVGRQNGVLESDIGVKF

DTRNFRLGLDPVTGLVMPGVYTNEAFHPDIILLPGCGVDFTYSRLSNLLGIRKRQPFQEGFRITYEDLEGG

NIPALLDVEAYQDSLKENEAGQEDTAPAASAAAEQGEDAADTAAADGAEADPAMVVEAPEQEEDMNDS

AVRGDTFVTRGEEKQAEAEAAAEEKQLAAAAAAALAAAEAESEGTKPAKEPVIKPLFEDSKKRSYNLL

KDSTNTAYRSWYLAYNYGDPSTGVRSWTLLCTPDVTCGSEQVYWSLPDMMQDPVTFRSTRQVSNFPVV

GAELLPVHSKSFYNDQAVYSQLIRQFTSLTHVFNRFPENQILARPPAPTITTVSENVPALTDHGTLPLRNSIG

GVQRVTVTDARRRTCPYVYKALGIVSPRVLSSRTF

Polynucleotide sequence encoding ChAd155 penton                           SEQ ID NO: 4

ATGCGGCGCGCGGCGATGTACCAGGAGGGACCTCCTCCCTCTTACGAGAGCGTGGTGGGCGCGGCGG

CGGCGGCGCCCTCTTCTCCCTTTGCGTCGCAGCTGCTGGAGCCGCCGTACGTGCCTCCGCGCTACCTG

CGGCCTACGGGGGGAGAAACAGCATCCGTTACTCGGAGCTGGCGCCCCTGTTCGACACCACCCGGG

TGTACCTGGTGGACAACAAGTCGGCGGACGTGGCCTCCCTGAACTACCAGAACGACCACAGCAATTT

TTTGACCACGGTCATCCAGAACAATGACTACAGCCCGAGCGAGGCCAGCACCCAGACCATCAATCTG

GATGACCGGTCGCACTGGGGCGGCGACCTGAAAACCATCCTGCACACCAACATGCCCAACGTGAAC

GAGTTCATGTTCACCAATAAGTTCAAGGCGCGGGTGATGGTGTCGCGCTCGCACACCAAGGAAGACC

GGGTGGAGCTGAAGTACGAGTGGGTGGAGTTCGAGCTGCCAGAGGGCAACTACTCCGAGACCATGA

CCATTGACCTGATGAACAACGCGATCGTGGAGCACTATCTGAAAGTGGGCAGGCAGAACGGGGTCCT

GGAGAGCGACATCGGGGTCAAGTTCGACACCAGGAACTTCCGCCTGGGGCTGGACCCCGTGACCGG

GCTGGTTATGCCCGGGGTGTACACCAACGAGGCCTTCCATCCCGACATCATCCTGCTGCCCGGCTGCG

GGGTGGACTTCACTTACAGCCGCCTGAGCAACCTCCTGGGCATCCGCAAGCGGCAGCCCTTCCAGGA

GGGCTTCAGGATCACCTACGAGGACCTGGAGGGGGGCAACATCCCCGCGCTCCTCGATGTGGAGGCC

TACCAGGATAGCTTGAAGGAAAATGAGGCGGGACAGGAGGATACCGCCCCCGCCGCCTCCGCCGCC

GCCGAGCAGGGCGAGGATGCTGCTGACACCGCGGCCGCGGACGGGGCAGAGGCCGACCCCGCTATG

GTGGTGGAGGCTCCCGAGCAGGAGGAGGACATGAATGACAGTGCGGTGCGCGGAGACACCTTCGTC

ACCCGGGGGGAGGAAAAGCAAGCGGAGGCCGAGGCCGCGGCCGAGGAAAAGCAACTGGCGGCAGC

AGCGGCGGCGGCGGCGTTGGCCGCGGCGGAGGCTGAGTCTGAGGGGACCAAGCCCGCCAAGGAGCC

CGTGATTAAGCCCCTGACCGAAGATAGCAAGAAGCGCAGTTACAACCTGCTCAAGGACAGCACCAA

CACCGCGTACCGCAGCTGGTACCTGGCCTACAACTACGGCGACCCGTCGACGGGGGTGCGCTCCTGG

ACCCTGCTGTGCACGCCGGACGTGACCTGCGGCTCGGAGCAGGTGTACTGGTCGCTGCCCGACATGA

TGCAAGACCCCGTGACCTTCCGCTCCACGCGGCAGGTCAGCAACTTCCCGGTGGTGGGCGCCGAGCT

```
GCTGCCCGTGCACTCCAAGAGCTTCTACAACGACCAGGCCGTCTACTCCCAGCTCATCCGCCAGTTCA

CCTCTCTGACCCACGTGTTCAATCGCTTTCCTGAGAACCAGATTCTGGCGCGCCCGCCCGCCCCCACC

ATCACCACCGTCAGTGAAAACGTTCCTGCTCTCACAGATCACGGGACGCTACCGCTGCGCAACAGCA

TCGGAGGAGTCCAGCGAGTGACCGTTACTGACGCCAGACGCCGCACCTGCCCCTACGTTTACAAGGC

CTTGGGCATAGTCTCGCCGCGCGTCCTTTCCAGCCGCACTTTT
```

Polypeptide sequence of ChAd155 hexon    SEQ ID NO: 5

```
MATPSMMPQWSYMHISGQDASEYLSPGLVQFARATDSYFSLSNKFRNPTVAPTHDVTTDRSQRLTLRFIP

VDREDTAYSYKARFTLAVGDNRVLDMASTYFDIRGVLDRGPTFKPYSGTAYNSLAPKGAPNSCEWEQEE

TQTAEEAQDEEEDEAEAEEEMPQEEQAPVKKTHVYAQAPLSGEKITKDGLQIGTDATATEQKPIYADPTF

QPEPQIGESQWNEADASVAGGRVLKKTTPMKPCYGSYARPTNANGGQGVLVEKDGGKMESQVDMQFFS

TSENARNEANNIQPKLVLYSEDVHMETPDTHISYKPAKSDDNSKVMLGQQSMPNRPNYIGERDNFIGLMY

YNSTGNMGVLAGQASQLNAVVDLQDRNTELSYQLLLDSMGDRTRYFSMVVNQAVDSYDPDVRIIENHGT

EDELPNYCFPLGGIGVTDTYQAIKTNGNGNGGGNTTWTKDETFADRNEIGVGNNFAMEINLSANLWRNF

LYSNVALYLPDKLKYNPSNVEISDNPNTYDYMNKRVVAPGLVDCYINLGARWSLDYMDNVNPFNHHRN

AGLRYRSMLLGNGRYVPFHIQVPQKFFAIKNLLLLPGSYTYEWNERKDVNMVLQSSLGNDLRVDGASIKE

ESICLYATFFPMAHNTASTLEAMLRNDTNDQSENDYLSAANMLYPIPANATNVPISIPSRNWAAFRGWAF

TRLKTKETPSLGSGFDPYYTYSGSIPYLDGTFYLNHTFKKVSVITDSSVSWPGNDRLLTPNEEEIKRSVDGE

GYNVAQCNMTKDWFLIQMLANYNIGYQGFYIPESYKDRMYSFERNFQPMSRQVVDETKYKDYQQVGII

HQHNNSGFVGYLAPTMREGQAYPANFPYPLIGKTAVDSVTQKKFLCDRTLWRIPFSSNFMSMGALTDLG

QNLLYANSAHALDMTFEVDPMDEPTLLYVLFEVEDVVRVHQPHRGVIETVYLRTPFSAGNATT
```

Polynucleotide sequence encoding ChAd155 hexon    SEQ ID NO: 6

```
ATGGCGACCCCATCGATGATGCCGCAGTGGTCGTACATGCACATCTCGGGCCAGGACGCCTCGGAGT

ACCTGAGCCCCGGGCTGGTGCAGTTCGCCCGCGCCACCGAGAGCTACTTCAGCCTGAGTAACAAGTT

TAGGAACCCCACGGTGGCGCCCACGCACGATGTGACCACCGACCGGTCTCAGCGCCTGACGCTGCGG

TTCATTCCCGTGGACCGCGAGGACACCGCGTACTCGTACAAGGCGCGGTTCACCCTGGCCGTGGGCG

ACAACCGCGTGCTGGACATGGCCTCCACCTACTTTGACATCCGCGGGGTGCTGGACCGGGGTCCCAC

TTTCAAGCCCTACTCTGGCACCGCCTACAACTCCCTGGCCCCCAAGGGCGCTCCCAACTCCTGCGAGT

GGGAGCAAGAGGAAACTCAGGCAGTTGAAGAAGCAGCAGAAGAGGAAGAAGAAGATGCTGACGGT

CAAGCTGAGGAAGAGCAAGCAGCTACCAAAAAGACTCATGTATATGCTCAGGCTCCCCTTTCTGGCG

AAAAAATTAGTAAAGATGGTCTGCAAATAGGAACGGACGCTACAGCTACAGAACAAAAACCTATTT

ATGCAGACCCTACATTCCAGCCCGAACCCCAAATCGGGGAGTCCCAGTGGAATGAGGCAGATGCTAC

AGTCGCCGGCGGTAGAGTGCTAAAGAAATCTACTCCCATGAAACCATGCTATGGTTCCTATGCAAGA

CCCACAAATGCTAATGGAGGTCAGGGTGTACTAACGGCAAATGCCCAGGGACAGCTAGAATCTCAG

GTTGAAATGCAATTCTTTTCAACTTCTGAAAACGCCCGTAACGAGGCTAACAACATTCAGCCCAAATT

GGTGCTGTATAGTGAGGATGTGCACATGGAGACCCCGGATACGCACCTTTCTTACAAGCCCGCAAAA

AGCGATGACAATTCAAAAATCATGCTGGGTCAGCAGTCCATGCCCAACAGACCTAATTACATCGGCT

TCAGAGACAACTTTATCGGCCTCATGTATTACAATAGCACTGGCAACATGGGAGTGCTTGCAGGTCA

GGCCTCTCAGTTGAATGCAGTGGTGGACTTGCAAGACAGAAACACAGAACTGTCCTACCAGCTCTTG

CTTGATTCCATGGGTGACAGAACCAGATACTTTTCCATGTGGAATCAGGCAGTGGACAGTTATGACC

CAGATGTTAGAATTATTGAAAATCATGGAACTGAAGACGAGCTCCCCAACTATTGTTTCCCTCTGGGT
```

```
GGCATAGGGGTAACTGACACTTACCAGGCTGTTAAAACCAACAATGGCAATAACGGGGGCCAGGTG

ACTTGGACAAAAGATGAAACTTTTGCAGATCGCAATGAAATAGGGGTGGGAAACAATTTCGCTATGG

AGATCAACCTCAGTGCCAACCTGTGGAGAAACTTCCTGTACTCCAACGTGGCGCTGTACCTACCAGA

CAAGCTTAAGTACAACCCCTCCAATGTGGACATCTCTGACAACCCCAACACCTACGATTACATGAAC

AAGCGAGTGGTGGCCCCGGGGCTGGTGGACTGCTACATCAACCTGGGCGCGCGCTGGTCGCTGGACT

ACATGGACAACGTCAACCCCTTCAACCACCACCGCAATGCGGGCCTGCGCTACCGCTCCATGCTCCT

GGGCAACGGGCGCTACGTGCCCTTCCACATCCAGGTGCCCCAGAAGTTCTTTGCCATCAAGAACCTC

CTCCTCCTGCCGGGCTCCTACACCTACGAGTGGAACTTCAGGAAGGATGTCAACATGGTCCTCCAGA

GCTCTCTGGGTAACGATCTCAGGGTGGACGGGGCCAGCATCAAGTTCGAGAGCATCTGCCTCTACGC

CACCTTCTTCCCCATGGCCCACAACACGGCCTCCACGCTCGAGGCCATGCTCAGGAACGACACCAAC

GACCAGTCCTTCAATGACTACCTCTCCGCCGCCAACATGCTCTACCCCATACCCGCCAACGCCACCAA

CGTCCCCATCTCCATCCCCTCGCGCAACTGGGCGGCCTTCCGCGGCTGGGCCTTCACCCGCCTCAAGA

CCAAGGAGACCCCCTCCCTGGGCTCGGGATTCGACCCCTACTACACCTACTCGGGCTCCATTCCCTAC

CTGGACGGCACCTTCTACCTCAACCACACTTTCAAGAAGGTCTCGGTCACCTTCGACTCCTCGGTCAG

CTGGCCGGGCAACGACCGTCTGCTCACCCCCAACGAGTTCGAGATCAAGCGCTCGGTCGACGGGGAG

GGCTACAACGTGGCCCAGTGCAACATGACCAAGGACTGGTTCCTGGTCCAGATGCTGGCCAACTACA

ACATCGGCTACCAGGGCTTCTACATCCCAGAGAGCTACAAGGACAGGATGTACTCCTTCTTCAGGAA

CTTCCAGCCCATGAGCCGGCAGGTGGTGGACCAGACCAAGTACAAGGACTACCAGGAGGTGGGCAT

CATCCACCAGCACAACAACTCGGGCTTCGTGGGCTACCTCGCCCCCACCATGCGCGAGGGACAGGCC

TACCCCGCCAACTTCCCCTATCCGCTCATAGGCAAGACCGCGGTCGACAGCATCACCCAGAAAAAGT

TCCTCTGCGACCGCACCCTCTGGCGCATCCCCTTCTCCAGCAACTTCATGTCCATGGGTGCGCTCTCG

GACCTGGGCCAGAACTTGCTCTACGCCAACTCCGCCCACGCCCTCGACATGACCTTCGAGGTCGACC

CCATGGACGAGCCCACCCTTCTCTATGTTCTGTTCGAAGTCTTTGACGTGGTCCGGGTCCACCAGCCG

CACCGCGGCGTCATCGAGACCGTGTACCTGCGTACGCCCTTCTCGGCCGGCAACGCCACCACC
```

Polynucleotide sequence encoding ChAd155#1434 backbone construct SEQ ID NO: 7

```
CATCATCAATAATATACCTTATTTTGGATTGAAGCCAATATGATAATGAGATGGGCGGCGCGGGGCG

GGGCGCGGGGCGGGAGGCGGGTTTGGGGGCGGGCCGGCGGGCGGGGCGGTGTGGCGGAAGTGGAC

TTTGTAAGTGTGGCGGATGTGACTTGCTAGTGCCGGGCGCGGTAAAAGTGACGTTTTCCGTGCGCGA

CAACGCCCCCGGGAAGTGCATTTTTCCCGCGGTTTTTACCGGATGTTGTAGTGAATTTGGGCGTAAC

CAAGTAAGATTTGGCCATTTTCGCGGGAAAACTGAAACGGGGAAGTGAAATCTGATTAATTTTGCGT

TAGTCATACCGCGTAATATTTGTCTAGGGCCGAGGGACTTTGGCCGATTACGTGGAGGACTCGCCCA

GGTGTTTTTTGAGGTGAATTTCCGCGTTCCGGGTCAAAGTCTGCGTTTTATTATTATAGGATATCCCAT

TGCATACGTTGTATCCATATCATAATATGTACATTTATATTGGCTCATGTCCAACATTACCGCCATGTT

GACATTGATTATTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAACGACCCCCGCCCAT

TGACGTCAATAATGACGTATGTTCCCATAGTAACGCCAATAGGGACTTTCCATTGACGTCAATGGGT

GGAGTATTTACGGTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCTTATGGGACTTTCC

TACTTGGCAGTACATCTACGTATTAGTCATCGCTATTACCATGGTGATGCGGTTTTGGCAGTACATCA

ATGGGCGTGGATAGCGGTTTGACTCACGGGGATTTCCAAGTCTCCACCCCATTGACGTCAATGGGAG

TTTGTTTTGGCACCAAAATCAACGGGACTTTCCAAAATGTCGTAACAACTCCGCCCCATTGACGCAAA
```

-continued

```
TGGGCGGTAGGCGTGTACGGTGGGAGGTCTATATAAGCAGAGCTCTCCCTATCAGTGATAGAGATCT

CCCTATCAGTGATAGAGATCGTCGACGAGCTCGTTTAGTGAACCGTCAGATCGCCTGGAGACGCCAT

CCACGCTGTTTTGACCTCCATAGAAGACACCGGGACCGATCCAGCCTCCGCGGCCGGGAACGGTGCA

TTGGAACGCGGATTCCCCGTGCCAAGAGTGAGATCTTCCGTTTATCTAGGTACCGGGCCCCCCCTCGA

GGTCGACGGTATCGATAAGCTTCACGCTGCCGCAAGCACTCAGGGCGCAAGGGCTGCTAAAGGAAG

CGGAACACGTAGAAAGCCAGTCCGCAGAAACGGTGCTGACCCCGGATGAATGTCAGCTACTGGGCT

ATCTGGACAAGGGAAAACGCAAGCGCAAAGAGAAAGCAGGTAGCTTGCAGTGGGCTTACATGGCGA

TAGCTAGACTGGGCGGTTTTATGGACAGCAAGCGAACCGGAATTGCCAGCTGGGGCGCCCTCTGGTA

AGGTTGGGAAGCCCTGCAAAGTAAACTGGATGGCTTTCTTGCCGCCAAGGATCTGATGGCGCAGGGG

ATCAAGATCTAACCAGGAGCTATTTAATGGCAACAGTTAACCAGCTGGTACGCAAACCACGTGCTCG

CAAAGTTGCGAAAAGCAACGTGCCTGCGCTGGAAGCATGCCCGCAAAAACGTGGCGTATGTACTCGT

GTATATACTACCACTCCTAAAAAACCGAACTCCGCGCTGCGTAAAGTATGCCGTGTTCGTCTGACTAA

CGGTTTCGAAGTGACTTCCTACATCGGTGGTGAAGGTCACAACCTGCAGGAGCACTCCGTGATCCTG

ATCCGTGGCGGTCGTGTTAAAGACCTCCCGGGTGTTCGTTACCACACCGTACGTGGTGCGCTTGACTG

CTCCGGCGTTAAAGACCGTAAGCAGGCTCGTTCCAAGTATGGCGTGAAGCGTCCTAAGGCTTAATGG

TAGATCTGATCAAGAGACAGGATGACGGTCGTTTCGCATGCTTGAACAAGATGGATTGCACGCAGGT

TCTCCGGCCGCTTGGGTGGAGAGGCTATTCGGCTATGACTGGGCACAACAGACAATCGGCTGCTCTG

ATGCCGCCGTGTTCCGGCTGTCAGCGCAGGGGCGCCCGGTTCTTTTTGTCAAGACCGACCTGTCCGGT

GCCCTGAATGAACTGCAGGACGAGGCAGCGCGGCTATCGTGGCTGGCCACGACGGGCGTTCCTTGCG

CAGCTGTGCTCGACGTTGTCACTGAAGCGGGAAGGGACTGGCTGCTATTGGGCGAAGTGCCGGGGCA

GGATCTCCTGTCATCTCACCTTGCTCCTGCCGAGAAAGTATCCATCATGGCTGATGCAATGCGGCGGC

TGCATACGCTTGATCCGGCTACCTGCCCATTCGACCACCAAGCGAAACATCGCATCGAGCGAGCACG

TACTCGGATGGAAGCCGGTCTTGTCGATCAGGATGATCTGGACGAAGAGCATCAGGGGCTCGCGCCA

GCCGAACTGTTCGCCAGGCTCAAGGCGCGCATGCCCGACGGCGAGGATCTCGTCGTGACCCATGGCG

ATGCCTGCTTGCCGAATATCATGGTGGAAAATGGCCGCTTTTCTGGATTCATCGACTGTGGCCGGCTG

GGTGTGGCGGACCGCTATCAGGACATAGCGTTGGCTACCCGTGATATTGCTGAAGAGCTTGGCGGCG

AATGGGCTGACCGCTTCCTCGTGCTTTACGGTATCGCCGCTCCCGATTCGCAGCGCATCGCCTTCTAT

CGCCTTCTTGACGAGTTCTTCTGAGCGGGACTCTGGGGTTCGAAATGACCGACCAAGCGACGCCCAA

CCTGCCATCACGAGATTTCGATTCCACCGCCGCCTTCTATGAAAGGTTGGGCTTCGGAATCGTTTTCC

GGGACGCCGGCTGGATGATCCTCCAGCGCGGGGATCTCATGCTGGAGTTCTTCGCCCACCCCGGGCT

CGATCCCCTCGGGGGGAATCAGAATTCAGTCGACAGCGGCCGCGATCTGCTGTGCCTTCTAGTTGCC

AGCCATCTGTTGTTTGCCCCTCCCCCGTGCCTTCCTTGACCCTGGAAGGTGCCACTCCCACTGTCCTTT

CCTAATAAAATGAGGAAATTGCATCGCATTGTCTGAGTAGGTGTCATTCTATTCTGGGGGGTGGGGT

GGGGCAGGACAGCAAGGGGGAGGATTGGGAAGACAATAGCAGGCATGCTGGGGATGCGGTGGGCT

CTATGGCCGATCAGCGATCGCTGAGGTGGGTGAGTGGGCGTGGCCTGGGGTGGTCATGAAAATATAT

AAGTTGGGGGTCTTAGGGTCTCTTTATTTGTGTTGCAGAGACCGCCGGAGCCATGAGCGGGAGCAGC

AGCAGCAGCAGTAGCAGCAGCGCCTTGGATGGCAGCATCGTGAGCCCTTATTTGACGACGCGGATGC

CCCACTGGGCCGGGGTGCGTCAGAATGTGATGGGCTCCAGCATCGACGGCCGACCCGTCCTGCCCGC

AAATTCCGCCACGCTGACCTATGCGACCGTCGCGGGACGCCGTTGGACGCCACCGCCGCCGCCGCC

GCCACCGCAGCCGCCTCGGCCGTGCGCAGCCTGGCCACGGACTTTGCATTCCTGGGACCACTGGCGA
```

-continued

```
CAGGGGCTACTTCTCGGGCCGCTGCTGCCGCCGTTCGCGATGACAAGCTGACCGCCCTGCTGGCGCA
GTTGGATGCGCTTACTCGGGAACTGGGTGACCTTTCTCAGCAGGTCATGGCCCTGCGCCAGCAGGTCT
CCTCCCTGCAAGCTGGCGGGAATGCTTCTCCCACAAATGCCGTTTAAGATAAATAAAACCAGACTCT
GTTTGGATTAAAGAAAAGTAGCAAGTGCATTGCTCTCTTTATTTCATAATTTTCCGCGCGCGATAGGC
CCTAGACCAGCGTTCTCGGTCGTTGAGGGTGCGGTGTATCTTCTCCAGGACGTGGTAGAGGTGGCTCT
GGACGTTGAGATACATGGGCATGAGCCCGTCCCGGGGGTGGAGGTAGCACCACTGCAGAGCTTCATG
CTCCGGGGTGGTGTTGTAGATGATCCAGTCGTAGCAGGAGCGCTGGGCATGGTGCCTAAAAATGTCC
TTCAGCAGCAGGCCGATGGCCAGGGGGAGGCCCTTGGTGTAAGTGTTTACAAAACGGTTAAGTTGGG
AAGGGTGCATTCGGGGAGAGATGATGTGCATCTTGGACTGTATTTTTAGATTGGCGATGTTTCCGCCC
AGATCCCTTCTGGGATTCATGTTGTGCAGGACCACCAGTACAGTGTATCCGGTGCACTTGGGGAATTT
GTCATGCAGCTTAGAGGGAAAAGCGTGGAAGAACTTGGAGACGCCTTTGTGGCCTCCCAGATTTTCC
ATGCATTCGTCCATGATGATGGCAATGGGCCCGCGGGAGGCAGCTTGGGCAAAGATATTTCTGGGGT
CGCTGACGTCGTAGTTGTGTTCCAGGGTGAGGTCGTCATAGGCCATTTTTACAAAGCGCGGGCGGAG
GGTGCCCGACTGGGGGATGATGGTCCCCTCTGGCCCTGGGGCGTAGTTGCCCTCGCAGATCTGCATTT
CCCAGGCCTTAATCTCGGAGGGGGGAATCATATCCACCTGCGGGGCGATGAAGAAAACGGTTTCCGG
AGCCGGGGAGATTAACTGGGATGAGAGCAGGTTTCTAAGCAGCTGTGATTTTCCACAACCGGTGGGC
CCATAAATAACACCTATAACCGGTTGCAGCTGGTAGTTTAGAGAGCTGCAGCTGCCGTCGTCCCGGA
GGAGGGGGGCCACCTCGTTGAGCATGTCCCTGACGCGCATGTTCTCCCCGACCAGATCCGCCAGAAG
GCGCTCGCCGCCCAGGGACAGCAGCTCTTGCAAGGAAGCAAAGTTTTTCAGCGGCTTGAGGCCGTCC
GCCGTGGGCATGTTTTTCAGGGTCTGGCTCAGCAGCTCCAGGCGGTCCCAGAGCTCGGTGACGTGCT
CTACGGCATCTCTATCCAGCATATCTCCTCGTTTCGCGGGTTGGGGCGACTTTCGCTGTAGGGCACCA
AGCGGTGGTCGTCCAGCGGGGCCAGAGTCATGTCCTTCCATGGGCGCAGGGTCCTCGTCAGGGTGGT
CTGGGTCACGGTGAAGGGGTGCGCTCCGGGCTGAGCGCTTGCCAAGGTGCGCTTGAGGCTGGTTCTG
CTGGTGCTGAAGCGCTGCCGGTCTTCGCCCTGCGCGTCGGCCAGGTAGCATTTGACCATGGTGTCATA
GTCCAGCCCCTCCGCGCGTGTCCCTTGGCGCGCAGCTTGCCCTTGGAGGTGGCGCCGCACGAGGGG
CAGAGCAGGCTCTTGAGCGCGTAGAGCTTGGGGGCGAGGAAGACCGATTCGGGGAGTAGGCGTCC
GCGCCGCAGACCCCGCACACGGTCTCGCACTCCACCAGCCAGGTGAGCTCGGGGCGCGCCGGGTCAA
AAACCAGGTTTCCCCCATGCTTTTTGATGCGTTTCTTACCTCGGGTCTCCATGAGGTGGTGTCCCCGCT
CGGTGACGAAGAGGCTGTCCGTGTCTCCGTAGACCGACTTGAGGGGTCTTTTCTCCAGGGGGTCCC
TCGGTCTTCCTCGTAGAGGAACTCGGACCACTCTGAGACGAAGGCCCGCGTCCAGGCCAGGACGAAG
GAGGCTATGTGGGAGGGGTAGCGGTCGTTGTCCACTAGGGGGTCCACCTTCTCCAAGGTGTGAAGAC
ACATGTCGCCTTCCTCGGCGTCCAGGAAGGTGATTGGCTTGTAGGTGTAGGCCACGTGACCGGGGGT
TCCTGACGGGGGGGTATAAAAGGGGGTGGGGGCGCGCTCGTCGTCACTCTCTTCCGCATCGCTGTCT
GCGAGGGCCAGCTGCTGGGGTGAGTATTCCCTCTCGAAGGCGGGCATGACCTCCGCGCTGAGGTTGT
CAGTTTCCAAAAACGAGGAGGATTTGATGTTCACCTGTCCCGAGGTGATACCTTTGAGGGTACCCGC
GTCCATCTGGTCAGAAAACACGATCTTTTATTGTCCAGCTTGGTGGCGAACGACCCGTAGAGGGCG
TTGGAGAGCAGCTTGGCGATGGAGCGCAGGGTCTGGTTCTTGTCCCTGTCGGCGCGCTCCTTGGCCGC
GATGTTGAGCTGCACGTACTCGCGCGCGACGCAGCGCCACTCGGGGAAGACGGTGGTGCGCTCGTCG
GGCACCAGGCGCACGCGCCAGCCGCGGTTGTGCAGGGTGACCAGGTCCACGCTGGTGGCGACCTCGC
CGCGCAGGCGCTCGTTGGTCCAGCAGAGACGGCCGCCCTTGCGCGAGCAGAAGGGGGCAGGGGGT
CGAGCTGGGTCTCGTCCGGGGGGTCCGCGTCCACGGTGAAAACCCCGGGGCGCAGGCGCGCGTCGA
```

-continued

```
AGTAGTCTATCTTGCAACCTTGCATGTCCAGCGCCTGCTGCCAGTCGCGGGCGGCGAGCGCGCTC
GTAGGGGTTGAGCGGCGGGCCCCAGGGCATGGGGTGGGTGAGTGCGGAGGCGTACATGCCGCAGAT
GTCATAGACGTAGAGGGGCTCCCGCAGGACCCCGATGTAGGTGGGGTAGCAGCGGCCGCCGCGGAT
GCTGGCGCGCACGTAGTCATACAGCTCGTGCGAGGGGGCGAGGAGGTCGGGGCCCAGGTTGGTGCG
GGCGGGGCGCTCCGCGCGGAAGACGATCTGCCTGAAGATGGCATGCGAGTTGGAAGAGATGGTGGG
GCGCTGGAAGACGTTGAAGCTGGCGTCCTGCAGGCCGACGGCGTCGCGCACGAAGGAGGCGTAGGA
GTCGCGCAGCTTGTGTACCAGCTCGGCGGTGACCTGCACGTCGAGCGCGCAGTAGTCGAGGGTCTCG
CGGATGATGTCATATTTAGCCTGCCCCTTCTTTTTCCACAGCTCGCGGTTGAGGACAAACTCTTCGCG
GTCTTTCCAGTACTCTTGGATCGGGAAACCGTCCGGTTCCGAACGGTAAGAGCCTAGCATGTAGAAC
TGGTTGACGGCCTGGTAGGCGCAGCAGCCCTTCTCCACGGGGAGGGCGTAGGCCTGCGCGGCCTTGC
GGAGCGAGGTGTGGGTCAGGGCGAAGGTGTCCCTGACCATGACTTTGAGGTACTGGTGCTTGAAGTC
GGAGTCGTCGCAGCCGCCCCGCTCCCAGAGCGAGAAGTCGGTGCGCTTCTTGGAGCGGGGGTTGGGC
AGAGCGAAGGTGACATCGTTGAAGAGGATTTTGCCCGCGCGGGGCATGAAGTTGCGGGTGATGCGG
AAGGGCCCCGGCACTTCAGAGCGGTTGTTGATGACCTGGGCGGCGAGCACGATCTCGTCGAAGCCGT
TGATGTTGTGGCCCACGATGTAGAGTTCCAGGAAGCGGGGCCGGCCCTTTACGGTGGGCAGCTTCTT
TAGCTCTTCGTAGGTGAGCTCCTCGGGCGAGGCGAGGCCGTGCTCGGCCAGGGCCCAGTCCGCGAGG
TGCGGGTTGTCTCTGAGGAAGGACTTCCAGAGGTCGCGGGCCAGGAGGGTCTGCAGGCGGTCTCTGA
AGGTCCTGAACTGGCGGCCCACGGCCATTTTTTCGGGGGTGATGCAGTAGAAGGTGAGGGGGTCTTG
CTGCCAGCGGTCCCAGTCGAGCTGCAGGGCGAGGTCGCGCGCGGCGGTGACCAGGCGCTCGTCGCCC
CCGAATTTCATGACCAGCATGAAGGGCACGAGCTGCTTTCCGAAGGCCCCCATCCAAGTGTAGGTCT
CTACATCGTAGGTGACAAAGAGGCGCTCCGTGCGAGGATGCGAGCCGATCGGGAAGAACTGGATCT
CCCGCCACCAGTTGGAGGAGTGGCTGTTGATGTGGTGGAAGTAGAAGTCCCGTCGCCGGGCCGAACA
CTCGTGCTGGCTTTTGTAAAAGCGAGCGCAGTACTGGCAGCGCTGCACGGGCTGTACCTCATGCACG
AGATGCACCTTTCGCCCGCGCACGAGGAAGCCGAGGGGAAATCTGAGCCCCCGCCTGGCTCGCGGC
ATGGCTGGTTCTCTTCTACTTTGGATGCGTGTCCGTCTCCGTCTGGCTCCTCGAGGGGTGTTACGGTG
GAGCGGACCACCACGCCGCGCGAGCCGCAGGTCCAGATATCGGCGCGCGGCGGTCGGAGTTTGATG
ACGACATCGCGCAGCTGGGAGCTGTCCATGGTCTGGAGCTCCCGCGGCGGCGGCAGGTCAGCCGGG
AGTTCTTGCAGGTTCACCTCGCAGAGTCGGGCCAGGGCGCGGGGCAGGTCTAGGTGGTACCTGATCT
CTAGGGGCGTGTTGGTGGCGGCGTCGATGGCTTGCAGGAGCCCGCAGCCCCGGGGGGCGACGACGG
TGCCCCGCGGGGTGGTGGTGGTGGCGGTGCAGCTCAGAAGCGGTGCCGCGGGCGGGCCCCCGG
AGGTAGGGGGGCTCCGGTCCCGCGGGCAGGGGCGGCAGCGGCACGTCGGCGTGGAGCGCGGGCAG
GAGTTGGTGCTGTGCCCGGAGGTTGCTGGCGAAGGCGACGACGCGGCGGTTGATCTCCTGGATCTGG
CGCCTCTGCGTGAAGACGACGGGCCCGGTGAGCTTGAACCTGAAAGAGAGTTCGACAGAATCAATCT
CGGTGTCATTGACCGCGGCCTGGCGCAGGATCTCCTGCACGTCTCCCGAGTTGTCTTGGTAGGCGATC
TCGGCCATGAACTGCTCGATCTCTTCCTCCTGGAGGTCTCCGCGTCCGGCGCGTTCCACGGTGGCCGC
CAGGTCGTTGGAGATGCGCCCCATGAGCTGCGAGAAGGCGTTGAGTCCGCCCTCGTTCCAGACTCGG
CTGTAGACCACGCCCCCCTGGTCATCGCGGGCGCGCATGACCACCTGCGCGAGGTTGAGCTCCACGT
GCCGCGCGAAGACGGCGTAGTTGCGCAGACGCTGGAAGAGGTAGTTGAGGGTGGTGGCGGTGTGCT
CGGCCACGAAGAAGTTCATGACCCAGCGGCGCAACGTGGATTCGTTGATGTCCCCCAAGGCCTCCAG
CCGTTCCATGGCCTCGTAGAAGTCCACGGCGAAGTTGAAAAACTGGGAGTTGCGCGCCGACACGGTC
```

```
AACTCCTCCTCCAGAAGACGGATGAGCTCGGCGACGGTGTCGCGCACCTCGCGCTCGAAGGCTATGG
GGATCTCTTCCTCCGCTAGCATCACCACCTCCTCCTCTTCCTCCTCTTCTGGCACTTCCATGATGGCTT
CCTCCTCTTCGGGGGGTGGCGGCGGCGGCGGTGGGGGAGGGGGCGCTCTGCGCCGGCGGCGGCGCA
CCGGGAGGCGGTCCACGAAGCGCGCGATCATCTCCCCGCGGCGGCGGCGCATGGTCTCGGTGACGGC
GCGGCCGTTCTCCCGGGGGCGCAGTTGGAAGACGCCGCCGGACATCTGGTGCTGGGGCGGGTGGCCG
TGAGGCAGCGAGACGGCGCTGACGATGCATCTCAACAATTGCTGCGTAGGTACGCCGCCGAGGGAC
CTGAGGGAGTCCATATCCACCGGATCCGAAAACCTTTCGAGGAAGGCGTCTAACCAGTCGCAGTCGC
AAGGTAGGCTGAGCACCGTGGCGGGCGGCGGGGGGTGGGGGAGTGTCTGGCGGAGGTGCTGCTGA
TGATGTAATTGAAGTAGGCGGACTTGACACGGCGGATGGTCGACAGGAGCACCATGTCCTTGGGTCC
GGCCTGCTGGATGCGGAGGCGGTCGGCTATGCCCCAGGCTTCGTTCTGGCATCGGCGCAGGTCCTTG
TAGTAGTCTTGCATGAGCCTTTCCACCGGCACCTCTTCTCCTTCCTCTTCTGCTTCTTCCATGTCTGCTT
CGGCCCTGGGGCGGCGCCGCGCCCCCTGCCCCCCATGCGCGTGACCCCGAACCCCCTGAGCGGTTG
GAGCAGGGCCAGGTCGGCGACGACGCGCTCGGCCAGGATGGCCTGCTGCACCTGCGTGAGGGTGGT
TTGGAAGTCATCCAAGTCCACGAAGCGGTGGTAGGCGCCCGTGTTGATGGTGTAGGTGCAGTTGGCC
ATGACGGACCAGTTGACGGTCTGGTGGCCCGGTTGCGACATCTCGGTGTACCTGAGTCGCGAGTAGG
CGCGGGAGTCGAAGACGTAGTCGTTGCAAGTCCGCACCAGGTACTGGTAGCCCACCAGGAAGTGCG
GCGGCGGCTGGCGGTAGAGGGGCCAGCGCAGGGTGGCGGGGGCTCCGGGGGCCAGGTCTTCCAGCA
TGAGGCGGTGGTAGGCGTAGATGTACCTGGACATCCAGGTGATACCCGCGGCGGTGGTGGAGGCGC
GCGGGAAGTCGCGCACCCGGTTCCAGATGTTGCGCAGGGGCAGAAAGTGCTCCATGGTAGGCGTGCT
CTGTCCAGTCAGACGCGCGCAGTCGTTGATACTCTAGACCAGGGAAAACGAAAGCCGGTCAGCGGG
CACTCTTCCGTGGTCTGGTGAATAGATCGCAAGGGTATCATGGCGGAGGGCCTCGGTTCGAGCCCCG
GGTCCGGGCCGGACGGTCCGCCATGATCCACGCGGTTACCGCCCGCGTGTCGAACCCAGGTGTGCGA
CGTCAGACAACGGTGGAGTGTTCCTTTTGGCGTTTTTCTGGCCGGGCGCCGGCGCCGCGTAAGAGAC
TAAGCCGCGAAAGCGAAAGCAGTAAGTGGCTCGCTCCCCGTAGCCGGAGGGATCCTTGCTAAGGGTT
GCGTTGCGGCGAACCCCGGTTCGAATCCCGTACTCGGGCCGGCCGGACCCGCGGCTAAGGTGTTGGA
TTGGCCTCCCCCTCGTATAAAGACCCCGCTTGCGGATTGACTCCGGACACGGGGACGAGCCCCTTTTA
TTTTTGCTTTCCCCAGATGCATCCGGTGCTGCGGCAGATGCGCCCCCGCCCCAGCAGCAGCAACAAC
ACCAGCAAGAGCGGCAGCAACAGCAGCGGGAGTCATGCAGGGCCCCCTCACCCACCCTCGGCGGGC
CGGCCACCTCGGCGTCCGCGGCCGTGTCTGGCGCCTGCGGCGGCGGCGGGGGCCGGCTGACGACCC
CGAGGAGCCCCCGCGGCGCAGGGCCAGACACTACCTGGACCTGGAGGAGGGCGAGGGCCTGGCGCG
GCTGGGGGCGCCGTCTCCCGAGCGCCACCCGCGGGTGCAGCTGAAGCGCGACTCGCGCGAGGCGTA
CGTGCCTCGGCAGAACCTGTTCAGGGACCGCGCGGGCGAGGAGCCCGAGGAGATGCGGGACAGGAG
GTTCAGCGCAGGGCGGGAGCTGCGGCAGGGGCTGAACCGCGAGCGGCTGCTGCGCGAGGAGGACTT
TGAGCCCGACGCGCGGACGGGGATCAGCCCCGCGCGCGCACGTGGCGGCCGCCGACCTGGTGAC
GGCGTACGAGCAGACGGTGAACCAGGAGATCAACTTCCAAAAGAGTTTCAACAACCACGTGCGCAC
GCTGGTGGCGCGCGAGGAGGTGACCATCGGGCTGATGCACCTGTGGGACTTTGTAAGCGCGCTGGTG
CAGAACCCCAACAGCAAGCCTCTGACGGCGCAGCTGTTCCTGATAGTGCAGCACAGCAGGGACAAC
GAGGCGTTTAGGGACGCGCTGCTGAACATCACCGAGCCCGAGGGTCGGTGGCTGCTGGACCTGATTA
ACATCCTGCAGAGCATAGTGGTGCAGGAGCGCAGCCTGAGCCTGGCCGACAAGGTGGCGGCCATCA
ACTACTCGATGCTGAGCCTGGGCAAGTTTTACGCGCGCAAGATCTACCAGACGCCGTACGTGCCCAT
AGACAAGGAGGTGAAGATCGACGGTTTTTACATGCGCATGGCGCTGAAGGTGCTCACCCTGAGCGAC
```

-continued

```
GACCTGGGCGTGTACCGCAACGAGCGCATCCACAAGGCCGTGAGCGTGAGCCGGCGGCGCGAGCTG

AGCGACCGCGAGCTGATGCACAGCCTGCAGCGGGCGCTGGCGGGCGCCGGCAGCGGCGACAGGGAG

GCGGAGTCCTACTTCGATGCGGGGGCGGACCTGCGCTGGGCGCCCAGCCGGCGGGCCCTGGAGGCC

GCGGGGGTCCGCGAGGACTATGACGAGGACGGCGAGGAGGATGAGGAGTACGAGCTAGAGGAGGG

CGAGTACCTGGACTAAACCGCGGGTGGTGTTTCCGGTAGATGCAAGACCCGAACGTGGTGGACCCGG

CGCTGCGGGCGGCTCTGCAGAGCCAGCCGTCCGGCCTTAACTCCTCAGACGACTGGCGACAGGTCAT

GGACCGCATCATGTCGCTGACGGCGCGTAACCCGGACGCGTTCCGGCAGCAGCCGCAGGCCAACAG

GCTCTCCGCCATCCTGGAGGCGGTGGTGCCTGCGCGCTCGAACCCCACGCACGAGAAGGTGCTGGCC

ATAGTGAACGCGCTGGCCGAGAACAGGGCCATCCGCCCGGACGAGGCCGGGCTGGTGTACGACGCG

CTGCTGCAGCGCGTGGCCCGCTACAACAGCGGCAACGTGCAGACCAACCTGGACCGGCTGGTGGGG

GACGTGCGCGAGGCGGTGGCGCAGCGCGAGCGCGCGGATCGGCAGGGCAACCTGGGCTCCATGGTG

GCGCTGAATGCCTTCCTGAGCACGCAGCCGGCCAACGTGCCGCGGGGGCAGGAAGACTACACCAAC

TTTGTGAGCGCGCTGCGGCTGATGGTGACCGAGACCCCCCAGAGCGAGGTGTACCAGTCGGGCCCGG

ACTACTTCTTCCAGACCAGCAGACAGGGCCTGCAGACGGTGAACCTGAGCCAGGCTTTCAAGAACCT

GCGGGGGCTGTGGGGCGTGAAGGCGCCCACCGGCGACCGGGCGACGGTGTCCAGCCTGCTGACGCC

CAACTCGCGCCTGCTGCTGCTGCTGATCGCGCCGTTCACGGACAGCGGCAGCGTGTCCCGGGACACC

TACCTGGGGCACCTGCTGACCCTGTACCGCGAGGCCATCGGGCAGGCGCAGGTGGACGAGCACACCT

TCCAGGAGATCACCAGCGTGAGCCGCGCGCTGGGGCAGGAGGACACGAGCAGCCTGGAGGCGACTC

TGAACTACCTGCTGACCAACCGGCGGCAGAAGATTCCCTCGCTGCACAGCCTGACCTCCGAGGAGGA

GCGCATCTTGCGCTACGTGCAGCAGAGCGTGAGCCTGAACCTGATGCGCGACGGGGTGACGCCCAGC

GTGGCGCTGGACATGACCGCGCGCAACATGGAACCGGGCATGTACGCCGCGCACCGGCCTTACATCA

ACCGCCTGATGGACTACCTGCATCGCGCGGCGGCCGTGAACCCCGAGTACTTTACCAACGCCATCCT

GAACCCGCACTGGCTCCCGCCGCCCGGGTTCTACAGCGGGGCTTCGAGGTCCCGGAGACCAACGAT

GGCTTCCTGTGGGACGACATGGACGACAGCGTGTTCTCCCCGCGGCCGCAGGCGCTGGCGGAAGCGT

CCCTGCTGCGTCCCAAGAAGGAGGAGGAGGAGGAGGCGAGTCGCCGCCGCGGCAGCAGCGGCGTGG

CTTCTCTGTCCGAGCTGGGGCGGCAGCCGCCGCGCGCCCCGGGTCCCTGGGCGGCAGCCCCTTTCC

GAGCCTGGTGGGGTCTCTGCACAGCGAGCGCACCACCCGCCCTCGGCTGCTGGGCGAGGACGAGTAC

CTGAATAACTCCCTGCTGCAGCCGGTGCGGGAGAAAAACCTGCCTCCCGCCTTCCCCAACAACGGGA

TAGAGAGCCTGGTGGACAAGATGAGCAGATGGAAGACCTATGCGCAGGAGCACAGGGACGCGCCTG

CGCTCCGGCCGCCCACGCGGCGCCAGCGCCACGACCGGCAGCGGGGCTGGTGTGGGATGACGAGG

ACTCCGCGGACGATAGCAGCGTGCTGGACCTGGGAGGGAGCGGCAACCCGTTCGCGCACCTGCGCCC

CCGCCTGGGGAGGATGTTTTAAAAAAAAAAAAAAAAAGCAAGAAGCATGATGCAAAAATTAAATAA

AACTCACCAAGGCCATGGCGACCGAGCGTTGGTTTCTTGTGTTCCCTTCAGTATGCGGCGCGCGGCG

ATGTACCAGGAGGGACCTCCTCCCTCTTACGAGAGCGTGGTGGGCGCGGCGGCGGCGGCGCCCTCTT

CTCCCTTTGCGTCGCAGCTGCTGGAGCCGCCGTACGTGCCTCCGCGCTACCTGCGGCCTACGGGGGG

GAGAAACAGCATCCGTTACTCGGAGCTGGCGCCCCTGTTCGACACCACCCGGGTGTACCTGGTGGAC

AACAAGTCGGCGGACGTGGCCTCCCTGAACTACCAGAACGACCACAGCAATTTTTTGACCACGGTCA

TCCAGAACAATGACTACAGCCCGAGCGAGGCCAGCACCCAGACCATCAATCTGGATGACCGGTCGC

ACTGGGCGGCGACCTGAAAACCATCCTGCACACCAACATGCCCAACGTGAACGAGTTCATGTTCAC

CAATAAGTTCAAGGCGCGGGTGATGGTGTCGCGCTCGCACACCAAGGAAGACCGGGTGGAGCTGAA
```

-continued

```
GTACGAGTGGGTGGAGTTCGAGCTGCCAGAGGGCAACTACTCCGAGACCATGACCATTGACCTGATG
AACAACGCGATCGTGGAGCACTATCTGAAAGTGGGCAGGCAGAACGGGGTCCTGGAGAGCGACATC
GGGGTCAAGTTCGACACCAGGAACTTCCGCCTGGGGCTGGACCCCGTGACCGGGCTGGTTATGCCCG
GGGTGTACACCAACGAGGCCTTCCATCCCGACATCATCCTGCTGCCCGGCTGCGGGGTGGACTTCAC
TTACAGCCGCCTGAGCAACCTCCTGGGCATCCGCAAGCGGCAGCCCTTCCAGGAGGGCTTCAGGATC
ACCTACGAGGACCTGGAGGGGGGCAACATCCCCGCGCTCCTCGATGTGGAGGCCTACCAGGATAGCT
TGAAGGAAAATGAGGCGGGACAGGAGGATACCGCCCCCGCCGCCTCCGCCGCCGCCGAGCAGGGCG
AGGATGCTGCTGACACCGCGGCCGCGACGGGGCAGAGGCCGACCCCGCTATGGTGGTGGAGGCTC
CCGAGCAGGAGGAGGACATGAATGACAGTGCGGTGCGCGGAGACACCTTCGTCACCCGGGGGGAGG
AAAAGCAAGCGGAGGCCGAGGCCGCGGCCGAGGAAAAGCAACTGGCGGCAGCAGCGGCGGCGGCG
GCGTTGGCCGCGGCGGAGGCTGAGTCTGAGGGGACCAAGCCCGCCAAGGAGCCCGTGATTAAGCCC
CTGACCGAAGATAGCAAGAAGCGCAGTTACAACCTGCTCAAGGACAGCACCAACACCGCGTACCGC
AGCTGGTACCTGGCCTACAACTACGGCGACCCGTCGACGGGGTGCGCTCCTGGACCCTGCTGTGCA
CGCCGGACGTGACCTGCGGCTCGGAGCAGGTGTACTGGTCGCTGCCCGACATGATGCAAGACCCCGT
GACCTTCCGCTCCACGCGGCAGGTCAGCAACTTCCCGGTGGTGGGCGCCGAGCTGCTGCCCGTGCAC
TCCAAGAGCTTCTACAACGACCAGGCCGTCTACTCCCAGCTCATCCGCCAGTTCACCTCTCTGACCCA
CGTGTTCAATCGCTTTCCTGAGAACCAGATTCTGGCGCGCCCGCCCGCCCCCACCATCACCACCGTCA
GTGAAAACGTTCCTGCTCTCACAGATCACGGGACGCTACCGCTGCGCAACAGCATCGGAGGAGTCCA
GCGAGTGACCGTTACTGACGCCAGACGCCGCACCTGCCCCTACGTTTACAAGGCCTTGGGCATAGTC
TCGCCGCGCGTCCTTTCCAGCCGCACTTTTTGAGCAACACCACCATCATGTCCATCCTGATCTCACCC
AGCAATAACTCCGGCTGGGGACTGCTGCGCGCGCCCAGCAAGATGTTCGGAGGGGCGAGGAAGCGT
TCCGAGCAGCACCCCGTGCGCGTGCGCGGGCACTTCCGCGCCCCCTGGGGAGCGCACAAACGCGGCC
GCGCGGGGCGCACCACCGTGGACGACGCCATCGACTCGGTGGTGGAGCAGGCGCGCAACTACAGGC
CCGCGGTCTCTACCGTGGACGCGGCCATCCAGACCGTGGTGCGGGGCGCGCGGCGGTACGCCAAGCT
GAAGAGCCGCCGGAAGCGCGTGGCCCGCCGCCACCGCCGCCGACCCGGGGCCGCCGCCAAACGCGC
CGCCGCGGCCCTGCTTCGCCGGGCCAAGCGCACGGGCCGCCGCGCCGCCATGAGGGCCGCGCGCCGC
TTGGCCGCCGGCATCACCGCCGCCACCATGGCCCCCCGTACCCGAAGACGCGCGGCCGCCGCCGCCG
CCGCCGCCATCAGTGACATGGCCAGCAGGCGCCGGGGCAACGTGTACTGGGTGCGCGACTCGGTGAC
CGGCACGCGCGTGCCCGTGCGCTTCCGCCCCCCGCGGACTTGAGATGATGTGAAAAAACAACACTGA
GTCTCCTGCTGTTGTGTGTATCCCAGCGGCGGCGGCGCGCAGCGTCATGTCCAAGCGCAAAATCA
AAGAAGAGATGCTCCAGGTCGTCGCGCCGGAGATCTATGGGCCCCCGAAGAAGGAAGAGCAGGATT
CGAAGCCCCGCAAGATAAAGCGGGTCAAAAAGAAAAAGAAAGATGATGACGATGCCGATGGGGAG
GTGGAGTTCCTGCGCGCCACGCGCCCCAGGCGCCCGGTGCAGTGGAAGGGCCGGCGCGTAAAGCGC
GTCCTGCGCCCCGGCACCGCGGTGGTCTTCACGCCCGGCGAGCGCTCCACCCGGACTTTCAAGCGCG
TCTATGACGAGGTGTACGGCGACGAAGACCTGCTGGAGCAGGCCAACGAGCGCTTCGGAGAGTTTGC
TTACGGGAAGCGTCAGCGGGCGCTGGGGAAGGAGGACCTGCTGGCGCTGCCGCTGGACCAGGGCAA
CCCCACCCCCAGTCTGAAGCCCGTGACCCTGCAGCAGGTGCTGCCGAGCAGCGCACCCTCCGAGGCG
AAGCGGGGTCTGAAGCGCGAGGGCGGCGACCTGGCGCCCACCGTGCAGCTCATGGTGCCCAAGCGG
CAGAGGCTGGAGGATGTGCTGGAGAAAATGAAAGTAGACCCCGGTCTGCAGCCGGACATCAGGGTC
CGCCCCATCAAGCAGGTGGCGCCGGGCCTCGGCGTGCAGACCGTGGACGTGGTCATCCCCACCGGCA
ACTCCCCCGCCGCCGCCACCACTACCGCTGCCTCCACGGACATGGAGACACAGACCGATCCCGCCGC
```

-continued

```
AGCCGCAGCCGCAGCCGCCGCCGCGACCTCCTCGGCGGAGGTGCAGACGGACCCCTGGCTGCCGCCG
GCGATGTCAGCTCCCCGCGCGCGTCGCGGGCGCAGGAAGTACGGCGCCGCCAACGCGCTCCTGCCCG
AGTACGCCTTGCATCCTTCCATCGCGCCCACCCCCGGCTACCGAGGCTATACCTACCGCCCGCGAAG
AGCCAAGGGTTCCACCCGCCGTCCCCGCCGACGCGCCGCCGCCACCACCCGCCGCCGCCGCCGCAGA
CGCCAGCCCGCACTGGCTCCAGTCTCCGTGAGGAAAGTGGCGCGCGACGGACACACCCTGGTGCTGC
CCAGGGCGCGCTACCACCCCAGCATCGTTTAAAAGCCTGTTGTGGTTCTTGCAGATATGGCCCTCACT
TGCCGCCTCCGTTTCCCGGTGCCGGGATACCGAGGAGGAAGATCGCGCCGCAGGAGGGGTCTGGCCG
GCCGCGGCCTGAGCGGAGGCAGCCGCCGCGCGCACCGGCGGCGACGCGCCACCAGCCGACGCATGC
GCGGCGGGGTGCTGCCCCTGTTAATCCCCCTGATCGCCGCGGCGATCGGCGCCGTGCCCGGGATCGC
CTCCGTGGCCTTGCAAGCGTCCCAGAGGCATTGACAGACTTGCAAACTTGCAAATATGGAAAAAAAA
ACCCCAATAAAAAAGTCTAGACTCTCACGCTCGCTTGGTCCTGTGACTATTTTGTAGAATGGAAGAC
ATCAACTTTGCGTCGCTGGCCCCGCGTCACGGCTCGCGCCCGTTCCTGGGACACTGGAACGATATCG
GCACCAGCAACATGAGCGGTGGCGCCTTCAGTTGGGGCTCTCTGTGGAGCGGCATTAAAAGTATCGG
GTCTGCCGTTAAAAATTACGGCTCCCGGGCCTGGAACAGCAGCACGGGCCAGATGTTGAGAGACAA
GTTGAAAGAGCAGAACTTCCAGCAGAAGGTGGTGGAGGGCCTGGCCTCCGGCATCAACGGGGTGGT
GGACCTGGCCAACCAGGCCGTGCAGAATAAGATCAACAGCAGACTGGACCCCCGGCCGCCGGTGGA
GGAGGTGCCGCCGGCGCTGGAGACGGTGTCCCCCGATGGGCGTGGCGAGAAGCGCCCGCGGCCCGA
TAGGGAAGAGACCACTCTGGTCACGCAGACCGATGAGCCGCCCCCGTATGAGGAGGCCCTGAAGCA
AGGTCTGCCCACCACGCGGCCCATCGCGCCCATGGCCACCGGGGTGGTGGGCCGCCACACCCCCGCC
ACGCTGGACTTGCCTCCGCCCGCCGATGTGCCGCAGCAGCAGAAGGCGGCACAGCCGGGCCCGCCCG
CGACCGCCTCCCGTTCCTCCGCCGGTCCTCTGCGCCGCGCGGCCAGCGGCCCCCGCGGGGGGTCGC
GAGGCACGGCAACTGGCAGAGCACGCTGAACAGCATCGTGGGTCTGGGGGTGCGGTCCGTGAAGCG
CCGCCGATGCTACTGAATAGCTTAGCTAACGTGTTGTATGTGTGTATGCGCCCTATGTCGCCGCCAGA
GGGAGCTGCTGAGTCGCCGCCGTTCGCGCGCCCACCACCACCGCCACTCCGCCCCTCAAGATGGCGAC
CCCATCGATGATGCCGCAGTGGTCGTACATGCACATCTCGGGCCAGGACGCCTCGGAGTACCTGAGC
CCCGGGCTGGTGCAGTTCGCCCGCGCCACCGAGAGCTACTTCAGCCTGAGTAACAAGTTTAGGAACC
CCACGGTGGCGCCCACGCACGATGTGACCACCGACCGGTCTCAGCGCCTGACGCTGCGGTTCATTCC
CGTGGACCGCGAGGACACCGCGTACTCGTACAAGGCGCGGTTCACCCTGGCCGTGGGCGACAACCGC
GTGCTGGACATGGCCTCCACCTACTTTGACATCCGCGGGGTGCTGGACCGGGGTCCCACTTTCAAGCC
CTACTCTGGCACCGCCTACAACTCCCTGGCCCCCAAGGGCGCTCCCAACTCCTGCGAGTGGGAGCAA
GAGGAAACTCAGGCAGTTGAAGAAGCAGCAGAAGAGGAAGAAGAAGATGCTGACGGTCAAGCTGA
GGAAGAGCAAGCAGCTACCAAAAAGACTCATGTATATGCTCAGGCTCCCCTTTCTGGCGAAAAAATT
AGTAAAGATGGTCTGCAAATAGGAACGGACGCTACAGCTACAGAACAAAAACCTATTTATGCAGAC
CCTACATTCCAGCCCGAACCCCAAATCGGGGAGTCCCAGTGGAATGAGGCAGATGCTACAGTCGCCG
GCGGTAGAGTGCTAAAGAAATCTACTCCCATGAAACCATGCTATGGTTCCTATGCAAGACCCACAAA
TGCTAATGGAGGTCAGGGTGTACTAACGGCAAATGCCCAGGGACAGCTAGAATCTCAGGTTGAAATG
CAATTCTTTTCAACTTCTGAAAACGCCCGTAACGAGGCTAACAACATTCAGCCCAAATTGGTGCTGTA
TAGTGAGGATGTGCACATGGAGACCCCGGATACGCACCTTTCTTACAAGCCCGCAAAAAGCGATGAC
AATTCAAAAATCATGCTGGGTCAGCAGTCCATGCCCAACAGACCTAATTACATCGGCTTCAGAGACA
ACTTTATCGGCCTCATGTATTACAATAGCACTGGCAACATGGGAGTGCTTGCAGGTCAGGCCTCTCAG
```

```
TTGAATGCAGTGGTGGACTTGCAAGACAGAAACACAGAACTGTCCTACCAGCTCTTGCTTGATTCCA

TGGGTGACAGAACCAGATACTTTTCCATGTGGAATCAGGCAGTGGACAGTTATGACCCAGATGTTAG

AATTATTGAAAATCATGGAACTGAAGACGAGCTCCCCAACTATTGTTTCCCTCTGGGTGGCATAGGG

GTAACTGACACTTACCAGGCTGTTAAAACCAACAATGGCAATAACGGGGGCCAGGTGACTTGGACA

AAAGATGAAACTTTTGCAGATCGCAATGAAATAGGGGTGGGAAACAATTTCGCTATGGAGATCAACC

TCAGTGCCAACCTGTGGAGAAACTTCCTGTACTCCAACGTGGCGCTGTACCTACCAGACAAGCTTAA

GTACAACCCCTCCAATGTGGACATCTCTGACAACCCCAACACCTACGATTACATGAACAAGCGAGTG

GTGGCCCCGGGGCTGGTGGACTGCTACATCAACCTGGGCGCGCGCTGGTCGCTGGACTACATGGACA

ACGTCAACCCCTTCAACCACCACCGCAATGCGGGCCTGCGCTACCGCTCCATGCTCCTGGGCAACGG

GCGCTACGTGCCCTTCCACATCCAGGTGCCCCAGAAGTTCTTTGCCATCAAGAACCTCCTCCTCCTGC

CGGGCTCCTACACCTACGAGTGGAACTTCAGGAAGGATGTCAACATGGTCCTCCAGAGCTCTCTGGG

TAACGATCTCAGGGTGGACGGGGCCAGCATCAAGTTCGAGAGCATCTGCCTCTACGCCACCTTCTTC

CCCATGGCCCACAACACGGCCTCCACGCTCGAGGCCATGCTCAGGAACGACACCAACGACCAGTCCT

TCAATGACTACCTCTCCGCCGCCAACATGCTCTACCCCATACCCGCCAACGCCACCAACGTCCCCATC

TCCATCCCCTCGCGCAACTGGGCGGCCTTCCGCGGCTGGGCCTTCACCCGCCTCAAGACCAAGGAGA

CCCCCTCCCTGGGCTCGGGATTCGACCCCTACTACACCTACTCGGGCTCCATTCCCTACCTGGACGGC

ACCTTCTACCTCAACCACACTTTCAAGAAGGTCTCGGTCACCTTCGACTCCTCGGTCAGCTGGCCGGG

CAACGACCGTCTGCTCACCCCCAACGAGTTCGAGATCAAGCGCTCGGTCGACGGGGAGGGCTACAAC

GTGGCCCAGTGCAACATGACCAAGGACTGGTTCCTGGTCCAGATGCTGGCCAACTACAACATCGGCT

ACCAGGGCTTCTACATCCCAGAGAGCTACAAGGACAGGATGTACTCCTTCTTCAGGAACTTCCAGCC

CATGAGCCGGCAGGTGGTGGACCAGACCAAGTACAAGGACTACCAGGAGGTGGGCATCATCCACCA

GCACAACAACTCGGGCTTCGTGGGCTACCTCGCCCCCACCATGCGCGAGGGACAGGCCTACCCCGCC

AACTTCCCCTATCCGCTCATAGGCAAGACCGCGGTCGACAGCATCACCCAGAAAAAGTTCCTCTGCG

ACCGCACCCTCTGGCGCATCCCCTTCTCCAGCAACTTCATGTCCATGGGTGCGCTCTCGGACCTGGGC

CAGAACTTGCTCTACGCCAACTCCGCCCACGCCCTCGACATGACCTTCGAGGTCGACCCCATGGACG

AGCCCACCCTTCTCTATGTTCTGTTCGAAGTCTTTGACGTGGTCCGGGTCCACCAGCCGCACCGCGGC

GTCATCGAGACCGTGTACCTGCGTACGCCCTTCTCGGCCGGCAACGCCACCACCTAAAGAAGCAAGC

CGCAGTCATCGCCGCCTGCATGCCGTCGGGTTCCACCGAGCAAGAGCTCAGGGCCATCGTCAGAGAC

CTGGGATGCGGGCCCTATTTTTTGGGCACCTTCGACAAGCGCTTCCCTGGCTTTGTCTCCCCACACAA

GCTGGCCTGCGCCATCGTCAACACGGCCGGCCGCGAGACCGGGGCGTGCACTGGCTGGCCTTCGCC

TGGAACCCGCGCTCCAAAACATGCTTCCTCTTTGACCCCTTCGGCTTTTCGGACCAGCGGCTCAAGCA

AATCTACGAGTTCGAGTACGAGGGCTTGCTGCGTCGCAGCGCCATCGCCTCCTCGCCCGACCGCTGC

GTCACCCTCGAAAAGTCCACCCAGACCGTGCAGGGGCCCGACTCGGCCGCCTGCGGTCTCTTCTGCT

GCATGTTTCTGCACGCCTTTGTGCACTGGCCTCAGAGTCCCATGGACCGCAACCCCACCATGAACTTG

CTGACGGGGTGCCCAACTCCATGCTCCAGAGCCCCCAGGTCGAGCCCACCCTGCGCCGCAACCAGG

AGCAGCTCTACAGCTTCCTGGAGCGCCACTCGCCTTACTTCCGCCGCCACAGCGCACAGATCAGGAG

GGCCACCTCCTTCTGCCACTTGCAAGAGATGCAAGAAGGGTAATAACGATGTACACACTTTTTTTCTC

AATAAATGGCATCTTTTTATTTATACAAGCTCTCTGGGGTATTCATTTCCCACCACCACCCGCCGTTGT

CGCCATCTGGCTCTATTTAGAAATCGAAAGGGTTCTGCCGGGAGTCGCCGTGCGCCACGGGCAGGGA

CACGTTGCGATACTGGTAGCGGGTGCCCCACTTGAACTCGGGCACCACCAGGCGAGGCAGCTCGGGG

AAGTTTTCGCTCCACAGGCTGCGGGTCAGCACCAGCGCGTTCATCAGGTCGGGCGCCGAGATCTTGA
```

-continued

```
AGTCGCAGTTGGGGCCGCCGCCCTGCGCGCGAGTTGCGGTACACCGGGTTGCAGCACTGGAACAC
CAACAGCGCCGGGTGCTTCACGCTGGCCAGCACGCTGCGGTCGGAGATCAGCTCGGCGTCCAGGTCC
TCCGCGTTGCTCAGCGCGAACGGGGTCATCTTGGGCACTTGCCGCCCCAGGAAGGGCGCGTGCCCCG
GTTTCGAGTTGCAGTCGCAGCGCAGCGGGATCAGCAGGTGCCCGTGCCCGGACTCGGCGTTGGGGTA
CAGCGCGCGCATGAAGGCCTGCATCTGGCGGAAGGCCATCTGGGCCTTGGCGCCCTCCGAGAAGAAC
ATGCCGCAGGACTTGCCCGAGAACTGGTTTGCGGGGCAGCTGGCGTCGTGCAGGCAGCAGCGCGCGT
CGGTGTTGGCGATCTGCACCACGTTGCGCCCCACCGGTTCTTCACGATCTTGGCCTTGGACGATTGC
TCCTTCAGCGCGCGCTGCCCGTTCTCGCTGGTCACATCCATCTCGATCACATGTTCCTTGTTCACCATG
CTGCTGCCGTGCAGACACTTCAGCTCGCCCTCCGTCTCGGTGCAGCGGTGCTGCCACAGCGCGCAGC
CCGTGGGCTCGAAAGACTTGTAGGTCACCTCCGCGAAGGACTGCAGGTACCCCTGCAAAAAGCGGCC
CATCATGGTCACGAAGGTCTTGTTGCTGCTGAAGGTCAGCTGCAGCCCGCGGTGCTCCTCGTTCAGCC
AGGTCTTGCACACGGCCGCCAGCGCCTCCACCTGGTCGGGCAGCATCTTGAAGTTCACCTTCAGCTCA
TTCTCCACGTGGTACTTGTCCATCAGCGTGCGCGCCGCCTCCATGCCCTTCTCCCAGGCCGACACCAG
CGGCAGGCTCACGGGGTTCTTCACCATCACCGTGGCCGCCGCCTCCGCCGCGCTTTCGCTTTCCGCCC
CGCTGTTCTCTTCCTCTTCCTCCTCTTCCTCGCCGCCGCCCACTCGCAGCCCCGCACCACGGGGTCGT
CTTCCTGCAGGCGCTGCACCTTGCGCTTGCCGTTGCGCCCCTGCTTGATGCGCACGGGCGGGTTGCTG
AAGCCCACCATCACCAGCGCGGCCTCTTCTTGCTCGTCCTCGCTGTCCAGAATGACCTCCGGGGAGG
GGGGGTTGGTCATCCTCAGTACCGAGGCACGCTTCTTTTTCTTCCTGGGGGCGTTCGCCAGCTCCGCG
GCTGCGGCCGCTGCCGAGGTCGAAGGCCGAGGGCTGGGCGTGCGCGGCACCAGCGCGTCCTGCGAG
CCGTCCTCGTCCTCCTCGGACTCGAGACGGAGGCGGGCCCGCTTCTTCGGGGGCGCGCGGGGCGGCG
GAGGCGGCGGCGGCGACGGAGACGGGGACGAGACATCGTCCAGGGTGGGTGGACGGCGGGCCGCG
CCGCGTCCGCGCTCGGGGGTGGTCTCGCGCTGGTCCTCTTCCCGACTGGCCATCTCCCACTGCTCCTT
CTCCTATAGGCAGAAAGAGATCATGGAGTCTCTCATGCGAGTCGAGAAGGAGGAGGACAGCCTAAC
CGCCCCCTCTGAGCCCTCCACCACCGCCGCCACCACCGCCAATGCCGCCGCGGACGACGCGCCCACC
GAGACCACCGCCAGTACCACCCTCCCCAGCGACGCACCCCCGCTCGAGAATGAAGTGCTGATCGAGC
AGGACCCGGGTTTTGTGAGCGGAGAGGAGGATGAGGTGGATGAGAAGGAGAAGGAGGAGGTCGCC
GCCTCAGTGCCAAAAGAGGATAAAAAGCAAGACCAGGACGACGCAGATAAGGATGAGACAGCAGT
CGGGCGGGGAACGGAAGCCATGATGCTGATGACGGCTACCTAGACGTGGGAGACGACGTGCTGCT
TAAGCACCTGCACCGCCAGTGCGTCATCGTCTGCGACGCGCTGCAGGAGCGCTGCGAAGTGCCCCTG
GACGTGGCGGAGGTCAGCCGCGCCTACGAGCGGCACCTCTTCGCGCCGCACGTGCCCCCCAAGCGCC
GGGAGAACGGCACCTGCGAGCCCAACCCGCGTCTCAACTTCTACCCGGTCTTCGCGGTACCCGAGGT
GCTGGCCACCTACCACATCTTTTTCCAAAACTGCAAGATCCCCCTCTCCTGCCGCGCCAACCGCACCC
GCGCCGACAAAACCCTGACCCTGCGGCAGGGCGCCCACATACCTGATATCGCCTCTCTGGAGGAAGT
GCCCAAGATCTTCGAGGGTCTCGGTCGCGACGAGAAACGGGCGGCGAACGCTCTGCACGGAGACAG
CGAAAACGAGAGTCACTCGGGGGTGCTGGTGGAGCTCGAGGGCGACAACGCGCGCCTGGCCGTACT
CAAGCGCAGCATAGAGGTCACCCACTTTGCCTACCCGGCGCTCAACCTGCCCCCCAAGGTCATGAGT
GTGGTCATGGGCGAGCTCATCATGCGCCGCGCCCAGCCCCTGGCCGCGGATGCAAACTTGCAAGAGT
CCTCCGAGGAAGGCCTGCCCGCGGTCAGCGACGAGCAGCTGGCGCGCTGGCTGGAGACCCGCGACC
CCGCGCAGCTGGAGGAGCGGCGCAAGCTCATGATGGCCGCGGTGCTGGTCACCGTGGAGCTCGAGT
GTCTGCAGCGCTTCTTCGCGGACCCCGAGATGCAGCGCAAGCTCGAGGAGACCCTGCACTACACCTT
```

-continued

```
CCGCCAGGGCTACGTGCGCCAGGCCTGCAAGATCTCCAACGTGGAGCTCTGCAACCTGGTCTCCTAC
CTGGGCATCCTGCACGAGAACCGCCTCGGGCAGAACGTCCTGCACTCCACCCTCAAAGGGGAGGCGC
GCCGCGACTACATCCGCGACTGCGCCTACCTCTTCCTCTGCTACACCTGGCAGACGGCCATGGGGGTC
TGGCAGCAGTGCCTGGAGGAGCGCAACCTCAAGGAGCTGGAAAAGCTCCTCAAGCGCACCCTCAGG
GACCTCTGGACGGGCTTCAACGAGCGCTCGGTGGCCGCCGCGCTGGCGGACATCATCTTTCCCGAGC
GCCTGCTCAAGACCCTGCAGCAGGGCCTGCCCGACTTCACCAGCCAGAGCATGCTGCAGAACTTCAG
GACTTTCATCCTGGAGCGCTCGGGCATCCTGCCGGCCACTTGCTGCGCGCTGCCCAGCGACTTCGTGC
CCATCAAGTACAGGGAGTGCCCGCCGCCGCTCTGGGGCCACTGCTACCTCTTCCAGCTGGCCAACTA
CCTCGCCTACCACTCGGACCTCATGGAAGACGTGAGCGGCGAGGGCCTGCTCGAGTGCCACTGCCGC
TGCAACCTCTGCACGCCCCACCGCTCTCTAGTCTGCAACCCGCAGCTGCTCAGCGAGAGTCAGATTAT
CGGTACCTTCGAGCTGCAGGGTCCCTCGCCTGACGAGAAGTCCGCGGCTCCAGGGCTGAAACTCACT
CCGGGGCTGTGGACTTCCGCCTACCTACGCAAATTTGTACCTGAGGACTACCACGCCCACGAGATCA
GGTTCTACGAAGACCAATCCCGCCCGCCCAAGGCGGAGCTCACCGCCTGCGTCATCACCCAGGGGCA
CATCCTGGGCCAATTGCAAGCCATCAACAAAGCCCGCCGAGAGTTCTTGCTGAAAAAGGGTCGGGGG
GTGTACCTGGACCCCCAGTCCGGCGAGGAGCTAAACCCGCTACCCCCGCCGCCGCCCCAGCAGCGGG
ACCTTGCTTCCCAGGATGGCACCCAGAAAGAAGCAGCAGCCGCCGCCGCCGCAGCCATACATGC
TTCTGGAGGAAGAGGAGGAGGACTGGGACAGTCAGGCAGAGGAGGTTTCGGACGAGGAGCAGGAG
GAGATGATGGAAGACTGGGAGGAGGACAGCAGCCTAGACGAGGAAGCTTCAGAGGCCGAAGAGGT
GGCAGACGCAACACCATCGCCCTCGGTCGCAGCCCCTCGCCGGGGCCCCTGAAATCCTCCGAACCC
AGCACCAGCGCTATAACCTCCGCTCCTCCGGCGCCGGCGCCACCCGCCCGCAGACCCAACCGTAGAT
GGGACACCACAGGAACCGGGGTCGGTAAGTCCAAGTGCCCGCCGCCGCCACCGCAGCAGCAGCAGC
AGCAGCGCCAGGGCTACCGCTCGTGGCGCGGGCACAAGAACGCCATAGTCGCCTGCTTGCAAGACTG
CGGGGGCAACATCTCTTTCGCCCGCCGCTTCCTGCTATTCCACCACGGGGTCGCCTTTCCCCGCAATG
TCCTGCATTACTACCGTCATCTCTACAGCCCCTACTGCAGCGGCGACCCAGAGGCGGCAGCGGCAGC
CACAGCGGCGACCACCACCTAGGAAGATATCCTCCGCGGGCAAGACAGCGGCAGCAGCGGCCAGGA
GACCCGCGGCAGCAGCGGCGGGAGCGGTGGGCGCACTGCGCCTCTCGCCCAACGAACCCCTCTCGAC
CCGGGAGCTCAGACACAGGATCTTCCCCACTTTGTATGCCATCTTCCAACAGAGCAGAGGCCAGGAG
CAGGAGCTGAAAATAAAAAACAGATCTCTGCGCTCCCTCACCCGCAGCTGTCTGTATCACAAAAGCG
AAGATCAGCTTCGGCGCACGCTGGAGGACGCGGAGGCACTCTTCAGCAAATACTGCGCGCTCACTCT
TAAAGACTAGCTCCGCGCCCTTCTCGAATTTAGGCGGGAGAAAACTACGTCATCGCCGGCCGCCGCC
CAGCCCGCCCAGCCGAGATGAGCAAAGAGATTCCCACGCCATACATGTGGAGCTACCAGCCGCAGA
TGGGACTCGCGGCGGGAGCGGCCCAGGACTACTCCACCCGCATGAACTACATGAGCGCGGGACCCC
ACATGATCTCACAGGTCAACGGGATCCGCGCCCAGCGAAACCAAATACTGCTGGAACAGGCGGCCA
TCACCGCCACGCCCCGCCATAATCTCAACCCCCGAAATTGGCCCGCCGCCCTCGTGTACCAGGAAAC
CCCCTCCGCCACCACCGTACTACTTCCGCGTGACGCCCAGGCCGAAGTCCAGATGACTAACTCAGGG
GCGCAGCTCGCGGGCGGCTTTCGTCACGGGGCGCGGCCGCTCCGACCAGGTATAAGACACCTGATGA
TCAGAGGCCGAGGTATCCAGCTCAACGACGAGTCGGTGAGCTCTTCGCTCGGTCTCCGTCCGGACGG
AACTTTCCAGCTCGCCGGATCCGGCCGCTCTTCGTTCACGCCCCGCCAGGCGTACCTGACTCTGCAGA
CCTCGTCCTCGGAGCCCCGCTCCGGCGGCATCGGAACCCTCCAGTTCGTGGAGGAGTTCGTGCCCTCG
GTCTACTTCAACCCCTTCTCGGGACCTCCCGGACGCTACCCCGACCAGTTCATTCCGAACTTTGACGC
GGTGAAGGACTCGGCGGACGGCTACGACTGAATGTCAGGTGTCGAGGCAGAGCAGCTTCGCCTGAG
```

```
ACACCTCGAGCACTGCCGCCGCCACAAGTGCTTCGCCCGCGGTTCTGGTGAGTTCTGCTACTTTCAGC

TACCCGAGGAGCATACCGAGGGGCCGGCGCACGGCGTCCGCCTGACCACCCAGGGCGAGGTTACCT

GTTCCCTCATCCGGGAGTTTACCCTCCGTCCCCTGCTAGTGGAGCGGGAGCGGGGTCCCTGTGTCCTA

ACTATCGCCTGCAACTGCCCTAACCCTGGATTACATCAAGATCTTTGCTGTCATCTCTGTGCTGAGTTT

AATAAACGCTGAGATCAGAATCTACTGGGGCTCCTGTCGCCATCCTGTGAACGCCACCGTCTTCACCC

ACCCCGACCAGGCCCAGGCGAACCTCACCTGCGGTCTGCATCGGAGGGCCAAGAAGTACCTCACCTG

GTACTTCAACGGCACCCCCTTTGTGGTTTACAACAGCTTCGACGGGACGGAGTCTCCCTGAAAGAC

CAGCTCTCCGGTCTCAGCTACTCCATCCACAAGAACACCACCCTCCAACTCTTCCCTCCCTACCTGCC

GGGAACCTACGAGTGCGTCACCGGCCGCTGCACCCACCTCACCCGCCTGATCGTAAACCAGAGCTTT

CCGGGAACAGATAACTCCCTCTTCCCCAGAACAGGAGGTGAGCTCAGGAAACTCCCCGGGGACCAG

GGCGGAGACGTACCTTCGACCCTTGTGGGGTTAGGATTTTTTATTACCGGGTTGCTGGCTCTTTTAAT

CAAAGTTTCCTTGAGATTTGTTCTTTCCTTCTACGTGTATGAACACCTCAACCTCCAATAACTCTACCC

TTTCTTCGGAATCAGGTGACTTCTCTGAAATCGGGCTTGGTGTGCTGCTTACTCTGTTGATTTTTTCC

TTATCATACTCAGCCTTCTGTGCCTCAGGCTCGCCGCCTGCTGCGCACACATCTATATCTACTGCTGGT

TGCTCAAGTGCAGGGGTCGCCACCCAAGATGAACAGGTACATGGTCCTATCGATCCTAGGCCTGCTG

GCCCTGGCGGCCTGCAGCGCCGCCAAAAAAGAGATTACCTTTGAGGAGCCCGCTTGCAATGTAACTT

TCAAGCCCGAGGGTGACCAATGCACCACCCTCGTCAAATGCGTTACCAATCATGAGAGGCTGCGCAT

CGACTACAAAAACAAAACTGGCCAGTTTGCGGTCTATAGTGTGTTTACGCCCGGAGACCCCTCTAAC

TACTCTGTCACCGTCTTCCAGGGCGGACAGTCTAAGATATTCAATTACACTTTCCCTTTTTATGAGTTA

TGCGATGCGGTCATGTACATGTCAAAACAGTACAACCTGTGGCCTCCCTCTCCCCAGGCGTGTGTGG

AAAATACTGGGTCTTACTGCTGTATGGCTTTCGCAATCACTACGCTCGCTCTAATCTGCACGGTGCTA

TACATAAAATTCAGGCAGAGGCGAATCTTTATCGATGAAAAGAAAATGCCTTGATCGCTAACACCGG

CTTTCTATCTGCAGAATGAATGCAATCACCTCCCTACTAATCACCACCACCCTCCTTGCGATTGCCCA

TGGGTTGACACGAATCGAAGTGCCAGTGGGGTCCAATGTCACCATGGTGGGCCCCGCCGGCAATTCC

ACCCTCATGTGGGAAAAATTTGTCCGCAATCAATGGGTTCATTTCTGCTCTAACCGAATCAGTATCAA

GCCCAGAGCCATCTGCGATGGGCAAAATCTAACTCTGATCAATGTGCAAATGATGGATGCTGGGTAC

TATTACGGGCAGCGGGAGAAATCATTAATTACTGGCGACCCCACAAGGACTACATGCTGCATGTAG

TCGAGGCACTTCCCACTACCACCCCCACTACCACCTCTCCCACCACCACCACCACTACTACTACTACT

ACTACTACTACTACTACCACTACCGCTGCCCGCCATACCCGCAAAAGCACCATGATTAGCACAA

AGCCCCCTCGTGCTCACTCCCACGCCGGCGGGCCCATCGGTGCGACCTCAGAAACCACCGAGCTTTG

CTTCTGCCAATGCACTAACGCCAGCGCTCATGAACTGTTCGACCTGGAGAATGAGGATGTCCAGCAG

AGCTCCGCTTGCCTGACCCAGGAGGCTGTGGAGCCCGTTGCCCTGAAGCAGATCGGTGATTCAATAA

TTGACTCTTCTTCTTTTGCCACTCCCGAATACCCTCCCGATTCTACTTTCCACATCACGGGTACCAAAG

ACCCTAACCTCTCTTTCTACCTGATGCTGCTGCTCTGTATCTCTGTGGTCTCTTCCGCGCTGATGTTAC

TGGGGATGTTCTGCTGCCTGATCTGCCGCAGAAAGAGAAAAGCTCGCTCTCAGGGCCAACCACTGAT

GCCCTTCCCTACCCCCGGATTTTGCAGATAACAAGATATGAGCTCGCTGCTGACACTAACCGCTTT

ACTAGCCTGCGCTCTAACCCTTGTCGCTTGCGACTCGAGATTCCACAATGTCACAGCTGTGGCAGGAG

AAAATGTTACTTTCAACTCCACGGCCGATACCCAGTGGTCGTGGAGTGGCTCAGGTAGCTACTTAACT

ATCTGCAATAGCTCCACTTCCCCCGGCATATCCCCAACCAAGTACCAATGCAATGCCAGCCTGTTCAC

CCTCATCAACGCTTCCACCCTGGACAATGGACTCTATGTAGGCTATGTACCCTTTGGTGGGCAAGGAA
```

-continued

```
AGACCCACGCTTACAACCTGGAAGTTCGCCAGCCCAGAACCACTACCCAAGCTTCTCCCACCACCAC
CACCACCACCACCATCACCAGCAGCAGCAGCAGCAGCAGCCACAGCAGCAGCAGCAGATTATTGAC
TTTGGTTTTGGCCAGCTCATCTGCCGCTACCCAGGCCATCTACAGCTCTGTGCCCGAAACCACTCAGA
TCCACCGCCCAGAAACGACCACCGCCACCACCCTACACACCTCCAGCGATCAGATGCCGACCAACAT
CACCCCCTTGGCTCTTCAAATGGGACTTACAAGCCCCACTCCAAAACCAGTGGATGCGGCCGAGGTC
TCCGCCCTCGTCAATGACTGGGCGGGGCTGGGAATGTGGTGGTTCGCCATAGGCATGATGGCGCTCT
GCCTGCTTCTGCTCTGGCTCATCTGCTGCCTCCACCGCAGGCGAGCCAGACCCCCCATCTATAGACCC
ATCATTGTCCTGAACCCCGATAATGATGGGATCCATAGATTGGATGGCCTGAAAAACCTACTTTTTTC
TTTTACAGTATGATAAATTGAGACATGCCTCGCATTTTCTTGTACATGTTCCTTCTCCCACCTTTTCTG
GGGTGTTCTACGCTGGCCGCTGTGTCTCACCTGGAGGTAGACTGCCTCTCACCCTTCACTGTCTACCT
GCTTTACGGATTGGTCACCCTCACTCTCATCTGCAGCCTAATCACAGTAATCATCGCCTTCATCCAGT
GCATTGATTACATCTGTGTGCGCCTCGCATACTTCAGACACCACCCGCAGTACCGAGACAGGAACAT
TGCCCAACTTCTAAGACTGCTCTAATCATGCATAAGACTGTGATCTGCCTTCTGATCCTCTGCATCCT
GCCCACCCTCACCTCCTGCCAGTACACCACAAAATCTCCGCGCAAAAGACATGCCTCCTGCCGCTTCA
CCCAACTGTGGAATATACCCAAATGCTACAACGAAAAGAGCGAGCTCTCCGAAGCTTGGCTGTATGG
GGTCATCTGTGTCTTAGTTTTCTGCAGCACTGTCTTTGCCCTCATAATCTACCCCTACTTTGATTTGGG
ATGGAACGCGATCGATGCCATGAATTACCCCACCTTTCCCGCACCCGAGATAATTCCACTGCGACAA
GTTGTACCCGTTGTCGTTAATCAACGCCCCCCATCCCCTACGCCCACTGAAATCAGCTACTTTAACCT
AACAGGCGGAGATGACTGACGCCCTAGATCTAGAAATGGACGGCATCAGTACCGAGCAGCGTCTCCT
AGAGAGGCGCAGGCAGGCGGCTGAGCAAGAGCGCCTCAATCAGGAGCTCCGAGATCTCGTTAACCT
GCACCAGTGCAAAAGAGGCATCTTTTGTCTGGTAAAGCAGGCCAAAGTCACCTACGAGAAGACCGG
CAACAGCCACCGCCTCAGTTACAAATTGCCCACCCAGCGCCAGAAGCTGGTGCTCATGGTGGGTGAG
AATCCCATCACCGTCACCCAGCACTCGGTAGAGACCGAGGGGTGTCTGCACTCCCCCTGTCGGGGTC
CAGAAGACCTCTGCACCCTGGTAAAGACCCTGTGCGGTCTCAGAGATTTAGTCCCCTTTAACTAATCA
AACACTGGAATCAATAAAAAGAATCACTTACTTAAAATCAGACAGCAGGTCTCTGTCCAGTTTATTC
AGCAGCACCTCCTTCCCCTCCTCCCAACTCTGGTACTCCAAACGCCTTCTGGCGGCAAACTTCCTCCA
CACCCTGAAGGGAATGTCAGATTCTTGCTCCTGTCCCTCCGCACCCACTATCTTCATGTTGTTGCAGA
TGAAGCGCACCAAAACGTCTGACGAGAGCTTCAACCCCGTGTACCCCTATGACACGGAAAGCGGCCC
TCCCTCCGTCCCTTTCCTCACCCCTCCCTTCGTGTCTCCCGATGGATTCCAAGAAAGTCCCCCCGGGGT
CCTGTCTCTGAACCTGGCCGAGCCCCTGGTCACTTCCCACGGCATGCTCGCCCTGAAAATGGGAAGT
GGCCTCTCCCTGGACGACGCTGGCAACCTCACCTCTCAAGATATCACCACCGCTAGCCCTCCCCTCAA
AAAAACCAAGACCAACCTCAGCCTAGAAACCTCATCCCCCCTAACTGTGAGCACCTCAGGCGCCCTC
ACCGTAGCAGCCGCCGCTCCCCTGGCGGTGGCCGGCACCTCCCTCACCATGCAATCAGAGGCCCCCC
TGACAGTACAGGATGCAAAACTCACCCTGGCCACCAAAGGCCCCCTGACCGTGTCTGAAGGCAAACT
GGCCTTGCAAACATCGGCCCCGCTGACGGCCGCTGACAGCAGCACCCTCACAGTCAGTGCCACACCA
CCCCTTAGCACAAGCAATGGCAGCTTGGGTATTGACATGCAAGCCCCCATTTACACCACCAATGGAA
AACTAGGACTTAACTTTGGCGCTCCCCTGCATGTGGTAGACAGCCTAAATGCACTGACTGTAGTTACT
GGCCAAGGTCTTACGATAAACGGAACAGCCCTACAAACTAGAGTCTCAGGTGCCCTCAACTATGACA
CATCAGGAAACCTAGAATTGAGAGCTGCAGGGGGTATGCGAGTTGATGCAAATGGTCAACTTATCCT
TGATGTAGCTTACCCATTTGATGCACAAAACAATCTCAGCCTTAGGCTTGGACAGGGACCCCTGTTTG
TTAACTCTGCCCACAACTTGGATGTTAACTACAACAGAGGCCTCTACCTGTTCACATCTGGAAATACC
```

```
AAAAAGCTAGAAGTTAATATCAAAACAGCCAAGGGTCTCATTTATGATGACACTGCTATAGCAATCA
ATGCGGGTGATGGGCTACAGTTTGACTCAGGCTCAGATACAAATCCATTAAAAACTAAACTTGGATT
AGGACTGGATTATGACTCCAGCAGAGCCATAATTGCTAAACTGGGAACTGGCCTAAGCTTTGACAAC
ACAGGTGCCATCACAGTAGGCAACAAAAATGATGACAAGCTTACCTTGTGGACCACACCAGACCCAT
CCCCTAACTGTAGAATCTATTCAGAGAAAGATGCTAAATTCACACTTGTTTTGACTAAATGCGGCAGT
CAGGTGTTGGCCAGCGTTTCTGTTTTATCTGTAAAAGGTAGCCTTGCGCCCATCAGTGGCACAGTAAC
TAGTGCTCAGATTGTCCTCAGATTTGATGAAAATGGAGTTCTACTAAGCAATTCTTCCCTTGACCCTC
AATACTGGAACTACAGAAAAGGTGACCTTACAGAGGGCACTGCATATACCAACGCAGTGGGATTTAT
GCCCAACCTCACAGCATACCCAAAAACACAGAGCCAAACTGCTAAAAGCAACATTGTAAGTCAGGTT
TACTTGAATGGGGACAAATCCAAACCCATGACCCTCACCATTACCCTCAATGGAACTAATGAAACAG
GAGATGCCACAGTAAGCACTTACTCCATGTCATTCTCATGGAACTGGAATGGAAGTAATTACATTAA
TGAAACGTTCCAAACCAACTCCTTCACCTTCTCCTACATCGCCCAAGAATAAAAAGCATGACGCTGTT
GATTTGATTCAATGTGTTTCTGTTTTATTTTCAAGCACAACAAAATCATTCAAGTCATTCTTCCATCTT
AGCTTAATAGACACAGTAGCTTAATAGACCCAGTAGTGCAAAGCCCCATTCTAGCTTATAACTAGTG
GAGAAGTACTCGCCTACATGGGGGTAGAGTCATAATCGTGCATCAGGATAGGGCGGTGGTGCTGCAG
CAGCGCGCGAATAAACTGCTGCCGCCGCCGCTCCGTCCTGCAGGAATACAACATGGCAGTGGTCTCC
TCAGCGATGATTCGCACCGCCCGCAGCATAAGGCGCCTTGTCCTCCGGGCACAGCAGCGCACCCTGA
TCTCACTTAAATCAGCACAGTAACTGCAGCACAGCACCACAATATTGTTCAAAATCCCACAGTGCAA
GGCGCTGTATCCAAAGCTCATGGCGGGGACCACAGAACCCACGTGGCCATCATACCACAAGCGCAG
GTAGATTAAGTGGCGACCCCTCATAAACACGCTGGACATAAACATTACCTCTTTTGGCATGTTGTAAT
TCACCACCTCCCGGTACCATATAAACCTCTGATTAAACATGGCGCCATCCACCACCATCCTAAACCAG
CTGGCCAAAACCTGCCCGCCGGCTATACACTGCAGGGAACCGGGACTGGAACAATGACAGTGGAGA
GCCCAGGACTCGTAACCATGGATCATCATGCTCGTCATGATATCAATGTTGGCACAACACAGGCACA
CGTGCATACACTTCCTCAGGATTACAAGCTCCTCCCGCGTTAGAACCATATCCCAGGGAACAACCCA
TTCCTGAATCAGCGTAAATCCCACACTGCAGGGAAGACCTCGCACGTAACTCACGTTGTGCATTGTC
AAAGTGTTACATTCGGGCAGCAGCGGATGATCCTCCAGTATGGTAGCGCGGGTTTCTGTCTCAAAAG
GAGGTAGACGATCCCTACTGTACGGAGTGCGCCGAGACAACCGAGATCGTGTTGGTCGTAGTGTCAT
GCCAAATGGAACGCCGGACGTAGTCATATTTCCTGAAGTCTTAGATCTCTCAACGCAGCACCAGCAC
CAACACTTCGCAGTGTAAAAGGCCAAGTGCCGAGAGAGTATATATAGGAATAAAAAGTGACGTAAA
CGGGCAAAGTCCAAAAAACGCCCAGAAAAACCGCACGCGAACCTACGCCCCGAAACGAAAGCCAAA
AAACACTAGACACTCCCTTCCGGCGTCAACTTCCGCTTTCCCACGCTACGTCACTTGCCCCAGTCAAA
CAAACTACATATCCCGAACTTCCAAGTCGCCACGCCCAAAACACCGCCTACACCTCCCCGCCCGCCG
GCCCGCCCCCAAACCCGCCTCCCGCCCCGCGCCCCGCCCCGCGCCGCCCATCTCATTATCATATTGGC
TTCAATCCAAAATAAGGTATATTATTGATGATGGTTTAAACGGATCCAATTCTTGAAGACGAAAGGG
CCTCGTGATACGCCTATTTTTATAGGTTAATGTCATGATAATAATGGTTTCTTAGACGTCAGGTGGCA
CTTTTCGGGGAAATGTGCGCGGAACCCCTATTTGTTTATTTTTCTAAATACATTCAAATATGTATCCGC
TCATGAGACAATAACCCTGATAAATGCTTCAATAATATTGAAAAGGAAGAGTATGAGTATTCAACA
TTTCCGTGTCGCCCTTATTCCCTTTTTTGCGGCATTTTGCCTTCCTGTTTTTGCTCACCCAGAAACGCTG
GTGAAAGTAAAAGATGCTGAAGATCAGTTGGGTGCACGAGTGGGTTACATCGAACTGGATCTCAACA
GCGGTAAGATCCTTGAGAGTTTTCGCCCCGAAGAACGTTTTCCAATGATGAGCACTTTTAAAGTTCTG
```

```
CTATGTGGCGCGGTATTATCCCGTGTTGACGCCGGGCAAGAGCAACTCGGTCGCCGCATACACTATT

CTCAGAATGACTTGGTTGAGTACTCACCAGTCACAGAAAAGCATCTTACGGATGGCATGACAGTAAG

AGAATTATGCAGTGCTGCCATAACCATGAGTGATAACACTGCGGCCAACTTACTTCTGACAACGATC

GGAGGACCGAAGGAGCTAACCGCTTTTTTGCACAACATGGGGGATCATGTAACTCGCCTTGATCGTT

GGGAACCGGAGCTGAATGAAGCCATACCAAACGACGAGCGTGACACCACGATGCCTGTAGCAATGG

CAACAACGTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTGGTTTATTG

CTGATAAATCTGGAGCCGGTGAGCGTGGGTCTCGCGGTATCATTGCAGCACTGGGGCCAGATGGTAA

GCCCTCCCGTATCGTAGTTATCTACACGACGGGGAGTCAGGCAACTATGGATGAACGAAATAGACAG

ATCGCTGAGATAGGTGCCTCACTGATTAAGCATTGGTAACTGTCAGACCAAGTTTACTCATATATACT

TTAGATTGATTTAAAAGGATCTAGGTGAAGATCCTTTTTGATAATCTCATGACCAAAATCCCTTAACG

TGAGTTTTCGTTCCACTGAGCGTCAGACCCCGTAGAAAAGATCAAAGGATCTTCTTGAGATCCTTTTT

TTCTGCGCGTAATCTGCTGCTTGCAAACAAAAAAACCACCGCTACCAGCGGTGGTTTGTTTGCCGGAT

CAAGAGCTACCAACTCTTTTTCCGAAGGTAACTGGCTTCAGCAGAGCGCAGATACCAAATACTGTCC

TTCTAGTGTAGCCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTGGACTCAAGACG

ATAGTTACCGGATAAGGCGCAGCGGTCGGGCTGAACGGGGGGTTCGTGCACACAGCCCAGCTTGGA

GCGAACGACCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACGAGGGAGC

TTCCAGGGGGAAACGCCTGGTATCTTTATAGTCCTGTCGGGTTTCGCCACCTCTGACTTGAGCGTCGA

TTTTTGTGATGCTCGTCAGGGGGGCGGAGCCTATGGAAAAACGCCAGCAACGCGGCCTTTTTACGGT

TCCTGGCCTTTTGCTGGCCTTGAAGCTGTCCCTGATGGTCGTCATCTACCTGCCTGGACAGCATGGCC

TGCAACGCGGGCATCCCGATGCCGCCGGAAGCGAGAAGAATCATAATGGGGAAGGCCATCCAGCCT

CGCGTCGCAGATCCGAATTCGTTTAAAC
```

Polynucleotide sequence encoding ChAd155#1390 backbone construct       SEQ ID NO: 8

```
CATCATCAATAATATACCTTATTTTGGATTGAAGCCAATATGATAATGAGATGGGCGGCGCGGGGCG

GGGCGCGGGGCGGGAGGCGGGTTTGGGGCGGGCCGGCGGGCGGGCGGTGTGGCGGAAGTGGAC

TTTGTAAGTGTGGCGGATGTGACTTGCTAGTGCCGGGCGCGGTAAAAGTGACGTTTTCCGTGCGCGA

CAACGCCCCGGGAAGTGCATTTTTCCCGCGGTTTTTACCGGATGTTGTAGTGAATTTGGGCGTAAC

CAAGTAAGATTTGGCCATTTTCGCGGGAAAACTGAAACGGGGAAGTGAAATCTGATTAATTTTGCGT

TAGTCATACCGCGTAATATTTGTCTAGGGCGAGGGACTTTGGCCGATTACGTGGAGGACTCGCCCA

GGTGTTTTTTGAGGTGAATTTCCGCGTTCCGGGTCAAAGTCTGCGTTTTATTATTATAGGATATCCCAT

TGCATACGTTGTATCCATATCATAATATGTACATTTATATTGGCTCATGTCCAACATTACCGCCATGTT

GACATTGATTATTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAACGACCCCCGCCCAT

TGACGTCAATAATGACGTATGTTCCCATAGTAACGCCAATAGGGACTTTCCATTGACGTCAATGGGT

GGAGTATTTACGGTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCTTATGGGACTTTCC

TACTTGGCAGTACATCTACGTATTAGTCATCGCTATTACCATGGTGATGCGGTTTTGGCAGTACATCA

ATGGGCGTGGATAGCGGTTTGACTCACGGGGATTTCCAAGTCTCCACCCCATTGACGTCAATGGGAG

TTTGTTTTGGCACCAAAATCAACGGGACTTTCCAAAATGTCGTAACAACTCCGCCCCATTGACGCAAA
```

-continued

```
TGGGCGGTAGGCGTGTACGGTGGGAGGTCTATATAAGCAGAGCTCTCCCTATCAGTGATAGAGATCT
CCCTATCAGTGATAGAGATCGTCGACGAGCTCGTTTAGTGAACCGTCAGATCGCCTGGAGACGCCAT
CCACGCTGTTTTGACCTCCATAGAAGACACCGGGACCGATCCAGCCTCCGCGGCCGGGAACGGTGCA
TTGGAACGCGGATTCCCCGTGCCAAGAGTGAGATCTTCCGTTTATCTAGGTACCGGGCCCCCCCTCGA
GGTCGACGGTATCGATAAGCTTCACGCTGCCGCAAGCACTCAGGGCGCAAGGGCTGCTAAAGGAAG
CGGAACACGTAGAAAGCCAGTCCGCAGAAACGGTGCTGACCCCGGATGAATGTCAGCTACTGGGCT
ATCTGGACAAGGGAAAACGCAAGCGCAAAGAGAAAGCAGGTAGCTTGCAGTGGGCTTACATGGCGA
TAGCTAGACTGGGCGGTTTTATGGACAGCAAGCGAACCGGAATTGCCAGCTGGGGCGCCCTCTGGTA
AGGTTGGGAAGCCCTGCAAAGTAAACTGGATGGCTTTCTTGCCGCCAAGGATCTGATGGCGCAGGGG
ATCAAGATCTAACCAGGAGCTATTTAATGGCAACAGTTAACCAGCTGGTACGCAAACCACGTGCTCG
CAAAGTTGCGAAAAGCAACGTGCCTGCGCTGGAAGCATGCCCGCAAAAACGTGGCGTATGTACTCGT
GTATATACTACCACTCCTAAAAAACCGAACTCCGCGCTGCGTAAAGTATGCCGTGTTCGTCTGACTAA
CGGTTTCGAAGTGACTTCCTACATCGGTGGTGAAGGTCACAACCTGCAGGAGCACTCCGTGATCCTG
ATCCGTGGCGGTCGTGTTAAAGACCTCCCGGGTGTTCGTTACCACACCGTACGTGGTGCGCTTGACTG
CTCCGGCGTTAAAGACCGTAAGCAGGCTCGTTCCAAGTATGGCGTGAAGCGTCCTAAGGCTTAATGG
TAGATCTGATCAAGAGACAGGATGACGGTCGTTTCGCATGCTTGAACAAGATGGATTGCACGCAGGT
TCTCCGGCCGCTTGGGTGGAGAGGCTATTCGGCTATGACTGGGCACAACAGACAATCGGCTGCTCTG
ATGCCGCCGTGTTCCGGCTGTCAGCGCAGGGGCGCCCGGTTCTTTTTGTCAAGACCGACCTGTCCGGT
GCCCTGAATGAACTGCAGGACGAGGCAGCGCGGCTATCGTGGCTGGCCACGACGGGCGTTCCTTGCG
CAGCTGTGCTCGACGTTGTCACTGAAGCGGGAAGGGACTGGCTGCTATTGGGCGAAGTGCCGGGGCA
GGATCTCCTGTCATCTCACCTTGCTCCTGCCGAGAAAGTATCCATCATGGCTGATGCAATGCGGCGGC
TGCATACGCTTGATCCGGCTACCTGCCCATTCGACCACCAAGCGAAACATCGCATCGAGCGAGCACG
TACTCGGATGGAAGCCGGTCTTGTCGATCAGGATGATCTGGACGAAGAGCATCAGGGGCTCGCGCCA
GCCGAACTGTTCGCCAGGCTCAAGGCGCGCATGCCCGACGGCGAGGATCTCGTCGTGACCCATGGCG
ATGCCTGCTTGCCGAATATCATGGTGGAAAATGGCCGCTTTTCTGGATTCATCGACTGTGGCCGGCTG
GGTGTGGCGGACCGCTATCAGGACATAGCGTTGGCTACCCGTGATATTGCTGAAGAGCTTGGCGGCG
AATGGGCTGACCGCTTCCTCGTGCTTTACGGTATCGCCGCTCCCGATTCGCAGCGCATCGCCTTCTAT
CGCCTTCTTGACGAGTTCTTCTGAGCGGGACTCTGGGGTTCGAAATGACCGACCAAGCGACGCCCAA
CCTGCCATCACGAGATTTCGATTCCACCGCCGCCTTCTATGAAAGGTTGGGCTTCGGAATCGTTTTCC
GGGACGCCGGCTGGATGATCCTCCAGCGCGGGGATCTCATGCTGGAGTTCTTCGCCCACCCCGGGCT
CGATCCCCTCGGGGGGAATCAGAATTCAGTCGACAGCGGCCGCGATCTGCTGTGCCTTCTAGTTGCC
AGCCATCTGTTGTTTGCCCCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTGGGGATGCGGTGGGCT
CTATGGCCGATCAGCGATCGCTGAGGTGGGTGAGTGGGCGTGGCCTGGGGTGGTCATGAAAATATAT
AAGTTGGGGGTCTTAGGGTCTCTTTATTTGTGTTGCAGAGACCGCCGGAGCCATGAGCGGGAGCAGC
AGCAGCAGCAGTAGCAGCAGCGCCTTGGATGGCAGCATCGTGAGCCCTTATTTGACGACGCGGATGC
CCCACTGGGCCGGGGTGCGTCAGAATGTGATGGGCTCCAGCATCGACGGCCGACCCGTCCTGCCCGC
AAATTCCGCCACGCTGACCTATGCGACCGTCGCGGGACGCCGTTGGACGCCACCGCCGCCGCCGCC
GCCACCGCAGCCGCCTCGGCCGTGCGCAGCCTGGCCACGGACTTTGCATTCCTGGGACCACTGGCGA
```

-continued

```
CAGGGGCTACTTCTCGGGCCGCTGCTGCCGCCGTTCGCGATGACAAGCTGACCGCCCTGCTGGCGCA
GTTGGATGCGCTTACTCGGGAACTGGGTGACCTTTCTCAGCAGGTCATGGCCCTGCGCCAGCAGGTCT
CCTCCCTGCAAGCTGGCGGGAATGCTTCTCCCACAAATGCCGTTTAAGATAAATAAAACCAGACTCT
GTTTGGATTAAAGAAAAGTAGCAAGTGCATTGCTCTCTTTATTTCATAATTTTCCGCGCGCGATAGGC
CCTAGACCAGCGTTCTCGGTCGTTGAGGGTGCGGTGTATCTTCTCCAGGACGTGGTAGAGGTGGCTCT
GGACGTTGAGATACATGGGCATGAGCCCGTCCCGGGGGTGGAGGTAGCACCACTGCAGAGCTTCATG
CTCCGGGGTGGTGTTGTAGATGATCCAGTCGTAGCAGGAGCGCTGGGCATGGTGCCTAAAAATGTCC
TTCAGCAGCAGGCCGATGGCCAGGGGGAGGCCCTTGGTGTAAGTGTTTACAAAACGGTTAAGTTGGG
AAGGGTGCATTCGGGGAGAGATGATGTGCATCTTGGACTGTATTTTTAGATTGGCGATGTTTCCGCCC
AGATCCCTTCTGGGATTCATGTTGTGCAGGACCACCAGTACAGTGTATCCGGTGCACTTGGGGAATTT
GTCATGCAGCTTAGAGGGAAAAGCGTGGAAGAACTTGGAGACGCCTTTGTGGCCTCCCAGATTTTCC
ATGCATTCGTCCATGATGATGGCAATGGGCCCGCGGGAGGCAGCTTGGGCAAAGATATTTCTGGGGT
CGCTGACGTCGTAGTTGTGTTCCAGGGTGAGGTCGTCATAGGCCATTTTTACAAAGCGCGGGCGGAG
GGTGCCCGACTGGGGGATGATGGTCCCCTCTGGCCCTGGGGCGTAGTTGCCCTCGCAGATCTGCATTT
CCCAGGCCTTAATCTCGGAGGGGGGAATCATATCCACCTGCGGGGCGATGAAGAAAACGGTTTCCGG
AGCCGGGGAGATTAACTGGGATGAGAGCAGGTTTCTAAGCAGCTGTGATTTTCCACAACCGGTGGGC
CCATAAATAACACCTATAACCGGTTGCAGCTGGTAGTTTAGAGAGCTGCAGCTGCCGTCGTCCCGGA
GGAGGGGGCCACCTCGTTGAGCATGTCCCTGACGCGCATGTTCTCCCCGACCAGATCCGCCAGAAG
GCGCTCGCCGCCCAGGGACAGCAGCTCTTGCAAGGAAGCAAAGTTTTTCAGCGGCTTGAGGCCGTCC
GCCGTGGGCATGTTTTTCAGGGTCTGGCTCAGCAGCTCCAGGCGGTCCCAGAGCTCGGTGACGTGCT
CTACGGCATCTCTATCCAGCATATCTCCTCGTTTCGCGGGTTGGGGCGACTTTCGCTGTAGGGCACCA
AGCGGTGGTCGTCCAGCGGGGCCAGAGTCATGTCCTTCCATGGGCGCAGGGTCCTCGTCAGGGTGGT
CTGGGTCACGGTGAAGGGGTGCGCTCCGGGCTGAGCGCTTGCCAAGGTGCGCTTGAGGCTGGTTCTG
CTGGTGCTGAAGCGCTGCCGGTCTTCGCCCTGCGCGTCGGCCAGGTAGCATTTGACCATGGTGTCATA
GTCCAGCCCCTCCGCGCGTGTCCCTTGGCGCGCAGCTTGCCCTTGGAGGTGGCGCCGCACGAGGGG
CAGAGCAGGCTCTTGAGCGCGTAGAGCTTGGGGGCGAGGAAGACCGATTCGGGGAGTAGGCGTCC
GCGCCGCAGACCCCGCACACGGTCTCGCACTCCACCAGCCAGGTGAGCTCGGGGCGCGCCGGGTCAA
AAACCAGGTTTCCCCCATGCTTTTTGATGCGTTTCTTACCTCGGGTCTCCATGAGGTGGTGTCCCCGCT
CGGTGACGAAGAGGCTGTCCGTGTCTCCGTAGACCGACTTGAGGGGTCTTTTCTCCAGGGGGTCCC
TCGGTCTTCCTCGTAGAGGAACTCGGACCACTCTGAGACGAAGGCCCGCGTCCAGGCCAGGACGAAG
GAGGCTATGTGGGAGGGGTAGCGGTCGTTGTCCACTAGGGGGTCCACCTTCTCCAAGGTGTGAAGAC
ACATGTCGCCTTCCTCGGCGTCCAGGAAGGTGATTGGCTTGTAGGTGTAGGCCACGTGACCGGGGGT
TCCTGACGGGGGGGTATAAAAGGGGGTGGGGGCGCGCTCGTCGTCACTCTCTTCCGCATCGCTGTCT
GCGAGGGCCAGCTGCTGGGGTGAGTATTCCCTCTCGAAGGCGGGCATGACCTCCGCGCTGAGGTTGT
CAGTTTCCAAAAACGAGGAGGATTTGATGTTCACCTGTCCCGAGGTGATACCTTTGAGGGTACCCGC
GTCCATCTGGTCAGAAAACACGATCTTTTATTGTCCAGCTTGGTGGCGAACGACCCGTAGAGGGCG
TTGGAGAGCAGCTTGGCGATGGAGCGCAGGGTCTGGTTCTTGTCCCTGTCGGCGCGCTCCTTGGCCGC
GATGTTGAGCTGCACGTACTCGCGCGCGACGCAGCGCCACTCGGGGAAGACGGTGGTGCGCTCGTCG
GGCACCAGGCGCACGCGCCAGCCGCGGTTGTGCAGGGTGACCAGGTCCACGCTGGTGGCGACCTCGC
CGCGCAGGCGCTCGTTGGTCCAGCAGAGACGGCCGCCCTTGCGCGAGCAGAAGGGGGGCAGGGGT
CGAGCTGGGTCTCGTCCGGGGGGTCCGCGTCCACGGTGAAAACCCCGGGGCGCAGGCGCGCGTCGA
```

```
AGTAGTCTATCTTGCAACCTTGCATGTCCAGCGCCTGCTGCCAGTCGCGGGCGGCGAGCGCGCGCTC
GTAGGGGTTGAGCGGCGGGCCCCAGGGCATGGGGTGGGTGAGTGCGGAGGCGTACATGCCGCAGAT
GTCATAGACGTAGAGGGGCTCCCGCAGGACCCCGATGTAGGTGGGGTAGCAGCGGCCGCCGCGGAT
GCTGGCGCGCACGTAGTCATACAGCTCGTGCGAGGGGGCGAGGAGGTCGGGGCCCAGGTTGGTGCG
GGCGGGGCGCTCCGCGCGGAAGACGATCTGCCTGAAGATGGCATGCGAGTTGGAAGAGATGGTGGG
GCGCTGGAAGACGTTGAAGCTGGCGTCCTGCAGGCCGACGGCGTCGCGCACGAAGGAGGCGTAGGA
GTCGCGCAGCTTGTGTACCAGCTCGGCGGTGACCTGCACGTCGAGCGCGCAGTAGTCGAGGGTCTCG
CGGATGATGTCATATTTAGCCTGCCCCTTCTTTTTCCACAGCTCGCGGTTGAGGACAAACTCTTCGCG
GTCTTTCCAGTACTCTTGGATCGGGAAACCGTCCGGTTCCGAACGGTAAGAGCCTAGCATGTAGAAC
TGGTTGACGGCCTGGTAGGCGCAGCAGCCCTTCTCCACGGGGAGGGCGTAGGCCTGCGCGGCCTTGC
GGAGCGAGGTGTGGGTCAGGGCGAAGGTGTCCCTGACCATGACTTTGAGGTACTGGTGCTTGAAGTC
GGAGTCGTCGCAGCCGCCCCGCTCCCAGAGCGAGAAGTCGGTGCGCTTCTTGGAGCGGGGGTTGGGC
AGAGCGAAGGTGACATCGTTGAAGAGGATTTTGCCCGCGCGGGGCATGAAGTTGCGGGTGATGCGG
AAGGGCCCCGGCACTTCAGAGCGGTTGTTGATGACCTGGGCGGCGAGCACGATCTCGTCGAAGCCGT
TGATGTTGTGGCCCACGATGTAGAGTTCCAGGAAGCGGGGCCGGCCCTTTACGGTGGGCAGCTTCTT
TAGCTCTTCGTAGGTGAGCTCCTCGGGCGAGGCGAGGCCGTGCTCGGCCAGGGCCCAGTCCGCGAGG
TGCGGGTTGTCTCTGAGGAAGGACTTCCAGAGGTCGCGGGCCAGGAGGGTCTGCAGGCGGTCTCTGA
AGGTCCTGAACTGGCGGCCCACGGCCATTTTTTCGGGGGTGATGCAGTAGAAGGTGAGGGGGTCTTG
CTGCCAGCGGTCCCAGTCGAGCTGCAGGGCGAGGTCGCGCGCGGCGGTGACCAGGCGCTCGTCGCCC
CCGAATTTCATGACCAGCATGAAGGGCACGAGCTGCTTTCCGAAGGCCCCCATCCAAGTGTAGGTCT
CTACATCGTAGGTGACAAAGAGGCGCTCCGTGCGAGGATGCGAGCCGATCGGGAAGAACTGGATCT
CCCGCCACCAGTTGGAGGAGTGGCTGTTGATGTGGTGGAAGTAGAAGTCCCGTCGCCGGGCCGAACA
CTCGTGCTGGCTTTTGTAAAAGCGAGCGCAGTACTGGCAGCGCTGCACGGGCTGTACCTCATGCACG
AGATGCACCTTTCGCCCGCGCACGAGGAAGCCGAGGGGAAATCTGAGCCCCCCGCCTGGCTCGCGGC
ATGGCTGGTTCTCTTCTACTTTGGATGCGTGTCCGTCTCCGTCTGGCTCCTCGAGGGGTGTTACGGTG
GAGCGGACCACCACGCCGCGCGAGCCGCAGGTCCAGATATCGGCGCGCGGCGGTCGGAGTTTGATG
ACGACATCGCGCAGCTGGGAGCTGTCCATGGTCTGGAGCTCCCGCGGCGGCGGCAGGTCAGCCGGG
AGTTCTTGCAGGTTCACCTCGCAGAGTCGGGCCAGGGCGCGGGGCAGGTCTAGGTGGTACCTGATCT
CTAGGGGCGTGTTGGTGGCGGCGTCGATGGCTTGCAGGAGCCCGCAGCCCCGGGGGGCGACGACGG
TGCCCCGCGGGGTGGTGGTGGTGGCGGTGCAGCTCAGAAGCGGTGCCGCGGGCGGGCCCCCGG
AGGTAGGGGGGGCTCCGGTCCCGCGGGCAGGGGCGGCAGCGGCACGTCGGCGTGGAGCGCGGGCAG
GAGTTGGTGCTGTGCCCGGAGGTTGCTGGCGAAGGCGACGACGCGGCGGTTGATCTCCTGGATCTGG
CGCCTCTGCGTGAAGACGACGGGCCCGGTGAGCTTGAACCTGAAAGAGAGTTCGACAGAATCAATCT
CGGTGTCATTGACCGCGGCCTGGCGCAGGATCTCCTGCACGTCTCCCGAGTTGTCTTGGTAGGCGATC
TCGGCCATGAACTGCTCGATCTCTTCCTCCTGGAGGTCTCCGCGTCCGGCGCGTTCCACGGTGGCCGC
CAGGTCGTTGGAGATGCGCCCCATGAGCTGCGAGAAGGCGTTGAGTCCGCCCTCGTTCCAGACTCGG
CTGTAGACCACGCCCCCCTGGTCATCGCGGGCGCGCATGACCACCTGCGCGAGGTTGAGCTCCACGT
GCCGCGCGAAGACGGCGTAGTTGCGCAGACGCTGGAAGAGGTAGTTGAGGGTGGTGGCGGTGTGCT
CGGCCACGAAGAAGTTCATGACCCAGCGGCGCAACGTGGATTCGTTGATGTCCCCCAAGGCCTCCAG
CCGTTCCATGGCCTCGTAGAAGTCCACGGCGAAGTTGAAAAACTGGGAGTTGCGCGCCGACACGGTC
```

-continued

```
AACTCCTCCTCCAGAAGACGGATGAGCTCGGCGACGGTGTCGCGCACCTCGCGCTCGAAGGCTATGG
GGATCTCTTCCTCCGCTAGCATCACCACCTCCTCCTCTTCCTCCTCTTCTGGCACTTCCATGATGGCTT
CCTCCTCTTCGGGGGGTGGCGGCGGCGGCGGTGGGGGAGGGGGCGCTCTGCGCCGGCGGCGGCGCA
CCGGGAGGCGGTCCACGAAGCGCGCGATCATCTCCCCGCGGCGGCGGCGCATGGTCTCGGTGACGGC
GCGGCCGTTCTCCCGGGGGCGCAGTTGGAAGACGCCGCCGGACATCTGGTGCTGGGGCGGGTGGCCG
TGAGGCAGCGAGACGGCGCTGACGATGCATCTCAACAATTGCTGCGTAGGTACGCCGCCGAGGGAC
CTGAGGGAGTCCATATCCACCGGATCCGAAAACCTTTCGAGGAAGGCGTCTAACCAGTCGCAGTCGC
AAGGTAGGCTGAGCACCGTGGCGGGCGGCGGGGGGTGGGGGGAGTGTCTGGCGGAGGTGCTGCTGA
TGATGTAATTGAAGTAGGCGGACTTGACACGGCGGATGGTCGACAGGAGCACCATGTCCTTGGGTCC
GGCCTGCTGGATGCGGAGGCGGTCGGCTATGCCCCAGGCTTCGTTCTGGCATCGGCGCAGGTCCTTG
TAGTAGTCTTGCATGAGCCTTTCCACCGGCACCTCTTCTCCTTCCTCTTCTGCTTCTTCCATGTCTGCTT
CGGCCCTGGGGCGGCGCCGCGCCCCCTGCCCCCCATGCGCGTGACCCCGAACCCCCTGAGCGGTTG
GAGCAGGGCCAGGTCGGCGACGACGCGCTCGGCCAGGATGGCCTGCTGCACCTGCGTGAGGGTGGT
TTGGAAGTCATCCAAGTCCACGAAGCGGTGGTAGGCGCCCGTGTTGATGGTGTAGGTGCAGTTGGCC
ATGACGGACCAGTTGACGGTCTGGTGGCCCGGTTGCGACATCTCGGTGTACCTGAGTCGCGAGTAGG
CGCGGGAGTCGAAGACGTAGTCGTTGCAAGTCCGCACCAGGTACTGGTAGCCCACCAGGAAGTGCG
GCGGCGGCTGGCGGTAGAGGGGCCAGCGCAGGGTGGCGGGGGCTCCGGGGGCCAGGTCTTCCAGCA
TGAGGCGGTGGTAGGCGTAGATGTACCTGGACATCCAGGTGATACCCGCGGCGGTGGTGGAGGCGC
GCGGGAAGTCGCGCACCCGGTTCCAGATGTTGCGCAGGGGCAGAAAGTGCTCCATGGTAGGCGTGCT
CTGTCCAGTCAGACGCGCGCAGTCGTTGATACTCTAGACCAGGGAAAACGAAAGCCGGTCAGCGGG
CACTCTTCCGTGGTCTGGTGAATAGATCGCAAGGGTATCATGGCGGAGGGCCTCGGTTCGAGCCCCG
GGTCCGGGCCGGACGGTCCGCCATGATCCACGCGGTTACCGCCCGCGTGTCGAACCCAGGTGTGCGA
CGTCAGACAACGGTGGAGTGTTCCTTTTGGCGTTTTTCTGGCCGGGCGCCGGCGCCGCGTAAGAGAC
TAAGCCGCGAAAGCGAAAGCAGTAAGTGGCTCGCTCCCCGTAGCCGGAGGGATCCTTGCTAAGGGTT
GCGTTGCGGCGAACCCCGGTTCGAATCCCGTACTCGGGCCGGCCGGACCCGCGGCTAAGGTGTTGGA
TTGGCCTCCCCCTCGTATAAAGACCCCGCTTGCGGATTGACTCCGGACACGGGGACGAGCCCCTTTTA
TTTTTGCTTTCCCCAGATGCATCCGGTGCTGCGGCAGATGCGCCCCCGCCCCAGCAGCAGCAACAAC
ACCAGCAAGAGCGGCAGCAACAGCAGCGGGAGTCATGCAGGGCCCCCTCACCCACCCTCGGCGGGC
CGGCCACCTCGGCGTCCGCGGCCGTGTCTGGCGCCTGCGGCGGCGGCGGGGGCCGGCTGACGACCC
CGAGGAGCCCCGCGGCGCAGGGCCAGACACTACCTGGACCTGGAGGAGGGCGAGGGCCTGGCGCG
GCTGGGGGCGCCGTCTCCCGAGCGCCACCCGCGGGTGCAGCTGAAGCGCGACTCGCGCGAGGCGTA
CGTGCCTCGGCAGAACCTGTTCAGGGACCGCGCGGGCGAGGAGCCCGAGGAGATGCGGGACAGGAG
GTTCAGCGCAGGGCGGGAGCTGCGGCAGGGGCTGAACCGCGAGCGGCTGCTGCGCGAGGAGGACTT
TGAGCCCGACGCGCGGACGGGGATCAGCCCCGCGCGCGCACGTGGCGGCCGCCGACCTGGTGAC
GGCGTACGAGCAGACGGTGAACCAGGAGATCAACTTCCAAAAGAGTTTCAACAACCACGTGCGCAC
GCTGGTGGCGCGCGAGGAGGTGACCATCGGGCTGATGCACCTGTGGGACTTTGTAAGCGCGCTGGTG
CAGAACCCCAACAGCAAGCCTCTGACGGCGCAGCTGTTCCTGATAGTGCAGCACAGCAGGGACAAC
GAGGCGTTTAGGGACGCGCTGCTGAACATCACCGAGCCCGAGGGTCGGTGGCTGCTGGACCTGATTA
ACATCCTGCAGAGCATAGTGGTGCAGGAGCGCAGCCTGAGCCTGGCCGACAAGGTGGCGGCCATCA
ACTACTCGATGCTGAGCCTGGGCAAGTTTTACGCGCGCAAGATCTACCAGACGCCGTACGTGCCCAT
AGACAAGGAGGTGAAGATCGACGGTTTTTACATGCGCATGGCGCTGAAGGTGCTCACCCTGAGCGAC
```

-continued

```
GACCTGGGCGTGTACCGCAACGAGCGCATCCACAAGGCCGTGAGCGTGAGCCGGCGGCGCGAGCTG

AGCGACCGCGAGCTGATGCACAGCCTGCAGCGGGCGCTGGCGGGCGCCGGCAGCGGCGACAGGGAG

GCGGAGTCCTACTTCGATGCGGGGGCGGACCTGCGCTGGGCGCCCAGCCGGCGGGCCCTGGAGGCC

GCGGGGGTCCGCGAGGACTATGACGAGGACGGCGAGGAGGATGAGGAGTACGAGCTAGAGGAGGG

CGAGTACCTGGACTAAACCGCGGGTGGTGTTTCCGGTAGATGCAAGACCCGAACGTGGTGGACCCGG

CGCTGCGGGCGGCTCTGCAGAGCCAGCCGTCCGGCCTTAACTCCTCAGACGACTGGCGACAGGTCAT

GGACCGCATCATGTCGCTGACGGCGCGTAACCCGGACGCGTTCCGGCAGCAGCCGCAGGCCAACAG

GCTCTCCGCCATCCTGGAGGCGGTGGTGCCTGCGCGCTCGAACCCCACGCACGAGAAGGTGCTGGCC

ATAGTGAACGCGCTGGCCGAGAACAGGGCCATCCGCCCGGACGAGGCCGGGCTGGTGTACGACGCG

CTGCTGCAGCGCGTGGCCCGCTACAACAGCGGCAACGTGCAGACCAACCTGGACCGGCTGGTGGGG

GACGTGCGCGAGGCGGTGGCGCAGCGCGAGCGCGCGGATCGGCAGGGCAACCTGGGCTCCATGGTG

GCGCTGAATGCCTTCCTGAGCACGCAGCCGGCCAACGTGCCGCGGGGGCAGGAAGACTACACCAAC

TTTGTGAGCGCGCTGCGGCTGATGGTGACCGAGACCCCCCAGAGCGAGGTGTACCAGTCGGGCCCGG

ACTACTTCTTCCAGACCAGCAGACAGGGCCTGCAGACGGTGAACCTGAGCCAGGCTTTCAAGAACCT

GCGGGGGCTGTGGGGCGTGAAGGCGCCCACCGGCGACCGGGCGACGGTGTCCAGCCTGCTGACGCC

CAACTCGCGCCTGCTGCTGCTGCTGATCGCGCCGTTCACGGACAGCGGCAGCGTGTCCCGGGACACC

TACCTGGGGCACCTGCTGACCCTGTACCGCGAGGCCATCGGGCAGGCGCAGGTGGACGAGCACACCT

TCCAGGAGATCACCAGCGTGAGCCGCGCGCTGGGGCAGGAGGACACGAGCAGCCTGGAGGCGACTC

TGAACTACCTGCTGACCAACCGGCGGCAGAAGATTCCCTCGCTGCACAGCCTGACCTCCGAGGAGGA

GCGCATCTTGCGCTACGTGCAGCAGAGCGTGAGCCTGAACCTGATGCGCGACGGGGTGACGCCCAGC

GTGGCGCTGGACATGACCGCGCGCAACATGGAACCGGGCATGTACGCCGCGCACCGGCCTTACATCA

ACCGCCTGATGGACTACCTGCATCGCGCGGCGGCCGTGAACCCCGAGTACTTTACCAACGCCATCCT

GAACCCGCACTGGCTCCCGCCGCCCGGGTTCTACAGCGGGGCTTCGAGGTCCCGGAGACCAACGAT

GGCTTCCTGTGGGACGACATGGACGACAGCGTGTTCTCCCCGCGGCCGCAGGCGCTGGCGGAAGCGT

CCCTGCTGCGTCCCAAGAAGGAGGAGGAGGAGGAGGCGAGTCGCCGCCGCGGCAGCAGCGGCGTGG

CTTCTCTGTCCGAGCTGGGGCGGCAGCCGCCGCGCGCCCCGGGTCCCTGGGCGGCAGCCCCTTTCC

GAGCCTGGTGGGGTCTCTGCACAGCGAGCGCACCACCCGCCCTCGGCTGCTGGGCGAGGACGAGTAC

CTGAATAACTCCCTGCTGCAGCCGGTGCGGGAGAAAAACCTGCCTCCCGCCTTCCCCAACAACGGGA

TAGAGAGCCTGGTGGACAAGATGAGCAGATGGAAGACCTATGCGCAGGAGCACAGGGACGCGCCTG

CGCTCCGGCCGCCCACGCGGCGCCAGCGCCACGACCGGCAGCGGGGCTGGTGTGGGATGACGAGG

ACTCCGCGGACGATAGCAGCGTGCTGGACCTGGGAGGGAGCGGCAACCCGTTCGCGCACCTGCGCCC

CCGCCTGGGGAGGATGTTTTAAAAAAAAAAAAAAAAAAGCAAGAAGCATGATGCAAAAATTAAATAA

AACTCACCAAGGCCATGGCGACCGAGCGTTGGTTTCTTGTGTTCCCTTCAGTATGCGGCGCGCGGCG

ATGTACCAGGAGGGACCTCCTCCCTCTTACGAGAGCGTGGTGGGCGCGGCGGCGGCGGCGCCCTCTT

CTCCCTTTGCGTCGCAGCTGCTGGAGCCGCCGTACGTGCCTCCGCGCTACCTGCGGCCTACGGGGGG

GAGAAACAGCATCCGTTACTCGGAGCTGGCGCCCCTGTTCGACACCACCCGGGTGTACCTGGTGGAC

AACAAGTCGGCGGACGTGGCCTCCCTGAACTACCAGAACGACCACAGCAATTTTTTGACCACGGTCA

TCCAGAACAATGACTACAGCCCGAGCGAGGCCAGCACCCAGACCATCAATCTGGATGACCGGTCGC

ACTGGGGCGGCGACCTGAAAACCATCCTGCACACCAACATGCCCAACGTGAACGAGTTCATGTTCAC

CAATAAGTTCAAGGCGCGGGTGATGGTGTCGCGCTCGCACACCAAGGAAGACCGGGTGGAGCTGAA
```

-continued

```
GTACGAGTGGGTGGAGTTCGAGCTGCCAGAGGGCAACTACTCCGAGACCATGACCATTGACCTGATG

AACAACGCGATCGTGGAGCACTATCTGAAAGTGGGCAGGCAGAACGGGGTCCTGGAGAGCGACATC

GGGGTCAAGTTCGACACCAGGAACTTCCGCCTGGGGCTGGACCCCGTGACCGGGCTGGTTATGCCCG

GGGTGTACACCAACGAGGCCTTCCATCCCGACATCATCCTGCTGCCCGGCTGCGGGGTGGACTTCAC

TTACAGCCGCCTGAGCAACCTCCTGGGCATCCGCAAGCGGCAGCCCTTCCAGGAGGGCTTCAGGATC

ACCTACGAGGACCTGGAGGGGGGCAACATCCCCGCGCTCCTCGATGTGGAGGCCTACCAGGATAGCT

TGAAGGAAAATGAGGCGGGACAGGAGGATACCGCCCCCGCCGCCTCCGCCGCCGCCGAGCAGGGCG

AGGATGCTGCTGACACCGCGGCCGCGGACGGGGCAGAGGCCGACCCCGCTATGGTGGTGGAGGCTC

CCGAGCAGGAGGAGGACATGAATGACAGTGCGGTGCGCGGAGACACCTTCGTCACCCGGGGGGAGG

AAAAGCAAGCGGAGGCCGAGGCCGCGGCCGAGGAAAAGCAACTGGCGGCAGCAGCGGCGGCGGCG

GCGTTGGCCGCGGCGGAGGCTGAGTCTGAGGGGACCAAGCCCGCCAAGGAGCCCGTGATTAAGCCC

CTGACCGAAGATAGCAAGAAGCGCAGTTACAACCTGCTCAAGGACAGCACCAACACCGCGTACCGC

AGCTGGTACCTGGCCTACAACTACGGCGACCCGTCGACGGGGGTGCGCTCCTGGACCCTGCTGTGCA

CGCCGGACGTGACCTGCGGCTCGGAGCAGGTGTACTGGTCGCTGCCCGACATGATGCAAGACCCCGT

GACCTTCCGCTCCACGCGGCAGGTCAGCAACTTCCCGGTGGTGGGCGCCGAGCTGCTGCCCGTGCAC

TCCAAGAGCTTCTACAACGACCAGGCCGTCTACTCCCAGCTCATCCGCCAGTTCACCTCTCTGACCCA

CGTGTTCAATCGCTTTCCTGAGAACCAGATTCTGGCGCGCCCGCCCGCCCCCACCATCACCACCGTCA

GTGAAAACGTTCCTGCTCTCACAGATCACGGGACGCTACCGCTGCGCAACAGCATCGGAGGAGTCCA

GCGAGTGACCGTTACTGACGCCAGACGCCGCACCTGCCCCTACGTTTACAAGGCCTTGGGCATAGTC

TCGCCGCGCGTCCTTTCCAGCCGCACTTTTTGAGCAACACCACCATCATGTCCATCCTGATCTCACCC

AGCAATAACTCCGGCTGGGGACTGCTGCGCGCGCCCAGCAAGATGTTCGGAGGGGCGAGGAAGCGT

TCCGAGCAGCACCCCGTGCGCGTGCGCGGGCACTTCCGCGCCCCCTGGGGAGCGCACAAACGCGGCC

GCGCGGGGCGCACCACCGTGGACGACGCCATCGACTCGGTGGTGGAGCAGGCGCGCAACTACAGGC

CCGCGGTCTCTACCGTGGACGCGGCCATCCAGACCGTGGTGCGGGCGCGCGGCGGTACGCCAAGCT

GAAGAGCCGCCGGAAGCGCGTGGCCCGCCGCCACCGCCGCCGACCCGGGGCCGCCGCCAAACGCGC

CGCCGCGGCCCTGCTTCGCCGGGCCAAGCGCACGGGCCGCCGCGCCGCCATGAGGGCCGCGCGCCGC

TTGGCCGCCGGCATCACCGCCGCCACCATGGCCCCCCGTACCCGAAGACGCGCGGCCGCCGCCGCCG

CCGCCGCCATCAGTGACATGGCCAGCAGGCGCCGGGGCAACGTGTACTGGGTGCGCGACTCGGTGAC

CGGCACGCGCGTGCCCGTGCGCTTCCGCCCCCCGCGGACTTGAGATGATGTGAAAAAACAACACTGA

GTCTCCTGCTGTTGTGTGTATCCCAGCGGCGGCGGCGCGCAGCGTCATGTCCAAGCGCAAAATCA

AAGAAGAGATGCTCCAGGTCGTCGCGCCGGAGATCTATGGGCCCCCGAAGAAGGAAGAGCAGGATT

CGAAGCCCCGCAAGATAAAGCGGGTCAAAAAGAAAAAGAAAGATGATGACGATGCCGATGGGGAG

GTGGAGTTCCTGCGCGCCACGCGCCCCAGGCGCCCGGTGCAGTGGAAGGGCCGGCGCGTAAAGCGC

GTCCTGCGCCCCGGCACCGCGGTGGTCTTCACGCCCGGCGAGCGCTCCACCCGGACTTTCAAGCGCG

TCTATGACGAGGTGTACGGCGACGAAGACCTGCTGGAGCAGGCCAACGAGCGCTTCGGAGAGTTTGC

TTACGGGAAGCGTCAGCGGGCGCTGGGGAAGGAGGACCTGCTGGCGCTGCCGCTGGACCAGGGCAA

CCCCACCCCCAGTCTGAAGCCCGTGACCCTGCAGCAGGTGCTGCCGAGCAGCGCACCCTCCGAGGCG

AAGCGGGGTCTGAAGCGCGAGGGCGGCGACCTGGCGCCCACCGTGCAGCTCATGGTGCCCAAGCGG

CAGAGGCTGGAGGATGTGCTGGAGAAAATGAAAGTAGACCCCGGTCTGCAGCCGGACATCAGGGTC

CGCCCCATCAAGCAGGTGGCGCCGGGCCTCGGCGTGCAGACCGTGGACGTGGTCATCCCCACCGGCA

ACTCCCCCGCCGCCGCCACCACTACCGCTGCCTCCACGGACATGGAGACACAGACCGATCCCGCCGC
```

-continued

```
AGCCGCAGCCGCAGCCGCCGCCGCGACCTCCTCGGCGGAGGTGCAGACGGACCCCTGGCTGCCGCCG
GCGATGTCAGCTCCCCGCGCGCGTCGCGGGCGCAGGAAGTACGGCGCCGCCAACGCGCTCCTGCCCG
AGTACGCCTTGCATCCTTCCATCGCGCCCACCCCCGGCTACCGAGGCTATACCTACCGCCCGCGAAG
AGCCAAGGGTTCCACCCGCCGTCCCCGCCGACGCGCCGCCGCCACCACCCGCCGCCGCCGCCGCAGA
CGCCAGCCCGCACTGGCTCCAGTCTCCGTGAGGAAAGTGGCGCGCGACGGACACACCCTGGTGCTGC
CCAGGGCGCGCTACCACCCCAGCATCGTTTAAAAGCCTGTTGTGGTTCTTGCAGATATGGCCCTCACT
TGCCGCCTCCGTTTCCCGGTGCCGGGATACCGAGGAGGAAGATCGCGCCGCAGGAGGGGTCTGGCCG
GCCGCGGCCTGAGCGGAGGCAGCCGCCGCGCGCACCGGCGGCGACGCGCCACCAGCCGACGCATGC
GCGGCGGGGTGCTGCCCCTGTTAATCCCCCTGATCGCCGCGGCGATCGGCGCCGTGCCCGGGATCGC
CTCCGTGGCCTTGCAAGCGTCCCAGAGGCATTGACAGACTTGCAAACTTGCAAATATGGAAAAAAAA
ACCCCAATAAAAAAGTCTAGACTCTCACGCTCGCTTGGTCCTGTGACTATTTTGTAGAATGGAAGAC
ATCAACTTTGCGTCGCTGGCCCCGCGTCACGGCTCGCGCCCGTTCCTGGGACACTGGAACGATATCG
GCACCAGCAACATGAGCGGTGGCGCCTTCAGTTGGGGCTCTCTGTGGAGCGGCATTAAAAGTATCGG
GTCTGCCGTTAAAAATTACGGCTCCCGGGCCTGGAACAGCAGCACGGGCCAGATGTTGAGAGACAA
GTTGAAAGAGCAGAACTTCCAGCAGAAGGTGGTGGAGGGCCTGGCCTCCGGCATCAACGGGGTGGT
GGACCTGGCCAACCAGGCCGTGCAGAATAAGATCAACAGCAGACTGGACCCCCGGCCGCCGGTGGA
GGAGGTGCCGCCGGCGCTGGAGACGGTGTCCCCCGATGGGCGTGGCGAGAAGCGCCCGCGGCCCGA
TAGGGAAGAGACCACTCTGGTCACGCAGACCGATGAGCCGCCCCCGTATGAGGAGGCCCTGAAGCA
AGGTCTGCCCACCACGCGGCCCATCGCGCCCATGGCCACCGGGGTGGTGGGCCGCCACACCCCCGCC
ACGCTGGACTTGCCTCCGCCCGCCGATGTGCCGCAGCAGCAGAAGGCGGCACAGCCGGGCCCGCCCG
CGACCGCCTCCCGTTCCTCCGCCGGTCCTCTGCGCCGCGCGGCCAGCGGCCCCCGCGGGGGGTCGC
GAGGCACGGCAACTGGCAGAGCACGCTGAACAGCATCGTGGGTCTGGGGGTGCGGTCCGTGAAGCG
CCGCCGATGCTACTGAATAGCTTAGCTAACGTGTTGTATGTGTGTATGCGCCCTATGTCGCCGCCAGA
GGAGCTGCTGAGTCGCCGCCGTTCGCGCGCCCACCACCACCGCCACTCCGCCCCTCAAGATGGCGAC
CCCATCGATGATGCCGCAGTGGTCGTACATGCACATCTCGGGCCAGGACGCCTCGGAGTACCTGAGC
CCCGGGCTGGTGCAGTTCGCCCGCGCCACCGAGAGCTACTTCAGCCTGAGTAACAAGTTTAGGAACC
CCACGGTGGCGCCCACGCACGATGTGACCACCGACCGGTCTCAGCGCCTGACGCTGCGGTTCATTCC
CGTGGACCGCGAGGACACCGCGTACTCGTACAAGGCGCGGTTCACCCTGGCCGTGGGCGACAACCGC
GTGCTGGACATGGCCTCCACCTACTTTGACATCCGCGGGGTGCTGGACCGGGGTCCCACTTTCAAGCC
CTACTCTGGCACCGCCTACAACTCCCTGGCCCCCAAGGGCGCTCCCAACTCCTGCGAGTGGGAGCAA
GAGGAAACTCAGGCAGTTGAAGAAGCAGCAGAAGAGGAAGAAGAAGATGCTGACGGTCAAGCTGA
GGAAGAGCAAGCAGCTACCAAAAAGACTCATGTATATGCTCAGGCTCCCCTTTCTGGCGAAAAATT
AGTAAAGATGGTCTGCAAATAGGAACGGACGCTACAGCTACAGAACAAAAACCTATTTATGCAGAC
CCTACATTCCAGCCCGAACCCCAAATCGGGGAGTCCCAGTGGAATGAGGCAGATGCTACAGTCGCCG
GCGGTAGAGTGCTAAAGAAATCTACTCCCATGAAACCATGCTATGGTTCCTATGCAAGACCCACAAA
TGCTAATGGAGGTCAGGGTGTACTAACGGCAAATGCCCAGGGACAGCTAGAATCTCAGGTTGAAATG
CAATTCTTTTCAACTTCTGAAAACGCCCGTAACGAGGCTAACAACATTCAGCCCAAATTGGTGCTGTA
TAGTGAGGATGTGCACATGGAGACCCCGGATACGCACCTTTCTTACAAGCCCGCAAAAAGCGATGAC
AATTCAAAAATCATGCTGGGTCAGCAGTCCATGCCCAACAGACCTAATTACATCGGCTTCAGAGACA
ACTTTATCGGCCTCATGTATTACAATAGCACTGGCAACATGGGAGTGCTTGCAGGTCAGGCCTCTCAG
```

-continued

```
TTGAATGCAGTGGTGGACTTGCAAGACAGAAACACAGAACTGTCCTACCAGCTCTTGCTTGATTCCA

TGGGTGACAGAACCAGATACTTTTCCATGTGGAATCAGGCAGTGGACAGTTATGACCCAGATGTTAG

AATTATTGAAAATCATGGAACTGAAGACGAGCTCCCCAACTATTGTTTCCCTCTGGGTGGCATAGGG

GTAACTGACACTTACCAGGCTGTTAAAACCAACAATGGCAATAACGGGGGCCAGGTGACTTGGACA

AAAGATGAAACTTTTGCAGATCGCAATGAAATAGGGGTGGGAAACAATTTCGCTATGGAGATCAACC

TCAGTGCCAACCTGTGGAGAAACTTCCTGTACTCCAACGTGGCGCTGTACCTACCAGACAAGCTTAA

GTACAACCCCTCCAATGTGGACATCTCTGACAACCCCAACACCTACGATTACATGAACAAGCGAGTG

GTGGCCCCGGGGCTGGTGGACTGCTACATCAACCTGGGCGCGCGCTGGTCGCTGGACTACATGGACA

ACGTCAACCCCTTCAACCACCACCGCAATGCGGGCCTGCGCTACCGCTCCATGCTCCTGGGCAACGG

GCGCTACGTGCCCTTCCACATCCAGGTGCCCCAGAAGTTCTTTGCCATCAAGAACCTCCTCCTCCTGC

CGGGCTCCTACACCTACGAGTGGAACTTCAGGAAGGATGTCAACATGGTCCTCCAGAGCTCTCTGGG

TAACGATCTCAGGGTGGACGGGGCCAGCATCAAGTTCGAGAGCATCTGCCTCTACGCCACCTTCTTC

CCCATGGCCCACAACACGGCCTCCACGCTCGAGGCCATGCTCAGGAACGACACCAACGACCAGTCCT

TCAATGACTACCTCTCCGCCGCCAACATGCTCTACCCCATACCCGCCAACGCCACCAACGTCCCCATC

TCCATCCCCTCGCGCAACTGGGCGGCCTTCCGCGGCTGGGCCTTCACCCGCCTCAAGACCAAGGAGA

CCCCCTCCCTGGGCTCGGGATTCGACCCCTACTACACCTACTCGGGCTCCATTCCCTACCTGGACGGC

ACCTTCTACCTCAACCACACTTTCAAGAAGGTCTCGGTCACCTTCGACTCCTCGGTCAGCTGGCCGGG

CAACGACCGTCTGCTCACCCCCAACGAGTTCGAGATCAAGCGCTCGGTCGACGGGGAGGGCTACAAC

GTGGCCCAGTGCAACATGACCAAGGACTGGTTCCTGGTCCAGATGCTGGCCAACTACAACATCGGCT

ACCAGGGCTTCTACATCCCAGAGAGCTACAAGGACAGGATGTACTCCTTCTTCAGGAACTTCCAGCC

CATGAGCCGGCAGGTGGTGGACCAGACCAAGTACAAGGACTACCAGGAGGTGGGCATCATCCACCA

GCACAACAACTCGGGCTTCGTGGGCTACCTCGCCCCCACCATGCGCGAGGGACAGGCCTACCCCGCC

AACTTCCCCTATCCGCTCATAGGCAAGACCGCGGTCGACAGCATCACCCAGAAAAAGTTCCTCTGCG

ACCGCACCCTCTGGCGCATCCCCTTCTCCAGCAACTTCATGTCCATGGGTGCGCTCTCGGACCTGGGC

CAGAACTTGCTCTACGCCAACTCCGCCCACGCCCTCGACATGACCTTCGAGGTCGACCCCATGGACG

AGCCCACCCTTCTCTATGTTCTGTTCGAAGTCTTTGACGTGGTCCGGGTCCACCAGCCGCACCGCGGC

GTCATCGAGACCGTGTACCTGCGTACGCCCTTCTCGGCCGGCAACGCCACCACCTAAAGAAGCAAGC

CGCAGTCATCGCCGCCTGCATGCCGTCGGGTTCCACCGAGCAAGAGCTCAGGGCCATCGTCAGAGAC

CTGGGATGCGGGCCCTATTTTTTGGGCACCTTCGACAAGCGCTTCCCTGGCTTTGTCTCCCCACACAA

GCTGGCCTGCGCCATCGTCAACACGGCCGGCCGCGAGACCGGGGGCGTGCACTGGCTGGCCTTCGCC

TGGAACCCGCGCTCCAAAACATGCTTCCTCTTTGACCCCTTCGGCTTTTCGGACCAGCGGCTCAAGCA

AATCTACGAGTTCGAGTACGAGGGCTTGCTGCGTCGCAGCGCCATCGCCTCCTCGCCCGACCGCTGC

GTCACCCTCGAAAAGTCCACCCAGACCGTGCAGGGGCCCGACTCGGCCGCCTGCGGTCTCTTCTGCT

GCATGTTTCTGCACGCCTTTGTGCACTGGCCTCAGAGTCCCATGGACCGCAACCCCACCATGAACTTG

CTGACGGGGTGCCCAACTCCATGCTCCAGAGCCCCCAGGTCGAGCCCACCCTGCGCCGCAACCAGG

AGCAGCTCTACAGCTTCCTGGAGCGCCACTCGCCTTACTTCCGCCGCCACAGCGCACAGATCAGGAG

GGCCACCTCCTTCTGCCACTTGCAAGAGATGCAAGAAGGGTAATAACGATGTACACACTTTTTTTCTC

AATAAATGGCATCTTTTTATTTATACAAGCTCTCTGGGGTATTCATTTCCCACCACCACCCGCCGTTGT

CGCCATCTGGCTCTATTTAGAAATCGAAAGGGTTCTGCCGGGAGTCGCCGTGCGCCACGGGCAGGGA

CACGTTGCGATACTGGTAGCGGGTGCCCCACTTGAACTCGGGCACCACCAGGCGAGGCAGCTCGGGG

AAGTTTTCGCTCCACAGGCTGCGGGTCAGCACCAGCGCGTTCATCAGGTCGGGCGCCGAGATCTTGA
```

-continued

```
AGTCGCAGTTGGGGCCGCCGCCCTGCGCGCGCGAGTTGCGGTACACCGGGTTGCAGCACTGGAACAC

CAACAGCGCCGGGTGCTTCACGCTGGCCAGCACGCTGCGGTCGGAGATCAGCTCGGCGTCCAGGTCC

TCCGCGTTGCTCAGCGCGAACGGGGTCATCTTGGGCACTTGCCGCCCCAGGAAGGGCGCGTGCCCCG

GTTTCGAGTTGCAGTCGCAGCGCAGCGGGATCAGCAGGTGCCCGTGCCCGGACTCGGCGTTGGGGTA

CAGCGCGCGCATGAAGGCCTGCATCTGGCGGAAGGCCATCTGGGCCTTGGCGCCCTCCGAGAAGAAC

ATGCCGCAGGACTTGCCCGAGAACTGGTTTGCGGGGCAGCTGGCGTCGTGCAGGCAGCAGCGCGCGT

CGGTGTTGGCGATCTGCACCACGTTGCGCCCCCACCGGTTCTTCACGATCTTGGCCTTGGACGATTGC

TCCTTCAGCGCGCGCTGCCCGTTCTCGCTGGTCACATCCATCTCGATCACATGTTCCTTGTTCACCATG

CTGCTGCCGTGCAGACACTTCAGCTCGCCCTCCGTCTCGGTGCAGCGGTGCTGCCACAGCGCGCAGC

CCGTGGGCTCGAAAGACTTGTAGGTCACCTCCGCGAAGGACTGCAGGTACCCCTGCAAAAAGCGGCC

CATCATGGTCACGAAGGTCTTGTTGCTGCTGAAGGTCAGCTGCAGCCCGCGGTGCTCCTCGTTCAGCC

AGGTCTTGCACACGGCCGCCAGCGCCTCCACCTGGTCGGGCAGCATCTTGAAGTTCACCTTCAGCTCA

TTCTCCACGTGGTACTTGTCCATCAGCGTGCGCGCCGCCTCCATGCCCTTCTCCCAGGCCGACACCAG

CGGCAGGCTCACGGGGTTCTTCACCATCACCGTGGCCGCCGCCTCCGCCGCGCTTTCGCTTTCCGCCC

CGCTGTTCTCTTCCTCTTCCTCCTCTTCCTCGCCGCCGCCCACTCGCAGCCCCGCACCACGGGGTCGT

CTTCCTGCAGGCGCTGCACCTTGCGCTTGCCGTTGCGCCCCTGCTTGATGCGCACGGGCGGGTTGCTG

AAGCCCACCATCACCAGCGCGGCCTCTTCTTGCTCGTCCTCGCTGTCCAGAATGACCTCCGGGGAGG

GGGGGTTGGTCATCCTCAGTACCGAGGCACGCTTCTTTTTCTTCCTGGGGGCGTTCGCCAGCTCCGCG

GCTGCGGCCGCTGCCGAGGTCGAAGGCCGAGGGCTGGGCGTGCGCGGCACCAGCGCGTCCTGCGAG

CCGTCCTCGTCCTCCTCGGACTCGAGACGGAGGCGGGCCCGCTTCTTCGGGGGCGCGCGGGGCGGCG

GAGGCGGCGGCGGCGACGGAGACGGGGACGAGACATCGTCCAGGGTGGGTGGACGGCGGGCCGCG

CCGCGTCCGCGCTCGGGGGTGGTCTCGCGCTGGTCCTCTTCCCGACTGGCCATCTCCCACTGCTCCTT

CTCCTATAGGCAGAAAGAGATCATGGAGTCTCTCATGCGAGTCGAGAAGGAGGAGGACAGCCTAAC

CGCCCCCTCTGAGCCCTCCACCACCGCCGCCACCACCGCCAATGCCGCCGCGGACGACGCGCCCACC

GAGACCACCGCCAGTACCACCCTCCCCAGCGACGCACCCCCGCTCGAGAATGAAGTGCTGATCGAGC

AGGACCCGGGTTTTGTGAGCGGAGAGGAGGATGAGGTGGATGAGAAGGAGAAGGAGGAGGTCGCC

GCCTCAGTGCCAAAAGAGGATAAAAAGCAAGACCAGGACGACGCAGATAAGGATGAGACAGCAGT

CGGGCGGGGAACGGAAGCCATGATGCTGATGACGGCTACCTAGACGTGGGAGACGACGTGCTGCT

TAAGCACCTGCACCGCCAGTGCGTCATCGTCTGCGACGCGCTGCAGGAGCGCTGCGAAGTGCCCCTG

GACGTGGCGGAGGTCAGCCGCGCCTACGAGCGGCACCTCTTCGCGCCGCACGTGCCCCCAAGCGCC

GGGAGAACGGCACCTGCGAGCCCAACCCGCGTCTCAACTTCTACCCGGTCTTCGCGGTACCCGAGGT

GCTGGCCACCTACCACATCTTTTTCCAAAACTGCAAGATCCCCCTCTCCTGCCGCGCCAACCGCACCC

GCGCCGACAAAACCCTGACCCTGCGGCAGGGCGCCCACATACCTGATATCGCCTCTCTGGAGGAAGT

GCCCAAGATCTTCGAGGGTCTCGGTCGCGACGAGAAACGGGCGGCGAACGCTCTGCACGGAGACAG

CGAAAACGAGAGTCACTCGGGGGTGCTGGTGGAGCTCGAGGGCGACAACGCGCGCCTGGCCGTACT

CAAGCGCAGCATAGAGGTCACCCACTTTGCCTACCCGGCGCTCAACCTGCCCCCAAGGTCATGAGT

GTGGTCATGGGCGAGCTCATCATGCGCCGCGCCCAGCCCCTGGCCGCGGATGCAAACTTGCAAGAGT

CCTCCGAGGAAGGCCTGCCCGCGGTCAGCGACGAGCAGCTGGCGCGCTGGCTGGAGACCCGCGACC

CCGCGCAGCTGGAGGAGCGGCGCAAGCTCATGATGGCCGCGGTGCTGGTCACCGTGGAGCTCGAGT

GTCTGCAGCGCTTCTTCGCGGACCCCGAGATGCAGCGCAAGCTCGAGGAGACCCTGCACTACACCTT
```

-continued

```
CCGCCAGGGCTACGTGCGCCAGGCCTGCAAGATCTCCAACGTGGAGCTCTGCAACCTGGTCTCCTAC
CTGGGCATCCTGCACGAGAACCGCCTCGGGCAGAACGTCCTGCACTCCACCCTCAAAGGGGAGGCGC
GCCGCGACTACATCCGCGACTGCGCCTACCTCTTCCTCTGCTACACCTGGCAGACGGCCATGGGGGTC
TGGCAGCAGTGCCTGGAGGAGCGCAACCTCAAGGAGCTGGAAAAGCTCCTCAAGCGCACCCTCAGG
GACCTCTGGACGGGCTTCAACGAGCGCTCGGTGGCCGCCGCGCTGGCGGACATCATCTTTCCCGAGC
GCCTGCTCAAGACCCTGCAGCAGGGCCTGCCCGACTTCACCAGCCAGAGCATGCTGCAGAACTTCAG
GACTTTCATCCTGGAGCGCTCGGGCATCCTGCCGGCCACTTGCTGCGCGCTGCCCAGCGACTTCGTGC
CCATCAAGTACAGGGAGTGCCCGCCGCCGCTCTGGGGCCACTGCTACCTCTTCCAGCTGGCCAACTA
CCTCGCCTACCACTCGGACCTCATGGAAGACGTGAGCGGCGAGGGCCTGCTCGAGTGCCACTGCCGC
TGCAACCTCTGCACGCCCCACCGCTCTCTAGTCTGCAACCCGCAGCTGCTCAGCGAGAGTCAGATTAT
CGGTACCTTCGAGCTGCAGGGTCCCTCGCCTGACGAGAAGTCCGCGGCTCCAGGGCTGAAACTCACT
CCGGGGCTGTGGACTTCCGCCTACCTACGCAAATTTGTACCTGAGGACTACCACGCCCACGAGATCA
GGTTCTACGAAGACCAATCCCGCCCGCCCAAGGCGGAGCTCACCGCCTGCGTCATCACCCAGGGGCA
CATCCTGGGCCAATTGCAAGCCATCAACAAAGCCCGCCGAGAGTTCTTGCTGAAAAAGGGTCGGGGG
GTGTACCTGGACCCCCAGTCCGGCGAGGAGCTAAACCCGCTACCCCCGCCGCCGCCCCAGCAGCGGG
ACCTTGCTTCCCAGGATGGCACCCAGAAAGAAGCAGCAGCCGCCGCCGCCGCAGCCATACATGC
TTCTGGAGGAAGAGGAGGAGGACTGGGACAGTCAGGCAGAGGAGGTTTCGGACGAGGAGCAGGAG
GAGATGATGGAAGACTGGGAGGAGGACAGCAGCCTAGACGAGGAAGCTTCAGAGGCCGAAGAGGT
GGCAGACGCAACACCATCGCCCTCGGTCGCAGCCCCTCGCCGGGGCCCCTGAAATCCTCCGAACCC
AGCACCAGCGCTATAACCTCCGCTCCTCCGGCGCCGGCGCCACCCGCCCGCAGACCCAACCGTAGAT
GGGACACCACAGGAACCGGGGTCGGTAAGTCCAAGTGCCCGCCGCCGCCACCGCAGCAGCAGCAGC
AGCAGCGCCAGGGCTACCGCTCGTGGCGCGGGCACAAGAACGCCATAGTCGCCTGCTTGCAAGACTG
CGGGGGCAACATCTCTTTCGCCCGCCGCTTCCTGCTATTCCACCACGGGGTCGCCTTTCCCCGCAATG
TCCTGCATTACTACCGTCATCTCTACAGCCCCTACTGCAGCGGCGACCCAGAGGCGGCAGCGGCAGC
CACAGCGGCGACCACCACCTAGGAAGATATCCTCCGCGGGCAAGACAGCGGCAGCAGCGGCCAGGA
GACCCGCGGCAGCAGCGGCGGGAGCGGTGGGCGCACTGCGCCTCTCGCCCAACGAACCCCTCTCGAC
CCGGGAGCTCAGACACAGGATCTTCCCCACTTTGTATGCCATCTTCCAACAGAGCAGAGGCCAGGAG
CAGGAGCTGAAAATAAAAAACAGATCTCTGCGCTCCCTCACCCGCAGCTGTCTGTATCACAAAAGCG
AAGATCAGCTTCGGCGCACGCTGGAGGACGCGGAGGCACTCTTCAGCAAATACTGCGCGCTCACTCT
TAAAGACTAGCTCCGCGCCCTTCTCGAATTTAGGCGGGAGAAAACTACGTCATCGCCGGCCGCCGCC
CAGCCCGCCCAGCCGAGATGAGCAAAGAGATTCCCACGCCATACATGTGGAGCTACCAGCCGCAGA
TGGGACTCGCGGCGGGAGCGGCCCAGGACTACTCCACCCGCATGAACTACATGAGCGCGGGACCCC
ACATGATCTCACAGGTCAACGGGATCCGCGCCCAGCGAAACCAAATACTGCTGGAACAGGCGGCCA
TCACCGCCACGCCCCGCCATAATCTCAACCCCCGAAATTGGCCCGCCGCCCTCGTGTACCAGGAAAC
CCCCTCCGCCACCACCGTACTACTTCCGCGTGACGCCCAGGCCGAAGTCCAGATGACTAACTCAGGG
GCGCAGCTCGCGGGCGGCTTTCGTCACGGGGCGCGGCCGCTCCGACCAGGTATAAGACACCTGATGA
TCAGAGGCCGAGGTATCCAGCTCAACGACGAGTCGGTGAGCTCTTCGCTCGGTCTCCGTCCGGACGG
AACTTTCCAGCTCGCCGGATCCGGCCGCTCTTCGTTCACGCCCCGCCAGGCGTACCTGACTCTGCAGA
CCTCGTCCTCGGAGCCCCGCTCCGGCGGCATCGGAACCCTCCAGTTCGTGGAGGAGTTCGTGCCCTCG
GTCTACTTCAACCCCTTCTCGGGACCTCCCGGACGCTACCCCGACCAGTTCATTCCGAACTTTGACGC
GGTGAAGGACTCGGCGGACGGCTACGACTGAATGTCAGGTGTCGAGGCAGAGCAGCTTCGCCTGAG
```

```
ACACCTCGAGCACTGCCGCCGCCACAAGTGCTTCGCCCGCGGTTCTGGTGAGTTCTGCTACTTTCAGC

TACCCGAGGAGCATACCGAGGGGCCGGCGCACGGCGTCCGCCTGACCACCCAGGGCGAGGTTACCT

GTTCCCTCATCCGGGAGTTTACCCTCCGTCCCCTGCTAGTGGAGCGGGAGCGGGGTCCCTGTGTCCTA

ACTATCGCCTGCAACTGCCCTAACCCTGGATTACATCAAGATCTTTGCTGTCATCTCTGTGCTGAGTTT

AATAAACGCTGAGATCAGAATCTACTGGGGCTCCTGTCGCCATCCTGTGAACGCCACCGTCTTCACCC

ACCCCGACCAGGCCCAGGCGAACCTCACCTGCGGTCTGCATCGGAGGGCCAAGAAGTACCTCACCTG

GTACTTCAACGGCACCCCCTTTGTGGTTTACAACAGCTTCGACGGGACGGAGTCTCCCTGAAAGAC

CAGCTCTCCGGTCTCAGCTACTCCATCCACAAGAACACCACCCTCCAACTCTTCCCTCCCTACCTGCC

GGGAACCTACGAGTGCGTCACCGGCCGCTGCACCCACCTCACCCGCCTGATCGTAAACCAGAGCTTT

CCGGGAACAGATAACTCCCTCTTCCCCAGAACAGGAGGTGAGCTCAGGAAACTCCCCGGGGACCAG

GGCGGAGACGTACCTTCGACCCTTGTGGGGTTAGGATTTTTTATTACCGGGTTGCTGGCTCTTTTAAT

CAAAGTTTCCTTGAGATTTGTTCTTTCCTTCTACGTGTATGAACACCTCAACCTCCAATAACTCTACCC

TTTCTTCGGAATCAGGTGACTTCTCTGAAATCGGGCTTGGTGTGCTGCTTACTCTGTTGATTTTTTCC

TTATCATACTCAGCCTTCTGTGCCTCAGGCTCGCCGCCTGCTGCGCACACATCTATATCTACTGCTGGT

TGCTCAAGTGCAGGGGTCGCCACCCAAGATGAACAGGTACATGGTCCTATCGATCCTAGGCCTGCTG

GCCCTGGCGGCCTGCAGCGCCGCCAAAAAAGAGATTACCTTTGAGGAGCCCGCTTGCAATGTAACTT

TCAAGCCCGAGGGTGACCAATGCACCACCCTCGTCAAATGCGTTACCAATCATGAGAGGCTGCGCAT

CGACTACAAAAACAAAACTGGCCAGTTTGCGGTCTATAGTGTGTTTACGCCCGGAGACCCCTCTAAC

TACTCTGTCACCGTCTTCCAGGGCGGACAGTCTAAGATATTCAATTACACTTTCCCTTTTTATGAGTTA

TGCGATGCGGTCATGTACATGTCAAAACAGTACAACCTGTGGCCTCCCTCTCCCCAGGCGTGTGTGG

AAAATACTGGGTCTTACTGCTGTATGGCTTTCGCAATCACTACGCTCGCTCTAATCTGCACGGTGCTA

TACATAAAATTCAGGCAGAGGCGAATCTTTATCGATGAAAAGAAAATGCCTTGATCGCTAACACCGG

CTTTCTATCTGCAGAATGAATGCAATCACCTCCCTACTAATCACCACCACCCTCCTTGCGATTGCCCA

TGGGTTGACACGAATCGAAGTGCCAGTGGGGTCCAATGTCACCATGGTGGGCCCCGCCGGCAATTCC

ACCCTCATGTGGGAAAAATTTGTCCGCAATCAATGGGTTCATTTCTGCTCTAACCGAATCAGTATCAA

GCCCAGAGCCATCTGCGATGGGCAAAATCTAACTCTGATCAATGTGCAAATGATGGATGCTGGGTAC

TATTACGGGCAGCGGGAGAAATCATTAATTACTGGCGACCCCACAAGGACTACATGCTGCATGTAG

TCGAGGCACTTCCCACTACCACCCCCACTACCACCTCTCCCACCACCACCACCACTACTACTACTACT

ACTACTACTACTACTACCACTACCGCTGCCCGCCATACCCGCAAAAGCACCATGATTAGCACAA

AGCCCCCTCGTGCTCACTCCCACGCCGGCGGGCCCATCGGTGCGACCTCAGAAACCACCGAGCTTTG

CTTCTGCCAATGCACTAACGCCAGCGCTCATGAACTGTTCGACCTGGAGAATGAGGATGTCCAGCAG

AGCTCCGCTTGCCTGACCCAGGAGGCTGTGGAGCCCGTTGCCCTGAAGCAGATCGGTGATTCAATAA

TTGACTCTTCTTCTTTTGCCACTCCCGAATACCCTCCCGATTCTACTTTCCACATCACGGGTACCAAAG

ACCCTAACCTCTCTTTCTACCTGATGCTGCTGCTCTGTATCTCTGTGGTCTCTTCCGCGCTGATGTTAC

TGGGGATGTTCTGCTGCCTGATCTGCCGCAGAAAGAGAAAAGCTCGCTCTCAGGGCCAACCACTGAT

GCCCTTCCCTACCCCCGGATTTTGCAGATAACAAGATATGAGCTCGCTGCTGACACTAACCGCTTT

ACTAGCCTGCGCTCTAACCCTTGTCGCTTGCGACTCGAGATTCCACAATGTCACAGCTGTGGCAGGAG

AAAATGTTACTTTCAACTCCACGGCCGATACCCAGTGGTCGTGGAGTGGCTCAGGTAGCTACTTAACT

ATCTGCAATAGCTCCACTTCCCCCGGCATATCCCCAACCAAGTACCAATGCAATGCCAGCCTGTTCAC

CCTCATCAACGCTTCCACCCTGGACAATGGACTCTATGTAGGCTATGTACCCTTTGGTGGGCAAGGAA
```

-continued

```
AGACCCACGCTTACAACCTGGAAGTTCGCCAGCCCAGAACCACTACCCAAGCTTCTCCCACCACCAC
CACCACCACCACCATCACCAGCAGCAGCAGCAGCAGCAGCCACAGCAGCAGCAGCAGATTATTGAC
TTTGGTTTTGGCCAGCTCATCTGCCGCTACCCAGGCCATCTACAGCTCTGTGCCCGAAACCACTCAGA
TCCACCGCCCAGAAACGACCACCGCCACCACCCTACACACCTCCAGCGATCAGATGCCGACCAACAT
CACCCCCTTGGCTCTTCAAATGGGACTTACAAGCCCCACTCCAAAACCAGTGGATGCGGCCGAGGTC
TCCGCCCTCGTCAATGACTGGGCGGGGCTGGGAATGTGGTGGTTCGCCATAGGCATGATGGCGCTCT
GCCTGCTTCTGCTCTGGCTCATCTGCTGCCTCCACCGCAGGCGAGCCAGACCCCCCATCTATAGACCC
ATCATTGTCCTGAACCCCGATAATGATGGGATCCATAGATTGGATGGCCTGAAAAACCTACTTTTTTC
TTTTACAGTATGATAAATTGAGACATGCCTCGCATTTTCTTGTACATGTTCCTTCTCCCACCTTTTCTG
GGGTGTTCTACGCTGGCCGCTGTGTCTCACCTGGAGGTAGACTGCCTCTCACCCTTCACTGTCTACCT
GCTTTACGGATTGGTCACCCTCACTCTCATCTGCAGCCTAATCACAGTAATCATCGCCTTCATCCAGT
GCATTGATTACATCTGTGTGCGCCTCGCATACTTCAGACACCACCCGCAGTACCGAGACAGGAACAT
TGCCCAACTTCTAAGACTGCTCTAATCATGCATAAGACTGTGATCTGCCTTCTGATCCTCTGCATCCT
GCCCACCCTCACCTCCTGCCAGTACACCACAAAATCTCCGCGCAAAAGACATGCCTCCTGCCGCTTCA
CCCAACTGTGGAATATACCCAAATGCTACAACGAAAAGAGCGAGCTCTCCGAAGCTTGGCTGTATGG
GGTCATCTGTGTCTTAGTTTTCTGCAGCACTGTCTTTGCCCTCATAATCTACCCCTACTTTGATTTGGG
ATGGAACGCGATCGATGCCATGAATTACCCCACCTTTCCCGCACCCGAGATAATTCCACTGCGACAA
GTTGTACCCGTTGTCGTTAATCAACGCCCCCCATCCCCTACGCCCACTGAAATCAGCTACTTTAACCT
AACAGGCGGAGATGACTGACGCCCTAGATCTAGAAATGGACGGCATCAGTACCGAGCAGCGTCTCCT
AGAGAGGCGCAGGCAGGCGGCTGAGCAAGAGCGCCTCAATCAGGAGCTCCGAGATCTCGTTAACCT
GCACCAGTGCAAAAGAGGCATCTTTTGTCTGGTAAAGCAGGCCAAAGTCACCTACGAGAAGACCGG
CAACAGCCACCGCCTCAGTTACAAATTGCCCACCCAGCGCCAGAAGCTGGTGCTCATGGTGGGTGAG
AATCCCATCACCGTCACCCAGCACTCGGTAGAGACCGAGGGGTGTCTGCACTCCCCCTGTCGGGGTC
CAGAAGACCTCTGCACCCTGGTAAAGACCCTGTGCGGTCTCAGAGATTTAGTCCCCTTTAACTAATCA
AACACTGGAATCAATAAAAAGAATCACTTACTTAAAATCAGACAGCAGGTCTCTGTCCAGTTTATTC
AGCAGCACCTCCTTCCCCTCCTCCCAACTCTGGTACTCCAAACGCCTTCTGGCGGCAAACTTCCTCCA
CACCCTGAAGGGAATGTCAGATTCTTGCTCCTGTCCCTCCGCACCCACTATCTTCATGTTGTTGCAGA
TGAAGCGCACCAAAACGTCTGACGAGAGCTTCAACCCCGTGTACCCCTATGACACGGAAAGCGGCCC
TCCCTCCGTCCCTTTCCTCACCCCTCCCTTCGTGTCTCCCGATGGATTCCAAGAAAGTCCCCCCGGGGT
CCTGTCTCTGAACCTGGCCGAGCCCCTGGTCACTTCCCACGGCATGCTCGCCCTGAAAATGGGAAGT
GGCCTCTCCCTGGACGACGCTGGCAACCTCACCTCTCAAGATATCACCACCGCTAGCCCTCCCCTCAA
AAAAACCAAGACCAACCTCAGCCTAGAAACCTCATCCCCCCTAACTGTGAGCACCTCAGGCGCCCTC
ACCGTAGCAGCCGCCGCTCCCCTGGCGGTGGCCGGCACCTCCCTCACCATGCAATCAGAGGCCCCCC
TGACAGTACAGGATGCAAAACTCACCCTGGCCACCAAAGGCCCCCTGACCGTGTCTGAAGGCAAACT
GGCCTTGCAAACATCGGCCCCGCTGACGGCCGCTGACAGCAGCACCCTCACAGTCAGTGCCACACCA
CCCCTTAGCACAAGCAATGGCAGCTTGGGTATTGACATGCAAGCCCCCATTTACACCACCAATGGAA
AACTAGGACTTAACTTTGGCGCTCCCCTGCATGTGGTAGACAGCCTAAATGCACTGACTGTAGTTACT
GGCCAAGGTCTTACGATAAACGGAACAGCCCTACAAACTAGAGTCTCAGGTGCCCTCAACTATGACA
CATCAGGAAACCTAGAATTGAGAGCTGCAGGGGGTATGCGAGTTGATGCAAATGGTCAACTTATCCT
TGATGTAGCTTACCCATTTGATGCACAAAACAATCTCAGCCTTAGGCTTGGACAGGGACCCCTGTTTG
TTAACTCTGCCCACAACTTGGATGTTAACTACAACAGAGGCCTCTACCTGTTCACATCTGGAAATACC
```

-continued

```
AAAAAGCTAGAAGTTAATATCAAAACAGCCAAGGGTCTCATTTATGATGACACTGCTATAGCAATCA
ATGCGGGTGATGGGCTACAGTTTGACTCAGGCTCAGATACAAATCCATTAAAAACTAAACTTGGATT
AGGACTGGATTATGACTCCAGCAGAGCCATAATTGCTAAACTGGGAACTGGCCTAAGCTTTGACAAC
ACAGGTGCCATCACAGTAGGCAACAAAAATGATGACAAGCTTACCTTGTGGACCACACCAGACCCAT
CCCCTAACTGTAGAATCTATTCAGAGAAAGATGCTAAATTCACACTTGTTTTGACTAAATGCGGCAGT
CAGGTGTTGGCCAGCGTTTCTGTTTTATCTGTAAAAGGTAGCCTTGCGCCCATCAGTGGCACAGTAAC
TAGTGCTCAGATTGTCCTCAGATTTGATGAAAATGGAGTTCTACTAAGCAATTCTTCCCTTGACCCTC
AATACTGGAACTACAGAAAAGGTGACCTTACAGAGGGCACTGCATATACCAACGCAGTGGGATTTAT
GCCCAACCTCACAGCATACCCAAAAACACAGAGCCAAACTGCTAAAAGCAACATTGTAAGTCAGGTT
TACTTGAATGGGGACAAATCCAAACCCATGACCCTCACCATTACCCTCAATGGAACTAATGAAACAG
GAGATGCCACAGTAAGCACTTACTCCATGTCATTCTCATGGAACTGGAATGGAAGTAATTACATTAA
TGAAACGTTCCAAACCAACTCCTTCACCTTCTCCTACATCGCCCAAGAATAAAAAGCATGACGCTGTT
GATTTGATTCAATGTGTTTCTGTTTTATTTTCAAGCACAACAAAATCATTCAAGTCATTCTTCCATCTT
AGCTTAATAGACACAGTAGCTTAATAGACCCAGTAGTGCAAAGCCCCATTCTAGCTTATAACTAGTG
GAGAAGTACTCGCCTACATGGGGGTAGAGTCATAATCGTGCATCAGGATAGGGCGGTGGTGCTGCAG
CAGCGCGCGAATAAACTGCTGCCGCCGCCGCTCCGTCCTGCAGGAATACAACATGGCAGTGGTCTCC
TCAGCGATGATTCGCACCGCCCGCAGCATAAGGCGCCTTGTCCTCCGGGCACAGCAGCGCACCCTGA
TCTCACTTAAATCAGCACAGTAACTGCAGCACAGCACCACAATATTGTTCAAAATCCCACAGTGCAA
GGCGCTGTATCCAAAGCTCATGGCGGGGACCACAGAACCCACGTGGCCATCATACCACAAGCGCAG
GTAGATTAAGTGGCGACCCCTCATAAACACGCTGGACATAAACATTACCTCTTTTGGCATGTTGTAAT
TCACCACCTCCCGGTACCATATAAACCTCTGATTAAACATGGCGCCATCCACCACCATCCTAAACCAG
CTGGCCAAAACCTGCCCGCCGGCTATACACTGCAGGGAACCGGGACTGGAACAATGACAGTGGAGA
GCCCAGGACTCGTAACCATGGATCATCATGCTCGTCATGATATCAATGTTGGCACAACACAGGCACA
CGTGCATACACTTCCTCAGGATTACAAGCTCCTCCCGCGTTAGAACCATATCCCAGGGAACAACCCA
TTCCTGAATCAGCGTAAATCCCACACTGCAGGGAAGACCTCGCACGTAACTCACGTTGTGCATTGTC
AAAGTGTTACATTCGGGCAGCAGCGGATGATCCTCCAGTATGGTAGCGCGGGTTTCTGTCTCAAAAG
GAGGTAGACGATCCCTACTGTACGGAGTGCGCCGAGACAACCGAGATCGTGTTGGTCGTAGTGTCAT
GCCAAATGGAACGCCGGACGTAGTCATATTTCCTGAAGTCTTAGATCTCTCAACGCAGCACCAGCAC
CAACACTTCGCAGTGTAAAAGGCCAAGTGCCGAGAGAGTATATATAGGAATAAAAAGTGACGTAAA
CGGGCAAAGTCCAAAAAACGCCCAGAAAAACCGCACGCGAACCTACGCCCCGAAACGAAAGCCAAA
AAACACTAGACACTCCCTTCCGGCGTCAACTTCCGCTTTCCCACGCTACGTCACTTGCCCCAGTCAAA
CAAACTACATATCCCGAACTTCCAAGTCGCCACGCCCAAAACACCGCCTACACCTCCCCGCCCGCCG
GCCCGCCCCAAACCCGCCTCCCGCCCCGCGCCCCGCCCCGCGCCGCCCATCTCATTATCATATTGGC
TTCAATCCAAAATAAGGTATATTATTGATGATGGTTTAAACGGATCCTCTAGAGTCGACCTGCAGGC
ATGCAAGCTTGAGTATTCTATAGTGTCACCTAAATAGCTTGGCGTAATCATGGTCATAGCTGTTTCCT
GTGTGAAATTGTTATCCGCTCACAATTCCACACAACATACGAGCCGGAAGCATAAAGTGTAAAGCCT
GGGGTGCCTAATGAGTGAGCTAACTCACATTAATTGCGTTGCGCTCACTGCCCGCTTTCCAGTCGGGA
AACCTGTCGTGCCAGCTGCATTAATGAATCGGCCAACGCGAACCCCTTGCGGCCGCCCGGGCCGTCG
ACCAATTCTCATGTTTGACAGCTTATCATCGAATTTCTGCCATTCATCCGCTTATTATCACTTATTCAG
GCGTAGCAACCAGGCGTTTAAGGGCACCAATAACTGCCTTAAAAAAATTACGCCCCGCCCTGCCACT
```

-continued

```
CATCGCAGTACTGTTGTAATTCATTAAGCATTCTGCCGACATGGAAGCCATCACAAACGGCATGATG

AACCTGAATCGCCAGCGGCATCAGCACCTTGTCGCCTTGCGTATAATATTTGCCCATGGTGAAAACG

GGGGCGAAGAAGTTGTCCATATTGGCCACGTTTAAATCAAAACTGGTGAAACTCACCCAGGGATTGG

CTGAGACGAAAAACATATTCTCAATAAACCCTTTAGGGAAATAGGCCAGGTTTTCACCGTAACACGC

CACATCTTGCGAATATATGTGTAGAAACTGCCGGAAATCGTCGTGGTATTCACTCCAGAGCGATGAA

AACGTTTCAGTTTGCTCATGGAAAACGGTGTAACAAGGGTGAACACTATCCCATATCACCAGCTCAC

CGTCTTTCATTGCCATACGGAATTCCGGATGAGCATTCATCAGGCGGGCAAGAATGTGAATAAAGGC

CGGATAAAACTTGTGCTTATTTTTCTTTACGGTCTTTAAAAAGGCCGTAATATCCAGCTGAACGGTCT

GGTTATAGGTACATTGAGCAACTGACTGAAATGCCTCAAAATGTTCTTTACGATGCCATTGGGATATA

TCAACGGTGGTATATCCAGTGATTTTTTTCTCCATTTTAGCTTCCTTAGCTCCTGAAAATCTCGATAAC

TCAAAAAATACGCCCGGTAGTGATCTTATTTCATTATGGTGAAAGTTGGAACCTCTTACGTGCCGATC

AACGTCTCATTTTCGCCAAAAGTTGGCCCAGGGCTTCCCGGTATCAACAGGGACACCAGGATTTATTT

ATTCTGCGAAGTGATCTTCCGTCACAGGTATTTATTCGCGATAAGCTCATGGAGCGGCGTAACCGTCG

CACAGGAAGGACAGAGAAAGCGCGGATCTGGGAAGTGACGGACAGAACGGTCAGGACCTGGATTG

GGGAGGCGGTTGCCGCCGCTGCTGCTGACGGTGTGACGTTCTCTGTTCCGGTCACACCACATACGTTC

CGCCATTCCTATGCGATGCACATGCTGTATGCCGGTATACCGCTGAAAGTTCTGCAAAGCCTGATGG

GACATAAGTCCATCAGTTCAACGGAAGTCTACACGAAGGTTTTTGCGCTGGATGTGGCTGCCCGGCA

CCGGGTGCAGTTTGCGATGCCGGAGTCTGATGCGGTTGCGATGCTGAAACAATTATCCTGAGAATAA

ATGCCTTGGCCTTTATATGGAAATGTGGAACTGAGTGGATATGCTGTTTTTGTCTGTTAAACAGAGAA

GCTGGCTGTTATCCACTGAGAAGCGAACGAAACAGTCGGGAAAATCTCCCATTATCGTAGAGATCCG

CATTATTAATCTCAGGAGCCTGTGTAGCGTTTATAGGAAGTAGTGTTCTGTCATGATGCCTGCAAGCG

GTAACGAAAACGATTTGAATATGCCTTCAGGAACAATAGAAATCTTCGTGCGGTGTTACGTTGAAGT

GGGAGCGGATTATGTCAGCAATGGACAGAACAACCTAATGAACACAGAACCATGATGTGGTCTGTCCT

TTTACAGCCAGTAGTGCTCGCCGCAGTCGAGCGACAGGGCGAAGCCCTCGAGTGAGCGAGGAAGCA

CCAGGGAACAGCACTTATATATTCTGCTTACACACGATGCCTGAAAAAACTTCCCTTGGGGTTATCCA

CTTATCCACGGGGATATTTTTATAATTATTTTTTTATAGTTTTAGATCTTCTTTTTTAGAGCGCCTTG

TAGGCCTTTATCCATGCTGGTTCTAGAGAAGGTGTTGTGACAAATTGCCCTTTCAGTGTGACAAATCA

CCCTCAAATGACAGTCCTGTCTGTGACAAATTGCCCTTAACCCTGTGACAAATTGCCCTCAGAAGAA

GCTGTTTTTTCACAAAGTTATCCCTGCTTATTGACTCTTTTTTATTTAGTGTGACAATCTAAAAACTTG

TCACACTTCACATGGATCTGTCATGGCGGAAACAGCGGTTATCAATCACAAGAAACGTAAAAATAGC

CCGCGAATCGTCCAGTCAAACGACCTCACTGAGGCGGCATATAGTCTCTCCCGGGATCAAAAACGTA

TGCTGTATCTGTTCGTTGACCAGATCAGAAAATCTGATGGCACCCTACAGGAACATGACGGTATCTG

CGAGATCCATGTTGCTAAATATGCTGAAATATTCGGATTGACCTCTGCGGAAGCCAGTAAGGATATA

CGGCAGGCATTGAAGAGTTTCGCGGGGAAGGAAGTGGTTTTTTATCGCCCTGAAGAGGATGCCGGCG

ATGAAAAAGGCTATGAATCTTTTCCTTGGTTTATCAAACGTGCGCACAGTCCATCCAGAGGGCTTTAC

AGTGTACATATCAACCCATATCTCATTCCCTTCTTTATCGGGTTACAGAACCGGTTTACGCAGTTTCG

GCTTAGTGAAACAAAAGAAATCACCAATCCGTATGCCATGCGTTTATACGAATCCCTGTGTCAGTAT

CGTAAGCCGGATGGCTCAGGCATCGTCTCTCTGAAAATCGACTGGATCATAGAGCGTTACCAGCTGC

CTCAAAGTTACCAGCGTATGCCTGACTTCCGCCGCCGCTTCCTGCAGGTCTGTGTTAATGAGATCAAC

AGCAGAACTCCAATGCGCCTCTCATACATTGAGAAAAAGAAAGGCCGCCAGACGACTCATATCGTAT

TTTCCTTCCGCGATATCACTTCCATGACGACAGGATAGTCTGAGGGTTATCTGTCACAGATTTGAGGG
```

```
TGGTTCGTCACATTTGTTCTGACCTACTGAGGGTAATTTGTCACAGTTTTGCTGTTTCCTTCAGCCTGC

ATGGATTTTCTCATACTTTTTGAACTGTAATTTTTAAGGAAGCCAAATTTGAGGGCAGTTTGTCACAG

TTGATTTCCTTCTCTTTCCCTTCGTCATGTGACCTGATATCGGGGGTTAGTTCGTCATCATTGATGAGG

GTTGATTATCACAGTTTATTACTCTGAATTGGCTATCCGCGTGTGTACCTCTACCTGGAGTTTTTCCCA

CGGTGGATATTTCTTCTTGCGCTGAGCGTAAGAGCTATCTGACAGAACAGTTCTTCTTTGCTTCCTCG

CCAGTTCGCTCGCTATGCTCGGTTACACGGCTGCGGCGAGCGCTAGTGATAATAAGTGACTGAGGTA

TGTGCTCTTCTTATCTCCTTTTGTAGTGTTGCTCTTATTTTAAACAACTTTGCGGTTTTTTGATGACTTT

GCGATTTTGTTGTTGCTTTGCAGTAAATTGCAAGATTTAATAAAAAAACGCAAAGCAATGATTAAAG

GATGTTCAGAATGAAACTCATGGAAACACTTAACCAGTGCATAAACGCTGGTCATGAAATGACGAAG

GCTATCGCCATTGCACAGTTTAATGATGACAGCCCGGAAGCGAGGAAAATAACCCGGCGCTGGAGA

ATAGGTGAAGCAGCGGATTTAGTTGGGGTTTCTTCTCAGGCTATCAGAGATGCCGAGAAAGCAGGGC

GACTACCGCACCCGGATATGGAAATTCGAGGACGGGTTGAGCAACGTGTTGGTTATACAATTGAACA

AATTAATCATATGCGTGATGTGTTTGGTACGCGATTGCGACGTGCTGAAGACGTATTTCCACCGGTGA

TCGGGGTTGCTGCCCATAAAGGTGGCGTTTACAAAACCTCAGTTTCTGTTCATCTTGCTCAGGATCTG

GCTCTGAAGGGGCTACGTGTTTTGCTCGTGGAAGGTAACGACCCCCAGGGAACAGCCTCAATGTATC

ACGGATGGGTACCAGATCTTCATATTCATGCAGAAGACACTCTCCTGCCTTTCTATCTTGGGGAAAAG

GACGATGTCACTTATGCAATAAAGCCCACTTGCTGGCCGGGGCTTGACATTATTCCTTCCTGTCTGGC

TCTGCACCGTATTGAAACTGAGTTAATGGGCAAATTTGATGAAGGTAAACTGCCCACCGATCCACAC

CTGATGCTCCGACTGGCCATTGAAACTGTTGCTCATGACTATGATGTCATAGTTATTGACAGCGCGCC

TAACCTGGGTATCGGCACGATTAATGTCGTATGTGCTGCTGATGTGCTGATTGTTCCCACGCCTGCTG

AGTTGTTTGACTACACCTCCGCACTGCAGTTTTTCGATATGCTTCGTGATCTGCTCAAGAACGTTGAT

CTTAAAGGGTTCGAGCCTGATGTACGTATTTTGCTTACCAAATACAGCAATAGTAATGGCTCTCAGTC

CCCGTGGATGGAGGAGCAAATTCGGGATGCCTGGGGAAGCATGGTTCTAAAAAATGTTGTACGTGAA

ACGGATGAAGTTGGTAAAGGTCAGATCCGGATGAGAACTGTTTTTGAACAGGCCATTGATCAACGCT

CTTCAACTGGTGCCTGGAGAAATGCTCTTTCTATTTGGGAACCTGTCTGCAATGAAATTTTCGATCGT

CTGATTAAACCACGCTGGGAGATTAGATAATGAAGCGTGCGCCTGTTATTCCAAAACATACGCTCAA

TACTCAACCGGTTGAAGATACTTCGTTATCGACACCAGCTGCCCCGATGGTGGATTCGTTAATTGCGC

GCGTAGGAGTAATGGCTCGCGGTAATGCCATTACTTTGCCTGTATGTGGTCGGGATGTGAAGTTTACT

CTTGAAGTGCTCCGGGGTGATAGTGTTGAGAAGACCTCTCGGGTATGGTCAGGTAATGAACGTGACC

AGGAGCTGCTTACTGAGGACGCACTGGATGATCTCATCCCTTCTTTTCTACTGACTGGTCAACAGACA

CCGGCGTTCGGTCGAAGAGTATCTGGTGTCATAGAAATTGCCGATGGGAGTCGCCGTCGTAAAGCTG

CTGCACTTACCGAAAGTGATTATCGTGTTCTGGTTGGCGAGCTGGATGATGAGCAGATGGCTGCATT

ATCCAGATTGGGTAACGATTATCGCCCAACAAGTGCTTATGAACGTGGTCAGCGTTATGCAAGCCGA

TTGCAGAATGAATTTGCTGGAAATATTTCTGCGCTGGCTGATGCGGAAATATTTCACGTAAGATTAT

TACCCGCTGTATCAACACCGCCAAATTGCCTAAATCAGTTGTTGCTCTTTTTTCTCACCCCGGTGAACT

ATCTGCCCGGTCAGGTGATGCACTTCAAAAAGCCTTTACAGATAAAGAGGAATTACTTAAGCAGCAG

GCATCTAACCTTCATGAGCAGAAAAAAGCTGGGGTGATATTTGAAGCTGAAGAAGTTATCACTCTTT

TAACTTCTGTGCTTAAAACGTCATCTGCATCAAGAACTAGTTTAAGCTCACGACATCAGTTTGCTCCT

GGAGCGACAGTATTGTATAAGGGCGATAAAATGGTGCTTAACCTGGACAGGTCTCGTGTTCCAACTG

AGTGTATAGAGAAAATTGAGGCCATTCTTAAGGAACTTGAAAAGCCAGCACCCTGATGCGACCACGT
```

-continued

```
TTTAGTCTACGTTTATCTGTCTTTACTTAATGTCCTTTGTTACAGGCCAGAAAGCATAACTGGCCTGAA
TATTCTCTCTGGGCCCACTGTTCCACTTGTATCGTCGGTCTGATAATCAGACTGGGACCACGGTCCCA
CTCGTATCGTCGGTCTGATTATTAGTCTGGGACCACGGTCCCACTCGTATCGTCGGTCTGATTATTAG
TCTGGGACCACGGTCCCACTCGTATCGTCGGTCTGATAATCAGACTGGGACCACGGTCCCACTCGTAT
CGTCGGTCTGATTATTAGTCTGGGACCATGGTCCCACTCGTATCGTCGGTCTGATTATTAGTCTGGGA
CCACGGTCCCACTCGTATCGTCGGTCTGATTATTAGTCTGGAACCACGGTCCCACTCGTATCGTCGGT
CTGATTATTAGTCTGGGACCACGGTCCCACTCGTATCGTCGGTCTGATTATTAGTCTGGGACCACGAT
CCCACTCGTGTTGTCGGTCTGATTATCGGTCTGGGACCACGGTCCCACTTGTATTGTCGATCAGACTA
TCAGCGTGAGACTACGATTCCATCAATGCCTGTCAAGGGCAAGTATTGACATGTCGTCGTAACCTGT
AGAACGGAGTAACCTCGGTGTGCGGTTGTATGCCTGCTGTGGATTGCTGCTGTGTCCTGCTTATCCAC
AACATTTTGCGCACGGTTATGTGGACAAAATACCTGGTTACCCAGGCCGTGCCGGCACGTTAACCGG
GCTGCATCCGATGCAAGTGTGTCGCTGTCGACGAGCTCGCGAGCTCGGACATGAGGTTGCCCCGTAT
TCAGTGTCGCTGATTTGTATTGTCTGAAGTTGTTTTTACGTTAAGTTGATGCAGATCAATTAATACGAT
ACCTGCGTCATAATTGATTATTTGACGTGGTTTGATGGCCTCCACGCACGTTGTGATATGTAGATGAT
AATCATTATCACTTTACGGGTCCTTTCCGGTGATCCGACAGGTTACGGGCGGCGACCTCGCGGGTTT
TCGCTATTTATGAAAATTTTCCGGTTTAAGGCGTTTCCGTTCTTCTTCGTCATAACTTAATGTTTTATT
TAAAATACCCTCTGAAAAGAAAGGAAACGACAGGTGCTGAAAGCGAGCTTTTTGGCCTCTGTCGTTT
CCTTTCTCTGTTTTTGTCCGTGGAATGAACAATGGAAGTCCGAGCTCATCGCTAATAACTTCGTATAG
CATACATTATACGAAGTTATATTCGATGCGGCCGCAAGGGGTTCGCGTCAGCGGGTGTTGGCGGGTG
TCGGGGCTGGCTTAACTATGCGGCATCAGAGCAGATTGTACTGAGAGTGCACCATATGCGGTGTGAA
ATACCGCACAGATGCGTAAGGAGAAAATACCGCATCAGGCGCCATTCGCCATTCAGGCTGCGCAACT
GTTGGGAAGGGCGATCGGTGCGGGCCTCTTCGCTATTACGCCAGCTGGCGAAAGGGGGATGTGCTGC
AAGGCGATTAAGTTGGGTAACGCCAGGGTTTTCCCAGTCACGACGTTGTAAAACGACGGCCAGTGAA
TTGTAATACGACTCACTATAGGGCGAATTCGAGCTCGGTACCCGGGGATCCTCGTTTAAAC
```

Polynucleotide sequence encoding ChAd155#1375 backbone construct    SEQ ID NO: 9

```
CATCATCAATAATATACCTTATTTTGGATTGAAGCCAATATGATAATGAGATGGGCGGCGCGGGGCG
GGGCGCGGGGCGGGAGGCGGGTTTGGGGGCGGGCCGGCGGGCGGGGCGGTGTGGCGGAAGTGGAC
TTTGTAAGTGTGGCGGATGTGACTTGCTAGTGCCGGGCGCGGTAAAAGTGACGTTTTCCGTGCGCGA
CAACGCCCCCGGGAAGTGCATTTTTCCCGCGGTTTTTACCGGATGTTGTAGTGAATTTGGGCGTAAC
CAAGTAAGATTTGGCCATTTTCGCGGGAAAACTGAAACGGGGAAGTGAAATCTGATTAATTTTGCGT
TAGTCATACCGCGTAATATTTGTCTAGGGCCGAGGGACTTTGGCCGATTACGTGGAGGACTCGCCCA
GGTGTTTTTTGAGGTGAATTTCCGCGTTCCGGGTCAAAGTCTGCGTTTTATTATTATAGGATATCCCAT
TGCATACGTTGTATCCATATCATAATATGTACATTTATATTGGCTCATGTCCAACATTACCGCCATGTT
GACATTGATTATTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGGGT
GGAGTATTTACGGTAAACTGCCCACTTGGCAGTACATCAAGTGTATCATATGCCAAGTACGCCCCCT
ATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCA
ATGGGCGTGGATAGCGGTTTGACTCACGGGGATTTCCAAGTCTCCACCCCATTGACGTCAATGGGAG
TTTGTTTTGGCACCAAAATCAACGGGACTTTCCAAAATGTCGTAACAACTCCGCCCCATTGACGCAAA
```

```
TGGGCGGTAGGCGTGTACGGTGGGAGGTCTATATAAGCAGAGCTCTCCCTATCAGTGATAGAGATCT
CCCTATCAGTGATAGAGATCGTCGACGAGCTCGTTTAGTGAACCGTCAGATCGCCTGGAGACGCCAT
CCACGCTGTTTTGACCTCCATAGAAGACACCGGGACCGATCCAGCCTCCGCGGCCGGGAACGGTGCA
TTGGAACGCGGATTCCCCGTGCCAAGAGTGAGATCTTCCGTTTATCTAGGTACCGGGCCCCCCCTCGA
GGTCGACGGTATCGATAAGCTTCACGCTGCCGCAAGCACTCAGGGCGCAAGGGCTGCTAAAGGAAG
CGGAACACGTAGAAAGCCAGTCCGCAGAAACGGTGCTGACCCCGGATGAATGTCAGCTACTGGGCT
ATCTGGACAAGGGAAAACGCAAGCGCAAAGAGAAAGCAGGTAGCTTGCAGTGGGCTTACATGGCGA
TAGCTAGACTGGGCGGTTTTATGGACAGCAAGCGAACCGGAATTGCCAGCTGGGGCGCCCTCTGGTA
AGGTTGGGAAGCCCTGCAAAGTAAACTGGATGGCTTTCTTGCCGCCAAGGATCTGATGGCGCAGGGG
ATCAAGATCTAACCAGGAGCTATTTAATGGCAACAGTTAACCAGCTGGTACGCAAACCACGTGCTCG
CAAAGTTGCGAAAAGCAACGTGCCTGCGCTGGAAGCATGCCCGCAAAAACGTGGCGTATGTACTCGT
GTATATACTACCACTCCTAAAAAACCGAACTCCGCGCTGCGTAAAGTATGCCGTGTTCGTCTGACTAA
CGGTTTCGAAGTGACTTCCTACATCGGTGGTGAAGGTCACAACCTGCAGGAGCACTCCGTGATCCTG
ATCCGTGGCGGTCGTGTTAAAGACCTCCCGGGTGTTCGTTACCACACCGTACGTGGTGCGCTTGACTG
CTCCGGCGTTAAAGACCGTAAGCAGGCTCGTTCCAAGTATGGCGTGAAGCGTCCTAAGGCTTAATGG
TAGATCTGATCAAGAGACAGGATGACGGTCGTTTCGCATGCTTGAACAAGATGGATTGCACGCAGGT
TCTCCGGCCGCTTGGGTGGAGAGGCTATTCGGCTATGACTGGGCACAACAGACAATCGGCTGCTCTG
ATGCCGCCGTGTTCCGGCTGTCAGCGCAGGGGCGCCCGGTTCTTTTTGTCAAGACCGACCTGTCCGGT
GCCCTGAATGAACTGCAGGACGAGGCAGCGCGGCTATCGTGGCTGGCCACGACGGGCGTTCCTTGCG
CAGCTGTGCTCGACGTTGTCACTGAAGCGGGAAGGGACTGGCTGCTATTGGGCGAAGTGCCGGGGCA
GGATCTCCTGTCATCTCACCTTGCTCCTGCCGAGAAAGTATCCATCATGGCTGATGCAATGCGGCGGC
TGCATACGCTTGATCCGGCTACCTGCCCATTCGACCACCAAGCGAAACATCGCATCGAGCGAGCACG
TACTCGGATGGAAGCCGGTCTTGTCGATCAGGATGATCTGGACGAAGAGCATCAGGGGCTCGCGCCA
GCCGAACTGTTCGCCAGGCTCAAGGCGCGCATGCCCGACGGCGAGGATCTCGTCGTGACCCATGGCG
ATGCCTGCTTGCCGAATATCATGGTGGAAAATGGCCGCTTTTCTGGATTCATCGACTGTGGCCGGCTG
GGTGTGGCGGACCGCTATCAGGACATAGCGTTGGCTACCCGTGATATTGCTGAAGAGCTTGGCGGCG
AATGGGCTGACCGCTTCCTCGTGCTTTACGGTATCGCCGCTCCCGATTCGCAGCGCATCGCCTTCTAT
CGCCTTCTTGACGAGTTCTTCTGAGCGGGACTCTGGGGTTCGAAATGACCGACCAAGCGACGCCCAA
CCTGCCATCACGAGATTTCGATTCCACCGCCGCCTTCTATGAAAGGTTGGGCTTCGGAATCGTTTTCC
GGGACGCCGGCTGGATGATCCTCCAGCGCGGGGATCTCATGCTGGAGTTCTTCGCCCACCCCGGGCT
CGATCCCCTCGGGGGAATCAGAATTCAGTCGACAGCGGCCGCGATCTGCTGTGCCTTCTAGTTGCC
AGCCATCTGTTGTTTGCCCCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTGGGGATGCGGTGGGCT
CTATGGCCGATCAGCGATCGCTGAGGTGGGTGAGTGGGCGTGGCCTGGGGTGGTCATGAAAATATAT
AAGTTGGGGGTCTTAGGGTCTCTTTATTTGTGTTGCAGAGACCGCCGGAGCCATGAGCGGGAGCAGC
AGCAGCAGCAGTAGCAGCAGCGCCTTGGATGGCAGCATCGTGAGCCCTTATTTGACGACGCGGATGC
CCCACTGGGCCGGGGTGCGTCAGAATGTGATGGGCTCCAGCATCGACGGCCGACCCGTCCTGCCCGC
AAATTCCGCCACGCTGACCTATGCGACCGTCGCGGGGACGCCGTTGGACGCCACCGCCGCCGCCGCC
GCCACCGCAGCCGCCTCGGCCGTGCGCAGCCTGGCCACGGACTTTGCATTCCTGGGACCACTGGCGA
```

-continued

```
CAGGGGCTACTTCTCGGGCCGCTGCTGCCGCCGTTCGCGATGACAAGCTGACCGCCCTGCTGGCGCA
GTTGGATGCGCTTACTCGGGAACTGGGTGACCTTTCTCAGCAGGTCATGGCCCTGCGCCAGCAGGTCT
CCTCCCTGCAAGCTGGCGGGAATGCTTCTCCCACAAATGCCGTTTAAGATAAATAAAACCAGACTCT
GTTTGGATTAAAGAAAAGTAGCAAGTGCATTGCTCTCTTTATTTCATAATTTTCCGCGCGCGATAGGC
CCTAGACCAGCGTTCTCGGTCGTTGAGGGTGCGGTGTATCTTCTCCAGGACGTGGTAGAGGTGGCTCT
GGACGTTGAGATACATGGGCATGAGCCCGTCCCGGGGGTGGAGGTAGCACCACTGCAGAGCTTCATG
CTCCGGGGTGGTGTTGTAGATGATCCAGTCGTAGCAGGAGCGCTGGGCATGGTGCCTAAAAATGTCC
TTCAGCAGCAGGCCGATGGCCAGGGGGAGGCCCTTGGTGTAAGTGTTTACAAAACGGTTAAGTTGGG
AAGGGTGCATTCGGGGAGAGATGATGTGCATCTTGGACTGTATTTTTAGATTGGCGATGTTTCCGCCC
AGATCCCTTCTGGGATTCATGTTGTGCAGGACCACCAGTACAGTGTATCCGGTGCACTTGGGGAATTT
GTCATGCAGCTTAGAGGGAAAAGCGTGGAAGAACTTGGAGACGCCTTTGTGGCCTCCCAGATTTTCC
ATGCATTCGTCCATGATGATGGCAATGGGCCCGCGGGAGGCAGCTTGGGCAAAGATATTCTGGGGT
CGCTGACGTCGTAGTTGTGTTCCAGGGTGAGGTCGTCATAGGCCATTTTTACAAAGCGCGGGCGGAG
GGTGCCCGACTGGGGGATGATGGTCCCCTCTGGCCCTGGGGCGTAGTTGCCCTCGCAGATCTGCATTT
CCCAGGCCTTAATCTCGGAGGGGGGAATCATATCCACCTGCGGGGCGATGAAGAAAACGGTTTCCGG
AGCCGGGGAGATTAACTGGGATGAGAGCAGGTTTCTAAGCAGCTGTGATTTTCCACAACCGGTGGGC
CCATAAATAACACCTATAACCGGTTGCAGCTGGTAGTTTAGAGAGCTGCAGCTGCCGTCGTCCCGGA
GGAGGGGGGCCACCTCGTTGAGCATGTCCCTGACGCGCATGTTCTCCCCGACCAGATCCGCCAGAAG
GCGCTCGCCGCCCAGGGACAGCAGCTCTTGCAAGGAAGCAAAGTTTTTCAGCGGCTTGAGGCCGTCC
GCCGTGGGCATGTTTTTCAGGGTCTGGCTCAGCAGCTCCAGGCGGTCCCAGAGCTCGGTGACGTGCT
CTACGGCATCTCTATCCAGCATATCTCCTCGTTTCGCGGGTTGGGGCGACTTTCGCTGTAGGGCACCA
AGCGGTGGTCGTCCAGCGGGGCCAGAGTCATGTCCTTCCATGGGCGCAGGGTCCTCGTCAGGGTGGT
CTGGGTCACGGTGAAGGGGTGCGCTCCGGGCTGAGCGCTTGCCAAGGTGCGCTTGAGGCTGGTTCTG
CTGGTGCTGAAGCGCTGCCGGTCTTCGCCCTGCGCGTCGGCCAGGTAGCATTTGACCATGGTGTCATA
GTCCAGCCCCTCCGCGCGTGTCCCTTGGCGCGCAGCTTGCCCTTGGAGGTGGCGCCGCACGAGGGG
CAGAGCAGGCTCTTGAGCGCGTAGAGCTTGGGGGCGAGGAAGACCGATTCGGGGAGTAGGCGTCC
GCGCCGCAGACCCCGCACACGGTCTCGCACTCCACCAGCCAGGTGAGCTCGGGGCGCGCCGGGTCAA
AAACCAGGTTTCCCCCATGCTTTTTGATGCGTTTCTTACCTCGGGTCTCCATGAGGTGGTGTCCCCGCT
CGGTGACGAAGAGGCTGTCCGTGTCTCCGTAGACCGACTTGAGGGGTCTTTTCTCCAGGGGGTCCC
TCGGTCTTCCTCGTAGAGGAACTCGGACCACTCTGAGACGAAGGCCCGCGTCCAGGCCAGGACGAAG
GAGGCTATGTGGGAGGGGTAGCGGTCGTTGTCCACTAGGGGGTCCACCTTCTCCAAGGTGTGAAGAC
ACATGTCGCCTTCCTCGGCGTCCAGGAAGGTGATTGGCTTGTAGGTGTAGGCCACGTGACCGGGGGT
TCCTGACGGGGGGGTATAAAAGGGGGTGGGGGCGCGCTCGTCGTCACTCTCTTCCGCATCGCTGTCT
GCGAGGGCCAGCTGCTGGGGTGAGTATTCCCTCTCGAAGGCGGGCATGACCTCCGCGCTGAGGTTGT
CAGTTTCCAAAAACGAGGAGGATTTGATGTTCACCTGTCCCGAGGTGATACCTTTGAGGGTACCCGC
GTCCATCTGGTCAGAAAACACGATCTTTTATTGTCCAGCTTGGTGGCGAACGACCCGTAGAGGGCG
TTGGAGAGCAGCTTGGCGATGGAGCGCAGGGTCTGGTTCTTGTCCCTGTCGGCGCGCTCCTTGGCCGC
GATGTTGAGCTGCACGTACTCGCGCGCGACGCAGCGCCACTCGGGGAAGACGGTGGTGCGCTCGTCG
GGCACCAGGCGCACGCGCCAGCCGCGGTTGTGCAGGGTGACCAGGTCCACGCTGGTGGCGACCTCGC
CGCGCAGGCGCTCGTTGGTCCAGCAGAGACGGCCGCCCTTGCGCGAGCAGAAGGGGGGCAGGGGGT
CGAGCTGGGTCTCGTCCGGGGGGTCCGCGTCCACGGTGAAAACCCCGGGGCGCAGGCGCGCGTCGA
```

-continued

```
AGTAGTCTATCTTGCAACCTTGCATGTCCAGCGCCTGCTGCCAGTCGCGGGCGGCGAGCGCGCTC
GTAGGGGTTGAGCGGCGGGCCCCAGGGCATGGGGTGGGTGAGTGCGGAGGCGTACATGCCGCAGAT
GTCATAGACGTAGAGGGGCTCCCGCAGGACCCCGATGTAGGTGGGGTAGCAGCGGCCGCCGCGGAT
GCTGGCGCGCACGTAGTCATACAGCTCGTGCGAGGGGCGAGGAGGTCGGGGCCCAGGTTGGTGCG
GGCGGGGCGCTCCGCGCGGAAGACGATCTGCCTGAAGATGGCATGCGAGTTGGAAGAGATGGTGGG
GCGCTGGAAGACGTTGAAGCTGGCGTCCTGCAGGCCGACGGCGTCGCGCACGAAGGAGGCGTAGGA
GTCGCGCAGCTTGTGTACCAGCTCGGCGGTGACCTGCACGTCGAGCGCGCAGTAGTCGAGGGTCTCG
CGGATGATGTCATATTTAGCCTGCCCCTTCTTTTTCCACAGCTCGCGGTTGAGGACAAACTCTTCGCG
GTCTTTCCAGTACTCTTGGATCGGGAAACCGTCCGGTTCCGAACGGTAAGAGCCTAGCATGTAGAAC
TGGTTGACGGCCTGGTAGGCGCAGCAGCCCTTCTCCACGGGGAGGGCGTAGGCCTGCGCGGCCTTGC
GGAGCGAGGTGTGGGTCAGGGCGAAGGTGTCCCTGACCATGACTTTGAGGTACTGGTGCTTGAAGTC
GGAGTCGTCGCAGCCGCCCCGCTCCCAGAGCGAGAAGTCGGTGCGCTTCTTGGAGCGGGGGTTGGGC
AGAGCGAAGGTGACATCGTTGAAGAGGATTTTGCCCGCGCGGGGCATGAAGTTGCGGGTGATGCGG
AAGGGCCCCGGCACTTCAGAGCGGTTGTTGATGACCTGGGCGGCGAGCACGATCTCGTCGAAGCCGT
TGATGTTGTGGCCCACGATGTAGAGTTCCAGGAAGCGGGGCCGGCCCTTTACGGTGGGCAGCTTCTT
TAGCTCTTCGTAGGTGAGCTCCTCGGGCGAGGCGAGGCCGTGCTCGGCCAGGGCCCAGTCCGCGAGG
TGCGGGTTGTCTCTGAGGAAGGACTTCCAGAGGTCGCGGGCCAGGAGGGTCTGCAGGCGGTCTCTGA
AGGTCCTGAACTGGCGGCCCACGGCCATTTTTTCGGGGGTGATGCAGTAGAAGGTGAGGGGGTCTTG
CTGCCAGCGGTCCCAGTCGAGCTGCAGGGCGAGGTCGCGCGCGGCGGTGACCAGGCGCTCGTCGCCC
CCGAATTTCATGACCAGCATGAAGGGCACGAGCTGCTTTCCGAAGGCCCCCATCCAAGTGTAGGTCT
CTACATCGTAGGTGACAAAGAGGCGCTCCGTGCGAGGATGCGAGCCGATCGGGAAGAACTGGATCT
CCCGCCACCAGTTGGAGGAGTGGCTGTTGATGTGGTGGAAGTAGAAGTCCCGTCGCCGGGCCGAACA
CTCGTGCTGGCTTTTGTAAAAGCGAGCGCAGTACTGGCAGCGCTGCACGGGCTGTACCTCATGCACG
AGATGCACCTTTCGCCCGCGCACGAGGAAGCCGAGGGGAAATCTGAGCCCCCGCCTGGCTCGCGGC
ATGGCTGGTTCTCTTCTACTTTGGATGCGTGTCCGTCTCCGTCTGGCTCCTCGAGGGGTGTTACGGTG
GAGCGGACCACCACGCCGCGCGAGCCGCAGGTCCAGATATCGGCGCGCGGCGGTCGGAGTTTGATG
ACGACATCGCGCAGCTGGGAGCTGTCCATGGTCTGGAGCTCCCGCGGCGGCGGCAGGTCAGCCGGG
AGTTCTTGCAGGTTCACCTCGCAGAGTCGGGCCAGGGCGCGGGGCAGGTCTAGGTGGTACCTGATCT
CTAGGGGCGTGTTGGTGGCGGCGTCGATGGCTTGCAGGAGCCCGCAGCCCCGGGGGCGACGACGG
TGCCCCGCGGGGTGGTGGTGGTGGCGGTGCAGCTCAGAAGCGGTGCCGCGGGCGGGCCCCCGG
AGGTAGGGGGGGCTCCGGTCCCGCGGGCAGGGGCGGCAGCGGCACGTCGGCGTGGAGCGCGGGCAG
GAGTTGGTGCTGTGCCCGGAGGTTGCTGGCGAAGGCGACGACGCGGCGGTTGATCTCCTGGATCTGG
CGCCTCTGCGTGAAGACGACGGGCCCGGTGAGCTTGAACCTGAAAGAGAGTTCGACAGAATCAATCT
CGGTGTCATTGACCGCGGCCTGGCGCAGGATCTCCTGCACGTCTCCCGAGTTGTCTTGGTAGGCGATC
TCGGCCATGAACTGCTCGATCTCTTCCTCCTGGAGGTCTCCGCGTCCGGCGCGTTCCACGGTGGCCGC
CAGGTCGTTGGAGATGCGCCCCATGAGCTGCGAGAAGGCGTTGAGTCCGCCCTCGTTCCAGACTCGG
CTGTAGACCACGCCCCCCTGGTCATCGCGGGCGCGCATGACCACCTGCGCGAGGTTGAGCTCCACGT
GCCGCGCGAAGACGGCGTAGTTGCGCAGACGCTGGAAGAGGTAGTTGAGGGTGGTGGCGGTGTGCT
CGGCCACGAAGAAGTTCATGACCCAGCGGCGCAACGTGGATTCGTTGATGTCCCCCAAGGCCTCCAG
CCGTTCCATGGCCTCGTAGAAGTCCACGGCGAAGTTGAAAAACTGGGAGTTGCGCGCCGACACGGTC
```

-continued

```
AACTCCTCCTCCAGAAGACGGATGAGCTCGGCGACGGTGTCGCGCACCTCGCGCTCGAAGGCTATGG
GGATCTCTTCCTCCGCTAGCATCACCACCTCCTCCTCTTCCTCCTCTTCTGGCACTTCCATGATGGCTT
CCTCCTCTTCGGGGGGTGGCGGCGGCGGCGGTGGGGGAGGGGGCGCTCTGCGCCGGCGGCGGCGCA
CCGGGAGGCGGTCCACGAAGCGCGCGATCATCTCCCCGCGGCGGCGGCGCATGGTCTCGGTGACGGC
GCGGCCGTTCTCCCGGGGGCGCAGTTGGAAGACGCCGCCGGACATCTGGTGCTGGGGCGGGTGGCCG
TGAGGCAGCGAGACGGCGCTGACGATGCATCTCAACAATTGCTGCGTAGGTACGCCGCCGAGGGAC
CTGAGGGAGTCCATATCCACCGGATCCGAAAACCTTTCGAGGAAGGCGTCTAACCAGTCGCAGTCGC
AAGGTAGGCTGAGCACCGTGGCGGGCGGCGGGGGGTGGGGGGAGTGTCTGGCGGAGGTGCTGCTGA
TGATGTAATTGAAGTAGGCGGACTTGACACGGCGGATGGTCGACAGGAGCACCATGTCCTTGGGTCC
GGCCTGCTGGATGCGGAGGCGGTCGGCTATGCCCCAGGCTTCGTTCTGGCATCGGCGCAGGTCCTTG
TAGTAGTCTTGCATGAGCCTTTCCACCGGCACCTCTTCTCCTTCCTCTTCTGCTTCTTCCATGTCTGCTT
CGGCCCTGGGGCGGCGCCGCGCCCCCTGCCCCCCATGCGCGTGACCCCGAACCCCCTGAGCGGTTG
GAGCAGGGCCAGGTCGGCGACGACGCGCTCGGCCAGGATGGCCTGCTGCACCTGCGTGAGGGTGGT
TTGGAAGTCATCCAAGTCCACGAAGCGGTGGTAGGCGCCCGTGTTGATGGTGTAGGTGCAGTTGGCC
ATGACGGACCAGTTGACGGTCTGGTGGCCCGGTTGCGACATCTCGGTGTACCTGAGTCGCGAGTAGG
CGCGGGAGTCGAAGACGTAGTCGTTGCAAGTCCGCACCAGGTACTGGTAGCCCACCAGGAAGTGCG
GCGGCGGCTGGCGGTAGAGGGGCCAGCGCAGGGTGGCGGGGGCTCCGGGGGCCAGGTCTTCCAGCA
TGAGGCGGTGGTAGGCGTAGATGTACCTGGACATCCAGGTGATACCCGCGGCGGTGGTGGAGGCGC
GCGGGAAGTCGCGCACCCGGTTCCAGATGTTGCGCAGGGGCAGAAAGTGCTCCATGGTAGGCGTGCT
CTGTCCAGTCAGACGCGCGCAGTCGTTGATACTCTAGACCAGGGAAAACGAAAGCCGGTCAGCGGG
CACTCTTCCGTGGTCTGGTGAATAGATCGCAAGGGTATCATGGCGGAGGGCCTCGGTTCGAGCCCCG
GGTCCGGGCCGGACGGTCCGCCATGATCCACGCGGTTACCGCCCGCGTGTCGAACCCAGGTGTGCGA
CGTCAGACAACGGTGGAGTGTTCCTTTTGGCGTTTTTCTGGCCGGGCGCCGGCGCCGCGTAAGAGAC
TAAGCCGCGAAAGCGAAAGCAGTAAGTGGCTCGCTCCCCGTAGCCGGAGGGATCCTTGCTAAGGGTT
GCGTTGCGGCGAACCCCGGTTCGAATCCCGTACTCGGGCCGGCCGGACCCGCGGCTAAGGTGTTGGA
TTGGCCTCCCCCTCGTATAAAGACCCCGCTTGCGGATTGACTCCGGACACGGGGACGAGCCCCTTTTA
TTTTTGCTTTCCCCAGATGCATCCGGTGCTGCGGCAGATGCGCCCCCGCCCCAGCAGCAGCAACAAC
ACCAGCAAGAGCGGCAGCAACAGCAGCGGGAGTCATGCAGGGCCCCCTCACCCACCCTCGGCGGGC
CGGCCACCTCGGCGTCCGCGGCCGTGTCTGGCGCCTGCGGCGGCGGCGGGGGGCCGGCTGACGACCC
CGAGGAGCCCCGCGGCGCAGGGCCAGACACTACCTGGACCTGGAGGAGGGCGAGGGCCTGGCGCG
GCTGGGGGCGCCGTCTCCCGAGCGCCACCCGCGGGTGCAGCTGAAGCGCGACTCGCGCGAGGCGTA
CGTGCCTCGGCAGAACCTGTTCAGGGACCGCGCGGGCGAGGAGCCCGAGGAGATGCGGGACAGGAG
GTTCAGCGCAGGGCGGGAGCTGCGGCAGGGGCTGAACCGCGAGCGGCTGCTGCGCGAGGAGGACTT
TGAGCCCGACGCGCGGACGGGGATCAGCCCCGCGCGCGCGCACGTGGCGGCCGCCGACCTGGTGAC
GGCGTACGAGCAGACGGTGAACCAGGAGATCAACTTCCAAAAGAGTTTCAACAACCACGTGCGCAC
GCTGGTGGCGCGCGAGGAGGTGACCATCGGGCTGATGCACCTGTGGGACTTTGTAAGCGCGCTGGTG
CAGAACCCCAACAGCAAGCCTCTGACGGCGCAGCTGTTCCTGATAGTGCAGCACAGCAGGGACAAC
GAGGCGTTTAGGGACGCGCTGCTGAACATCACCGAGCCCGAGGGTCGGTGGCTGCTGGACCTGATTA
ACATCCTGCAGAGCATAGTGGTGCAGGAGCGCAGCCTGAGCCTGGCCGACAAGGTGGCGGCCATCA
ACTACTCGATGCTGAGCCTGGGCAAGTTTTACGCGCGCAAGATCTACCAGACGCCGTACGTGCCCAT
AGACAAGGAGGTGAAGATCGACGGTTTTTACATGCGCATGGCGCTGAAGGTGCTCACCCTGAGCGAC
```

-continued

```
GACCTGGGCGTGTACCGCAACGAGCGCATCCACAAGGCCGTGAGCGTGAGCCGGCGGCGCGAGCTG

AGCGACCGCGAGCTGATGCACAGCCTGCAGCGGGCGCTGGCGGGCGCCGGCAGCGGCGACAGGGAG

GCGGAGTCCTACTTCGATGCGGGGGCGGACCTGCGCTGGGCGCCCAGCCGGCGGGCCCTGGAGGCC

GCGGGGGTCCGCGAGGACTATGACGAGGACGGCGAGGAGGATGAGGAGTACGAGCTAGAGGAGGG

CGAGTACCTGGACTAAACCGCGGGTGGTGTTTCCGGTAGATGCAAGACCCGAACGTGGTGGACCCGG

CGCTGCGGGCGGCTCTGCAGAGCCAGCCGTCCGGCCTTAACTCCTCAGACGACTGGCGACAGGTCAT

GGACCGCATCATGTCGCTGACGGCGCGTAACCCGGACGCGTTCCGGCAGCAGCCGCAGGCCAACAG

GCTCTCCGCCATCCTGGAGGCGGTGGTGCCTGCGCGCTCGAACCCCACGCACGAGAAGGTGCTGGCC

ATAGTGAACGCGCTGGCCGAGAACAGGGCCATCCGCCCGGACGAGGCCGGGCTGGTGTACGACGCG

CTGCTGCAGCGCGTGGCCCGCTACAACAGCGGCAACGTGCAGACCAACCTGGACCGGCTGGTGGGG

GACGTGCGCGAGGCGGTGGCGCAGCGCGAGCGCGCGGATCGGCAGGGCAACCTGGGCTCCATGGTG

GCGCTGAATGCCTTCCTGAGCACGCAGCCGGCCAACGTGCCGCGGGGGCAGGAAGACTACACCAAC

TTTGTGAGCGCGCTGCGGCTGATGGTGACCGAGACCCCCCAGAGCGAGGTGTACCAGTCGGGCCCGG

ACTACTTCTTCCAGACCAGCAGACAGGGCCTGCAGACGGTGAACCTGAGCCAGGCTTTCAAGAACCT

GCGGGGGCTGTGGGCGTGAAGGCGCCCACCGGCGACCGGGCGACGGTGTCCAGCCTGCTGACGCC

CAACTCGCGCCTGCTGCTGCTGCTGATCGCGCCGTTCACGGACAGCGGCAGCGTGTCCCGGGACACC

TACCTGGGGCACCTGCTGACCCTGTACCGCGAGGCCATCGGGCAGGCGCAGGTGGACGAGCACACCT

TCCAGGAGATCACCAGCGTGAGCCGCGCGCTGGGGCAGGAGGACACGAGCAGCCTGGAGGCGACTC

TGAACTACCTGCTGACCAACCGGCGGCAGAAGATTCCCTCGCTGCACAGCCTGACCTCCGAGGAGGA

GCGCATCTTGCGCTACGTGCAGCAGAGCGTGAGCCTGAACCTGATGCGCGACGGGGTGACGCCCAGC

GTGGCGCTGGACATGACCGCGCGCAACATGGAACCGGGCATGTACGCCGCGCACCGGCCTTACATCA

ACCGCCTGATGGACTACCTGCATCGCGCGGCGGCCGTGAACCCCGAGTACTTTACCAACGCCATCCT

GAACCCGCACTGGCTCCCGCCGCCCGGGTTCTACAGCGGGGCTTCGAGGTCCCGGAGACCAACGAT

GGCTTCCTGTGGGACGACATGGACGACAGCGTGTTCTCCCCGCGGCCGCAGGCGCTGGCGGAAGCGT

CCCTGCTGCGTCCCAAGAAGGAGGAGGAGGAGGAGGCGAGTCGCCGCCGCGGCAGCAGCGGCGTGG

CTTCTCTGTCCGAGCTGGGGCGGCAGCCGCCGCGCGCCCCGGGTCCCTGGGCGGCAGCCCCTTTCC

GAGCCTGGTGGGGTCTCTGCACAGCGAGCGCACCACCCGCCCTCGGCTGCTGGGCGAGGACGAGTAC

CTGAATAACTCCCTGCTGCAGCCGGTGCGGGAGAAAAACCTGCCTCCCGCCTTCCCCAACAACGGGA

TAGAGAGCCTGGTGGACAAGATGAGCAGATGGAAGACCTATGCGCAGGAGCACAGGGACGCGCCTG

CGCTCCGGCCGCCCACGCGGCGCCAGCGCCACGACCGGCAGCGGGGCTGGTGTGGGATGACGAGG

ACTCCGCGGACGATAGCAGCGTGCTGGACCTGGGAGGGAGCGGCAACCCCGTTCGCGCACCTGCGCCC

CCGCCTGGGGAGGATGTTTTAAAAAAAAAAAAAAAAGCAAGAAGCATGATGCAAAAATTAAATAA

AACTCACCAAGGCCATGGCGACCGAGCGTTGGTTTCTTGTGTTCCCTTCAGTATGCGGCGCGCGGCG

ATGTACCAGGAGGGACCTCCTCCCTCTTACGAGAGCGTGGTGGGCGCGGCGGCGGCGCGCCCTCTT

CTCCCTTTGCGTCGCAGCTGCTGGAGCCGCCGTACGTGCCTCCGCGCTACCTGCGGCCTACGGGGGG

GAGAAACAGCATCCGTTACTCGGAGCTGGCGCCCCTGTTCGACACCACCCGGGTGTACCTGGTGGAC

AACAAGTCGGCGGACGTGGCCTCCCTGAACTACCAGAACGACCACAGCAATTTTTTGACCACGGTCA

TCCAGAACAATGACTACAGCCCGAGCGAGGCCAGCACCCAGACCATCAATCTGGATGACCGGTCGC

ACTGGGCGGCGACCTGAAAACCATCCTGCACACCAACATGCCCAACGTGAACGAGTTCATGTTCAC

CAATAAGTTCAAGGCGCGGGTGATGGTGTCGCGCTCGCACACCAAGGAAGACCGGGTGGAGCTGAA
```

-continued

```
GTACGAGTGGGTGGAGTTCGAGCTGCCAGAGGGCAACTACTCCGAGACCATGACCATTGACCTGATG
AACAACGCGATCGTGGAGCACTATCTGAAAGTGGGCAGGCAGAACGGGGTCCTGGAGAGCGACATC
GGGGTCAAGTTCGACACCAGGAACTTCCGCCTGGGGCTGGACCCCGTGACCGGGCTGGTTATGCCCG
GGGTGTACACCAACGAGGCCTTCCATCCCGACATCATCCTGCTGCCCGGCTGCGGGGTGGACTTCAC
TTACAGCCGCCTGAGCAACCTCCTGGGCATCCGCAAGCGGCAGCCCTTCCAGGAGGGCTTCAGGATC
ACCTACGAGGACCTGGAGGGGGGCAACATCCCCGCGCTCCTCGATGTGGAGGCCTACCAGGATAGCT
TGAAGGAAAATGAGGCGGGACAGGAGGATACCGCCCCCGCCGCCTCCGCCGCCGCCGAGCAGGGCG
AGGATGCTGCTGACACCGCGGCCGCGGACGGGGCAGAGGCCGACCCCGCTATGGTGGTGGAGGCTC
CCGAGCAGGAGGAGGACATGAATGACAGTGCGGTGCGCGGAGACACCTTCGTCACCCGGGGGGAGG
AAAAGCAAGCGGAGGCCGAGGCCGCGGCCGAGGAAAAGCAACTGGCGGCAGCAGCGGCGGCGGCG
GCGTTGGCCGCGGCGGAGGCTGAGTCTGAGGGGACCAAGCCCGCCAAGGAGCCCGTGATTAAGCCC
CTGACCGAAGATAGCAAGAAGCGCAGTTACAACCTGCTCAAGGACAGCACCAACACCGCGTACCGC
AGCTGGTACCTGGCCTACAACTACGGCGACCCGTCGACGGGGTGCGCTCCTGGACCCTGCTGTGCA
CGCCGGACGTGACCTGCGGCTCGGAGCAGGTGTACTGGTCGCTGCCCGACATGATGCAAGACCCCGT
GACCTTCCGCTCCACGCGGCAGGTCAGCAACTTCCCGGTGGTGGGCGCCGAGCTGCTGCCCGTGCAC
TCCAAGAGCTTCTACAACGACCAGGCCGTCTACTCCCAGCTCATCCGCCAGTTCACCTCTCTGACCCA
CGTGTTCAATCGCTTTCCTGAGAACCAGATTCTGGCGCGCCCGCCCGCCCCCACCATCACCACCGTCA
GTGAAAACGTTCCTGCTCTCACAGATCACGGGACGCTACCGCTGCGCAACAGCATCGGAGGAGTCCA
GCGAGTGACCGTTACTGACGCCAGACGCCGCACCTGCCCCTACGTTTACAAGGCCTTGGGCATAGTC
TCGCCGCGCGTCCTTTCCAGCCGCACTTTTTGAGCAACACCACCATCATGTCCATCCTGATCTCACCC
AGCAATAACTCCGGCTGGGGACTGCTGCGCGCGCCCAGCAAGATGTTCGGAGGGGCGAGGAAGCGT
TCCGAGCAGCACCCCGTGCGCGTGCGCGGGCACTTCCGCGCCCCCTGGGGAGCGCACAAACGCGGCC
GCGCGGGGCGCACCACCGTGGACGACGCCATCGACTCGGTGGTGGAGCAGGCGCGCAACTACAGGC
CCGCGGTCTCTACCGTGGACGCGGCCATCCAGACCGTGGTGCGGGGCGCGCGGCGGTACGCCAAGCT
GAAGAGCCGCCGGAAGCGCGTGGCCCGCCGCCACCGCCGCCGACCCGGGGCCGCCGCCAAACGCGC
CGCCGCGGCCCTGCTTCGCCGGGCCAAGCGCACGGGCCGCCGCGCCGCCATGAGGGCCGCGCGCCGC
TTGGCCGCCGGCATCACCGCCGCCACCATGGCCCCCCGTACCCGAAGACGCGCGGCCGCCGCCGCCG
CCGCCGCCATCAGTGACATGGCCAGCAGGCGCCGGGGCAACGTGTACTGGGTGCGCGACTCGGTGAC
CGGCACGCGCGTGCCCGTGCGCTTCCGCCCCCCGCGGACTTGAGATGATGTGAAAAAACAACACTGA
GTCTCCTGCTGTTGTGTGTATCCCAGCGGCGGCGGCGCGCAGCGTCATGTCCAAGCGCAAAATCA
AAGAAGAGATGCTCCAGGTCGTCGCGCCGGAGATCTATGGGCCCCGAAGAAGGAAGAGCAGGATT
CGAAGCCCCGCAAGATAAAGCGGGTCAAAAAGAAAAAGAAAGATGATGACGATGCCGATGGGGAG
GTGGAGTTCCTGCGCGCCACGCGCCCAGGCGCCCGGTGCAGTGGAAGGGCCGGCGCGTAAAGCGC
GTCCTGCGCCCCGGCACCGCGGTGGTCTTCACGCCCGGCGAGCGCTCCACCCGGACTTTCAAGCGCG
TCTATGACGAGGTGTACGCGACGAAGACCTGCTGGAGCAGGCCAACGAGCGCTTCGGAGAGTTTGC
TTACGGGAAGCGTCAGCGGGCGCTGGGGAAGGAGGACCTGCTGGCGCTGCCGCTGGACCAGGGCAA
CCCCACCCCAGTCTGAAGCCCGTGACCCTGCAGCAGGTGCTGCCGAGCAGCGCACCCTCCGAGGCG
AAGCGGGGTCTGAAGCGCGAGGGCGGCGACCTGGCGCCCACCGTGCAGCTCATGGTGCCCAAGCGG
CAGAGGCTGGAGGATGTGCTGGAGAAAATGAAAGTAGACCCCGGTCTGCAGCCGGACATCAGGGTC
CGCCCCATCAAGCAGGTGGCGCCGGGCCTCGGCGTGCAGACCGTGGACGTGGTCATCCCCACCGGCA
ACTCCCCCGCCGCCGCCACCACTACCGCTGCCTCCACGGACATGGAGACACAGACCGATCCCGCCGC
```

-continued

```
AGCCGCAGCCGCAGCCGCCGCCGCGACCTCCTCGGCGGAGGTGCAGACGGACCCCTGGCTGCCGCCG
GCGATGTCAGCTCCCCGCGCGCGTCGCGGGCGCAGGAAGTACGGCGCCGCCAACGCGCTCCTGCCCG
AGTACGCCTTGCATCCTTCCATCGCGCCCACCCCCGGCTACCGAGGCTATACCTACCGCCCGCGAAG
AGCCAAGGGTTCCACCCGCCGTCCCCGCCGACGCGCCGCCGCCACCACCCGCCGCCGCCGCCGCAGA
CGCCAGCCCGCACTGGCTCCAGTCTCCGTGAGGAAAGTGGCGCGCGACGGACACACCCTGGTGCTGC
CCAGGGCGCGCTACCACCCCAGCATCGTTTAAAAGCCTGTTGTGGTTCTTGCAGATATGGCCCTCACT
TGCCGCCTCCGTTTCCCGGTGCCGGGATACCGAGGAGGAAGATCGCGCCGCAGGAGGGGTCTGGCCG
GCCGCGGCCTGAGCGGAGGCAGCCGCCGCGCGCACCGGCGGCGACGCGCCACCAGCCGACGCATGC
GCGGCGGGGTGCTGCCCCTGTTAATCCCCCTGATCGCCGCGGCGATCGGCGCCGTGCCCGGGATCGC
CTCCGTGGCCTTGCAAGCGTCCCAGAGGCATTGACAGACTTGCAAACTTGCAAATATGGAAAAAAAA
ACCCCAATAAAAAAGTCTAGACTCTCACGCTCGCTTGGTCCTGTGACTATTTTGTAGAATGGAAGAC
ATCAACTTTGCGTCGCTGGCCCCGCGTCACGGCTCGCGCCCGTTCCTGGGACACTGGAACGATATCG
GCACCAGCAACATGAGCGGTGGCGCCTTCAGTTGGGGCTCTCTGTGGAGCGGCATTAAAAGTATCGG
GTCTGCCGTTAAAAATTACGGCTCCCGGGCCTGGAACAGCAGCACGGGCCAGATGTTGAGAGACAA
GTTGAAAGAGCAGAACTTCCAGCAGAAGGTGGTGGAGGGCCTGGCCTCCGGCATCAACGGGGTGGT
GGACCTGGCCAACCAGGCCGTGCAGAATAAGATCAACAGCAGACTGGACCCCCGGCCGCCGGTGGA
GGAGGTGCCGCCGGCGCTGGAGACGGTGTCCCCCGATGGGCGTGGCGAGAAGCGCCCGCGGCCCGA
TAGGGAAGAGACCACTCTGGTCACGCAGACCGATGAGCCGCCCCCGTATGAGGAGGCCCTGAAGCA
AGGTCTGCCCACCACGCGGCCCATCGCGCCCATGGCCACCGGGGTGGTGGGCCGCCACACCCCCGCC
ACGCTGGACTTGCCTCCGCCCGCCGATGTGCCGCAGCAGCAGAAGGCGGCACAGCCGGGCCCGCCCG
CGACCGCCTCCCGTTCCTCCGCCGGTCCTCTGCGCCGCGCGGCCAGCGGCCCCCGCGGGGGGTCGC
GAGGCACGGCAACTGGCAGAGCACGCTGAACAGCATCGTGGGTCTGGGGGTGCGGTCCGTGAAGCG
CCGCCGATGCTACTGAATAGCTTAGCTAACGTGTTGTATGTGTGTATGCGCCCTATGTCGCCGCCAGA
GGGAGCTGCTGAGTCGCCGCCGTTCGCGCGCCCACCACCACCGCCACTCCGCCCCTCAAGATGGCGAC
CCCATCGATGATGCCGCAGTGGTCGTACATGCACATCTCGGGCCAGGACGCCTCGGAGTACCTGAGC
CCCGGGCTGGTGCAGTTCGCCCGCGCCACCGAGAGCTACTTCAGCCTGAGTAACAAGTTTAGGAACC
CCACGGTGGCGCCCACGCACGATGTGACCACCGACCGGTCTCAGCGCCTGACGCTGCGGTTCATTCC
CGTGGACCGCGAGGACACCGCGTACTCGTACAAGGCGCGGTTCACCCTGGCCGTGGGCGACAACCGC
GTGCTGGACATGGCCTCCACCTACTTTGACATCCGCGGGGTGCTGGACCGGGGTCCCACTTTCAAGCC
CTACTCTGGCACCGCCTACAACTCCCTGGCCCCCAAGGGCGCTCCCAACTCCTGCGAGTGGGAGCAA
GAGGAAACTCAGGCAGTTGAAGAAGCAGCAGAAGAGGAAGAAGAAGATGCTGACGGTCAAGCTGA
GGAAGAGCAAGCAGCTACCAAAAAGACTCATGTATATGCTCAGGCTCCCCTTTCTGGCGAAAAATT
AGTAAAGATGGTCTGCAAATAGGAACGGACGCTACAGCTACAGAACAAAAACCTATTTATGCAGAC
CCTACATTCCAGCCCGAACCCCAAATCGGGGAGTCCCAGTGGAATGAGGCAGATGCTACAGTCGCCG
GCGGTAGAGTGCTAAAGAAATCTACTCCCATGAAACCATGCTATGGTTCCTATGCAAGACCCACAAA
TGCTAATGGAGGTCAGGGTGTACTAACGGCAAATGCCCAGGGACAGCTAGAATCTCAGGTTGAAATG
CAATTCTTTTCAACTTCTGAAAACGCCCGTAACGAGGCTAACAACATTCAGCCCAAATTGGTGCTGTA
TAGTGAGGATGTGCACATGGAGACCCCGGATACGCACCTTTCTTACAAGCCCGCAAAAAGCGATGAC
AATTCAAAAATCATGCTGGGTCAGCAGTCCATGCCCAACAGACCTAATTACATCGGCTTCAGAGACA
ACTTTATCGGCCTCATGTATTACAATAGCACTGGCAACATGGGAGTGCTTGCAGGTCAGGCCTCTCAG
```

-continued

```
TTGAATGCAGTGGTGGACTTGCAAGACAGAAACACAGAACTGTCCTACCAGCTCTTGCTTGATTCCA

TGGGTGACAGAACCAGATACTTTTCCATGTGGAATCAGGCAGTGGACAGTTATGACCCAGATGTTAG

AATTATTGAAAATCATGGAACTGAAGACGAGCTCCCCAACTATTGTTTCCCTCTGGGTGGCATAGGG

GTAACTGACACTTACCAGGCTGTTAAAACCAACAATGGCAATAACGGGGGCCAGGTGACTTGGACA

AAAGATGAAACTTTTGCAGATCGCAATGAAATAGGGGTGGGAAACAATTTCGCTATGGAGATCAACC

TCAGTGCCAACCTGTGGAGAAACTTCCTGTACTCCAACGTGGCGCTGTACCTACCAGACAAGCTTAA

GTACAACCCCTCCAATGTGGACATCTCTGACAACCCCAACACCTACGATTACATGAACAAGCGAGTG

GTGGCCCCGGGGCTGGTGGACTGCTACATCAACCTGGGCGCGCGCTGGTCGCTGGACTACATGGACA

ACGTCAACCCCTTCAACCACCACCGCAATGCGGGCCTGCGCTACCGCTCCATGCTCCTGGGCAACGG

GCGCTACGTGCCCTTCCACATCCAGGTGCCCCAGAAGTTCTTTGCCATCAAGAACCTCCTCCTCCTGC

CGGGCTCCTACACCTACGAGTGGAACTTCAGGAAGGATGTCAACATGGTCCTCCAGAGCTCTCTGGG

TAACGATCTCAGGGTGGACGGGGCCAGCATCAAGTTCGAGAGCATCTGCCTCTACGCCACCTTCTTC

CCCATGGCCCACAACACGGCCTCCACGCTCGAGGCCATGCTCAGGAACGACACCAACGACCAGTCCT

TCAATGACTACCTCTCCGCCGCCAACATGCTCTACCCCATACCCGCCAACGCCACCAACGTCCCCATC

TCCATCCCCTCGCGCAACTGGGCGGCCTTCCGCGGCTGGGCCTTCACCCGCCTCAAGACCAAGGAGA

CCCCCTCCCTGGGCTCGGGATTCGACCCCTACTACACCTACTCGGGCTCCATTCCCTACCTGGACGGC

ACCTTCTACCTCAACCACACTTTCAAGAAGGTCTCGGTCACCTTCGACTCCTCGGTCAGCTGGCCGGG

CAACGACCGTCTGCTCACCCCCAACGAGTTCGAGATCAAGCGCTCGGTCGACGGGGAGGGCTACAAC

GTGGCCCAGTGCAACATGACCAAGGACTGGTTCCTGGTCCAGATGCTGGCCAACTACAACATCGGCT

ACCAGGGCTTCTACATCCCAGAGAGCTACAAGGACAGGATGTACTCCTTCTTCAGGAACTTCCAGCC

CATGAGCCGGCAGGTGGTGGACCAGACCAAGTACAAGGACTACCAGGAGGTGGGCATCATCCACCA

GCACAACAACTCGGGCTTCGTGGGCTACCTCGCCCCCACCATGCGCGAGGGACAGGCCTACCCCGCC

AACTTCCCCTATCCGCTCATAGGCAAGACCGCGGTCGACAGCATCACCCAGAAAAAGTTCCTCTGCG

ACCGCACCCTCTGGCGCATCCCCTTCTCCAGCAACTTCATGTCCATGGGTGCGCTCTCGGACCTGGGC

CAGAACTTGCTCTACGCCAACTCCGCCCACGCCCTCGACATGACCTTCGAGGTCGACCCCATGGACG

AGCCCACCCTTCTCTATGTTCTGTTCGAAGTCTTTGACGTGGTCCGGGTCCACCAGCCGCACCGCGGC

GTCATCGAGACCGTGTACCTGCGTACGCCCTTCTCGGCCGGCAACGCCACCACCTAAAGAAGCAAGC

CGCAGTCATCGCCGCCTGCATGCCGTCGGGTTCCACCGAGCAAGAGCTCAGGGCCATCGTCAGAGAC

CTGGGATGCGGGCCCTATTTTTTGGGCACCTTCGACAAGCGCTTCCCTGGCTTTGTCTCCCCACACAA

GCTGGCCTGCGCCATCGTCAACACGGCCGGCCGCGAGACCGGGGGCGTGCACTGGCTGGCCTTCGCC

TGGAACCCGCGCTCCAAAACATGCTTCCTCTTTGACCCCTTCGGCTTTTCGGACCAGCGGCTCAAGCA

AATCTACGAGTTCGAGTACGAGGGCTTGCTGCGTCGCAGCGCCATCGCCTCCTCGCCCGACCGCTGC

GTCACCCTCGAAAAGTCCACCCAGACCGTGCAGGGGCCCGACTCGGCCGCCTGCGGTCTCTTCTGCT

GCATGTTTCTGCACGCCTTTGTGCACTGGCCTCAGAGTCCCATGGACCGCAACCCCACCATGAACTTG

CTGACGGGGTGCCCAACTCCATGCTCCAGAGCCCCCAGGTCGAGCCCACCCTGCGCCGCAACCAGG

AGCAGCTCTACAGCTTCCTGGAGCGCCACTCGCCTTACTTCCGCCGCCACAGCGCACAGATCAGGAG

GGCCACCTCCTTCTGCCACTTGCAAGAGATGCAAGAAGGGTAATAACGATGTACACACTTTTTTTCTC

AATAAATGGCATCTTTTTATTTATACAAGCTCTCTGGGGTATTCATTTCCCACCACCACCCGCCGTTGT

CGCCATCTGGCTCTATTTAGAAATCGAAAGGGTTCTGCCGGGAGTCGCCGTGCGCCACGGGCAGGGA

CACGTTGCGATACTGGTAGCGGGTGCCCCACTTGAACTCGGGCACCACCAGGCGAGGCAGCTCGGGG

AAGTTTTCGCTCCACAGGCTGCGGGTCAGCACCAGCGCGTTCATCAGGTCGGGCGCCGAGATCTTGA
```

-continued

```
AGTCGCAGTTGGGGCCGCCGCCCTGCGCGCGCGAGTTGCGGTACACCGGGTTGCAGCACTGGAACAC

CAACAGCGCCGGGTGCTTCACGCTGGCCAGCACGCTGCGGTCGGAGATCAGCTCGGCGTCCAGGTCC

TCCGCGTTGCTCAGCGCGAACGGGGTCATCTTGGGCACTTGCCGCCCCAGGAAGGGCGCGTGCCCCG

GTTTCGAGTTGCAGTCGCAGCGCAGCGGGATCAGCAGGTGCCCGTGCCCGGACTCGGCGTTGGGGTA

CAGCGCGCGCATGAAGGCCTGCATCTGGCGGAAGGCCATCTGGGCCTTGGCGCCCTCCGAGAAGAAC

ATGCCGCAGGACTTGCCCGAGAACTGGTTTGCGGGGCAGCTGGCGTCGTGCAGGCAGCAGCGCGCGT

CGGTGTTGGCGATCTGCACCACGTTGCGCCCCACCGGTTCTTCACGATCTTGGCCTTGGACGATTGC

TCCTTCAGCGCGCGCTGCCCGTTCTCGCTGGTCACATCCATCTCGATCACATGTTCCTTGTTCACCATG

CTGCTGCCGTGCAGACACTTCAGCTCGCCCTCCGTCTCGGTGCAGCGGTGCTGCCACAGCGCGCAGC

CCGTGGGCTCGAAAGACTTGTAGGTCACCTCCGCGAAGGACTGCAGGTACCCCTGCAAAAAGCGGCC

CATCATGGTCACGAAGGTCTTGTTGCTGCTGAAGGTCAGCTGCAGCCCGCGGTGCTCCTCGTTCAGCC

AGGTCTTGCACACGGCCGCCAGCGCCTCCACCTGGTCGGGCAGCATCTTGAAGTTCACCTTCAGCTCA

TTCTCCACGTGGTACTTGTCCATCAGCGTGCGCGCCGCCTCCATGCCCTTCTCCCAGGCCGACACCAG

CGGCAGGCTCACGGGGTTCTTCACCATCACCGTGGCCGCCGCCTCCGCCGCGCTTTCGCTTTCCGCCC

CGCTGTTCTCTTCCTCTTCCTCCTCTTCCTCGCCGCCGCCCACTCGCAGCCCCGCACCACGGGGTCGT

CTTCCTGCAGGCGCTGCACCTTGCGCTTGCCGTTGCGCCCCTGCTTGATGCGCACGGGCGGGTTGCTG

AAGCCCACCATCACCAGCGCGGCCTCTTCTTGCTCGTCCTCGCTGTCCAGAATGACCTCCGGGGAGG

GGGGGTTGGTCATCCTCAGTACCGAGGCACGCTTCTTTTTCTTCCTGGGGGCGTTCGCCAGCTCCGCG

GCTGCGGCCGCTGCCGAGGTCGAAGGCCGAGGGCTGGGCGTGCGCGGCACCAGCGCGTCCTGCGAG

CCGTCCTCGTCCTCCTCGGACTCGAGACGGAGGCGGGCCCGCTTCTTCGGGGGCGCGCGGGGCGGCG

GAGGCGGCGGCGGCGACGGAGACGGGGACGAGACATCGTCCAGGGTGGGTGGACGGCGGGCCGCG

CCGCGTCCGCGCTCGGGGGTGGTCTCGCGCTGGTCCTCTTCCCGACTGGCCATCTCCCACTGCTCCTT

CTCCTATAGGCAGAAAGAGATCATGGAGTCTCTCATGCGAGTCGAGAAGGAGGAGGACAGCCTAAC

CGCCCCCTCTGAGCCCTCCACCACCGCCGCCACCACCGCCAATGCCGCCGCGGACGACGCGCCCACC

GAGACCACCGCCAGTACCACCCTCCCCAGCGACGCACCCCCGCTCGAGAATGAAGTGCTGATCGAGC

AGGACCCGGGTTTTGTGAGCGGAGAGGAGGATGAGGTGGATGAGAAGGAGAAGGAGGAGGTCGCC

GCCTCAGTGCCAAAAGAGGATAAAAAGCAAGACCAGGACGACGCAGATAAGGATGAGACAGCAGT

CGGGCGGGGAACGGAAGCCATGATGCTGATGACGGCTACCTAGACGTGGGAGACGACGTGCTGCT

TAAGCACCTGCACCGCCAGTGCGTCATCGTCTGCGACGCGCTGCAGGAGCGCTGCGAAGTGCCCCTG

GACGTGGCGGAGGTCAGCCGCGCCTACGAGCGGCACCTCTTCGCGCCGCACGTGCCCCCAAGCGCC

GGGAGAACGGCACCTGCGAGCCCAACCCGCGTCTCAACTTCTACCCGGTCTTCGCGGTACCCGAGGT

GCTGGCCACCTACCACATCTTTTTCCAAAACTGCAAGATCCCCCTCTCCTGCCGCGCCAACCGCACCC

GCGCCGACAAAACCCTGACCCTGCGGCAGGGCGCCCACATACCTGATATCGCCTCTCTGGAGGAAGT

GCCCAAGATCTTCGAGGGTCTCGGTCGCGACGAGAAACGGGCGGCGAACGCTCTGCACGGAGACAG

CGAAAACGAGAGTCACTCGGGGGTGCTGGTGGAGCTCGAGGGCGACAACGCGCGCCTGGCCGTACT

CAAGCGCAGCATAGAGGTCACCCACTTTGCCTACCCGGCGCTCAACCTGCCCCCAAGGTCATGAGT

GTGGTCATGGGCGAGCTCATCATGCGCCGCGCCCAGCCCCTGGCCGCGGATGCAAACTTGCAAGAGT

CCTCCGAGGAAGGCCTGCCCGCGGTCAGCGACGAGCAGCTGGCGCGCTGGCTGGAGACCCGCGACC

CCGCGCAGCTGGAGGAGCGGCGCAAGCTCATGATGGCCGCGGTGCTGGTCACCGTGGAGCTCGAGT

GTCTGCAGCGCTTCTTCGCGGACCCCGAGATGCAGCGCAAGCTCGAGGAGACCCTGCACTACACCTT
```

-continued

```
CCGCCAGGGCTACGTGCGCCAGGCCTGCAAGATCTCCAACGTGGAGCTCTGCAACCTGGTCTCCTAC
CTGGGCATCCTGCACGAGAACCGCCTCGGGCAGAACGTCCTGCACTCCACCCTCAAAGGGGAGGCGC
GCCGCGACTACATCCGCGACTGCGCCTACCTCTTCCTCTGCTACACCTGGCAGACGGCCATGGGGGTC
TGGCAGCAGTGCCTGGAGGAGCGCAACCTCAAGGAGCTGGAAAAGCTCCTCAAGCGCACCCTCAGG
GACCTCTGGACGGGCTTCAACGAGCGCTCGGTGGCCGCCGCGCTGGCGGACATCATCTTTCCCGAGC
GCCTGCTCAAGACCCTGCAGCAGGGCCTGCCCGACTTCACCAGCCAGAGCATGCTGCAGAACTTCAG
GACTTTCATCCTGGAGCGCTCGGGCATCCTGCCGGCCACTTGCTGCGCGCTGCCCAGCGACTTCGTGC
CCATCAAGTACAGGGAGTGCCCGCCGCCGCTCTGGGGCCACTGCTACCTCTTCCAGCTGGCCAACTA
CCTCGCCTACCACTCGGACCTCATGGAAGACGTGAGCGGCGAGGGCCTGCTCGAGTGCCACTGCCGC
TGCAACCTCTGCACGCCCCACCGCTCTCTAGTCTGCAACCCGCAGCTGCTCAGCGAGAGTCAGATTAT
CGGTACCTTCGAGCTGCAGGGTCCCTCGCCTGACGAGAAGTCCGCGGCTCCAGGGCTGAAACTCACT
CCGGGGCTGTGGACTTCCGCCTACCTACGCAAATTTGTACCTGAGGACTACCACGCCCACGAGATCA
GGTTCTACGAAGACCAATCCCGCCCGCCCAAGGCGGAGCTCACCGCCTGCGTCATCACCCAGGGGCA
CATCCTGGGCCAATTGCAAGCCATCAACAAAGCCCGCCGAGAGTTCTTGCTGAAAAAGGGTCGGGGG
GTGTACCTGGACCCCCAGTCCGGCGAGGAGCTAAACCCGCTACCCCCGCCGCCGCCCCAGCAGCGGG
ACCTTGCTTCCCAGGATGGCACCCAGAAAGAAGCAGCAGCCGCCGCCGCCGCAGCCATACATGC
TTCTGGAGGAAGAGGAGGAGGACTGGGACAGTCAGGCAGAGGAGGTTTCGGACGAGGAGCAGGAG
GAGATGATGGAAGACTGGGAGGAGGACAGCAGCCTAGACGAGGAAGCTTCAGAGGCCGAAGAGGT
GGCAGACGCAACACCATCGCCCTCGGTCGCAGCCCCTCGCCGGGGCCCCTGAAATCCTCCGAACCC
AGCACCAGCGCTATAACCTCCGCTCCTCCGGCGCCGGCGCCACCCGCCCGCAGACCCAACCGTAGAT
GGGACACCACAGGAACCGGGGTCGGTAAGTCCAAGTGCCCGCCGCCGCCACCGCAGCAGCAGCAGC
AGCAGCGCCAGGGCTACCGCTCGTGGCGCGGGCACAAGAACGCCATAGTCGCCTGCTTGCAAGACTG
CGGGGGCAACATCTCTTTCGCCCGCCGCTTCCTGCTATTCCACCACGGGGTCGCCTTTCCCCGCAATG
TCCTGCATTACTACCGTCATCTCTACAGCCCCTACTGCAGCGGCGACCCAGAGGCGGCAGCGGCAGC
CACAGCGGCGACCACCACCTAGGAAGATATCCTCCGCGGGCAAGACAGCGGCAGCAGCGGCCAGGA
GACCCGCGGCAGCAGCGGCGGGAGCGGTGGGCGCACTGCGCCTCTCGCCCAACGAACCCCTCTCGAC
CCGGGAGCTCAGACACAGGATCTTCCCCACTTTGTATGCCATCTTCCAACAGAGCAGAGGCCAGGAG
CAGGAGCTGAAAATAAAAACAGATCTCTGCGCTCCCTCACCCGCAGCTGTCTGTATCACAAAAGCG
AAGATCAGCTTCGGCGCACGCTGGAGGACGCGGAGGCACTCTTCAGCAAATACTGCGCGCTCACTCT
TAAAGACTAGCTCCGCGCCCTTCTCGAATTTAGGCGGGAGAAAACTACGTCATCGCCGGCCGCCGCC
CAGCCCGCCCAGCCGAGATGAGCAAAGAGATTCCCACGCCATACATGTGGAGCTACCAGCCGCAGA
TGGGACTCGCGGCGGGAGCGGCCCAGGACTACTCCACCCGCATGAACTACATGAGCGCGGGACCCC
ACATGATCTCACAGGTCAACGGGATCCGCGCCCAGCGAAACCAAATACTGCTGGAACAGGCGGCCA
TCACCGCCACGCCCCGCCATAATCTCAACCCCCGAAATTGGCCCGCCGCCCTCGTGTACCAGGAAAC
CCCCTCCGCCACCACCGTACTACTTCCGCGTGACGCCCAGGCCGAAGTCCAGATGACTAACTCAGGG
GCGCAGCTCGCGGGCGGCTTTCGTCACGGGGCGCGGCCGCTCCGACCAGGTATAAGACACCTGATGA
TCAGAGGCCGAGGTATCCAGCTCAACGACGAGTCGGTGAGCTCTTCGCTCGGTCTCCGTCCGGACGG
AACTTTCCAGCTCGCCGGATCCGGCCGCTCTTCGTTCACGCCCCGCCAGGCGTACCTGACTCTGCAGA
CCTCGTCCTCGGAGCCCCGCTCCGGCGGCATCGGAACCCTCCAGTTCGTGGAGGAGTTCGTGCCCTCG
GTCTACTTCAACCCCTTCTCGGGACCTCCCGGACGCTACCCCGACCAGTTCATTCCGAACTTTGACGC
GGTGAAGGACTCGGCGGACGGCTACGACTGAATGTCAGGTGTCGAGGCAGAGCAGCTTCGCCTGAG
```

-continued

```
ACACCTCGAGCACTGCCGCCGCCACAAGTGCTTCGCCCGCGGTTCTGGTGAGTTCTGCTACTTTCAGC

TACCCGAGGAGCATACCGAGGGGCCGGCGCACGGCGTCCGCCTGACCACCCAGGGCGAGGTTACCT

GTTCCCTCATCCGGGAGTTTACCCTCCGTCCCCTGCTAGTGGAGCGGGAGCGGGGTCCCTGTGTCCTA

ACTATCGCCTGCAACTGCCCTAACCCTGGATTACATCAAGATCTTTGCTGTCATCTCTGTGCTGAGTTT

AATAAACGCTGAGATCAGAATCTACTGGGGCTCCTGTCGCCATCCTGTGAACGCCACCGTCTTCACCC

ACCCCGACCAGGCCCAGGCGAACCTCACCTGCGGTCTGCATCGGAGGGCCAAGAAGTACCTCACCTG

GTACTTCAACGGCACCCCCTTTGTGGTTTACAACAGCTTCGACGGGACGGAGTCTCCCTGAAAGAC

CAGCTCTCCGGTCTCAGCTACTCCATCCACAAGAACACCACCCTCCAACTCTTCCCTCCCTACCTGCC

GGGAACCTACGAGTGCGTCACCGGCCGCTGCACCCACCTCACCCGCCTGATCGTAAACCAGAGCTTT

CCGGGAACAGATAACTCCCTCTTCCCCAGAACAGGAGGTGAGCTCAGGAAACTCCCCGGGGACCAG

GGCGGAGACGTACCTTCGACCCTTGTGGGGTTAGGATTTTTTATTACCGGGTTGCTGGCTCTTTTAAT

CAAAGTTTCCTTGAGATTTGTTCTTTCCTTCTACGTGTATGAACACCTCAACCTCCAATAACTCTACCC

TTTCTTCGGAATCAGGTGACTTCTCTGAAATCGGGCTTGGTGTGCTGCTTACTCTGTTGATTTTTTCC

TTATCATACTCAGCCTTCTGTGCCTCAGGCTCGCCGCCTGCTGCGCACACATCTATATCTACTGCTGGT

TGCTCAAGTGCAGGGGTCGCCACCCAAGATGAACAGGTACATGGTCCTATCGATCCTAGGCCTGCTG

GCCCTGGCGGCCTGCAGCGCCGCCAAAAAAGAGATTACCTTTGAGGAGCCCGCTTGCAATGTAACTT

TCAAGCCCGAGGGTGACCAATGCACCACCCTCGTCAAATGCGTTACCAATCATGAGAGGCTGCGCAT

CGACTACAAAAACAAAACTGGCCAGTTTGCGGTCTATAGTGTGTTTACGCCCGGAGACCCCTCTAAC

TACTCTGTCACCGTCTTCCAGGGCGGACAGTCTAAGATATTCAATTACACTTTCCCTTTTTATGAGTTA

TGCGATGCGGTCATGTACATGTCAAAACAGTACAACCTGTGGCCTCCCTCTCCCCAGGCGTGTGTGG

AAAATACTGGGTCTTACTGCTGTATGGCTTTCGCAATCACTACGCTCGCTCTAATCTGCACGGTGCTA

TACATAAAATTCAGGCAGAGGCGAATCTTTATCGATGAAAAGAAAATGCCTTGATCGCTAACACCGG

CTTTCTATCTGCAGAATGAATGCAATCACCTCCCTACTAATCACCACCACCCTCCTTGCGATTGCCCA

TGGGTTGACACGAATCGAAGTGCCAGTGGGGTCCAATGTCACCATGGTGGGCCCCGCCGGCAATTCC

ACCCTCATGTGGGAAAAATTTGTCCGCAATCAATGGGTTCATTTCTGCTCTAACCGAATCAGTATCAA

GCCCAGAGCCATCTGCGATGGGCAAAATCTAACTCTGATCAATGTGCAAATGATGGATGCTGGGTAC

TATTACGGGCAGCGGGAGAAATCATTAATTACTGGCGACCCCACAAGGACTACATGCTGCATGTAG

TCGAGGCACTTCCCACTACCACCCCCACTACCACCTCTCCCACCACCACCACCACTACTACTACTACT

ACTACTACTACTACTACCACTACCGCTGCCCGCCATACCCGCAAAAGCACCATGATTAGCACAA

AGCCCCCTCGTGCTCACTCCCACGCCGGCGGGCCCATCGGTGCGACCTCAGAAACCACCGAGCTTTG

CTTCTGCCAATGCACTAACGCCAGCGCTCATGAACTGTTCGACCTGGAGAATGAGGATGTCCAGCAG

AGCTCCGCTTGCCTGACCCAGGAGGCTGTGGAGCCCGTTGCCCTGAAGCAGATCGGTGATTCAATAA

TTGACTCTTCTTCTTTTGCCACTCCCGAATACCCTCCCGATTCTACTTTCCACATCACGGGTACCAAAG

ACCCTAACCTCTCTTTCTACCTGATGCTGCTGCTCTGTATCTCTGTGGTCTCTTCCGCGCTGATGTTAC

TGGGGATGTTCTGCTGCCTGATCTGCCGCAGAAAGAGAAAAGCTCGCTCTCAGGGCCAACCACTGAT

GCCCTTCCCCTACCCCCGGATTTTGCAGATAACAAGATATGAGCTCGCTGCTGACACTAACCGCTTT

ACTAGCCTGCGCTCTAACCCTTGTCGCTTGCGACTCGAGATTCCACAATGTCACAGCTGTGGCAGGAG

AAAATGTTACTTTCAACTCCACGGCCGATACCCAGTGGTCGTGGAGTGGCTCAGGTAGCTACTTAACT

ATCTGCAATAGCTCCACTTCCCCCGGCATATCCCCAACCAAGTACCAATGCAATGCCAGCCTGTTCAC

CCTCATCAACGCTTCCACCCTGGACAATGGACTCTATGTAGGCTATGTACCCTTTGGTGGGCAAGGAA
```

-continued

```
AGACCCACGCTTACAACCTGGAAGTTCGCCAGCCCAGAACCACTACCCAAGCTTCTCCCACCACCAC
CACCACCACCACCATCACCAGCAGCAGCAGCAGCAGCAGCCACAGCAGCAGCAGCAGATTATTGAC
TTTGGTTTTGGCCAGCTCATCTGCCGCTACCCAGGCCATCTACAGCTCTGTGCCCGAAACCACTCAGA
TCCACCGCCCAGAAACGACCACCGCCACCACCCTACACACCTCCAGCGATCAGATGCCGACCAACAT
CACCCCCTTGGCTCTTCAAATGGGACTTACAAGCCCCACTCCAAAACCAGTGGATGCGGCCGAGGTC
TCCGCCCTCGTCAATGACTGGGCGGGGCTGGGAATGTGGTGGTTCGCCATAGGCATGATGGCGCTCT
GCCTGCTTCTGCTCTGGCTCATCTGCTGCCTCCACCGCAGGCGAGCCAGACCCCCCATCTATAGACCC
ATCATTGTCCTGAACCCCGATAATGATGGGATCCATAGATTGGATGGCCTGAAAAACCTACTTTTTTC
TTTTACAGTATGATAAATTGAGACATGCCTCGCATTTTCTTGTACATGTTCCTTCTCCCACCTTTTCTG
GGGTGTTCTACGCTGGCCGCTGTGTCTCACCTGGAGGTAGACTGCCTCTCACCCTTCACTGTCTACCT
GCTTTACGGATTGGTCACCCTCACTCTCATCTGCAGCCTAATCACAGTAATCATCGCCTTCATCCAGT
GCATTGATTACATCTGTGTGCGCCTCGCATACTTCAGACACCACCCGCAGTACCGAGACAGGAACAT
TGCCCAACTTCTAAGACTGCTCTAATCATGCATAAGACTGTGATCTGCCTTCTGATCCTCTGCATCCT
GCCCACCCTCACCTCCTGCCAGTACACCACAAAATCTCCGCGCAAAAGACATGCCTCCTGCCGCTTCA
CCCAACTGTGGAATATACCCAAATGCTACAACGAAAAGAGCGAGCTCTCCGAAGCTTGGCTGTATGG
GGTCATCTGTGTCTTAGTTTTCTGCAGCACTGTCTTTGCCCTCATAATCTACCCCTACTTTGATTTGGG
ATGGAACGCGATCGATGCCATGAATTACCCCACCTTTCCCGCACCCGAGATAATTCCACTGCGACAA
GTTGTACCCGTTGTCGTTAATCAACGCCCCCCATCCCCTACGCCCACTGAAATCAGCTACTTTAACCT
AACAGGCGGAGATGACTGACGCCCTAGATCTAGAAATGGACGGCATCAGTACCGAGCAGCGTCTCCT
AGAGAGGCGCAGGCAGGCGGCTGAGCAAGAGCGCCTCAATCAGGAGCTCCGAGATCTCGTTAACCT
GCACCAGTGCAAAAGAGGCATCTTTTGTCTGGTAAAGCAGGCCAAAGTCACCTACGAGAAGACCGG
CAACAGCCACCGCCTCAGTTACAAATTGCCCACCCAGCGCCAGAAGCTGGTGCTCATGGTGGGTGAG
AATCCCATCACCGTCACCCAGCACTCGGTAGAGACCGAGGGGTGTCTGCACTCCCCCTGTCGGGGTC
CAGAAGACCTCTGCACCCTGGTAAAGACCCTGTGCGGTCTCAGAGATTTAGTCCCCTTTAACTAATCA
AACACTGGAATCAATAAAAAGAATCACTTACTTAAAATCAGACAGCAGGTCTCTGTCCAGTTTATTC
AGCAGCACCTCCTTCCCCTCCTCCCAACTCTGGTACTCCAAACGCCTTCTGGCGGCAAACTTCCTCCA
CACCCTGAAGGGAATGTCAGATTCTTGCTCCTGTCCCTCCGCACCCACTATCTTCATGTTGTTGCAGA
TGAAGCGCACCAAAACGTCTGACGAGAGCTTCAACCCCGTGTACCCCTATGACACGGAAAGCGGCCC
TCCCTCCGTCCCTTTCCTCACCCCTCCCTTCGTGTCTCCCGATGGATTCCAAGAAAGTCCCCCCGGGGT
CCTGTCTCTGAACCTGGCCGAGCCCCTGGTCACTTCCCACGGCATGCTCGCCCTGAAAATGGGAAGT
GGCCTCTCCCTGGACGACGCTGGCAACCTCACCTCTCAAGATATCACCACCGCTAGCCCTCCCCTCAA
AAAAACCAAGACCAACCTCAGCCTAGAAACCTCATCCCCCCTAACTGTGAGCACCTCAGGCGCCCTC
ACCGTAGCAGCCGCCGCTCCCCTGGCGGTGGCCGGCACCTCCCTCACCATGCAATCAGAGGCCCCCC
TGACAGTACAGGATGCAAAACTCACCCTGGCCACCAAAGGCCCCCTGACCGTGTCTGAAGGCAAACT
GGCCTTGCAAACATCGGCCCCGCTGACGGCCGCTGACAGCAGCACCCTCACAGTCAGTGCCACACCA
CCCCCTTAGCACAAGCAATGGCAGCTTGGGTATTGACATGCAAGCCCCCATTTACACCACCAATGGAA
AACTAGGACTTAACTTTGGCGCTCCCCTGCATGTGGTAGACAGCCTAAATGCACTGACTGTAGTTACT
GGCCAAGGTCTTACGATAAACGGAACAGCCCTACAAACTAGAGTCTCAGGTGCCCTCAACTATGACA
CATCAGGAAACCTAGAATTGAGAGCTGCAGGGGGTATGCGAGTTGATGCAAATGGTCAACTTATCCT
TGATGTAGCTTACCCATTTGATGCACAAAACAATCTCAGCCTTAGGCTTGGACAGGGACCCCTGTTTG
TTAACTCTGCCCACAACTTGGATGTTAACTACAACAGAGGCCTCTACCTGTTCACATCTGGAAATACC
```

```
AAAAAGCTAGAAGTTAATATCAAAACAGCCAAGGGTCTCATTTATGATGACACTGCTATAGCAATCA

ATGCGGGTGATGGGCTACAGTTTGACTCAGGCTCAGATACAAATCCATTAAAAACTAAACTTGGATT

AGGACTGGATTATGACTCCAGCAGAGCCATAATTGCTAAACTGGGAACTGGCCTAAGCTTTGACAAC

ACAGGTGCCATCACAGTAGGCAACAAAAATGATGACAAGCTTACCTTGTGGACCACACCAGACCCAT

CCCCTAACTGTAGAATCTATTCAGAGAAAGATGCTAAATTCACACTTGTTTTGACTAAATGCGGCAGT

CAGGTGTTGGCCAGCGTTTCTGTTTTATCTGTAAAAGGTAGCCTTGCGCCCATCAGTGGCACAGTAAC

TAGTGCTCAGATTGTCCTCAGATTTGATGAAAATGGAGTTCTACTAAGCAATTCTTCCCTTGACCCTC

AATACTGGAACTACAGAAAAGGTGACCTTACAGAGGGCACTGCATATACCAACGCAGTGGGATTTAT

GCCCAACCTCACAGCATACCCAAAAACACAGAGCCAAACTGCTAAAAGCAACATTGTAAGTCAGGTT

TACTTGAATGGGGACAAATCCAAACCCATGACCCTCACCATTACCCTCAATGGAACTAATGAAACAG

GAGATGCCACAGTAAGCACTTACTCCATGTCATTCTCATGGAACTGGAATGGAAGTAATTACATTAA

TGAAACGTTCCAAACCAACTCCTTCACCTTCTCCTACATCGCCCAAGAATAAAAAGCATGACGCTGTT

GATTTGATTCAATGTGTTTCTGTTTTATTTTCAAGCACAACAAAATCATTCAAGTCATTCTTCCATCTT

AGCTTAATAGACACAGTAGCTTAATAGACCCAGTAGTGCAAAGCCCCATTCTAGCTTATAGATCAGA

CAGTGATAATTAACCACCACCACCACCATACCTTTTGATTCAGGAAATCATGATCATCACAGGATCCT

AGTCTTCAGGCCGCCCCCTCCCTCCCAAGACACAGAATACACAGTCCTCTCCCCCCGACTGGCTTTAA

ATAACACCATCTGGTTGGTCACAGACATGTTCTTAGGGGTTATATTCCACACGGTCTCCTGCCGCGCC

AGGCGCTCGTCGGTGATGTTGATAAACTCTCCCGGCAGCTCGCTCAAGTTCACGTCGCTGTCCAGCGG

CTGAACCTCCGGCTGACGCGATAACTGTGCGACCGGCTGCTGGACGAACGGAGGCCGCGCCTACAAG

GGGGTAGAGTCATAATCCTCGGTCAGGATAGGGCGGTGATGCAGCAGCAGCGAGCGAAACATCTGC

TGCCGCCGCCGCTCCGTCCGGCAGGAAAACAACACGCCGGTGGTCTCCTCCGCGATAATCCGCACCG

CCCGCAGCATCAGCTTCCTCGTTCTCCGCGCGCAGCACCTCACCCTTATCTCGCTCAAATCGGCGCAG

TAGGTACAGCACAGCACCACGATGTTATTCATGATCCCACAGTGCAGGGCGCTGTATCCAAAGCTCA

TGCCGGGAACCACCGCCCCCACGTGGCCATCGTACCACAAGCGCACGTAAATCAAGTGTCGACCCCT

CATGAACGCGCTGGACACAAACATTACTTCCTTGGGCATGTTGTAATTCACCACCTCCCGGTACCAGA

TAAACCTCTGGTTGAACAGGGCACCTTCCACCACCATCCTGAACCAAGAGGCCAGAACCTGCCCACC

GGCTATGCACTGCAGGGAACCCGGGTTGGAACAATGACAATGCAGACTCCAAGGCTCGTAACCGTG

GATCATCCGGCTGCTGAAGGCATCGATGTTGGCACAACACAGACACACGTGCATGCACTTTCTCATG

ATTAGCAGCTCTTCCCTCGTCAGGATCATATCCCAAGGAATAACCCATTCTTGAATCAACGTAAAACC

CACACAGCAGGGAAGGCCTCGCACATAACTCACGTTGTGCATGGTCAGCGTGTTGCATTCCGGAAAC

AGCGGATGATCCTCAGTATCGAGGCGCGGGTCTCCTTCTCACAGGGAGGTAAAGGGTCCCTGCTGT

ACGGACTGCGCCGGGACGACCGAGATCGTGTTGAGCGTAGTGTCATGGAAAAGGGAACGCCGGACG

TGGTCATACTTCTTGAAGCAGAACCAGGTTCGCGCGTGGCAGGCCTCCTTGCGTCTGCGGTCTCGCCG

TCTAGCTCGCTCCGTGTGATAGTTGTAGTACAGCCACTCCCGCAGAGCGTCGAGGCGCACCCTGGCTT

CCGGATCTATGTAGACTCCGTCTTGCACCGCGGCCCTGATAATATCCACCACCGTAGAATAAGCAAC

ACCCAGCCAAGCAATACACTCGCTCTGCGAGCGGCAGACAGGAGGAGCGGGCAGAGATGGGAGAAC

CATGATAAAAAACTTTTTTTAAAGAATATTTTCCAATTCTTCGAAAGTAAGATCTATCAAGTGGCAGC

GCTCCCCTCCACTGGCGCGGTCAAACTCTACGGCCAAAGCACAGACAACGGCATTTCTAAGATGTTC

CTTAATGGCGTCCAAAAGACACACCGCTCTCAAGTTGCAGTAAACTATGAATGAAAACCCATCCGGC

TGATTTTCCAATATAGACGCGCCGGCAGCGTCCACCAAACCCAGATAATTTTCTTCTCTCCAGCGGTT
```

-continued

```
TACGATCTGTCTAAGCAAATCCCTTATATCAAGTCCGACCATGCCAAAAATCTGCTCAAGAGCGCCCT

CCACCTTCATGTACAAGCAGCGCATCATGATTGCAAAAATTCAGGTTCTTCAGAGACCTGTATAAGA

TTCAAAATGGGAACATTAACAAAAATTCCTCTGTCGCGCAGATCCCTTCGCAGGGCAAGCTGAACAT

AATCAGACAGGTCCGAACGGACCAGTGAGGCCAAATCCCCACCAGGAACCAGATCCAGAGACCCTA

TACTGATTATGACGCGCATACTCGGGGCTATGCTGACCAGCGTAGCGCCGATGTAGGCGTGCTGCAT

GGGCGGCGAGATAAAATGCAAAGTGCTGGTTAAAAAATCAGGCAAAGCCTCGCGCAAAAAAGCTAA

CACATCATAATCATGCTCATGCAGGTAGTTGCAGGTAAGCTCAGGAACCAAAACGGAATAACACACG

ATTTTCCTCTCAAACATGACTTCGCGGATACTGCGTAAAACAAAAAATTATAAATAAAAAATTAATT

AAATAACTTAAACATTGGAAGCCTGTCTCACAACAGGAAAAACCACTTTAATCAACATAAGACGGGC

CACGGGCATGCCGGCATAGCCGTAAAAAAATTGGTCCCCGTGATTAACAAGTACCACAGACAGCTCC

CCGGTCATGTCGGGGGTCATCATGTGAGACTCTGTATACACGTCTGGATTGTGAACATCAGACAAAC

AAAGAAATCGAGCCACGTAGCCCGGAGGTATAATCACCCGCAGGCGGAGGTACAGCAAAACGACCC

CCATAGGAGGAATCACAAAATTAGTAGGAGAAAAAAATACATAAACACCAGAAAAACCCTGTTGCT

GAGGCAAAATAGCGCCCTCCCGATCCAAAACAACATAAAGCGCTTCCACAGGAGCAGCCATAACAA

AGACCCGAGTCTTACCAGTAAAAGAAAAAAGATCTCTCAACGCAGCACCAGCACCAACACTTCGCA

GTGTAAAAGGCCAAGTGCCGAGAGAGTATATATAGGAATAAAAAGTGACGTAAACGGGCAAAGTCC

AAAAAACGCCCAGAAAAACCGCACGCGAACCTACGCCCCGAAACGAAAGCCAAAAAACACTAGAC

ACTCCCTTCCGGCGTCAACTTCCGCTTTCCCACGCTACGTCACTTGCCCCAGTCAAACAAACTACATA

TCCCGAACTTCCAAGTCGCCACGCCCAAAACACCGCCTACACCTCCCCGCCCGCCGGCCCGCCCCCA

AACCCGCCTCCCGCCCCGCGCCCCGCCCCGCGCCGCCCATCTCATTATCATATTGGCTTCAATCCAAA

ATAAGGTATATTATTGATGATGGTTTAAACGGATCCTCTAGAGTCGACCTGCAGGCATGCAAGCTTG

AGTATTCTATAGTGTCACCTAAATAGCTTGGCGTAATCATGGTCATAGCTGTTTCCTGTGTGAAATTG

TTATCCGCTCACAATTCCACACAACATACGAGCCGGAAGCATAAAGTGTAAAGCCTGGGGTGCCTAA

TGAGTGAGCTAACTCACATTAATTGCGTTGCGCTCACTGCCCGCTTTCCAGTCGGGAAACCTGTCGTG

CCAGCTGCATTAATGAATCGGCCAACGCGAACCCCTTGCGGCCGCCCGGGCCGTCGACCAATTCTCA

TGTTTGACAGCTTATCATCGAATTTCTGCCATTCATCCGCTTATTATCACTTATTCAGGCGTAGCAACC

AGGCGTTTAAGGGCACCAATAACTGCCTTAAAAAAATTACGCCCCGCCCTGCCACTCATCGCAGTAC

TGTTGTAATTCATTAAGCATTCTGCCGACATGGAAGCCATCACAAACGGCATGATGAACCTGAATCG

CCAGCGGCATCAGCACCTTGTCGCCTTGCGTATAATATTTGCCCATGGTGAAAACGGGGGCGAAGAA

GTTGTCCATATTGGCCACGTTTAAATCAAAACTGGTGAAACTCACCCAGGGATTGGCTGAGACGAAA

AACATATTCTCAATAAACCCTTTAGGGAAATAGGCCAGGTTTTCACCGTAACACGCCACATCTTGCG

AATATATGTGTAGAAACTGCCGGAAATCGTCGTGGTATTCACTCCAGAGCGATGAAAACGTTTCAGT

TTGCTCATGGAAAACGGTGTAACAAGGGTGAACACTATCCCATATCACCAGCTCACCGTCTTTCATTG

CCATACGGAATTCCGGATGAGCATTCATCAGGCGGGCAAGAATGTGAATAAAGGCCGGATAAAACT

TGTGCTTATTTTTCTTTACGGTCTTTAAAAAGGCCGTAATATCCAGCTGAACGGTCTGGTTATAGGTA

CATTGAGCAACTGACTGAAATGCCTCAAAATGTTCTTTACGATGCCATTGGGATATATCAACGGTGGT

ATATCCAGTGATTTTTTTCTCCATTTTAGCTTCCTTAGCTCCTGAAAATCTCGATAACTCAAAAAATAC

GCCCGGTAGTGATCTTATTTCATTATGGTGAAAGTTGGAACCTCTTACGTGCCGATCAACGTCTCATT

TTCGCCAAAAGTTGGCCCAGGGCTTCCCGGTATCAACAGGGACACCAGGATTTATTTATTCTGCGAA

GTGATCTTCCGTCACAGGTATTTATTCGCGATAAGCTCATGGAGCGGCGTAACCGTCGCACAGGAAG

GACAGAGAAAGCGCGGATCTGGGAAGTGACGGACAGAACGGTCAGGACCTGGATTGGGGAGGCGGT
```

```
TGCCGCCGCTGCTGCTGACGGTGTGACGTTCTCTGTTCCGGTCACACCACATACGTTCCGCCATTCCT

ATGCGATGCACATGCTGTATGCCGGTATACCGCTGAAAGTTCTGCAAAGCCTGATGGGACATAAGTC

CATCAGTTCAACGGAAGTCTACACGAAGGTTTTTGCGCTGGATGTGGCTGCCCGGCACCGGGTGCAG

TTTGCGATGCCGGAGTCTGATGCGGTTGCGATGCTGAAACAATTATCCTGAGAATAAATGCCTTGGC

CTTTATATGGAAATGTGGAACTGAGTGGATATGCTGTTTTTGTCTGTTAAACAGAGAAGCTGGCTGTT

ATCCACTGAGAAGCGAACGAAACAGTCGGGAAAATCTCCCATTATCGTAGAGATCCGCATTATTAAT

CTCAGGAGCCTGTGTAGCGTTTATAGGAAGTAGTGTTCTGTCATGATGCCTGCAAGCGGTAACGAAA

ACGATTTGAATATGCCTTCAGGAACAATAGAAATCTTCGTGCGGTGTTACGTTGAAGTGGAGCGGAT

TATGTCAGCAATGGACAGAACAACCTAATGAACACAGAACCATGATGTGGTCTGTCCTTTTACAGCC

AGTAGTGCTCGCCGCAGTCGAGCGACAGGGCGAAGCCCTCGAGTGAGCGAGGAAGCACCAGGGAAC

AGCACTTATATATTCTGCTTACACACGATGCCTGAAAAAACTTCCCTTGGGGTTATCCACTTATCCAC

GGGGATATTTTTATAATTATTTTTTTTATAGTTTTTAGATCTTCTTTTTTAGAGCGCCTTGTAGGCCTTT

ATCCATGCTGGTTCTAGAGAAGGTGTTGTGACAAATTGCCCTTTCAGTGTGACAAATCACCCTCAAAT

GACAGTCCTGTCTGTGACAAATTGCCCTTAACCCTGTGACAAATTGCCCTCAGAAGAAGCTGTTTTTT

CACAAAGTTATCCCTGCTTATTGACTCTTTTTTATTTAGTGTGACAATCTAAAAACTTGTCACACTTCA

CATGGATCTGTCATGGCGGAAACAGCGGTTATCAATCACAAGAAACGTAAAAATAGCCCGCGAATC

GTCCAGTCAAACGACCTCACTGAGGCGGCATATAGTCTCTCCCGGGATCAAAAACGTATGCTGTATC

TGTTCGTTGACCAGATCAGAAAATCTGATGGCACCCTACAGGAACATGACGGTATCTGCGAGATCCA

TGTTGCTAAATATGCTGAAATATTCGGATTGACCTCTGCGGAAGCCAGTAAGGATATACGGCAGGCA

TTGAAGAGTTTCGCGGGGAAGGAAGTGGTTTTTTATCGCCCTGAAGAGGATGCCGGCGATGAAAAAG

GCTATGAATCTTTTCCTTGGTTTATCAAACGTGCGCACAGTCCATCCAGAGGGCTTTACAGTGTACAT

ATCAACCCATATCTCATTCCCTTCTTTATCGGGTTACAGAACCGGTTTACGCAGTTTCGGCTTAGTGA

AACAAAAGAAATCACCAATCCGTATGCCATGCGTTTATACGAATCCCTGTGTCAGTATCGTAAGCCG

GATGGCTCAGGCATCGTCTCTCTGAAAATCGACTGGATCATAGAGCGTTACCAGCTGCCTCAAAGTT

ACCAGCGTATGCCTGACTTCCGCCGCCGCTTCCTGCAGGTCTGTGTTAATGAGATCAACAGCAGAACT

CCAATGCGCCTCTCATACATTGAGAAAAAGAAAGGCCGCCAGACGACTCATATCGTATTTTCCTTCC

GCGATATCACTTCCATGACGACAGGATAGTCTGAGGGTTATCTGTCACAGATTTGAGGGTGGTTCGTC

ACATTTGTTCTGACCTACTGAGGGTAATTTGTCACAGTTTTGCTGTTTCCTTCAGCCTGCATGGATTTT

CTCATACTTTTTGAACTGTAATTTTTAAGGAAGCCAAATTTGAGGGCAGTTTGTCACAGTTGATTTCC

TTCTCTTTCCCTTCGTCATGTGACCTGATATCGGGGGTTAGTTCGTCATCATTGATGAGGGTTGATTAT

CACAGTTATTACTCTGAATTGGCTATCCGCGTGTGTACCTCTACCTGGAGTTTTTCCCACGGTGGAT

ATTTCTTCTTGCGCTGAGCGTAAGAGCTATCTGACAGAACAGTTCTTCTTTGCTTCCTCGCCAGTTCGC

TCGCTATGCTCGGTTACACGGCTGCGGCGAGCGCTAGTGATAATAAGTGACTGAGGTATGTGCTCTTC

TTATCTCCTTTTGTAGTGTTGCTCTTATTTTAAACAACTTTGCGGTTTTTTGATGACTTTGCGATTTTGT

TGTTGCTTTGCAGTAAATTGCAAGATTTAATAAAAAAACGCAAAGCAATGATTAAAGGATGTTCAGA

ATGAAACTCATGGAAACACTTAACCAGTGCATAAACGCTGGTCATGAAATGACGAAGGCTATCGCCA

TTGCACAGTTTAATGATGACAGCCCGGAAGCGAGGAAAATAACCCGGCGCTGGAGAATAGGTGAAG

CAGCGGATTTAGTTGGGGTTTCTTCTCAGGCTATCAGAGATGCCGAGAAAGCAGGGCGACTACCGCA

CCCGGATATGGAAATTCGAGGACGGGTTGAGCAACGTGTTGGTTATACAATTGAACAAATTAATCAT

ATGCGTGATGTGTTTGGTACGCGATTGCGACGTGCTGAAGACGTATTTCCACCGGTGATCGGGGTTGC
```

-continued

```
TGCCCATAAAGGTGGCGTTTACAAAACCTCAGTTTCTGTTCATCTTGCTCAGGATCTGGCTCTGAAGG

GGCTACGTGTTTTGCTCGTGGAAGGTAACGACCCCCAGGGAACAGCCTCAATGTATCACGGATGGGT

ACCAGATCTTCATATTCATGCAGAAGACACTCTCCTGCCTTTCTATCTTGGGGAAAAGGACGATGTCA

CTTATGCAATAAAGCCCACTTGCTGGCCGGGGCTTGACATTATTCCTTCCTGTCTGGCTCTGCACCGT

ATTGAAACTGAGTTAATGGGCAAATTTGATGAAGGTAAACTGCCCACCGATCCACACCTGATGCTCC

GACTGGCCATTGAAACTGTTGCTCATGACTATGATGTCATAGTTATTGACAGCGCGCCTAACCTGGGT

ATCGGCACGATTAATGTCGTATGTGCTGCTGATGTGCTGATTGTTCCCACGCCTGCTGAGTTGTTTGA

CTACACCTCCGCACTGCAGTTTTTCGATATGCTTCGTGATCTGCTCAAGAACGTTGATCTTAAAGGGT

TCGAGCCTGATGTACGTATTTTGCTTACCAAATACAGCAATAGTAATGGCTCTCAGTCCCCGTGGATG

GAGGAGCAAATTCGGGATGCCTGGGGAAGCATGGTTCTAAAAAATGTTGTACGTGAAACGGATGAA

GTTGGTAAAGGTCAGATCCGGATGAGAACTGTTTTTGAACAGGCCATTGATCAACGCTCTTCAACTG

GTGCCTGGAGAAATGCTCTTTCTATTTGGGAACCTGTCTGCAATGAAATTTTCGATCGTCTGATTAAA

CCACGCTGGGAGATTAGATAATGAAGCGTGCGCCTGTTATTCCAAAACATACGCTCAATACTCAACC

GGTTGAAGATACTTCGTTATCGACACCAGCTGCCCCGATGGTGGATTCGTTAATTGCGCGCGTAGGA

GTAATGGCTCGCGGTAATGCCATTACTTTGCCTGTATGTGGTCGGGATGTGAAGTTTACTCTTGAAGT

GCTCCGGGGTGATAGTGTTGAGAAGACCTCTCGGGTATGGTCAGGTAATGAACGTGACCAGGAGCTG

CTTACTGAGGACGCACTGGATGATCTCATCCCTTCTTTTCTACTGACTGGTCAACAGACACCGGCGTT

CGGTCGAAGAGTATCTGGTGTCATAGAAATTGCCGATGGGAGTCGCCGTCGTAAAGCTGCTGCACTT

ACCGAAAGTGATTATCGTGTTCTGGTTGGCGAGCTGGATGATGAGCAGATGGCTGCATTATCCAGAT

TGGGTAACGATTATCGCCCAACAAGTGCTTATGAACGTGGTCAGCGTTATGCAAGCCGATTGCAGAA

TGAATTTGCTGGAAATATTTCTGCGCTGGCTGATGCGGAAAATATTTCACGTAAGATTATTACCCGCT

GTATCAACACCGCCAAATTGCCTAAATCAGTTGTTGCTCTTTTTTCTCACCCCGGTGAACTATCTGCCC

GGTCAGGTGATGCACTTCAAAAAGCCTTTACAGATAAAGAGGAATTACTTAAGCAGCAGGCATCTAA

CCTTCATGAGCAGAAAAAAGCTGGGGTGATATTTGAAGCTGAAGAAGTTATCACTCTTTTAACTTCTG

TGCTTAAAACGTCATCTGCATCAAGAACTAGTTTAAGCTCACGACATCAGTTTGCTCCTGGAGCGACA

GTATTGTATAAGGGCGATAAAATGGTGCTTAACCTGGACAGGTCTCGTGTTCCAACTGAGTGTATAG

AGAAAATTGAGGCCATTCTTAAGGAACTTGAAAAGCCAGCACCCTGATGCGACCACGTTTTAGTCTA

CGTTTATCTGTCTTTACTTAATGTCCTTTGTTACAGGCCAGAAAGCATAACTGGCCTGAATATTCTCTC

TGGGCCCACTGTTCCACTTGTATCGTCGGTCTGATAATCAGACTGGGACCACGGTCCCACTCGTATCG

TCGGTCTGATTATTAGTCTGGGACCACGGTCCCACTCGTATCGTCGGTCTGATTATTAGTCTGGGACC

ACGGTCCCACTCGTATCGTCGGTCTGATAATCAGACTGGGACCACGGTCCCACTCGTATCGTCGGTCT

GATTATTAGTCTGGGACCATGGTCCCACTCGTATCGTCGGTCTGATTATTAGTCTGGGACCACGGTCC

CACTCGTATCGTCGGTCTGATTATTAGTCTGGAACCACGGTCCCACTCGTATCGTCGGTCTGATTATT

AGTCTGGGACCACGGTCCCACTCGTATCGTCGGTCTGATTATTAGTCTGGGACCACGATCCCACTCGT

GTTGTCGGTCTGATTATCGGTCTGGGACCACGGTCCCACTTGTATTGTCGATCAGACTATCAGCGTGA

GACTACGATTCCATCAATGCCTGTCAAGGGCAAGTATTGACATGTCGTCGTAACCTGTAGAACGGAG

TAACCTCGGTGTGCGGTTGTATGCCTGCTGTGGATTGCTGCTGTGTCCTGCTTATCCACAACATTTTGC

GCACGGTTATGTGGACAAAATACCTGGTTACCCAGGCCGTGCCGGCACGTTAACCGGGCTGCATCCG

ATGCAAGTGTGTCGCTGTCGACGAGCTCGCGAGCTCGGACATGAGGTTGCCCCGTATTCAGTGTCGC

TGATTTGTATTGTCTGAAGTTGTTTTTACGTTAAGTTGATGCAGATCAATTAATACGATACCTGCGTC

ATAATTGATTATTTGACGTGGTTTGATGGCCTCCACGCACGTTGTGATATGTAGATGATAATCATTAT
```

```
CACTTTACGGGTCCTTTCCGGTGATCCGACAGGTTACGGGGCGGCGACCTCGCGGGTTTTCGCTATTT

ATGAAAATTTTCCGGTTTAAGGCGTTTCCGTTCTTCTTCGTCATAACTTAATGTTTTTATTTAAAATAC

CCTCTGAAAAGAAAGGAAACGACAGGTGCTGAAAGCGAGCTTTTTGGCCTCTGTCGTTTCCTTTCTCT

GTTTTTGTCCGTGGAATGAACAATGGAAGTCCGAGCTCATCGCTAATAACTTCGTATAGCATACATTA

TACGAAGTTATATTCGATGCGGCCGCAAGGGGTTCGCGTCAGCGGGTGTTGGCGGGTGTCGGGGCTG

GCTTAACTATGCGGCATCAGAGCAGATTGTACTGAGAGTGCACCATATGCGGTGTGAAATACCGCAC

AGATGCGTAAGGAGAAAATACCGCATCAGGCGCCATTCGCCATTCAGGCTGCGCAACTGTTGGGAAG

GGCGATCGGTGCGGGCCTCTTCGCTATTACGCCAGCTGGCGAAAGGGGGATGTGCTGCAAGGCGATT

AAGTTGGGTAACGCCAGGGTTTTCCCAGTCACGACGTTGTAAAACGACGGCCAGTGAATTGTAATAC

GACTCACTATAGGGCGAATTCGAGCTCGGTACCCGGGGATCCTCGTTTAAAC
```

Polynucleotide sequence encoding wild type ChAd155

SEQ ID NO: 10

```
CATCATCAATAATATACCTTATTTTGGATTGAAGCCAATATGATAATGAGATGGGCGGCGCGGGGCG

GGAGGCGGGTCCGGGGCGGGCCGGCGGGCGGGGCGGTGTGGCGGAAGTGGACTTTGTAAGTGTGG

CGGATGTGACTTGCTAGTGCCGGGCGCGGTAAAAGTGACGTTTTCCGTGCGCGACAACGCCCACGGG

AAGTGACATTTTTCCCGCGGTTTTTACCGGATGTTGTAGTGAATTTGGGCGTAACCAAGTAAGATTTG

GCCATTTTCGCGGGAAAACTGAAACGGGGAAGTGAAATCTGATTAATTTCGCGTTAGTCATACCGCG

TAATATTTGTCGAGGGCCGAGGGACTTTGGCCGATTACGTGGAGGACTCGCCCAGGTGTTTTTTGAG

GTGAATTTCCGCGTTCCGGGTCAAAGTCTCCGTTTTATTATTATAGTCAGCTGACGCGGAGTGTATTT

ATACCCTCTGATCTCGTCAAGTGGCCACTCTTGAGTGCCAGCGAGTAGAGTTTTCTCCTCTGCCGCTC

TCCGCTCCGCTCCGCTCGGCTCTGACACCGGGGAAAAAATGAGACATTTCACCTACGATGGCGGTGT

GCTCACCGGCCAGCTGGCTGCTGAAGTCCTGGACACCCTGATCGAGGAGGTATTGGCCGATAATTAT

CCTCCCTCGACTCCTTTTGAGCCACCTACACTTCACGAACTCTACGATCTGGATGTGGTGGGGCCCAG

CGATCCGAACGAGCAGGCGGTTTCCAGTTTTTTTCCAGAGTCCATGTTGTTGGCCAGCCAGGAGGGG

GTCGAACTTGAGACCCCTCCTCCGATCGTGGATTCCCCCGATCCGCCGCAGCTGACTAGGCAGCCCG

AGCGCTGTGCGGGACCTGAGACTATGCCCCAGCTGCTACCTGAGGTGATCGATCTCACCTGTAATGA

GTCTGGTTTTCCACCCAGCGAGGATGAGGACGAAGAGGGTGAGCAGTTTGTGTTAGATTCTGTGGAA

CAACCCGGGCGAGGATGCAGGTCTTGTCAATATCACCGGAAAAACACAGGAGACTCCCAGATTATGT

GTTCTCTGTGTTATATGAAGATGACCTGTATGTTTATTTACAGTAAGTTTATCATCTGTGGGCAGGTG

GGCTATAGTGTGGGTGGTGGTCTTTGGGGGGTTTTTTAATATATGTCAGGGGTTATGCTGAAGACTTT

TTTATTGTGATTTTTAAAGGTCCAGTGTCTGAGCCCGAGCAAGAACCTGAACCGGAGCCTGAGCCTTC

TCGCCCCAGGAGAAAGCCTGTAATCTTAACTAGACCCAGCGCACCGGTAGCGAGAGGCCTCAGCAGC

GCGGAGACCACCGACTCCGGTGCTTCCTCATCACCCCCGGAGATTCACCCCCTGGTGCCCCTGTGTCC

CGTTAAGCCCGTTGCCGTGAGAGTCAGTGGGCGGCGGTCTGCTGTGGAGTGCATTGAGGACTTGCTT

TTTGATTCACAGGAACCTTTGGACTTGAGCTTGAAACGCCCCAGGCATTAAACCTGGTCACCTGGACT

GAATGAGTTGACGCCTATGTTTGCTTTTGAATGACTTAATGTGTATAGATAATAAAGAGTGAGATAAT

GTTTTAATTGCATGGTGTGTTTAACTTGGGCGGAGTCTGCTGGGTATATAAGCTTCCCTGGGCTAAAC

TTGGTTACACTTGACCTCATGGAGGCCTGGGAGTGTTTGGAGAACTTTGCCGGAGTTCGTGCCTTGCT

GGACGAGAGCTCTAACAATACCTCTTGGTGGTGGAGGTATTTGTGGGGCTCTCCCCAGGGCAAGTTA

GTTTGTAGAATCAAGGAGGATTACAAGTGGGAATTTGAAGAGCTTTTGAAATCCTGTGGTGAGCTAT

TGGATTCTTTGAATCTAGGCCACCAGGCTCTCTTCCAGGAGAAGGTCATCAGGACTTTGGATTTTTCC
```

-continued

ACACCGGGGCGCATTGCAGCCGCGGTTGCTTTTCTAGCTTTTTTGAAGGATAGATGGAGCGAAGAGA

CCCACTTGAGTTCGGGCTACGTCCTGGATTTTCTGGCCATGCAACTGTGGAGAGCATGGATCAGACA

CAAGAACAGGCTGCAACTGTTGTCTTCCGTCCGCCCGTTGCTGATTCCGGCGGAGGAGCAACAGGCC

GGGTCAGAGGACCGGGCCCGTCGGGATCCGGAGGAGAGGGCACCGAGGCCGGGCGAGAGGAGCGC

GCTGAACCTGGGAACCGGGCTGAGCGGCCATCCACATCGGGAGTGAATGTCGGGCAGGTGGTGGAT

CTTTTTCCAGAACTGCGGCGGATTTTGACTATTAGGGAGGATGGGCAATTTGTTAAGGGTCTTAAGAG

GGAGAGGGGGCTTCTGAGCATAACGAGGAGGCCAGTAATTTAGCTTTTAGCTTGATGACCAGACAC

CGTCCAGAGTGCATCACTTTTCAGCAGATTAAGGACAATTGTGCCAATGAGTTGGATCTGTTGGGTCA

GAAGTATAGCATAGAGCAGCTGACCACTTACTGGCTGCAGCCGGGTGATGATCTGGAGGAAGCTATT

AGGGTGTATGCTAAGGTGGCCCTGCGGCCCGATTGCAAGTACAAGCTCAAGGGGCTGGTGAATATCA

GGAATTGTTGCTACATTTCTGGCAACGGGGCGGAGGTGGAGATAGAGACCGAAGACAGGGTGGCTTT

CAGATGCAGCATGATGAATATGTGGCCGGGGGTGCTGGGCATGGACGGGGTGGTGATTATGAATGTG

AGGTTCACGGGGCCCAACTTTAACGGCACGGTGTTTTTGGGGAACACCAACCTGGTCCTGCACGGGG

TGAGCTTCTATGGGTTTAACAACACCTGTGTGGAGGCCTGGACCGATGTGAAGGTCCGCGGTTGCGC

CTTTTATGGATGTTGGAAGGCCATAGTGAGCCGCCCTAAGAGCAGGAGTTCCATTAAGAAATGCTTG

TTTGAGAGGTGCACCTTGGGGATCCTGGCCGAGGGCAACTGCAGGGTGCGCCACAATGTGGCCTCCG

AGTGCGGTTGCTTCATGCTAGTCAAGAGCGTGGCGGTAATCAAGCATAATATGGTGTGCGGCAACAG

CGAGGACAAGGCCTCACAGATGCTGACCTGCACGGATGGCAACTGCCACTTGCTGAAGACCATCCAT

GTAACCAGCCACAGCCGGAAGGCCTGGCCCGTGTTCGAGCACAACTTGCTGACCCGCTGCTCCTTGC

ATCTGGGCAACAGGCGGGGGGTGTTCCTGCCCTATCAATGCAACTTTAGTCACACCAAGATCTTGCT

AGAGCCCGAGAGCATGTCCAAGGTGAACTTGAACGGGGTGTTTGACATGACCATGAAGATCTGGAA

GGTGCTGAGGTACGACGAGACCAGGTCCCGGTGCAGACCCTGCGAGTGCGGGGGCAAGCATATGAG

GAACCAGCCCGTGATGCTGGATGTGACCGAGGAGCTGAGGACAGACCACTTGGTTCTGGCCTGCACC

AGGGCCGAGTTTGGTTCTAGCGATGAAGACACAGATTGAGGTGGGTGAGTGGGCGTGGCCTGGGGT

GGTCATGAAAATATATAAGTTGGGGGTCTTAGGGTCTCTTTATTTGTGTTGCAGAGACCGCCGGAGCC

ATGAGCGGGAGCAGCAGCAGCAGTAGCAGCAGCGCCTTGGATGGCAGCATCGTGAGCCCTTAT

TTGACGACGCGGATGCCCCACTGGGCCGGGGTGCGTCAGAATGTGATGGGCTCCAGCATCGACGGCC

GACCCGTCCTGCCCGCAAATTCCGCCACGCTGACCTATGCGACCGTCGCGGGGACGCCGTTGGACGC

CACCGCCGCCGCCGCCACCGCAGCCGCCTCGGCCGTGCGCAGCCTGGCCACGGACTTTGCATTC

CTGGGACCACTGGCGACAGGGGCTACTTCTCGGGCCGCTGCTGCCGCCGTTCGCGATGACAAGCTGA

CCGCCCTGCTGGCGCAGTTGGATGCGCTTACTCGGGAACTGGGTGACCTTTCTCAGCAGGTCATGGCC

CTGCGCCAGCAGGTCTCCTCCCTGCAAGCTGGCGGGAATGCTTCTCCCACAAATGCCGTTTAAGATA

AATAAAACCAGACTCTGTTTGGATTAAAGAAAAGTAGCAAGTGCATTGCTCTCTTTATTTCATAATTT

TCCGCGCGCGATAGGCCCTAGACCAGCGTTCTCGGTCGTTGAGGGTGCGGTGTATCTTCTCCAGGAC

GTGGTAGAGGTGGCTCTGGACGTTGAGATACATGGGCATGAGCCCGTCCCGGGGGTGGAGGTAGCA

CCACTGCAGAGCTTCATGCTCCGGGGTGGTGTTGTAGATGATCCAGTCGTAGCAGGAGCGCTGGGCA

TGGTGCCTAAAAATGTCCTTCAGCAGCAGGCCGATGGCCAGGGGGAGGCCCTTGGTGTAAGTGTTTA

CAAAACGGTTAAGTTGGGAAGGGTGCATTCGGGGAGAGATGATGTGCATCTTGGACTGTATTTTTAG

ATTGGCGATGTTTCCGCCCAGATCCCTTCTGGGATTCATGTTGTGCAGGACCACCAGTACAGTGTATC

CGGTGCACTTGGGGAATTTGTCATGCAGCTTAGAGGGAAAAGCGTGGAAGAACTTGGAGACGCCTTT

GTGGCCTCCCAGATTTTCCATGCATTCGTCCATGATGATGGCAATGGGCCCGCGGGAGGCAGCTTGG

```
GCAAAGATATTTCTGGGGTCGCTGACGTCGTAGTTGTGTTCCAGGGTGAGGTCGTCATAGGCCATTTT

TACAAAGCGCGGGCGGAGGGTGCCCGACTGGGGGATGATGGTCCCCTCTGGCCCTGGGGCGTAGTTG

CCCTCGCAGATCTGCATTTCCCAGGCCTTAATCTCGGAGGGGGGAATCATATCCACCTGCGGGGCGA

TGAAGAAAACGGTTTCCGGAGCCGGGGAGATTAACTGGGATGAGAGCAGGTTTCTAAGCAGCTGTG

ATTTTCCACAACCGGTGGGCCCATAAATAACACCTATAACCGGTTGCAGCTGGTAGTTTAGAGAGCT

GCAGCTGCCGTCGTCCCGGAGGAGGGGGGCCACCTCGTTGAGCATGTCCCTGACGCGCATGTTCTCC

CCGACCAGATCCGCCAGAAGGCGCTCGCCGCCCAGGGACAGCAGCTCTTGCAAGGAAGCAAAGTTTT

TCAGCGGCTTGAGGCCGTCCGCCGTGGGCATGTTTTTCAGGGTCTGGCTCAGCAGCTCCAGGCGGTCC

CAGAGCTCGGTGACGTGCTCTACGGCATCTCTATCCAGCATATCTCCTCGTTTCGCGGGTTGGGGCGA

CTTTCGCTGTAGGGCACCAAGCGGTGGTCGTCCAGCGGGGCCAGAGTCATGTCCTTCCATGGGCGCA

GGGTCCTCGTCAGGGTGGTCTGGGTCACGGTGAAGGGGTGCGCTCCGGGCTGAGCGCTTGCCAAGGT

GCGCTTGAGGCTGGTTCTGCTGGTGCTGAAGCGCTGCCGGTCTTCGCCCTGCGCGTCGGCCAGGTAGC

ATTTGACCATGGTGTCATAGTCCAGCCCCTCCGCGGCGTGTCCCTTGGCGCGCAGCTTGCCCTTGGAG

GTGGCGCCGCACGAGGGGCAGAGCAGGCTCTTGAGCGCGTAGAGCTTGGGGGCGAGGAAGACCGAT

TCGGGGGAGTAGGCGTCCGCGCCGCAGACCCCGCACACGGTCTCGCACTCCACCAGCCAGGTGAGCT

CGGGGCGCGCCGGGTCAAAAACCAGGTTTCCCCCATGCTTTTTGATGCGTTTCTTACCTCGGGTCTCC

ATGAGGTGGTGTCCCCGCTCGGTGACGAAGAGGCTGTCCGTGTCTCCGTAGACCGACTTGAGGGGTC

TTTTCTCCAGGGGGGTCCCTCGGTCTTCCTCGTAGAGGAACTCGGACCACTCTGAGACGAAGGCCCG

CGTCCAGGCCAGGACGAAGGAGGCTATGTGGGAGGGGTAGCGGTCGTTGTCCACTAGGGGGTCCAC

CTTCTCCAAGGTGTGAAGACACATGTCGCCTTCCTCGGCGTCCAGGAAGGTGATTGGCTTGTAGGTGT

AGGCCACGTGACCGGGGGTTCCTGACGGGGGGGTATAAAAGGGGGTGGGGCGCGCTCGTCGTCAC

TCTCTTCCGCATCGCTGTCTGCGAGGGCCAGCTGCTGGGGTGAGTATTCCCTCTCGAAGGCGGGCATG

ACCTCCGCGCTGAGGTTGTCAGTTTCCAAAAACGAGGAGGATTTGATGTTCACCTGTCCCGAGGTGA

TACCTTTGAGGGTACCCGCGTCCATCTGGTCAGAAAACACGATCTTTTTATTGTCCAGCTTGGTGGCG

AACGACCCGTAGAGGGCGTTGGAGAGCAGCTTGGCGATGGAGCGCAGGGTCTGGTTCTTGTCCCTGT

CGGCGCGCTCCTTGGCCGCGATGTTGAGCTGCACGTACTCGCGCGCGACGCAGCGCCACTCGGGGAA

GACGGTGGTGCGCTCGTCGGGCACCAGGCGCACGCGCCAGCCGCGGTTGTGCAGGGTGACCAGGTCC

ACGCTGGTGGCGACCTCGCCGCGCAGGCGCTCGTTGGTCCAGCAGAGACGGCCGCCCTTGCGCGAGC

AGAAGGGGGCAGGGGGTCGAGCTGGGTCTCGTCCGGGGGTCCGCGTCCACGGTGAAAACCCCGG

GGCGCAGGCGCGCGTCGAAGTAGTCTATCTTGCAACCTTGCATGTCCAGCGCCTGCTGCCAGTCGCG

GGCGGCGAGCGCGCGCTCGTAGGGGTTGAGCGGCGGGCCCCAGGGCATGGGGTGGGTGAGTGCGGA

GGCGTACATGCCGCAGATGTCATAGACGTAGAGGGGCTCCCGCAGGACCCCGATGTAGGTGGGGTA

GCAGCGGCCGCCGCGGATGCTGGCGCGCACGTAGTCATACAGCTCGTGCGAGGGGCGAGGAGGTC

GGGGCCCAGGTTGGTGCGGGCGGGCGCTCCGCGCGGAAGACGATCTGCCTGAAGATGGCATGCGA

GTTGGAAGAGATGGTGGGGCGCTGGAAGACGTTGAAGCTGGCGTCCTGCAGGCCGACGGCGTCGCG

CACGAAGGAGGCGTAGGAGTCGCGCAGCTTGTGTACCAGCTCGGCGGTGACCTGCACGTCGAGCGC

GCAGTAGTCGAGGGTCTCGCGGATGATGTCATATTTAGCCTGCCCCTTCTTTTTCCACAGCTCGCGGT

TGAGGACAAACTCTTCGCGGTCTTTCCAGTACTCTTGGATCGGGAAACCGTCCGGTTCCGAACGGTA

AGAGCCTAGCATGTAGAACTGGTTGACGGCCTGGTAGGCGCAGCAGCCCTTCTCCACGGGGAGGGCG

TAGGCCTGCGCGGCCTTGCGGAGCGAGGTGTGGGTCAGGGCGAAGGTGTCCCTGACCATGACTTTGA
```

-continued

```
GGTACTGGTGCTTGAAGTCGGAGTCGTCGCAGCCGCCCCGCTCCCAGAGCGAGAAGTCGGTGCGCTT
CTTGGAGCGGGGGTTGGGCAGAGCGAAGGTGACATCGTTGAAGAGGATTTTGCCCGCGCGGGGCAT
GAAGTTGCGGGTGATGCGGAAGGGCCCCGGCACTTCAGAGCGGTTGTTGATGACCTGGGCGGCGAG
CACGATCTCGTCGAAGCCGTTGATGTTGTGGCCCACGATGTAGAGTTCCAGGAAGCGGGGCCGGCCC
TTTACGGTGGGCAGCTTCTTTAGCTCTTCGTAGGTGAGCTCCTCGGGCGAGGCGAGGCCGTGCTCGGC
CAGGGCCCAGTCCGCGAGGTGCGGGTTGTCTCTGAGGAAGGACTTCCAGAGGTCGCGGGCCAGGAG
GGTCTGCAGGCGGTCTCTGAAGGTCCTGAACTGGCGGCCCACGGCCATTTTTTCGGGGGTGATGCAG
TAGAAGGTGAGGGGGTCTTGCTGCCAGCGGTCCCAGTCGAGCTGCAGGGCGAGGTCGCGCGCGGCG
GTGACCAGGCGCTCGTCGCCCCCGAATTTCATGACCAGCATGAAGGGCACGAGCTGCTTTCCGAAGG
CCCCCATCCAAGTGTAGGTCTCTACATCGTAGGTGACAAAGAGGCGCTCCGTGCGAGGATGCGAGCC
GATCGGGAAGAACTGGATCTCCCGCCACCAGTTGGAGGAGTGGCTGTTGATGTGGTGGAAGTAGAA
GTCCCGTCGCCGGGCCGAACACTCGTGCTGGCTTTTGTAAAAGCGAGCGCAGTACTGGCAGCGCTGC
ACGGGCTGTACCTCATGCACGAGATGCACCTTTCGCCCGCGCACGAGGAAGCCGAGGGGAAATCTGA
GCCCCCGCCTGGCTCGCGGCATGGCTGGTTCTCTTCTACTTTGGATGCGTGTCCGTCTCCGTCTGGCT
CCTCGAGGGGTGTTACGGTGGAGCGGACCACCACGCCGCGCGAGCCGCAGGTCCAGATATCGGCGC
GCGGCGGTCGGAGTTTGATGACGACATCGCGCAGCTGGGAGCTGTCCATGGTCTGGAGCTCCCGCGG
CGGCGGCAGGTCAGCCGGGAGTTCTTGCAGGTTCACCTCGCAGAGTCGGGCCAGGGCGCGGGGCAG
GTCTAGGTGGTACCTGATCTCTAGGGGCGTGTTGGTGGCGGCGTCGATGGCTTGCAGGAGCCCGCAG
CCCCGGGGGGCGACGACGGTGCCCCGCGGGGTGGTGGTGGTGGCGGTGCAGCTCAGAAGCGGT
GCCGCGGGCGGGCCCCCGGAGGTAGGGGGGGCTCCGGTCCCGCGGGCAGGGGCGGCAGCGGCACGT
CGGCGTGGAGCGCGGGCAGGAGTTGGTGCTGTGCCCGGAGGTTGCTGGCGAAGGCGACGACGCGGC
GGTTGATCTCCTGGATCTGGCGCCTCTGCGTGAAGACGACGGGCCCGGTGAGCTTGAACCTGAAAGA
GAGTTCGACAGAATCAATCTCGGTGTCATTGACCGCGGCCTGGCGCAGGATCTCCTGCACGTCTCCC
GAGTTGTCTTGGTAGGCGATCTCGGCCATGAACTGCTCGATCTCTTCCTCCTGGAGGTCTCCGCGTCC
GGCGCGTTCCACGGTGGCCGCCAGGTCGTTGGAGATGCGCCCCATGAGCTGCGAGAAGGCGTTGAGT
CCGCCCTCGTTCCAGACTCGGCTGTAGACCACGCCCCCCTGGTCATCGCGGGCGCGCATGACCACCT
GCGCGAGGTTGAGCTCCACGTGCCGCGCGAAGACGGCGTAGTTGCGCAGACGCTGGAAGAGGTAGT
TGAGGGTGGTGGCGGTGTGCTCGGCCACGAAGAAGTTCATGACCCAGCGGCGCAACGTGGATTCGTT
GATGTCCCCAAGGCCTCCAGCCGTTCCATGGCCTCGTAGAAGTCCACGGCGAAGTTGAAAAACTGG
GAGTTGCGCGCCGACACGGTCAACTCCTCCTCCAGAAGACGGATGAGCTCGGCGACGGTGTCGCGCA
CCTCGCGCTCGAAGGCTATGGGGATCTCTTCCTCCGCTAGCATCACCACCTCCTCCTCTTCCTCCTCTT
CTGGCACTTCCATGATGGCTTCCTCCTCTTCGGGGGGTGGCGGCGGCGGCGGTGGGGAGGGGCGC
TCTGCGCCGGCGGCGGCGCACCGGGAGGCGGTCCACGAAGCGCGCGATCATCTCCCCGCGGCGGCG
GCGCATGGTCTCGGTGACGGCGCGGCCGTTCTCCCGGGGGCGCAGTTGGAAGACGCCGCCGGACATC
TGGTGCTGGGGCGGGTGGCCGTGAGGCAGCGAGACGGCGCTGACGATGCATCTCAACAATTGCTGCG
TAGGTACGCCGCCGAGGGACCTGAGGGAGTCCATATCCACCGGATCCGAAAACCTTTCGAGGAAGG
CGTCTAACCAGTCGCAGTCGCAAGGTAGGCTGAGCACCGTGGCGGGCGGCGGGGGGTGGGGGAGT
GTCTGGCGGAGGTGCTGCTGATGATGTAATTGAAGTAGGCGGACTTGACACGGCGGATGGTCGACAG
GAGCACCATGTCCTTGGGTCCGGCCTGCTGGATGCGGAGGCGGTCGGCTATGCCCCAGGCTTCGTTCT
GGCATCGGCGCAGGTCCTTGTAGTAGTCTTGCATGAGCCTTTCCACCGGCACCTCTTCTCCTTCCTCTT
CTGCTTCTTCCATGTCTGCTTCGGCCCTGGGGCGGCGCCGCGCCCCCCTGCCCCCCATGCGCGTGACC
```

-continued

```
CCGAACCCCCTGAGCGGTTGGAGCAGGGCCAGGTCGGCGACGACGCGCTCGGCCAGGATGGCCTGC

TGCACCTGCGTGAGGGTGGTTTGGAAGTCATCCAAGTCCACGAAGCGGTGGTAGGCGCCCGTGTTGA

TGGTGTAGGTGCAGTTGGCCATGACGGACCAGTTGACGGTCTGGTGGCCCGGTTGCGACATCTCGGT

GTACCTGAGTCGCGAGTAGGCGCGGGAGTCGAAGACGTAGTCGTTGCAAGTCCGCACCAGGTACTGG

TAGCCCACCAGGAAGTGCGGCGGCGGCTGGCGGTAGAGGGGCCAGCGCAGGGTGGCGGGGGCTCCG

GGGGCCAGGTCTTCCAGCATGAGGCGGTGGTAGGCGTAGATGTACCTGGACATCCAGGTGATACCCG

CGGCGGTGGTGGAGGCGCGCGGGAAGTCGCGCACCCGGTTCCAGATGTTGCGCAGGGGCAGAAAGT

GCTCCATGGTAGGCGTGCTCTGTCCAGTCAGACGCGCGCAGTCGTTGATACTCTAGACCAGGGAAAA

CGAAAGCCGGTCAGCGGGCACTCTTCCGTGGTCTGGTGAATAGATCGCAAGGGTATCATGGCGGAGG

GCCTCGGTTCGAGCCCCGGGTCCGGGCCGGACGGTCCGCCATGATCCACGCGGTTACCGCCCGCGTG

TCGAACCCAGGTGTGCGACGTCAGACAACGGTGGAGTGTTCCTTTTGGCGTTTTTCTGGCCGGGCGCC

GGCGCCGCGTAAGAGACTAAGCCGCGAAAGCGAAAGCAGTAAGTGGCTCGCTCCCCGTAGCCGGAG

GGATCCTTGCTAAGGGTTGCGTTGCGGCGAACCCCGGTTCGAATCCCGTACTCGGGCCGGCCGGACC

CGCGGCTAAGGTGTTGGATTGGCCTCCCCCTCGTATAAAGACCCCGCTTGCGGATTGACTCCGGACA

CGGGGACGAGCCCCTTTTATTTTTGCTTTCCCCAGATGCATCCGGTGCTGCGGCAGATGCGCCCCCG

CCCCAGCAGCAGCAACAACACCAGCAAGAGCGGCAGCAACAGCAGCGGGAGTCATGCAGGGCCCCC

TCACCCACCCTCGGCGGGCCGGCCACCTCGGCGTCCGCGGCCGTGTCTGGCGCCTGCGGCGGCGGCG

GGGGGCCGGCTGACGACCCCGAGGAGCCCCCGCGGCGCAGGGCCAGACACTACCTGGACCTGGAGG

AGGGCGAGGGCCTGGCGCGGCTGGGGGCGCCGTCTCCCGAGCGCCACCCGCGGGTGCAGCTGAAGC

GCGACTCGCGCGAGGCGTACGTGCCTCGGCAGAACCTGTTCAGGGACCGCGCGGGCGAGGAGCCCG

AGGAGATGCGGGACAGGAGGTTCAGCGCAGGGCGGGAGCTGCGGCAGGGGCTGAACCGCGAGCGG

CTGCTGCGCGAGGAGGACTTTGAGCCCGACGCGCGGACGGGGATCAGCCCCGCGCGCGCACGTG

GCGGCCGCCGACCTGGTGACGGCGTACGAGCAGACGGTGAACCAGGAGATCAACTTCCAAAAGAGT

TTCAACAACCACGTGCGCACGCTGGTGGCGCGCGAGGAGGTGACCATCGGGCTGATGCACCTGTGGG

ACTTTGTAAGCGCGCTGGTGCAGAACCCCAACAGCAAGCCTCTGACGGCGCAGCTGTTCCTGATAGT

GCAGCACAGCAGGGACAACGAGGCGTTTAGGGACGCGCTGCTGAACATCACCGAGCCCGAGGGTCG

GTGGCTGCTGGACCTGATTAACATCCTGCAGAGCATAGTGGTGCAGGAGCGCAGCCTGAGCCTGGCC

GACAAGGTGGCGGCCATCAACTACTCGATGCTGAGCCTGGGCAAGTTTTACGCGCGCAAGATCTACC

AGACGCCGTACGTGCCCATAGACAAGGAGGTGAAGATCGACGGTTTTTACATGCGCATGGCGCTGAA

GGTGCTCACCCTGAGCGACGACCTGGGCGTGTACCGCAACGAGCGCATCCACAAGGCCGTGAGCGTG

AGCCGGCGGCGCGAGCTGAGCGACCGCGAGCTGATGCACAGCCTGCAGCGGGCGCTGGCGGGCGCC

GGCAGCGGCGACAGGGAGGCGGAGTCCTACTTCGATGCGGGGCGGACCTGCGCTGGGCGCCCAGC

CGGCGGGCCCTGGAGGCCGCGGGGTCCGCGAGGACTATGACGAGGACGGCGAGGAGGATGAGGA

GTACGAGCTAGAGGAGGGCGAGTACCTGGACTAAACCGCGGGTGGTGTTTCCGGTAGATGCAAGAC

CCGAACGTGGTGGACCCGGCGCTGCGGGCGGCTCTGCAGAGCCAGCCGTCCGGCCTTAACTCCTCAG

ACGACTGGCGACAGGTCATGGACCGCATCATGTCGCTGACGGCGCGTAACCCGGACGCGTTCCGGCA

GCAGCCGCAGGCCAACAGGCTCTCCGCCATCCTGGAGGCGGTGGTGCCTGCGCGCTCGAACCCCACG

CACGAGAAGGTGCTGGCCATAGTGAACGCGCTGGCCGAGAACAGGGCCATCCGCCCGGACGAGGCC

GGGCTGGTGTACGACGCGCTGCTGCAGCGCGTGGCCCGCTACAACAGCGGCAACGTGCAGACCAAC

CTGGACCGGCTGGTGGGGGACGTGCGCGAGGCGGTGGCGCAGCGCGAGCGCGCGGATCGGCAGGGC
```

-continued

```
AACCTGGGCTCCATGGTGGCGCTGAATGCCTTCCTGAGCACGCAGCCGGCCAACGTGCCGCGGGGC

AGGAAGACTACACCAACTTTGTGAGCGCGCTGCGGCTGATGGTGACCGAGACCCCCCAGAGCGAGG

TGTACCAGTCGGGCCCGGACTACTTCTTCCAGACCAGCAGACAGGGCCTGCAGACGGTGAACCTGAG

CCAGGCTTTCAAGAACCTGCGGGGGCTGTGGGGCGTGAAGGCGCCCACCGGCGACCGGGCGACGGT

GTCCAGCCTGCTGACGCCCAACTCGCGCCTGCTGCTGCTGCTGATCGCGCCGTTCACGGACAGCGGC

AGCGTGTCCCGGGACACCTACCTGGGGCACCTGCTGACCCTGTACCGCGAGGCCATCGGGCAGGCGC

AGGTGGACGAGCACACCTTCCAGGAGATCACCAGCGTGAGCCGCGCGCTGGGGCAGGAGGACACGA

GCAGCCTGGAGGCGACTCTGAACTACCTGCTGACCAACCGGCGGCAGAAGATTCCCTCGCTGCACAG

CCTGACCTCCGAGGAGGAGCGCATCTTGCGCTACGTGCAGCAGAGCGTGAGCCTGAACCTGATGCGC

GACGGGGTGACGCCCAGCGTGGCGCTGGACATGACCGCGCGCAACATGGAACCGGGCATGTACGCC

GCGCACCGGCCTTACATCAACCGCCTGATGGACTACCTGCATCGCGCGGCGGCCGTGAACCCCGAGT

ACTTTACCAACGCCATCCTGAACCCGCACTGGCTCCCGCCGCCCGGGTTCTACAGCGGGGGCTTCGA

GGTCCCGGAGACCAACGATGGCTTCCTGTGGGACGACATGGACGACAGCGTGTTCTCCCCGCGGCCG

CAGGCGCTGGCGGAAGCGTCCCTGCTGCGTCCCAAGAAGGAGGAGGAGGAGGAGGCGAGTCGCCGC

CGCGGCAGCAGCGGCGTGGCTTCTCTGTCCGAGCTGGGGCGGCAGCCGCCGCGCGCCCCGGGTCCC

TGGGCGGCAGCCCCTTTCCGAGCCTGGTGGGGTCTCTGCACAGCGAGCGCACCACCCGCCCTCGGCT

GCTGGGCGAGGACGAGTACCTGAATAACTCCCTGCTGCAGCCGGTGCGGGAGAAAAACCTGCCTCCC

GCCTTCCCCAACAACGGGATAGAGAGCCTGGTGGACAAGATGAGCAGATGGAAGACCTATGCGCAG

GAGCACAGGGACGCGCCTGCGCTCCGGCCGCCCACGCGGCGCCAGCGCCACGACCGGCAGCGGGGG

CTGGTGTGGGATGACGAGGACTCCGCGGACGATAGCAGCGTGCTGGACCTGGGAGGGAGCGGCAAC

CCGTTCGCGCACCTGCGCCCCCGCCTGGGGAGGATGTTTTAAAAAAAAAAAAAAAAGCAAGAAGC

ATGATGCAAAAATTAAATAAAACTCACCAAGGCCATGGCGACCGAGCGTTGGTTTCTTGTGTTCCCTT

CAGTATGCGGCGCGCGGCGATGTACCAGGAGGGACCTCCTCCCTCTTACGAGAGCGTGGTGGGCGCG

GCGGCGGCGGCGCCCTCTTCTCCCTTTGCGTCGCAGCTGCTGGAGCCGCCGTACGTGCCTCCGCGCTA

CCTGCGGCCTACGGGGGGGAGAAACAGCATCCGTTACTCGGAGCTGGCGCCCCTGTTCGACACCACC

CGGGTGTACCTGGTGGACAACAAGTCGGCGGACGTGGCCTCCCTGAACTACCAGAACGACCACAGC

AATTTTTTGACCACGGTCATCCAGAACAATGACTACAGCCCGAGCGAGGCCAGCACCCAGACCATCA

ATCTGGATGACCGGTCGCACTGGGGCGGCGACCTGAAAACCATCCTGCACACCAACATGCCCAACGT

GAACGAGTTCATGTTCACCAATAAGTTCAAGGCGCGGGTGATGGTGTCGCGCTCGCACACCAAGGAA

GACCGGGTGGAGCTGAAGTACGAGTGGGTGGAGTTCGAGCTGCCAGAGGGCAACTACTCCGAGACC

ATGACCATTGACCTGATGAACAACGCGATCGTGGAGCACTATCTGAAAGTGGGCAGGCAGAACGGG

GTCCTGGAGAGCGACATCGGGGTCAAGTTCGACACCAGGAACTTCCGCCTGGGGCTGGACCCCGTGA

CCGGGCTGGTTATGCCCGGGGTGTACACCAACGAGGCCTTCCATCCCGACATCATCCTGCTGCCCGG

CTGCGGGGTGGACTTCACTTACAGCCGCCTGAGCAACCTCCTGGGCATCCGCAAGCGGCAGCCCTTC

CAGGAGGGCTTCAGGATCACCTACGAGGACCTGGAGGGGGGCAACATCCCCGCGCTCCTCGATGTGG

AGGCCTACCAGGATAGCTTGAAGGAAAATGAGGCGGGACAGGAGGATACCGCCCCCGCCGCCTCCG

CCGCCGCCGAGCAGGGCGAGGATGCTGCTGACACCGCGGCCGCGGACGGGGCAGAGGCCGACCCCG

CTATGGTGGTGGAGGCTCCCGAGCAGGAGGAGGACATGAATGACAGTGCGGTGCGCGGAGACACCT

TCGTCACCCGGGGGGAGGAAAAGCAAGCGGAGGCCGAGGCCGCGGCCGAGGAAAAGCAACTGGCG

GCAGCAGCGGCGGCGGCGGCGTTGGCCGCGGCGGAGGCTGAGTCTGAGGGGACCAAGCCCGCCAAG

GAGCCCGTGATTAAGCCCCTGACCGAAGATAGCAAGAAGCGCAGTTACAACCTGCTCAAGGACAGC
```

-continued

```
ACCAACACCGCGTACCGCAGCTGGTACCTGGCCTACAACTACGGCGACCCGTCGACGGGGGTGCGCT

CCTGGACCCTGCTGTGCACGCCGGACGTGACCTGCGGCTCGGAGCAGGTGTACTGGTCGCTGCCCGA

CATGATGCAAGACCCCGTGACCTTCCGCTCCACGCGGCAGGTCAGCAACTTCCCGGTGGTGGGCGCC

GAGCTGCTGCCCGTGCACTCCAAGAGCTTCTACAACGACCAGGCCGTCTACTCCCAGCTCATCCGCC

AGTTCACCTCTCTGACCCACGTGTTCAATCGCTTTCCTGAGAACCAGATTCTGGCGCGCCCGCCCGCC

CCCACCATCACCACCGTCAGTGAAAACGTTCCTGCTCTCACAGATCACGGGACGCTACCGCTGCGCA

ACAGCATCGGAGGAGTCCAGCGAGTGACCGTTACTGACGCCAGACGCCGCACCTGCCCCTACGTTTA

CAAGGCCTTGGGCATAGTCTCGCCGCGCGTCCTTTCCAGCCGCACTTTTTGAGCAACACCACCATCAT

GTCCATCCTGATCTCACCCAGCAATAACTCCGGCTGGGGACTGCTGCGCGCGCCCAGCAAGATGTTC

GGAGGGGCGAGGAAGCGTTCCGAGCAGCACCCCGTGCGCGTGCGCGGGCACTTCCGCGCCCCTGG

GGAGCGCACAAACGCGGCCGCGCGGGGCGCACCACCGTGGACGACGCCATCGACTCGGTGGTGGAG

CAGGCGCGCAACTACAGGCCCGCGGTCTCTACCGTGGACGCGGCCATCCAGACCGTGGTGCGGGCG

CGCGGCGGTACGCCAAGCTGAAGAGCCGCCGGAAGCGCGTGGCCCGCCGCCACCGCCGCCGACCCG

GGGCCGCCGCCAAACGCGCCGCCGCGCCCTGCTTCGCCGGGCCAAGCGCACGGGCCGCCGCGCCG

CCATGAGGGCCGCGCGCCGCTTGGCCGCCGGCATCACCGCCGCCACCATGGCCCCCCGTACCCGAAG

ACGCGCGGCCGCCGCCGCCGCCGCCGCCATCAGTGACATGGCCAGCAGGCGCCGGGGCAACGTGTA

CTGGGTGCGCGACTCGGTGACCGGCACGCGCGTGCCCGTGCGCTTCCGCCCCCCGCGGACTTGAGAT

GATGTGAAAAAACAACACTGAGTCTCCTGCTGTTGTGTGTATCCCAGCGGCGGCGGCGCGCGCAGCG

TCATGTCCAAGCGCAAAATCAAAGAAGAGATGCTCCAGGTCGTCGCGCCGGAGATCTATGGGCCCCC

GAAGAAGGAAGAGCAGGATTCGAAGCCCCGCAAGATAAAGCGGGTCAAAAAGAAAAAGAAAGATG

ATGACGATGCCGATGGGGAGGTGGAGTTCCTGCGCGCCACGGCGCCCAGGCGCCCGGTGCAGTGGA

AGGGCCGGCGCGTAAAGCGCGTCCTGCGCCCCGGCACCGCGGTGGTCTTCACGCCCGGCGAGCGCTC

CACCCGGACTTTCAAGCGCGTCTATGACGAGGTGTACGGCGACGAAGACCTGCTGGAGCAGGCCAAC

GAGCGCTTCGGAGAGTTTGCTTACGGGAAGCGTCAGCGGGCGCTGGGGAAGGAGGACCTGCTGGCG

CTGCCGCTGGACCAGGGCAACCCCACCCCCAGTCTGAAGCCCGTGACCCTGCAGCAGGTGCTGCCGA

GCAGCGCACCCTCCGAGGCGAAGCGGGGTCTGAAGCGCGAGGGCGGCGACCTGGCGCCCACCGTGC

AGCTCATGGTGCCCAAGCGGCAGAGGCTGGAGGATGTGCTGGAGAAAATGAAAGTAGACCCCGGTC

TGCAGCCGGACATCAGGGTCCGCCCCATCAAGCAGGTGGCGCCGGGCCTCGGCGTGCAGACCGTGG

ACGTGGTCATCCCCACCGGCAACTCCCCCGCCGCCGCCACCACTACCGCTGCCTCCACGGACATGGA

GACACAGACCGATCCCGCCGCAGCCGCAGCCGCAGCCGCCGCCGCGACCTCCTCGGCGGAGGTGCA

GACGGACCCCTGGCTGCCGCCGGCGATGTCAGCTCCCCGCGCGCGTCGCGGGCGCAGGAAGTACGGC

GCCGCCAACGCGCTCCTGCCCGAGTACGCCTTGCATCCTTCCATCGCGCCCACCCCCGGCTACCGAGG

CTATACCTACCGCCCGCGAAGAGCCAAGGGTTCCACCCGCCGTCCCCGCCGACGCGCCGCCGCCACC

ACCCGCCGCCGCCGCCGCAGACGCCAGCCCGCACTGGCTCCAGTCTCCGTGAGGAAAGTGGCGCGCG

ACGGACACACCCTGGTGCTGCCCAGGGCGCGCTACCACCCCAGCATCGTTTAAAAGCCTGTTGTGGT

TCTTGCAGATATGGCCCTCACTTGCCGCCTCCGTTTCCCGGTGCCGGGATACCGAGGAGGAAGATCG

CGCCGCAGGAGGGGTCTGGCCGGCCGCGGCCTGAGCGGAGGCAGCCGCCGCGCGCACCGGCGGCGA

CGCGCCACCAGCCGACGCATGCGCGGCGGGGTGCTGCCCCTGTTAATCCCCCTGATCGCCGCGGCGA

TCGGCGCCGTGCCCGGGATCGCCTCCGTGGCCTTGCAAGCGTCCCAGAGGCATTGACAGACTTGCAA

ACTTGCAAATATGGAAAAAAAAACCCCAATAAAAAAGTCTAGACTCTCACGCTCGCTTGGTCCTGTG
```

-continued

```
ACTATTTTGTAGAATGGAAGACATCAACTTTGCGTCGCTGGCCCCGCGTCACGGCTCGCGCCCGTTCC
TGGGACACTGGAACGATATCGGCACCAGCAACATGAGCGGTGGCGCCTTCAGTTGGGGCTCTCTGTG
GAGCGGCATTAAAAGTATCGGGTCTGCCGTTAAAAATTACGGCTCCCGGGCCTGGAACAGCAGCACG
GGCCAGATGTTGAGAGACAAGTTGAAAGAGCAGAACTTCCAGCAGAAGGTGGTGGAGGGCCTGGCC
TCCGGCATCAACGGGGTGGTGGACCTGGCCAACCAGGCCGTGCAGAATAAGATCAACAGCAGACTG
GACCCCCGGCCGCCGGTGGAGGAGGTGCCGCCGGCGCTGGAGACGGTGTCCCCCGATGGGCGTGGC
GAGAAGCGCCCGCGGCCCGATAGGGAAGAGACCACTCTGGTCACGCAGACCGATGAGCCGCCCCCG
TATGAGGAGGCCCTGAAGCAAGGTCTGCCCACCACGCGGCCCATCGCGCCCATGGCCACCGGGGTGG
TGGGCCGCCACACCCCCGCCACGCTGGACTTGCCTCCGCCCGCCGATGTGCCGCAGCAGCAGAAGGC
GGCACAGCCGGGCCCGCCCGCGACCGCCTCCCGTTCCTCCGCCGGTCCTCTGCCGCGCGCGGCCAGC
GGCCCCCGCGGGGGGTCGCGAGGCACGGCAACTGGCAGAGCACGCTGAACAGCATCGTGGGTCTG
GGGGTGCGGTCCGTGAAGCGCCGCCGATGCTACTGAATAGCTTAGCTAACGTGTTGTATGTGTGTAT
GCGCCCTATGTCGCCGCCAGAGGAGCTGCTGAGTCGCCGCCGTTCGCGCGCCCACCACCACCGCCAC
TCCGCCCCTCAAGATGGCGACCCCATCGATGATGCCGCAGTGGTCGTACATGCACATCTCGGGCCAG
GACGCCTCGGAGTACCTGAGCCCCGGGCTGGTGCAGTTCGCCCGCGCCACCGAGAGCTACTTCAGCC
TGAGTAACAAGTTTAGGAACCCCACGGTGGCGCCCACGCACGATGTGACCACCGACCGGTCTCAGCG
CCTGACGCTGCGGTTCATTCCCGTGGACCGCGAGGACACCGCGTACTCGTACAAGGCGCGGTTCACC
CTGGCCGTGGGCGACAACCGCGTGCTGGACATGGCCTCCACCTACTTTGACATCCGCGGGGTGCTGG
ACCGGGGTCCCACTTTCAAGCCCTACTCTGGCACCGCCTACAACTCCCTGGCCCCCAAGGGCGCTCCC
AACTCCTGCGAGTGGGAGCAAGAGGAAACTCAGGCAGTTGAAGAAGCAGCAGAAGAGGAAGAAGA
AGATGCTGACGGTCAAGCTGAGGAAGAGCAAGCAGCTACCAAAAAGACTCATGTATATGCTCAGGC
TCCCCTTTCTGGCGAAAAAATTAGTAAAGATGGTCTGCAAATAGGAACGGACGCTACAGCTACAGAA
CAAAAACCTATTTATGCAGACCCTACATTCCAGCCCGAACCCCAAATCGGGGAGTCCCAGTGGAATG
AGGCAGATGCTACAGTCGCCGGCGGTAGAGTGCTAAAGAAATCTACTCCCATGAAACCATGCTATGG
TTCCTATGCAAGACCCACAAATGCTAATGGAGGTCAGGGTGTACTAACGGCAAATGCCCAGGGACAG
CTAGAATCTCAGGTTGAAATGCAATTCTTTTCAACTTCTGAAAACGCCCGTAACGAGGCTAACAACA
TTCAGCCCAAATTGGTGCTGTATAGTGAGGATGTGCACATGGAGACCCCGGATACGCACCTTTCTTAC
AAGCCCGCAAAAAGCGATGACAATTCAAAAATCATGCTGGGTCAGCAGTCCATGCCCAACAGACCT
AATTACATCGGCTTCAGAGACAACTTTATCGGCCTCATGTATTACAATAGCACTGGCAACATGGGAG
TGCTTGCAGGTCAGGCCTCTCAGTTGAATGCAGTGGTGGACTTGCAAGACAGAAACACAGAACTGTC
CTACCAGCTCTTGCTTGATTCCATGGGTGACAGAACCAGATACTTTTCCATGTGGAATCAGGCAGTGG
ACAGTTATGACCCAGATGTTAGAATTATTGAAAATCATGGAACTGAAGACGAGCTCCCCAACTATTG
TTTCCCTCTGGGTGGCATAGGGGTAACTGACACTTACCAGGCTGTTAAAACCAACAATGGCAATAAC
GGGGGCCAGGTGACTTGGACAAAAGATGAAACTTTTGCAGATCGCAATGAAATAGGGGTGGGAAAC
AATTTCGCTATGGAGATCAACCTCAGTGCCAACCTGTGGAGAAACTTCCTGTACTCCAACGTGGCGCT
GTACCTACCAGACAAGCTTAAGTACAACCCCTCCAATGTGGACATCTCTGACAACCCCAACACCTAC
GATTACATGAACAAGCGAGTGGTGGCCCCGGGGCTGGTGGACTGCTACATCAACCTGGGCGCGCGCT
GGTCGCTGGACTACATGGACAACGTCAACCCCTTCAACCACCACCGCAATGCGGGCCTGCGCTACCG
CTCCATGCTCCTGGGCAACGGGCGCTACGTGCCCTTCCACATCCAGGTGCCCCAGAAGTTCTTTGCCA
TCAAGAACCTCCTCCTCCTGCCGGGCTCCTACACCTACGAGTGGAACTTCAGGAAGGATGTCAACAT
GGTCCTCCAGAGCTCTCTGGGTAACGATCTCAGGGTGGACGGGGCCAGCATCAAGTTCGAGAGCATC
```

-continued

```
TGCCTCTACGCCACCTTCTTCCCCATGGCCCACAACACGGCCTCCACGCTCGAGGCCATGCTCAGGAA

CGACACCAACGACCAGTCCTTCAATGACTACCTCTCCGCCGCCAACATGCTCTACCCCATACCCGCCA

ACGCCACCAACGTCCCCATCTCCATCCCCTCGCGCAACTGGGCGGCCTTCCGCGGCTGGGCCTTCACC

CGCCTCAAGACCAAGGAGACCCCTCCCTGGGCTCGGGATTCGACCCCTACTACACCTACTCGGGCT

CCATTCCCTACCTGGACGGCACCTTCTACCTCAACCACACTTTCAAGAAGGTCTCGGTCACCTTCGAC

TCCTCGGTCAGCTGGCCGGGCAACGACCGTCTGCTCACCCCCAACGAGTTCGAGATCAAGCGCTCGG

TCGACGGGGAGGGCTACAACGTGGCCCAGTGCAACATGACCAAGGACTGGTTCCTGGTCCAGATGCT

GGCCAACTACAACATCGGCTACCAGGGCTTCTACATCCCAGAGAGCTACAAGGACAGGATGTACTCC

TTCTTCAGGAACTTCCAGCCCATGAGCCGGCAGGTGGTGGACCAGACCAAGTACAAGGACTACCAGG

AGGTGGGCATCATCCACCAGCACAACAACTCGGGCTTCGTGGGCTACCTCGCCCCCACCATGCGCGA

GGGACAGGCCTACCCCGCCAACTTCCCCTATCCGCTCATAGGCAAGACCGCGGTCGACAGCATCACC

CAGAAAAAGTTCCTCTGCGACCGCACCCTCTGGCGCATCCCCTTCTCCAGCAACTTCATGTCCATGGG

TGCGCTCTCGGACCTGGGCCAGAACTTGCTCTACGCCAACTCCGCCCACGCCCTCGACATGACCTTCG

AGGTCGACCCCATGGACGAGCCCACCCTTCTCTATGTTCTGTTCGAAGTCTTTGACGTGGTCCGGGTC

CACCAGCCGCACCGCGGCGTCATCGAGACCGTGTACCTGCGTACGCCCTTCTCGGCCGGCAACGCCA

CCACCTAAAGAAGCAAGCCGCAGTCATCGCCGCCTGCATGCCGTCGGGTTCCACCGAGCAAGAGCTC

AGGGCCATCGTCAGAGACCTGGGATGCGGGCCCTATTTTTTGGGCACCTTCGACAAGCGCTTCCCTG

GCTTTGTCTCCCCACACAAGCTGGCCTGCGCCATCGTCAACACGGCCGGCCGCGAGACCGGGGCGT

GCACTGGCTGGCCTTCGCCTGGAACCCGCGCTCCAAAACATGCTTCCTCTTTGACCCCTTCGGCTTTT

CGGACCAGCGGCTCAAGCAAATCTACGAGTTCGAGTACGAGGGCTTGCTGCGTCGCAGCGCCATCGC

CTCCTCGCCCGACCGCTGCGTCACCCTCGAAAAGTCCACCCAGACCGTGCAGGGGCCCGACTCGGCC

GCCTGCGGTCTCTTCTGCTGCATGTTTCTGCACGCCTTTGTGCACTGGCCTCAGAGTCCCATGGACCG

CAACCCCACCATGAACTTGCTGACGGGGGTGCCCAACTCCATGCTCCAGAGCCCCCAGGTCGAGCCC

ACCCTGCGCCGCAACCAGGAGCAGCTCTACAGCTTCCTGGAGCGCCACTCGCCTTACTTCCGCCGCC

ACAGCGCACAGATCAGGAGGGCCACCTCCTTCTGCCACTTGCAAGAGATGCAAGAAGGGTAATAAC

GATGTACACACTTTTTTTCTCAATAAATGGCATCTTTTTATTTATACAAGCTCTCTGGGGTATTCATTT

CCCACCACCACCCGCCGTTGTCGCCATCTGGCTCTATTTAGAAATCGAAAGGGTTCTGCCGGGAGTCG

CCGTGCGCCACGGGCAGGGACACGTTGCGATACTGGTAGCGGGTGCCCCACTTGAACTCGGGCACCA

CCAGGCGAGGCAGCTCGGGGAAGTTTTCGCTCCACAGGCTGCGGGTCAGCACCAGCGCGTTCATCAG

GTCGGGCGCCGAGATCTTGAAGTCGCAGTTGGGGCCGCCGCCCTGCGCGCGCGAGTTGCGGTACACC

GGGTTGCAGCACTGGAACACCAACAGCGCCGGGTGCTTCACGCTGGCCAGCACGCTGCGGTCGGAG

ATCAGCTCGGCGTCCAGGTCCTCCGCGTTGCTCAGCGCGAACGGGGTCATCTTGGGCACTTGCCGCCC

CAGGAAGGGCGCGTGCCCCGGTTTCGAGTTGCAGTCGCAGCGCAGCGGGATCAGCAGGTGCCCGTGC

CCGGACTCGGCGTTGGGGTACAGCGCGCGCATGAAGGCCTGCATCTGGCGGAAGGCCATCTGGGCCT

TGGCGCCCTCCGAGAAGAACATGCCGCAGGACTTGCCCGAGAACTGGTTTGCGGGGCAGCTGGCGTC

GTGCAGGCAGCAGCGCGCGTCGGTGTTGGCGATCTGCACCACGTTGCGCCCCCACCGGTTCTTCACG

ATCTTGGCCTTGGACGATTGCTCCTTCAGCGCGCGCTGCCCGTTCTCGCTGGTCACATCCATCTCGAT

CACATGTTCCTTGTTCACCATGCTGCTGCCGTGCAGACACTTCAGCTCGCCCTCCGTCTCGGTGCAGC

GGTGCTGCCACAGCGCGCAGCCCGTGGGCTCGAAAGACTTGTAGGTCACCTCCGCGAAGGACTGCAG

GTACCCCTGCAAAAAGCGGCCCATCATGGTCACGAAGGTCTTGTTGCTGCTGAAGGTCAGCTGCAGC
```

-continued

CCGCGGTGCTCCTCGTTCAGCCAGGTCTTGCACACGGCCGCCAGCGCCTCCACCTGGTCGGGCAGCA

TCTTGAAGTTCACCTTCAGCTCATTCTCCACGTGGTACTTGTCCATCAGCGTGCGCGCCGCCTCCATG

CCCTTCTCCCAGGCCGACACCAGCGGCAGGCTCACGGGGTTCTTCACCATCACCGTGGCCGCCGCCTC

CGCCGCGCTTTCGCTTTCCGCCCCGCTGTTCTCTTCCTCTTCCTCCTCTTCCTCGCCGCCGCCCACTCGC

AGCCCCCGCACCACGGGGTCGTCTTCCTGCAGGCGCTGCACCTTGCGCTTGCCGTTGCGCCCCTGCTT

GATGCGCACGGGCGGGTTGCTGAAGCCCACCATCACCAGCGCGGCCTCTTCTTGCTCGTCCTCGCTGT

CCAGAATGACCTCCGGGGAGGGGGGGTTGGTCATCCTCAGTACCGAGGCACGCTTCTTTTTCTTCCTG

GGGGCGTTCGCCAGCTCCGCGGCTGCGGCCGCTGCCGAGGTCGAAGGCCGAGGGCTGGGCGTGCGC

GGCACCAGCGCGTCCTGCGAGCCGTCCTCGTCCTCCTCGGACTCGAGACGGAGGCGGGCCCGCTTCT

TCGGGGCGCGCGGGCGGCGGAGGCGGCGGCGGCGACGGAGACGGGGACGAGACATCGTCCAGG

GTGGGTGGACGGCGGGCCGCGCCGCGTCCGCGCTCGGGGGTGGTCTCGCGCTGGTCCTCTTCCCGAC

TGGCCATCTCCCACTGCTCCTTCTCCTATAGGCAGAAAGAGATCATGGAGTCTCTCATGCGAGTCGAG

AAGGAGGAGGACAGCCTAACCGCCCCCTCTGAGCCCTCCACCACCGCCGCCACCACCGCCAATGCCG

CCGCGGACGACGCGCCCACCGAGACCACCGCCAGTACCACCCTCCCCAGCGACGCACCCCCGCTCGA

GAATGAAGTGCTGATCGAGCAGGACCCGGGTTTTGTGAGCGGAGAGGAGGATGAGGTGGATGAGAA

GGAGAAGGAGGAGGTCGCCGCCTCAGTGCCAAAAGAGGATAAAAAGCAAGACCAGGACGACGCAG

ATAAGGATGAGACAGCAGTCGGGCGGGGGAACGGAAGCCATGATGCTGATGACGGCTACCTAGACG

TGGGAGACGACGTGCTGCTTAAGCACCTGCACCGCCAGTGCGTCATCGTCTGCGACGCGCTGCAGGA

GCGCTGCGAAGTGCCCCTGGACGTGGCGGAGGTCAGCCGCGCCTACGAGCGGCACCTCTTCGCGCCG

CACGTGCCCCCCAAGCGCCGGGAGAACGGCACCTGCGAGCCCAACCCGCGTCTCAACTTCTACCCGG

TCTTCGCGGTACCCGAGGTGCTGGCCACCTACCACATCTTTTTCCAAAACTGCAAGATCCCCCTCTCC

TGCCGCGCCAACCGCACCCGCGCCGACAAAACCCTGACCCTGCGGCAGGGCGCCCACATACCTGATA

TCGCCTCTCTGGAGGAAGTGCCCCAAGATCTTCGAGGGTCTCGGTCGCGACGAGAAACGGGCGGCGAA

CGCTCTGCACGGAGACAGCGAAAACGAGAGTCACTCGGGGGTGCTGGTGGAGCTCGAGGGCGACAA

CGCGCGCCTGGCCGTACTCAAGCGCAGCATAGAGGTCACCCACTTTGCCTACCCGGCGCTCAACCTG

CCCCCCAAGGTCATGAGTGTGGTCATGGGCGAGCTCATCATGCGCCGCGCCCAGCCCCTGGCCGCGG

ATGCAAACTTGCAAGAGTCCTCCGAGGAAGGCCTGCCCGCGGTCAGCGACGAGCAGCTGGCGCGCT

GGCTGGAGACCCGCGACCCCGCGCAGCTGGAGGAGCGGCGCAAGCTCATGATGGCCGCGGTGCTGG

TCACCGTGGAGCTCGAGTGTCTGCAGCGCTTCTTCGCGGACCCCGAGATGCAGCGCAAGCTCGAGGA

GACCCTGCACTACACCTTCCGCCAGGGCTACGTGCGCCAGGCCTGCAAGATCTCCAACGTGGAGCTC

TGCAACCTGGTCTCCTACCTGGGCATCCTGCACGAGAACCGCCTCGGGCAGAACGTCCTGCACTCCA

CCCTCAAAGGGGAGGCGCGCCGCGACTACATCCGCGACTGCGCCTACCTCTTCCTCTGCTACACCTG

GCAGACGGCCATGGGGGTCTGGCAGCAGTGCCTGGAGGAGCGCAACCTCAAGGAGCTGGAAAAGCT

CCTCAAGCGCACCCTCAGGGACCTCTGGACGGGCTTCAACGAGCGCTCGGTGGCCGCCGCGCTGGCG

GACATCATCTTTCCCGAGCGCCTGCTCAAGACCCTGCAGCAGGGCCTGCCCGACTTCACCAGCCAGA

GCATGCTGCAGAACTTCAGGACTTTCATCCTGGAGCGCTCGGGCATCCTGCCGGCCACTTGCTGCGCG

CTGCCCAGCGACTTCGTGCCCATCAAGTACAGGGAGTGCCCGCCGCCGCTCTGGGGCCACTGCTACC

TCTTCCAGCTGGCCAACTACCTCGCCTACCACTCGGACCTCATGGAAGACGTGAGCGGCGAGGGCCT

GCTCGAGTGCCACTGCCGCTGCAACCTCTGCACGCCCCACCGCTCTCTAGTCTGCAACCCGCAGCTGC

TCAGCGAGAGTCAGATTATCGGTACCTTCGAGCTGCAGGGTCCCTCGCCTGACGAGAAGTCCGCGGC

TCCAGGGCTGAAACTCACTCCGGGGCTGTGGACTTCCGCCTACCTACGCAAATTTGTACCTGAGGACT

```
ACCACGCCCACGAGATCAGGTTCTACGAAGACCAATCCCGCCCGCCCAAGGCGGAGCTCACCGCCTG

CGTCATCACCCAGGGGCACATCCTGGGCCAATTGCAAGCCATCAACAAAGCCCGCCGAGAGTTCTTG

CTGAAAAAGGGTCGGGGGGTGTACCTGGACCCCCAGTCCGGCGAGGAGCTAAACCCGCTACCCCCG

CCGCCGCCCAGCAGCGGGACCTTGCTTCCCAGGATGGCACCCAGAAAGAAGCAGCAGCCGCCGCC

GCCGCCGCAGCCATACATGCTTCTGGAGGAAGAGGAGGAGGACTGGGACAGTCAGGCAGAGGAGGT

TTCGGACGAGGAGCAGGAGGAGATGATGGAAGACTGGGAGGAGGACAGCAGCCTAGACGAGGAAG

CTTCAGAGGCCGAAGAGGTGGCAGACGCAACACCATCGCCCTCGGTCGCAGCCCCTCGCCGGGGCC

CCTGAAATCCTCCGAACCCAGCACCAGCGCTATAACCTCCGCTCCTCCGGCGCCGGCGCCACCCGCC

CGCAGACCCAACCGTAGATGGGACACCACAGGAACCGGGGTCGGTAAGTCCAAGTGCCCGCCGCCG

CCACCGCAGCAGCAGCAGCAGCGCCAGGGCTACCGCTCGTGGCGCGGGCACAAGAACGCCATA

GTCGCCTGCTTGCAAGACTGCGGGGGCAACATCTCTTTCGCCCGCCGCTTCCTGCTATTCCACCACGG

GGTCGCCTTTCCCCGCAATGTCCTGCATTACTACCGTCATCTCTACAGCCCCTACTGCAGCGGCGACC

CAGAGGCGGCAGCGGCAGCCACAGCGGCGACCACCACCTAGGAAGATATCCTCCGCGGGCAAGACA

GCGGCAGCAGCGGCCAGGAGACCCGCGGCAGCAGCGGCGGGAGCGGTGGGCGCACTGCGCCTCTCG

CCCAACGAACCCCTCTCGACCCGGGAGCTCAGACACAGGATCTTCCCCACTTTGTATGCCATCTTCCA

ACAGAGCAGAGGCCAGGAGCAGGAGCTGAAAATAAAAAACAGATCTCTGCGCTCCCTCACCCGCAG

CTGTCTGTATCACAAAAGCGAAGATCAGCTTCGGCGCACGCTGGAGGACGCGGAGGCACTCTTCAGC

AAATACTGCGCGCTCACTCTTAAAGACTAGCTCCGCGCCCTTCTCGAATTTAGGCGGGAGAAAACTA

CGTCATCGCCGGCCGCCGCCCAGCCCGCCCAGCCGAGATGAGCAAAGAGATTCCCACGCCATACATG

TGGAGCTACCAGCCGCAGATGGGACTCGCGGCGGGAGCGGCCCAGGACTACTCCACCCGCATGAAC

TACATGAGCGCGGGACCCCACATGATCTCACAGGTCAACGGGATCCGCGCCCAGCGAAACCAAATA

CTGCTGGAACAGGCGGCCATCACCGCCACGCCCCGCCATAATCTCAACCCCCGAAATTGGCCCGCCG

CCCTCGTGTACCAGGAAACCCCCTCCGCCACCACCGTACTACTTCCGCGTGACGCCCAGGCCGAAGT

CCAGATGACTAACTCAGGGGCGCAGCTCGCGGGCGGCTTTCGTCACGGGGCGCGGCCGCTCCGACCA

GGTATAAGACACCTGATGATCAGAGGCCGAGGTATCCAGCTCAACGACGAGTCGGTGAGCTCTTCGC

TCGGTCTCCGTCCGGACGGAACTTTCCAGCTCGCCGGATCCGGCCGCTCTTCGTTCACGCCCCGCCAG

GCGTACCTGACTCTGCAGACCTCGTCCTCGGAGCCCCGCTCCGGCGGCATCGGAACCCTCCAGTTCGT

GGAGGAGTTCGTGCCCTCGGTCTACTTCAACCCCTTCTCGGGACCTCCCGGACGCTACCCCGACCAGT

TCATTCCGAACTTTGACGCGGTGAAGGACTCGGCGGACGGCTACGACTGAATGTCAGGTGTCGAGGC

AGAGCAGCTTCGCCTGAGACACCTCGAGCACTGCCGCCGCCACAAGTGCTTCGCCCGCGGTTCTGGT

GAGTTCTGCTACTTTCAGCTACCCGAGGAGCATACCGAGGGGCCGGCGCACGGCGTCCGCCTGACCA

CCCAGGGCGAGGTTACCTGTTCCCTCATCCGGGAGTTTACCCTCCGTCCCCTGCTAGTGGAGCGGGAG

CGGGGTCCCTGTGTCCTAACTATCGCCTGCAACTGCCCTAACCCTGGATTACATCAAGATCTTTGCTG

TCATCTCTGTGCTGAGTTTAATAAACGCTGAGATCAGAATCTACTGGGGCTCCTGTCGCCATCCTGTG

AACGCCACCGTCTTCACCCACCCCGACCAGGCCCAGGCGAACCTCACCTGCGGTCTGCATCGGAGGG

CCAAGAAGTACCTCACCTGGTACTTCAACGGCACCCCCTTTGTGGTTTACAACAGCTTCGACGGGGA

CGGAGTCTCCCTGAAAGACCAGCTCTCCGGTCTCAGCTACTCCATCCACAAGAACACCACCCTCCAA

CTCTTCCCTCCCTACCTGCCGGGAACCTACGAGTGCGTCACCGGCCGCTGCACCCACCTCACCCGCCT

GATCGTAAACCAGAGCTTTCCGGGAACAGATAACTCCCTCTTCCCCAGAACAGGAGGTGAGCTCAGG

AAACTCCCCGGGGACCAGGGCGGAGACGTACCTTCGACCCTTGTGGGGTTAGGATTTTTTATTACCG
```

-continued

```
GGTTGCTGGCTCTTTTAATCAAAGTTTCCTTGAGATTTGTTCTTTCCTTCTACGTGTATGAACACCTCA
ACCTCCAATAACTCTACCCTTTCTTCGGAATCAGGTGACTTCTCTGAAATCGGGCTTGGTGTGCTGCT
TACTCTGTTGATTTTTTCCTTATCATACTCAGCCTTCTGTGCCTCAGGCTCGCCGCCTGCTGCGCACA
CATCTATATCTACTGCTGGTTGCTCAAGTGCAGGGGTCGCCACCCAAGATGAACAGGTACATGGTCC
TATCGATCCTAGGCCTGCTGGCCCTGGCGGCCTGCAGCGCCGCCAAAAAAGAGATTACCTTTGAGGA
GCCCGCTTGCAATGTAACTTTCAAGCCCGAGGGTGACCAATGCACCACCCTCGTCAAATGCGTTACC
AATCATGAGAGGCTGCGCATCGACTACAAAAACAAAACTGGCCAGTTTGCGGTCTATAGTGTGTTTA
CGCCCGGAGACCCCTCTAACTACTCTGTCACCGTCTTCCAGGGCGGACAGTCTAAGATATTCAATTAC
ACTTTCCCTTTTTATGAGTTATGCGATGCGGTCATGTACATGTCAAAACAGTACAACCTGTGGCCTCC
CTCTCCCCAGGCGTGTGTGGAAAATACTGGGTCTTACTGCTGTATGGCTTTCGCAATCACTACGCTCG
CTCTAATCTGCACGGTGCTATACATAAAATTCAGGCAGAGGCGAATCTTTATCGATGAAAAGAAAAT
GCCTTGATCGCTAACACCGGCTTTCTATCTGCAGAATGAATGCAATCACCTCCCTACTAATCACCACC
ACCCTCCTTGCGATTGCCCATGGGTTGACACGAATCGAAGTGCCAGTGGGGTCCAATGTCACCATGG
TGGGCCCCGCCGGCAATTCCACCCTCATGTGGGAAAAATTTGTCCGCAATCAATGGGTTCATTTCTGC
TCTAACCGAATCAGTATCAAGCCCAGAGCCATCTGCGATGGGCAAAATCTAACTCTGATCAATGTGC
AAATGATGGATGCTGGGTACTATTACGGGCAGCGGGAGAAATCATTAATTACTGGCGACCCCACAA
GGACTACATGCTGCATGTAGTCGAGGCACTTCCCACTACCACCCCCACTACCACCTCTCCCACCACCA
CCACCACTACTACTACTACTACTACTACTACTACTACCACTACCGCTGCCCGCCATACCCGCAAA
AGCACCATGATTAGCACAAAGCCCCCTCGTGCTCACTCCCACGCCGGCGGGCCCATCGGTGCGACCT
CAGAAACCACCGAGCTTTGCTTCTGCCAATGCACTAACGCCAGCGCTCATGAACTGTTCGACCTGGA
GAATGAGGATGTCCAGCAGAGCTCCGCTTGCCTGACCCAGGAGGCTGTGGAGCCCGTTGCCCTGAAG
CAGATCGGTGATTCAATAATTGACTCTTCTTCTTTTGCCACTCCCGAATACCCTCCCGATTCTACTTTC
CACATCACGGGTACCAAAGACCCTAACCTCTCTTTCTACCTGATGCTGCTGCTCTGTATCTCTGTGGT
CTCTTCCGCGCTGATGTTACTGGGGATGTTCTGCTGCCTGATCTGCCGCAGAAAGAGAAAAGCTCGCT
CTCAGGGCCAACCACTGATGCCCTTCCCCTACCCCCCGGATTTTGCAGATAACAAGATATGAGCTCGC
TGCTGACACTAACCGCTTTACTAGCCTGCGCTCTAACCCTTGTCGCTTGCGACTCGAGATTCCACAAT
GTCACAGCTGTGGCAGGAGAAAATGTTACTTTCAACTCCACGGCCGATACCCAGTGGTCGTGGAGTG
GCTCAGGTAGCTACTTAACTATCTGCAATAGCTCCACTTCCCCCGGCATATCCCCAACCAAGTACCAA
TGCAATGCCAGCCTGTTCACCCTCATCAACGCTTCCACCCTGGACAATGGACTCTATGTAGGCTATGT
ACCCTTTGGTGGGCAAGGAAAGACCCACGCTTACAACCTGGAAGTTCGCCAGCCCAGAACCACTACC
CAAGCTTCTCCCACCACCACCACCACCACCATCACCAGCAGCAGCAGCAGCAGCCACAGCA
GCAGCAGCAGATTATTGACTTTGGTTTTGGCCAGCTCATCTGCCGCTACCCAGGCCATCTACAGCTCT
GTGCCCGAAACCACTCAGATCCACCGCCCAGAAACGACCACCGCCACCACCCTACACACCTCCAGCG
ATCAGATGCCGACCAACATCACCCCCTTGGCTCTTCAAATGGGACTTACAAGCCCCACTCCAAAACC
AGTGGATGCGGCCGAGGTCTCCGCCCTCGTCAATGACTGGGCGGGCTGGGAATGTGGTGGTTCGCC
ATAGGCATGATGGCGCTCTGCCTGCTTCTGCTCTGGCTCATCTGCTGCCTCCACCGCAGGCGAGCCAG
ACCCCCCATCTATAGACCCATCATTGTCCTGAACCCCGATAATGATGGGATCCATAGATTGGATGGCC
TGAAAAACCTACTTTTTTCTTTTACAGTATGATAAATTGAGACATGCCTCGCATTTTCTTGTACATGTT
CCTTCTCCCACCTTTTCTGGGGTGTTCTACGCTGGCCGCTGTGTCTCACCTGGAGGTAGACTGCCTCTC
ACCCTTCACTGTCTACCTGCTTTACGGATTGGTCACCCTCACTCTCATCTGCAGCCTAATCACAGTAAT
CATCGCCTTCATCCAGTGCATTGATTACATCTGTGTGCGCCCTCGCATACTTCAGACACCACCCGCAGT
```

-continued

```
ACCGAGACAGGAACATTGCCCAACTTCTAAGACTGCTCTAATCATGCATAAGACTGTGATCTGCCTTC

TGATCCTCTGCATCCTGCCCACCCTCACCTCCTGCCAGTACACCACAAAATCTCCGCGCAAAAGACAT

GCCTCCTGCCGCTTCACCCAACTGTGGAATATACCCAAATGCTACAACGAAAAGAGCGAGCTCTCCG

AAGCTTGGCTGTATGGGGTCATCTGTGTCTTAGTTTTCTGCAGCACTGTCTTTGCCCTCATAATCTACC

CCTACTTTGATTTGGGATGGAACGCGATCGATGCCATGAATTACCCCACCTTTCCCGCACCCGAGATA

ATTCCACTGCGACAAGTTGTACCCGTTGTCGTTAATCAACGCCCCCCATCCCCTACGCCCACTGAAAT

CAGCTACTTTAACCTAACAGGCGGAGATGACTGACGCCCTAGATCTAGAAATGGACGGCATCAGTAC

CGAGCAGCGTCTCCTAGAGAGGCGCAGGCAGGCGGCTGAGCAAGAGCGCCTCAATCAGGAGCTCCG

AGATCTCGTTAACCTGCACCAGTGCAAAAGAGGCATCTTTTGTCTGGTAAAGCAGGCCAAAGTCACC

TACGAGAAGACCGGCAACAGCCACCGCCTCAGTTACAAATTGCCCACCCAGCGCCAGAAGCTGGTGC

TCATGGTGGGTGAGAATCCCATCACCGTCACCCAGCACTCGGTAGAGACCGAGGGGTGTCTGCACTC

CCCCTGTCGGGGTCCAGAAGACCTCTGCACCCTGGTAAAGACCCTGTGCGGTCTCAGAGATTTAGTC

CCCTTTAACTAATCAAACACTGGAATCAATAAAAAGAATCACTTACTTAAAATCAGACAGCAGGTCT

CTGTCCAGTTTATTCAGCAGCACCTCCTTCCCCTCCTCCCAACTCTGGTACTCCAAACGCCTTCTGGCG

GCAAACTTCCTCCACACCCTGAAGGGAATGTCAGATTCTTGCTCCTGTCCCTCCGCACCCACTATCTT

CATGTTGTTGCAGATGAAGCGCACCAAAACGTCTGACGAGAGCTTCAACCCCGTGTACCCCTATGAC

ACGGAAAGCGGCCCTCCCTCCGTCCCTTTCCTCACCCCTCCCTTCGTGTCTCCCGATGGATTCCAAGA

AAGTCCCCCGGGGTCCTGTCTCTGAACCTGGCCGAGCCCCTGGTCACTTCCCACGGCATGCTCGCCC

TGAAAATGGGAAGTGGCCTCTCCCTGGACGACGCTGGCAACCTCACCTCTCAAGATATCACCACCGC

TAGCCCTCCCCTCAAAAAAACCAAGACCAACCTCAGCCTAGAAACCTCATCCCCCCTAACTGTGAGC

ACCTCAGGCGCCCTCACCGTAGCAGCCGCCGCTCCCCTGGCGGTGGCCGGCACCTCCCTCACCATGC

AATCAGAGGCCCCCCTGACAGTACAGGATGCAAAACTCACCCTGGCCACCAAAGGCCCCCTGACCGT

GTCTGAAGGCAAACTGGCCTTGCAAACATCGGCCCCGCTGACGGCCGCTGACAGCAGCACCCTCACA

GTCAGTGCCACACCACCCCTTAGCACAAGCAATGGCAGCTTGGGTATTGACATGCAAGCCCCCATTT

ACACCACCAATGGAAAACTAGGACTTAACTTTGGCGCTCCCCTGCATGTGGTAGACAGCCTAAATGC

ACTGACTGTAGTTACTGGCCAAGGTCTTACGATAAACGGAACAGCCCTACAAACTAGAGTCTCAGGT

GCCCTCAACTATGACACATCAGGAAACCTAGAATTGAGAGCTGCAGGGGGTATGCGAGTTGATGCAA

ATGGTCAACTTATCCTTGATGTAGCTTACCCATTTGATGCACAAAACAATCTCAGCCTTAGGCTTGGA

CAGGGACCCCTGTTTGTTAACTCTGCCCACAACTTGGATGTTAACTACAACAGAGGCCTCTACCTGTT

CACATCTGGAAATACCAAAAAGCTAGAAGTTAATATCAAAACAGCCAAGGGTCTCATTTATGATGAC

ACTGCTATAGCAATCAATGCGGGTGATGGGCTACAGTTTGACTCAGGCTCAGATACAAATCCATTAA

AAACTAAACTTGGATTAGGACTGGATTATGACTCCAGCAGAGCCATAATTGCTAAACTGGGAACTGG

CCTAAGCTTTGACAACACAGGTGCCATCACAGTAGGCAACAAAAATGATGACAAGCTTACCTTGTGG

ACCACACCAGACCCATCCCCTAACTGTAGAATCTATTCAGAGAAAGATGCTAAATTCACACTTGTTTT

GACTAAATGCGGCAGTCAGGTGTTGGCCAGCGTTTCTGTTTTATCTGTAAAAGGTAGCCTTGCGCCCA

TCAGTGGCACAGTAACTAGTGCTCAGATTGTCCTCAGATTTGATGAAAATGGAGTTCTACTAAGCAA

TTCTTCCCTTGACCCTCAATACTGGAACTACAGAAAAGGTGACCTTACAGAGGGCACTGCATATACC

AACGCAGTGGGATTTATGCCCAACCTCACAGCATACCCAAAAACACAGAGCCAAACTGCTAAAAGC

AACATTGTAAGTCAGGTTTACTTGAATGGGGACAAATCCAAACCCATGACCCTCACCATTACCCTCA

ATGGAACTAATGAAACAGGAGATGCCACAGTAAGCACTTACTCCATGTCATTCTCATGGAACTGGAA
```

-continued

```
TGGAAGTAATTACATTAATGAAACGTTCCAAACCAACTCCTTCACCTTCTCCTACATCGCCCAAGAAT

AAAAAGCATGACGCTGTTGATTTGATTCAATGTGTTTCTGTTTTATTTTCAAGCACAACAAAATCATT

CAAGTCATTCTTCCATCTTAGCTTAATAGACACAGTAGCTTAATAGACCCAGTAGTGCAAAGCCCCAT

TCTAGCTTATAGATCAGACAGTGATAATTAACCACCACCACCACCATACCTTTTGATTCAGGAAATCA

TGATCATCACAGGATCCTAGTCTTCAGGCCGCCCCCTCCCTCCCAAGACACAGAATACACAGTCCTCT

CCCCCCGACTGGCTTTAAATAACACCATCTGGTTGGTCACAGACATGTTCTTAGGGGTTATATTCCAC

ACGGTCTCCTGCCGCGCCAGGCGCTCGTCGGTGATGTTGATAAACTCTCCCGGCAGCTCGCTCAAGTT

CACGTCGCTGTCCAGCGGCTGAACCTCCGGCTGACGCGATAACTGTGCGACCGGCTGCTGGACGAAC

GGAGGCCGCGCCTACAAGGGGGTAGAGTCATAATCCTCGGTCAGGATAGGGCGGTGATGCAGCAGC

AGCGAGCGAAACATCTGCTGCCGCCGCCGCTCCGTCCGGCAGGAAAACAACACGCCGGTGGTCTCCT

CCGCGATAATCCGCACCGCCCGCAGCATCAGCTTCCTCGTTCTCCGCGCGCAGCACCTCACCCTTATC

TCGCTCAAATCGGCGCAGTAGGTACAGCACAGCACCACGATGTTATTCATGATCCCACAGTGCAGGG

CGCTGTATCCAAAGCTCATGCCGGGAACCACCGCCCCACGTGGCCATCGTACCACAAGCGCACGTA

AATCAAGTGTCGACCCCTCATGAACGCGCTGGACACAAACATTACTTCCTTGGGCATGTTGTAATTCA

CCACCTCCCGGTACCAGATAAACCTCTGGTTGAACAGGGCACCTTCCACCACCATCCTGAACCAAGA

GGCCAGAACCTGCCCACCGGCTATGCACTGCAGGGAACCCGGGTTGGAACAATGACAATGCAGACT

CCAAGGCTCGTAACCGTGGATCATCCGGCTGCTGAAGGCATCGATGTTGGCACAACACAGACACACG

TGCATGCACTTTCTCATGATTAGCAGCTCTTCCCTCGTCAGGATCATATCCCAAGGAATAACCCATTC

TTGAATCAACGTAAAACCCACACAGCAGGGAAGGCCTCGCACATAACTCACGTTGTGCATGGTCAGC

GTGTTGCATTCCGGAAACAGCGGATGATCCTCCAGTATCGAGGCGCGGGTCTCCTTCTCACAGGGAG

GTAAAGGGTCCCTGCTGTACGGACTGCGCCGGGACGACCGAGATCGTGTTGAGCGTAGTGTCATGGA

AAAGGGAACGCCGGACGTGGTCATACTTCTTGAAGCAGAACCAGGTTCGCGCGTGGCAGGCCTCCTT

GCGTCTGCGGTCTCGCCGTCTAGCTCGCTCCGTGTGATAGTTGTAGTACAGCCACTCCCGCAGAGCGT

CGAGGCGCACCCTGGCTTCCGGATCTATGTAGACTCCGTCTTGCACCGCGGCCCTGATAATATCCACC

ACCGTAGAATAAGCAACACCCAGCCAAGCAATACACTCGCTCTGCGAGCGGCAGACAGGAGGAGCG

GGCAGAGATGGGAGAACCATGATAAAAAACTTTTTTTAAAGAATATTTTCCAATTCTTCGAAAGTAA

GATCTATCAAGTGGCAGCGCTCCCCTCCACTGGCGCGGTCAAACTCTACGGCCAAAGCACAGACAAC

GGCATTTCTAAGATGTTCCTTAATGGCGTCCAAAAGACACACCGCTCTCAAGTTGCAGTAAACTATG

AATGAAAACCCATCCGGCTGATTTTCCAATATAGACGCGCCGGCAGCGTCCACCAAACCCAGATAAT

TTTCTTCTCTCCAGCGGTTTACGATCTGTCTAAGCAAATCCCTTATATCAAGTCCGACCATGCCAAAA

ATCTGCTCAAGAGCGCCCTCCACCTTCATGTACAAGCAGCGCATCATGATTGCAAAAATTCAGGTTCT

TCAGAGACCTGTATAAGATTCAAAATGGGAACATTAACAAAAATTCCTCTGTCGCGCAGATCCCTTC

GCAGGGCAAGCTGAACATAATCAGACAGGTCCGAACGGACCAGTGAGGCCAAATCCCCACCAGGAA

CCAGATCCAGAGACCCTATACTGATTATGACGCGCATACTCGGGGCTATGCTGACCAGCGTAGCGCC

GATGTAGGCGTGCTGCATGGGCGGCGAGATAAAATGCAAAGTGCTGGTTAAAAAATCAGGCAAAGC

CTCGCGCAAAAAAGCTAACACATCATAATCATGCTCATGCAGGTAGTTGCAGGTAAGCTCAGGAACC

AAAACGGAATAACACACGATTTTCCTCTCAAACATGACTTCGCGGATACTGCGTAAAACAAAAAATT

ATAAATAAAAAATTAATTAAATAACTTAAACATTGGAAGCCTGTCTCACAACAGGAAAAACCACTTT

AATCAACATAAGACGGGCCACGGGCATGCCGGCATAGCCGTAAAAAATTGGTCCCCGTGATTAAC

AAGTACCACAGACAGCTCCCCGGTCATGTCGGGGTCATCATGTGAGACTCTGTATACACGTCTGGA

TTGTGAACATCAGACAAACAAAGAAATCGAGCCACGTAGCCCGGAGGTATAATCACCCGCAGGCGG
```

-continued

```
AGGTACAGCAAAACGACCCCCATAGGAGGAATCACAAAATTAGTAGGAGAAAAAAATACATAAACA

CCAGAAAAACCCTGTTGCTGAGGCAAAATAGCGCCCTCCCGATCCAAAACAACATAAAGCGCTTCCA

CAGGAGCAGCCATAACAAAGACCCGAGTCTTACCAGTAAAAGAAAAAAGATCTCTCAACGCAGCAC

CAGCACCAACACTTCGCAGTGTAAAAGGCCAAGTGCCGAGAGAGTATATATAGGAATAAAAAGTGA

CGTAAACGGGCAAAGTCCAAAAAACGCCCAGAAAAACCGCACGCGAACCTACGCCCCGAAACGAAA

GCCAAAAAACACTAGACACTCCCTTCCGGCGTCAACTTCCGCTTTCCCACGCTACGTCACTTCCCCCG

GTCAAACAAACTACATATCCCGAACTTCCAAGTCGCCACGCCCAAAACACCGCCTACACCTCCCCGC

CCGCCGGCCCGCCCCCGGACCCGCCTCCCGCCCCGCGCCGCCCATCTCATTATCATATTGGCTTCAAT

CCAAAATAAGGTATATTATTGATGATG
```

Polynucleotide sequence encoding ChAd155/RSV    SEQ ID NO: 11

```
CATCATCAATAATATACCTTATTTTGGATTGAAGCCAATATGATAATGAGATGGGCGGCGCGGGGCG

GGGCGCGGGGCGGGAGGCGGGTTTGGGGGCGGGCCGGCGGGCGGGGCGGTGTGGCGGAAGTGGAC

TTTGTAAGTGTGGCGGATGTGACTTGCTAGTGCCGGGCGCGGTAAAAGTGACGTTTTCCGTGCGCGA

CAACGCCCCCGGGAAGTGACATTTTTCCCGCGGTTTTTACCGGATGTTGTAGTGAATTTGGGCGTAAC

CAAGTAAGATTTGGCCATTTTCGCGGGAAAACTGAAACGGGGAAGTGAAATCTGATTAATTTTGCGT

TAGTCATACCGCGTAATATTTGTCTAGGGCCGAGGGACTTTGGCCGATTACGTGGAGGACTCGCCCA

GGTGTTTTTTGAGGTGAATTTCCGCGTTCCGGGTCAAAGTCTGCGTTTTATTATTATAGGATATCCCAT

TGCATACGTTGTATCCATATCATAATATGTACATTTATATTGGCTCATGTCCAACATTACCGCCATGTT

GACATTGATTATTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAACGACCCCCGCCCAT

TGACGTCAATAATGACGTATGTTCCCATAGTAACGCCAATAGGGACTTTCCATTGACGTCAATGGGT

GGAGTATTTACGGTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCTTATGGGACTTTCC

TACTTGGCAGTACATCTACGTATTAGTCATCGCTATTACCATGGTGATGCGGTTTTGGCAGTACATCA

ATGGGCGTGGATAGCGGTTTGACTCACGGGGATTTCCAAGTCTCCACCCCATTGACGTCAATGGGAG

TTTGTTTTGGCACCAAAATCAACGGGACTTTCCAAAATGTCGTAACAACTCCGCCCCATTGACGCAAA

TGGGCGGTAGGCGTGTACGGTGGGAGGTCTATATAAGCAGAGCTCTCCCTATCAGTGATAGAGATCT

CCCTATCAGTGATAGAGATCGTCGACGAGCTCGTTTAGTGAACCGTCAGATCGCCTGGAGACGCCAT

CCACGCTGTTTTGACCTCCATAGAAGACACCGGGACCGATCCAGCCTCCGCGGCCGGGAACGGTGCA

TTGGAACGCGGATTCCCCGTGCCAAGAGTGAGATCTTCCGTTTATCTAGGTACCAGATATCGCCACCA

TGGAACTGCTGATCCTGAAGGCCAACGCCATCACCACCATCCTGACCGCCGTGACCTTCTGCTTCGCC

AGCGGCCAGAACATCACCGAGGAATTCTACCAGAGCACCTGTAGCGCCGTGAGCAAGGGCTACCTG

AGCGCCCTGAGAACCGGCTGGTACACCAGCGTGATCACCATCGAGCTGAGCAACATCAAAGAAAAC

AAGTGCAACGGCACCGACGCCAAAGTGAAGCTGATCAAGCAGGAACTGGACAAGTACAAGAACGCC

GTGACCGAGCTGCAGCTGCTGATGCAGAGCACCCCCGCCACCAACAACCGGGCCAGACGGGAGCTG

CCCCGGTTCATGAACTACACCCTGAACAACGCCAAAAAGACCAACGTGACCCTGAGCAAGAAGCGG

AAGCGGCGGTTCCTGGGCTTTCTGCTGGGCGTGGGCAGCGCCATTGCCAGCGGCGTGGCCGTGTCTA

AGGTGCTGCACCTGGAAGGCGAAGTGAACAAGATCAAGAGCGCCCTGCTGAGCACCAACAAGGCCG

TGGTGTCCCTGAGCAACGGCGTGAGCGTGCTGACCAGCAAGGTGCTGGATCTGAAGAACTACATCGA

CAAGCAGCTGCTGCCCATCGTGAACAAGCAGAGCTGCAGCATCAGCAACATCGAGACAGTGATCGA
```

-continued

```
GTTCCAGCAGAAGAACAACCGGCTGCTGGAAATCACCCGGGAGTTCAGCGTGAACGCCGGCGTGAC

CACCCCTGTGTCCACCTACATGCTGACCAACAGCGAGCTGCTGAGCCTGATCAACGACATGCCCATC

ACCAACGACCAGAAAAAGCTGATGAGCAACAACGTGCAGATCGTGCGGCAGCAGAGCTACTCCATC

ATGTCCATCATCAAAGAAGAGGTGCTGGCCTACGTGGTCAGCTGCCCCTGTACGGCGTGATCGACA

CCCCCTGCTGGAAGCTGCACACCAGCCCCCTGTGCACCACCAACACCAAAGAGGGCAGCAACATCTG

CCTGACCCGGACCGACAGAGGCTGGTACTGCGACAACGCCGGCAGCGTGTCATTCTTTCCACAGGCC

GAGACATGCAAGGTGCAGAGCAACCGGGTGTTCTGCGACACCATGAACAGCCTGACCCTGCCCTCCG

AAGTGAACCTGTGCAACGTGGACATCTTCAACCCCAAGTACGACTGCAAGATCATGACCTCCAAGAC

CGACGTGTCCAGCTCCGTGATCACCTCCCTGGGCGCCATCGTGTCCTGCTACGGCAAGACCAAGTGC

ACCGCCAGCAACAAGAACCGGGGCATCATCAAGACCTTCAGCAACGGCTGCGACTACGTGTCCAAC

AAGGGGGTGGACACCGTGTCCGTGGGCAACACCCTGTACTACGTGAACAAACAGGAAGGCAAGAGC

CTGTACGTGAAGGGCGAGCCCATCATCAACTTCTACGACCCCCTGGTGTTCCCCAGCGACGAGTTCG

ACGCCAGCATCAGCCAGGTGAACGAGAAGATCAACCAGAGCCTGGCCTTCATCCGGAAGTCCGACG

AGCTGCTGCACAATGTGAATGCCGGCAAGTCCACCACCAACCGGAAGCGGAGAGCCCCTGTGAAGC

AGACCCTGAACTTCGACCTGCTGAAGCTGGCCGGCGACGTGGAGAGCAATCCCGGCCCTATGGCCCT

GAGCAAAGTGAAACTGAACGATACACTGAACAAGGACCAGCTGCTGTCCAGCAGCAAGTACACCAT

CCAGCGGAGCACCGGCGACAGCATCGATACCCCCAACTACGACGTGCAGAAGCACATCAACAAGCT

GTGCGGCATGCTGCTGATCACAGAGGACGCCAACCACAAGTTCACCGGCCTGATCGGCATGCTGTAC

GCCATGAGCCGGCTGGGCCGGGAGGACACCATCAAGATCCTGCGGGACGCCGGCTACCACGTGAAG

GCCAATGGCGTGGACGTGACCACACACCGGCAGGACATCAACGGCAAAGAAATGAAGTTCGAGGTG

CTGACCCTGGCCAGCCTGACCACCGAGATCCAGATCAATATCGAGATCGAGAGCCGGAAGTCCTACA

AGAAAATGCTGAAAGAAATGGGCGAGGTGGCCCCCGAGTACAGACACGACAGCCCCGACTGCGGCA

TGATCATCCTGTGTATCGCCGCCCTGGTGATCACAAAGCTGGCCGCTGGCGACAGATCTGGCCTGAC

AGCCGTGATCAGACGGGCCAACAATGTGCTGAAGAACGAGATGAAGCGGTACAAGGGCCTGCTGCC

CAAGGACATTGCCAACAGCTTCTACGAGGTGTTCGAGAAGTACCCCCACTTCATCGACGTGTTCGTG

CACTTCGGCATTGCCCAGAGCAGCACCAGAGGCGGCTCCAGAGTGGAGGGCATCTTCGCCGGCCTGT

TCATGAACGCCTACGGCGCTGGCCAGGTGATGCTGAGATGGGGCGTGCTGGCCAAGAGCGTGAAGA

ACATCATGCTGGGCCACGCCAGCGTGCAGGCCGAGATGGAACAGGTGGTGGAGGTGTACGAGTACG

CCCAGAAGCTGGGCGGAGAGGCCGGCTTCTACCACATCCTGAACAACCCTAAGGCCTCCCTGCTGTC

CCTGACCCAGTTCCCCCACTTCTCCAGCGTGGTGCTGGGAAATGCCGCCGGACTGGGCATCATGGGC

GAGTACCGGGGCACCCCCAGAAACCAGGACCTGTACGACGCCGCCAAGGCCTACGCCGAGCAGCTG

AAAGAAAACGGCGTGATCAACTACAGCGTGCTGGACCTGACCGCTGAGGAACTGGAAGCCATCAAG

CACCAGCTGAACCCCAAGGACAACGACGTGGAGCTGGGAGGCGGAGGATCTGGCGGCGGAGGCATG

AGCAGACGGAACCCCTGCAAGTTCGAGATCCGGGCCACTGCCTGAACGGCAAGCGGTGCCACTTCA

GCCACAACTACTTCGAGTGGCCCCCTCATGCTCTGCTGGTGCGGCAGAACTTCATGCTGAACCGGATC

CTGAAGTCCATGGACAAGAGCATCGACACCCTGAGCGAGATCAGCGGAGCCGCCGAGCTGGACAGA

ACCGAGGAATATGCCCTGGGCGTGGTGGGAGTGCTGGAAAGCTACATCGGCTCCATCAACAACATCA

CAAAGCAGAGCGCCTGCGTGGCCATGAGCAAGCTGCTGACAGAGCTGAACAGCGACGACATCAAGA

AGCTGAGGGACAACGAGGAACTGAACAGCCCCAAGATCCGGGTGTACAACACCGTGATCAGCTACA

TTGAGAGCAACCGCAAGAACAACAAGCAGACCATCCATCTGCTGAAGCGGCTGCCCGCCGACGTGCT

GAAAAAGACCATCAAGAACACCCTGGACATCCACAAGTCCATCACCATCAACAATCCCAAAGAAAG
```

-continued

```
CACCGTGTCTGACACCAACGATCACGCCAAGAACAACGACACCACCTGATGAGCGGCCGCGATCTGC

TGTGCCTTCTAGTTGCCAGCCATCTGTTGTTTGCCCCTCCCCCGTGCCTTCCTTGACCCTGGAAGGTGC

CACTCCCACTGTCCTTTCCTAATAAAATGAGGAAATTGCATCGCATTGTCTGAGTAGGTGTCATTCTA

TTCTGGGGGTGGGGTGGGGCAGGACAGCAAGGGGGAGGATTGGGAAGACAATAGCAGGCATGCTG

GGGATGCGGTGGGCTCTATGGCCGATCAGCGATCGCTGAGGTGGGTGAGTGGGCGTGGCCTGGGGTG

GTCATGAAAATATATAAGTTGGGGGTCTTAGGGTCTCTTTATTTGTGTTGCAGAGACCGCCGGAGCCA

TGAGCGGGAGCAGCAGCAGCAGCAGTAGCAGCAGCGCCTTGGATGGCAGCATCGTGAGCCCTTATTT

GACGACGCGGATGCCCCACTGGGCCGGGGTGCGTCAGAATGTGATGGGCTCCAGCATCGACGGCCG

ACCCGTCCTGCCCGCAAATTCCGCCACGCTGACCTATGCGACCGTCGCGGGGACGCCGTTGGACGCC

ACCGCCGCCGCCGCCGCCACCGCAGCCGCCTCGGCCGTGCGCAGCCTGGCCACGGACTTTGCATTCC

TGGGACCACTGGCGACAGGGGCTACTTCTCGGGCCGCTGCTGCCGCCGTTCGCGATGACAAGCTGAC

CGCCCTGCTGGCGCAGTTGGATGCGCTTACTCGGGAACTGGGTGACCTTTCTCAGCAGGTCATGGCCC

TGCGCCAGCAGGTCTCCTCCCTGCAAGCTGGCGGGAATGCTTCTCCCACAAATGCCGTTTAAGATAA

ATAAAACCAGACTCTGTTTGGATTAAAGAAAAGTAGCAAGTGCATTGCTCTCTTTATTTCATAATTTT

CCGCGCGCGATAGGCCCTAGACCAGCGTTCTCGGTCGTTGAGGGTGCGGTGTATCTTCTCCAGGACG

TGGTAGAGGTGGCTCTGGACGTTGAGATACATGGGCATGAGCCCGTCCCGGGGGTGGAGGTAGCACC

ACTGCAGAGCTTCATGCTCCGGGGTGGTGTTGTAGATGATCCAGTCGTAGCAGGAGCGCTGGGCATG

GTGCCTAAAAATGTCCTTCAGCAGCAGGCCGATGGCCAGGGGAGGCCCTTGGTGTAAGTGTTTACA

AAACGGTTAAGTTGGGAAGGGTGCATTCGGGGAGAGATGATGTGCATCTTGGACTGTATTTTTAGAT

TGGCGATGTTTCCGCCCAGATCCCTTCTGGGATTCATGTTGTGCAGGACCACCAGTACAGTGTATCCG

GTGCACTTGGGGAATTTGTCATGCAGCTTAGAGGGAAAAGCGTGGAAGAACTTGGAGACGCCTTTGT

GGCCTCCCAGATTTTCCATGCATTCGTCCATGATGATGGCAATGGGCCCGCGGGAGGCAGCTTGGGC

AAAGATATTTCTGGGGTCGCTGACGTCGTAGTTGTGTTCCAGGGTGAGGTCGTCATAGGCCATTTTTA

CAAAGCGCGGGCGGAGGGTGCCCGACTGGGGGATGATGGTCCCCTCTGGCCCTGGGGCGTAGTTGCC

CTCGCAGATCTGCATTTCCCAGGCCTTAATCTCGGAGGGGGGAATCATATCCACCTGCGGGGCGATG

AAGAAAACGGTTTCCGGAGCCGGGGAGATTAACTGGGATGAGAGCAGGTTTCTAAGCAGCTGTGATT

TTCCACAACCGGTGGGCCCATAAATAACACCTATAACCGGTTGCAGCTGGTAGTTTAGAGAGCTGCA

GCTGCCGTCGTCCCGGAGGAGGGGGCCACCTCGTTGAGCATGTCCCTGACGCGCATGTTCTCCCCG

ACCAGATCCGCCAGAAGGCGCTCGCCGCCCAGGGACAGCAGCTCTTGCAAGGAAGCAAAGTTTTTCA

GCGGCTTGAGGCCGTCCGCCGTGGGCATGTTTTTCAGGGTCTGGCTCAGCAGCTCCAGGCGGTCCCA

GAGCTCGGTGACGTGCTCTACGGCATCTCTATCCAGCATATCTCCTCGTTTCGCGGGTTGGGCGACT

TTCGCTGTAGGGCACCAAGCGGTGGTCGTCCAGCGGGGCCAGAGTCATGTCCTTCCATGGGCGCAGG

GTCCTCGTCAGGGTGGTCTGGGTCACGGTGAAGGGGTGCGCTCCGGGCTGAGCGCTTGCCAAGGTGC

GCTTGAGGCTGGTTCTGCTGGTGCTGAAGCGCTGCCGGTCTTCGCCCTGCGCGTCGGCCAGGTAGCAT

TTGACCATGGTGTCATAGTCCAGCCCCTCCGCGGCGTGTCCCTTGGCGCGCAGCTTGCCCTTGGAGGT

GGCGCCGCACGAGGGGCAGAGCAGGCTCTTGAGCGCGTAGAGCTTGGGGGCGAGGAAGACCGATTC

GGGGGAGTAGGCGTCCGCGCCGCAGACCCCGCACACGGTCTCGCACTCCACCAGCCAGGTGAGCTCG

GGGCGCGCCGGGTCAAAAACCAGGTTTCCCCCATGCTTTTTGATGCGTTTCTTACCTCGGGTCTCCAT

GAGGTGGTGTCCCCGCTCGGTGACGAAGAGGCTGTCCGTGTCTCCGTAGACCGACTTGAGGGGTCTT

TTCTCCAGGGGGGTCCCTCGGTCTTCCTCGTAGAGGAACTCGGACCACTCTGAGACGAAGGCCCGCG
```

-continued

```
TCCAGGCCAGGACGAAGGAGGCTATGTGGGAGGGGTAGCGGTCGTTGTCCACTAGGGGGTCCACCTT

CTCCAAGGTGTGAAGACACATGTCGCCTTCCTCGGCGTCCAGGAAGGTGATTGGCTTGTAGGTGTAG

GCCACGTGACCGGGGGTTCCTGACGGGGGGGTATAAAAGGGGGTGGGGGCGCGCTCGTCGTCACTCT

CTTCCGCATCGCTGTCTGCGAGGGCCAGCTGCTGGGGTGAGTATTCCCTCTCGAAGGCGGGCATGAC

CTCCGCGCTGAGGTTGTCAGTTTCCAAAAACGAGGAGGATTTGATGTTCACCTGTCCCGAGGTGATA

CCTTTGAGGGTACCCGCGTCCATCTGGTCAGAAAACACGATCTTTTTATTGTCCAGCTTGGTGGCGAA

CGACCCGTAGAGGGCGTTGGAGAGCAGCTTGGCGATGGAGCGCAGGGTCTGGTTCTTGTCCCTGTCG

GCGCGCTCCTTGGCCGCGATGTTGAGCTGCACGTACTCGCGCGCGACGCAGCGCCACTCGGGGAAGA

CGGTGGTGCGCTCGTCGGGCACCAGGCGCACGCGCCAGCCGCGGTTGTGCAGGGTGACCAGGTCCAC

GCTGGTGGCGACCTCGCCGCGCAGGCGCTCGTTGGTCCAGCAGAGACGGCCGCCCTTGCGCGAGCAG

AAGGGGGGCAGGGGGTCGAGCTGGGTCTCGTCCGGGGGGTCCGCGTCCACGGTGAAAACCCCGGGG

CGCAGGCGCGCGTCGAAGTAGTCTATCTTGCAACCTTGCATGTCCAGCGCCTGCTGCCAGTCGCGGG

CGGCGAGCGCGCGCTCGTAGGGGTTGAGCGGCGGGCCCCAGGGCATGGGGTGGGTGAGTGCGGAGG

CGTACATGCCGCAGATGTCATAGACGTAGAGGGGCTCCCGCAGGACCCCGATGTAGGTGGGGTAGC

AGCGGCCGCCGCGGATGCTGGCGCGCACGTAGTCATACAGCTCGTGCGAGGGGGCGAGGAGGTCGG

GGCCCAGGTTGGTGCGGGCGGGGCGCTCCGCGCGGAAGACGATCTGCCTGAAGATGGCATGCGAGT

TGGAAGAGATGGTGGGGCGCTGGAAGACGTTGAAGCTGGCGTCCTGCAGGCCGACGGCGTCGCGCA

CGAAGGAGGCGTAGGAGTCGCGCAGCTTGTGTACCAGCTCGGCGGTGACCTGCACGTCGAGCGCGC

AGTAGTCGAGGGTCTCGCGGATGATGTCATATTTAGCCTGCCCCTTCTTTTTCCACAGCTCGCGGTTG

AGGACAAACTCTTCGCGGTCTTTCCAGTACTCTTGGATCGGGAAACCGTCCGGTTCCGAACGGTAAG

AGCCTAGCATGTAGAACTGGTTGACGGCCTGGTAGGCGCAGCAGCCCTTCTCCACGGGGAGGGCGTA

GGCCTGCGCGGCCTTGCGGAGCGAGGTGTGGGTCAGGGCGAAGGTGTCCCTGACCATGACTTTGAGG

TACTGGTGCTTGAAGTCGGAGTCGTCGCAGCCGCCCCGCTCCCAGAGCGAGAAGTCGGTGCGCTTCT

TGGAGCGGGGGTTGGGCAGAGCGAAGGTGACATCGTTGAAGAGGATTTTGCCCGCGCGGGGCATGA

AGTTGCGGGTGATGCGGAAGGGCCCCGGCACTTCAGAGCGGTTGTTGATGACCTGGGCGGCGAGCAC

GATCTCGTCGAAGCCGTTGATGTTGTGGCCCACGATGTAGAGTTCCAGGAAGCGGGGCCGGCCCTTT

ACGGTGGGCAGCTTCTTTAGCTCTTCGTAGGTGAGCTCCTCGGGCGAGGCGAGGCCGTGCTCGGCCA

GGGCCCAGTCCGCGAGGTGCGGGTTGTCTCTGAGGAAGGACTTCCAGAGGTCGCGGGCCAGGAGGG

TCTGCAGGCGGTCTCTGAAGGTCCTGAACTGGCGGCCCACGGCCATTTTTTCGGGGGTGATGCAGTA

GAAGGTGAGGGGGTCTTGCTGCCAGCGGTCCCAGTCGAGCTGCAGGGCGAGGTCGCGCGCGGCGGT

GACCAGGCGCTCGTCGCCCCCGAATTTCATGACCAGCATGAAGGGCACGAGCTGCTTTCCGAAGGCC

CCCATCCAAGTGTAGGTCTCTACATCGTAGGTGACAAAGAGGCGCTCCGTGCGAGGATGCGAGCCGA

TCGGGAAGAACTGGATCTCCCGCCACCAGTTGGAGGAGTGGCTGTTGATGTGGTGGAAGTAGAAGTC

CCGTCGCCGGGCCGAACACTCGTGCTGGCTTTTGTAAAAGCGAGCGCAGTACTGGCAGCGCTGCACG

GGCTGTACCTCATGCACGAGATGCACCTTTCGCCCGCGCACGAGGAAGCCGAGGGGAAATCTGAGCC

CCCCGCCTGGCTCGCGGCATGGCTGGTTCTCTTCTACTTTGGATGCGTGTCCGTCTCCGTCTGGCTCCT

CGAGGGGTGTTACGGTGGAGCGGACCACCACGCCGCGCGAGCCGCAGGTCCAGATATCGGCGCGCG

GCGGTCGGAGTTTGATGACGACATCGCGCAGCTGGGAGCTGTCCATGGTCTGGAGCTCCCGCGGCGG

CGGCAGGTCAGCCGGGAGTTCTTGCAGGTTCACCTCGCAGAGTCGGGCCAGGGCGCGGGGCAGGTCT

AGGTGGTACCTGATCTCTAGGGGCGTGTTGGTGGCGGCGTCGATGGCTTGCAGGAGCCCGCAGCCCC

GGGGGGCGACGACGGTGCCCCGCGGGGTGGTGGTGGTGGTGGCGGTGCAGCTCAGAAGCGGTGCCG
```

-continued

```
CGGGCGGGCCCCCGGAGGTAGGGGGGGCTCCGGTCCCGCGGGCAGGGGCGGCAGCGGCACGTCGGC

GTGGAGCGCGGGCAGGAGTTGGTGCTGTGCCCGGAGGTTGCTGGCGAAGGCGACGACGCGGCGGTT

GATCTCCTGGATCTGGCGCCTCTGCGTGAAGACGACGGGCCCGGTGAGCTTGAACCTGAAAGAGAGT

TCGACAGAATCAATCTCGGTGTCATTGACCGCGGCCTGGCGCAGGATCTCCTGCACGTCTCCCGAGTT

GTCTTGGTAGGCGATCTCGGCCATGAACTGCTCGATCTCTTCCTCCTGGAGGTCTCCGCGTCCGGCGC

GTTCCACGGTGGCCGCCAGGTCGTTGGAGATGCGCCCCATGAGCTGCGAGAAGGCGTTGAGTCCGCC

CTCGTTCCAGACTCGGCTGTAGACCACGCCCCCCTGGTCATCGCGGGCGCGCATGACCACCTGCGCG

AGGTTGAGCTCCACGTGCCGCGCGAAGACGGCGTAGTTGCGCAGACGCTGGAAGAGGTAGTTGAGG

GTGGTGGCGGTGTGCTCGGCCACGAAGAAGTTCATGACCCAGCGGCGCAACGTGGATTCGTTGATGT

CCCCCAAGGCCTCCAGCCGTTCCATGGCCTCGTAGAAGTCCACGGCGAAGTTGAAAAACTGGGAGTT

GCGCGCCGACACGGTCAACTCCTCCTCCAGAAGACGGATGAGCTCGGCGACGGTGTCGCGCACCTCG

CGCTCGAAGGCTATGGGATCTCTTCCTCCGCTAGCATCACCACCTCCTCCTCTTCCTCCTCTTCTGGC

ACTTCCATGATGGCTTCCTCCTCTTCGGGGGGTGGCGGCGGCGGCGGTGGGGGAGGGGCGCTCTGC

GCCGGCGGCGGCGCACCGGGAGGCGGTCCACGAAGCGCGCGATCATCTCCCCGCGGCGGCGGCGCA

TGGTCTCGGTGACGGCGCGGCCGTTCTCCCGGGGGCGCAGTTGGAAGACGCCGCCGGACATCTGGTG

CTGGGGCGGGTGGCCGTGAGGCAGCGAGACGCGCTGACGATGCATCTCAACAATTGCTGCGTAGGT

ACGCCGCCGAGGGACCTGAGGGAGTCCATATCCACCGGATCCGAAAACCTTTCGAGGAAGGCGTCTA

ACCAGTCGCAGTCGCAAGGTAGGCTGAGCACCGTGGCGGGCGGCGGGGGGTGGGGGAGTGTCTGG

CGGAGGTGCTGCTGATGATGTAATTGAAGTAGGCGGACTTGACACGGCGGATGGTCGACAGGAGCA

CCATGTCCTTGGGTCCGGCCTGCTGGATGCGGAGGCGGTCGGCTATGCCCCAGGCTTCGTTCTGGCAT

CGGCGCAGGTCCTTGTAGTAGTCTTGCATGAGCCTTTCCACCGGCACCTCTTCTCCTTCCTCTTCTGCT

TCTTCCATGTCTGCTTCGGCCCTGGGGCGGCGCCGCGCCCCCTGCCCCCCATGCGCGTGACCCCGAA

CCCCCTGAGCGGTTGGAGCAGGGCCAGGTCGGCGACGACGCGCTCGGCCAGGATGGCCTGCTGCACC

TGCGTGAGGGTGGTTTGGAAGTCATCCAAGTCCACGAAGCGGTGGTAGGCGCCCGTGTTGATGGTGT

AGGTGCAGTTGGCCATGACGGACCAGTTGACGGTCTGGTGGCCCGGTTGCGACATCTCGGTGTACCT

GAGTCGCGAGTAGGCGCGGGAGTCGAAGACGTAGTCGTTGCAAGTCCGCACCAGGTACTGGTAGCC

CACCAGGAAGTGCGGCGGCGGCTGGCGGTAGAGGGGCCAGCGCAGGGTGGCGGGGGCTCCGGGGGC

CAGGTCTTCCAGCATGAGGCGGTGGTAGGCGTAGATGTACCTGGACATCCAGGTGATACCCGCGGCG

GTGGTGGAGGCGCGCGGGAAGTCGCGCACCCGGTTCCAGATGTTGCGCAGGGGCAGAAAGTGCTCC

ATGGTAGGCGTGCTCTGTCCAGTCAGACGCGCGCAGTCGTTGATACTCTAGACCAGGGAAAACGAAA

GCCGGTCAGCGGGCACTCTTCCGTGGTCTGGTGAATAGATCGCAAGGGTATCATGGCGGAGGGCCTC

GGTTCGAGCCCCGGGTCCGGGCCGGACGGTCCGCCATGATCCACGCGGTTACCGCCCGCGTGTCGAA

CCCAGGTGTGCGACGTCAGACAACGGTGGAGTGTTCCTTTTGGCGTTTTTCTGGCCGGGCGCCGGCGC

CGCGTAAGAGACTAAGCCGCGAAAGCGAAAGCAGTAAGTGGCTCGCTCCCCGTAGCCGGAGGGATC

CTTGCTAAGGGTTGCGTTGCGGCGAACCCCGGTTCGAATCCCGTACTCGGGCCGGCCGGACCCGCGG

CTAAGGTGTTGGATTGGCCTCCCCCTCGTATAAAGACCCCGCTTGCGGATTGACTCCGGACACGGGG

ACGAGCCCCTTTTATTTTTGCTTTCCCCAGATGCATCCGGTGCTGCGGCAGATGCGCCCCCCGCCCCA

GCAGCAGCAACAACACCAGCAAGAGCGGCAGCAACAGCAGCGGGAGTCATGCAGGGCCCCCTCACC

CACCCTCGGCGGGCCGGCCACCTCGGCGTCCGCGGCCGTGTCTGGCGCCTGCGGCGGCGGCGGGGGG

CCGGCTGACGACCCCGAGGAGCCCCCGCGGCGCAGGGCCAGACACTACCTGGACCTGGAGGAGGGC
```

-continued

```
GAGGGCCTGGCGCGGCTGGGGGCGCCGTCTCCCGAGCGCCACCCGCGGGTGCAGCTGAAGCGCGAC

TCGCGCGAGGCGTACGTGCCTCGGCAGAACCTGTTCAGGGACCGCGCGGGCGAGGAGCCCGAGGAG

ATGCGGGACAGGAGGTTCAGCGCAGGGCGGGAGCTGCGGCAGGGGCTGAACCGCGAGCGGCTGCTG

CGCGAGGAGGACTTTGAGCCCGACGCGCGGACGGGGATCAGCCCCGCGCGCGCACGTGGCGGCC

GCCGACCTGGTGACGGCGTACGAGCAGACGGTGAACCAGGAGATCAACTTCCAAAAGAGTTTCAAC

AACCACGTGCGCACGCTGGTGGCGCGCGAGGAGGTGACCATCGGGCTGATGCACCTGTGGGACTTTG

TAAGCGCGCTGGTGCAGAACCCCAACAGCAAGCCTCTGACGGCGCAGCTGTTCCTGATAGTGCAGCA

CAGCAGGGACAACGAGGCGTTTAGGGACGCGCTGCTGAACATCACCGAGCCCGAGGGTCGGTGGCT

GCTGGACCTGATTAACATCCTGCAGAGCATAGTGGTGCAGGAGCGCAGCCTGAGCCTGGCCGACAAG

GTGGCGGCCATCAACTACTCGATGCTGAGCCTGGGCAAGTTTTACGCGCGCAAGATCTACCAGACGC

CGTACGTGCCCATAGACAAGGAGGTGAAGATCGACGGTTTTTACATGCGCATGGCGCTGAAGGTGCT

CACCCTGAGCGACGACCTGGGCGTGTACCGCAACGAGCGCATCCACAAGGCCGTGAGCGTGAGCCG

GCGGCGCGAGCTGAGCGACCGCGAGCTGATGCACAGCCTGCAGCGGGCGCTGGCGGGCGCCGGCAG

CGGCGACAGGGAGGCGGAGTCCTACTTCGATGCGGGGGCGGACCTGCGCTGGGCGCCCAGCCGGCG

GGCCCTGGAGGCCGCGGGGGTCCGCGAGGACTATGACGAGGACGGCGAGGAGGATGAGGAGTACG

AGCTAGAGGAGGGCGAGTACCTGGACTAAACCGCGGGTGGTGTTTCCGGTAGATGCAAGACCCGAA

CGTGGTGGACCCGGCGCTGCGGGCGGCTCTGCAGAGCCAGCCGTCCGGCCTTAACTCCTCAGACGAC

TGGCGACAGGTCATGGACCGCATCATGTCGCTGACGGCGCGTAACCCGGACGCGTTCCGGCAGCAGC

CGCAGGCCAACAGGCTCTCCGCCATCCTGGAGGCGGTGGTGCCTGCGCGCTCGAACCCCACGCACGA

GAAGGTGCTGGCCATAGTGAACGCGCTGGCCGAGAACAGGGCCATCCGCCCGGACGAGGCCGGGCT

GGTGTACGACGCGCTGCTGCAGCGCGTGGCCCGCTACAACAGCGGCAACGTGCAGACCAACCTGGA

CCGGCTGGTGGGGGACGTGCGCGAGGCGGTGGCGCAGCGCGAGCGCGCGGATCGGCAGGGCAACCT

GGGCTCCATGGTGGCGCTGAATGCCTTCCTGAGCACGCAGCCGGCCAACGTGCCGCGGGGGCAGGA

AGACTACACCAACTTTGTGAGCGCGCTGCGGCTGATGGTGACCGAGACCCCCCAGAGCGAGGTGTAC

CAGTCGGGCCCGGACTACTTCTTCCAGACCAGCAGACAGGGCCTGCAGACGGTGAACCTGAGCCAGG

CTTTCAAGAACCTGCGGGGGCTGTGGGCGTGAAGGCGCCCACCGGCGACCGGGCGACGGTGTCCA

GCCTGCTGACGCCCAACTCGCGCCTGCTGCTGCTGCTGATCGCGCCGTTCACGGACAGCGGCAGCGT

GTCCCGGGACACCTACCTGGGGCACCTGCTGACCCTGTACCGCGAGGCCATCGGGCAGGCGCAGGTG

GACGAGCACACCTTCCAGGAGATCACCAGCGTGAGCCGCGCGCTGGGGCAGGAGGACACGAGCAGC

CTGGAGGCGACTCTGAACTACCTGCTGACCAACCGGCGGCAGAAGATTCCCTCGCTGCACAGCCTGA

CCTCCGAGGAGGAGCGCATCTTGCGCTACGTGCAGCAGAGCGTGAGCCTGAACCTGATGCGCGACGG

GGTGACGCCCAGCGTGGCGCTGGACATGACCGCGCGCAACATGGAACCGGGCATGTACGCCGCGCA

CCGGCCTTACATCAACCGCCTGATGGACTACCTGCATCGCGCGGCGGCCGTGAACCCCGAGTACTTT

ACCAACGCCATCCTGAACCCGCACTGGCTCCCGCCGCCCGGGTTCTACAGCGGGGGCTTCGAGGTCC

CGGAGACCAACGATGGCTTCCTGTGGGACGACATGGACGACAGCGTGTTCTCCCCGCGGCCGCAGGC

GCTGGCGGAAGCGTCCCTGCTGCGTCCCAAGAAGGAGGAGGAGGAGGAGGCGAGTCGCCGCCGCGG

CAGCAGCGGCGTGGCTTCTCTGTCCGAGCTGGGGCGGCAGCCGCCGCGCGCCCCGGGTCCCTGGGC

GGCAGCCCCTTTCCGAGCCTGGTGGGGTCTCTGCACAGCGAGCGCACCACCCGCCCTCGGCTGCTGG

GCGAGGACGAGTACCTGAATAACTCCCTGCTGCAGCCGGTGCGGGAGAAAAACCTGCCTCCCGCCTT

CCCCAACAACGGGATAGAGAGCCTGGTGGACAAGATGAGCAGATGGAAGACCTATGCGCAGGAGCA

CAGGGACGCGCCTGCGCTCCGGCCGCCCACGCGGCGCCAGCGCCACGACCGGCAGCGGGGGCTGGT
```

-continued

```
GTGGGATGACGAGGACTCCGCGGACGATAGCAGCGTGCTGGACCTGGGAGGGAGCGGCAACCCGTT

CGCGCACCTGCGCCCCGCCTGGGGAGGATGTTTTAAAAAAAAAAAAAAAAAGCAAGAAGCATGAT

GCAAAAATTAAATAAAACTCACCAAGGCCATGGCGACCGAGCGTTGGTTTCTTGTGTTCCCTTCAGT

ATGCGGCGCGCGGCGATGTACCAGGAGGGACCTCCTCCCTCTTACGAGAGCGTGGTGGGCGCGGCGG

CGGCGGCGCCCTCTTCTCCCTTTGCGTCGCAGCTGCTGGAGCCGCCGTACGTGCCTCCGCGCTACCTG

CGGCCTACGGGGGGGAGAAACAGCATCCGTTACTCGGAGCTGGCGCCCCTGTTCGACACCACCCGGG

TGTACCTGGTGGACAACAAGTCGGCGGACGTGGCCTCCCTGAACTACCAGAACGACCACAGCAATTT

TTTGACCACGGTCATCCAGAACAATGACTACAGCCCGAGCGAGGCCAGCACCCAGACCATCAATCTG

GATGACCGGTCGCACTGGGCGGCGACCTGAAAACCATCCTGCACACCAACATGCCCAACGTGAAC

GAGTTCATGTTCACCAATAAGTTCAAGGCGCGGGTGATGGTGTCGCGCTCGCACACCAAGGAAGACC

GGGTGGAGCTGAAGTACGAGTGGGTGGAGTTCGAGCTGCCAGAGGGCAACTACTCCGAGACCATGA

CCATTGACCTGATGAACAACGCGATCGTGGAGCACTATCTGAAAGTGGGCAGGCAGAACGGGGTCCT

GGAGAGCGACATCGGGGTCAAGTTCGACACCAGGAACTTCCGCCTGGGGCTGGACCCCGTGACCGG

GCTGGTTATGCCCGGGGTGTACACCAACGAGGCCTTCCATCCCGACATCATCCTGCTGCCCGGCTGCG

GGGTGGACTTCACTTACAGCCGCCTGAGCAACCTCCTGGGCATCCGCAAGCGGCAGCCCTTCCAGGA

GGGCTTCAGGATCACCTACGAGGACCTGGAGGGGGGCAACATCCCCGCGCTCCTCGATGTGGAGGCC

TACCAGGATAGCTTGAAGGAAAATGAGGCGGGACAGGAGGATACCGCCCCCGCCGCCTCCGCCGCC

GCCGAGCAGGGCGAGGATGCTGCTGACACCGCGGCCGCGGACGGGGCAGAGGCCGACCCCGCTATG

GTGGTGGAGGCTCCCGAGCAGGAGGAGGACATGAATGACAGTGCGGTGCGCGGAGACACCTTCGTC

ACCCGGGGGGAGGAAAAGCAAGCGGAGGCCGAGGCCGCGGCCGAGGAAAAGCAACTGGCGGCAGC

AGCGGCGGCGGCGGCGTTGGCCGCGGCGGAGGCTGAGTCTGAGGGGACCAAGCCCGCCAAGGAGCC

CGTGATTAAGCCCCTGACCGAAGATAGCAAGAAGCGCAGTTACAACCTGCTCAAGGACAGCACCAA

CACCGCGTACCGCAGCTGGTACCTGGCCTACAACTACGGCGACCCGTCGACGGGGTGCGCTCCTGG

ACCCTGCTGTGCACGCCGGACGTGACCTGCGGCTCGGAGCAGGTGTACTGGTCGCTGCCCGACATGA

TGCAAGACCCCGTGACCTTCCGCTCCACGCGGCAGGTCAGCAACTTCCCGGTGGTGGGCGCCGAGCT

GCTGCCCGTGCACTCCAAGAGCTTCTACAACGACCAGGCCGTCTACTCCCAGCTCATCCGCCAGTTCA

CCTCTCTGACCCACGTGTTCAATCGCTTTCCTGAGAACCAGATTCTGGCGCGCCCGCCCGCCCCCACC

ATCACCACCGTCAGTGAAAACGTTCCTGCTCTCACAGATCACGGGACGCTACCGCTGCGCAACAGCA

TCGGAGGAGTCCAGCGAGTGACCGTTACTGACGCCAGACGCCGCACCTGCCCCTACGTTTACAAGGC

CTTGGGCATAGTCTCGCCGCGCGTCCTTTCCAGCCGCACTTTTTGAGCAACACCACCATCATGTCCAT

CCTGATCTCACCCAGCAATAACTCCGGCTGGGGACTGCTGCGCGCGCCCAGCAAGATGTTCGGAGGG

GCGAGGAAGCGTTCCGAGCAGCACCCCGTGCGCGTGCGCGGGCACTTCCGCGCCCCTGGGGAGCGC

ACAAACGCGGCCGCGCGGGGCGCACCACCGTGGACGACGCCATCGACTCGGTGGTGGAGCAGGCGC

GCAACTACAGGCCCGCGGTCTCTACCGTGGACGCGGCCATCCAGACCGTGGTGCGGGGCGCGCGGCG

GTACGCCAAGCTGAAGAGCCGCCGGAAGCGCGTGGCCCGCCGCCACCGCCGCCGACCCGGGGCCGC

CGCCAAACGCGCCGCCGCGGCCCTGCTTCGCCGGGCCAAGCGCACGGGCCGCCGCGCCGCCATGAG

GGCCGCGCGCCGCTTGGCCGCCGGCATCACCGCCGCCACCATGGCCCCCCGTACCCGAAGACGCGCG

GCCGCCGCCGCCGCCGCCGCATCAGTGACATGGCCAGCAGGCGCCGGGGCAACGTGTACTGGGTGC

GCGACTCGGTGACCGGCACGCGCGTGCCCGTGCGCTTCCGCCCCCCGCGGACTTGAGATGATGTGAA

AAAACAACACTGAGTCTCCTGCTGTTGTGTGTATCCCAGCGGCGGCGGCGCGCGCAGCGTCATGTCC
```

-continued

```
AAGCGCAAAATCAAAGAAGAGATGCTCCAGGTCGTCGCGCCGGAGATCTATGGGCCCCCGAAGAAG
GAAGAGCAGGATTCGAAGCCCCGCAAGATAAAGCGGGTCAAAAAGAAAAAGAAAGATGATGACGA
TGCCGATGGGGAGGTGGAGTTCCTGCGCGCCACGGCGCCCAGGCGCCCGGTGCAGTGGAAGGGCCG
GCGCGTAAAGCGCGTCCTGCGCCCCGGCACCGCGGTGGTCTTCACGCCCGGCGAGCGCTCCACCCGG
ACTTTCAAGCGCGTCTATGACGAGGTGTACGGCGACGAAGACCTGCTGGAGCAGGCCAACGAGCGCT
TCGGAGAGTTTGCTTACGGGAAGCGTCAGCGGGCGCTGGGGAAGGAGGACCTGCTGGCGCTGCCGCT
GGACCAGGGCAACCCCACCCCCAGTCTGAAGCCCGTGACCCTGCAGCAGGTGCTGCCGAGCAGCGC
ACCCTCCGAGGCGAAGCGGGGTCTGAAGCGCGAGGGCGGCGACCTGGCGCCCACCGTGCAGCTCAT
GGTGCCCAAGCGGCAGAGGCTGGAGGATGTGCTGGAGAAAATGAAAGTAGACCCCGGTCTGCAGCC
GGACATCAGGGTCCGCCCCATCAAGCAGGTGGCGCCGGGCCTCGGCGTGCAGACCGTGGACGTGGTC
ATCCCCACCGGCAACTCCCCCGCCGCCGCCACCACTACCGCTGCCTCCACGGACATGGAGACACAGA
CCGATCCCGCCGCAGCCGCAGCCGCAGCCGCCGCCGCGACCTCCTCGGCGGAGGTGCAGACGGACCC
CTGGCTGCCGCCGGCGATGTCAGCTCCCCGCGCGCGTCGCGGGCGCAGGAAGTACGGCGCCGCCAAC
GCGCTCCTGCCCGAGTACGCCTTGCATCCTTCCATCGCGCCCACCCCCGGCTACCGAGGCTATACCTA
CCGCCCCGCGAAGAGCCAAGGGTTCCACCCGCCGTCCCCGCCGACGCGCCGCCGCCACCACCCGCCGC
CGCCGCCGCAGACGCCAGCCCGCACTGGCTCCAGTCTCCGTGAGGAAAGTGGCGCGCGACGGACAC
ACCCTGGTGCTGCCCAGGGCGCGCTACCACCCCAGCATCGTTTAAAAGCCTGTTGTGGTTCTTGCAGA
TATGGCCCTCACTTGCCGCCTCCGTTTCCCGGTGCCGGGATACCGAGGAGGAAGATCGCGCCGCAGG
AGGGGTCTGGCCGGCCGCGGCCTGAGCGGAGGCAGCCGCCGCGCGCACCGGCGGCGACGCGCCACC
AGCCGACGCATGCGCGGCGGGGTGCTGCCCCTGTTAATCCCCCTGATCGCCGCGGCGATCGGCGCCG
TGCCCGGGATCGCCTCCGTGGCCTTGCAAGCGTCCCAGAGGCATTGACAGACTTGCAAACTTGCAAA
TATGGAAAAAAAAACCCCAATAAAAAAGTCTAGACTCTCACGCTCGCTTGGTCCTGTGACTATTTTGT
AGAATGGAAGACATCAACTTTGCGTCGCTGGCCCCGCGTCACGGCTCGCGCCCGTTCCTGGGACACT
GGAACGATATCGGCACCAGCAACATGAGCGGTGGCGCCTTCAGTTGGGGCTCTCTGTGGAGCGGCAT
TAAAAGTATCGGGTCTGCCGTTAAAAATTACGGCTCCCGGGCCTGGAACAGCAGCACGGGCCAGATG
TTGAGAGACAAGTTGAAAGAGCAGAACTTCCAGCAGAAGGTGGTGGAGGGCCTGGCCTCCGGCATC
AACGGGGTGGTGGACCTGGCCAACCAGGCCGTGCAGAATAAGATCAACAGCAGACTGGACCCCCGG
CCGCCGGTGGAGGAGGTGCCGCCGGCGCTGGAGACGGTGTCCCCCGATGGGCGTGGCGAGAAGCGC
CCGCGGCCCGATAGGGAAGAGACCACTCTGGTCACGCAGACCGATGAGCCGCCCCCGTATGAGGAG
GCCCTGAAGCAAGGTCTGCCCACCACGCGGCCCATCGCGCCCATGGCCACCGGGGTGGTGGGCCGCC
ACACCCCCGCCACGCTGGACTTGCCTCCGCCCGCCGATGTGCCGCAGCAGCAGAAGGCGGCACAGCC
GGGCCCGCCCGCGACCGCCTCCCGTTCCTCCGCCGGTCCTCTGCGCCGCGCGGCCAGCGGCCCCCGC
GGGGGGGTCGCGAGGCACGGCAACTGGCAGAGCACGCTGAACAGCATCGTGGGTCTGGGGGTGCGG
TCCGTGAAGCGCCGCCGATGCTACTGAATAGCTTAGCTAACGTGTTGTATGTGTGTATGCGCCCTATG
TCGCCGCCAGAGGAGCTGCTGAGTCGCCGCCGTTCGCGCGCCCACCACCACCGCCACTCCGCCCCTC
AAGATGGCGACCCCATCGATGATGCCGCAGTGGTCGTACATGCACATCTCGGGCCAGGACGCCTCGG
AGTACCTGAGCCCCGGGCTGGTGCAGTTCGCCCGCGCCACCGAGAGCTACTTCAGCCTGAGTAACAA
GTTTAGGAACCCCACGGTGGCGCCCACGCACGATGTGACCACCGACCGGTCTCAGCGCCTGACGCTG
CGGTTCATTCCCGTGGACCGCGAGGACACCGCGTACTCGTACAAGGCGCGGTTCACCCTGGCCGTGG
GCGACAACCGCGTGCTGGACATGGCCTCCACCTACTTTGACATCCGCGGGGTGCTGGACCGGGGTCC
CACTTTCAAGCCCTACTCTGGCACCGCCTACAACTCCCTGGCCCCCAAGGGCGCTCCCAACTCCTGCG
```

```
AGTGGGAGCAAGAGGAAACTCAGGCAGTTGAAGAAGCAGCAGAAGAGGAAGAAGAAGATGCTGAC

GGTCAAGCTGAGGAAGAGCAAGCAGCTACCAAAAAGACTCATGTATATGCTCAGGCTCCCCTTCTG

GCGAAAAAATTAGTAAAGATGGTCTGCAAATAGGAACGGACGCTACAGCTACAGAACAAAAACCTA

TTTATGCAGACCCTACATTCCAGCCCGAACCCCAAATCGGGGAGTCCCAGTGGAATGAGGCAGATGC

TACAGTCGCCGGCGGTAGAGTGCTAAAGAAATCTACTCCCATGAAACCATGCTATGGTTCCTATGCA

AGACCCACAAATGCTAATGGAGGTCAGGGTGTACTAACGGCAAATGCCCAGGGACAGCTAGAATCT

CAGGTTGAAATGCAATTCTTTTCAACTTCTGAAAACGCCCGTAACGAGGCTAACAACATTCAGCCCA

AATTGGTGCTGTATAGTGAGGATGTGCACATGGAGACCCCGGATACGCACCTTTCTTACAAGCCCGC

AAAAAGCGATGACAATTCAAAAATCATGCTGGGTCAGCAGTCCATGCCCAACAGACCTAATTACATC

GGCTTCAGAGACAACTTTATCGGCCTCATGTATTACAATAGCACTGGCAACATGGGAGTGCTTGCAG

GTCAGGCCTCTCAGTTGAATGCAGTGGTGGACTTGCAAGACAGAAACACAGAACTGTCCTACCAGCT

CTTGCTTGATTCCATGGGTGACAGAACCAGATACTTTTCCATGTGGAATCAGGCAGTGGACAGTTATG

ACCCAGATGTTAGAATTATTGAAAATCATGGAACTGAAGACGAGCTCCCCAACTATTGTTTCCCTCTG

GGTGGCATAGGGGTAACTGACACTTACCAGGCTGTTAAAACCAACAATGGCAATAACGGGGGCCAG

GTGACTTGGACAAAAGATGAAACTTTTGCAGATCGCAATGAAATAGGGGTGGGAAACAATTTCGCTA

TGGAGATCAACCTCAGTGCCAACCTGTGGAGAAACTTCCTGTACTCCAACGTGGCGCTGTACCTACC

AGACAAGCTTAAGTACAACCCCTCCAATGTGGACATCTCTGACAACCCCAACACCTACGATTACATG

AACAAGCGAGTGGTGGCCCCGGGGCTGGTGGACTGCTACATCAACCTGGGCGCGCGCTGGTCGCTGG

ACTACATGGACAACGTCAACCCCTTCAACCACCACCGCAATGCGGGCCTGCGCTACCGCTCCATGCT

CCTGGGCAACGGGCGCTACGTGCCCTTCCACATCCAGGTGCCCCAGAAGTTCTTTGCCATCAAGAAC

CTCCTCCTCCTGCCGGGCTCCTACACCTACGAGTGGAACTTCAGGAAGGATGTCAACATGGTCCTCCA

GAGCTCTCTGGGTAACGATCTCAGGGTGGACGGGGCCAGCATCAAGTTCGAGAGCATCTGCCTCTAC

GCCACCTTCTTCCCCATGGCCCACAACACGGCCTCCACGCTCGAGGCCATGCTCAGGAACGACACCA

ACGACCAGTCCTTCAATGACTACCTCTCCGCCGCCAACATGCTCTACCCCATACCCGCCAACGCCACC

AACGTCCCCATCTCCATCCCCTCGCGCAACTGGGCGGCCTTCCGCGGCTGGGCCTTCACCCGCCTCAA

GACCAAGGAGACCCCCTCCCTGGGCTCGGGATTCGACCCCTACTACACCTACTCGGGCTCCATTCCCT

ACCTGGACGGCACCTTCTACCTCAACCACACTTTCAAGAAGGTCTCGGTCACCTTCGACTCCTCGGTC

AGCTGGCCGGGCAACGACCGTCTGCTCACCCCCAACGAGTTCGAGATCAAGCGCTCGGTCGACGGGG

AGGGCTACAACGTGGCCCAGTGCAACATGACCAAGGACTGGTTCCTGGTCCAGATGCTGGCCAACTA

CAACATCGGCTACCAGGGCTTCTACATCCCAGAGAGCTACAAGGACAGGATGTACTCCTTCTTCAGG

AACTTCCAGCCCATGAGCCGGCAGGTGGTGGACCAGACCAAGTACAAGGACTACCAGGAGGTGGGC

ATCATCCACCAGCACAACAACTCGGGCTTCGTGGGCTACCTCGCCCCCACCATGCGCGAGGGACAGG

CCTACCCCGCCAACTTCCCCTATCCGCTCATAGGCAAGACCGCGGTCGACAGCATCACCCAGAAAAA

GTTCCTCTGCGACCGCACCCTCTGGCGCATCCCCTTCTCCAGCAACTTCATGTCCATGGGTGCGCTCT

CGGACCTGGGCCAGAACTTGCTCTACGCCAACTCCGCCCACGCCCTCGACATGACCTTCGAGGTCGA

CCCCATGGACGAGCCCACCCTTCTCTATGTTCTGTTCGAAGTCTTTGACGTGGTCCGGGTCCACCAGC

CGCACCGCGGCGTCATCGAGACCGTGTACCTGCGTACGCCCTTCTCGGCCGGCAACGCCACCACCTA

AAGAAGCAAGCCGCAGTCATCGCCGCCTGCATGCCGTCGGGTTCCACCGAGCAAGAGCTCAGGGCC

ATCGTCAGAGACCTGGATGCGGGCCCTATTTTTTGGGCACCTTCGACAAGCGCTTCCCTGGCTTTGT

CTCCCCACACAAGCTGGCCTGCGCCATCGTCAACACGGCCGGCCGCGAGACCGGGGCGTGCACTGG
```

-continued

```
CTGGCCTTCGCCTGGAACCCGCGCTCCAAAACATGCTTCCTCTTTGACCCCTTCGGCTTTTCGGACCA

GCGGCTCAAGCAAATCTACGAGTTCGAGTACGAGGGCTTGCTGCGTCGCAGCGCCATCGCCTCCTCG

CCCGACCGCTGCGTCACCCTCGAAAAGTCCACCCAGACCGTGCAGGGGCCCGACTCGGCCGCCTGCG

GTCTCTTCTGCTGCATGTTTCTGCACGCCTTTGTGCACTGGCCTCAGAGTCCCATGGACCGCAACCCC

ACCATGAACTTGCTGACGGGGGTGCCCAACTCCATGCTCCAGAGCCCCCAGGTCGAGCCCACCCTGC

GCCGCAACCAGGAGCAGCTCTACAGCTTCCTGGAGCGCCACTCGCCTTACTTCCGCCGCCACAGCGC

ACAGATCAGGAGGGCCACCTCCTTCTGCCACTTGCAAGAGATGCAAGAAGGGTAATAACGATGTACA

CACTTTTTTCTCAATAAATGGCATCTTTTTATTTATACAAGCTCTCTGGGGTATTCATTTCCCACCAC

CACCCGCCGTTGTCGCCATCTGGCTCTATTTAGAAATCGAAAGGGTTCTGCCGGGAGTCGCCGTGCGC

CACGGGCAGGGACACGTTGCGATACTGGTAGCGGGTGCCCCACTTGAACTCGGGCACCACCAGGCG

AGGCAGCTCGGGGAAGTTTTCGCTCCACAGGCTGCGGGTCAGCACCAGCGCGTTCATCAGGTCGGGC

GCCGAGATCTTGAAGTCGCAGTTGGGGCCGCCGCCCTGCGCGCGCGAGTTGCGGTACACCGGGTTGC

AGCACTGGAACACCAACAGCGCCGGGTGCTTCACGCTGGCCAGCACGCTGCGGTCGGAGATCAGCTC

GGCGTCCAGGTCCTCCGCGTTGCTCAGCGCGAACGGGGTCATCTTGGGCACTTGCCGCCCCAGGAAG

GGCGCGTGCCCCGGTTTCGAGTTGCAGTCGCAGCGCAGCGGGATCAGCAGGTGCCCGTGCCCGGACT

CGGCGTTGGGGTACAGCGCGCGCATGAAGGCCTGCATCTGGCGGAAGGCCATCTGGGCCTTGGCGCC

CTCCGAGAAGAACATGCCGCAGGACTTGCCCGAGAACTGGTTTGCGGGGCAGCTGGCGTCGTGCAGG

CAGCAGCGCGCGTCGGTGTTGGCGATCTGCACCACGTTGCGCCCCCACCGGTTCTTCACGATCTTGGC

CTTGGACGATTGCTCCTTCAGCGCGCGCTGCCCGTTCTCGCTGGTCACATCCATCTCGATCACATGTT

CCTTGTTCACCATGCTGCTGCCGTGCAGACACTTCAGCTCGCCCTCCGTCTCGGTGCAGCGGTGCTGC

CACAGCGCGCAGCCCGTGGGCTCGAAAGACTTGTAGGTCACCTCCGCGAAGGACTGCAGGTACCCCT

GCAAAAAGCGGCCCATCATGGTCACGAAGGTCTTGTTGCTGCTGAAGGTCAGCTGCAGCCCGCGGTG

CTCCTCGTTCAGCCAGGTCTTGCACACGGCCGCCAGCGCCTCCACCTGGTCGGGCAGCATCTTGAAGT

TCACCTTCAGCTCATTCTCCACGTGGTACTTGTCCATCAGCGTGCGCGCCGCCTCCATGCCCTTCTCCC

AGGCCGACACCAGCGGCAGGCTCACGGGGTTCTTCACCATCACCGTGGCCGCCGCCTCCGCCGCGCT

TTCGCTTTCCGCCCCGCTGTTCTCTTCCTCTTCCTCCTCTTCCTCGCCGCCGCCCACTCGCAGCCCCCG

CACCACGGGGTCGTCTTCCTGCAGGCGCTGCACCTTGCGCTTGCCGTTGCGCCCCTGCTTGATGCGCA

CGGGCGGGTTGCTGAAGCCCACCATCACCAGCGCGGCCTCTTCTTGCTCGTCCTCGCTGTCCAGAATG

ACCTCCGGGAGGGGGGGTTGGTCATCCTCAGTACCGAGGCACGCTTCTTTTTCTTCCTGGGGGCGTT

CGCCAGCTCCGCGGCTGCGGCCGCTGCCGAGGTCGAAGGCCGAGGGCTGGGCGTGCGCGGCACCAG

CGCGTCCTGCGAGCCGTCCTCGTCCTCCTCGGACTCGAGACGGAGGCGGGCCCGCTTCTTCGGGGGC

GCGCGGGCGGCGGAGGCGGCGGCGGCGACGGAGACGGGGACGAGACATCGTCCAGGGTGGGTGG

ACGGCGGGCCGCGCCGCGTCCGCGCTCGGGGGTGGTCTCGCGCTGGTCCTCTTCCCGACTGGCCATCT

CCCACTGCTCCTTCTCCTATAGGCAGAAAGAGATCATGGAGTCTCTCATGCGAGTCGAGAAGGAGGA

GGACAGCCTAACCGCCCCCTCTGAGCCCTCCACCACCGCCGCCACCACCGCCAATGCCGCCGCGGAC

GACGCGCCCACCGAGACCACCGCCAGTACCACCCTCCCCAGCGACGCACCCCCGCTCGAGAATGAAG

TGCTGATCGAGCAGGACCCGGGTTTTGTGAGCGGAGAGGAGGATGAGGTGGATGAGAAGGAGAAGG

AGGAGGTCGCCGCCTCAGTGCCAAAAGAGGATAAAAAGCAAGACCAGGACGACGCAGATAAGGAT

GAGACAGCAGTCGGGCGGGGAACGGAAGCCATGATGCTGATGACGGCTACCTAGACGTGGGAGAC

GACGTGCTGCTTAAGCACCTGCACCGCCAGTGCGTCATCGTCTGCGACGCGCTGCAGGAGCGCTGCG

AAGTGCCCCTGGACGTGGCGGAGGTCAGCCGCGCCTACGAGCGGCACCTCTTCGCGCCGCACGTGCC
```

-continued

```
CCCCAAGCGCCGGGAGAACGGCACCTGCGAGCCCAACCCGCGTCTCAACTTCTACCCGGTCTTCGCG
GTACCCGAGGTGCTGGCCACCTACCACATCTTTTTCCAAAACTGCAAGATCCCCCTCTCCTGCCGCGC
CAACCGCACCCGCGCCGACAAAACCCTGACCCTGCGGCAGGGCGCCCACATACCTGATATCGCCTCT
CTGGAGGAAGTGCCCAAGATCTTCGAGGGTCTCGGTCGCGACGAGAAACGGGCGGCGAACGCTCTG
CACGGAGACAGCGAAAACGAGAGTCACTCGGGGGTGCTGGTGGAGCTCGAGGGCGACAACGCGCGC
CTGGCCGTACTCAAGCGCAGCATAGAGGTCACCCACTTTGCCTACCCGGCGCTCAACCTGCCCCCCA
AGGTCATGAGTGTGGTCATGGGCGAGCTCATCATGCGCCGCGCCCAGCCCCTGGCCGCGGATGCAAA
CTTGCAAGAGTCCTCCGAGGAAGGCCTGCCCGCGGTCAGCGACGAGCAGCTGGCGCGCTGGCTGGA
GACCCGCGACCCCGCGCAGCTGGAGGAGCGGCGCAAGCTCATGATGGCCGCGGTGCTGGTCACCGT
GGAGCTCGAGTGTCTGCAGCGCTTCTTCGCGGACCCCGAGATGCAGCGCAAGCTCGAGGAGACCCTG
CACTACACCTTCCGCCAGGGCTACGTGCGCCAGGCCTGCAAGATCTCCAACGTGGAGCTCTGCAACC
TGGTCTCCTACCTGGGCATCCTGCACGAGAACCGCCTCGGGCAGAACGTCCTGCACTCCACCCTCAA
AGGGGAGGCGCGCCGCGACTACATCCGCGACTGCGCCTACCTCTTCCTCTGCTACACCTGGCAGACG
GCCATGGGGGTCTGGCAGCAGTGCCTGGAGGAGCGCAACCTCAAGGAGCTGGAAAAGCTCCTCAAG
CGCACCCTCAGGGACCTCTGGACGGGCTTCAACGAGCGCTCGGTGGCCGCCGCGCTGGCGGACATCA
TCTTTCCCGAGCGCCTGCTCAAGACCCTGCAGCAGGGCCTGCCCGACTTCACCAGCCAGAGCATGCT
GCAGAACTTCAGGACTTTCATCCTGGAGCGCTCGGGCATCCTGCCGGCCACTTGCTGCGCGCTGCCCA
GCGACTTCGTGCCCATCAAGTACAGGGAGTGCCCGCCGCCGCTCTGGGCCACTGCTACCTCTTCCA
GCTGGCCAACTACCTCGCCTACCACTCGGACCTCATGGAAGACGTGAGCGGCGAGGGCCTGCTCGAG
TGCCACTGCCGCTGCAACCTCTGCACGCCCCACCGCTCTCTAGTCTGCAACCCGCAGCTGCTCAGCGA
GAGTCAGATTATCGGTACCTTCGAGCTGCAGGGTCCCTCGCCTGACGAGAAGTCCGCGGCTCCAGGG
CTGAAACTCACTCCGGGGCTGTGGACTTCCGCCTACCTACGCAAATTTGTACCTGAGGACTACCACGC
CCACGAGATCAGGTTCTACGAAGACCAATCCCGCCCGCCCAAGGCGGAGCTCACCGCCTGCGTCATC
ACCCAGGGGCACATCCTGGGCCAATTGCAAGCCATCAACAAAGCCCGCCGAGAGTTCTTGCTGAAAA
AGGGTCGGGGGTGTACCTGGACCCCCAGTCCGGCGAGGAGCTAAACCCGCTACCCCCGCCGCCGCC
CCAGCAGCGGGACCTTGCTTCCCAGGATGGCACCCAGAAAGAAGCAGCAGCCGCCGCCGCCGCCGC
AGCCATACATGCTTCTGGAGGAAGAGGAGGAGGACTGGGACAGTCAGGCAGAGGAGGTTTCGGACG
AGGAGCAGGAGGAGATGATGGAAGACTGGGAGGAGGACAGCAGCCTAGACGAGGAAGCTTCAGAG
GCCGAAGAGGTGGCAGACGCAACACCATCGCCCTCGGTCGCAGCCCCCTCGCCGGGGCCCCTGAAAT
CCTCCGAACCCAGCACCAGCGCTATAACCTCCGCTCCTCCGGCGCCGGCGCCACCCGCCCGCAGACC
CAACCGTAGATGGGACACCACAGGAACCGGGGTCGGTAAGTCCAAGTGCCCGCCGCCGCCACCGCA
GCAGCAGCAGCAGCGCCAGGGCTACCGCTCGTGGCGCGGGCACAAGAACGCCATAGTCGCCTG
CTTGCAAGACTGCGGGGCAACATCTCTTTCGCCCGCCGCTTCCTGCTATTCCACCACGGGTCGCCT
TTCCCCGCAATGTCCTGCATTACTACCGTCATCTCTACAGCCCCTACTGCAGCGGCGACCCAGAGGCG
GCAGCGGCAGCCACAGCGGCGACCACCACCTAGGAAGATATCCTCCGCGGGCAAGACAGCGGCAGC
AGCGGCCAGGAGACCCGCGGCAGCAGCGGCGGGAGCGGTGGGCGCACTGCGCCTCTCGCCCAACGA
ACCCCTCTCGACCCGGGAGCTCAGACACAGGATCTTCCCCACTTTGTATGCCATCTTCCAACAGAGCA
GAGGCCAGGAGCAGGAGCTGAAAATAAAAAACAGATCTCTGCGCTCCCTCACCCGCAGCTGTCTGTA
TCACAAAAGCGAAGATCAGCTTCGGCGCACGCTGGAGGACGCGGAGGCACTCTTCAGCAAATACTG
CGCGCTCACTCTTAAAGACTAGCTCCGCGCCCTTCTCGAATTTAGGCGGGAGAAAACTACGTCATCG
```

-continued

CCGGCCGCCGCCCAGCCCGCCCAGCCGAGATGAGCAAAGAGATTCCCACGCCATACATGTGGAGCTA

CCAGCCGCAGATGGGACTCGCGGCGGGAGCGGCCCAGGACTACTCCACCCGCATGAACTACATGAG

CGCGGGACCCCACATGATCTCACAGGTCAACGGGATCCGCGCCCAGCGAAACCAAATACTGCTGGA

ACAGGCGGCCATCACCGCCACGCCCCGCCATAATCTCAACCCCCGAAATTGGCCCGCCGCCCTCGTG

TACCAGGAAACCCCCTCCGCCACCACCGTACTACTTCCGCGTGACGCCCAGGCCGAAGTCCAGATGA

CTAACTCAGGGGCGCAGCTCGCGGGCGGCTTTCGTCACGGGGCGCGGCCGCTCCGACCAGGTATAAG

ACACCTGATGATCAGAGGCCGAGGTATCCAGCTCAACGACGAGTCGGTGAGCTCTTCGCTCGGTCTC

CGTCCGGACGGAACTTTCCAGCTCGCCGGATCCGGCCGCTCTTCGTTCACGCCCCGCCAGGCGTACCT

GACTCTGCAGACCTCGTCCTCGGAGCCCCGCTCCGGCGGCATCGGAACCCTCCAGTTCGTGGAGGAG

TTCGTGCCCTCGGTCTACTTCAACCCCTTCTCGGGACCTCCCGGACGCTACCCCGACCAGTTCATTCC

GAACTTTGACGCGGTGAAGGACTCGGCGGACGGCTACGACTGAATGTCAGGTGTCGAGGCAGAGCA

GCTTCGCCTGAGACACCTCGAGCACTGCCGCCGCCACAAGTGCTTCGCCCGCGGTTCTGGTGAGTTCT

GCTACTTTCAGCTACCCGAGGAGCATACCGAGGGGCCGGCGCACGGCGTCCGCCTGACCACCCAGGG

CGAGGTTACCTGTTCCCTCATCCGGGAGTTTACCCTCCGTCCCCTGCTAGTGGAGCGGGAGCGGGGTC

CCTGTGTCCTAACTATCGCCTGCAACTGCCCTAACCCTGGATTACATCAAGATCTTTGCTGTCATCTCT

GTGCTGAGTTTAATAAACGCTGAGATCAGAATCTACTGGGGCTCCTGTCGCCATCCTGTGAACGCCA

CCGTCTTCACCCACCCCGACCAGGCCCAGGCGAACCTCACCTGCGGTCTGCATCGGAGGGCAAGAA

GTACCTCACCTGGTACTTCAACGGCACCCCCTTTGTGGTTTACAACAGCTTCGACGGGGACGGAGTCT

CCCTGAAAGACCAGCTCTCCGGTCTCAGCTACTCCATCCACAAGAACACCACCCTCCAACTCTTCCCT

CCCTACCTGCCGGGAACCTACGAGTGCGTCACCGGCCGCTGCACCCACCTCACCCGCCTGATCGTAA

ACCAGAGCTTTCCGGGAACAGATAACTCCCTCTTCCCCAGAACAGGAGGTGAGCTCAGGAAACTCCC

CGGGGACCAGGGCGGAGACGTACCTTCGACCCTTGTGGGGTTAGGATTTTTTATTACCGGGTTGCTG

GCTCTTTTAATCAAAGTTTCCTTGAGATTTGTTCTTTCCTTCTACGTGTATGAACACCTCAACCTCCAA

TAACTCTACCCTTTCTTCGGAATCAGGTGACTTCTCTGAAATCGGGCTTGGTGTGCTGCTTACTCTGTT

GATTTTTTCCTTATCATACTCAGCCTTCTGTGCCTCAGGCTCGCCGCCTGCTGCGCACACATCTATAT

CTACTGCTGGTTGCTCAAGTGCAGGGGTCGCCACCCAAGATGAACAGGTACATGGTCCTATCGATCC

TAGGCCTGCTGGCCCTGGCGGCCTGCAGCGCCGCCAAAAAAGAGATTACCTTTGAGGAGCCCGCTTG

CAATGTAACTTTCAAGCCCGAGGGTGACCAATGCACCACCCTCGTCAAATGCGTTACCAATCATGAG

AGGCTGCGCATCGACTACAAAAACAAAACTGGCCAGTTTGCGGTCTATAGTGTGTTTACGCCCGGAG

ACCCCTCTAACTACTCTGTCACCGTCTTCCAGGGCGGACAGTCTAAGATATTCAATTACACTTTCCCT

TTTTATGAGTTATGCGATGCGGTCATGTACATGTCAAAACAGTACAACCTGTGGCCTCCCTCTCCCCA

GGCGTGTGTGGAAAATACTGGGTCTTACTGCTGTATGGCTTTCGCAATCACTACGCTCGCTCTAATCT

GCACGGTGCTATACATAAAATTCAGGCAGAGGCGAATCTTTATCGATGAAAAGAAAATGCCTTGATC

GCTAACACCGGCTTTCTATCTGCAGAATGAATGCAATCACCTCCCTACTAATCACCACCACCCTCCTT

GCGATTGCCCATGGGTTGACACGAATCGAAGTGCCAGTGGGGTCCAATGTCACCATGGTGGGCCCCG

CCGGCAATTCCACCCTCATGTGGGAAAAATTTGTCCGCAATCAATGGGTTCATTTCTGCTCTAACCGA

ATCAGTATCAAGCCCAGAGCCATCTGCGATGGGCAAAATCTAACTCTGATCAATGTGCAAATGATGG

ATGCTGGGTACTATTACGGGCAGCGGGAGAAATCATTAATTACTGGCGACCCCACAAGGACTACAT

GCTGCATGTAGTCGAGGCACTTCCCACTACCACCCCCACTACCACCTCTCCCACCACCACCACCACTA

CTACTACTACTACTACTACTACTACTACCACTACCGCTGCCCGCCATACCCGCAAAAGCACCATG

ATTAGCACAAAGCCCCCTCGTGCTCACTCCCACGCCGGCGGGCCCATCGGTGCGACCTCAGAAACCA

-continued

```
CCGAGCTTTGCTTCTGCCAATGCACTAACGCCAGCGCTCATGAACTGTTCGACCTGGAGAATGAGGA
TGTCCAGCAGAGCTCCGCTTGCCTGACCCAGGAGGCTGTGGAGCCCGTTGCCCTGAAGCAGATCGGT
GATTCAATAATTGACTCTTCTTCTTTTGCCACTCCCGAATACCCTCCCGATTCTACTTTCCACATCACG
GGTACCAAAGACCCTAACCTCTCTTTCTACCTGATGCTGCTGCTCTGTATCTCTGTGGTCTCTTCCGCG
CTGATGTTACTGGGGATGTTCTGCTGCCTGATCTGCCGCAGAAAGAGAAAAGCTCGCTCTCAGGGCC
AACCACTGATGCCCTTCCCCTACCCCCCGGATTTTGCAGATAACAAGATATGAGCTCGCTGCTGACAC
TAACCGCTTTACTAGCCTGCGCTCTAACCCTTGTCGCTTGCGACTCGAGATTCCACAATGTCACAGCT
GTGGCAGGAGAAAATGTTACTTTCAACTCCACGGCCGATACCCAGTGGTCGTGGAGTGGCTCAGGTA
GCTACTTAACTATCTGCAATAGCTCCACTTCCCCCGGCATATCCCCAACCAAGTACCAATGCAATGCC
AGCCTGTTCACCCTCATCAACGCTTCCACCCTGGACAATGGACTCTATGTAGGCTATGTACCCTTTGG
TGGGCAAGGAAAGACCCACGCTTACAACCTGGAAGTTCGCCAGCCCAGAACCACTACCCAAGCTTCT
CCCACCACCACCACCACCACCACCATCACCAGCAGCAGCAGCAGCAGCAGCCACAGCAGCAGCAGC
AGATTATTGACTTTGGTTTTGGCCAGCTCATCTGCCGCTACCCAGGCCATCTACAGCTCTGTGCCCGA
AACCACTCAGATCCACCGCCCAGAAACGACCACCGCCACCACCCTACACACCTCCAGCGATCAGATG
CCGACCAACATCACCCCCTTGGCTCTTCAAATGGGACTTACAAGCCCCACTCCAAAACCAGTGGATG
CGGCCGAGGTCTCCGCCCTCGTCAATGACTGGGCGGGCTGGGAATGTGGTGGTTCGCCATAGGCAT
GATGGCGCTCTGCCTGCTTCTGCTCTGGCTCATCTGCTGCCTCCACCGCAGGCGAGCCAGACCCCCA
TCTATAGACCCATCATTGTCCTGAACCCCGATAATGATGGGATCCATAGATTGGATGGCCTGAAAAA
CCTACTTTTTTCTTTTACAGTATGATAAATTGAGACATGCCTCGCATTTTCTTGTACATGTTCCTTCTCC
CACCTTTTCTGGGGTGTTCTACGCTGGCCGCTGTGTCTCACCTGGAGGTAGACTGCCTCTCACCCTTC
ACTGTCTACCTGCTTTACGGATTGGTCACCCTCACTCTCATCTGCAGCCTAATCACAGTAATCATCGC
CTTCATCCAGTGCATTGATTACATCTGTGTGCGCCTCGCATACTTCAGACACCACCCGCAGTACCGAG
ACAGGAACATTGCCCAACTTCTAAGACTGCTCTAATCATGCATAAGACTGTGATCTGCCTTCTGATCC
TCTGCATCCTGCCCACCCTCACCTCCTGCCAGTACACCACAAAATCTCCGCGCAAAAGACATGCCTCC
TGCCGCTTCACCCAACTGTGGAATATACCCAAATGCTACAACGAAAAGAGCGAGCTCTCCGAAGCTT
GGCTGTATGGGGTCATCTGTGTCTTAGTTTTCTGCAGCACTGTCTTTGCCCTCATAATCTACCCCTACT
TTGATTTGGGATGGAACGCGATCGATGCCATGAATTACCCCACCTTTCCCGCACCCGAGATAATTCCA
CTGCGACAAGTTGTACCCGTTGTCGTTAATCAACGCCCCCCATCCCCTACGCCCACTGAAATCAGCTA
CTTTAACCTAACAGGCGGAGATGACTGACGCCCTAGATCTAGAAATGGACGGCATCAGTACCGAGCA
GCGTCTCCTAGAGAGGCGCAGGCAGGCGGCTGAGCAAGAGCGCCTCAATCAGGAGCTCCGAGATCT
CGTTAACCTGCACCAGTGCAAAAGAGGCATCTTTTGTCTGGTAAAGCAGGCCAAAGTCACCTACGAG
AAGACCGGCAACAGCCACCGCCTCAGTTACAAATTGCCCACCCAGCGCCAGAAGCTGGTGCTCATGG
TGGGTGAGAATCCCATCACCGTCACCCAGCACTCGGTAGAGACCGAGGGGTGTCTGCACTCCCCCTG
TCGGGGTCCAGAAGACCTCTGCACCCTGGTAAAGACCCTGTGCGGTCTCAGAGATTTAGTCCCCTTTA
ACTAATCAAACACTGGAATCAATAAAAAGAATCACTTACTTAAAATCAGACAGCAGGTCTCTGTCCA
GTTTATTCAGCAGCACCTCCTTCCCCTCCTCCCAACTCTGGTACTCCAAACGCCTTCTGGCGGCAAAC
TTCCTCCACACCCTGAAGGGAATGTCAGATTCTTGCTCCTGTCCCTCCGCACCCACTATCTTCATGTTG
TTGCAGATGAAGCGCACCAAAACGTCTGACGAGAGCTTCAACCCCGTGTACCCCTATGACACGGAAA
GCGGCCCTCCCTCCGTCCCTTTCCTCACCCCTCCCTTCGTGTCTCCCGATGGATTCCAAGAAAGTCCCC
CCGGGGTCCTGTCTCTGAACCTGGCCGAGCCCCTGGTCACTTCCCACGGCATGCTCGCCCTGAAAATG
```

-continued

```
GGAAGTGGCCTCTCCCTGGACGACGCTGGCAACCTCACCTCTCAAGATATCACCACCGCTAGCCCTC
CCCTCAAAAAAACCAAGACCAACCTCAGCCTAGAAACCTCATCCCCCCTAACTGTGAGCACCTCAGG
CGCCCTCACCGTAGCAGCCGCCGCTCCCCTGGCGGTGGCCGGCACCTCCCTCACCATGCAATCAGAG
GCCCCCCTGACAGTACAGGATGCAAAACTCACCCTGGCCACCAAAGGCCCCCTGACCGTGTCTGAAG
GCAAACTGGCCTTGCAAACATCGGCCCCGCTGACGGCCGCTGACAGCAGCACCCTCACAGTCAGTGC
CACACCACCCCTTAGCACAAGCAATGGCAGCTTGGGTATTGACATGCAAGCCCCCATTTACACCACC
AATGGAAAACTAGGACTTAACTTTGGCGCTCCCCTGCATGTGGTAGACAGCCTAAATGCACTGACTG
TAGTTACTGGCCAAGGTCTTACGATAAACGGAACAGCCCTACAAACTAGAGTCTCAGGTGCCCTCAA
CTATGACACATCAGGAAACCTAGAATTGAGAGCTGCAGGGGGTATGCGAGTTGATGCAAATGGTCA
ACTTATCCTTGATGTAGCTTACCCATTTGATGCACAAAACAATCTCAGCCTTAGGCTTGGACAGGGAC
CCCTGTTTGTTAACTCTGCCCACAACTTGGATGTTAACTACAACAGAGGCCTCTACCTGTTCACATCT
GGAAATACCAAAAAGCTAGAAGTTAATATCAAAACAGCCAAGGGTCTCATTTATGATGACACTGCTA
TAGCAATCAATGCGGGTGATGGGCTACAGTTTGACTCAGGCTCAGATACAAATCCATTAAAAACTAA
ACTTGGATTAGGACTGGATTATGACTCCAGCAGAGCCATAATTGCTAAACTGGGAACTGGCCTAAGC
TTTGACAACACAGGTGCCATCACAGTAGGCAACAAAAATGATGACAAGCTTACCTTGTGGACCACAC
CAGACCCATCCCCTAACTGTAGAATCTATTCAGAGAAAGATGCTAAATTCACACTTGTTTTGACTAAA
TGCGGCAGTCAGGTGTTGGCCAGCGTTTCTGTTTTATCTGTAAAAGGTAGCCTTGCGCCCATCAGTGG
CACAGTAACTAGTGCTCAGATTGTCCTCAGATTTGATGAAAATGGAGTTCTACTAAGCAATTCTTCCC
TTGACCCTCAATACTGGAACTACAGAAAAGGTGACCTTACGAGGGCACTGCATATACCAACGCAGT
GGGATTTATGCCCAACCTCACAGCATACCCAAAAACACAGAGCCAAACTGCTAAAAGCAACATTGTA
AGTCAGGTTTACTTGAATGGGACAAATCCAAACCCATGACCCTCACCATTACCCTCAATGGAACTA
ATGAAACAGGAGATGCCACAGTAAGCACTTACTCCATGTCATTCTCATGGAACTGGAATGGAAGTAA
TTACATTAATGAAACGTTCCAAACCAACTCCTTCACCTTCTCCTACATCGCCCAAGAATAAAAGCAT
GACGCTGTTGATTTGATTCAATGTGTTTCTGTTTTATTTTCAAGCACAACAAAATCATTCAAGTCATTC
TTCCATCTTAGCTTAATAGACACAGTAGCTTAATAGACCCAGTAGTGCAAAGCCCCATTCTAGCTTAT
AACTAGTGGAGAAGTACTCGCCTACATGGGGGTAGAGTCATAATCGTGCATCAGGATAGGGCGGTG
GTGCTGCAGCAGCGCGCGAATAAACTGCTGCCGCCGCCGCTCCGTCCTGCAGGAATACAACATGGCA
GTGGTCTCCTCAGCGATGATTCGCACCGCCCGCAGCATAAGGCGCCTTGTCCTCCGGGCACAGCAGC
GCACCCTGATCTCACTTAAATCAGCACAGTAACTGCAGCACAGCACCACAATATTGTTCAAAATCCC
ACAGTGCAAGGCGCTGTATCCAAAGCTCATGGCGGGGACCACAGAACCCACGTGGCCATCATACCAC
AAGCGCAGGTAGATTAAGTGGCGACCCCTCATAAACACGCTGGACATAAACATTACCTCTTTTGGCA
TGTTGTAATTCACCACCTCCCGGTACCATATAAACCTCTGATTAAACATGGCGCCATCCACCACCATC
CTAAACCAGCTGGCCAAAACCTGCCCGCCGGCTATACACTGCAGGGAACCGGGACTGGAACAATGA
CAGTGGAGAGCCCAGGACTCGTAACCATGGATCATCATGCTCGTCATGATATCAATGTTGGCACAAC
ACAGGCACACGTGCATACACTTCCTCAGGATTACAAGCTCCTCCCGCGTTAGAACCATATCCCAGGG
AACAACCCATTCCTGAATCAGCGTAAATCCCACACTGCAGGGAAGACCTCGCACGTAACTCACGTTG
TGCATTGTCAAAGTGTTACATTCGGGCAGCAGCGGATGATCCTCCAGTATGGTAGCGCGGGTTTCTGT
CTCAAAAGGAGGTAGACGATCCCTACTGTACGGAGTGCGCCGAGACAACCGAGATCGTGTTGGTCGT
AGTGTCATGCCAAATGGAACGCCGGACGTAGTCATATTTCCTGAAGTCTTAGATCTCTCAACGCAGC
ACCAGCACCAACACTTCGCAGTGTAAAAGGCCAAGTGCCGAGAGAGTATATATAGGAATAAAAAGT
GACGTAAACGGGCAAAGTCCAAAAAACGCCCAGAAAAACCGCACGCGAACCTACGCCCCGAAACGA
```

```
AAGCCAAAAAACACTAGACACTCCCTTCCGGCGTCAACTTCCGCTTTCCCACGCTACGTCACTTGCCC

CAGTCAAACAAACTACATATCCCGAACTTCCAAGTCGCCACGCCCAAAACACCGCCTACACCTCCCC

GCCCGCCGGCCCGCCCCCAAACCCGCCTCCCGCCCCGCGCCCCGCCCCGCGCCGCCCATCTCATTATC

ATATTGGCTTCAATCCAAAATAAGGTATATTATTGATGATG
```

Polynucleotide sequence encoding the CASI promoter                          SEQ ID NO: 12
```
GGAGTTCCGCGTTACATAACTTACGGTAAATGGCCCGCCTGGCTGACCGCCCAACGACCCCCGCCCA

TTGACGTCAATAATGACGTATGTTCCCATAGTAACGCCAATAGGGACTTTCCATTGACGTCAATGGGT

GGAGTATTTACGGTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCTTATGGGACTTTCC

TACTTGGCAGTACATCTACGTATTAGTCATCGCTATTACCATGGTCGAGGTGAGCCCCACGTTCTGCT

TCACTCTCCCCATCTCCCCCCCCTCCCCACCCCCAATTTTGTATTTATTTATTTTTTAATTATTTTGTGC

AGCGATGGGGGCGGGGGGGGGGGGGCGCGCGCCAGGCGGGGCGGGGCGGGGCGAGGGCGGGG

CGGGGCGAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCTCCCTATCAGTGATAGAGATCTCC

CTATCAGTGATAGAGATCGTCGACGAGCTCGCGGCGGGCGGGAGTCGCTGCGCGCTGCCTTCGCCCC

GTGCCCCGCTCCGCCGCCGCCTCGCGCCGCCCGCCCCGGCTCTGACTGACCGCGTTACTAAAACAGG

TAAGTCCGGCCTCCGCGCCGGGTTTTGGCGCCTCCCGCGGGCGCCCCCCTCCTCACGGCGAGCGCTGC

CACGTCAGACGAAGGGCGCAGCGAGCGTCCTGATCCTTCCGCCCGGACGCTCAGGACAGCGGCCCGC

TGCTCATAAGACTCGGCCTTAGAACCCCAGTATCAGCAGAAGGACATTTTAGGACGGGACTTGGGTG

ACTCTAGGGCACTGGTTTTCTTTCCAGAGAGCGGAACAGGCGAGGAAAAGTAGTCCCTTCTCGGCGA

TTCTGCGGAGGGATCTCCGTGGGGCGGTGAACGCCGATGATGCCTCTACTAACCATGTTCATGTTTTC

TTTTTTTTCTACAGGTCCTGGGTGACGAACAG
```

Ad5orf6 primer 1 polynucleotide sequence                                    SEQ ID NO: 13
```
ATACGGACTAGTGGAGAAGTACTCGCCTACATG
```

Ad5orf6 primer 2 polynucleotide sequence                                    SEQ ID NO: 14
```
ATACGGAAGATCTAAGACTTCAGGAAATATGACTAC
```

BAC/CHAd155 ΔE1_TetO hCMV RpsL-Kana primer 1 polynucleotide sequence        SEQ ID NO: 15
```
ATTCAGTGTACAGGCGCGCCAAAGCATGACGCTGTTGATTTGATTC
```

BAC/CHAd155 ΔE1_TetO hCMV RpsL-Kana (#1375) primer 2 polynucleotide sequence   SEQ ID NO: 16
```
ACTAGGACTAGTTATAAGCTAGAATGGGGCTTTGC
```

1021-FW E4 Del Step1 primer polynucleotide sequence                         SEQ ID NO: 17
```
TTAATAGACACAGTAGCTTAATAGACCCAGTAGTGCAAAGCCCCATTCTAGCTTATAACCCCTATTTG
TTTATTTTTCT
```

1022-RW E4 Del Step1 primer polynucleotide sequence                         SEQ ID NO: 18
```
ATATATACTCTCTCGGCACTTGGCCTTTTACACTGCGAAGTGTTGGTGCTGGTGCTGCGTTGAGAGAT
CTTTATTTGTTAACTGTTAATTGTC
```

1025-FW E4 Del Step2 primer polynucleotide sequence                         SEQ ID NO: 19
```
TTAATAGACACAGTAGCTTAATA
```

1026-RW E4 Del Step2 primer polynucleotide sequence                         SEQ ID NO: 20
```
GGAAGGGAGTGTCTAGTGTT
```

91-SubMonte FW primer polynucleotide sequence                               SEQ ID NO: 21

CAATGGGCGTGGATAGCGGTTTGAC

90-BghPolyA RW primer polynucleotide sequence  SEQ ID NO: 22

CAGCATGCCTGCTATTGTC

CMVfor primer polynucleotide sequence  SEQ ID NO: 23

CATCTACGTATTAGTCATCGCTATTACCA

CMVrev primer polynucleotide sequence  SEQ ID NO: 24

GACTTGGAAATCCCCGTGAGT

CMVFAM-TAMRA qPCR probe polynucleotide sequence  SEQ ID NO: 25

ACATCAATGGGCGTGGATAGCGGTT

Woodchuck Hepatitis Virus Posttranscriptional Regulatory Element (WPRE) polynucleotide sequence  SEQ ID NO: 26

TAATCAACCTCTGGATTACAAAATTTGTGAAAGATTGACTGGTATTCTTAACTATGTTGCTCCTTTTAC

GCTATGTGGATACGCTGCTTTAATGCCTTTGTATCATGCTATTGCTTCCCGTATGGCTTTCATTTTCTC

CTCCTTGTATAAATCCTGGTTGCTGTCTCTTTATGAGGAGTTGTGGCCCGTTGTCAGGCAACGTGGCG

TGGTGTGCACTGTGTTTGCTGACGCAACCCCCACTGGTTGGGGCATTGCCACCACCTGTCAGCTCCTT

TCCGGGACTTTCGCTTTCCCCCTCCCTATTGCCACGGCGGAACTCATCGCCGCCTGCCTTGCCCGCTG

CTGGACAGGGGCTCGGCTGTTGGGCACTGACAATTCCGTGGTGTTGTCGGGGAAATCATCGTCCTTTC

CTTGGCTGCTCGCCTGTGTTGCCACCTGGATTCTGCGCGGGACGTCCTTCTGCTACGTCCCTTCGGCCC

TCAATCCAGCGGACCTTCCTTCCCGCGGCCTGCTGCCGGCTCTGCGGCCTCTTCCGCGTCTTCGCCTTC

GCCCTCAGACGAGTCGGATCTCCCTTTGGGCCGCCTCCCCGCCT

ChAd3 fiber amino acid sequence  SEQ ID NO: 27

MKRTKTSDESFNPVYPYDTESGPPSVPFLTPPPFVSPDGFQESPPGVLSLNLAEPLVTSHGMLALKMGSGLS

LDDAGNLTSQDITTASPPLKKTKTNLSLETSSPLTVSTSGALTVAAAAPLAVAGTSLTMQSEAPLTVQDAK

LTLATKGPLTVSEGKLALQTSAPLTAADSSTLTVSATPPINVSSGSLGLDMEDPMYTHDGKLGIRIGGPLR

VVDSLHTLTVVTGNGLTVDNNALQTRVTGALGYDTSGNLQLRAAGGMRIDANGQLILNVAYPFDAQNN

LSLRLGQGPLYINTDHNLDLNCNRGLTTTTTNNTKKLETKISSGLDYDTNGAVIIKLGTGLSFDNTGALTV

GNTGDDKLTLWTTPDPSPNCRIHSDKDCKFTLVLTKCGSQILASVAALAVSGNLASITGTVASVTIFLRFD

QNGVLMENSSLDRQYWNFRNGNSTNAAPYTNAVGFMPNLAAYPKTQSQTAKNNIVSQVYLNGDKSKP

MTLTITLNGTNESSETSQVSHYSMSFTWAWESGQYAFETFATNSFTFSYIAEQ

PanAd3 fiber amino acid sequence  SEQ ID NO: 28

MKRAKTSDETFNPVYPYDTENGPPSVPFLTPPPFVSPDGFQESPPGVLSLRLSEPLVTSHGMLALKMGNGLS

LDDAGNLTSQDVTTVTPPLKKTKTNLSLQTSAPLTVSSGSLTVAAAAPLAVAGTSLTMQSQAPLTVQDAK

LGLATQGPLTVSEGKLTLQTSAPLTAADSSTLTVGTTPPISVSSGSLGLDMEDPMYTHDGKLGIRIGGPLQ

VVDSLHTLTVVTGNGITVANNALQTKVAGALGYDSSGNLELRAAGGMRINTGGQLILDVAYPFDAQNNL

SLRLGQGPLYVNTNHNLDLNCNRGLTTTTSSNTTKLETKIDSGLDYNANGAIIAKLGTGLTFDNTGAITVG

NTGDDKLTLWTTPDPSPNCRIHADKDKFTLVLTKCGSQILASVAALAVSGNLSSMTGTVSSVTIFLRFDQN

GVLMENSSLDKEYWNFRNGNSTNATPYTNAVGFMPNLSAYPKTQSQTAKNNIVSEVYLHGDKSKPMILT

ITLNGTNESSETSQVSHYSMSFTWSWDSGKYATETFATNSFTFSYIAEQ

ChAd17 fiber amino acid sequence  SEQ ID NO: 29

MKRTKTSDESFNPVYPYDTESGPPSVPFLTPPPFVSPDGFQESPPGVLSLNLAEPLVTSHGMLALKMGSGLS

LDDAGNLTSQDITSTTPPLKKTKTNLSLETSSPLTVSTSGALTVAAAAPLAVAGTSLTMQSEAPLAVQDAK

-continued

LTLATKGPLTVSEGKLALQTSAPLTAADSSTLTVSSTPPISVSSGSLGLDMEDPMYTHDGKLGIRIGGPLRV

VDSLHTLTVVTGNGLTVDNNALQTRVTGALGYDTSGNLQLRAAGGMRIDANGQLILDVAYPFDAQNNL

SLRLGQGPLYVNTDHNLDLNCNRGLTTTTTNNTKKLETKISSGLDYDTNGAVIIKLGTGLSFDNTGALTV

GNTGDDKLTLWTTPDPSPNCRIHSDKDCKFTLVLTKCGSQILASVAALAVSGNLASITGTVASVTIFLRFD

QNGVLMENSSLDKQYWNFRNGNSTNAAPYTNAVGFMPNLAAYPKTQSQTAKNNIVSQVYLNGDKSKP

MTLTITLNGTNESSETSQVSHYSMSFTWAWESGQYATETFATNSFTFSYIAEQ

ChAd19 fiber amino acid sequence SEQ ID NO: 30

MKRTKTSDKSFNPVYPYDTENGPPSVPFLTPPFVSPDGFQESPPGVLSLNLAEPLVTSHGMLALKMGSGLS

LDDAGNLTSQDVTTTTPPLKKTKTNLSLETSAPLTVSTSGALTLAAAAPLAVAGTSLTMQSEAPLTVQDA

KLTLATKGPLTVSEGKLALQTSAPLTAADSSTLTVSATPPISVSSGSLGLDMEDPMYTHDGKLGIRIGGPLR

VVDSLHTLTVVTGNGIAVDNNALQTRVTGALGYDTSGNLQLRAAGGMRIDANGQLILDVAYPFDAQNN

LSLRLGQGPLYVNTDHNLDLNCNRGLTTTTTNNTKKLETKIGSGLDYDTNGAVIIKLGTGVSFDSTGALS

VGNTGDDKLTLWTTPDPSPNCRIHSDKDCKFTLVLTKCGSQILASVAALAVSGNLASITGTVSSVTIFLRFD

QNGVLMENSSLDKQYWNFRNGNSTNATPYTNAVGFMPNLAAYPKTQSQTAKNNIVSQVYLNGDKSKP

MTLTITLNGTNESSETSQVSHYSMSFTWAWESGQYATETFATNSFTFSYIAEQ

ChAd24 fiber amino acid sequence SEQ ID NO: 31

MKRTKTSDESFNPVYPYDTENGPPSVPFLTPPFVSPDGFQESPPGVLSLNLAEPLVTSHGMLALKMGSGLS

LDDAGNLTSQDVTTTTPPLKKTKTNLSLETSAPLTVSTSGALTLAAAAPLAVAGTSLTMQSEAPLTVQDA

KLTLATKGPLTVSEGKLALQTSAPLTAADSSTLTVSATPPINVSSGSLGLDMENPMYTHDGKLGIRIGGPL

RVVDSLHTLTVVTGNGIAVDNNALQTRVTGALGYDTSGNLQLRAAGGMRIDANGQLILDVAYPFDAQN

NLSLRLGQGPLYVNTDHNLDLNCNRGLTTTTTNNTKKLETKIGSGLDYDTNGAVIIKLGTGVSFDSTGAL

SVGNTGDDKLTLWTTPDPSPNCRIHSDKDCKFTLVLTKCGSQILASVAALAVSGNLASITGTVSSVTIFLRF

DQNGVLMENSSLDKQYWNFRNGNSTNATPYTNAVGFMPNLAAYPKTQSQTAKNNIVSQVYLNGDKSKP

MILTITLNGTNESSETSQVSHYSMSFTWAWESGQYATETFATNSFTFSYIAEQ

ChAd11 fiber amino acid sequence SEQ ID NO: 32

MKRTKTSDESFNPVYPYDTENGPPSVPFLTPPFVSPDGFQESPPGVLSLNLAEPLVTSHGMLALKMGSGLS

LDDAGNLTSQDVTTTTPPLKKTKTNLSLETSAPLTVSTSGALTLAAAVPLAVAGTSLTMQSEAPLTVQDA

KLTLATKGPLTVSEGKLALQTSAPLTAADSSTLTISATPPLSTSNGSLGIDMQAPIYTTNGKLGLNFGAPLH

VVDSLNALTVVTGQGLTINGTALQTRVSGALNYDSSGNLELRAAGGMRVDANGKLILDVAYPFDAQNN

LSLRLGQGPLFVNSAHNLDVNYNRGLYLFTSGNTKKLEVNIKTAKGLIYDDTAIAINPGDGLEFGSGSDTN

PLKTKLGLGLEYDSSRAIIAKLGTGLSFDNTGAITVGNKNDDKLTLWTTPDPSPNCRIYSEKDAKFTLVLT

KCGSQVLASVSVLSVKGSLAPISGTVTSAQIILRFDENGVLLSNSSLDPQYWNYRKGDLTEGTAYTNAVGF

MPNLTAYPKTQSQTAKSNIVSQVYLNGDKSKPMILTITLNGTNETGDATVSTYSMSFSWNWNGSNYINET

FQTNSFTFSYIAQE

ChAd20 fiber amino acid sequence SEQ ID NO: 33

MKRTKTSDESFNPVYPYDTESGPPSVPFLTPPFVSPDGFQESPPGVLSLNLAEPLVTSHGMLALKMGSGLS

LDDAGNLTSQDITTASPPLKKTKTNLSLETSSPLTVSTSGALTVAAAAPLAVAGTSLTMQSEAPLTVQDAK

LTLATKGPLTVSEGKLALQTSAPLTAADSSTLTVSATPPLSTSNGSLGIDMQAPIYTTNGKLGLNFGAPLH

VVDSLNALTVVTGQGLTINGTALQTRVSGALNYDTSGNLELRAAGGMRVDANGQLILDVAYPFDAQNN

LSLRLGQGPLFVNSAHNLDVNYNRGLYLFTSGNTKKLEVNIKTAKGLIYDDTAIAINAGDGLQFDSGSDT

NPLKTKLGLGLDYDSSRAIIAKLGTGLSFDNTGAITVGNKNDDKLTLWTTPDPSPNCRIYSEKDAKFTLVL

```
TKCGSQVLASVSVLSVKGSLAPISGTVTSAQIVLRFDENGVLLSNSSLDPQYWNYRKGDLTGTAYTNAV

GFMPNLTAYPKTQSQTAKSNIVSQVYLNGDKSKPMTLTITLNGTNETGDATVSTYSMSFSWNWNGSNYI

NETFQTNSFTFSYIAQE
```

ChAd31 fiber amino acid sequence                                                   SEQ ID NO: 34

```
MKRTKTSDESFNPVYPYDTESGPPSVPFLTPPFVSPDGFQESPPGVLSLNLAEPLVTSHGMLALKMGSGLS

LDDAGNLTSQDITTASPPLKKTKTNLSLETSSPLTVSTSGALTVAAAAPLAVAGTSLTMQSEAPLTVQDAK

LTLATKGPLTVSEGKLALQTSAPLTAADSSTLTVSATPPLSTSNGSLGIDMQAPIYTTNGKLGLNFGAPLH

VVDSLNALTVVTGQGLTINGTALQTRVSGALNYDTSGNLELRAAGGMRVDANGQLILDVAYPFDAQNN

LSLRLGQGPLFVNSAHNLDVNYNRGLYLFTSGNTKKLEVNIKTAKGLIYDDTAIAINAGDGLQFDSGSDT

NPLKTKLGLGLDYDSSRAIIAKLGTGLSFDNTGAITVGNKNDDKLTLWTTPDPSPNCRIYSEKDAKFTLVL

TKCGSQVLASVSVLSVKGSLAPISGTVTSAQIVLRFDENGVLLSNSSLDPQYWNYRKGDLTEGTAYTNAV

GFMPNLTAYPKTQSQTAKSNIVSQVYLNGDKSKPMTLTITLNGTNETGDATVSTYSMSFSWNWNGSNYI

NETFQTNSFTFSYIAQE
```

PanAd1 fiber amino acid sequence                                                   SEQ ID NO: 35

```
MKRAKTSDETFNPVYPYDTENGPPSVPFLTPPFVSPDGFQESPPGVLSLRLSEPLVTSHGMLALKMGNGLS

LDDAGNLTSQDVTTVTPPLKKTKTNLSLQTSAPLTVSSGSLTVAAAAPLAVAGTSLTMQSQAPLTVQDAK

LGLATQGPLTVSEGKLTLQTSAPLTAADSSTLTVSATPPLSTSNGSLSIDMQAPIYTTNGKLALNIGAPLHV

VDTLNALTVVTGQGLTINGRALQTRVTGALSYDTEGNIQLQAGGGMRIDNNGQLILNVAYPFDAQNNLS

LRLGQGPLIVNSAHNLDLNLNRGLYLFTSGNTKKLEVNIKTAKGLFYDGTAIAINAGDGLQFGSGSDTNPL

QTKLGLGLEYDSNKAIITKLGTGLSFDNTGAITVGNKNDDKLTLWTTPDPSPNCRINSEKDAKLTLVLTKC

GSQVLASVSVLSVKGSLAPISGTVTSAQIVLRFDENGVLLSNSSLDPQYWNYRKGDSTEGTAYTNAVGFM

PNLTAYPKTQSQTAKSNIVSQVYLNGDKTKPMTLTITLNGTNETGDATVSTYSMSFSWNWNGSNYINDTF

QTNSFTFSYIAQE
```

PanAd2 fiber amino acid sequence                                                   SEQ ID NO: 36

```
MKRAKTSDETFNPVYPYDTENGPPSVPFLTPPFVSPDGFQESPPGVLSLRLSEPLVTSHGMLALKMGNGLS

LDDAGNLTSQDVTTVTPPLKKTKTNLSLQTSAPLTVSSGSLTVAAAAPLAVAGTSLTMQSQAPLTVQDAK

LGLATQGPLTVSEGKLTLQTSAPLTAADSSTLTVSATPPLSTSNGSLSIDMQAPIYTTNGKLALNIGAPLHV

VDTLNALTVVTGQGLTINGRALQTRVTGALSYDTEGNIQLQAGGGMRIDNNGQLILNVAYPFDAQNNLS

LRLGQGPLIVNSAHNLDLNLNRGLYLFTSGNTKKLEVNIKTAKGLFYDGTAIAINAGDGLQFGSGSDTNPL

QTKLGLGLEYDSNKAIITKLGTGLSFDNTGAITVGNKNDDKLTLWTTPDPSPNCRINSEKDAKLTLVLTKC

GSQVLASVSVLSVKGSLAPISGTVTSAQIVLRFDENGVLLSNSSLDPQYWNYRKGDSTEGTAYTNAVGFM

PNLTAYPKTQSQTAKSNIVSQVYLNGDKTKPMTLTITLNGTNETGDATVSTYSMSFSWNWNGSNYINDTF

QTNSFTFSYIAQE
```

RSV FΔTM-N-M2-1 amino acid sequence                                                SEQ ID NO: 37

```
MELLILKANAITTILTAVTFCFASGQNITEEFYQSTCSAVSKGYLSALRTGWYTSVITIELSNIKENKCNGTD

AKVKLIKQELDKYKNAVTELQLLMQSTPATNNRARRELPRFMNYTLNNAKKTNVTLSKKRKRRFLGFLL

GVGSAIASGVAVSKVLHLEGEVNKIKSALLSTNKAVVSLSNGVSVLTSKVLDLKNYIDKQLLPIVNKQSCS

ISNIETVIEFQQKNNRLLEITREFSVNAGVTTPVSTYMLTNSELLSLNDMPITNDQKKLMSNNVQIVRQQSY

SIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKN
```

RGIIKTFSNGCDYVSNKGVDTVSVGNTLYYVNKQEGKSLYVKGEPIINFYDPLVFPSDEFDASISQVNEKIN

QSLAFIRKSDELLHNVNAGKSTTNRKRRAPVKQTLNFDLLKLAGDVESNPGPMALSKVKLNDTLNKDQL

LSSSKYTIQRSTGDSIDTPNYDVQKHINKLCGMLLITEDANHKFTGLIGMLYAMSRLGREDTIKILRDAGY

HVKANGVDVTTHRQDINGKEMKIALVLTLASLTTEIQINIEIESRKSYKKMLKEMGEVAPEYRHDSPDCGM

IILCIAALVITKLAAGDRSGLTAVIRRANNVLKNEMKRYKGLLPKDIANS

FYEVIALKYPHFIDVFVHFGIAQSSTRGGSRVEGIFAGLFMNAYGAGQVMLRWGVLAKSVKNIMLGHASV

QAEMEQVVEVYEYAQKLGGEAGFYHILNNPKASLLSLTQFPHFSSVVLGNAAGLGIMGEYRGTPRNQDL

YDAAKAYAEQLKENGVINYSVLDLTAEELEAIKHQLNPKDNDVELGGGGSGGGGMSRRNPCKFEIRGHC

LNGKRCHFSHNYFEWPPHALLVRQNFMLNRILKSMDKSIDTLSEISGAAELDRTEEYALGVVGVLESYIGS

INNITKQSACVAMSKLLILLNSDDIKKLRDNEELNSPKIRVYNTVISYIESNRKNNKQTIHLLKRLPADVLK

KTIKNTLDIHKSITINNPKESTVSDTNDHAKNNDTT

HIV Gag polynucleotide sequence

SEQ ID NO: 38

ATGGGTGCTAGGGCTTCTGTGCTGTCTGGTGGTGAGCTGGACAAGTGGGAGAAGATCAGGCTGAGGC

CTGGTGGCAAGAAGAAGTACAAGCTAAAGCACATTGTGTGGGCCTCCAGGGAGCTGGAGAGGTTTG

CTGTGAACCCTGGCCTGCTGGAGACCTCTGAGGGGTGCAGGCAGATCCTGGGCCAGCTCCAGCCCTC

CCTGCAAACAGGCTCTGAGGAGCTGAGGTCCCTGTACAACACAGTGGCTACCCTGTACTGTGTGCAC

CAGAAGATTGATGTGAAGGACACCAAGGAGGCCCTGGAGAAGATTGAGGAGGAGCAGAACAAGTCC

AAGAAGAAGGCCCAGCAGGCTGCTGCTGGCACAGGCAACTCCAGCCAGGTGTCCCAGAACTACCCC

ATTGTGCAGAACCTCCAGGGCCAGATGGTGCACCAGGCCATCTCCCCCCGGACCCTGAATGCCTGGG

TGAAGGTGGTGGAGGAGAGGCCTTCTCCCCTGAGGTGATCCCCATGTTCTCTGCCCTGTCTGAGGGTG

CCACCCCCCAGGACCTGAACACCATGCTGAACACAGTGGGGGCCATCAGGCTGCCATGCAGATGCT

GAAGGAGACCATCAATGAGGAGGCTGCTGAGTGGACAGGCTGCATCCTGTGCACGCTGGCCCCATT

GCCCCCGGCCAGATGAGGGAGCCCAGGGGCTCTGACATTGCTGGCACCACCTCCACCCTCCAGGAGC

AGATTGGCTGGATGACCAACAACCCCCCCATCCCTGTGGGGGAAATCTACAAGAGGTGGATCATCCT

GGGCCTGAACAAGATTGTGAGGATGTACTCCCCCACCTCCATCCTGGACATCAGGCAGGGCCCCAAG

GAGCCCTTCAGGGACTATGTGGACAGGTTCTACAAGACCCTGAGGGCTGAGCAGGCCTCCCAGGAGG

TGAAGAACTGGATGACAGAGACCCTGCTGGTGCAGAATGCCAACCCTGACTGCAAGACCATCCTGAA

GGCCCTGGGCCCTGCTGCCACCCTGGAGGAGATGATGACAGCCTGCCAGGGGGTGGGGGCCCTGGT

CACAAGGCCAGGGTGCTGGCTGAGGCCATGTCCCAGGTGACCAACTCCGCCACCATCATGATGCAGA

GGGGCAACTTCAGGAACCAGAGGAAGACAGTGAAGTGCTTCAACTGTGGCAAGGTGGGCCACATTG

CCAAGAACTGTAGGGCCCCCAGGAAGAAGGGCTGCTGGAAGTGTGGCAAGGAGGGCCACCAGATGA

AGGACTGCAATGAGAGGCAGGCCAACTTCCTGGGCAAAATCTGGCCCTCCCACAAGGGCAGGCCTG

GCAACTTCCTCCAGTCCAGGCCTGAGCCCACAGCCCCTCCCGAGGAGTCCTTCAGGTTTGGGGAGGA

GAAGACCACCCCCAGCCAGAAGCAGGAGCCCATTGACAAGGAGCTGTACCCCCTGGCCTCCCTGAG

GTCCCTGTTTGGCAACGACCCCTCCTCCCAGTAA

---

What is claimed is:

1. A recombinant vector comprising a polynucleotide selected from the group consisting of:
   (a) a polynucleotide which encodes a polypeptide having the amino acid sequence according to SEQ ID NO: 1,
   (b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
   (c) a polynucleotide which encodes a polypeptide having the amino acid sequence according to SEQ ID NO: 3, wherein the recombinant vector comprises a nucleic acid sequence encoding a heterologous protein, wherein the nucleic acid sequence is operatively linked to one or more sequences which direct expression of said heterologous protein in a host cell, wherein the heterologous protein comprises the amino acid sequence according to SEQ ID NO: 37.

2. A recombinant adenovirus comprising at least one polynucleotide or polypeptide selected from the group consisting of:
   (a) a polynucleotide which encodes a polypeptide having the amino acid sequence according to SEQ ID NO: 1,
   (b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
   (c) a polynucleotide which encodes a polypeptide having the amino acid sequence according to SEQ ID NO: 3,
   (d) a polypeptide having the amino acid sequence according to SEQ ID NO: 1,
   (e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
   (f) a polypeptide having the amino acid sequence according to SEQ ID NO: 3,
   wherein the recombinant adenovirus comprises a nucleic acid sequence encoding a heterologous protein, wherein the nucleic acid sequence is operatively linked to one or more sequences which direct expression of said heterologous protein in a host cell, wherein the heterologous protein comprises the amino acid sequence according to SEQ ID NO: 37.

3. A composition comprising at least one of the following:
(a) a recombinant vector according to claim 1, and
(b) a recombinant adenovirus according to claim 2;
and a pharmaceutically acceptable excipient.

4. The recombinant vector according to claim 1, wherein the polynucleotide encodes a polypeptide having the amino acid sequence according to SEQ ID NO: 1.

5. The recombinant vector according to claim 4, wherein the polynucleotide has a sequence according to SEQ ID NO: 2.

6. The recombinant vector according to claim 1, wherein the polynucleotide comprises at least one of the following:
(a) an adenoviral 5' inverted terminal repeat;
(b) an adenoviral E1A region, or a fragment thereof selected from among the E1A 280R and E1A 243R regions;
(c) an adenoviral E1B or IX region, or a fragment thereof selected from among the group consisting of the E1B_19K, E1B_55K or IX regions;
(d) an adenoviral E2b region; or a fragment thereof selected from among the group consisting of the E2B_pTP, E2B_Polymerase and E2B_IVa2 regions;
(e) an adenoviral L1 region, or a fragment thereof, said fragment encoding an adenoviral protein selected from the group consisting of the L1_13.6k protein, L1_52k and L1_IIIa protein;
an adenoviral L2 region, or a fragment thereof, said fragment encoding an adenoviral protein selected from the group consisting of the L2_penton protein, L2_pVII, L2_V, and L2_pX protein;
(g) an adenoviral L3 region, or a fragment thereof, said fragment encoding an adenoviral protein selected from the group consisting of the L3_pVI protein, L3_hexon protein and L3_protease;
(h) an adenoviral E2A region;
(i) an adenoviral L4 region, or a fragment thereof said fragment encoding an adenoviral protein selected from the group consisting of the L4_100k protein, the L4_33k protein and protein L4_VIII;
(j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region, or a fragment thereof said fragment encoding the L5_fiber fiber protein;
(l) an adenoviral E4 region, or a fragment thereof selected from the group consisting of E4 ORF7, E4 ORF6, E4 ORF4, E4 ORF3, E4 ORF2, and E4 ORF1;
(m) an adenoviral 3'-end; and/or
(n) an adenoviral VAI or VAII RNA region.

7. The recombinant vector according to claim 1, wherein the polynucleotide comprises a polynucleotide which is identical over its entire length to a sequence selected from the group consisting of: SEQ ID NO:s 7, 8 and 9.

8. The recombinant adenovirus according to claim 2, wherein the recombinant adenovirus is replication-incompetent.

9. The recombinant adenovirus according to claim 2, wherein the adenovirus is capable of infecting a mammalian cell.

10. The composition according to claim 3, comprising an organic adjuvant.

11. The composition according to claim 10, wherein the organic adjuvant is QS21.

12. A method of inducing an immune response in a subject comprising administering the recombinant adenovirus of claim 2 to the subject.

13. The method according to claim 12 wherein the immune response is directed against respiratory syncytial virus (RSV).

14. A method of inducing an immune response in a subject comprising administering the composition of claim 3 to the subject.

15. The method according to claim 14, wherein the immune response is directed against respiratory syncytial virus (RSV).

16. An isolated polynucleotide comprising or consisting of the sequence according to SEQ ID NO: 11.

\* \* \* \* \*